(12) United States Patent
Shimizu et al.

(10) Patent No.: US 10,053,446 B2
(45) Date of Patent: Aug. 21, 2018

(54) HETEROBICYCLIC COMPOUNDS AND THEIR USE FOR THE TREATMENT OF TUBERCULOSIS

(71) Applicant: OTSUKA PHARMACEUTICAL CO., LTD., Tokyo (JP)

(72) Inventors: Hiroshi Shimizu, Higashikagawa (JP); Yoshikazu Kawano, Tokushima (JP); Shunpei Ishikawa, Tokushima (JP); Yukitaka Uematsu, Kitajima-cho (JP); Toshio Shinohara, Tokushima (JP); Motohiro Itotani, Tokushima (JP); Yoshikazu Haraguchi, Tokushima (JP); Isao Takemura, Naruto (JP); Atsunori Kaneshige, Ann Arbor, MI (US); Yuya Nakai, Matsushige-cho (JP); Norimitsu Hariguchi, Kitajima-cho (JP); Yohei Hayashi, Brussels (BE); Makoto Matsumoto, Millbrae, CA (US)

(73) Assignee: OTSUKA PHARMACEUTICAL CO., LTD., Tokyo (JP)

( * ) Notice: Subject to any disclaimer, the term of this patent is extended or adjusted under 35 U.S.C. 154(b) by 0 days.

(21) Appl. No.: 15/506,887

(22) PCT Filed: Aug. 28, 2015

(86) PCT No.: PCT/JP2015/004371
§ 371 (c)(1),
(2) Date: Feb. 27, 2017

(87) PCT Pub. No.: WO2016/031255
PCT Pub. Date: Mar. 3, 2016

(65) Prior Publication Data
US 2017/0253576 A1 Sep. 7, 2017

(30) Foreign Application Priority Data
Aug. 28, 2014 (JP) .................. 2014-174528

(51) Int. Cl.
*C07D 401/14* (2006.01)
*C07D 401/06* (2006.01)
*C07D 215/227* (2006.01)

(52) U.S. Cl.
CPC ....... *C07D 401/14* (2013.01); *C07D 215/227* (2013.01); *C07D 401/06* (2013.01)

(58) Field of Classification Search
CPC . C07D 401/14; C07D 215/227; C07D 401/06
USPC ...................................................... 546/157
See application file for complete search history.

(56) References Cited

U.S. PATENT DOCUMENTS

| 5,668,127 | A | 9/1997 | Baker et al. |
| 2006/0094767 | A1 | 5/2006 | Tsubouchi et al. |
| 2008/0119478 | A1 | 5/2008 | Tsubouchi et al. |
| 2009/0062261 | A1 | 3/2009 | Masui et al. |
| 2011/0028466 | A1 | 2/2011 | Thompson et al. |
| 2011/0059979 | A1* | 3/2011 | Jamieson .............. C04B 35/632 514/252.03 |
| 2011/0212939 | A1 | 9/2011 | Bertram et al. |
| 2014/0031342 | A1 | 1/2014 | Kawano et al. |

FOREIGN PATENT DOCUMENTS

| EP | 2532650 A2 * | 12/2012 |
| JP | 11-508270 A | 7/1999 |
| JP | 2004-149527 A | 5/2004 |
| JP | 2005-320316 A | 11/2005 |
| WO | 97/01562 A1 | 1/1997 |
| WO | 2005/042542 A1 | 5/2005 |
| WO | 2007/099828 A1 | 9/2007 |
| WO | 2010/004347 A1 | 1/2010 |
| WO | WO 2010/004347 A1 * | 1/2010 |
| WO | 2010/045987 A1 | 4/2010 |
| WO | 2011/014776 A1 | 2/2011 |

(Continued)

OTHER PUBLICATIONS

Kanabus, A. TB Prevention—Vaccine, drug treatment, isolation. TBFacts.org, 2017, first paragraph, p. 1.*
National Center for HIV/AIDS, Viral Hepatitis, STD, and TB Prevention—Division of Tuberculosis Elimination. TB Elimination—Diagnosis of Tuberculosis Disease. US Center for Disease Control, 2011, p. 1, right column, part 3.*
Iseman, Michael D., A Clinician's Guide to Tuberculosis, Lippincott Williams & Wilkins, printed in the USA, 2000, ISBN 0-7817-1749-3 (28 pgs. total).

(Continued)

*Primary Examiner* — Daniel R Carcanague
(74) *Attorney, Agent, or Firm* — Sughrue Mion, PLLC

(57) ABSTRACT

It is an object of the present invention to provide a compound having an excellent antibacterial activity against tuberculosis bacteria, multidrug-resistant tuberculosis bacteria and/or non-tuberculous mycobacteria. Disclosed is a compound of the general formula (1):

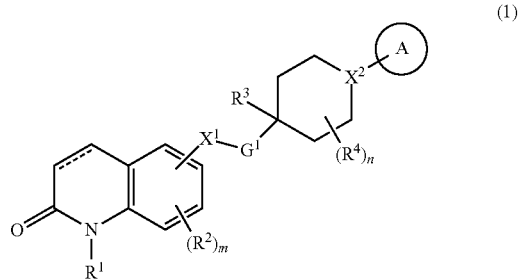

wherein each symbol is defined as described in the attached specification, or a salt thereof.

21 Claims, No Drawings

(56) References Cited

FOREIGN PATENT DOCUMENTS

WO 2012/141338 A1 10/2012
WO WO 2017146246 * 8/2017

OTHER PUBLICATIONS

Kekkaku 2nd edition, Fumiyuki Kuze, Takahide Izumi, Igaku-shoin, 1992 (8 pgs. total).
International Preliminary Report on Patentability dated Mar. 9, 2017, mailed from the International Bureau in counterpart International Application No. PCT/JP2015/004371.
International Search Report (ISR), issued by International Searching Authority in corresponding International Application No. PCT/JP2015/004371, dated Oct. 20, 2015.
Naik, M. et al., 4-Aminoquinolone Piperidine Amides: Noncovalent Inhibitors of DprE1 with Long Residence Time and Potent Antimycobacterial Activity, Journal of Medical Chemistry, 2014, vol. 57, 5419-5434 (16 pages total).
The Global Plan to Stop TB, Transforming the Fight Towards Elimination of Tuberculosis, World Health Organization, 2011-2015, (101 total pages).
Verma, S. et al, HIV-Tuberculosis Co-Infection, The Internet Journal of Pulmonary Medicine, 2007, vol. 10, No. 1 (5 pages total).
World Health Organization, Global Tuberculosis Report 2013, ISBN 978 92 4 156465 6 (306 pages total).
Kekkaku, Prospects for Development of New Antimicrobials for Clinical Control of Tuberculosis, vol. 74, No. 1, 77-82, 1999 (38 pages total).

* cited by examiner

HETEROBICYCLIC COMPOUNDS AND THEIR USE FOR THE TREATMENT OF TUBERCULOSIS

CROSS REFERENCE TO RELATED APPLICATIONS

This application is a National Stage of International Application No. PCT/JP2015/004371, filed on Aug. 28, 2015, which claims priority from Japanese Patent Application No. 2014-174528, filed on Aug. 28, 2014, the contents of all of which are incorporated herein by reference in their entirety.

TECHNICAL FIELD

The present invention relates to a fused heterocyclic compound.

BACKGROUND ART

Human tuberculosis bacteria (*Mycobacterium tuberculosis*) is widely known among mycobacteria, with which third part of human beings are said to be infected. *Mycobacterium africanum, Mycobacterium bovis, Mycobacterium caprae, Mycobacterium pinnipedii*, and *Mycobacterium microti* are known to belong to the tuberculosis bacteria group like human tuberculosis bacteria, and are known as mycobacteria having pathogenicity against human.

Multidrug chemotherapy for 6 months has been recommended as a treatment for these tuberculosis bacteria. A typical therapy comprises a treatment with 4 agents of rifampicin, isoniazid, pyrazinamide, and ethambutol (or streptomycin) for the first 2 months; and a treatment with 2 agents of rifampicin and isoniazid for the remaining 4 months.

It has been pointed out however that the medication compliance in the treatment for tuberculosis is poor due to such long-term treatment and adverse effects of the used drugs often cause the treatment to discontinue.

The adverse effects of these drugs have been reported (Nonpatent Literatures 1 and 2), for example, rifampicin has hepatic disorder, flu syndrome, drug allergy, and contraindication to combination use with other drugs caused by P450-related enzymes; isoniazid has peripheral neuropathy and serious hepatic disorder induced with a combination use with rifampicin; ethambutol has visual loss caused by optic nerve disorder; streptomycin has hearing loss caused by eighth cranial nerve involvement; pyrazinamide has hepatic disorder, gouty attack associated with the uric acid level, and vomiting. Amongst the adverse effects of the above 5 agents used as a first-line drug, in particular, hepatotoxicity commonly-caused by rifampicin, isoniazid, and pyrazinamide is known as the most frequent adverse effect.

It has been in fact reported that the cases where the standard chemotherapy cannot be carried out due to the adverse effects account for 70% of the cases where the drug administration is discontinued (about 23%, 52 cases) of the total (the total of 228 inpatient cases surveyed) (Nonpatent Literature 3).

Tuberculosis bacteria resistant to antitubercular agents, multidrug-resistant tuberculosis bacteria, for example have been recently increasing, which has made the treatment of tuberculosis more difficult.

The World Health Organization (WHO) has reported that among those who have been infected with multidrug-resistant tuberculosis (MDR-TB) resistant to potent rifampicin and isoniazid, 450,000 people have newly developed and 170,000 people have died per year, and multidrug-resistant tuberculosis patients are currently estimated as 1,500,000 in the world. An extensively-drug-resistant tuberculosis (XDR-TB) which has been resistant to many drugs has been identified, which has become a threat to public health in the world (Nonpatent Literature 4).

Third part of those who have been infected with HIV in the world has been suspected of co-infection with tuberculosis even though not progressing to active tuberculosis (Nonpatent Literature 5). Co-infection of HIV and tuberculosis is fatal, in which one disease can accelerate the progression of the other disease and tuberculosis can easily progress to active tuberculosis. In 2012, about 320,000 people died of tuberculosis associated with HIV, which means that about 25% of the death of HIV infected people were caused by tuberculosis. It has been also reported that patients infected with both HIV and tuberculosis can develop tuberculosis in 20 to 37 times higher risk than usual (Nonpatent Literature 6).

The American Thoracic Society and Centers for Disease Control and Prevention have recently reported the concept that carriage state itself of tuberculosis bacteria is a potential disease even though not developing to tuberculosis, and the usefulness of active treatment has been established for patients with a higher risk of developing to the disease.

In view of the current circumstances, a desired profile for antitubercular agents includes (1) those effective for multidrug-resistant tuberculosis bacteria, (2) those which enable a short-term chemotherapy, (3) those with less adverse effects, (4) those effective for latent tuberculosis infection (LTBI).

*Mycobacterium avium* and *Mycobacterium intracellulare*, which are responsible bacteria for recently increasing MAC symptom (*Mycobacterium avium-intracellulare* complex symptom), as well as other non-tuberculous mycobacteria such as *Mycobacterium kansasii, Mycobacterium marinum, Mycobacterium simiae, Mycobacterium scrofulaceum, Mycobacterium szulgai, Mycobacterium xenopi, Mycobacterium malmoense, Mycobacterium haemophilum, Mycobacterium ulcerans, Mycobacterium shimoidei, Mycobacterium fortuitum, Mycobacterium chelonae, Mycobacterium smegmatis*, and *Mycobacterium aurum* have been known as bacteria having pathogenicity in human.

A typical chemotherapy of lung MAC symptom is polypharmacy based on three drugs of rifampicin, ethambutol, and clarithromycin, and streptomycin or kanamycin is, if needed, used in combination. Another treatment for non-tuberculous mycobacteria symptom currently includes combination use with an antitubercular agent such as rifampicin, isoniazid, ethambutol, streptomycin, kanamycin, a therapeutic agent for common bacterial infection such as a new quinolone agent, a macrolide antibacterial agent, an aminoglycoside antibacterial agent, and a tetracycline antibacterial agent.

It has been reported however that the treatment for non-tuberculous mycobacteria needs a longer-term medication than that in common bacterial infection, the treatment tends to become refractory, and some have resulted in death. To solve the circumstances, a development of more potent drugs has been desired.

For example, Patent Literature 1 discloses that 6-nitro-1,2,3,4-tetrahydro[2,1-b]imidazopyrane compounds have a bactericidal activity against tuberculosis bacteria (H37Rv strain) and multidrug-resistant tuberculosis bacteria in vitro and a therapeutic effect in oral administration for a tuberculosis-infected animal model, and thus they are useful as an antitubercular agent.

Patent Literatures 2 and 3 disclose that 2,3-dihydroimidazo[2,1-b]oxazole compounds have a bactericidal activity against tuberculosis bacteria, multidrug-resistant tuberculosis bacteria, and atypical mycobacteria.

Patent Literature 4 discloses that nitroimidazooxazine and nitroimidazooxazole compounds can be used as a medicament against human tuberculosis bacteria (*Mycobacterium tuberculosis*).

Patent Literature 5 discloses that 6,7-dihydroimidazo[2,1-b][1,3]oxazine compounds have an excellent bactericidal activity against tuberculosis bacteria and multidrug-resistant tuberculosis bacteria.

The compounds disclosed in the above references, however, structurally differ from and are not similar to the compound of the present invention.

CITATION LIST

Patent Literature

[PTL 1] WO 97/01562 (JP-A-11-508270)
[PTL 2] JP-A-2004-149527
[PTL 3] JP-A-2005-320316
[PTL 4] WO 2011/014776
[PTL 5] WO 2012/141338

Non Patent Literature

[NPL 1] A Clinician's Guide To Tuberculosis, Michael D. Iseman 2000 by Lippincott Williams & Wilkins, printed in the USA, ISBN 0-7817-1749-3
[NPL 2] Kekkaku 2nd edition, Fumiyuki Kuze, Takahide Izumi, Igaku-shoin 1992
[NPL 3] Kekkaku Vol. 74: 77-82, 1999
[NPL 4] Global tuberculosis report 2013
[NPL 5] The Internet Journal of Pulmonary Medicine 2008: Volume 10 Number 1
[NPL 6] The Global Plan To Stop TB 2011-2015

SUMMARY OF INVENTION

Technical Problem

It is an object of the present invention to provide compounds having an excellent antibacterial activity against tuberculosis bacteria and multidrug-resistant tuberculosis bacteria. It is another object of the present invention to provide compounds having an excellent antibacterial activity against non-tuberculous mycobacteria.

Solution to Problem

The present inventors have achieved syntheses of novel fused heterocyclic compounds having an excellent bactericidal activity against tuberculosis bacteria, multidrug-resistant tuberculosis bacteria, and non-tuberculous mycobacteria as a result of extensive studies to solve the problem. The present invention has been accomplished on the basis of this finding.

In one aspect, the present invention includes a compound of the general formula (1):

[Chem. 1]

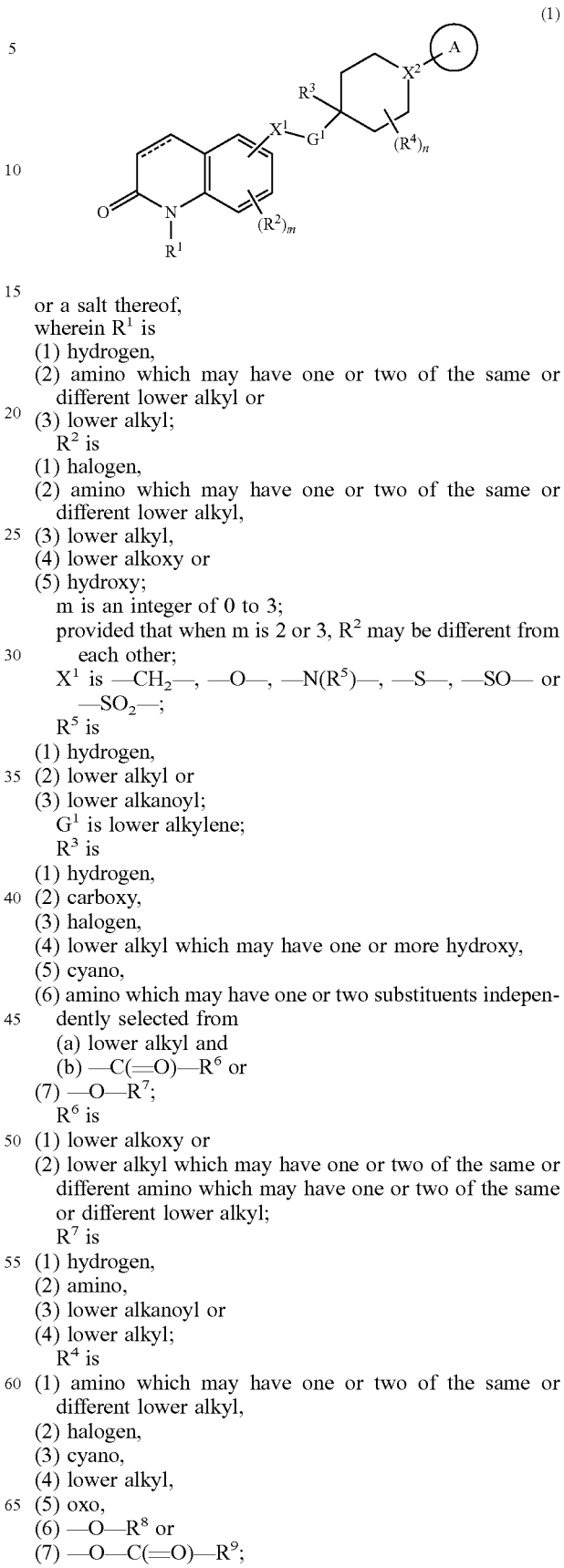

(1)

or a salt thereof,
wherein $R^1$ is
(1) hydrogen,
(2) amino which may have one or two of the same or different lower alkyl or
(3) lower alkyl;
$R^2$ is
(1) halogen,
(2) amino which may have one or two of the same or different lower alkyl,
(3) lower alkyl,
(4) lower alkoxy or
(5) hydroxy;
m is an integer of 0 to 3;
provided that when m is 2 or 3, $R^2$ may be different from each other;
$X^1$ is —$CH_2$—, —O—, —N($R^5$)—, —S—, —SO— or —$SO_2$—;
$R^5$ is
(1) hydrogen,
(2) lower alkyl or
(3) lower alkanoyl;
$G^1$ is lower alkylene;
$R^3$ is
(1) hydrogen,
(2) carboxy,
(3) halogen,
(4) lower alkyl which may have one or more hydroxy,
(5) cyano,
(6) amino which may have one or two substituents independently selected from
 (a) lower alkyl and
 (b) —C(=O)—$R^6$ or
(7) —O—$R^7$;
$R^6$ is
(1) lower alkoxy or
(2) lower alkyl which may have one or two of the same or different amino which may have one or two of the same or different lower alkyl;
$R^7$ is
(1) hydrogen,
(2) amino,
(3) lower alkanoyl or
(4) lower alkyl;
$R^4$ is
(1) amino which may have one or two of the same or different lower alkyl,
(2) halogen,
(3) cyano,
(4) lower alkyl,
(5) oxo,
(6) —O—$R^8$ or
(7) —O—C(=O)—$R^9$;

$R^8$ is
(1) hydrogen,
(2) lower alkyl,
(3) —PH(=O)OH or
(4) benzyl which may have one or more of the same or different lower alkoxy;
$R^9$ is
(1) lower alkyl,
(2) -$G^2$-COOH,
(3) amino which may have one or two of the same or different lower alkyl,
(4) lower alkoxy or
(5) pyrazinyl;
$G^2$ is lower alkylene;
n is an integer of 0 to 8;
provided that when n is 2 or more, each of $R^4$, $R^8$, $R^9$, and $G^2$ may be different from each other and may be substituted on the same carbon atom;
$X^2$ is N or CH;
provided that when $X^2$ is CH, H of the group may be substituted with $R^4$ which is defined as above or may be different from the other $R^4$;
Ring A is
(1) aryl which may have one or more substituents, or
(2) heterocyclyl which may have one or more substituents; a moiety of formula:
[Chem. 2]

- - - - represents a single bond or a double bond; which is referred hereinafter to as Compound (1).

Advantageous Effects of Invention

Compound (1) in the present invention has specific activities in particular against mycobacteria (such as tuberculosis bacterial genus and non-tuberculous mycobacterial genus), and also has excellent activities against multidrug-resistant tuberculosis bacteria.

Compound (1) in the present invention shows not only the activities in vitro but also the activities in vivo in oral administration because the administered compound is favorably distributed in lung tissues which are the primary organ infected with the mycobacterial infectious disease.

Compound (1) in the present invention does not induce diarrhea as seen in known antibacterial agents with a wide spectrum for common bacteria such as gram-positive bacteria and gram-negative bacteria, and thereby may become a medicinal substance which allows for a long-term administration.

Compound (1) in the present invention is effective for intracellular parasitic bacteria such as human-origin tuberculosis bacteria which is parasitic in macrophage, and has a stronger bactericidal activity in a low concentration even in a bactericidal test than conventional antitubercular agents. It is thus expected that the relapse rate in tuberculosis will be reduced, which eventually allows for a short-term chemotherapy.

Compound (1) in the present invention shows a low inhibitory activity against a drug-metabolizing enzyme, a low possibility for an enzyme induction of CYP3A, and a low concerns about drug interaction. Thus, the compound is expected for a combination use with conventional drugs or HIV drugs.

In addition, Compound (1) has a lower toxicity than conventional drugs, and hence the compound is also expected for long-term use in the treatment for latent tuberculosis.

DESCRIPTION OF EMBODIMENTS

The phrases and terms used herein are described in detail as below.

Examples of "lower alkyl" include straight or branched chain alkyl groups having 1 to 6 carbon atoms, and in particular include, for example, methyl, ethyl, propyl, isopropyl, butyl, isobutyl, sec-butyl, tert-butyl, pentyl, isopentyl, neopentyl, hexyl, isohexyl, and 3-methylpentyl.

Examples of "lower alkenyl" include straight or branched chain alkenyl groups having 2 to 6 carbon atoms and 1 to 3 double bonds, and include, for example, vinyl (ethenyl), 1-propenyl, 2-propenyl, 2-methyl-1-propenyl, 1-butenyl, 2-butenyl, 3-butenyl, 3-methyl-2-butenyl, 1-pentenyl, 2-pentenyl, 3-pentenyl, 4-pentenyl, 4-methyl-3-pentenyl, 1-hexenyl, 3-hexenyl, and 5-hexenyl.

Examples of "lower alkynyl" include straight or branched chain alkynyl groups having 2 to 6 carbon atoms and 1 to 3 triple bonds, and include, for example, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, and 5-hexynyl.

Examples of "lower alkoxy" include straight or branched chain alkoxy groups having 1 to 6 carbon atoms, and include, for example, methoxy, ethoxy, propoxy, isopropoxy, butoxy, isobutoxy, sec-butoxy, tert-butoxy, pentyloxy, isopentyloxy, neopentyloxy, hexyloxy, isohexyloxy, and 3-methylpentyloxy.

Examples of "lower alkenyloxy" include straight or branched chain alkenyloxy groups having 2 to 6 carbon atoms and 1 to 3 double bonds, and include, for example, vinyloxy (ethenyloxy), 1-propenyloxy, 2-propenyloxy, 2-methyl-1-propenyloxy, 1-butenyloxy, 2-butenyloxy, 3-butenyloxy, 3-methyl-2-butenyloxy, 1-pentenyloxy, 2-pentenyloxy, 3-pentenyloxy, 4-pentenyloxy, 4-methyl-3-pentenyloxy, 1-hexenyloxy, 3-hexenyloxy, and 5-hexenyloxy.

Examples of "lower alkynyloxy" include straight or branched chain alkynyloxy groups having 2 to 6 carbon atoms and 1 to 3 triple bonds, and include, for example, ethynyloxy, 1-propynyloxy, 2-propynyloxy, 1-butynyloxy, 2-butynyloxy, 3-butynyloxy, 1-pentynyloxy, 2-pentynyloxy, 3-pentynyloxy, 4-pentynyloxy, 1-hexynyloxy, 2-hexynyloxy, 3-hexynyloxy, 4-hexynyloxy, and 5-hexynyloxy.

Examples of "lower alkanoyl" include straight or branched chain alkanoyl groups having 1 to 7 carbon atoms, and include, for example, formyl, acetyl, propionyl, butyryl, isobutyryl, pentanoyl, tert-butylcarbonyl, and hexanoyl.

Examples of "lower alkenylcarbonyl" include straight or branched chain alkenylcarbonyl groups having 3 to 7 carbon atoms and 1 to 3 double bonds, and include, for example, vinylcarbonyl (ethenylcarbonyl), 1-propenylcarbonyl, 2-propenylcarbonyl, 2-methyl-1-propenylcarbonyl, 1-butenylcarbonyl, 2-butenylcarbonyl, 3-butenylcarbonyl, 3-methyl-2-butenylcarbonyl, 1-pentenylcarbonyl, 2-pentenylcarbonyl, 3-pentenylcarbonyl, 4-pentenylcarbonyl, 4-methyl-3-pentenylcarbonyl, 1-hexenylcarbonyl, 3-hexenylcarbonyl, and 5-hexenylcarbonyl.

Examples of "lower alkynylcarbonyl" include straight or branched chain alkynylcarbonyl groups having 3 to 7 carbon atoms and 1 to 3 triple bonds, and include, for example, ethynylcarbonyl, 1-propynylcarbonyl, 2-propynylcarbonyl, 1-butynylcarbonyl, 2-butynylcarbonyl, 3-butynylcarbonyl, 1-pentynylcarbonyl, 2-pentynylcarbonyl, 3-pentynylcarbonyl, 4-pentynylcarbonyl, 1-hexynylcarbonyl, 2-hexynylcarbonyl, 3-hexynylcarbonyl, 4-hexynylcarbonyl, and 5-hexynylcarbonyl.

Examples of "lower alkanoyloxy" include straight or branched chain alkanoyloxy groups having 1 to 7 carbon atoms, and include, for example, formyloxy, acetyloxy, propionyloxy, butyryloxy, isobutyryloxy, pentanoyloxy, tert-butylcarbonyloxy, and hexanoyloxy.

Examples of "lower alkoxycarbonyl" include straight or branched chain alkoxycarbonyl groups having 2 to 7 carbon atoms, and include, for example, methoxycarbonyl, ethoxycarbonyl, propoxycarbonyl, isopropoxycarbonyl, butoxycarbonyl, tert-butoxycarbonyl, pentyloxycarbonyl, and hexyloxycarbonyl.

Examples of "lower alkylsulfanyl" include straight or branched chain alkylsulfanyl groups having 1 to 6 carbon atoms, and include, for example, methylsulfanyl, ethylsulfanyl, propylsulfanyl, isopropylsulfanyl, butylsulfanyl, tert-butylsulfanyl, pentylsulfanyl, and hexylsulfanyl.

Examples of "lower alkylsulfinyl" include straight or branched chain alkylsulfinyl groups having 1 to 6 carbon atoms, and include, for example, methylsulfinyl, ethylsulfinyl, propylsulfinyl, isopropylsulfinyl, butylsulfinyl, tert-butylsulfinyl, pentylsulfinyl, and hexylsulfinyl.

Examples of "lower alkylsulfonyl" include straight or branched chain alkylsulfonyl groups having 1 to 6 carbon atoms, and include, for example, methylsulfonyl, ethylsulfonyl, propylsulfonyl, isopropylsulfonyl, butylsulfonyl, tert-butylsulfonyl, pentylsulfonyl, and hexylsulfonyl.

Examples of "cyclo-lower-alkyl" include cycloalkyl groups having 3 to 6 carbon atoms, and include, for example, cyclopropyl, cyclobutyl, cyclopentyl, and cyclohexyl.

Examples of "cyclo-lower-alkenyl" include cycloalkenyl groups having 3 to 6 carbon atoms, and include, for example, 2-cyclopentenyl, 3-cyclopentenyl, 2-cyclohexenyl, and 3-cyclohexenyl.

Examples of "cyclo-lower-alkoxy" include cycloalkoxy groups having 3 to 6 carbon atoms, and include, for example, cyclopropyloxy, cyclobutyloxy, cyclopentyloxy, and cyclohexyloxy.

Examples of "cyclo-lower-alkenyloxy" include cycloalkenyloxy groups having 3 to 6 carbon atoms, and include, for example, 2-cyclopentenyloxy, 3-cyclopentenyloxy, 2-cyclohexenyloxy, and 3-cyclohexenyloxy.

Examples of "cyclo-lower-alkylcarbonyl" include cycloalkylcarbonyl groups having 4 to 7 carbon atoms, and include, for example, cyclopropylcarbonyl, cyclobutylcarbonyl, cyclopentylcarbonyl, and cyclohexylcarbonyl.

Examples of "cyclo-lower-alkoxycarbonyl" include cycloalkoxycarbonyl group having 4 to 7 carbon atoms, and include, for example, cyclopropyloxycarbonyl, cyclobutyloxycarbonyl, cyclopentyloxycarbonyl, and cyclohexyloxycarbonyl.

Examples of "aryl" include mono-, bi-, or tri-cyclic aromatic hydrocarbon groups, and include, for example, phenyl, naphthyl, anthryl, and phenanthryl.

Examples of "aryloxy" include mono-, bi-, or tri-cyclic aromatic hydrocarbon-oxy groups, and include, for example, phenyloxy, naphthyloxy, anthryloxy, and phenanthryloxy.

Examples of "arylcarbonyl" include mono-, bi-, or tri-cyclic aromatic hydrocarbon-carbonyl groups, and include, for example, phenylcarbonyl, naphthylcarbonyl, anthrylcarbonyl, and phenanthrylcarbonyl.

Examples of "aryloxycarbonyl" include mono-, bi-, or tri-cyclic aromatic hydrocarbon-oxycarbonyl groups, and include, for example, phenyloxycarbonyl, naphthyloxycarbonyl, anthryloxycarbonyl, and phenanthryloxycarbonyl.

Examples of "aralkyl" include straight or branched chain alkyl groups having 1 to 3 carbon atoms which are substituted with mono-, bi-, or tri-cyclic aromatic hydrocarbon groups, and include, for example, benzyl, 1-phenylethyl, 2-phenylethyl, 1-naphthylmethyl, and 2-naphthylmethyl.

Examples of "aralkyloxy" include straight or branched chain alkoxy groups having 1 to 3 carbon atoms which are substituted with mono-, bi-, or tri-cyclic aromatic hydrocarbon groups, and include, for example, benzyloxy, 1-phenylethyloxy, 2-phenylethyloxy, 1-naphthylmethyloxy, and 2-naphthylmethyloxy.

Examples of "aralkylcarbonyl" include straight or branched chain alkylcarbonyl groups having 2 to 4 carbon atoms which are substituted with mono-, bi-, or tri-cyclic aromatic hydrocarbon groups, and include, for example, benzylcarbonyl, 1-phenylethylcarbonyl, 2-phenylethylcarbonyl, 1-naphthylmethylcarbonyl, and 2-naphthylmethylcarbonyl.

Examples of "aralkyloxycarbonyl" include straight or branched chain alkyloxycarbonyl groups having 2 to 4 carbon atoms which are substituted with mono-, bi-, or tri-cyclic aromatic hydrocarbon groups, and include, for example, benzyloxycarbonyl, 1-phenylethyloxycarbonyl, 2-phenylethyloxycarbonyl, 1-naphthylmethyloxycarbonyl, 2-naphthylmethyloxycarbonyl, and biphenylylmethyloxycarbonyl.

Examples of "heterocyclyl" include saturated or unsaturated monocyclic or polycyclic (e.g. bicyclic, tricyclic, spiro-form, or bicyclo-form) heterocyclyl groups comprising at least one (e.g. 1 to 5) heteroatom selected as a ring-constituent atom from oxygen atom, sulfur atom (which may form sulfoxide), and nitrogen atom (which may form amine oxide) besides carbon atoms, and for example include:

(a) saturated or unsaturated 3- to 8-membered (preferably 5- or 6-membered) heteromonocyclic groups comprising 1 to 4 nitrogen atoms, for example, pyrrolyl, pyrrolinyl, imidazolyl, pyrazolyl, pyridyl, N-oxide pyridyl, tetrahydropyridyl, pyrimidinyl, pyrazinyl, pyridazinyl, triazolyl, tetrazolyl, dihydrotriazinyl, azetidinyl, pyrrolidinyl, imidazolidinyl, piperidyl, pyrazolidinyl, piperazinyl, azepanyl, 1,4-diazepanyl;

(b) saturated or unsaturated 7- to 12-membered fused heterocyclyl groups comprising 1 to 5 nitrogen atoms, for example, decahydroquinolyl, indolyl, dihydroindolyl, isoindolyl, indolizinyl, benzoimidazolyl, dihydrobenzoimidazolyl, quinolyl, dihydroquinolyl, tetrahydroquinolyl, isoquinolyl, dihydroisoquinolyl, tetrahydroisoquinolyl, carbostyryl, dihydrocarbostyryl, indazolyl, benzotriazolyl, tetrazolopyridyl, tetrazolopyridazinyl, dihydrotriazolopyridazinyl, imidazopyridyl, naphthyridinyl, cinnolinyl, quinoxalinyl, quinazolinyl, pyrazolopyridyl, tetrahydropyridoindolyl;

(c) saturated or unsaturated 3- to 8-membered (preferably 5- or 6-membered) heteromonocyclic groups comprising 1 or 2 oxygen atoms, for example, furyl, tetrahydropyranyl, tetrahydrofuryl, dioxanyl;

(d) saturated or unsaturated 7- to 12-membered fused heterocyclyl groups comprising 1 to 3 oxygen atoms, for example, benzofuryl, dihydrobenzofuryl, chromanyl, benzodioxanyl, benzodioxolyl;

(e) saturated or unsaturated 3- to 8-membered (preferably 5- or 6-membered) heteromonocyclic groups comprising 1 or 2 oxygen atoms and 1 to 3 nitrogen atoms, for example, oxazolyl, isoxazolyl, oxadiazolyl, morpholinyl;

(f) saturated or unsaturated 7- to 12-membered fused heterocyclyl groups comprising 1 or 2 oxygen atoms and 1 to 3 nitrogen atoms, for example, benzooxazolyl, benzooxadiazolyl, benzoisoxazolyl, dihydrobenzooxazinyl, furopyridyl, furopyrrolyl;

(g) saturated or unsaturated 3- to 8-membered (preferably 5- or 6-membered) heteromonocyclic groups comprising 1 or 2 sulfur atoms and 1 to 3 nitrogen atoms, for example, thiazolyl, thiazolinyl, thiadiazolyl, isothiazolyl, thiazolidinyl;

(h) saturated or unsaturated 7- to 12-membered fused heterocyclyl groups comprising 1 or 2 sulfur atoms and 1 to 3 nitrogen atoms, for example, benzothiazolyl, benzothiadiazolyl, thienopyridyl, imidazothiazolyl, dihydroimidazothiazolyl, thienopyrazinyl;

(i) saturated or unsaturated 3- to 8-membered (preferably 5- or 6-membered) heteromonocyclic groups comprising 1 sulfur atom, for example, thienyl;

(j) saturated or unsaturated 7- to 12-membered fused heterocyclyl groups comprising 1 to 3 sulfur atoms, for example, benzothienyl;

(k) saturated or unsaturated 7- to 12-membered heterocyclic spiro groups, for example, azaspiroundecanyl; and (l) saturated or unsaturated 7- to 12-membered bicyclo heterocyclyl groups, for example, azabicyclo-cyclooctanyl.

"Heterocyclyloxy" refers to a group of "(heterocyclyl)-O—", and examples of heterocyclyl group include groups as illustrated above in "heterocyclyl".

"Heterocyclylcarbonyl" refers to a group of "(heterocyclyl)-CO—", and examples of heterocyclyl group include groups as illustrated above in "heterocyclyl".

"Heterocyclyloxycarbonyl" refers to a group of "(heterocyclyl)-O—CO—", and examples of heterocyclyl include groups as illustrated above in "heterocyclyl".

Examples of "mono- or di-lower alkylamino" include amino groups which are mono- or di-substituted with straight or branched chain alkyl groups having 1 to 6 carbon atoms, and for example, include mono-lower alkylamino groups such as methylamino, ethylamino, propylamino, isopropylamino, butylamino, isobutylamino, sec-butylamino, and tert-butylamino; di-lower alkylamino groups such as dimethylamino, diethylamino, dipropylamino, dibutylamino, diisobutylamino, di-sec-butylamino, di-tert-butylamino, and N-ethyl-N-methylamino.

Examples of "mono- or di-lower alkanoylamino" include amino groups which are mono- or di-substituted with straight or branched chain alkanoyl groups having 1 to 7 carbon atoms, for example, mono-lower alkanoylamino groups such as formylamino, acetylamino, propionylamino, butyrylamino, isobutyrylamino, pentanoylamino, tert-butylcarbonylamino, and hexanoylamino; di-lower alkanoylamino groups such as diformylamino, diacetylamino, dipropionylamino, dibutyrylamino, diisobutyrylamino, dipentanoylamino, di-tert-butylcarbonylamino, and dihexanoylamino.

Examples of "tri-lower alkylsilyl" include silyl groups which are tri-substituted with straight or branched chain alkyl groups having 1 to 6 carbon atoms, for example, trimethylsilyl, triethylsilyl, triisopropylsilyl, tert-butyldimethylsilyl.

Examples of "lower alkylene" include straight or branched chain alkylene groups having 1 to 6 carbon atoms, for example, —$CH_2$—, —$(CH_2)_2$—, —$(CH_2)_3$—, —$(CH_2)_4$—, —$(CH_2)_5$—, —$(CH_2)_6$—, —$CH(CH_3)$—, —$C(CH_3)_2$—, —$CH(CH_2CH_3)$—, —$C(CH_3)(CH_2CH_3)$—, —$C(CH_2CH_3)_2$—, —$CH(CH_2CH_2CH_3)$—, —$C(CH_3)(CH_2CH_2CH_3)$—, —$CH(CH(CH_3)_2)$—, —$C(CH_3)(CH(CH_3)_2)$—, —$C(CH_2CH_3)(CH(CH_3)_2)$—, —$CH_2$—$CH(CH_3)$—, —$CH(CH_3)$—$CH_2$—, —$CH_2$—$CH(CH_2CH_3)$—, —$CH(CH_2CH_3)$—$CH_2$—, —$(CH(CH_3))_2$—, —$CH(CH_3)$—$CH_2$—$CH_2$—, —$CH_2$—$CH(CH_3)$—$CH_2$—, —$CH_2$—$CH_2$—$CH(CH_3)$—, —$CH_2$—$CH_2$—$C(CH_3)_2$—, —$C(CH_3)_2$—$CH_2$—$CH_2$—, —$CH_2$—$CH_2$—$CH_2$—$C(CH_3)_2$—, —$C(CH_3)_2$—$CH_2$—$CH_2$—$CH_2$—.

Examples of "halogen" include fluorine, chlorine, bromine, and iodine.

The phrase "β which may have α" means that β may be substituted with at least one (usually 1 to 10, preferably 1 to 6, more preferably 1 to 3, and 1 or 2 in the case where β is amino or carbamoyl) α, each of β being displaceable at the same or different positions.

Examples of "substituent" in the phrase "may have one or more substituents" include groups independently selected from:

(A) halogen,
(B) cyano,
(C) nitro,
(D) hydroxy,
(E) carboxy,
(F) sulfo,
(G) sulfanyl,
(H) lower alkyl which may have one or more substituents selected from groups (Ia) and (Ib),
(I) lower alkenyl which may have one or more substituents selected from groups (Ia) and (Ib),
(J) lower alkynyl which may have one or more substituents selected from groups (Ia) and (Ib),
(K) lower alkoxy which may have one or more substituents selected from groups (Ia) and (Ib),
(L) lower alkenyloxy which may have one or more substituents selected from groups (Ia) and (Ib),
(M) lower alkynyloxy which may have one or more substituents selected from groups (Ia) and (Ib),
(N) lower alkanoyl which may have one or more substituents selected from groups (Ia) and (Ib),
(O) lower alkenylcarbonyl which may have one or more substituents selected from groups (Ia) and (Ib),
(P) lower alkynylcarbonyl which may have one or more substituents selected from groups (Ia) and (Ib),
(Q) lower alkanoyloxy which may have one or more substituents selected from groups (Ia) and (Ib),
(R) lower alkoxycarbonyl which may have one or more substituents selected from groups (Ia) and (Ib),
(S) lower alkylsulfanyl which may have one or more substituents selected from groups (Ia) and (Ib),
(T) lower alkylsulfinyl which may have one or more substituents selected from groups (Ia) and (Ib),
(U) lower alkylsulfonyl which may have one or more substituents selected from groups (Ia) and (Ib),
(V) cyclo-lower-alkyl which may have one or more substituents selected from groups (Ia), (Ib), (Ic), and oxo,
(W) cyclo-lower-alkoxy which may have one or more substituents selected from groups (Ia), (Ib), (Ic), and oxo,
(X) cyclo-lower-alkenyl which may have one or more substituents selected from groups (Ia), (Ib), (Ic), and oxo,
(Y) cyclo-lower-alkenyloxy which may have one or more substituents selected from groups (Ia), (Ib), (Ic), and oxo,
(Z) cyclo-lower-alkylcarbonyl which may have one or more substituents selected from groups (Ia), (Ib), (Ic), and oxo,
(AA) cyclo-lower-alkoxycarbonyl group which may have one or more substituents selected from groups (Ia), (Ib), (Ic), and oxo,
(BB) aryl which may have one or more substituents selected from groups (Ia), (Ib), and (Ic), (CC) aryloxy which may have one or more substituents selected from groups (Ia), (Ib), and (Ic),
(DD) arylcarbonyl which may have one or more substituents selected from groups (Ia), (Ib), and (Ic),
(EE) aryloxycarbonyl which may have one or more substituents selected from groups (Ia), (Ib), and (Ic),
(FF) aralkyl which may have one or more substituents selected from groups (Ia), (Ib), and (Ic),
(GG) aralkyloxy which may have one or more substituents selected from groups (Ia), (Ib), and (Ic),
(HH) aralkylcarbonyl which may have one or more substituents selected from groups (Ia), (Ib), and (Ic),
(II) aralkyloxycarbonyl which may have one or more substituents selected from groups (Ia), (Ib), and (Ic),
(JJ) heterocyclyl which may have one or more substituents selected from groups (Ia), (Ib), (Ic), and oxo,
(KK) heterocyclyloxy which may have one or more substituents selected from groups (Ia), (Ib), (Ic), and oxo,
(LL) heterocyclylcarbonyl which may have one or more substituents selected from groups (Ia), (Ib), (Ic), and oxo,
(MM) heterocyclyloxycarbonyl which may have one or more substituents selected from groups (Ia), (Ib), (Ic), and oxo,
(NN) amino which may have one or more substituents selected from groups (Ia) and (Ic), and
(OO) carbamoyl which may have one or more substituents selected from groups (Ia) and (Ic).

The number of any substituents in Compound (1) is not limited as long as chemically applicable, unless otherwise specified.

The "group (Ia)" includes substituents selected from:
(a) lower alkanoyl which may have one or more substituents selected from groups (IIa) and (IIb),
(b) lower alkenylcarbonyl which may have one or more substituents selected from groups (IIa) and (IIb),
(c) lower alkynylcarbonyl which may have one or more substituents selected from groups (IIa) and (IIb),
(d) lower alkoxycarbonyl which may have one or more substituents selected from groups (IIa) and (IIb),
(e) lower alkylsulfanyl which may have one or more substituents selected from groups (IIa) and (IIb),
(f) lower alkylsulfinyl which may have one or more substituents selected from groups (IIa) and (IIb),
(g) lower alkylsulfonyl which may have one or more substituents selected from groups (IIa) and (IIb),
(h) cyclo-lower-alkyl which may have one or more substituents selected from groups (IIa), (IIb), (IIc), and oxo,
(i) cyclo-lower-alkoxy which may have one or more substituents selected from groups (IIa), (Ib), (IIc), and oxo,
(j) cyclo-lower-alkenyl which may have one or more substituents selected from groups (IIa), (IIb), (IIc), and oxo,
(k) cyclo-lower-alkylcarbonyl which may have one or more substituents selected from groups (IIa), (IIb), (IIc), and oxo,
(l) cyclo-lower-alkoxycarbonyl which may have one or more substituents selected from groups (IIa), (IIb), (IIc), and oxo,
(m) aryl which may have one or more substituents selected from groups (IIa), (IIb), and (IIc),
(n) arylcarbonyl which may have one or more substituents selected from groups (IIa), (IIb), and (IIc),
(o) aryloxycarbonyl which may have one or more substituents selected from groups (IIa), (IIb), and (IIc),
(p) aralkyl which may have one or more substituents selected from groups (IIa), (IIb), and (IIc),
(q) aralkylcarbonyl which may have one or more substituents selected from groups (IIa), (IIb), and (IIc),
(r) aralkyloxycarbonyl which may have one or more substituents selected from groups (IIa), (IIb), and (IIc),
(s) heterocyclyl which may have one or more substituents selected from groups (IIa), (IIb), (IIc), and oxo,
(t) heterocyclylcarbonyl which may have one or more substituents selected from groups (IIa), (IIb), (IIc), and oxo,
(v) heterocyclyloxycarbonyl which may have one or more substituents selected from groups (IIa), (IIb), (IIc), and oxo, and
(w) carbamoyl which may have one or more substituents selected from groups (IIa) and (IIc).

The "group (Ib)" includes substituents selected from:
(a) halogen,
(b) cyano,
(c) nitro,
(d) hydroxy,
(e) carboxy,
(f) sulfo,
(g) sulfanyl,
(h) lower alkoxy which may have one or more substituents selected from groups (IIa) and (IIb),
(i) lower alkenyloxy which may have one or more substituents selected from groups (IIa) and (IIb),
(j) lower alkynyloxy which may have one or more substituents selected from groups (IIa) and (IIb),
(k) lower alkanoyloxy which may have one or more substituents selected from groups (IIa) and (IIb),
(l) cyclo-lower-alkenyloxy which may have one or more substituents selected from groups (IIa), (Ib), (IIc), and oxo,
(m) aryloxy which may have one or more substituents selected from groups (IIa), (IIb), and (IIc),
(n) aralkyloxy which may have one or more substituents selected from groups (IIa), (IIb), and (IIc),
(o) heterocyclyloxy which may have one or more substituents selected from groups (IIa), (IIb), (IIc), and oxo, and
(p) amino which may have one or more substituents selected from groups (IIa) and (IIc).

The "group (Ic)" includes substituents selected from:
(a) lower alkyl which may have one or more substituents selected from groups (IIa) and (IIb),
(b) lower alkenyl which may have one or more substituents selected from groups (IIa) and (IIb), and
(c) lower alkynyl which may have one or more substituents selected from groups (IIa) and (IIb).

The "group (IIa)" includes substituents selected from lower alkanoyl, lower alkenylcarbonyl, lower alkynylcarbonyl, lower alkoxycarbonyl, lower alkylsulfonyl, cyclo-lower-alkyl, cyclo-lower-alkoxy, cyclo-lower-alkenyl, cyclo-lower-alkylcarbonyl, cyclo-lower-alkoxycarbonyl, aryl, arylcarbonyl, aryloxycarbonyl, aralkyl, aralkylcarbonyl, aralkyloxycarbonyl, heterocyclyl, heterocyclylcarbonyl, heterocyclyloxycarbonyl, mono- or di-lower alkanoylcarbamoyl, and mono- or di-lower alkylcarbamoyl.

The "group (IIb)" includes substituents selected from halogen, cyano, nitro, hydroxy, carboxy, sulfo, sulfanyl, amino, lower alkoxy, lower alkenyloxy, lower alkynyloxy, lower alkanoyloxy, lower alkylsulfanyl, lower alkylsulfinyl, cyclo-lower-alkenyloxy, aryloxy, aralkyloxy, heterocyclyloxy, mono- or di-lower alkylamino, and mono- or di-lower alkanoylamino.

The "group (IIc)" includes substituents selected from lower alkyl, lower alkenyl, and lower alkynyl.

Each of symbols and structures in the general formula (1) is explained in detail as below.

In one aspect, the present invention includes the following embodiments:

[1] A compound of the general formula (1):

[Chem. 3]

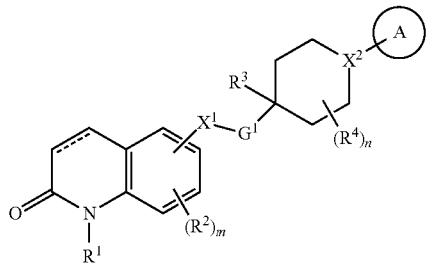

or a salt thereof,
wherein $R^1$ is
(1) hydrogen,
(2) amino which may have one or two of the same or different lower alkyl or
(3) lower alkyl;
$R^2$ is
(1) halogen,
(2) amino which may have one or two of the same or different lower alkyl,
(3) lower alkyl,
(4) lower alkoxy or
(5) hydroxy;
m is an integer of 0 to 3;
provided that when m is 2 or 3, $R^2$ may be different from each other;
$X^1$ is —$CH_2$—, —O—, —N($R^5$)—, —S—, —SO— or —$SO_2$—;
$R^5$ is
(1) hydrogen,
(2) lower alkyl or
(3) lower alkanoyl;
$G^1$ is lower alkylene;
$R^3$ is
(1) hydrogen,
(2) carboxy,
(3) halogen,
(4) lower alkyl which may have one or more hydroxy,
(5) cyano,
(6) amino which may have one or two substituents independently selected from:
 (a) lower alkyl and
 (b) —C(=O)—$R^6$ or
(7) —O—$R^7$;
$R^6$ is
(1) lower alkoxy or
(2) lower alkyl which may have one or two of the same or different amino which may have one or two of the same or different lower alkyl;
$R^7$ is
(1) hydrogen,
(2) amino,
(3) lower alkanoyl or
(4) lower alkyl;
$R^4$ is
(1) amino which may have one or two of the same or different lower alkyl,
(2) halogen,
(3) cyano,
(4) lower alkyl,
(5) oxo,
(6) —O—$R^8$ or
(7) —O—C(=O)—$R^9$;
$R^8$ is
(1) hydrogen,
(2) lower alkyl,
(3) —PH(=O)OH or
(4) benzyl which may have one or more of the same or different lower alkoxy;
$R^9$ is
(1) lower alkyl,
(2) -$G^2$-COOH,
(3) amino which may have one or two of the same or different lower alkyl,
(4) lower alkoxy or
(5) pyrazinyl;
$G^2$ is lower alkylene;
n is an integer of 0 to 8;
provided that when n is 2 or more, each of $R^4$, $R^8$, $R^9$, and $G^2$ may be different from each other and may be substituted on the same carbon atom;
$X^2$ is N or CH;
provided that when $X^2$ is CH, H of the group may be substituted with $R^4$ which is defined as above or may be different from the other $R^4$;
Ring A is
(1) aryl which may have one or more substituents, or
(2) heterocyclyl which may have one or more substituents;
a moiety of formula:
[Chem. 4]
----
represents a single bond or a double bond.
[2] The compound of [1], or a salt thereof, wherein the partial structure (X):

[Chem. 5]

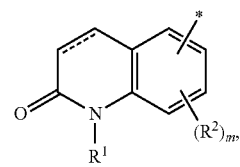

wherein * is a binding point to $X^1$; and other symbols are as defined in [1],
is any one of the structures selected from the group consisting of the following formulae (X1) to (X6):

[Chem. 6]

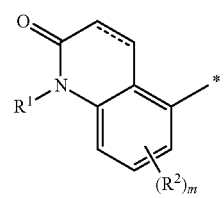

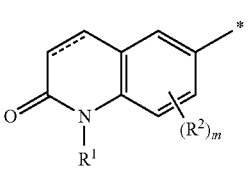

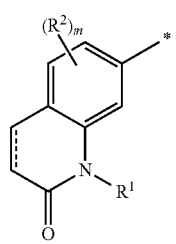 (X3)
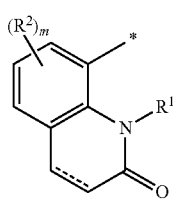 (X4)
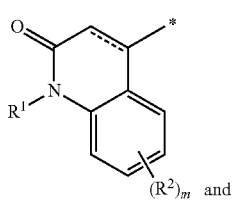 (X5)
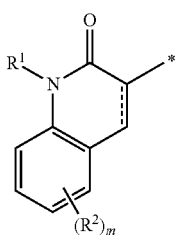 (X6)
wherein the symbols are as defined in the above and [1].
[2A] The compound of [1], or a salt thereof, wherein the partial structure (X):
[Chem. 7]
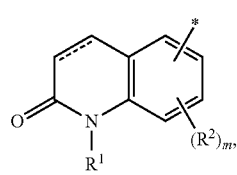 (X)
wherein * is a binding point to $X^1$; and other symbols are as defined in [1],
is any one of the structures selected from the group consisting of the following formulae (X1-1) to (X5-1):
[Chem. 8]
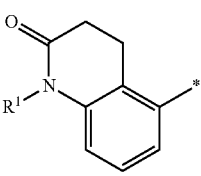 (X1-1)
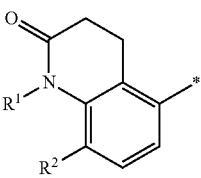 (X1-2)
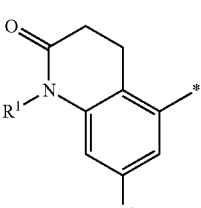 (X1-3)
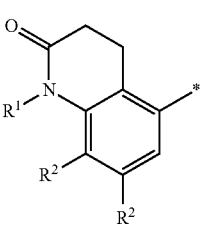 (X1-4)
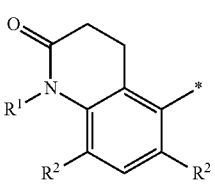 (X1-5)
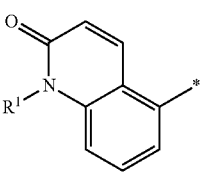 (X1-6)
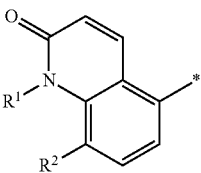 (X1-7)
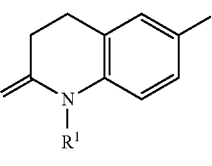 (X2-1)

-continued (X3-1)
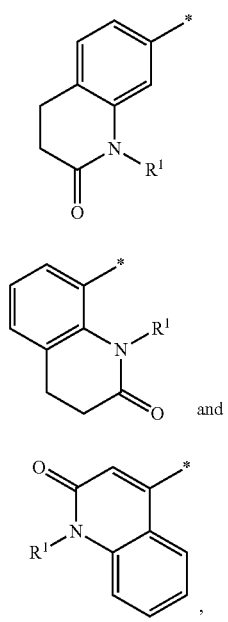

(X4-1)

(X5-1)

wherein the symbols are as defined in the above and [1].

[3] The compound of any one of [1], [2] or [2A], or a salt thereof, wherein the partial structure (Y):

[Chem. 9]

(Y)
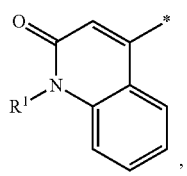

wherein *1 is a binding point to the partial structure of Formula (X); *2 is a binding point to Ring A; and other symbols are as defined in [1], is any one of the structures selected from the group consisting of the following formulae (Y1) to (Y8):

[Chem. 10]

(Y1)
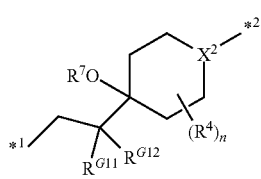

(Y2)
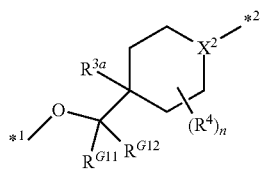

-continued (Y3)
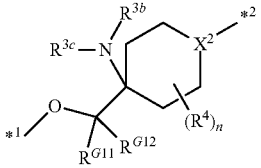

(Y4)
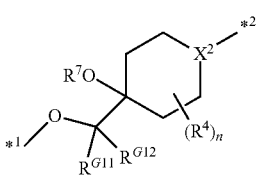

(Y5)
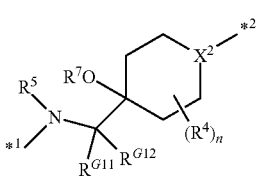

(Y6)
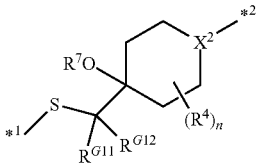

(Y7)
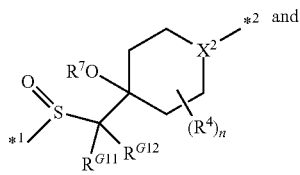

(Y8)
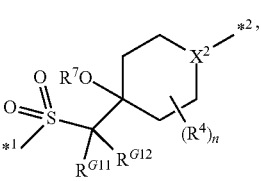

wherein $R^{3a}$ is (1) hydrogen, (2) carboxy, (3) halogen, (4) lower alkyl which may have one or more hydroxy, or (5) cyano;

$R^{3b}$ and $R^{3c}$ are each independently (1) hydrogen, (2) lower alkyl, or (3) —C(=O)—$R^6$;

$R^{G11}$ and $R^{G12}$ are each independently hydrogen or lower alkyl;

the total number of carbon atoms in $R^{G11}$ and $R^{G12}$ is 0 to 5; and other symbols are as defined in [1].

[3A] The compound of any one of [1], [2] or [2A], or a salt thereof, wherein the partial structure (Y):

[Chem. 11]

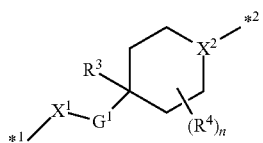
(Y)

wherein *1 is a binding point to the partial structure of Formula (X); *2 is a binding point to Ring A; and other symbols are as defined in [1], is any one of the structures selected from the group consisting of the following formulae (Y1-1) to (Y8-1):

[Chem. 12]

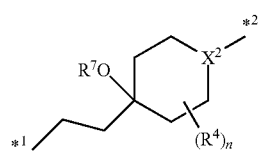
(Y1-1)

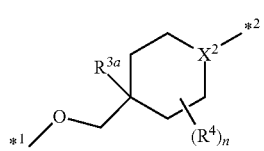
(Y2-1)

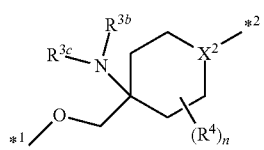
(Y3-1)

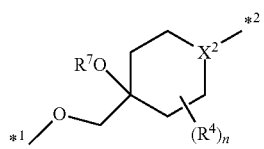
(Y4-1)

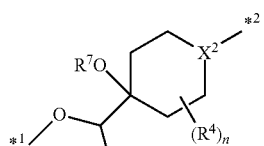
(Y4-2)

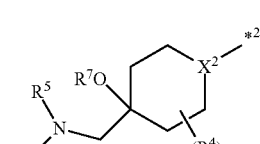
(Y5-1)

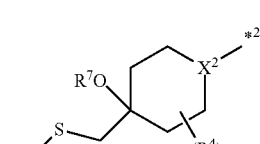
(Y6-1)

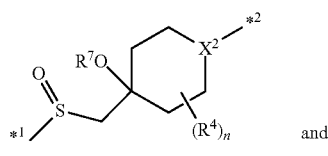
(Y7-1)

and

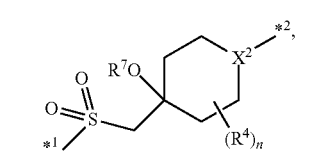
(Y8-1)

wherein $R^{3a}$ is (1) hydrogen, (2) carboxy, (3) halogen, (4) lower alkyl which may have one or more hydroxy, or (5) cyano;

$R^{3b}$ and $R^{3c}$ are each independently (1) hydrogen, (2) lower alkyl, or (3) —C(=O)—$R^6$; and other symbols are as defined in [1].

[4] The compound of any one of [1], [2], [2A], [3] or [3A], or a salt thereof, wherein Ring A is aryl or heterocyclyl which may have 1 to 5 substituents independently selected from:
(a) halogen;
(b) cyano;
(c) nitro;
(d) hydroxy;
(e) lower alkyl which may have one or more substituents independently selected from:
  (i) halogen,
  (ii) hydroxy,
  (iii) lower alkoxy, and
  (iv) aryloxy which may have one or more of the same or different halogen;
(f) lower alkoxy which may have one or more substituents independently selected from:
  (i) halogen,
  (ii) lower alkoxy which may have one or more of the same or different lower alkoxy,
  (iii) aryloxy which may have one or more of the same or different halogen,
  (iv) heterocyclyl which may have one or more of the same or different lower alkyl which may have one or more of the same or different halogen, and
  (v) amino which may have one or two of the same or different lower alkyl;
(g) lower alkoxycarbonyl;
(h) lower alkylsulfanyl;
(i) aryl which may have one or more of the same or different halogen;
(j) aryloxy; and
(k) aralkyloxy which may have one or more substituents independently selected from:
  (i) halogen,
  (ii) lower alkyl which may have one or more of the same or different halogen, and
  (iii) lower alkoxy which may have one or more of the same or different halogen.

[4A] The compound of any one of [1], [2], [2A], [3] or [3A], or a salt thereof, wherein Ring A is aryl, or saturated or unsaturated mono- or bi-cyclic heterocyclyl which comprises 1 to 5 heteroatoms independently selected from oxygen, sulfur, and nitrogen, which may have 1 to 5 substituents independently selected from:

(a) halogen;
(b) cyano;
(c) nitro;
(d) hydroxy;
(e) lower alkyl which may have one or more substituents independently selected from:
  (i) halogen,
  (ii) hydroxy,
  (iii) lower alkoxy, and
  (iv) aryloxy which may have one or more of the same or different halogen;
(f) lower alkoxy which may have one or more of the same or different substituents independently selected from:
  (i) halogen,
  (ii) lower alkoxy which may have one or more of the same or different lower alkoxy,
  (iii) aryloxy which may have one or more of the same or different halogen,
  (iv) heterocyclyl (e.g. pyridyl) which may have one or more of the same or different lower alkyl which may have one or more of the same or different halogen, and
  (v) amino which may have one or two of the same or different lower alkyl;
(g) lower alkoxycarbonyl;
(h) lower alkylsulfanyl;
(i) aryl which may have one or more of the same or different halogen;
(j) aryloxy; and
(k) aralkyloxy which may have one or more substituents independently selected from:
  (i) halogen,
  (ii) lower alkyl which may have one or more of the same or different halogen, and
  (iii) lower alkoxy which may have one or more of the same or different halogen.

[4B] The compound of any one of [1], [2], [2A], [3] or [3A], or a salt thereof, wherein Ring A is:
(1) aryl;
(2) saturated or unsaturated 5- or 6-membered heteromonocyclic group comprising 1 to 4 nitrogen;
(3) saturated or unsaturated 7- to 12-membered fused heterocyclyl group comprising 1 to 5 nitrogen;
(4) saturated or unsaturated 7- to 12-membered fused heterocyclyl group comprising 1 to 3 oxygen;
(5) saturated or unsaturated 7- to 12-membered fused heterocyclyl group comprising 1 or 2 oxygen and 1 to 3 nitrogen;
(6) saturated or unsaturated 5- or 6-membered heteromonocyclic group comprising 1 sulfur; or
(7) saturated or unsaturated 7- to 12-membered fused heterocyclyl group comprising 1 to 3 sulfur,
which may have 1 to 5 substituents independently selected from:
(a) halogen;
(b) cyano;
(c) nitro;
(d) hydroxy;
(e) lower alkyl which may have one or more substituents independently selected from:
  (i) halogen,
  (ii) hydroxy,
  (iii) lower alkoxy, and
  (iv) aryloxy which may have one or more of the same or different halogen;
(f) lower alkoxy which may have one or more substituents independently selected from:
  (i) halogen,
  (ii) lower alkoxy which may have one or more of the same or different lower alkoxy,
  (iii) aryloxy which may have one or more of the same or different halogens,
  (iv) heterocyclyl (e.g. pyridyl) which may have one or more of the same or different lower alkyl which may have one or more of the same or different halogen, and
  (v) amino which may have one or more of the same or different lower alkyl;
(g) lower alkoxycarbonyl;
(h) lower alkylsulfanyl;
(i) aryl which may have one or more of the same or different halogen;
(j) aryloxy; and
(k) aralkyloxy which may have one or more substituents independently selected from:
  (i) halogen,
  (ii) lower alkyl which may have one or more of the same or different halogen, and
  (iii) lower alkoxy which may have one or more of the same or different halogen.

[4C] The compound of any one of [1], [2], [2A], [3] or [3A], or a salt thereof, wherein Ring A is a group selected from:
(a1) phenyl,
(a2) pyridyl,
(a3) N-oxide pyridyl,
(a4) thienyl,
(a5) quinolyl,
(a6) isoquinolyl,
(a7) benzothienyl,
(a8) quinoxalinyl,
(a9) benzofuryl,
(a10) benzodioxolyl,
(a11) benzoxazolyl, and
(a12) benzimidazolyl,
which may have the same or different 1 to 5 substituents.

[4D] The compound of any one of [1], [2], [2A], [3] or [3A], or a salt thereof, wherein Ring A is a group selected from:
(a1) phenyl,
(a2) pyridyl,
(a3) N-oxide pyridyl,
(a4) thienyl,
(a5) quinolyl,
(a6) isoquinolyl,
(a7) benzothienyl,
(a8) quinoxalinyl,
(a9) benzofuryl,
(a10) benzodioxolyl,
(a11) benzoxazolyl, and
(a12) benzimidazolyl,
which may have 1 to 5 substituents independently selected from:
(a) halogen;
(b) cyano;
(c) nitro;
(d) hydroxy;
(e) lower alkyl which may have one or more substituents independently selected from:
  (i) halogen,
  (ii) hydroxy,
  (iii) lower alkoxy, and
  (iv) aryloxy which may have one or more of the same or different halogen;
(f) lower alkoxy which may have one or more substituents independently selected from:

23

(i) halogen,
(ii) lower alkoxy which may have one or more of the same or different lower alkoxy,
(iii) aryloxy which may have one or more of the same or different halogen,
(iv) heterocyclyl (e.g. pyridyl) which may have one or more of the same or different lower alkyls which may have one or more of the same or different halogen, and
(v) amino which may have one or more of the same or different lower alkyl;
(g) lower alkoxycarbonyl;
(h) lower alkylsulfanyl;
(i) aryl which may have one or more of the same or different halogen;
(j) aryloxy; and
(k) aralkyloxy which may have one or more substituents independently selected from:
(i) halogen,
(ii) lower alkyl which may have one or more of the same or different halogens, and
(iii) lower alkoxy which may have one or more of the same or different halogen.

[4E] The compound of any one of [1], [2], [2A], [3] or [3A], or a salt thereof, wherein Ring A is:
(A1) phenyl which may have 1 to 5 substituents independently selected from:
(a) halogen;
(b) cyano;
(c) nitro;
(d) hydroxy;
(e) lower alkyl which may have one or more substituents independently selected from:
(i) halogen,
(ii) hydroxy,
(iii) lower alkoxy, and
(iv) aryloxy which may have one or more of the same or different halogen;
(f) lower alkoxy which may have one or more substituents independently selected from:
(i) halogen,
(ii) lower alkoxy which may have one or more of the same or different lower alkoxy,
(iii) aryloxy which may have one or more of the same or different halogen,
(iv) heterocyclyl (e.g. pyridyl) which may have one or more of the same or different lower alkyls which may have one or more of the same or different halogen, and
(v) amino which may have one or two of the same or different lower alkyl;
(g) lower alkoxycarbonyl;
(h) lower alkylsulfanyl;
(i) aryl which may have one or more of the same or different halogen;
(j) aryloxy; and
(k) aralkyloxy which may have one or more substituents independently selected from:
(i) halogen,
(ii) lower alkyl which may have one or more of the same or different halogen, and
(iii) lower alkoxy which may have one or more of the same or different halogen;
(A2) pyridyl which may have 1 to 2 substituents independently selected from:
(a) halogen;
(b) cyano;

24

(c) lower alkyl which may have one or more of the same or different halogen; and
(d) lower alkoxy;
(A3) N-oxide pyridyl which may have 1 to 2 halogen;
(A4) thienyl;
(A5) quinolyl which may have 1 to 2 halogen;
(A6) isoquinolyl;
(A7) benzothienyl;
(A8) quinoxalinyl;
(A9) benzofuryl;
(A10) benzodioxolyl which may have 1 to 3 halogen;
(A11) benzoxazolyl which may have 1 to 2 halogen; or
(A12) benzimidazolyl which may have 1 to 3 substituents independently selected from:
(a) halogen; and
(b) lower alkyl which may have one or more of the same or different lower alkoxy.

[5] The compound of any one of [1], [2], [2A], [3], [3A], [4], [4A], [4B], [4C], [4D], or [4E], or a salt thereof, wherein $R^1$ is hydrogen.

[6] The compound of any one of [1], [2], [2A], [3], [3A], [4], [4A], [4B], [4C], [4D], [4E], or [5], or a salt thereof, wherein $R^2$ is halogen.

[7] The compound of any one of [1], [2], [2A], [3], [3A], [4], [4A], [4B], [4C], [4D], [4E], [5], or [6], wherein m is 0, 1 or 2, or a salt thereof.

[8] The compound of any one of [1], [2], [2A], [3], [3A], [4], [4A], [4B], [4C], [4D], [4E], [5], [6], or [7], or a salt thereof, wherein n is 0, 1 or 2.

[9] The compound of [1], or a salt thereof, wherein the partial structure (X) is a structure of a formula selected from the group consisting of the formulae (X1-1), (X1-2), (X1-3), (X1-4), (X1-6), and (X1-7):

[Chem. 13]

(X1-1)

(X1-2)

(X1-3)

-continued

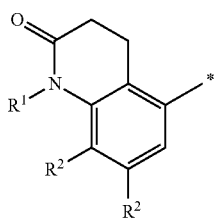
(X1-4)

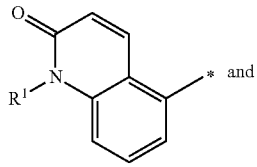
(X1-6)

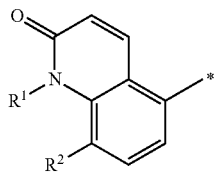
(X1-7)

wherein * is a binding point to $X^1$;

$R^1$ is hydrogen;

$R^2$ is a substituent selected from (1) halogen or (2) lower alkyl;

provided that when $R^2$ may be multiple, each of them may be different from each other;

the partial structure (Y) is a structure of a formula selected from the group consisting of the formulae (Y1-1), (Y2-1), (Y3-1), (Y4-1), (Y5-1), and (Y6-1):

[Chem. 14]

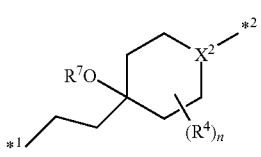
(Y1-1)

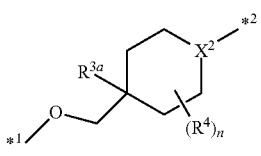
(Y2-1)

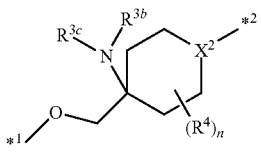
(Y3-1)

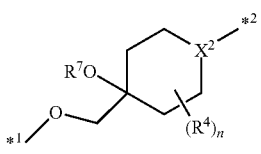
(Y4-1)

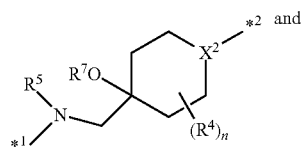
(Y5-1)

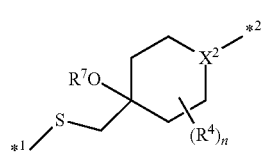
(Y6-1)

wherein *1 is a binding point to the partial structure of Formula (X);

*2 is a binding point to Ring A;

$R^5$ is hydrogen;

$R^{3a}$ is (1) hydrogen or (2) halogen;

$R^{3b}$ and $R^{3c}$ are each hydrogen;

$R^7$ is hydrogen;

$R^4$ is a substituent selected from (1) halogen, (2) —O—$R^8$, (3) —O—C(=O)—$R^9$, or (4) cyano;

$R^8$ is (1) hydrogen or (2) lower alkyl;

$R^9$ is (1) lower alkyl or (2) lower alkoxy;

n is an integer of 0 to 2;

provided that when n is 2, each of $R^4$, $R^8$, and $R^9$ may be different from each other and may be substituted on the same carbon atom;

$X^2$ is N or CH;

provided that when $X^2$ is CH, H of the group may be substituted with $R^4$ which is defined as above or may be different from the other $R^4$; and Ring A is phenyl or pyridyl which may have 1 to 3 substituents independently selected from:

(a) halogen;

(b) lower alkoxy which may have (i) one or more halogen and (ii) one or more lower alkoxy; or (c) aralkyloxy which may have one or more of the same or different lower alkoxy which may have one or more of the same or different halogen; or quinolyl which may have 1 to 2 halogen.

[10] The compound of [1], which is selected from the group consisting of the following compounds:

5-{[4-amino-1-(3,5-dichloropyridin-2-yl)piperidin-4-yl]methoxy}-8-fluoro-3,4-dihydroquinolin-2(1H)-one, 5-{[4-amino-1-(4-chloro-2-fluorophenyl)piperidin-4-yl]methoxy}-8-chloro-3,4-dihydroquinolin-2(1H)-one, 5-{[4-amino-1-(4-chloro-2-fluorophenyl)piperidin-4-yl]methoxy}-8-chloroquinolin-2(1H)-one, 5-{[1-(4-chlorophenyl)-4-hydroxypiperidin-4-yl]methoxy}-8-fluoro-3,4-dihydroquinolin-2(1H)-one, 5-{[1-(4-chloro-2-fluorophenyl)-4-hydroxypiperidin-4-yl]methoxy}-8-fluoro-3,4-dihydroquinolin-2(1H)-one, 5-{[1-(4-ethoxy-2-fluorophenyl)-4-hydroxypiperidin-4-yl]methoxy}-8-fluoro-3,4-dihydroquinolin-2(1H)-one, 8-chloro-5-{[1-(4-chloro-2,6-difluorophenyl)-4-hydroxypiperidin-4-yl]methoxy}-3,4-dihydroquinolin-2(1H)-one, 5-{[1-(4-bromo-2-fluorophenyl)-4-hydroxypiperidin-4-yl]methoxy}-7,8-difluoro-3,4-dihydroquinolin-2(1H)-one, 5-{[1-(4-chloro-2-fluorophenyl)-4-hydroxypiperidin-4-yl]methoxy}quinolin-2(1H)-one, 8-chloro-5-{[1-(3,5-dichloropyridin-2-yl)-4-hydroxypiperidin-4-yl]methoxy}-3,4-dihydroquinolin-2(1H)-one, 8-fluoro-5-{[1-(2-fluoro-4-{[4-(trifluoromethoxy)benzyl]oxy}phenyl)-4-hydroxypiperidin-4-yl]methoxy}-3,4-dihydroquinolin-2(1H)-one,
8-chloro-5-({1-[4-chloro-2-fluoro-5-(2-methoxyethoxy)phenyl]-4-hydroxypiperidin-4-yl}methoxy)-3,4-dihydroquinolin-2(1H)-one,
5-{[1-(4-chloro-2-fluorophenyl)-4-hydroxypiperidin-4-yl]methoxy}-7-fluoro-3,4-dihydroquinolin-2(1H)-one,
5-{[1-(2,4-dichloro-5-fluorophenyl)-4-hydroxypiperidin-4-yl]methoxy}-7-fluoro-8-methyl-3,4-dihydroquinolin-2(1H)-one,
8-chloro-7-fluoro-5-{[4-hydroxy-1-(2,4,6-trifluorophenyl)piperidin-4-yl]methoxy}-3,4-dihydroquinolin-2(1H)-one,
5-{[(3R,4R)-1-(3,5-dichloropyridin-2-yl)-3,4-dihydroxypiperidin-4-yl]methoxy}-8-fluoro-3,4-dihydroquinolin-2(1H)-one,
5-{[(3S,4S)-1-(3,5-dichloropyridin-2-yl)-3,4-dihydroxypiperidin-4-yl]methoxy}-8-fluoro-3,4-dihydroquinolin-2(1H)-one,
5-{[(3R,4R)-1-(4-chloro-2-fluorophenyl)-3,4-dihydroxypiperidin-4-yl]methoxy}-8-fluoro-3,4-dihydroquinolin-2(1H)-one,
5-{[(3R,4R)-1-(4-chloro-2,6-difluorophenyl)-3,4-dihydroxypiperidin-4-yl]methoxy}-8-fluoro-3,4-dihydroquinolin-2(1H)-one,
5-{[(3S,4S)-1-(4-chloro-2-fluorophenyl)-3,4-dihydroxypiperidin-4-yl]methoxy}-8-fluoro-3,4-dihydroquinolin-2(1H)-one,
5-{[(3R,4R)-1-(3-bromo-6-chloroquinolin-2-yl)-3,4-dihydroxypiperidin-4-yl]methoxy}-8-fluoro-3,4-dihydroquinolin-2(1H)-one,
5-{[(3R,4R)-1-(4-bromo-2-fluorophenyl)-3,4-dihydroxypiperidin-4-yl]methoxy}-3,4-dihydroquinolin-2(1H)-one,
5-{[(3S,4R)-1-(4-chloro-2,6-difluorophenyl)-3,4-dihydroxypiperidin-4-yl]methoxy}-8-fluoro-3,4-dihydroquinolin-2(1H)-one,
5-{[(3R,4S)-1-(4-bromo-2-fluorophenyl)-3,4-dihydroxypiperidin-4-yl]methoxy}-8-chloro-3,4-dihydroquinolin-2(1H)-one,
5-{[(3R*,4R*)-1-(4-bromo-2-fluorophenyl)-3,4-dihydroxypiperidin-4-yl]methoxy}-8-fluoroquinolin-2(1H)-one,
5-({[1-(3,5-dichloropyridin-2-yl)-4-hydroxypiperidin-4-yl]methyl}amino)-8-fluoro-3,4-dihydroquinolin-2(1H)-one,
5-{[1-(3,5-dichloropyridin-2-yl)piperidin-4-yl]methoxy}-8-fluoro-3,4-dihydroquinolin-2(1H)-one,
5-{[1-(3,5-dichloropyridin-2-yl)-4-fluoropiperidin-4-yl]methoxy}-8-fluoro-3,4-dihydroquinolin-2(1H)-one,
5-{[(3R*,4R*)-1-(4-chloro-2-fluorophenyl)-3-hydroxypiperidin-4-yl]methoxy}-8-fluoro-3,4-dihydroquinolin-2(1H)-one,
5-{[(3R,4S)-1-(4-chloro-2,6-difluorophenyl)-3-fluoro-4-hydroxypiperidin-4-yl]methoxy}-8-fluoro-3,4-dihydroquinolin-2(1H)-one,
5-{[(3S,4R)-1-(4-chloro-2,6-difluorophenyl)-3-fluoro-4-hydroxypiperidin-4-yl]methoxy}-8-fluoro-3,4-dihydroquinolin-2(1H)-one,
5-{[(3R,4R)-1-(4-chloro-2,6-difluorophenyl)-3-fluoro-4-hydroxypiperidin-4-yl]methoxy}-8-fluoro-3,4-dihydroquinolin-2(1H)-one,
5-{[(3S,4S)-1-(4-chloro-2,6-difluorophenyl)-3-fluoro-4-hydroxypiperidin-4-yl]methoxy}-8-fluoro-3,4-dihydroquinolin-2(1H)-one,
(3R,4R)-1-(4-chloro-2,6-difluorophenyl)-4-{[(8-fluoro-2-oxo-1,2,3,4-tetrahydroquinolin-5-yl)oxy]methyl}-4-hydroxypiperidin-3-yl ethyl carbonate,
(3R,4R)-1-(4-chloro-2-fluorophenyl)-4-{[(8-fluoro-2-oxo-1,2,3,4-tetrahydroquinolin-5-yl)oxy]methyl}-4-hydroxypiperidin-3-yl acetate,
5-({[1-(4-chloro-2-fluorophenyl)-4-hydroxypiperidin-4-yl]methyl}sulfanyl)-8-fluoro-3,4-dihydroquinolin-2(1H)-one,
5-{2-[1-(4-chloro-2,6-difluorophenyl)-4-hydroxypiperidin-4-yl]ethyl}-8-fluoro-3,4-dihydroquinolin-2(1H)-one,
5-{[trans-4-(4-chloro-2-fluorophenyl)-1,4-dihydroxycyclohexyl]methoxy}-8-fluoro-3,4-dihydroquinolin-2(1H)-one,
5-{[cis-4-(4-chloro-2-fluorophenyl)-1-hydroxycyclohexyl]methoxy}-8-fluoro-3,4-dihydroquinolin-2(1H)-one,
5-{[(1R*,2R*,4R*)-4-(4-chloro-2-fluorophenyl)-1,2-dihydroxycyclohexyl]methoxy}-8-fluoro-3,4-dihydroquinolin-2(1H)-one,
5-{[(1R,2R,4S)-4-(4-chloro-2-fluorophenyl)-1,2,4-trihydroxycyclohexyl]methoxy}-8-fluoro-3,4-dihydroquinolin-2(1H)-one,
trans-1-(4-chloro-2-fluorophenyl)-4-{[(8-fluoro-2-oxo-1,2,3,4-tetrahydroquinolin-5-yl)oxy]methyl}-4-hydroxycyclohexanecarbonitrile, and
5-{[trans-4-(4-chloro-2-fluorophenyl)-1-hydroxy-4-methoxycyclohexyl]methoxy}-8-fluoro-3,4-dihydroquinolin-2(1H)-one, or a salt thereof.

[11] The compound of [1], which is selected from the group consisting of the following compounds:
5-{[4-amino-1-(3,5-dichloropyridin-2-yl)piperidin-4-yl]methoxy}-8-fluoro-3,4-dihydroquinolin-2(1H)-one,
5-{[4-amino-1-(4-chloro-2-fluorophenyl)piperidin-4-yl]methoxy}-8-chloro-3,4-dihydroquinolin-2(1H)-one,
5-{[4-amino-1-(4-chloro-2-fluorophenyl)piperidin-4-yl]methoxy}-8-chloroquinolin-2(1H)-one,
5-{[1-(4-chlorophenyl)-4-hydroxypiperidin-4-yl]methoxy}-8-fluoro-3,4-dihydroquinolin-2(1H)-one,
5-{[1-(4-chloro-2-fluorophenyl)-4-hydroxypiperidin-4-yl]methoxy}-8-fluoro-3,4-dihydroquinolin-2(1H)-one,
5-{[1-(4-ethoxy-2-fluorophenyl)-4-hydroxypiperidin-4-yl]methoxy}-8-fluoro-3,4-dihydroquinolin-2(1H)-one,
8-chloro-5-{[1-(4-chloro-2,6-difluorophenyl)-4-hydroxypiperidin-4-yl]methoxy}-3,4-dihydroquinolin-2(1H)-one,
5-{[1-(4-bromo-2-fluorophenyl)-4-hydroxypiperidin-4-yl]methoxy}-7,8-difluoro-3,4-dihydroquinolin-2(1H)-one,
5-{[1-(4-chloro-2-fluorophenyl)-4-hydroxypiperidin-4-yl]methoxy}quinolin-2(1H)-one,
8-chloro-5-{[1-(3,5-dichloropyridin-2-yl)-4-hydroxypiperidin-4-yl]methoxy}-3,4-dihydroquinolin-2(1H)-one,
8-fluoro-5-{[1-(2-fluoro-4-{[4-(trifluoromethoxy)benzyl]oxy}phenyl)-4-hydroxypiperidin-4-yl]methoxy}-3,4-dihydroquinolin-2(1H)-one,
8-chloro-5-({1-[4-chloro-2-fluoro-5-(2-methoxyethoxy)phenyl]-4-hydroxypiperidin-4-yl}methoxy)-3,4-dihydroquinolin-2(1H)-one,
5-{[1-(4-chloro-2-fluorophenyl)-4-hydroxypiperidin-4-yl]methoxy}-7-fluoro-3,4-dihydroquinolin-2(1H)-one,
5-{[1-(2,4-dichloro-5-fluorophenyl)-4-hydroxypiperidin-4-yl]methoxy}-7-fluoro-8-methyl-3,4-dihydroquinolin-2(1H)-one,
8-chloro-7-fluoro-5-{[4-hydroxy-1-(2,4,6-trifluorophenyl)piperidin-4-yl]methoxy}-3,4-dihydroquinolin-2(1H)-one,
5-{[(3R,4R)-1-(3,5-dichloropyridin-2-yl)-3,4-dihydroxypiperidin-4-yl]methoxy}-8-fluoro-3,4-dihydroquinolin-2(1H)-one,
5-{[(3S,4S)-1-(3,5-dichloropyridin-2-yl)-3,4-dihydroxypiperidin-4-yl]methoxy}-8-fluoro-3,4-dihydroquinolin-2(1H)-one, 5-{[(3R,4R)-1-(4-chloro-2-fluorophenyl)-3,4-dihydroxypiperidin-4-yl]methoxy}-8-fluoro-3,4-dihydroquinolin-2(1H)-one, 5-{[(3R,4R)-1-(4-chloro-2,6-difluorophenyl)-3,4-dihydroxypiperidin-4-yl]methoxy}-8-fluoro-3,4-dihydroquinolin-2(1H)-one, 5-{[(3S,4S)-1-(4-chloro-2-fluorophenyl)-3,4-dihydroxypiperidin-4-yl]methoxy}-8-fluoro-3,4-dihydroquinolin-2(1H)-one, 5-{[(3R,4R)-1-(3-bromo-6-chloroquinolin-2-yl)-3,4-dihydroxypiperidin-4-yl]methoxy}-8-fluoro-3,4-dihydroquinolin-2(1H)-one, 5-{[(3R,4R)-1-(4-bromo-2-fluorophenyl)-3,4-dihydroxypiperidin-4-yl]methoxy}-3,4-dihydroquinolin-2(1H)-one, 5-{[(3S,4R)-1-(4-chloro-2,6-difluorophenyl)-3,4-dihydroxypiperidin-4-yl]methoxy}-8-fluoro-3,4-dihydroquinolin-2(1H)-one, 5-{[(3R,4S)-1-(4-bromo-2-fluorophenyl)-3,4-dihydroxypiperidin-4-yl]methoxy}-8-chloro-3,4-dihydroquinolin-2(1H)-one, 5-{[(3R*,4R*)-1-(4-bromo-2-fluorophenyl)-3,4-dihydroxypiperidin-4-yl]methoxy}-8-fluoroquinolin-2(1H)-one, 5-({[1-(3,5-dichloropyridin-2-yl)-4-hydroxypiperidin-4-yl]methyl}amino)-8-fluoro-3,4-dihydroquinolin-2(1H)-one, 5-{[1-(3,5-dichloropyridin-2-yl)piperidin-4-yl]methoxy}-8-fluoro-3,4-dihydroquinolin-2(1H)-one, 5-{[1-(3,5-dichloropyridin-2-yl)-4-fluoropiperidin-4-yl]methoxy}-8-fluoro-3,4-dihydroquinolin-2(1H)-one, 5-{[(3R*,4R*)-1-(4-chloro-2-fluorophenyl)-3-hydroxypiperidin-4-yl]methoxy}-8-fluoro-3,4-dihydroquinolin-2(1H)-one, 5-{[(3R,4S)-1-(4-chloro-2,6-difluorophenyl)-3-fluoro-4-hydroxypiperidin-4-yl]methoxy}-8-fluoro-3,4-dihydroquinolin-2(1H)-one, 5-{[(3S,4R)-1-(4-chloro-2,6-difluorophenyl)-3-fluoro-4-hydroxypiperidin-4-yl]methoxy}-8-fluoro-3,4-dihydroquinolin-2(1H)-one, 5-{[(3R,4R)-1-(4-chloro-2,6-difluorophenyl)-3-fluoro-4-hydroxypiperidin-4-yl]methoxy}-8-fluoro-3,4-dihydroquinolin-2(1H)-one, 5-{[(3S,4S)-1-(4-chloro-2,6-difluorophenyl)-3-fluoro-4-hydroxypiperidin-4-yl]methoxy}-8-fluoro-3,4-dihydroquinolin-2(1H)-one, (3R,4R)-1-(4-chloro-2,6-difluorophenyl)-4-{[(8-fluoro-2-oxo-1,2,3,4-tetrahydroquinolin-5-yl)oxy]methyl}-4-hydroxypiperidin-3-yl ethyl carbonate, (3R,4R)-1-(4-chloro-2-fluorophenyl)-4-{[(8-fluoro-2-oxo-1,2,3,4-tetrahydroquinolin-5-yl)oxy]methyl}-4-hydroxypiperidin-3-yl acetate, 5-({[1-(4-chloro-2-fluorophenyl)-4-hydroxypiperidin-4-yl]methyl}sulfanyl)-8-fluoro-3,4-dihydroquinolin-2(1H)-one, 5-{2-[1-(4-chloro-2,6-difluorophenyl)-4-hydroxypiperidin-4-yl]ethyl}-8-fluoro-3,4-dihydroquinolin-2(1H)-one, 5-{[trans-4-(4-chloro-2-fluorophenyl)-1,4-dihydroxycyclohexyl]methoxy}-8-fluoro-3,4-dihydroquinolin-2(1H)-one, 5-{[cis-4-(4-chloro-2-fluorophenyl)-1-hydroxycyclohexyl]methoxy}-8-fluoro-3,4-dihydroquinolin-2(1H)-one, 5-{[(1R*,2R*,4R*)-4-(4-chloro-2-fluorophenyl)-1,2-dihydroxycyclohexyl]methoxy}-8-fluoro-3,4-dihydroquinolin-2(1H)-one, 5-{[(1R,2R,4S)-4-(4-chloro-2-fluorophenyl)-1,2,4-trihydroxycyclohexyl]methoxy}-8-fluoro-3,4-dihydroquinolin-2(1H)-one, trans-1-(4-chloro-2-fluorophenyl)-4-{[(8-fluoro-2-oxo-1,2,3,4-tetrahydroquinolin-5-yl)oxy]methyl}-4-hydroxycyclohexanecarbonitrile, and 5-{[trans-4-(4-chloro-2-fluorophenyl)-1-hydroxy-4-methoxycyclohexyl]methoxy}-8-fluoro-3,4-dihydroquinolin-2(1H)-one.

[12] A pharmaceutical composition, comprising the compound of any one of [1], [2], [2A], [3], [3A], [4], [4A], [4B], [4C], [4D], [4E], [5], [6], [7], [8], [9], [10], or [11], or a salt thereof and a pharmaceutically acceptable carrier.

[13] An agent for diagnosing, preventing, and/or treating tuberculosis, comprising the compound of any one of [1], [2], [2A], [3], [3A], [4], [4A], [4B], [4C], [4D], [4E], [5], [6], [7], [8], [9], [10], or [11], or a salt thereof and a pharmaceutically acceptable carrier.

[14] The compound of any one of [1], [2], [2A], [3], [3A], [4], [4A], [4B], [4C], [4D], [4E], [5], [6], [7], [8], [9], [10], or [11], or a salt thereof, for use of diagnosing, preventing, and/or treating tuberculosis.

[15] Use of the compound of any one of [1], [2], [2A], [3], [3A], [4], [4A], [4B], [4C], [4D], [4E], [5], [6], [7], [8], [9], [10], or [11], or a salt thereof, in the manufacture of a medicament for diagnosing, preventing, and/or treating tuberculosis.

[16] Use of the compound of any one of [1], [2], [2A], [3], [3A], [4], [4A], [4B], [4C], [4D], [4E], [5], [6], [7], [8], [9], [10], or [11], or a salt thereof, as a pharmaceutical composition.

[17] A method of diagnosing, preventing, and/or treating tuberculosis, comprising administering to a patient an effective amount of the compound of any one of [1], [2], [2A], [3], [3A], [4], [4A], [4B], [4C], [4D], [4E], [5], [6], [7], [8], [9], [10], or [11], or a salt thereof.

In one embodiment, m is preferably 0, 1, or 2.

In another embodiment, $G^1$ is preferably —C($R^{G11}$)($R^{G12}$)—; more preferably —CH$_2$— or —CH(CH$_3$)—.

In another embodiment, $R^{G11}$ and $R^{G12}$ are each independently hydrogen or lower alkyl; and the total number of carbon atoms in $R^{G11}$ and $R^{G12}$ is 0 to 5. Preferably $R^{G11}$ and $R^{G12}$ are each independently hydrogen or methyl; more preferably $R^{GU}$ is hydrogen or methyl, and $R^{G12}$ is hydrogen.

Examples of "—C($R^{G11}$)($R^{G12}$)—" in $G^1$ include, for example, —CH$_2$—, —CH(CH$_3$)—, —C(CH$_3$)$_2$—, —CH(CH$_2$CH$_3$)—, —C(CH$_3$)(CH$_2$CH$_3$)—, —C(CH$_2$CH$_3$)$_2$—, —CH(CH$_2$CH$_2$CH$_3$)—, C(CH$_3$)(CH$_2$CH$_2$CH$_3$)—, —C(CH$_2$CH$_3$)(CH$_2$CH$_2$CH$_3$)—, —CH(CH(CH$_3$)$_2$)—, —C(CH$_3$)(CH(CH$_3$)$_2$)—, —C(CH$_2$CH$_3$)(CH(CH$_3$)$_2$)—.

In another embodiment, n is preferably 0, 1, or 2.

The "aryl" of "(1) aryl which may have one or more substituents" in Ring A is preferably (a1) phenyl.

The "heterocyclyl" of "(2) heterocyclyl which may have one or more substituents" in Ring A is preferably selected from:

(a2) pyridyl (e.g. 2-pyridyl, 3-pyridyl, 4-pyridyl),
(a3) N-oxide pyridyl (e.g. N-oxide pyridin-2-yl),
(a4) thienyl (e.g. 3-thienyl),
(a5) quinolyl (e.g. 2-quinolyl, 6-quinolyl),
(a6) isoquinolyl (e.g. 1-isoquinolyl),
(a7) benzothienyl (e.g. benzo[b]thiophen-5-yl),
(a8) quinoxalinyl (e.g. 6-quinoxalinyl),
(a9) benzofuryl (e.g. benzo[b]furan-5-yl),
(a10) benzodioxolyl (e.g. benzo[1,3]dioxol-5-yl),
(a11) benzooxazolyl (e.g. 2-benzooxazolyl), and
(a12) benzoimidazolyl (e.g. 2-benzoimidazolyl).

Ring A is preferably aryl or heterocyclyl, which is preferably a group selected from the above (a1) to (a12), each of which may have one or more substituents selected from:
(a) halogen (e.g. fluorine, chlorine, bromine, iodine);
(b) cyano;
(c) nitro;
(d) hydroxy;
(e) lower alkyl which may have one or more substituents selected from groups (Ia) and (Ib) (e.g. methyl, ethyl, propyl, isopropyl, trifluoromethyl, hydroxymethyl, methoxymethyl, ethoxymethyl, 2-methoxyethyl, 2-(4-fluorophenoxy)ethyl);
(f) lower alkoxy which may have one or more substituents selected from groups (Ia) and (Ib) (e.g. methoxy, ethoxy, propoxy, isopropoxy, butoxy, difluoromethoxy, trifluoromethoxy, 2-fluoroethoxy, 2,2,2-trifluoroethoxy, 2-(2-methoxyethoxy)ethoxy, 2-methoxyethoxy, 2-(4-fluorophenoxy)ethoxy, 5-(trifluoromethyl)pyridin-2-ylmethoxy, 2-(dimethylamino)ethoxy);
(g) lower alkoxycarbonyl which may have one or more substituents selected from groups (Ia) and (Ib) (e.g. ethoxycarbonyl);
(h) lower alkylsulfanyl which may have one or more substituents selected from groups (Ia) and (Ib) (e.g. methylsulfanyl, ethylsulfanyl);
(i) aryl which may have one or more substituents selected from groups (Ia), (Ib), and (Ic) (e.g. 2,4-dichlorophenyl, 4-chloro-2-fluorophenyl);
(j) aryloxy which may have one or more substituents selected from groups (Ia), (Ib), and (Ic) (e.g. phenoxy); and
(k) aralkyloxy which may have one or more substituents selected from groups (Ia), (Ib), and (Ic) (e.g. benzyloxy, 4-fluorobenzyloxy, 4-chlorobenzyloxy, 2,4-dichlorobenzyloxy, 4-(trifluoromethyl)benzyloxy, 4-(trifluoromethoxy)benzyloxy).

Ring A is more preferably aryl or heterocyclyl, which is preferably a group selected from the above (a1) to (a12), each of which may have one or more substituents selected from:
(a) halogen (e.g. fluorine, chlorine, bromine, iodine);
(b) cyano;
(c) nitro;
(d) hydroxy;
(e) lower alkyl (e.g. methyl, ethyl, propyl, isopropyl) which may have one or more substituents selected from (i) halogen (e.g. fluorine), (ii) hydroxy, (iii) lower alkoxy (e.g. methoxy, ethoxy), and (iv) aryloxy (e.g. phenoxy) which may have halogen (e.g. fluorine) (e.g. methyl, ethyl, propyl, isopropyl, trifluoromethyl, hydroxymethyl, methoxymethyl, ethoxymethyl, 2-methoxyethyl, 2-(4-fluorophenoxy)ethyl);
(f) lower alkoxy (e.g. methoxy, ethoxy, propoxy, isopropoxy, butoxy) which may have one or more substituents selected from (i) halogen (e.g. fluorine), (ii) lower alkoxy (e.g. methoxy, ethoxy) which may have lower alkoxy (e.g. methoxy), (iii) aryloxy (e.g. phenoxy) which may have halogen (e.g. fluorine), (iv) heterocyclyl (e.g. pyridyl) which may have lower alkyl (e.g. methyl) which may have halogen (e.g. fluorine), and (v) amino which may have lower alkyl (e.g. methyl) (e.g. methoxy, ethoxy, propoxy, isopropoxy, butoxy, difluoromethoxy, trifluoromethoxy, 2-fluoroethoxy, 2,2,2-trifluoroethoxy, 2-(2-methoxyethoxy)ethoxy, 2-methoxyethoxy, 2-(4-fluorophenoxy)ethoxy, 5-(trifluoromethyl)pyridin-2-ylmethoxy, 2-(dimethylamino)ethoxy);
(g) lower alkoxycarbonyl (e.g. ethoxycarbonyl);
(h) lower alkylsulfanyl (e.g. methylsulfanyl, ethylsulfanyl);
(i) aryl (e.g. phenyl) which may have halogen (e.g. fluorine, chlorine) (e.g. 2,4-dichlorophenyl, 4-chloro-2-fluorophenyl);
(j) aryloxy (e.g. phenoxy); and
(k) aralkyloxy (e.g. benzyloxy) which may have one or more substituents selected from (i) halogen (e.g. fluorine, chlorine), (ii) lower alkyl (e.g. methyl) which may have halogen (e.g. fluorine), and (iii) lower alkoxy (e.g. methoxy) which may have halogen (e.g. fluorine) (e.g. benzyloxy, 4-fluorobenzyloxy, 4-chlorobenzyloxy, 2,4-dichlorobenzyloxy, 4-(trifluoromethyl)benzyloxy, 4-(trifluoromethoxy)benzyloxy).

Ring A is further preferably
(1) aryl, which is preferably the group of the above (a1), which may have one or more substituents selected from:
(a) halogen (e.g. fluorine, chlorine, bromine);
(b) cyano;
(c) nitro;
(d) hydroxy;
(e) lower alkyl (e.g. methyl, ethyl, propyl, isopropyl) which may have one or more substituents selected from (i) halogen (e.g. fluorine), (ii) hydroxy, (iii) lower alkoxy (e.g. methoxy, ethoxy), and (iv) aryloxy (e.g. phenoxy) which may have halogen (e.g. fluorine) (e.g. methyl, ethyl, propyl, isopropyl, trifluoromethyl, hydroxymethyl, ethoxymethyl, 2-methoxyethyl, 2-(4-fluorophenoxy)ethyl);
(f) lower alkoxy (e.g. methoxy, ethoxy, propoxy, isopropoxy, butoxy) which may have one or more substituents selected from (i) halogen (e.g. fluorine), (ii) lower alkoxy (e.g. methoxy, ethoxy) which may have lower alkoxy (e.g. methoxy), (iii) aryloxy (e.g. phenoxy) which may have halogen (e.g. fluorine), (iv) heterocyclyl (e.g. pyridyl) which may have lower alkyl (e.g. methyl) which may have halogen (e.g. fluorine), and (v) amino which may have lower alkyl (e.g. methyl) (e.g. methoxy, ethoxy, propoxy, isopropoxy, butoxy, difluoromethoxy, trifluoromethoxy, 2-fluoroethoxy, 2,2,2-trifluoroethoxy, 2-(2-methoxyethoxy)ethoxy, 2-methoxyethoxy, 2-(4-fluorophenoxy)ethoxy, 5-(trifluoromethyl)pyridin-2-ylmethoxy, 2-(dimethylamino)ethoxy);
(g) lower alkoxycarbonyl (e.g. ethoxycarbonyl);
(h) lower alkylsulfanyl (e.g. methylsulfanyl, ethylsulfanyl);
(i) aryl (e.g. phenyl) which may have halogen (e.g. fluorine, chlorine) (e.g. 2,4-dichlorophenyl, 4-chloro-2-fluorophenyl);
(j) aryloxy (e.g. phenoxy); and
(k) aralkyloxy (e.g. benzyloxy) which may have one or more substituents selected from (i) halogen (e.g. fluorine, chlorine), (ii) lower alkyl (e.g. methyl) which may have halogen (e.g. fluorine), and (iii) lower alkoxy (e.g. methoxy) which may have halogen (e.g. fluorine) (e.g. benzyloxy, 4-fluorobenzyloxy, 4-chlorobenzyloxy, 2,4-dichlorobenzyloxy, 4-(trifluoromethyl)benzyloxy, 4-(trifluoromethoxy)benzyloxy); or
(2) heterocyclyl, which is preferably a group selected from the above (a2) to (a12), which may have one or more substituents selected from:
(a) halogen (e.g. fluorine, chlorine, bromine, iodine);
(b) cyano;
(c) lower alkyl (e.g. methyl) which may have one or more substituents selected from (i) halogen (e.g. fluorine), and (ii) lower alkoxy (e.g. methoxy) (e.g. methyl, trifluoromethyl, methoxymethyl); and (d) lower alkoxy (e.g. ethoxy).

Ring A is particularly preferably (A1) phenyl which may have one or more substituents selected from:
- (a) halogen (e.g. fluorine, chlorine, bromine);
- (b) cyano;
- (c) nitro;
- (d) hydroxy;
- (e) lower alkyl (e.g. methyl, ethyl, propyl, isopropyl) which may have one or more substituents selected from (i) halogen (e.g. fluorine), (ii) hydroxy, (iii) lower alkoxy (e.g. methoxy, ethoxy), and (iv) aryloxy (e.g. phenoxy) which may have halogen (e.g. fluorine) (e.g. methyl, ethyl, propyl, isopropyl, trifluoromethyl, hydroxymethyl, ethoxymethyl, 2-methoxyethyl, 2-(4-fluorophenoxy)ethyl);
- (f) lower alkoxy (e.g. methoxy, ethoxy, propoxy, isopropoxy, butoxy) which may have one or more substituents selected from (i) halogen (e.g. fluorine), (ii) lower alkoxy (e.g. methoxy, ethoxy) which may have lower alkoxy (e.g. methoxy), (iii) aryloxy (e.g. phenoxy) which may have halogen (e.g. fluorine), (iv) heterocyclyl (e.g. pyridyl) which may have lower alkyl (e.g. methyl) which may have halogen (e.g. fluorine), and (v) amino which may have lower alkyl (e.g. methyl) (e.g. methoxy, ethoxy, propoxy, isopropoxy, butoxy, difluoromethoxy, trifluoromethoxy, 2-fluoroethoxy, 2,2,2-trifluoroethoxy, 2-(2-methoxyethoxy)ethoxy, 2-methoxyethoxy, 2-(4-fluorophenoxy)ethoxy, 5-(trifluoromethyl)pyridin-2-ylmethoxy, 2-(dimethylamino)ethoxy);
- (g) lower alkoxycarbonyl (e.g. ethoxycarbonyl);
- (h) lower alkylsulfanyl (e.g. methylsulfanyl, ethylsulfanyl);
- (i) aryl (e.g. phenyl) which may have halogen (e.g. fluorine, chlorine) (e.g. 2,4-dichlorophenyl, 4-chloro-2-fluorophenyl);
- (j) aryloxy (e.g. phenoxy); and
- (k) aralkyloxy (e.g. benzyloxy) which may have one or more substituents selected from (i) halogen (e.g. fluorine, chlorine), (ii) lower alkyl (e.g. methyl) which may have halogen (e.g. fluorine), and (iii) lower alkoxy (e.g. methoxy) which may have halogen (e.g. fluorine) (e.g. benzyloxy, 4-fluorobenzyloxy, 4-chlorobenzyloxy, 2,4-dichlorobenzyloxy, 4-(trifluoromethyl)benzyloxy, 4-(trifluoromethoxy)benzyloxy);

(A2) pyridyl (e.g. 2-pyridyl, 3-pyridyl, 4-pyridyl) which may have one or more substituents selected from:
- (a) halogen (e.g. fluorine, chlorine, bromine, iodine);
- (b) cyano;
- (c) lower alkyl (e.g. methyl) which may have halogen (e.g. fluorine) (e.g. methyl, trifluoromethyl); and
- (d) lower alkoxy (e.g. ethoxy);

(A3) N-oxide pyridyl (e.g. N-oxide pyridin-2-yl) which may have halogen (e.g. chlorine);

(A4) thienyl (e.g. 3-thienyl);

(A5) quinolyl (e.g. 2-quinolyl, 6-quinolyl) which may have halogen (e.g. chlorine, bromine);

(A6) isoquinolyl (e.g. 1-isoquinolyl);

(A7) benzothienyl (e.g. benzo[b]thiophen-5-yl);

(A8) quinoxalinyl (e.g. 6-quinoxalinyl);

(A9) benzofuryl (e.g. benzo[b]furan-5-yl);

(A10) benzodioxolyl (e.g. benzo[1,3]dioxol-5-yl) which may have halogen (e.g. fluorine);

(A11) benzoxazolyl (e.g. 2-benzooxazolyl) which may have halogen (e.g. chlorine); or (A12) benzimidazolyl (e.g. 2-benzoimidazolyl) which may have one or more substituents selected from:
- (a) halogen (e.g. fluorine); and
- (b) lower alkyl (e.g. methyl) which may have lower alkoxy (e.g. methoxy) (e.g. methyl, methoxymethyl).

In the general formula (1), the partial structure (X):

[Chem. 15]

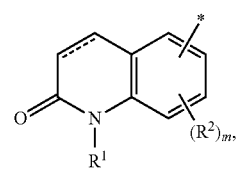

wherein * is the binding point to $X^1$ and other symbols are the same as defined above, includes a structure selected from the group consisting of the following formulae (X1) to (X6):

[Chem. 16]

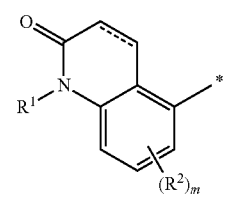

(X1)

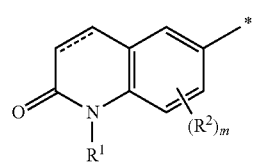

(X2)

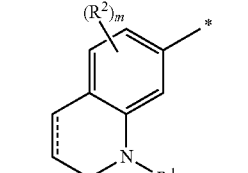

(X3)

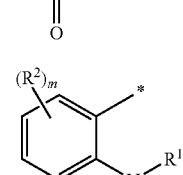

(X4)

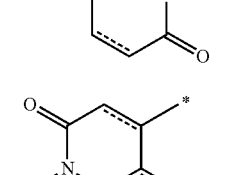

(X5)

and (X6) 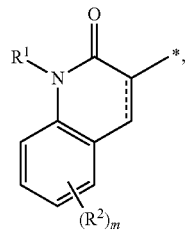

wherein each symbol is the same as defined above;
preferably a structure of Formula (X1), (X2), (X3), (X4), or (X5); and
more preferably a structure selected from the group consisting of the following formulae (X1-1) to (X5-1):

[Chem. 17]

(X1-1) 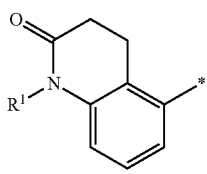

(X1-2) 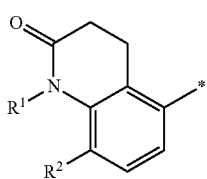

(X1-3) 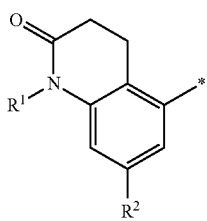

(X1-4) 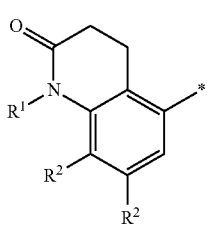

(X1-5) 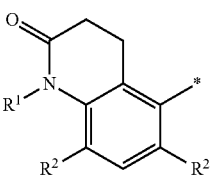

(X1-6)

(X1-7)

(X2-1)

(X3-1)

(X4-1) and (X5-1)

wherein each symbol is the same as defined above.

In the general formula (1), the partial structure (Y):

[Chem. 18]

(Y) 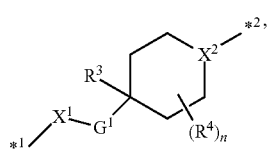

wherein *1 is the binding point to the partial structure of Formula (X); *2 represents the binding point to Ring A; and other symbols are the same as defined above, is preferably a structure selected from the group consisting of the following formulae (Y1) to (Y8):

[Chem. 19]

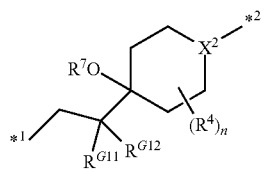 (Y1)

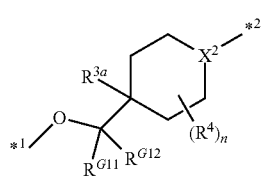 (Y2)

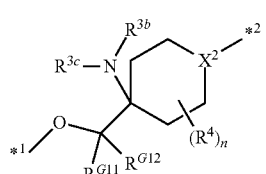 (Y3)

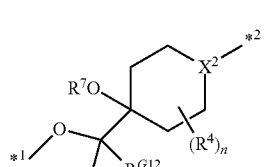 (Y4)

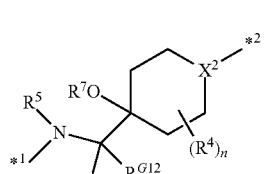 (Y5)

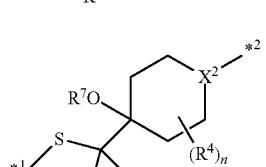 (Y6)

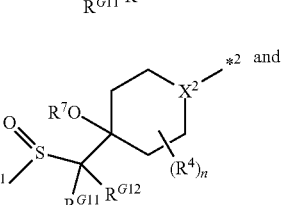 (Y7) and

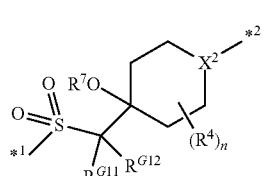 (Y8)

wherein $R^{3a}$ is (1) hydrogen, (2) carboxy, (3) halogen (e.g. fluorine), (4) lower alkyl (e.g. methyl) which may have hydroxy (e.g. hydroxymethyl), or (5) cyano; $R^{3b}$ and $R^{3c}$ are each independently (1) hydrogen, (2) lower alkyl (e.g. methyl), or (3) —C(=O)—$R^6$ (e.g. methoxycarbonyl, acetyl, dimethylaminoacetyl); and other symbols are the same as defined above;

more preferably a structure selected from the group consisting of the following formulae (Y1-1) to (Y8-1):

[Chem. 20]

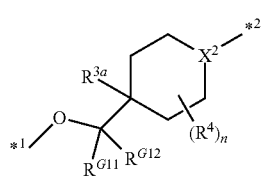 (Y1-1)

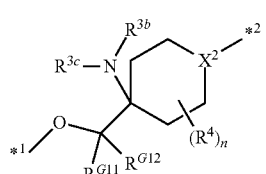 (Y2-1)

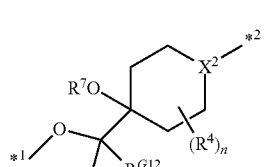 (Y3-1)

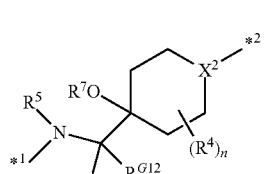 (Y4-1)

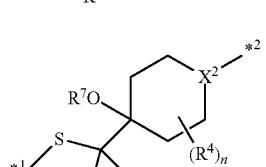 (Y4-2)

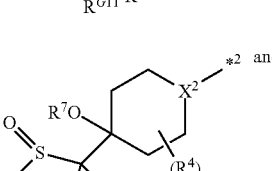 (Y5-1)

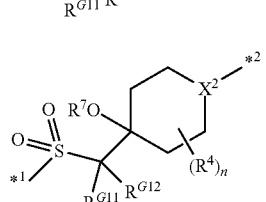 (Y6-1)

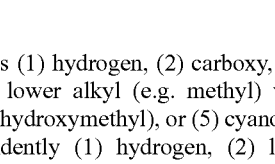 (Y7-1)

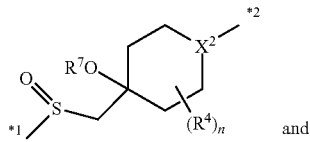 and (Y8-1)

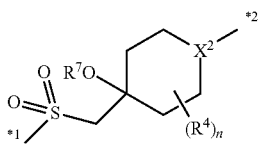

wherein each symbol is the same as defined above.

In one preferable embodiment, in Formula (I), the partial structure (X) is a structure selected from the group consisting of the formulae (X1-1), (X1-2), (X1-3), (X1-4), (X1-5), (X1-6), (X1-7), (X2-1), (X3-1), (X4-1), and (X5-1);

the partial structure (Y) is a structure selected from the group consisting of the formulae (Y1-1), (Y2-1), (Y3-1), (Y4-1), (Y4-2), (Y5-1), (Y6-1), (Y7-1), and (Y8-1);

$R^1$ is (1) hydrogen, (2) amino (e.g. amino) which may have one or more of the same or different lower alkyl, or (3) lower alkyl (e.g. methyl);

$R^2$ is a substituent selected from (1) halogen (e.g. fluorine, chlorine, bromine, iodine), (2) amino (e.g. amino) which may have one or two of the same or different lower alkyl, (3) lower alkyl (e.g. methyl, ethyl), (4) lower alkoxy (e.g. ethoxy), and (5) hydroxy;

each of $R^2$ may be different when it exists plurally;

$R^5$ is (1) hydrogen, (2) lower alkyl (e.g. methyl), or (3) lower alkanoyl (e.g. acetyl);

$R^{3a}$ is (1) hydrogen, (2) carboxy, (3) halogen (e.g. fluorine), (4) lower alkyl (e.g. methyl) which may have one or more of hydroxy (e.g. hydroxymethyl), or (5) cyano;

$R^{3b}$ and $R^{3c}$ are each independently (1) hydrogen, (2) lower alkyl (e.g. methyl), or (3) —C(=O)—$R^6$ (e.g. methoxycarbonyl, acetyl, dimethylaminoacetyl);

$R^6$ is (1) lower alkoxy (e.g. methoxy), or (2) lower alkyl (e.g. methyl) which may have one or more of the same or different amino which may have one or more of the same or different lower alkyl (e.g. methyl) (e.g. methyl, dimethylaminomethyl);

$R^7$ is (1) hydrogen, (2) amino, (3) lower alkanoyl (e.g. acetyl), or (4) lower alkyl (e.g. methyl);

$R^4$ is a substituent selected from (1) amino (e.g. amino, methylamino) which may have one or two of the same or different lower alkyl (e.g. methyl), (2) halogen (e.g. fluorine), (3) cyano, (4) lower alkyl (e.g. methyl), (5) oxo, (6) —O—$R^8$ (e.g. hydroxy, methoxy, 4-methoxybenzyloxy, —O—PH(=O)OH), and (7) —O—C(=O)—$R^9$ (e.g. acetoxy, pyrazinylcarbonyloxy, ethoxycarbonyloxy, ethylaminocarbonyloxy, 3-carboxypropionyloxy);

$R^8$ is (1) hydrogen, (2) lower alkyl (e.g. methyl), (3) —PH(=O)OH, or (4) benzyl which may have one or more of the same or different lower alkoxy (e.g. methoxy) (e.g. 4-methoxybenzyl);

$R^9$ is (1) lower alkyl (e.g. methyl), (2) -$G^2$-COOH (e.g. 2-carboxyethyl), (3) amino which may have one or two of the same or different lower alkyl (e.g. ethyl) (e.g. ethylamino), (4) lower alkoxy (e.g. ethoxy), or (5) pyrazinyl;

$G^2$ is lower alkylene (e.g. —$(CH_2)_2$—);

n is 0, 1, or 2;

provided that when n is 2, each of $R^4$, $R^8$, $R^9$, and $G^2$ may be different from each other and may be substituted on the same carbon atom;

$X^2$ is N or CH;

provided that when $X^2$ is CH, H of the group may be substituted with $R^4$ which is defined as above or may be different from the other $R^4$; and Ring A is (1) aryl, which is preferably (a1) phenyl, which may have one or more substituents independently selected from:
(a) halogen (e.g. fluorine, chlorine, bromine);
(b) cyano;
(c) nitro;
(d) hydroxy;
(e) lower alkyl (e.g. methyl, ethyl, propyl, isopropyl) which may have one or more substituents independently selected from (i) halogen (e.g. fluorine), (ii) hydroxy, (iii) lower alkoxy (e.g. methoxy, ethoxy), and (iv) aryloxy (e.g. phenoxy) which may have one or more of the same or different halogen (e.g. fluorine) (e.g. methyl, ethyl, propyl, isopropyl, trifluoromethyl, hydroxymethyl, ethoxymethyl, 2-methoxyethyl, 2-(4-fluorophenoxy)ethyl];
(f) lower alkoxy (e.g. methoxy, ethoxy, propoxy, isopropoxy, butoxy) which may have one or more substituents independently selected from (i) halogen (e.g. fluorine), (ii) lower alkoxy (e.g. methoxy, ethoxy) which may have one or more of the same or different lower alkoxy (e.g. methoxy), (iii) aryloxy (e.g. phenoxy) which may have one or more of the same or different halogen (e.g. fluorine), (iv) heterocyclyl (e.g. pyridyl) which may have one or more of the same or different lower alkyl (e.g. methyl) which may have halogen (e.g. fluorine), and (v) amino which may have one or two of the same or different lower alkyl (e.g. methyl) (e.g. methoxy, ethoxy, propoxy, isopropoxy, butoxy, difluoromethoxy, trifluoromethoxy, 2-fluoroethoxy, 2,2,2-trifluoroethoxy, 2-(2-methoxyethoxy) ethoxy, 2-methoxyethoxy, 2-(4-fluorophenoxy)ethoxy, 5-(trifluoromethyl)pyridin-2-ylmethoxy, 2-(dimethylamino)ethoxy);
(g) lower alkoxycarbonyl (e.g. ethoxycarbonyl);
(h) lower alkylsulfanyl (e.g. methylsulfanyl, ethylsulfanyl);
(i) aryl (e.g. phenyl) which may have one or more of the same or different halogen (e.g. fluorine, chlorine) (e.g. 2,4-dichlorophenyl, 4-chloro-2-fluorophenyl);
(j) aryloxy (e.g. phenoxy); and
(k) aralkyloxy (e.g. benzyloxy) which may have one or more substituents independently selected from (i) halogen (e.g. fluorine, chlorine), (ii) lower alkyl (e.g. methyl) which may have one or more of the same or different halogen (e.g. fluorine), and (iii) lower alkoxy (e.g. methoxy) which may have one or more of the same or different halogen (e.g. fluorine) (e.g. benzyloxy, 4-fluorobenzyloxy, 4-chlorobenzyloxy, 2,4-dichlorobenzyloxy, 4-(trifluoromethyl)benzyloxy, 4-(trifluoromethoxy)benzyloxy); or (2) heterocyclyl, which is preferably a group selected from (a2) pyridyl (e.g. 2-pyridyl, 3-pyridyl, 4-pyridyl), (a3) N-oxide pyridyl (e.g. N-oxidepyridin-2-yl), (a4) thienyl (e.g. 3-thienyl), (a5) quinolyl (e.g. 2-quinolyl, 6-quinolyl), (a6) isoquinolyl (e.g. 1-isoquinolyl), (a7) benzothienyl (e.g. benzo[b]thiophen-5-yl), (a8) quinoxalinyl (e.g. 6-quinoxalinyl), (a9) benzofuryl (e.g. benzo[b]furan-5-yl), (a10) benzodioxolyl (e.g. benzo[1,3]dioxol-5-yl), (a11) benzoxazolyl (e.g. 2-benzoxazolyl), and (a12) benzimidazolyl (e.g. 2-benzimidazolyl), which may have one or more substituents independently selected from:
(a) halogen (e.g. fluorine, chlorine, bromine, iodine);
(b) cyano;

(c) lower alkyl (e.g. methyl) which may have one or more substituents independently selected from (i) halogen (e.g. fluorine), and (ii) lower alkoxy (e.g. methoxy) (e.g. methyl, trifluoromethyl, methoxymethyl); and (d) lower alkoxy (e.g. ethoxy).

A method of preparing Compound (1) in the present invention is explained as below. Compound (1) in the present invention may be for example prepared according to the preparation methods as below. The preparation methods as below are illustrative and a method of preparing Compound (1) is not limited thereto.

Examples of "hydrocarbons" as a solvent include, for example, aliphatic hydrocarbons such as hexane and pentane; alicyclic hydrocarbons such as cyclopentane and cyclohexane; aromatic hydrocarbons such as benzene and toluene.

Examples of "halogenated hydrocarbons" as a solvent include, for example, chloroform, dichloromethane.

Examples of "alcohols" as a solvent include, for example, methanol, ethanol, isopropanol, propanol, tert-butanol.

Examples of "ethers" as a solvent include, for example, chain ethers such as diethyl ether, diisopropyl ether, dibutyl ether, and diphenyl ether; circular ethers such as 1,4-dioxane and tetrahydrofurane.

Examples of "esters" as a solvent include, for example, ethyl acetate, ethyl propionate.

Examples of "ketones" as a solvent include, for example, acetone, methyl ethyl ketone, methyl isobutyl ketone.

Examples of "amides" as a solvent include, for example, N,N-dimethylformamide, N,N-dimethylacetamide, N-methyl-2-pyrrolidone.

Examples of "nitriles" as a solvent include, for example, acetonitrile, propionitrile.

Examples of "sulfoxides" as a solvent include, for example, dimethylsulfoxide.

Examples of "alkali metal hydroxides" as a base include, for example, sodium hydroxide, potassium hydroxide, cesium hydroxide.

Examples of "alkali metal hydrides" as a base include, for example, sodium hydride, potassium hydride, cesium hydride.

Examples of "alkali metal carboxylates" as a base include, for example, sodium acetate, potassium acetate, sodium butyrate.

Examples of "alkali metal carbonates" as a base include, for example, sodium carbonate, potassium carbonate, cesium carbonate, lithium carbonate.

Examples of "alkali metal hydrogencarbonates" as a base include, for example, sodium hydrogencarbonate, potassium hydrogencarbonate, cesium hydrogencarbonate.

Examples of "alkali metal phosphates" as a base include, for example, sodium phosphate, potassium phosphate.

Examples of "aromatic amines" as a base include, for example, pyridine, lutidine.

Examples of "tertiary amines" as a base include, for example, triethylamine, tripropylamine, tributylamine, diisopropylethylamine, cyclohexyldimethylamine, 4-dimethylaminopyridine, N,N-dimethylaniline, N-methylpiperidine, N-methylpyrrolidine, N-methylmorpholine, tetramethylethylenediamine, tetramethylpropylenediamine, 1,8-diazabicyclo[5,4,0]undec-7-ene (diazabicycloundecene).

Examples of "metal amides" as a base include, for example, lithium diisopropylamide, lithium hexamethyldisilazide.

Examples of "metal alkoxides" as a base include, for example, sodium methoxide, sodium ethoxide, sodium tert-butoxide, potassium tert-butoxide, sodium phenoxide.

Examples of "protecting group of hydroxy" include, but not limited to, any protecting groups of hydroxy used in the field of synthetic organic chemistry, and include, for example, alkyl (e.g. methyl, ethyl, isopropyl, tert-butyl, trifluoromethyl, hydroxymethyl, 2-hydroxyethyl, acetylmethyl); alkenyl (e.g. ethenyl, 1-propenyl, 2-propenyl, 1-methyl-2-propenyl); alkynyl (e.g. ethynyl, 1-propynyl, 2-propynyl, 1-methyl-2-propynyl); formyl; alkyl (alkenyl) carbonyls (e.g. acetyl, propionyl, butyryl, isobutyryl, pentanoyl, pivaloyl, valeryl, isovaleryl, chloroacetyl, dichloroacetyl, trichloroacetyl, trifluoroacetyl, methoxyacetyl, acryloyl, propioloyl, methacryloyl, crotonoyl, isocrotonoyl, (E)-2-methyl-2-butenoyl); arylcarbonyl (e.g. benzoyl, α-naphthoyl, β-naphthoyl, 2-bromobenzoyl, 4-chlorobenzoyl, 2,4,6-trimethylbenzoyl, 4-toluoyl, 4-anisoyl, 4-nitrobenzoyl, 2-nitrobenzoyl, 2-(methoxycarbonyl)benzoyl, 4-phenylbenzoyl); alkoxycarbonyl (e.g. methoxycarbonyl, tert-butoxycarbonyl, 2,2,2-trichloroethoxycarbonyl, 2-trimethylsilylethoxycarbonyl, 9-fluorenylmethyloxycarbonyl); tetrahydro (thio) pyranyl (furanyl) (e.g. tetrahydropyran-2-yl, 3-bromotetrahydropyran-2-yl, 4-methoxytetrahydropyran-4-yl, tetrahydrothiopyran-2-yl, 4-methoxytetrahydrothiopyran-4-yl, tetrahydrofuran-2-yl, tetrahydrothiofuran-2-yl); silyl (e.g. trimethylsilyl, triethylsilyl, isopropyl dimethylsilyl, tert-butyldimethyl silyl, methyldiisopropyl silyl, methyl di-tert-butylsilyl, triisopropylsilyl, diphenylmethyl silyl, diphenylbutyl silyl, diphenylisopropyl silyl, phenyldiisopropyl silyl); alkoxymethyl (e.g. methoxymethyl, 1,1-dimethyl-1-methoxymethyl, ethoxymethyl, propoxymethyl, isopropoxymethyl, butoxymethyl, tert-butoxymethyl, 2-methoxyethoxymethyl, 2,2,2-trichloroethoxymethyl, bis(2-chloroethoxy)methyl); alkoxyethyl (e.g. 1-ethoxyethyl, 1-(isopropoxy)ethyl); halogenated ethyl (e.g. 2,2,2-trichloroethyl); aralkyl (e.g. benzyl, α-naphthylmethyl, β-naphthylmethyl, diphenylmethyl, triphenylmethyl, α-naphthyldiphenylmethyl, 9-anthrylmethyl, 4-methylbenzyl, 2,4,6-trimethylbenzyl, 3,4,5-trimethylbenzyl, 4-methoxybenzyl, 4-methoxyphenyldiphenylmethyl, 2-nitrobenzyl, 4-nitrobenzyl, 4-chlorobenzyl, 4-bromobenzyl, 4-cyanobenzyl); alkenyloxycarbonyl (e.g. vinyloxycarbonyl, allyloxycarbonyl); aralkyloxycarbonyl (e.g. benzyloxycarbonyl, 4-methoxybenzyloxycarbonyl, 3,4-dimethoxybenzyloxycarbonyl, 2-nitrobenzyloxycarbonyl, 4-nitrobenzyloxycarbonyl).

Examples of "protecting group of carboxy" include, but not limited to, any protecting groups of carboxy used in the field of synthetic organic chemistry, and include, for example, similar groups to the above "alkyl", "alkenyl", "alkynyl", "aralkyl", and "silyl" illustrated in the "protecting group of hydroxy".

Examples of "protecting group of amino" include, but not limited to, any protecting groups of amino used in the field of synthetic organic chemistry, and include, for example, similar groups to the above "alkyl (alkenyl) carbonyl", "arylcarbonyl", "alkoxycarbonyl", "silyl", "aralkyl", "alkenyloxycarbonyl", and "aralkyloxycarbonyl" illustrated in the "protecting group of hydroxy".

Examples of "protecting group of terminal acetylene" include, but not limited to, any protecting groups of terminal acetylene used in the field of synthetic organic chemistry, and include, for example, similar groups to the above "silyl" illustrated in the "protecting group of hydroxy".

Examples of "leaving group" include, for example, halogen (e.g. chlorine, bromine, iodine), alkylsulfonyloxy (e.g. methylsulfonyloxy, ethylsulfonyloxy, trifluoromethylsulfonyloxy), arylsulfonyloxy (e.g. benzenesulfonyloxy, p-toluenesulfonyloxy, 2,4,6-trimethylbenzenesulfonyloxy, 2-nitrobenzenesulfonyloxy, 4-nitrobenzenesulfonyloxy).

For the avoidance of doubt it is confirmed that in the general description above, in the usual way the proposal of general preferences and options in respect of different features of the compounds, methods, and compositions constitutes the proposal of general combinations of those general preferences and options for the different features, insofar as they are combinable and compatible and are put forward in the same context.

Preparation Method A: General Synthetic Route 1

Scheme A-1

[Chem. 21]

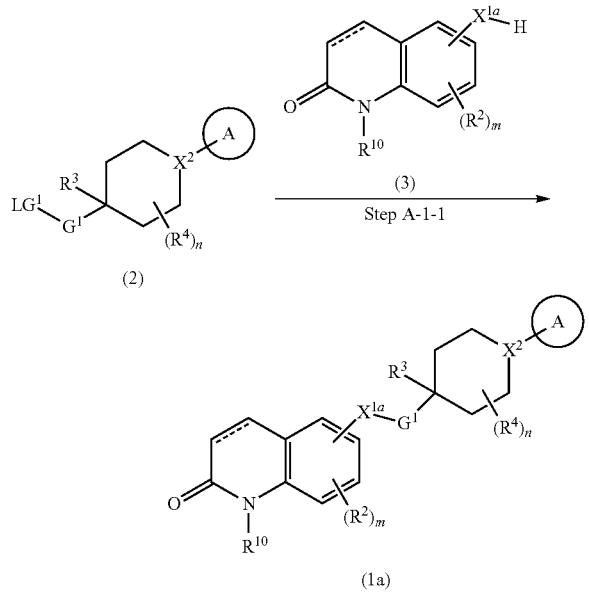

wherein $X^{1a}$ represents —O—, —N($R^5$)— or —S—; $R^{10}$ represents hydrogen or an amino protective group; $LG^1$ represents a leaving group; and other symbols are as defined above.

In the compound having $R^{10}$, instead of protecting the amino of the amide with $R^{10}$, it is possible to protect the imidic acid (hydroxyl thereof) which is a tautomer of the amide. Namely, a substructure represented by formula (aa):

[Chem. 22]

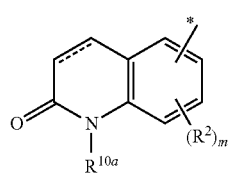

wherein $R^{10a}$ represents an amino protecting group; * represents a binding point to $X^{1a}$ ($X^1$); and other symbols are as defined above can be formula (aa1):

[Chem. 23]

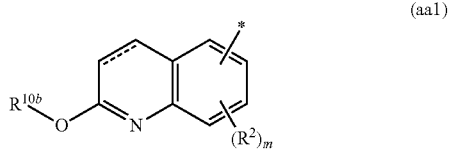

wherein $R^{10b}$ represents lower alkyl; and other symbols are as defined above.

(Step A-1-1: (2)+(3)→(1a))

Among the compounds represented as formula (1), compound (1a) can be obtained, for example, by reacting compound (2) and compound (3) in an inert solvent in the presence of a base.

The amount of compound (3) used is typically 0.1 to 10 molar equivalents, preferably 0.2 to 5 molar equivalents relative to compound (2).

Examples of the base include, for example, alkali metal hydroxides, alkali metal hydrides, alkali metal carbonates, alkali metal hydrogen carbonates, alkali metal hydrogen phosphates, aromatic amines, tertiary amines, metal amides and metal alkoxides, and it is also possible to use any two or more of them in an appropriate ratio. The amount of the base used is typically 1 to 10 molar equivalents, preferably 1 to 5 molar equivalents relative to compound (2).

Examples of the inert solvent include, for example, hydrocarbons, halogenated hydrocarbons, ethers, esters, ketones, alcohols, water, amides, nitriles and sulfoxides, and it is also possible to use any two or more of them in an appropriate ratio.

The reaction temperature is typically −80 to 150° C. The reaction time is typically 0.1 to 200 hours.

Scheme A-2

[Chem. 24]

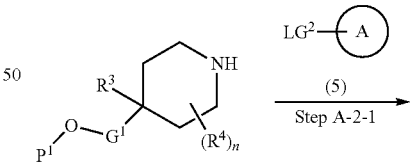

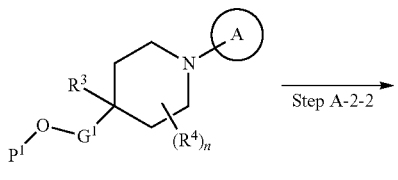

-continued

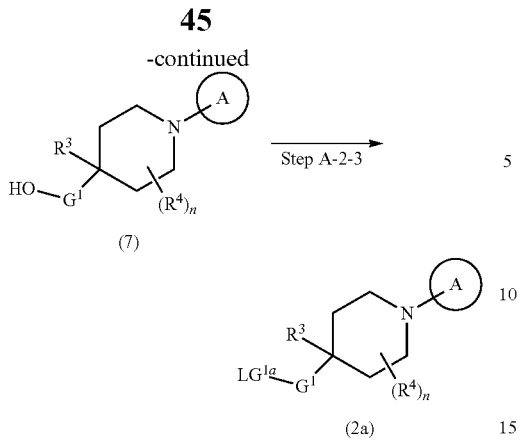

(7)

(2a)

wherein $LG^2$ and $LG^{1a}$ each independently represents a leaving group; $P^1$ represents a hydroxy protecting group; and other symbols are as defined above.

(Step A-2-1: (4)+(5)→(6))

Compound (6) can be obtained, for example, by reacting compound (4) and compound (5) in an inert solvent in the presence of a base. The amount of compound (5) used is typically 0.1 to 10 molar equivalents, preferably 0.2 to 5 molar equivalents relative to compound (4).

Examples of the base include, for example, alkali metal hydroxides, alkali metal hydrides, alkali metal carbonates, alkali metal hydrogen carbonates, alkali metal hydrogen phosphates, aromatic amines, tertiary amines, metal amides, alkoxides, and it is also possible to use any two or more of them in an appropriate ratio. The amount of the base used is typically 1 to 10 molar equivalents, preferably 1 to 5 molar equivalents relative to compound (4).

Transition metal catalyst can be used as necessary.

Examples of the transition metal catalyst include, for example, palladium catalysts such as palladium (II) acetate, palladium (II) chloride, tetrakis(triphenylphosphine)palladium (0), tris(dibenzylideneacetone)dipalladium (0), 1,1-bis(diphenylphosphino)ferrocene dichloropalladium (II), dichlorobis(triphenylphosphine)palladium (II), bis(tri-(tert-butylphosphine))palladium (0), phenylallylchloro[1,3-bis(diisopropylphenyl)-2-imidazol-2-ylidene]palladium (II) and phenylallylchloro-[1,3-bis(diisopropylphenyl)-2-imidazolidinylidene]palladium (II); copper catalysts such as copper (I) iodide and copper (I) oxide; rhodium catalysts such as tris(triphenylphosphine)rhodium (III) chloride; nickel catalysts such as tetrakis(triphenylphosphine)nickel (0), and it is also possible to use any two or more of them in an appropriate ratio. The amount of the transition metal catalyst used is typically 0.001 to 3 molar equivalents relative to compound (4).

In addition, a ligand can be added as necessary. Examples of the ligand include, for example, triphenylphosphine, tri(tert-butyl)phosphine, 2,2'-bis(diphenylphosphino)-1,1'-binaphthyl, 2-(dicyclohexylphosphino)-2',4',6'-triisopropyl-1,1'-biphenyl, 4,5'-bis(diphenylphosphino)-9,9'-dimethylxanthene. The amount of the ligand used is typically 0.001 to 3 molar equivalents relative to compound (4).

Examples of the inert solvent include, for example, hydrocarbons, halogenated hydrocarbons, ethers, esters, ketones, alcohols, water, amides, nitriles and sulfoxides, and it is also possible to use any two or more of them in an appropriate ratio.

The reaction temperature is typically −80 to 150° C. The reaction time is typically 0.1 to 200 hours.

(Step A-2-2: (6)→(7))

Compound (7) can be obtained by subjecting compound (6) to a deprotection reaction.

Any of known reactions may be used as the deprotection reaction, for example, when $P^1$ is silyl, compound (6) can be deprotected in an inert solvent in the presence of a fluoride source or an acid to give compound (7).

Examples of the fluoride source include tetrabutylammonium fluoride, hydrofluoric acid and cesium fluoride. The amount of the fluoride source used is typically 1 to 10 molar equivalents, preferably 1 to 5 molar equivalents relative to compound (6).

Examples of the acid include, for example, inorganic acids such as hydrochloric acid, sulfuric acid, nitric acid, hydrobromic acid and phosphoric acid; organic acids such as acetic acid, trifluoroacetic acid, oxalic acid, phthalic acid, fumaric acid, tartaric acid, maleic acid, citric acid, succinic acid, methanesulfonic acid, p-toluenesulfonic acid and 10-camphorsulfonic acid, and it is also possible to use any two or more of them in an appropriate ratio. The amount of the acid used is typically 1 molar equivalent to excessive amounts relative to compound (6).

Examples of the inert solvent include, for example, hydrocarbons, halogenated hydrocarbons, water, alcohols, ethers, esters, ketones, amides, nitriles and sulfoxides, and it is also possible to use any two or more of them in an appropriate ratio.

The reaction temperature is typically −80 to 150° C. The reaction time is typically 0.1 to 200 hours.

(Step A-2-3: (7)→(2a))

Among the compounds represented as formula (2), compound (2a) can be obtained by transforming hydroxy in compound (7) to a leaving group by using any known method.

For example, when the leaving group in compound (2a) is alkylsulfonyloxy or arylsulfonyloxy, compound (7) can be reacted with corresponding sulfonic anhydride (such as trifluoromethanesulfonic anhydride) or sulfonyl halide (such as benzenesulfonyl chloride, p-toluenesulfonyl chloride and methylsulfonyl chloride) etc. in an inert solvent in the presence of a base to provide compound (2a). The amount of sulfonic anhydride or sulfonyl halide used is typically 1 to 10 molar equivalents, preferably 1 to 5 molar equivalents relative to compound (7).

Examples of the base include, for example, alkali metal hydroxides, alkali metal hydrides, alkali metal carbonates, alkali metal hydrogen carbonates, alkali metal hydrogen phosphates, aromatic amines, tertiary amines, metal amides and metal alkoxides, and it is also possible to use any two or more of them in an appropriate ratio. The amount of the base used is typically 1 to 10 molar equivalents, preferably 1 to 5 molar equivalents relative to compound (7).

Examples of the inert solvent include, for example, hydrocarbons, halogenated hydrocarbons, ethers, esters, ketones, amides, nitriles and sulfoxides, and it is also possible to use any two or more of them in an appropriate ratio.

The reaction temperature is typically −80 to 150° C. The reaction time is typically 0.1 to 200 hours.

Scheme A-3

[Chem. 25]

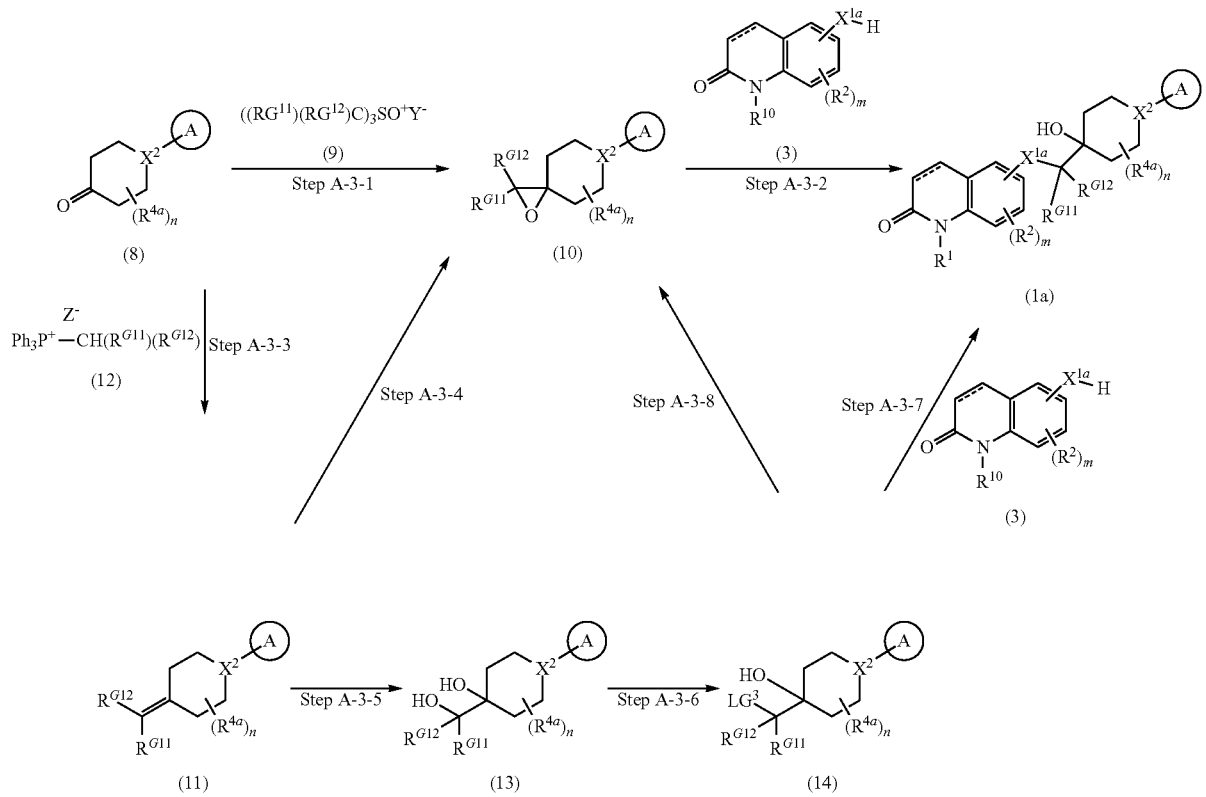

wherein each $R^{4a}$ independently represents amino optionally having one or more lower alkyl, halogen, cyano, lower alkyl, —O—$R^8$ or —O—C(=O)—$R^9$; $Y^-$ and $Z^-$ each independently represents halide ion; $LG^3$ represents a leaving group; and other symbols are as defined above.

(Step A-3-1: (8)+(9)→(10))

Compound (10) can be obtained, for example, by reacting compound (8) with compound (9) in an inert solvent in the presence of a base (Corey-Chaykovsky reaction).

The amount of compound (9) used is typically 0.1 to 10 molar equivalents, preferably 0.2 to 5 molar equivalents relative to compound (8).

Examples of the base include, for example, alkali metal hydroxides, alkali metal hydrides, alkali metal carbonates, alkali metal hydrogen carbonates, alkali metal hydrogen phosphates, aromatic amines, tertiary amines, metal amides and metal alkoxides, and it is also possible to use any two or more of them in an appropriate ratio. The amount of the base used is typically 1 to 10 molar equivalents, preferably 1 to 5 molar equivalents relative to compound (8).

In addition, as necessary, a salt can be added.

Examples of the salt include, for example, halogenated alkali metals such as cesium fluoride, cesium chloride, cesium bromide, cesium iodide, potassium fluoride, potassium chloride, potassium bromide, potassium iodide, sodium fluoride, sodium chloride, sodium bromide, sodium iodide, lithium fluoride, lithium chloride, lithium bromide and lithium iodide. The amount of the salt used is typically 1 to 10 molar equivalents, preferably 1 to 5 molar equivalents relative to compound (8).

Examples of the inert solvent include, for example, hydrocarbons, halogenated hydrocarbons, water, alcohols, ethers, esters, amides and sulfoxides, and it is also possible to use any two or more of them in an appropriate ratio.

The reaction temperature is typically −80 to 150° C. The reaction time is typically 0.1 to 200 hours.

(Step A-3-2: (10)+(3)→(1b))

Among the compounds represented as formula (1), compound (1b) can be obtained, for example, by reacting compound (10) with compound (3) in an inert solvent in the presence of a base or in the presence of an acid.

The amount of compound (3) used is typically 0.1 to 10 molar equivalents, preferably 0.2 to 5 molar equivalents relative to compound (10).

Examples of the base include, for example, alkali metal hydroxides, alkali metal hydrides, alkali metal carbonates, alkali metal hydrogen carbonates, alkali metal hydrogen phosphates, aromatic amines, tertiary amines, metal amides and metal alkoxides, and it is also possible to use any two or more of them in an appropriate ratio. The amount of the base used is typically 0.01 to 10 molar equivalents, preferably 0.1 to 5 molar equivalents relative to compound (10).

Examples of the acid include, for example, inorganic acids such as hydrochloric acid, sulfuric acid, nitric acid, hydrobromic acid and phosphoric acid; organic acids such as acetic acid, trifluoroacetic acid, oxalic acid, phthalic acid, fumaric acid, tartaric acid, maleic acid, citric acid, succinic acid, methanesulfonic acid, p-toluenesulfonic acid and 10-camphorsulfonic acid, and it is also possible to use any two or more of them in an appropriate ratio. The amount of the acid used is typically 1 molar equivalent to excessive amounts relative to compound (10).

Examples of the inert solvent include, for example, hydrocarbons, halogenated hydrocarbons, ethers, esters, ketones, alcohols, water, amides, nitriles and sulfoxides, and it is also possible to use any two or more of them in an appropriate ratio.

The reaction temperature is typically 40 to 150° C. The reaction time is typically 0.1 to 200 hours.

(Step A-3-3: (8)+(12)→(11))

Compound (11) can be obtained, for example, by reacting compound (8) with compound (12) in an inert solvent in the presence of a base (Wittig reaction).

The amount of compound (12) used is typically 0.1 to 10 molar equivalents, preferably 0.2 to 5 molar equivalents relative to compound (8).

Examples of the base include, for example, alkali metal hydrides, metal amides, metal alkoxides and organolithium reagent, and it is also possible to use any two or more of them in an appropriate ratio. The amount of the base used is typically 1 to 10 molar equivalents, preferably 1 to 5 molar equivalents relative to compound (8).

Examples of the inert solvent include, for example, hydrocarbons, halogenated hydrocarbons and ethers, and it is also possible to use any two or more of them in an appropriate ratio.

The reaction temperature is typically −80 to 150° C. The reaction time is typically 0.1 to 200 hours.

(Step A-3-4: (11)→(10))

Compound (10) can be obtained, for example, by reacting compound (11) in an inert solvent in the presence of an oxidizing agent.

Examples of the oxidizing agent include inorganic peroxides (such as hydrogen peroxide, sodium hypochlorite and sodium periodate), organic peroxides (such as m-chloroperbenzoic acid, perbenzoic acid, peracetic acid and trifluoroperacetic acid) and dioxiranes (such as dimethyldioxirane). The amount of the oxidizing agent used is typically 1 to 10 molar equivalents, preferably 1 to 5 molar equivalents relative to compound (11).

In addition, a base can be used, as necessary.

Examples of the base include, for example, alkali metal hydroxides, alkali metal hydrides, alkali metal carbonates, alkali metal hydrogen carbonates, alkali metal hydrogen phosphates, aromatic amines, tertiary amines, metal amides and metal alkoxides, and it is also possible to use any two or more of them in an appropriate ratio. The amount of the base used is typically 1 to 10 molar equivalents, preferably 1 to 5 molar equivalents relative to compound (11).

Examples of the inert solvent include, for example, hydrocarbons, halogenated hydrocarbons, water, alcohols, ethers, esters, ketones, amides, nitriles and sulfoxides, and it is also possible to use any two or more of them in an appropriate ratio.

The reaction temperature is typically −80 to 150° C. The reaction time is typically 0.1 to 200 hours.

(Step A-3-5: (11)→(13))

Compound (13) can be obtained, for example, by reacting compound (11) with in an inert solvent in the presence of osmium tetraoxide and a reoxidizing agent.

The amount of osmium tetraoxide used is typically 0.01 to 0.5 molar equivalents relative to compound (11). Also, potassium osmate ($K_2OsO_2(OH)_4$) may be used as an alternative to osmium tetraoxide. In addition, it is possible to use an immobilized catalyst in which osmium tetraoxide is supported on a solvent resistant polymer. Example of immobilized catalyst includes "Osmium Oxide, Immobilized Catalyst I (Os IC-I)" (trade name) (Wako Pure Chemical Industries, Ltd.).

Examples of the reoxidizing agent include, for example, N-methylmorpholine oxide, trimethylamine oxide, tert-butyl hydroperoxide and potassium ferricyanide ($K_3Fe(CN)_6$), and it is also possible to use any two or more of them in an appropriate ratio. The amount of the reoxidizing agent used is typically 1 to 10 molar equivalents, preferably 1 to 5 molar equivalents relative to compound (11).

Examples of the inert solvent include, for example, hydrocarbons, halogenated hydrocarbons, water, alcohols, ethers, esters, ketones, amides, nitriles and sulfoxides, and it is also possible to use any two or more of them in an appropriate ratio.

The reaction temperature is typically −80 to 150° C. The reaction time is typically 0.1 to 200 hours.

(Step A-3-6: (13)→(14))

Compound (14) can be obtained by transforming a specific hydroxy group in compound (13) to a leaving group. Said reaction can be performed under the conditions similar to above step A-2-3.

(Step A-3-7: (14)+(3)→(1b))

Among the compounds represented as formula (1), compound (1b) can be obtained, for example, by reacting compound (14) with compound (3) in an inert solvent in the presence of a base. Said reaction can be performed under the conditions similar to above step A-1-1.

(Step A-3-8: (14)→(10))

Compound (10) can be obtained, for example, by reacting compound (14) in an inert solvent in the presence of a base.

Examples of the base include, for example, alkali metal hydroxides, alkali metal hydrides, alkali metal carbonates, alkali metal hydrogen carbonates, alkali metal hydrogen phosphates, aromatic amines, tertiary amines, metal amides and metal alkoxides, and it is also possible to use any two or more of them in an appropriate ratio. The amount of the base used is typically 1 to 10 molar equivalents, preferably 1 to 5 molar equivalents relative to compound (14).

Examples of the inert solvent include, for example, hydrocarbons, halogenated hydrocarbons, ethers, esters, ketones, amides, nitriles and sulfoxides, and it is also possible to use any two or more of them in an appropriate ratio.

The reaction temperature is typically −80 to 150° C. The reaction time is typically 0.1 to 200 hours.

Scheme A-4

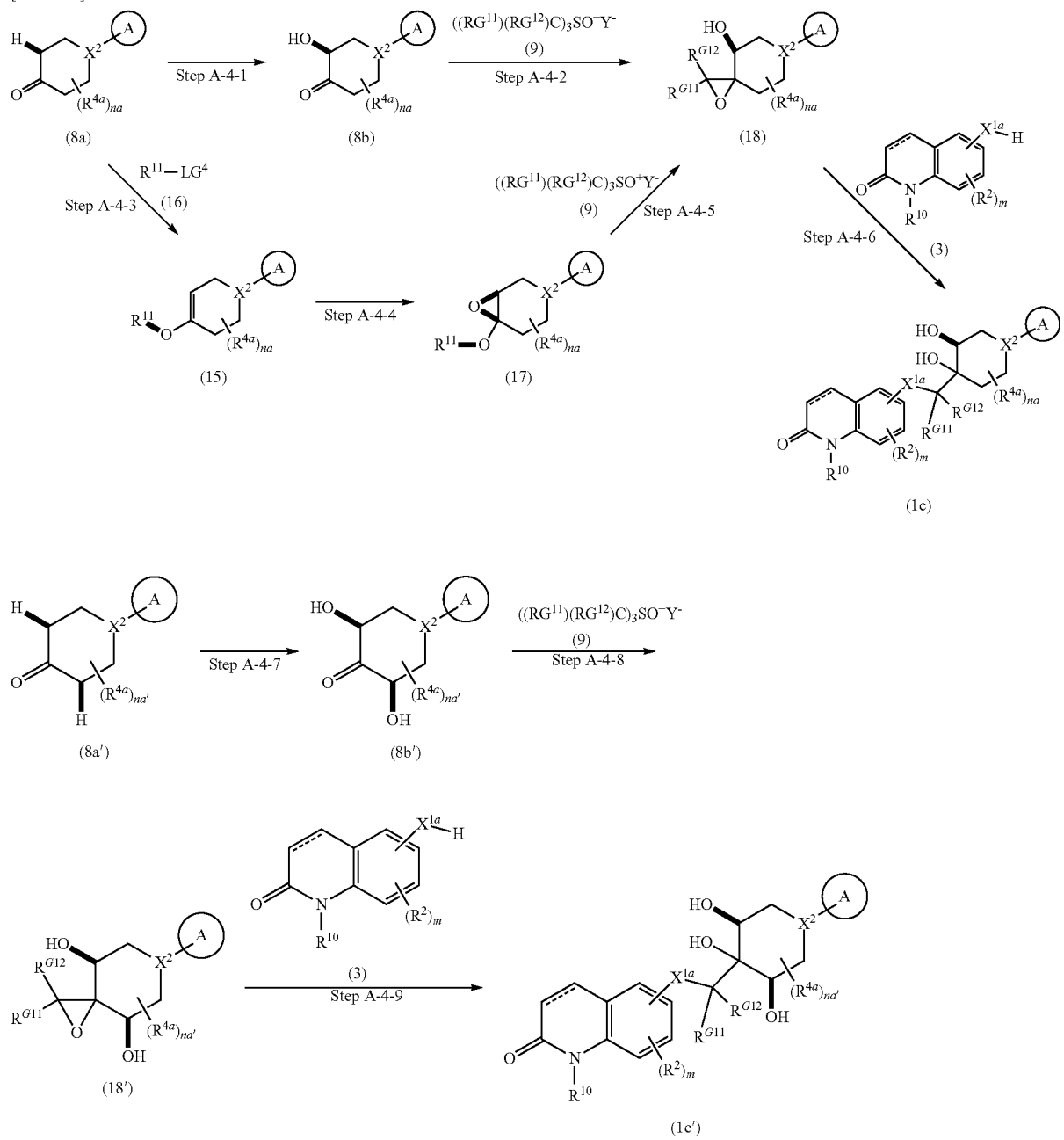

wherein $R^{11}$ represents tri-lower alkyl-silyl; $LG^4$ represents a leaving group; na is an integer from 0 to 7; na' is an integer from 0 to 6; and other symbols are as defined above.

(Step A-4-1: (8a)→(8b))

Among the compounds represented as formula (8), compound (8b) can be obtained, for example, by subjecting α-aminooxylation by reacting compound (8a) with a nitroso compound in an inert solvent in the presence of a catalyst of proline or a derivative thereof, followed by hydrolysis in the presence of copper (II) sulfate catalyst.

The amount of copper (II) sulfate used is typically 0.001 to 3 molar equivalents relative to compound (8a).

Example of the nitroso compound includes nitrosobenzene optionally having one or more substituents. The amount of the nitroso compound used is typically 1 to 10 molar equivalents, preferably 1 to 2 molar equivalents relative to compound (8a).

Examples of proline or a derivative thereof include LD-proline and 5-(pyrrolidin-2-yl)-1H-tetrazole. The amount of proline or a derivative thereof used is typically 0.001 to 3 molar equivalents relative to compound (8a).

In addition, by using L-proline and (S)-5-(pyrrolidin-2-yl)-1H-tetrazole etc. as proline or a derivative thereof, typically, it is possible to obtain mostly a compound represented as formula (8ba):

[Chem. 27]

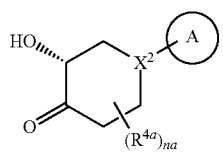

(8ba)

as compound (8b).

Alternatively, by using D-proline and (R)-5-(pyrrolidin-2-yl)-1H-tetrazole etc. as proline or a derivative thereof, typically, it is possible to obtain mostly a compound represented as formula (8bb):

[Chem. 28]

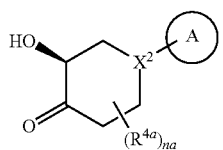

(8bb)

as compound (8b).

Examples of the inert solvent include, for example, hydrocarbons, halogenated hydrocarbons, water, alcohols, ethers, amides and sulfoxides, and it is also possible to use any two or more of them in an appropriate ratio.

The reaction temperature is typically −80 to 150° C. The reaction time is typically 0.1 to 200 hours.

(Step A-4-2: (8b)+(9)→(18))

Compound (18) can be obtained, for example, by reacting compound (8b) with compound (9) in an inert solvent in the presence of a base (Corey-Chaykovsky reaction). Said reaction can be performed under the conditions similar to above step A-3-1.

(Step A-4-3: (8a)+(16)→(15))

Compound (15) can be obtained, for example, by reacting compound (8a) with compound (16) in an inert solvent in the presence of a base.

The amount of compound (16) used is typically 1 to 10 molar equivalents, preferably 1 to 5 molar equivalents relative to compound (8a).

In addition, it may possible to add sodium iodide, as necessary. The amount of sodium iodide used is typically 0.01 to 10 molar equivalents, preferably 0.1 to 5 molar equivalents relative to compound (8a).

Examples of the base include, for example, alkali metal hydroxides, alkali metal hydrides, alkali metal carbonates, alkali metal hydrogen carbonates, alkali metal hydrogen phosphates, aromatic amines, tertiary amines and metal amides, and it is also possible to use any two or more of them in an appropriate ratio. The amount of the base used is typically 1 to 10 molar equivalents, preferably 1 to 5 molar equivalents relative to compound (8a).

Examples of the inert solvent include, for example, hydrocarbons, halogenated hydrocarbons, ethers, esters, ketones, amides, nitriles and sulfoxides, and it is also possible to use any two or more of them in an appropriate ratio.

The reaction temperature is typically −80 to 150° C. The reaction time is typically 0.1 to 200 hours.

(Step A-4-4: (15)→(17))

Compound (17) can be obtained, for example, by reacting compound (15) in an inert solvent in the presence of an oxidizing agent.

Examples of the oxidizing agent include inorganic peroxides (such as hydrogen peroxide, sodium hypochlorite and sodium periodate), organic peroxides (such as m-chloroperbenzoic acid, perbenzoic acid, peracetic acid and trifluoroperacetic acid) and dioxiranes (such as dimethyldioxirane). The amount of the oxidizing agent used is typically 1 to 10 molar equivalents, preferably 1 to 5 molar equivalents relative to compound (15).

In addition, Shi asymmetric epoxidation is performed by using Shi epoxidizing catalyst (1-O,2-O:4-O,5-O-diisopropylidene-β-D-erythro-2,3-hexodiuro-2,6-pyranose), and it may possible to obtain, mainly, formula (17a):

[Chem. 29]

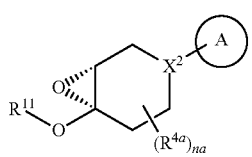

(17a)

wherein each symbol is as defined above as compound (17). The amount of Shi epoxidizing catalyst used is typically 0.001 to 3 molar equivalents relative to compound (15).

In addition, when using a ketone compound such as Shi epoxidizing catalyst, an oxidation auxiliary can be used in place of an oxidizing agent. Example of the oxidation auxiliary includes Oxone (registered trade name). The amount of the oxidation auxiliary used is typically 1 to 10 molar equivalents, preferably 1 to 5 molar equivalents relative to compound (15).

In addition, a base can be used, as necessary.

Examples of the base include, for example, alkali metal hydroxides, alkali metal hydrides, alkali metal carbonates, alkali metal hydrogen carbonates, alkali metal hydrogen phosphates, aromatic amines, tertiary amines, metal amides and metal alkoxides, and it is also possible to use any two or more of them in an appropriate ratio. The amount of the base used is typically 1 to 10 molar equivalents, preferably 1 to 5 molar equivalents relative to compound (15).

In addition, an additive agent can be added, as necessary. Example of the additive agent includes ethylenediaminetetraacetic acid disodium salt. The amount of the additive agent used is typically 0.001 to 3 molar equivalents relative to compound (15).

Examples of the inert solvent include, for example, hydrocarbons, halogenated hydrocarbons, water, alcohols, ethers, esters, ketones, amides, nitriles and sulfoxides, and it is also possible to use any two or more of them in an appropriate ratio.

The reaction temperature is typically −80 to 150° C. The reaction time is typically 0.1 to 200 hours.

(Step A-4-5: (17)+(9)→(18))

Compound (18) can be obtained, for example, by reacting compound (17) with compound (9) in an inert solvent in the presence of a base (Corey-Chaykovsky reaction). Said reaction can be performed under the conditions similar to above step A-3-1.

(Step A-4-6: (18)+(3)→(1c))

Among the compounds represented as formula (1), compound (1c) can be obtained, for example, by reacting compound (18) with compound (3) in an inert solvent in the presence of a base. Said reaction can be performed under the conditions similar to above step A-3-2.

(Step A-4-7: (8a')→(8b'))

Among the compounds represented as formula (8), compound (8b') can be obtained, for example, by subjecting α-aminohydroxylation by reacting compound (8a') with a nitroso compound in an inert solvent in the presence of a catalyst of proline or a derivative thereof, followed by hydrolysis in the presence of copper (II) sulfate catalyst. Said reaction can be performed under the conditions similar to above step A-4-1. The amount of the nitroso compound used is typically 2 to 10 molar equivalents, preferably 2 to 5 molar equivalents relative to compound (8a').

(Step A-4-8: (8b')+(9)→(18'))

Compound (18') can be obtained, for example, by reacting compound (8b') with compound (9) in an inert solvent in the presence of a base (Corey-Chaykovsky reaction). Said reaction can be performed under the conditions similar to above step A-3-1.

(Step A-4-9: (18')+(3)→(1c'))

Among the compounds represented as formula (1), compound (1c') can be obtained, for example, by reacting compound (18') with compound (3) in an inert solvent in the presence of a base. Said reaction can be performed under the conditions similar to above step A-3-2.

Scheme A-5

[Chem. 30]

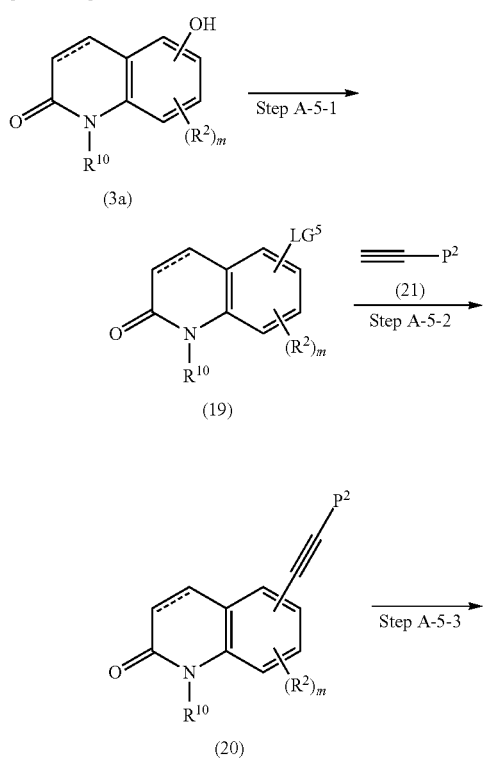

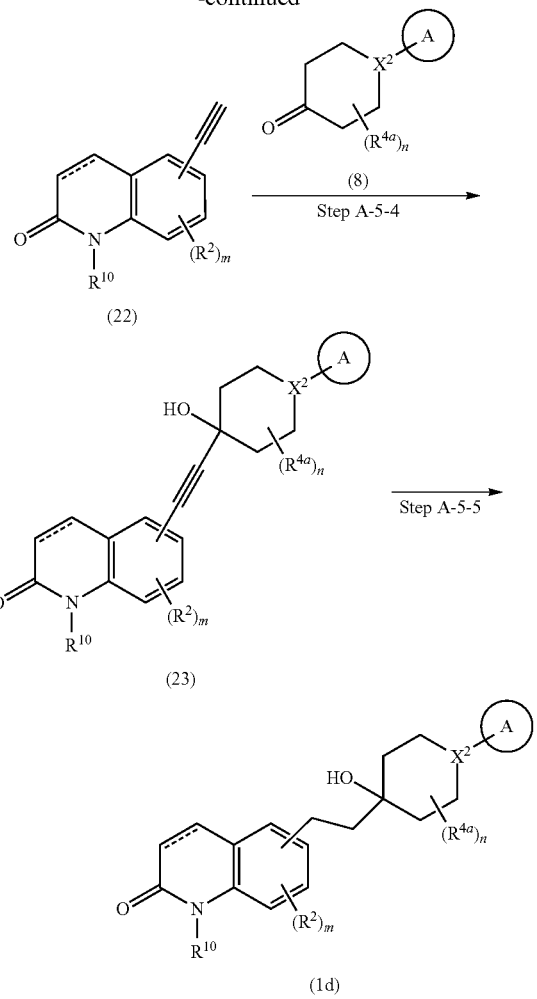

wherein $LG^5$ represents a leaving group; $P^2$ represents a protecting group on terminal acetylene; and other symbols are as defined above.

(Step A-5-1: (3a)→(19))

Compound (19) can be obtained by transforming hydroxy of compound (3a) to a leaving group by using any known method. For example, said reaction can be performed under the conditions similar to above step A-2-3.

(Step A-5-2: (19)+(21)→(20))

Compound (20) can be obtained, for example, by reacting compound (19) with compound (21) in an inert solvent, in the presence of base and transition metal catalyst. The amount of compound (21) used is typically 0.1 to 10 molar equivalents, preferably 0.2 to 5 molar equivalents relative to compound (19).

Examples of the base include, for example, alkali metal hydroxides, alkali metal hydrides, alkali metal carbonates, alkali metal hydrogen carbonates, alkali metal hydrogen phosphates, aromatic amines, tertiary amines, metal amides and metal alkoxides, and it is also possible to use any two or more of them in an appropriate ratio. The amount of the base used is typically 1 to 10 molar equivalents, preferably 1 to 5 molar equivalents relative to compound (19).

Examples of the transition metal catalyst include, for example, palladium catalysts such as palladium (II) acetate, palladium (II) chloride, tetrakis(triphenylphosphine)palladium (0), tris(dibenzylideneacetone)dipalladium (0), 1,1-bis (diphenylphosphino)ferrocene dichloropalladium (II), dichlorobis(triphenylphosphine)palladium (II), bis(tri-(tert-butylphosphine))palladium (0), phenylallylchloro[1,3-bis (diisopropylphenyl)-2-imidazol-2-ylidene]palladium (II) and phenylallylchloro-[1,3-bis(diisopropylphenyl)-2-imidazolidinylidene]palladium (II); copper catalysts such as copper (I) iodide and copper (I) oxide; rhodium catalysts such as tris(triphenylphosphine)rhodium (III) chloride; nickel catalysts such as tetrakis(triphenylphosphine)nickel (0), and it is also possible to use any two or more of them in an appropriate ratio. The amount of the transition metal catalyst used is typically 0.001 to 3 molar equivalents relative to compound (19).

In addition, a ligand can be added as necessary. Examples of the ligand include, for example, triphenylphosphine, tri(tert-butyl)phosphine, 2,2'-bis(diphenylphosphino)-1,1'-binaphthyl, 2-(dicyclohexylphosphino)-2',4',6'-triisopropyl-1,1'-biphenyl, 4,5'-bis(diphenylphosphino)-9,9'-dimethylxanthene. The amount of the ligand used is typically 0.001 to 3 molar equivalents relative to compound (19).

Examples of the inert solvent include, for example, hydrocarbons, halogenated hydrocarbons, ethers, esters, ketones, alcohols, water, amides, nitriles and sulfoxides, and it is also possible to use any two or more of them in an appropriate ratio.

The reaction temperature is typically −80 to 150° C. The reaction time is typically 0.1 to 200 hours.

(Step A-5-3: (20)→(22))

Compound (22) can be obtained by subjecting compound (20) to a deprotection reaction.

Any of known reactions may be used as the deprotection reaction, for example, when $P^2$ is silyl, compound (20) can be deprotected in the presence of a fluoride source or an acid to give compound (22).

Examples of the fluoride source include tetrabutylammonium fluoride, hydrofluoric acid and cesium fluoride. The amount of the fluoride source used is typically 1 to 10 molar equivalents, preferably 1 to 5 molar equivalents relative to compound (20).

Examples of the acid include, for example, inorganic acids such as hydrochloric acid, sulfuric acid, nitric acid and hydrobromic acid; organic acids such as methanesulfonic acid, p-toluenesulfonic acid and 10-camphorsulfonic acid, and it is also possible to use any two or more of them in an appropriate ratio. The amount of the acid used is typically 1 molar equivalent to excessive amounts relative to compound (20).

The acid can be used as a solvent, or an additional inert solvent can be used.

Examples of the inert solvent include, for example, hydrocarbons, halogenated hydrocarbons, water, alcohols, ethers, esters, ketones, amides, nitriles and sulfoxides, and it is also possible to use any two or more of them in an appropriate ratio.

The reaction temperature is typically −80 to 150° C. The reaction time is typically 0.1 to 200 hours.

(Step A-5-4: (22)+(8)→(23))

Compound (23) can be obtained, by treating compound (22) with a base in an inert solvent, followed by a reaction with compound (8).

The amount of compound (8) used is typically 0.1 to 10 molar equivalents, preferably 0.2 to 5 molar equivalents relative to compound (22).

Examples of the base include, for example, alkali metal hydroxides, alkali metal hydrides, alkali metal carbonates, alkali metal hydrogen carbonates, alkali metal hydrogen phosphates, aromatic amines, tertiary amines, metal amides, organic lithium reagent and a Grignard reagent of secondary or tertiary alkyl, and it is also possible to use any two or more of them in an appropriate ratio. The amount of the base used is typically 1 to 10 molar equivalents, preferably 1 to 5 molar equivalents relative to compound (22).

Examples of the Grignard reagent of secondary or tertiary alkyl include for example, isopropylmagnesium chloride, isopropylmagnesium bromide and tert-butylmagnesium bromide. Examples of the organic lithium reagent include, for example, isopropyllithium, propyllithium and tert-butyllithium.

Examples of the inert solvent include, for example, hydrocarbons, halogenated hydrocarbons, water, alcohols, ethers, esters, amides and sulfoxides, and it is also possible to use any two or more of them in an appropriate ratio.

The reaction temperature is typically −80 to 150° C. The reaction time is typically 0.1 to 200 hours.

(Step A-5-5: (23)→(1d))

Among the compounds represented as formula (1), compound (1d) can be obtained by subjecting compound (23) in the reduction reaction in an inert solvent, in the presence of a hydrogen source and a metal catalyst.

Examples of the hydrogen source include, for example, hydrogen gas, formic acid, sodium formate, ammonium formate, cyclohexene, phosphinic acid salt and hydrazine. When using hydrogen gas as the hydrogen source, the reaction can be done under the hydrogen pressure of about 1 to 10 atm. The amount of another hydrogen source used is typically 1 to 10 molar equivalents, preferably 1 to 5 molar equivalents relative to compound (23).

Examples of the metal catalyst include, for example, palladium on carbon, palladium black, palladium chloride, palladium hydroxide on carbon, platinum oxide, platinum black, platinum-palladium, platinum-carbon, Raney nickel and Raney cobalt. The amount of the metal catalyst used is typically 0.001 to 1000 molar equivalents, preferably 0.01 to 100 molar equivalents relative to compound (23).

Examples of the inert solvent include, for example, hydrocarbons, halogenated hydrocarbons, water, alcohols, ethers, esters, ketones, amides, nitriles and sulfoxides, and it is also possible to use any two or more of them in an appropriate ratio.

The reaction temperature is typically −80 to 150° C. The reaction time is typically 0.1 to 200 hours.

Scheme A-6

[Chem. 31]

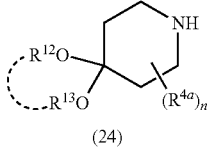
(24)

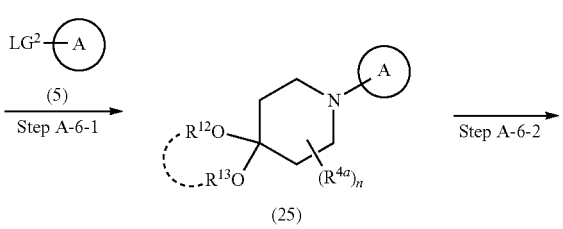
(25)

Step A-6-2

-continued

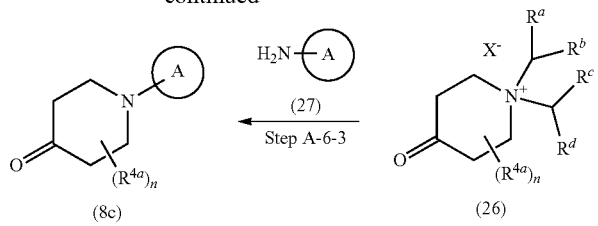

(8c)      Step A-6-3      (26)

wherein $R^{12}$ and $R^{13}$ each independently represents lower alkyl, or $R^{12}$ and $R^{13}$ may unitedly form an acetal ring; $R^a$, $R^b$, $R^c$ and $R^d$ each independently represents hydrogen, lower alkyl optionally having one or more substituents, lower alkenyl optionally having one or more substituents, lower alkoxycarbonyl optionally having one or more substituents, and aryl optionally having one or more substituents or carboxy; $X^-$ represents an inert anion such as halide ion; and other symbols are as defined above.

(Step A-6-1: (24)+(5)→(25))

Compound (25) can be obtained, for example, by reacting compound (24) with compound (5) in an inert solvent in the presence of a base. Said reaction can be performed under the conditions similar to above step A-2-1.

(Step A-6-2: (25)→(8c))

Among the compounds represented as formula (8), compound (8c) can be obtained, for example, by treating compound (25) with an acid.

Examples of the acid include, for example, inorganic acids such as hydrochloric acid, sulfuric acid, nitric acid, hydrobromic acid and phosphoric acid; organic acids such as acetic acid, trifluoroacetic acid, oxalic acid, phthalic acid, fumaric acid, tartaric acid, maleic acid, citric acid, succinic acid, methanesulfonic acid, p-toluenesulfonic acid and 10-camphorsulfonic acid, and it is also possible to use any two or more of them in an appropriate ratio. The amount of the acid used is typically 1 molar equivalent to excessive amounts relative to compound (25).

The acid can be used as a solvent, or an additional inert solvent can be used.

Examples of the inert solvent include, for example, hydrocarbons, halogenated hydrocarbons, water, alcohols, ethers, ketones, amides and sulfoxides, and it is also possible to use any two or more of them in an appropriate ratio.

The reaction temperature is typically −80 to 150° C. The reaction time is typically 0.1 to 200 hours.

(Step A-6-3: (26)+(27)→(8c))

Among the compounds represented as formula (8), compound (8c) can be obtained, for example, by reacting compound (26) with compound (27) in an inert solvent.

The amount of compound (27) used is typically 0.1 to 10 molar equivalents, preferably 0.2 to 5 molar equivalents relative to compound (26).

In addition, an additive agent can be added, as necessary. Examples of the additive agent include, for example, sodium acetate, sodium hydrogen carbonate, potassium carbonate, proline, thioureas, tertiary amines, acetic acid. The amount of the additive agent used is typically 0.01 to 10 molar equivalents, preferably 0.02 to 5 molar equivalents relative to compound (26).

Examples of the inert solvent include, for example, water, alcohols, hydrocarbons, halogenated hydrocarbons, ethers, esters, ketones, amides, nitriles and sulfoxides, and it is also possible to use any two or more of them in an appropriate ratio.

The reaction temperature is typically 40 to 150° C. The reaction time is typically 0.1 to 200 hours.

Scheme A-7

[Chem. 32]

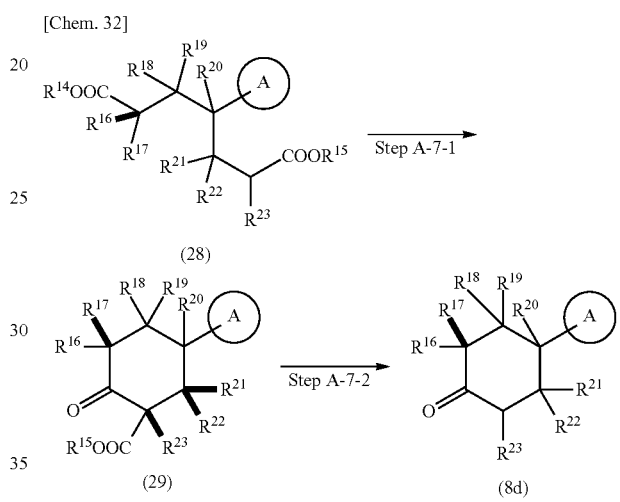

wherein $R^{14}$ and $R^{15}$ each independently represents lower alkyl; $R^{16}$, $R^{17}$, $R^8$, $R^{19}$, $R^{20}$, $R^{21}$ and $R^{22}$ each independently represents hydrogen, amino optionally having one or more lower alkyl, halogen, cyano, lower alkyl, —O—$R^8$ or —O—C(=O)—$R^9$; $R^{23}$ represents hydrogen, cyano or lower alkyl; and other symbols are as defined above.

(Step A-7-1: (28)→(29))

Compound (29) can be obtained, for example, by subjecting compound (28) to Claisen condensation reaction in an inert solvent in the presence of a base.

Examples of the base include, for example, alkali metal hydroxides, alkali metal hydrides, alkali metal carbonates, alkali metal hydrogen carbonates, alkali metal hydrogen phosphates, aromatic amines, tertiary amines, metal amides and metal alkoxides, and it is also possible to use any two or more of them in an appropriate ratio. The amount of the base used is typically 1 to 10 molar equivalents, preferably 1 to 5 molar equivalents relative to compound (28).

Examples of the inert solvent include, for example, hydrocarbons, halogenated hydrocarbons, water, alcohols, ethers, amides and sulfoxides, and it is also possible to use any two or more of them in an appropriate ratio.

The reaction temperature is typically 40 to 150° C. The reaction time is typically 0.1 to 200 hours.

(Step A-7-2: (29)→(8d))

Compound (8d) can be obtained, for example, by subjecting compound (29) to decarbonation reaction in an inert solvent.

An acid, a base or a salt can be added, as necessary.

Examples of the acid include, for example, inorganic acids such as hydrochloric acid, sulfuric acid, nitric acid, hydrobromic acid and phosphoric acid; organic acids such as acetic acid, trifluoroacetic acid, oxalic acid, phthalic acid, fumaric acid, tartaric acid, maleic acid, citric acid, succinic acid, methanesulfonic acid, p-toluenesulfonic acid and 10-camphorsulfonic acid, and it is also possible to use any two or more of them in an appropriate ratio.

Examples of the base include, for example, alkali metal hydroxides, alkali metal hydrides, alkali metal carbonates, alkali metal hydrogen carbonates, alkali metal hydrogen phosphates, aromatic amines, tertiary amines, metal amides and metal alkoxides, and it is also possible to use any two or more of them in an appropriate ratio.

Examples of the salt include, for example, halogenated alkali metals such as cesium fluoride, cesium chloride, cesium bromide, cesium iodide, potassium fluoride, potassium chloride, potassium bromide, potassium iodide, sodium fluoride, sodium chloride, sodium bromide, sodium iodide, lithium fluoride, lithium chloride, lithium bromide and lithium iodide.

The amount of the acid, base or salt used is typically 1 molar equivalent to excessive amounts relative to compound (29).

Examples of the inert solvent include, for example, hydrocarbons, halogenated hydrocarbons, water, alcohols, ethers, esters, ketones, amides, nitriles and sulfoxides, and it is also possible to use any two or more of them in an appropriate ratio.

The reaction temperature is typically 40 to 150° C. The reaction time is typically 0.1 to 200 hours.

Scheme A-8

[Chem. 33]

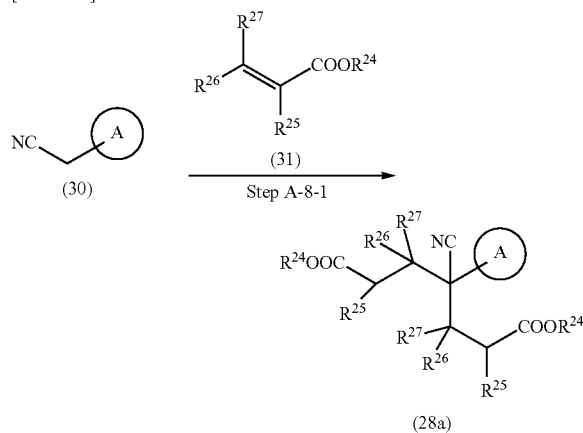

wherein $R^{24}$ represents lower alkyl; $R^{25}$ represents hydrogen, cyano or lower alkyl; $R^{26}$ and $R^{27}$ each independently represents hydrogen, amino optionally having one or more lower alkyl, halogen, cyano, lower alkyl, —O—$R^8$ or —O—C(=O)—$R^9$; and other symbols are as defined above.

(Step A-8-1: (30)+(31)→(28a))

Among the compounds represented as formula (28), compound (28a) can be obtained, for example, by reacting compound (30) with compound (31) in an inert solvent in the presence of a base (Michael addition reaction).

The amount of compound (31) used is typically 0.1 to 10 molar equivalents, preferably 0.2 to 5 molar equivalents relative to compound (30).

Examples of the base include, for example, basic ammonium salts, alkali metal hydroxides, alkali metal hydrides, alkali metal carbonates, alkali metal hydrogen carbonates, alkali metal hydrogen phosphates, aromatic amines, tertiary amines, metal amides and metal alkoxides, and it is also possible to use any two or more of them in an appropriate ratio. The amount of the base used is typically 1 to 10 molar equivalents, preferably 1 to 5 molar equivalents relative to compound (30).

Examples of the basic ammonium salt include tetramethylammonium hydoxide, tetraethylammonium hydoxide, tetra-n-propylammonium hydoxide, tetraisopropylammonium hydoxide, tetra-n-butylammonium hydroxide and benzyltrimethylammonium hydoxide (Triton-B).

Examples of the inert solvent include, for example, hydrocarbons, halogenated hydrocarbons, alcohols, ethers, amides, sulfoxides and nitriles, and it is also possible to use any two or more of them in an appropriate ratio.

The reaction temperature is typically 40 to 150° C. The reaction time is typically 0.1 to 200 hours.

Scheme A-9

[Chem. 34]

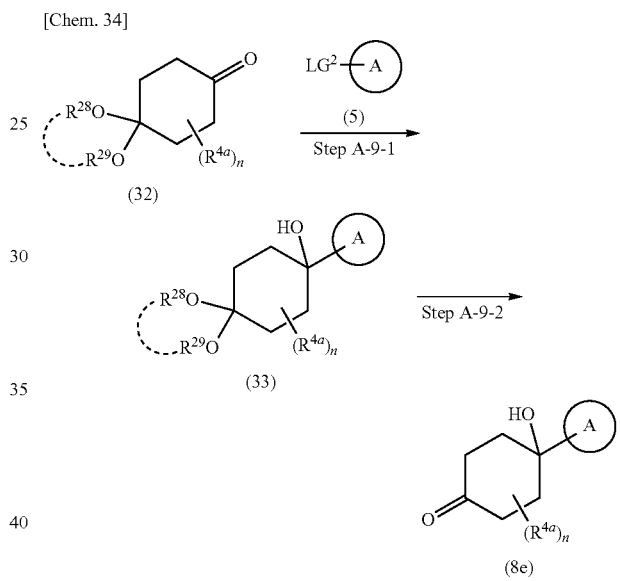

wherein $R^{28}$ and $R^{29}$ each independently represents a lower alkyl group, or $R^{28}$ and $R^{29}$ may unitedly form an acetal ring; and other symbols are as defined above.

(Step A-9-1: (32)+(5)→(33))

Compound (33) can be obtained, for example, by a magnesiation or lithiation of compound (5) using a method such as halogen-metal exchange method employing a Grignard reagent of secondary or tertiary alkyl or organic lithium reagent, and then reacting the obtained compound with compound (32).

The amount of compound (5) used is typically 0.1 to 10 molar equivalents, preferably 0.2 to 5 molar equivalents relative to compound (32).

Examples of the Grignard reagent of secondary or tertiary alkyl include for example, isopropylmagnesium chloride, isopropylmagnesium bromide and tert-butylmagnesium bromide. Examples of the organic lithium reagent include, for example, isopropyllithium, propyllithium and tert-butyllithium. The amount of the Grignard reagent of secondary or tertiary alkyl or organic lithium reagent used is typically 1 to 10 molar equivalents, preferably 1 to 5 molar equivalents relative to compound (32).

Examples of the inert solvent include, for example, hydrocarbons, ethers, amides and sulfoxides, and it is also possible to use any two or more of them in an appropriate ratio. The reaction temperature is typically −80 to 150° C. The reaction time is typically 0.1 to 200 hours.

(Step A-9-2: (33)→(8e))

Among the compounds represented as formula (8), compound (8e) can be obtained, for example, by treating compound (33) with an acid. Said reaction can be performed under the conditions similar to above step A-6-2.

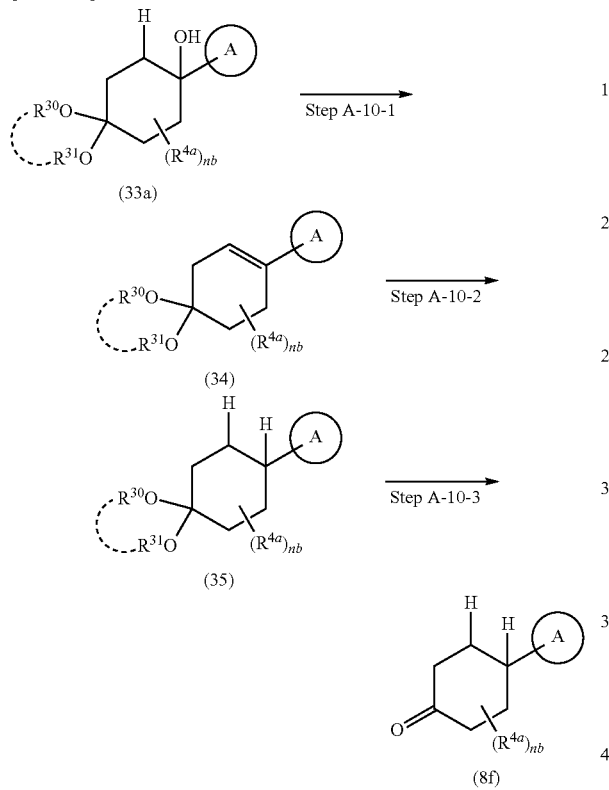

wherein $R^{30}$ and $R^{31}$ each independently represents lower alkyl, or $R^{30}$ and $R^{31}$ may unitedly form an acetal ring; nb is an integer of 0 to 7; and other symbols are as defined above.

(Step A-10-1: (33a)→(34))

Compound (34) can be obtained, for example, by transforming hydroxy in compound (33a) to a leaving group by using any known method followed by olefination reaction.

For example, hydroxy of compound (33a) can be transformed to a leaving group by reacting it with sulfonic anhydride (such as trifluoromethanesulfonic anhydride) or sulfonyl halide (such as benzenesulfonyl chloride, p-toluenesulfonyl chloride and methylsulfonyl chloride) in an inert solvent in the presence of a base, followed by an elimination reaction to give compound (34). The amount of sulfonic anhydride or sulfonyl halide used is typically 1 to 10 molar equivalents, preferably 1 to 5 molar equivalents relative to compound (33a).

Examples of the base include, for example, alkali metal hydroxides, alkali metal hydrides, alkali metal carbonates, alkali metal hydrogen carbonates, alkali metal hydrogen phosphates, aromatic amines, tertiary amines, metal amides and metal alkoxides, and it is also possible to use any two or more of them in an appropriate ratio. The amount of the base used is typically 1 to 10 molar equivalents, preferably 1 to 5 molar equivalents relative to compound (33a).

Examples of the inert solvent include, for example, hydrocarbons, halogenated hydrocarbons, ethers, esters, ketones, amides, nitriles and sulfoxides, and it is also possible to use any two or more of them in an appropriate ratio.

The reaction temperature is typically −80 to 150° C. The reaction time is typically 0.1 to 200 hours.

(Step A-10-2: (34)→(35))

Compound (35) can be obtained by subjecting compound (34) to reduction reaction in an inert solvent, in the presence of a hydrogen source and a metal catalyst. Said reaction can be performed under the conditions similar to above step A-5-5.

(Step A-10-3: (35)→(8f))

Among the compounds represented as formula (8), compound (8f) can be obtained, for example, by treating compound (35) with an acid. Said reaction can be performed under the conditions similar to above step A-6-2.

[Preparation Method B: General Synthetic Route 2]

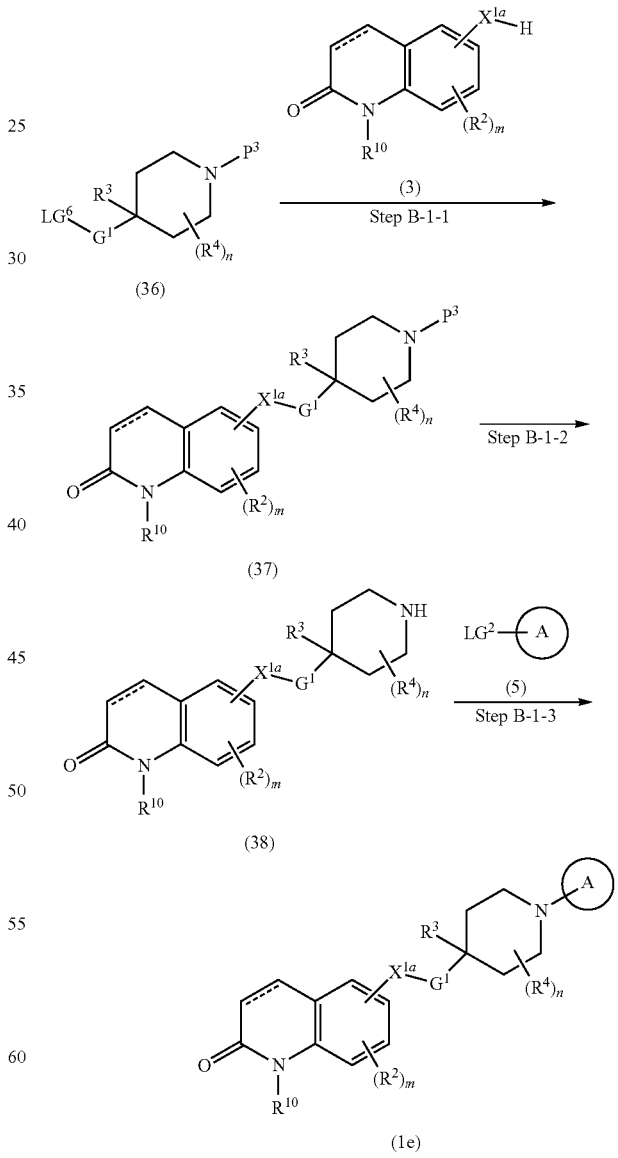

wherein $LG^6$ represents a leaving group; $P^3$ represents an amino protecting group; and other symbols are as defined above.

(Step B-1-1: (36)+(3)→(37))

Compound (37) can be obtained, for example, by reacting compound (36) with compound (3) in an inert solvent in the presence of a base. Said reaction can be performed under the conditions similar to above step A-1-1.

(Step B-1-2: (37)→(38))

Compound (38) can be obtained by subjecting compound (37) to a deprotection reaction.

Any of known reactions may be used as the deprotection reaction, for example, when $P^2$ is tert-butoxycarbonyl group (Boc), compound (37) can be deprotected in an inert solvent or in the absence of solvent in the presence of an acid (such as hydrochloric acid and trifluoroacetic acid) to give compound (38).

Examples of the inert solvent include, for example, hydrocarbons, halogenated hydrocarbons, water, alcohols, ethers, esters, ketones, amides, nitriles and sulfoxides, and it is also possible to use any two or more of them in an appropriate ratio.

The reaction temperature is typically −80 to 150° C. The reaction time is typically 0.1 to 200 hours.

(Step B-1-3: (38)+(5)→(1e))

Among the compounds represented as formula (1), compound (1e) can be obtained, for example, by reacting compound (38) with compound (5) in an inert solvent in the presence of a base. Said reaction can be performed under the conditions similar to above step A-2-1.

Scheme B-2

[Chem. 37]

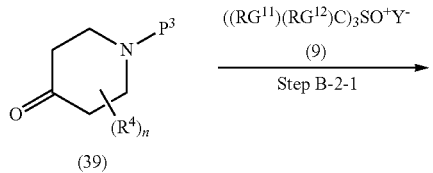

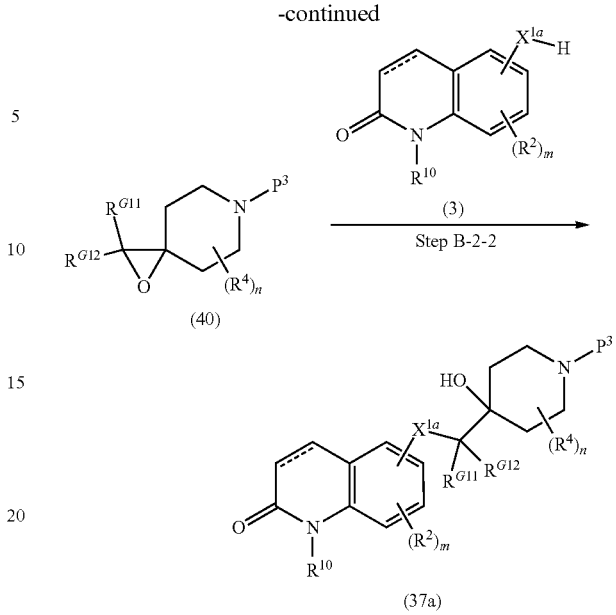

wherein each symbol is as defined above.

(Step B-2-1: (39)+(9)→(40))

Compound (40) can be obtained, for example, by reacting compound (39) with compound (9) in an inert solvent in the presence of a base (Corey-Chaykovsky reaction). Said reaction can be performed under the conditions similar to above step A-3-1.

(Step B-2-2: (40)+(3)→(37a))

Among the compounds represented as formula (37), compound (37a) can be obtained, for example, by reacting compound (40) with compound (3) in an inert solvent in the presence of a base. Said reaction can be performed under the conditions similar to above step A-3-2.

Scheme B-3

[Chem. 38]

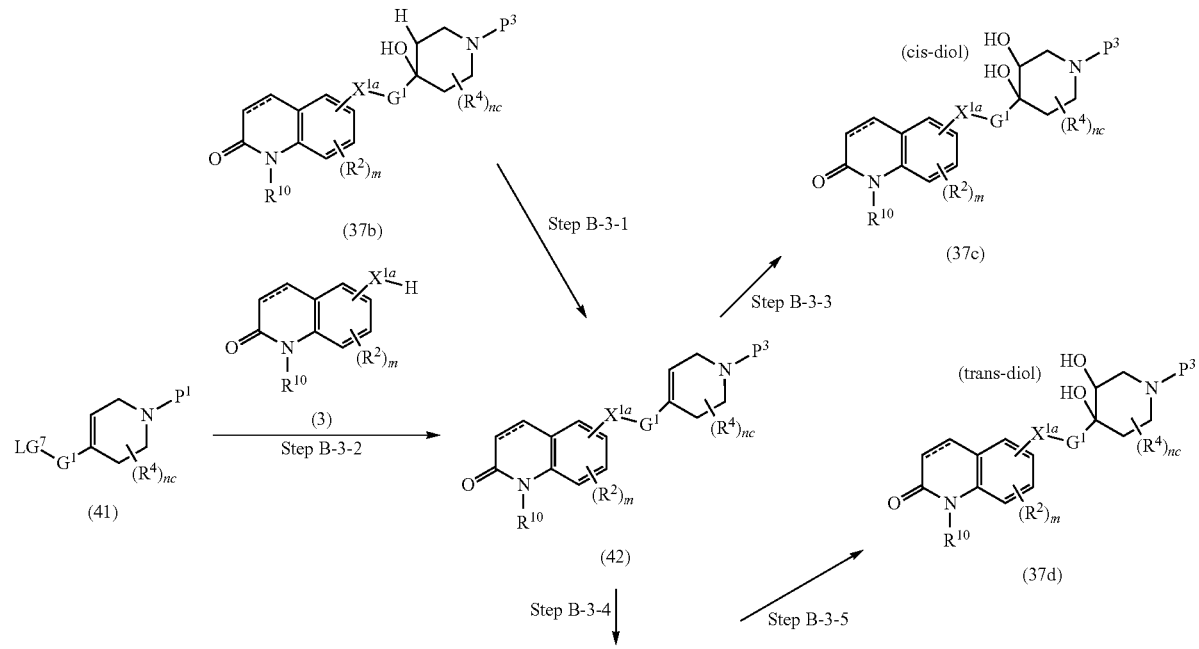

-continued

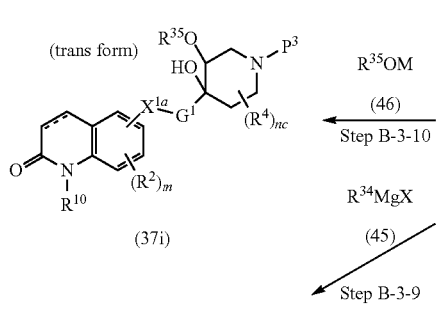
(37i)

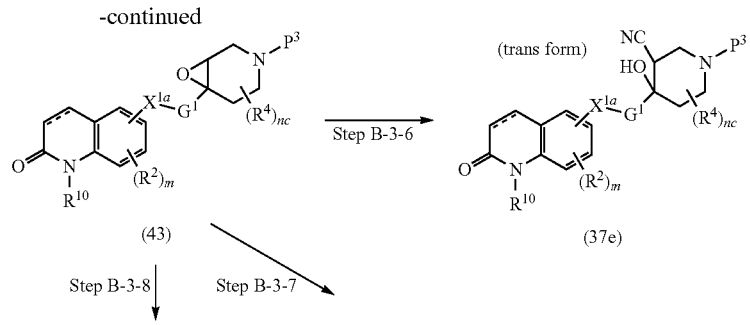
(43) (37e)

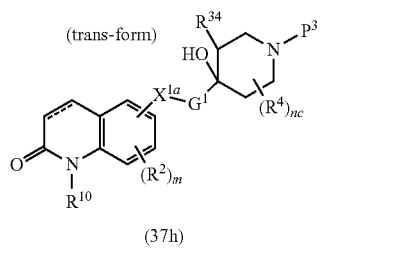
(37h)

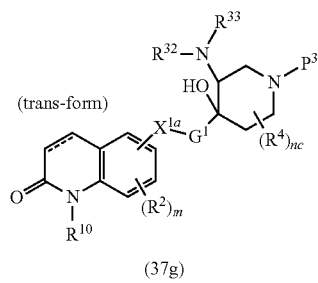
(37g)

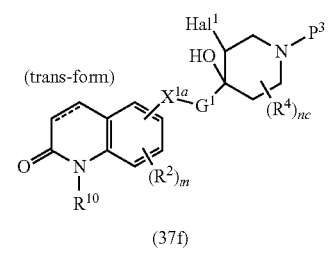
(37f)

wherein LG⁷ represents a leaving group; Hal¹ represents halogen; $R^{32}$ and $R^{33}$ each independently represents hydrogen or lower alkyl; $R^{34}$ represents lower alkyl; $R^{35}$ represents lower alkyl; M represents an alkali metal atom; X represents halogen; nc is an integer of 0 to 7; and other symbols are as defined above.

(Step B-3-1: (37b)→(42))

Compound (42) can be obtained, for example, by transforming hydroxy in compound (37b) to a leaving group by using any known method followed by olefination reaction. Said reaction can be performed under the conditions similar to above step A-10-1.

(Step B-3-2: (41)+(3)→(42))

Compound (42) can be obtained, for example, by reacting compound (41) with compound (3) in an inert solvent in the presence of a base. Said reaction can be performed under the conditions similar to above step A-1-1.

(Step B-3-3: (42)→(37c))

Among the compounds represented as formula (37), compound (37c) can be obtained, for example, by reacting compound (42) in an inert solvent, in the presence of osmium tetraoxide and a reoxidizing agent.

The amount of osmium tetraoxide used is typically 0.01 to 0.5 molar equivalents relative to compound (42). Also, potassium osmate ($K_2OsO_2(OH)_4$) may be used as an alternative to osmium tetraoxide. In addition, it is possible to use an immobilized catalyst in which osmium tetraoxide is support on a solvent resistant polymer. Example of immobilized catalyst includes "Osmium Oxide, Immobilized Catalyst I (Os IC-I)" (trade name) (Wako Pure Chemical Industries, Ltd.).

Examples of the reoxidizing agent include, for example, N-methylmorpholine oxide, trimethylamine oxide, tert-butyl hydroperoxide and potassium ferricyanide ($K_3Fe(CN)_6$), and it is also possible to use any two or more of them in an appropriate ratio. The amount of the reoxidizing agent used is typically 1 to 10 molar equivalents, preferably 1 to 5 molar equivalents relative to compound (42).

In addition, Sharpless asymmetric dihydroxylation reaction can be done by using an asymmetric amine ligand.

Examples of the asymmetric amine ligand include, for example, hydroquinine ethers such as hydroquinine anthraquinone-1,4-diyl diether [(DHQ)₂AQN], hydroquinine 2,5-diphenyl-4,6-pyrimidinediyl diether [(DHQ)₂PYR] and hydroquinine 1,4-phthalazinediyl diether [(DHQ)₂PHAL] and; hydroquinidine ethers such as hydroquinidine anthraquinone-1,4-diyl diether [(DHQD)₂AQN], hydroquinidine 2,5-diphenyl-4,6-pyrimidinediyl diether [(DHQD)₂PYR] and hydroquinidine 1,4-phthalazinediyl diether [(DHQD)₂PHAL]. The amount of the asymmetric amine ligand used is typically 0.001 to 1 molar equivalent relative to compound (42).

For example, when employing a hydroquinine ether, typically, it is possible to obtain mainly, a compound represented as formula (37ca):

[Chem. 39]

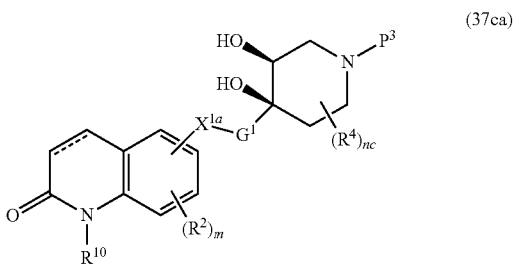
(37ca)

wherein each symbol is as defined above as compound (37c).

For example, when using a hydroquinidine ether, typically, it is possible to obtain mainly, a compound represented as formula (37cb):

[Chem. 40]

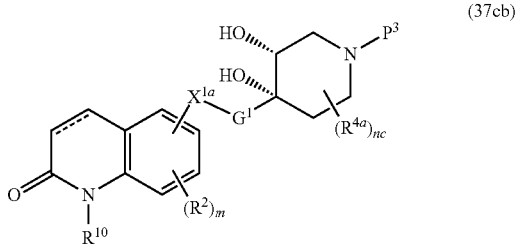

(37cb)

wherein each symbol is as defined above as compound (37c).

In addition, it is possible to add a base, as necessary. Examples of the base include alkali metal carbonates, alkali metal hydrogen carbonates, alkali metal hydroxides, aromatic amines and tertiary amines. The amount of the base used is typically 0.001 to 3 molar equivalents relative to compound (42).

In addition, an additive agent can be added, as necessary. Example of the additive agent includes methanesulfonamide. The amount of the additive agent used is typically 0.001 to 3 molar equivalents relative to compound (42).

In addition, a commercially available reagent kit such as AD-mix-α (comprising $K_2OsO_2(OH)_4$, $(DHQ)_2PHAL$, $K_3Fe(CN)_6$ and $K_2CO_3$) or AD-mix-β (comprising $K_2OsO_2(OH)_4$, $(DHQD)_2PHAL$, $K_3Fe(CN)_6$ and $K_2CO_3$) can be used.

Examples of the inert solvent include, for example, hydrocarbons, halogenated hydrocarbons, water, alcohols, ethers, esters, ketones, amides, nitriles and sulfoxides, and it is also possible to use any two or more of them in an appropriate ratio.

The reaction temperature is typically −80 to 150° C. The reaction time is typically 0.1 to 200 hours.

(Step B-3-4: (42)→(43))

Compound (43) can be obtained, for example, by reacting compound (42) in an inert solvent in the presence of an oxidizing agent. Said reaction can be performed under the conditions similar to above step A-4-4.

(Step B-3-5: (43)→(37d))

Among the compounds represented as formula (37), compound (37d) can be obtained, for example, by treating compound (43) with an acid.

Examples of the acid include, for example, inorganic acids such as hydrochloric acid, sulfuric acid, nitric acid, hydrobromic acid and phosphoric acid; organic acids such as acetic acid, trifluoroacetic acid, oxalic acid, phthalic acid, fumaric acid, tartaric acid, maleic acid, citric acid, succinic acid, methanesulfonic acid, p-toluenesulfonic acid and 10-camphorsulfonic acid, and it is also possible to use any two or more of them in an appropriate ratio. The amount of the acid used is typically 1 molar equivalent to excessive amounts relative to compound (43).

The acid can be used as a solvent, or an additional inert solvent can be used.

Examples of the inert solvent include, for example, hydrocarbons, halogenated hydrocarbons, water, alcohols, ethers, esters, ketones, amides, nitriles and sulfoxides, and it is also possible to use any two or more of them in an appropriate ratio.

The reaction temperature is typically −80 to 150° C. The reaction time is typically 0.1 to 200 hours.

(Step B-3-6: (43)→(37e))

Among the compounds represented as formula (37), compound (37e) can be obtained, for example, treating compound (43) with a cyane source and a base.

Examples of the cyane source include, for example, α-cyanohydrins such as α-hydroxyisobutyronitrile. The amount of the cyane source used is typically 1 to 10 molar equivalents, preferably 1 to 5 molar equivalents relative to compound (43).

Examples of the base include, for example, alkali metal hydroxides, alkali metal hydrides, alkali metal carbonates, alkali metal hydrogen carbonates, alkali metal hydrogen phosphates, aromatic amines, tertiary amines and metal amides, and it is also possible to use any two or more of them in an appropriate ratio. The amount of the base used is typically 1 to 10 molar equivalents, preferably 1 to 5 molar equivalents relative to compound (43).

Examples of the inert solvent include, for example, hydrocarbons, halogenated hydrocarbons, water, alcohols, ethers, esters, ketones, amides, nitriles and sulfoxides, and it is also possible to use any two or more of them in an appropriate ratio.

The reaction temperature is typically −80 to 150° C. The reaction time is typically 0.1 to 200 hours.

(Step B-3-7: (43)→(37f))

Among the compounds represented as formula (37), compound (37f) can be obtained, by reacting for example, compound (43) with hydrogen halide in an inert solvent or in the absence of solvent.

When $Hal^1$ is fluorine, tetrabutylammonium dihydrogen trifluoride can be used as the hydrogen halide.

The amount of the hydrogen halide used is typically 1 molar equivalent to excessive amounts relative to compound (43).

Examples of the inert solvent include, for example, hydrocarbons, halogenated hydrocarbons, water, alcohols, ethers, esters, ketones, amides, nitriles and sulfoxides, and it is also possible to use any two or more of them in an appropriate ratio.

The reaction temperature is typically −80 to 150° C. The reaction time is typically 0.1 to 200 hours.

(Step B-3-8: (43)+(44)→(37g))

Among the compounds represented as formula (37), compound (37g) can be obtained, for example, by reacting compound (43) with compound (44).

The amount of compound (44) used is typically 1 molar equivalent to excessive amounts relative to compound (43).

Compound (44) can be used as a solvent, or an additional inert solvent can be used.

Examples of the inert solvent include, for example, hydrocarbons, halogenated hydrocarbons, water, alcohols, ethers, esters, ketones, amides, nitriles and sulfoxides, and it is also possible to use any two or more of them in an appropriate ratio.

The reaction temperature is typically −80 to 150° C. The reaction time is typically 0.1 to 200 hours.

(Step B-3-9: (43)+(45)→(37h))

Among the compounds represented as formula (37), compound (37h) can be obtained, for example, by reacting compound (43) with compound (45) in an inert solvent.

The amount of compound (45) used is typically 1 to 10 molar equivalents, preferably 1 to 5 molar equivalents relative to compound (43).

In addition, a copper compound can be used as a catalyst, as necessary.

Examples of the copper compound include for example, copper (I) chloride, copper (II) chloride, copper (I) bromide, copper (II) bromide, copper (I) iodide, copper (I) oxide, copper (II) oxide, copper (I) acetate, copper (II) acetate, copper (I) cyanide, copper (II) sulfate, or a dimethyl sulfide complex thereof. The amount of the copper compound used is typically 0.001 to 3 molar equivalents relative to compound (43).

Examples of the inert solvent include, for example, hydrocarbons, ethers, amides and sulfoxides, and it is also possible to use any two or more of them in an appropriate ratio.

The reaction temperature is typically −80 to 150° C. The reaction time is typically 0.1 to 200 hours.

(Step B-3-10: (43)+(46)→(37i))

Among the compounds represented as formula (37), compound (37i) can be obtained, for example, by reacting compound (43) with compound (46) in an inert solvent.

The amount of compound (46) used is typically 1 molar equivalent to excessive amounts relative to compound (43).

Examples of the alkali metal represented as M include potassium, sodium and cesium.

Examples of the inert solvent include, for example, alcohols corresponding to compound (46), or hydrocarbons, halogenated hydrocarbons, ethers, esters, ketones, amides, nitriles and sulfoxides, and it is also possible to use any two or more of them in an appropriate ratio.

The reaction temperature is typically −80 to 150° C. The reaction time is typically 0.1 to 200 hours.

Scheme B-4

[Chem. 41]

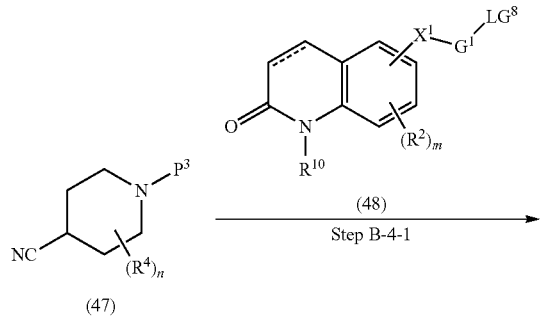

-continued

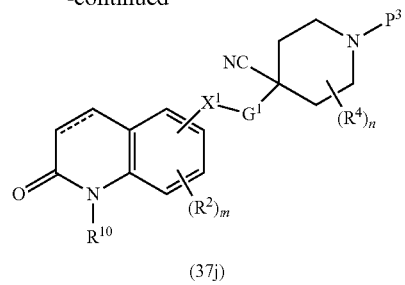

(37j)

wherein $LG^8$ represents a leaving group; and other symbols are as defined above.

(Step B-4-1: (47)+(48)→(37j))

Among the compounds represented as formula (37), compound (37j) can be obtained, for example, by reacting compound (47) with compound (48) in an inert solvent in the presence of a base.

The amount of compound (48) used is typically 0.1 to 10 molar equivalents, preferably 0.2 to 5 molar equivalents relative to compound (47).

Examples of the base include, for example, alkali metal hydroxides, alkali metal hydrides, alkali metal carbonates, alkali metal hydrogen carbonates, alkali metal hydrogen phosphates, aromatic amines, tertiary amines and metal amides, and it is also possible to use any two or more of them in an appropriate ratio. The amount of the base used is typically 1 to 10 molar equivalents, preferably 1 to 5 molar equivalents relative to compound (47).

Examples of the inert solvent include, for example, hydrocarbons, halogenated hydrocarbons, ethers, amides and sulfoxides, and it is also possible to use any two or more of them in an appropriate ratio.

The reaction temperature is typically −80 to 150° C. The reaction time is typically 0.1 to 200 hours.

Scheme B-5

[Chem. 42]

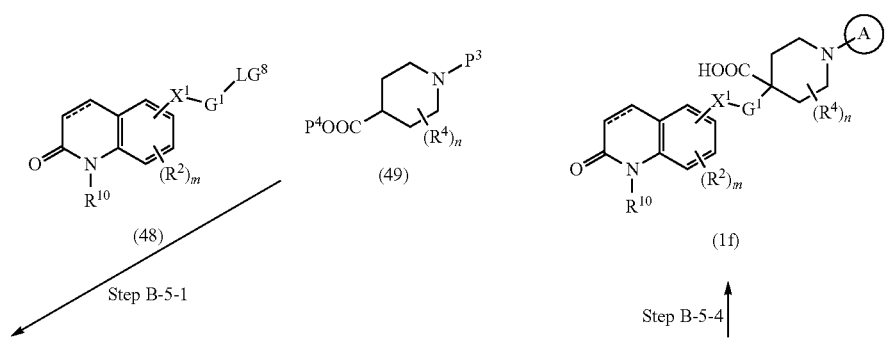

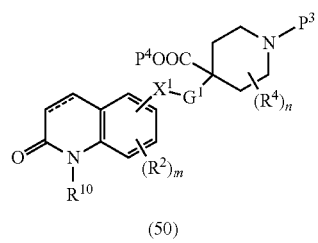 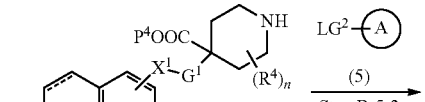 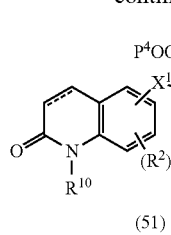

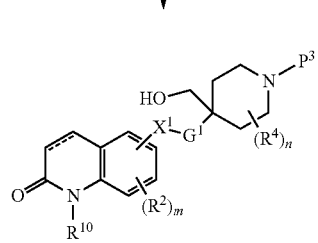 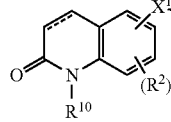

wherein P⁴ represents a carboxy protecting group; and other symbols are as defined above.

(Step B-5-1: (49)+(48)→(50))

Compound (50) can be obtained, for example, by reacting compound (49) with compound (48) in an inert solvent in the presence of a base. Said reaction can be performed under the conditions similar to above step B-4-1.

(Step B-5-2: (50)→(51))

Compound (51) can be obtained by subjecting compound (50) to a deprotection reaction. For example, said reaction can be performed under the conditions similar to above step B-1-2.

(Step B-5-3: (51)+(5)→(52))

Compound (52) can be obtained, for example, by reacting compound (51) with compound (5) in an inert solvent in the presence of a base. Said reaction can be performed under the conditions similar to above step A-2-1.

(Step B-5-4: (52)→(1f))

Among the compounds represented as formula (1), compound (1f) can be obtained by subjecting compound (52) to a deprotection reaction.

Any of known reactions may be used as the deprotection reaction, for example, when P⁴ is lower alkyl, said group can be deprotected by reacting the compound in an inert solvent in the presence of a base.

Examples of the base include, for example, alkali metal hydroxides, alkali metal hydrides, alkali metal carbonates, alkali metal hydrogen phosphates and metal amides, and it is also possible to use any two or more of them in an appropriate ratio. The amount of the base used is typically 1 to 10 molar equivalents, preferably 1 to 5 molar equivalents relative to compound (50).

Examples of the inert solvent include, for example, hydrocarbons, halogenated hydrocarbons, water, alcohols, ethers, esters, ketones, amides, nitriles and sulfoxides, and it is also possible to use any two or more of them in an appropriate ratio.

The reaction temperature is typically −80 to 150° C. The reaction time is typically 0.1 to 200 hours.

(Step B-5-5: (51)→(53))

Compound (53) can be obtained by subjecting P⁴ of compound (51) to the deprotection reaction by using similar reaction to those of the above step B-5-4 to give carboxylic acid, and then subjecting the obtained compound to a reduction reaction in an inert solvent, in the presence of a reducing agent, alternatively, subjecting compound (51) directly to a reduction reaction in an inert solvent in the presence of a reducing agent.

Examples of the reducing agent include sodium borohydride, lithium borohydride, sodium cyanoborohydride, sodium triacetoxyborohydride, sodium triethylborohydride, lithium triethylborohydride, lithium aluminum hydride, sodium dihydridobis(2-methoxyethoxy)-aluminate, borane-tetrahydrofuran complex and diisobutylaluminium hydride. The amount of the reducing agent used is typically 1 to 10 molar equivalents, preferably 1 to 5 molar equivalents relative to compound (51).

Examples of the inert solvent include, for example, hydrocarbons, halogenated hydrocarbons, alcohols, ethers, amides and sulfoxides, and it is also possible to use any two or more of them in an appropriate ratio.

The reaction temperature is typically −80 to 150° C. The reaction time is typically 0.1 to 200 hours.

(Step B-5-6: (53)+(5)→(1g))

Compound (1g) can be obtained, for example, by reacting compound (53) with compound (5) in an inert solvent in the presence of a base. Said reaction can be performed under the conditions similar to above step A-2-1.

(Step B-5-7: (52)→(1g))

Among the compounds represented as formula (1), compound (1g) can be obtained by subjecting P⁴ of compound (52) to the deprotection reaction by using similar reaction to those of the above step B-5-4 to give carboxylic acid, and then subjecting the obtained compound to a reduction reaction in an inert solvent, in the presence of a reducing agent, alternatively, subjecting compound (52) directly to a reduction reaction in an inert solvent in the presence of a reducing agent. Said reaction can be performed under the conditions similar to above step B-5-5.

(Step B-5-8: (50)→(54))

Compound (54) can be obtained by subjecting P⁴ of compound (50)) to the deprotection reaction by using similar reaction to those of the above step B-5-4 to give carboxylic acid, and then subjecting the obtained compound to a reduction reaction in an inert solvent, in the presence of a reducing agent, alternatively, subjecting compound (50) directly to a reduction reaction in an inert solvent, in the presence of a reducing agent. Said reaction can be performed under the conditions similar to above step B-5-5.

(Step B-5-9: (54)→(53))

Compound (53) can be obtained by subjecting compound (54) to a deprotection reaction. For example, said reaction can be performed under the conditions similar to above step B-1-2.

[Preparation Method C: Various Derivatizations]

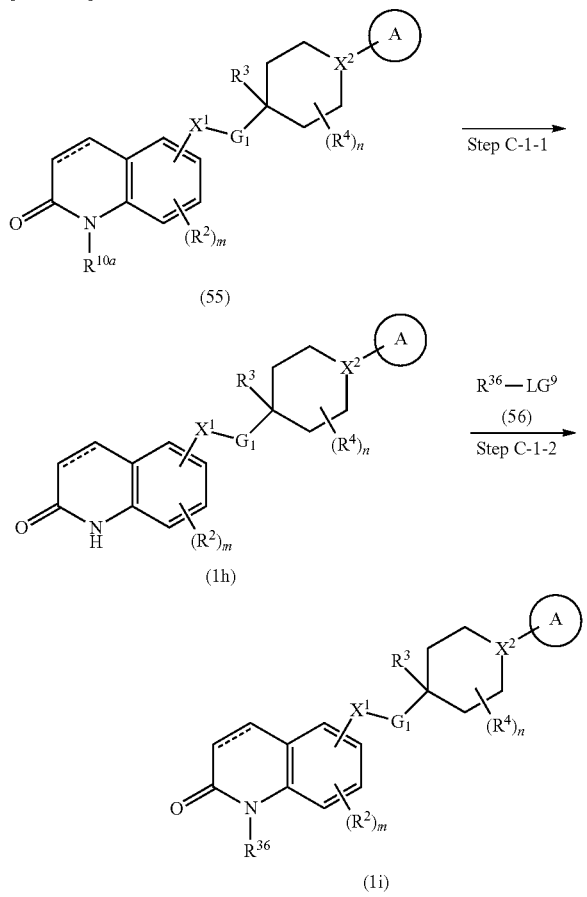

Scheme C-1

[Chem. 43]

wherein $R^{10a}$ represents an amino protecting group; $LG^9$ represents a leaving group; $R^{36}$ represents amino optionally having one or more lower alkyl or lower alkyl; and other symbols are as defined above.

(Step C-1-1: (55)→(1h))

Among the compounds represented as formula (1), compound (1h) can be obtained by subjecting compound (55) to a deprotection reaction.

Any of known reactions may be used as the deprotection reaction, for example, when $R^{10a}$ is 4-methoxybenzyl (PMB), compound (1h) can be obtained by hydrogenation in the presence of a hydrogen source and a metal catalyst, treatment with an oxidizing agent, or treatment under strong acid conditions.

When a subformula of the above formula (aa) is the formula represented as above formula (aa1), namely, compound (55) is protected as the imidic acid (lower alkyl protection), compound (1h) can be obtained by treating it under a strong acid condition.

Examples of the hydrogen source include, for example, hydrogen gas, formic acid, sodium formate, ammonium formate, cyclohexene, phosphinic acid salt and hydrazine. When using hydrogen gas as the hydrogen source, the reaction can be done under the hydrogen pressure of about 1 to 10 atm. The amount of another hydrogen source used is typically 1 molar equivalent to excessive amounts, preferably 1 to 10 molar equivalents relative to compound (55).

Examples of the metal catalyst include, for example, palladium on carbon, palladium black, palladium chloride, palladium hydroxide on carbon, platinum oxide, platinum black, platinum-palladium, platinum-carbon, Raney nickel and Raney cobalt. The amount of the metal catalyst used is typically 0.001 to 1000 molar equivalents, preferably 0.01 to 100 molar equivalents relative to compound (55).

Examples of the oxidizing agent include quinone oxidizing agents such as 2,3-dichloro-5,6-dicyano-p-benzoquinone (DDQ) and; metalic oxidizing agents such as ammonium hexanitratocerate (IV) (CAN). The amount of the oxidizing agent used is typically 1 to 10 molar equivalents, preferably 1 to 5 molar equivalents relative to compound (55).

Examples of the strong acid include inorganic acids such as hydrochloric acid, sulfuric acid, nitric acid and hydrobromic acid and; organic acids such as trifluoroacetic acid and trifluoromethanesulfonic acid. The amount of the strong acid used is typically 1 molar equivalent to excessive amounts relative to compound (55).

In addition, when using the strong acid, it is possible to use a cation scavenger, as necessary. Examples of the cation scavenger include, for example, anisole, thioanisole, phenol, m-cresol, p-cresol and dimethyl sulfide. The amount of the cation scavenger used is typically 1 to 10 molar equivalents, preferably 1 to 5 molar equivalents relative to compound (55).

The strong acid can be used as a solvent, or an inert solvent can be used.

Examples of the inert solvent include, for example, hydrocarbons, halogenated hydrocarbons, water, alcohols, ethers, ketones, amides and sulfoxides, and it is also possible to use any two or more of them in an appropriate ratio.

The reaction temperature is typically −80 to 150° C. The reaction time is typically 0.1 to 200 hours.

(Step C-1-2: (1h)+(56)→(1i))

Among the compounds represented as formula (1), compound (1i) can be obtained, for example, by reacting compound (1h) with compound (56) in an inert solvent in the presence of a base.

The amount of compound (56) used is typically 0.1 to 10 molar equivalents, preferably 0.2 to 5 molar equivalents relative to compound (1h).

Examples of the base include, for example, alkali metal hydroxides, alkali metal hydrides, alkali metal carbonates, alkali metal hydrogen carbonates, alkali metal hydrogen phosphates, aromatic amines, tertiary amines and metal amides, and it is also possible to use any two or more of them in an appropriate ratio. The amount of the base used is typically 1 to 10 molar equivalents, preferably 1 to 5 molar equivalents relative to compound (1h).

Examples of the inert solvent include, for example, hydrocarbons, halogenated hydrocarbons, ethers, esters, ketones, amides, nitriles and sulfoxides, and it is also possible to use any two or more of them in an appropriate ratio.

The reaction temperature is typically −80 to 150° C. The reaction time is typically 0.1 to 200 hours.

Scheme C-2

[Chem. 44]

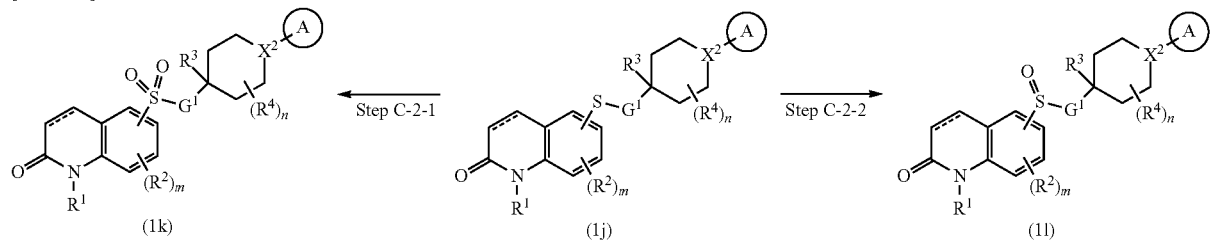

wherein each symbol is as defined above.

(Step C-2-1: (1j)→(1k))

Compound (1k) can be obtained, for example, by reacting compound (1j) in an inert solvent in the presence of an oxidizing agent.

Examples of the oxidizing agent include for example, inorganic peroxides (such as hydrogen peroxide, sodium hypochlorite and sodium periodate), organic peroxides (such as m-chloroperbenzoic acid, perbenzoic acid, peracetic acid and trifluoroperacetic acid) and dioxiranes (such as dimethyldioxirane). The amount of the oxidizing agent used is typically 2 to 10 molar equivalents, preferably 2 to 5 molar equivalents relative to compound (1j).

Examples of the inert solvent include, for example, hydrocarbons, halogenated hydrocarbons, ethers, esters, ketones, amides, nitriles and sulfoxides, and it is also possible to use any two or more of them in an appropriate ratio.

The reaction temperature is typically −80 to 150° C. The reaction time is typically 0.1 to 200 hours.

(Step C-2-2: (1j)→(1l))

Compound (1l) can be obtained, for example, by reacting compound (1j) in an inert solvent in the presence of an oxidizing agent. Said reaction can be performed under the conditions similar to above step C-2-1. The amount of the oxidizing agent used is typically 1 to 10 molar equivalents, preferably 1 to 1.5 molar equivalents relative to compound (1j).

Scheme C-3

[Chem. 45]

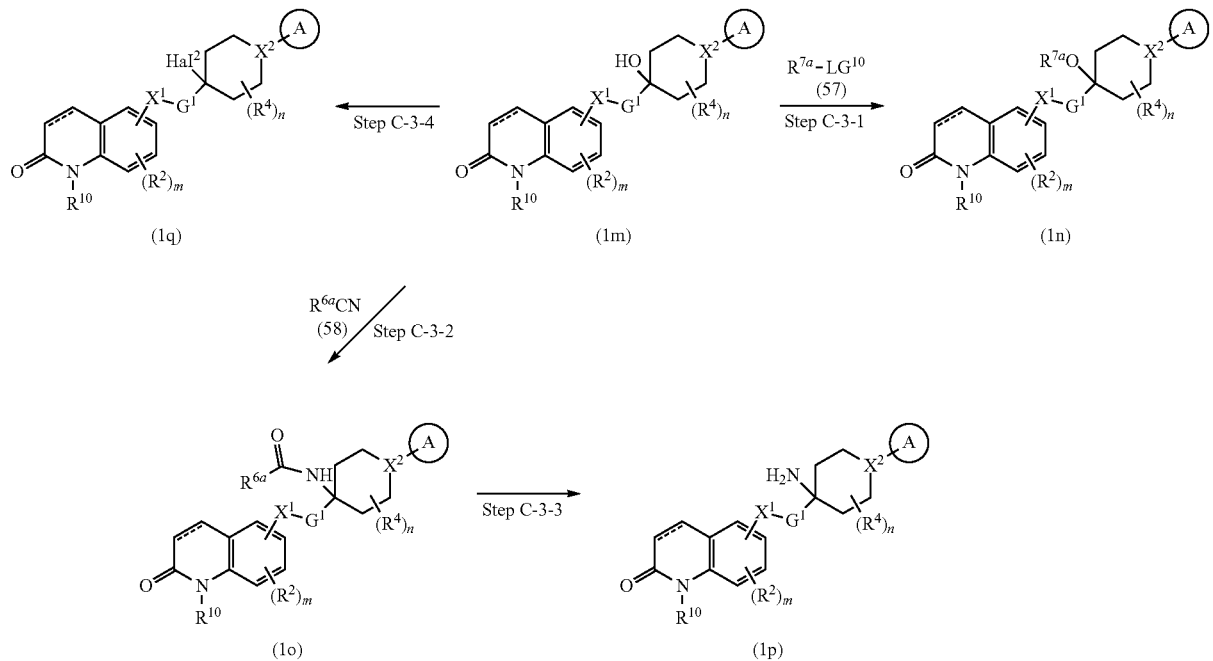

wherein $R^{6a}$ represents lower alkyl optionally having one or more amino which optionally having one or more lower alkyl; $R^{7a}$ represents amino, lower alkanoyl or lower alkyl; $Hal^2$ represents halogen; $LG^{10}$ represents a leaving group; and other symbols are as defined above.

(Step C-3-1: (1m)+(57)→(1n))

Compound (1n) can be obtained, for example, by reacting compound (1m) with compound (57) in an inert solvent in the presence of a base. Said reaction can be performed under the conditions similar to above step A-1-1.

In addition, when $R^{7a}$ is lower alkanoyl, it is possible to use carboxylic acid anhydride such as $(R^{7a})_2O$ in place of compound (57).

(Step C-3-2: (1m)+(58)→(1o))

Compound (1o) can be obtained, for example, reacting compound (1m) with compound (58) in the presence of an acid.

The amount of compound (58) used is typically 1 molar equivalent to excessive amounts relative to compound (1m).

Examples of the acid include, for example, inorganic acids such as hydrochloric acid, sulfuric acid, nitric acid and hydrobromic acid and; organic acids such as trifluoroacetic acid and trifluoromethanesulfonic acid, and it is also possible to use any two or more of them in an appropriate ratio. The amount of the acid used is typically 1 molar equivalent to excessive amounts relative to compound (1m).

The acid or compound (58) can be used as a solvent, or an additional inert solvent can be used.

Examples of the inert solvent include, for example, hydrocarbons, halogenated hydrocarbons, ethers, ketones, amides, sulfoxides and nitriles, and it is also possible to use any two or more of them in an appropriate ratio.

The reaction temperature is typically −80 to 150° C. The reaction time is typically 0.1 to 200 hours.
(Step C-3-3: (1o)→(1p))

Compound (1p) can be obtained, for example, by treating compound (1o) with an acid.

Examples of the acid include, for example, inorganic acids such as hydrochloric acid, sulfuric acid, nitric acid and hydrobromic acid and; organic acids such as trifluoroacetic acid and trifluoromethanesulfonic acid and it is also possible to use any two or more of them in an appropriate ratio. The amount of the acid used is typically 1 molar equivalent to excessive amounts relative to compound (1o).

The acid can be used as a solvent, or an additional inert solvent can be used.

Examples of the inert solvent include, for example, hydrocarbons, halogenated hydrocarbons, water, alcohols, ethers, ketones, amides and sulfoxides, and it is also possible to use any two or more of them in an appropriate ratio.

The reaction temperature is typically −80 to 150° C. The reaction time is typically 0.1 to 200 hours.
(Step C-3-4: (1m)→(1q))

Compound (1q) can be obtained, for example, by reacting compound (1m) with a halogenating agent in an inert solvent.

Examples of the halogenating agent include, for example, thionyl chloride, oxalyl chloride, phosgene, phosphorus oxychloride and phosphorus pentachloride, phosphorus trichloride for chlorination; thionyl bromide and phosphorus tribromide for bromination; and bis(2-methoxyethyl)aminosulfur trifluoride and diethylaminosulfur trifluoride for fluorination. The amount of the halogenating agent used is typically 1 to 10 molar equivalents relative to compound (1m).

Examples of the inert solvent include, for example, hydrocarbons, halogenated hydrocarbons, ethers, ketones, amides, nitriles and sulfoxides, and it is also possible to use any two or more of them in an appropriate ratio.

The reaction temperature is typically −80 to 150° C. The reaction time is typically 0.1 to 200 hours.

Scheme C-4

[Chem. 46]

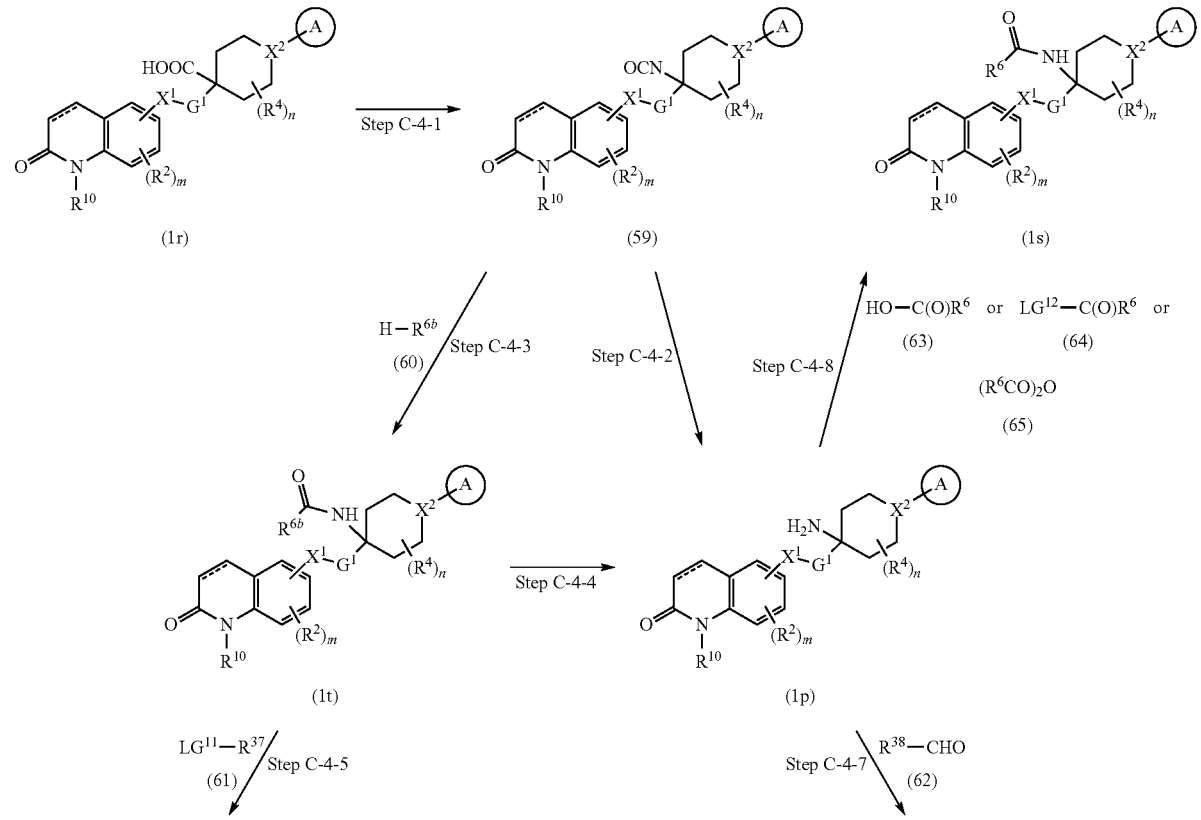

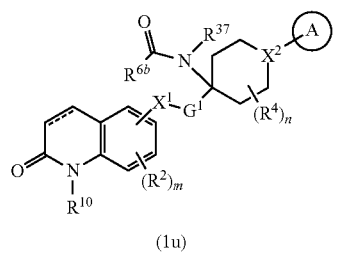 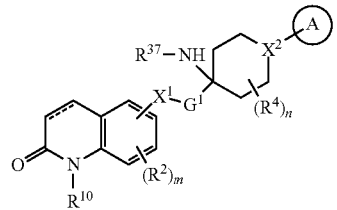 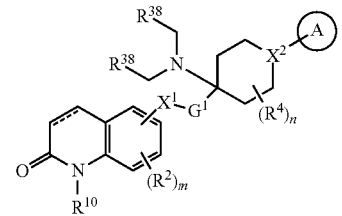

(1u) (1v) (1w)

wherein $R^{6b}$ represents lower alkoxy; $R^{37}$ represents lower alkyl; $R^{38}$ represents hydrogen or alkyl having 1 to 5 carbon atoms; $LG^{11}$ or $LG^{12}$ each independently represents a leaving group; and other symbols are as defined above.

(Step C-4-1: (1r)→(59))

Compound (59) can be obtained, for example, by reacting compound (1r) with a phosphoryl azide compound in an inert solvent in the presence of a base.

Examples of the phosphoryl azide compound include, for example, diphenylphosphoryl azide, bis(p-nitrophenyl)phosphoryl azide and diethylphosphoryl azide. The amount of the phosphoryl azide compound used is typically 0.1 to 10 molar equivalents, preferably 0.2 to 5 molar equivalents relative to compound (1r).

Examples of the base include, for example, alkali metal hydroxides, alkali metal hydrides, alkali metal carbonates, alkali metal hydrogen carbonates, alkali metal hydrogen phosphates, aromatic amines, tertiary amines and metal amides, preferably, tertiary amines, and it is also possible to use any two or more of them in an appropriate ratio. The amount of the base used is typically 1 to 10 molar equivalents, preferably 1 to 5 molar equivalents relative to compound (1r).

Examples of the inert solvent include, for example, hydrocarbons, halogenated hydrocarbons, ethers, esters, ketones, amides, nitriles and sulfoxides, and it is also possible to use any two or more of them in an appropriate ratio.

The reaction temperature is typically 40 to 150° C. The reaction time is typically 0.1 to 200 hours.

(Step C-4-2: (59)→(1p))

Among the compounds represented as formula (1), compound (1p) can be obtained, for example, by treating compound (59) with an acid.

Examples of the acid include, for example, inorganic acids such as hydrochloric acid, sulfuric acid, nitric acid, hydrobromic acid and phosphoric acid; organic acids such as acetic acid, trifluoroacetic acid, oxalic acid, phthalic acid, fumaric acid, tartaric acid, maleic acid, citric acid, succinic acid, methanesulfonic acid, p-toluenesulfonic acid and 10-camphorsulfonic acid, and it is also possible to use any two or more of them in an appropriate ratio. The amount of the acid used is typically 1 molar equivalent to excessive amounts relative to compound (59).

The acid can be used as a solvent, or an additional inert solvent can be used.

Examples of the inert solvent include, for example, hydrocarbons, halogenated hydrocarbons, water, alcohols, ethers, ketones, amides, nitriles and sulfoxides, and it is also possible to use any two or more of them in an appropriate ratio.

The reaction temperature is typically −80 to 150° C. The reaction time is typically 0.1 to 200 hours.

(Step C-4-3: (59)+(60)→(1t))

Among the compounds represented as formula (1), compound (1t) can be obtained, for example, by reacting compound (59) with compound (60).

The amount of compound (60) used is typically 1 molar equivalent to excessive amounts relative to compound (59).

Compound (60) can be used as a solvent, or an inert solvent can be used in addition to compound (60).

Examples of the inert solvent include, for example, hydrocarbons, halogenated hydrocarbons, ethers, ketones, amides, nitriles and sulfoxides, and it is also possible to use any two or more of them in an appropriate ratio.

The reaction temperature is typically −80 to 150° C. The reaction time is typically 0.1 to 200 hours.

(Step C-4-4: (1t)→(1p))

Among the compounds represented as formula (1), compound (1p) can be obtained, for example, by treating compound (1t) with an acid.

Examples of the acid include, for example, inorganic acids such as hydrochloric acid, sulfuric acid, nitric acid and hydrobromic acid; and organic acids such as acetic acid, trifluoroacetic acid and trifluoromethanesulfonic acid, and it is also possible to use any two or more of them in an appropriate ratio. The amount of the acid used is typically 1 molar equivalent to excessive amounts relative to compound (1t).

The acid can be used as a solvent, or an additional inert solvent can be used.

Examples of the inert solvent include, for example, hydrocarbons, halogenated hydrocarbons, ethers, water, alcohols, ketones, amides, nitriles and sulfoxides, and it is also possible to use any two or more of them in an appropriate ratio.

The reaction temperature is typically −80 to 150° C. The reaction time is typically 0.1 to 200 hours.

(Step C-4-5: (1t)+(61)→(1u))

Among the compounds represented as formula (1), compound (1u) can be obtained, for example, by reacting compound (1t) with compound (61) in an inert solvent in the presence of a base.

The amount of compound (61) used is typically 1 to 10 molar equivalents, preferably 1 to 5 molar equivalents relative to compound (1t).

Examples of the base include, for example, alkali metal hydrides and metal amides, and it is also possible to use any two or more of them in an appropriate ratio. The amount of the base used is typically 1 to 10 molar equivalents, preferably 1 to 5 molar equivalents relative to compound (1t).

Examples of the inert solvent include, for example, hydrocarbons, halogenated hydrocarbons, ethers, esters, ketones, amides, nitriles and sulfoxides, and it is also possible to use any two or more of them in an appropriate ratio.

The reaction temperature is typically −40 to 150° C. The reaction time is typically 0.1 to 200 hours.

(Step C-4-6: (1u)→(1v))

Among the compounds represented as formula (1), compound (1v) can be obtained, for example, by treating compound (1u) with an acid. Said reaction can be performed under the conditions similar to above step C-4-4.

(Step C-4-7: (1p)+(62)→(1w))

Among the compounds represented as formula (1), compound (1w) can be obtained by reacting compound (1p) with compound (62) in an inert solvent, in the presence of a reducing agent (reductive amination reaction).

The amount of compound (62) used is typically 2 molar equivalents to excessive amounts relative to compound (1p).

Examples of the reducing agent include sodium borohydride, lithium borohydride, sodium cyanoborohydride, sodium triacetoxyborohydride, sodium triethylborohydride, lithium triethylborohydride, lithium aluminum hydride, sodium dihydridobis(2-methoxyethoxy)-aluminate, borane-tetrahydrofuran complex, diisobutylaluminium hydride, formic acid, sodium formate and ammonium formate. The amount of the reducing agent used is typically 1 to 10 molar equivalents, preferably 1 to 5 molar equivalents relative to compound (1p).

Examples of the inert solvent include, for example, hydrocarbons, halogenated hydrocarbons, alcohols, ethers, ketones, amides, nitriles and sulfoxides, and it is also possible to use any two or more of them in an appropriate ratio.

The reaction temperature is typically −80 to 150° C. The reaction time is typically 0.1 to 200 hours.

(Step C-4-8: (1p)+(63) or (64) or (65)→(1s))

Among the compounds represented as formula (1), compound (1s) can be obtained by the condensation reaction of compound (1p) with compound (63), (64) or (65) in an inert solvent.

The respective amount of compound (63), (64) or (65) used is typically 1 to 10 molar equivalents, preferably 1 to 5 molar equivalents relative to compound (1p).

In addition, it is possible to add a base, as necessary. Example of the base include, for example, alkali metal hydroxides, alkali metal hydrides, alkali metal carbonates, alkali metal hydrogen carbonates, alkali metal hydrogen phosphates, aromatic amines, tertiary amines and metal amides, and it is also possible to use any two or more of them in an appropriate ratio. The amount of the base used is typically 1 to 10 molar equivalents, preferably 1 to 5 molar equivalents relative to compound (1p).

In addition, a basic active agent can be used, as necessary. Examples of the basic active agent include N,N-dimethyl-4-aminopyridine (DMAP) and pyridine. The amount of the basic active agent used is typically 0.01 molar equivalents to excessive amounts relative to compound (1p).

In addition, especially when condensation reaction is performed with compound (63), it is preferred to use a condensation agent in the condensation. Examples of the condensation agent include, for example, carbodiimides such as 1,3-dicyclohexylcarbodiimide, 1-cyclohexyl-3-morpholinoethylcarbodiimide, 1-cyclohexyl-3-(4-diethylaminocyclohexyl)carbodiimide, 1,3-diethylcarbodiimide, 1,3-diisopropylcarbodiimide and 1-ethyl-3-(3-dimethylaminopropyl)carbodiimide or salts thereof. The amount of the condensation agent used is typically 1 to 10 molar equivalents, preferably 1 to 5 molar equivalents relative to compound (1p).

In addition, a condensation accelerator can be added in addition to the condensation agent. Examples of the condensation accelerator include, for example, 1-hydroxybenzotriazole (HOBt), N-hydroxysuccinimide (HOSu), 1-hydroxy-7-azabenzotriazole (HOAt) and hydroxy-3,4-dihydro-4-oxo-1,2,3-benzotriazine (HOOBt). The amount of the condensation accelerator used is typically 1 to 10 molar equivalents, preferably 1 to 5 molar equivalents relative to compound (1p).

In addition, tertiary amines such as pyridine can be used as a solvent, or an inert solvent can be used.

Examples of the inert solvent include, for example, hydrocarbons, halogenated hydrocarbons, ethers, ketones, amides, nitriles and sulfoxides, and it is also possible to use any two or more of them in an appropriate ratio.

The reaction temperature is typically −80 to 150° C. The reaction time is typically 0.1 to 200 hours.

Scheme C-5

[Chem. 47]

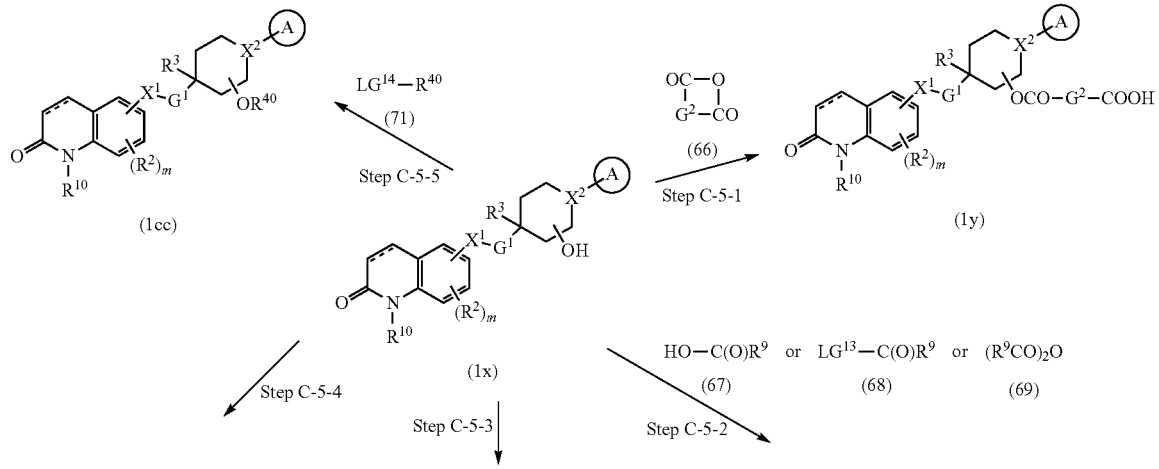

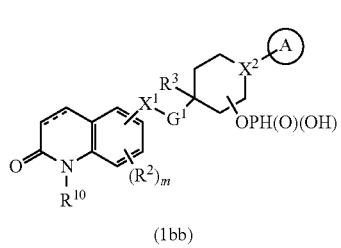 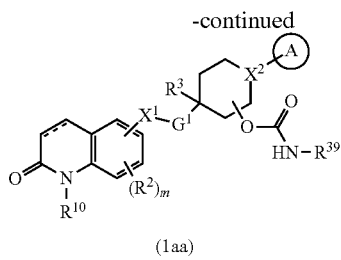 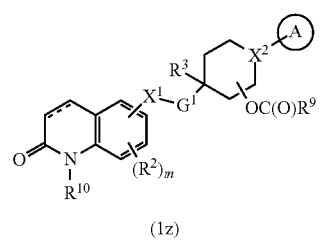

(1bb)  (1aa)  (1z)

wherein $R^{39}$ represents alkyl; $R^{40}$ represents benzyl optionally having one or more lower alkoxy, or lower alkyl; $LG^{13}$ or $LG^{14}$ each independently represents a leaving group; and other symbols are as defined above.

(Step C-5-1: (1x)+(66)→(1y))

Among the compounds represented as formula (1), compound (1y) can be obtained by reacting compound (1x) with compound (66) in an inert solvent.

The amount of compound (66) used is typically 1 to 10 molar equivalents, preferably 1 to 5 molar equivalents relative to compound (1x).

In addition, a basic active agent can be used, as necessary. Examples of the basic active agent include, N,N-dimethyl-4-aminopyridine (DMAP) and pyridine. The amount of the basic active agent used is typically 1 molar equivalent to excessive amounts relative to compound (1x).

In addition, pyridine etc. can be used as a solvent, or an inert solvent can be used.

Examples of the inert solvent include, for example, hydrocarbons, halogenated hydrocarbons, ethers, ketones, amides, nitriles and sulfoxides, and it is also possible to use any two or more of them in an appropriate ratio.

The reaction temperature is typically −80 to 150° C. The reaction time is typically 0.1 to 200 hours.

(Step C-5-2: (1x)+(67) or (68) or (69)→(1z))

Among the compounds represented as formula (1), compound (1z) can be obtained by the condensation reaction of compound (1x) with compound (67), (68) or (69) in an inert solvent.

The respective amount of compound (67), (68) or (69) used is typically 1 to 10 molar equivalents, preferably 1 to 5 molar equivalents relative to compound (1x).

In addition, it is possible to add a base, as necessary. Example of the base include, for example, alkali metal hydroxides, alkali metal hydrides, alkali metal carbonates, alkali metal hydrogen carbonates, alkali metal hydrogen phosphates, aromatic amines, tertiary amines and metal amides, and it is also possible to use any two or more of them in an appropriate ratio. The amount of the base used is typically 1 to 10 molar equivalents, preferably 1 to 5 molar equivalents relative to compound (1x).

In addition, a basic active agent can be used, as necessary. Examples of the basic active agent include, N,N-dimethyl-4-aminopyridine (DMAP) and pyridine. The amount of the basic active agent used is typically 0.01 molar equivalents to excessive amounts relative to compound (1x).

In addition, especially when condensation reaction is performed with compound (67), it is preferred to use a condensation agent in the condensation. Examples of the condensation agent include, for example, carbodiimides such as 1,3-dicyclohexylcarbodiimide, 1-cyclohexyl-3-morpholinoethylcarbodiimide, 1-cyclohexyl-3-(4-diethylaminocyclohexyl)-carbodiimide, 1,3-diethylcarbodiimide, 1,3-diisopropylcarbodiimide and 1-ethyl-3-(3-dimethylaminopropyl)carbodiimide or salts thereof. The amount of the condensation agent used is typically 1 to 10 molar equivalents, preferably 1 to 5 molar equivalents relative to compound (1x).

In addition, a condensation accelerator can be added in addition to the condensation agent. Examples of the condensation accelerator include, for example, 1-hydroxybenzotriazole (HOBt), N-hydroxysuccinimide (HOSu), 1-hydroxy-7-azabenzotriazole (HOAt) and hydroxy-3,4-dihydro-4-oxo-1,2,3-benzotriazine (HOOBt). The amount of the condensation accelerator used is typically 1 to 10 molar equivalents, preferably 1 to 5 molar equivalents relative to compound (1x).

In addition, tertiary amines such as pyridine can be used as a solvent, or an inert solvent can be used.

Examples of the inert solvent include, for example, hydrocarbons, halogenated hydrocarbons, ethers, ketones, amides, nitriles and sulfoxides, and it is also possible to use any two or more of them in an appropriate ratio.

The reaction temperature is typically −80 to 150° C. The reaction time is typically 0.1 to 200 hours.

(Step C-5-3: (1x)+(70)→(1aa))

Among the compounds represented as formula (1), compound (1aa) can be obtained, for example, by reacting compound (1x) with compound (70) in an inert solvent.

The amount of compound (70) used is typically 1 molar equivalent to excessive amounts relative to compound (1x).

In addition, a basic active agent can be used, as necessary. Examples of the basic active agent include, N,N-dimethyl-4-aminopyridine (DMAP) and pyridine. The amount of the basic active agent used is typically 1 molar equivalent to excessive amounts relative to compound (1x).

Examples of the inert solvent include, for example, hydrocarbons, halogenated hydrocarbons, ethers, ketones, amides, nitriles and sulfoxides, and it is also possible to use any two or more of them in an appropriate ratio.

The reaction temperature is typically −80 to 150° C. The reaction time is typically 0.1 to 200 hours.

(Step C-5-4: (1x)→(1bb))

Among the compounds represented as formula (1), compound (1bb) can be obtained, for example, reacting compound (1x) with diphenyl phosphite in an inert solvent in the presence of a base.

The amount of diphenyl phosphite used is typically 1 molar equivalent to excessive amounts relative to compound (1x).

Examples of the base include, for example, alkali metal hydroxides, alkali metal hydrides, alkali metal carbonates, alkali metal hydrogen carbonates, alkali metal hydrogen phosphates, aromatic amines, tertiary amines and metal amides, and it is also possible to use any two or more of them in an appropriate ratio. The amount of the base used is typically 1 to 10 molar equivalents, preferably 1 to 5 molar equivalents relative to compound (1x).

Examples of the inert solvent include, for example, hydrocarbons, halogenated hydrocarbons, ethers, ketones, amides, nitriles and sulfoxides, and it is also possible to use any two or more of them in an appropriate ratio.

The reaction temperature is typically −80 to 150° C. The reaction time is typically 0.1 to 200 hours.

(Step C-5-5: (1x)+(71)→(1cc))

Among the compounds represented as formula (1), compound (1cc) can be obtained, for example, by reacting compound (1x) with compound (71) in an inert solvent in the presence of a base. Said reaction can be performed under the conditions similar to above step A-1-1.

(Step C-6-1: (1dd)→(72))

Compound (72) can be obtained, for example, by transforming hydroxy in compound (1dd) to a leaving group by using any known method followed by olefination reaction. Said reaction can be performed under the conditions similar to above step A-10-1.

(Step C-6-2: (72)→(1ee))

Among the compounds represented as formula (1), compound (1ee) can be obtained, for example, reacting compound (72) in an inert solvent in the presence of osmium tetraoxide and a reoxidizing agent. Said reaction can be performed under the conditions similar to above step B-3-3.

Similar to the above step B-3-3, when, for example, a hydroquinine ether is used as a catalyst, typically, it is possible to obtain, mainly, a compound represented as formula (1eea):

[Chem. 49]

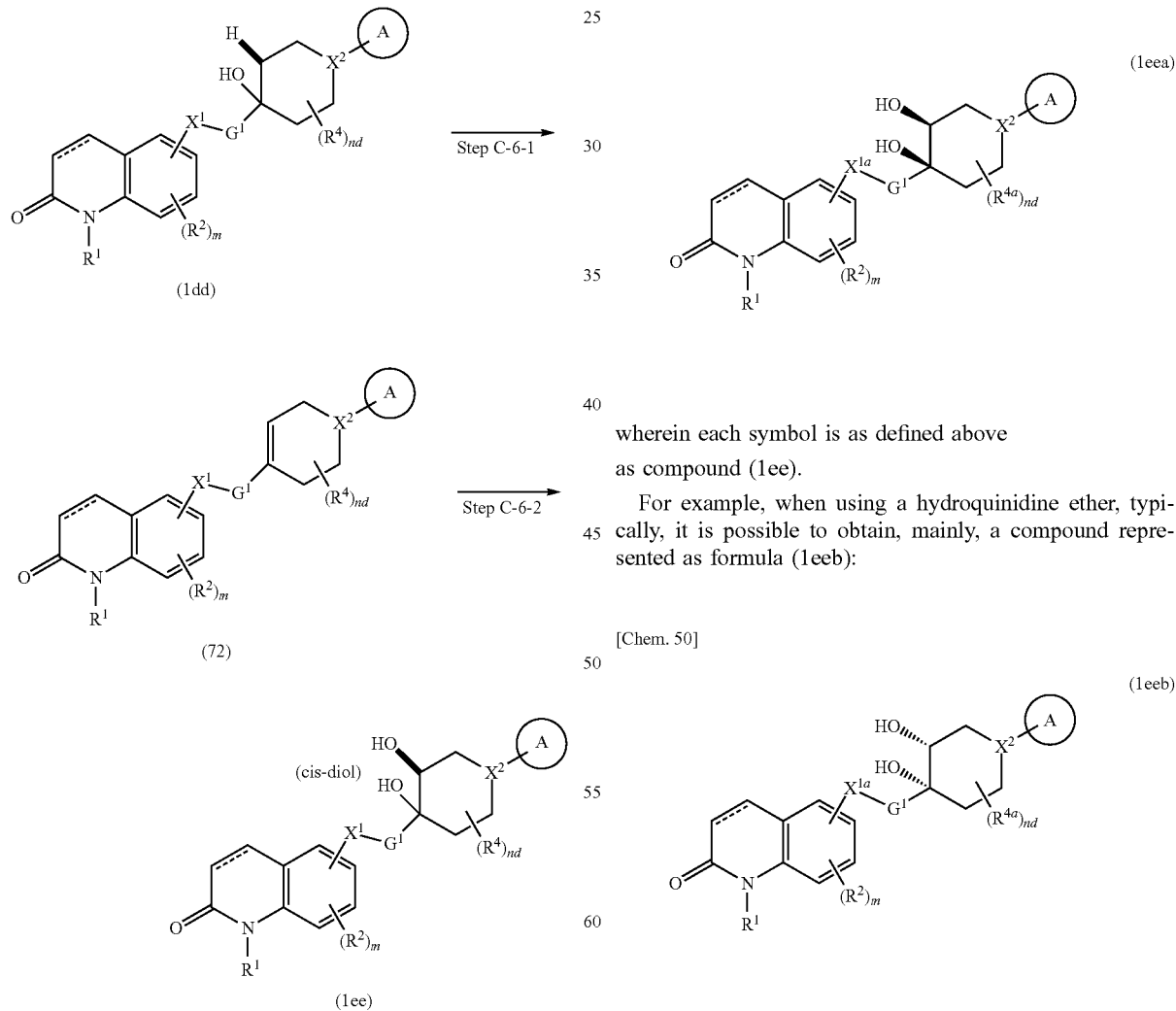

Scheme C-6

[Chem. 48]

wherein each symbol is as defined above as compound (1ee).

For example, when using a hydroquinidine ether, typically, it is possible to obtain, mainly, a compound represented as formula (1eeb):

[Chem. 50]

wherein nd is an integer of 0 to 7; and other symbols are as defined above.

wherein each symbol is as defined above as compound (1ee).

Scheme C-7

[Chem. 51]

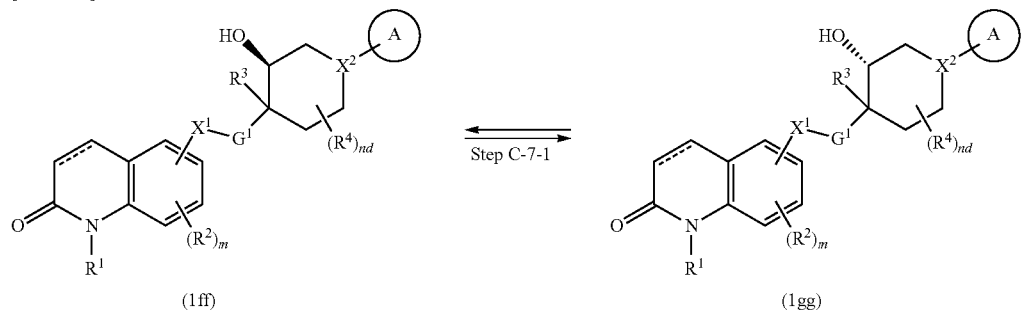

wherein each symbol is as defined above
(Step C-7-1: (1ff)←→(1gg))

Among the compounds represented as formula (1), compound (1gg) can be obtained from compound (1ff) by Mitsunobu reaction followed by a hydrolysis reaction.

Mitsunobu reaction can be performed, for example, by reacting compound (1ff) with carboxylic acid in an inert solvent, in the presence of azodicarboxylic acid ester and phosphine.

Examples of the azodicarboxylic acid ester include, for example, dimethyl azodicarboxylate, diethyl azodicarboxylate, diisopropyl azodicarboxylate, dibenzyl azodicarboxylate, di-tert-butyl azodicarboxylate and 1,1'-(azodicarbonyl)dipiperidine. The amount of the azodicarboxylic acid ester used is typically 0.1 to 10 molar equivalents, preferably 0.2 to 5 molar equivalents relative to compound (1ff).

Examples of the phosphine include, for example, triphenylphosphine, tricyclohexylphosphine and tributylphosphine. The amount of the phosphine used is typically 0.1 to 10 molar equivalents, preferably 0.2 to 5 molar equivalents relative to compound (1ff).

Examples of the carboxylic acid include benzoic acid, p-nitrobenzoic acid and p-methoxybenzoic acid. The amount of the carboxylic acid used is typically 0.1 to 10 molar equivalents, preferably 0.2 to 5 molar equivalents relative to compound (1ff).

In addition, hydrolysis reaction after Mitsunobu reaction can be done, for example, by reacting the compound in an inert solvent in the presence of a base.

Examples of the base include, for example, alkali metal hydroxides, alkali metal hydrides, alkali metal carbonates, alkali metal hydrogen phosphates and metal amides, and it is also possible to use any two or more of them in an appropriate ratio. The amount of the base used is typically 1 molar equivalent to excessive amounts relative to compound (1ff).

Examples of the inert solvent include, for example, hydrocarbons, halogenated hydrocarbons, ethers, esters, ketones, amides, nitriles and sulfoxides, and it is also possible to use any two or more of them in an appropriate ratio.

The reaction temperature is typically −80 to 150° C. The reaction time is typically 0.1 to 200 hours.

In addition, compound (1ff) can be obtained from compound (1gg) by using a similar method.

[Preparation Method D: Synthesis of Starting Materials]

Scheme D-1

[Chem. 52]

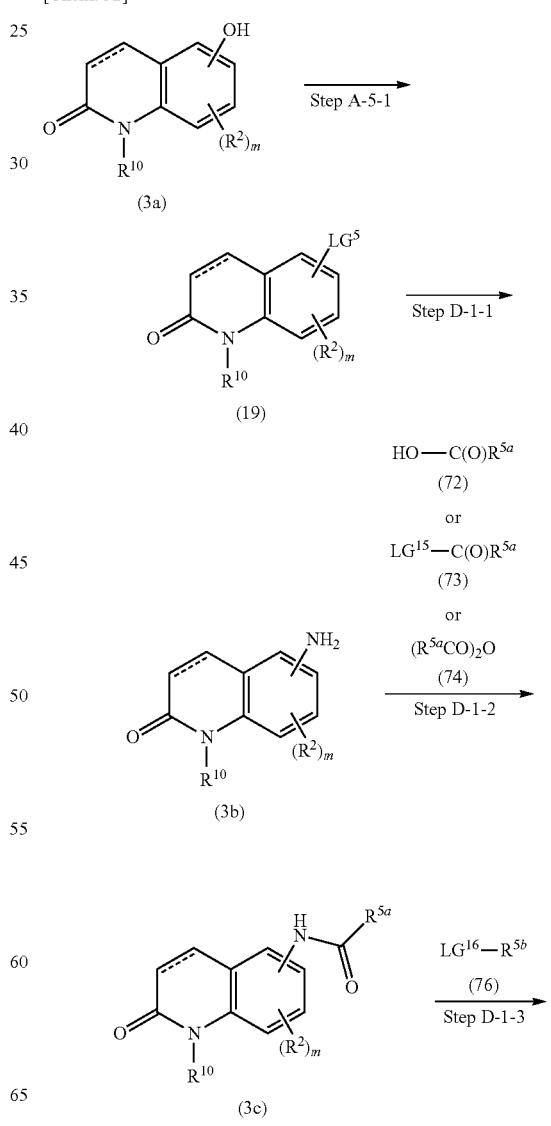

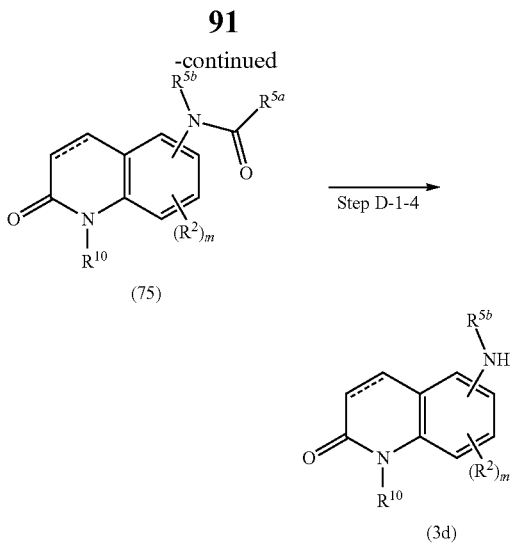

wherein $R^{5a}$ represents hydrogen or lower alkyl; $R^{5b}$ represents lower alkyl; $LG^{15}$ and $LG^{16}$ each independently represents a leaving group; and other symbols are as defined above.

(Step D-1-1: (19)→(3b))

Among the compounds represented as formula (3), compound (3b) can be obtained from compound (19) by using any known method for introducing amino, for example, by reacting compound (19) with benzophenone imine or hexamethyldisilazane in an inert solvent, in the presence of base and transition metal catalyst, followed by the hydrolysis of the obtained compound.

Examples of the benzophenone imine include, for example, benzophenone imine and 4,4'-dimethoxybenzophenone imine.

The amount of the benzophenone imine or hexamethyldisilazane used is typically 1 to 10 molar equivalents, preferably 1 to 5 molar equivalents relative to compound (19).

Examples of the base include, for example, alkali metal hydroxides, alkali metal hydrides, alkali metal carbonates, alkali metal hydrogen carbonates, alkali metal hydrogen phosphates, aromatic amines, tertiary amines, metal amides and metal alkoxides, and it is also possible to use any two or more of them in an appropriate ratio. The amount of the base used is typically 1 to 10 molar equivalents, preferably 1 to 5 molar equivalents relative to compound (19).

Examples of the transition metal catalyst include, for example, palladium catalysts such as palladium (II) acetate, palladium (II) chloride, tetrakis(triphenylphosphine)palladium (0), tris(dibenzylideneacetone)dipalladium (0), 1,1-bis(diphenylphosphino)ferrocene dichloropalladium (II), dichlorobis(triphenylphosphine)palladium (II), bis(tri-(tert-butylphosphine))palladium (0), phenylallylchloro[1,3-bis(diisopropylphenyl)-2-imidazol-2-ylidene]palladium (II) and phenylallylchloro-[1,3-bis(diisopropylphenyl)-2-imidazolidinylidene]palladium (II); copper catalysts such as copper (I) iodide and copper (I) oxide; rhodium catalysts such as tris(triphenylphosphine)rhodium (III) chloride; nickel catalysts such as tetrakis(triphenylphosphine)nickel (0), and it is also possible to use any two or more of them in an appropriate ratio. The amount of the transition metal catalyst used is typically 0.001 to 3 molar equivalents relative to compound (19).

In addition, a ligand can be added as necessary. Examples of the ligand include, for example, triphenylphosphine, tri(tert-butyl)phosphine, 2,2'-bis(diphenylphosphino)-1,1'-binaphthyl, 2-(dicyclohexylphosphino)-2',4',6'-triisopropyl-1,1'-biphenyl, 4,5'-bis(diphenylphosphino)-9,9'-dimethylxanthene. The amount of the ligand used is typically 0.001 to 3 molar equivalents relative to compound (19).

Examples of the inert solvent include, for example, hydrocarbons, halogenated hydrocarbons, ethers, esters, ketones, alcohols, water, amides, nitriles and sulfoxides, and it is also possible to use any two or more of them in an appropriate ratio.

The reaction temperature is typically −80 to 150° C. The reaction time is typically 0.1 to 200 hours.

(Step D-1-2: (3b)+(72) or (73) or (74)→(3c))

Among the compounds represented as formula (3), compound (3c) can be obtained by the condensation reaction of compound (3b) with compound (72), (73) or (74) in an inert solvent. Said reaction can be performed under the conditions similar to above step C-4-8.

(Step D-1-3: (3c)+(76)→(75))

Compound (75) can be obtained, for example, by reacting compound (3c) with compound (76) in an inert solvent in the presence of a base. Said reaction can be performed under the conditions similar to above step C-4-5.

(Step D-1-4: (75)→(3d))

Among the compounds represented as formula (3), compound (3d) can be obtained, for example, by treating compound (75) with an acid.

Examples of the acid include, for example, inorganic acids such as hydrochloric acid, sulfuric acid, nitric acid and hydrobromic acid; and organic acids such as acetic acid, trifluoroacetic acid and trifluoromethanesulfonic acid, and it is also possible to use any two or more of them in an appropriate ratio. The amount of the acid used is typically 1 molar equivalent to excessive amounts relative to compound (75).

The acid can be used as a solvent, or an additional inert solvent can be used.

Examples of the inert solvent include, for example, hydrocarbons, halogenated hydrocarbons, ethers, water, alcohols, ketones, amides, nitriles and sulfoxides, and it is also possible to use any two or more of them in an appropriate ratio.

The reaction temperature is typically −80 to 150° C. The reaction time is typically 0.1 to 200 hours.

Scheme D-2

[Chem. 53]

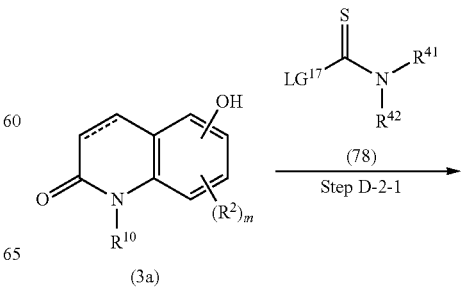

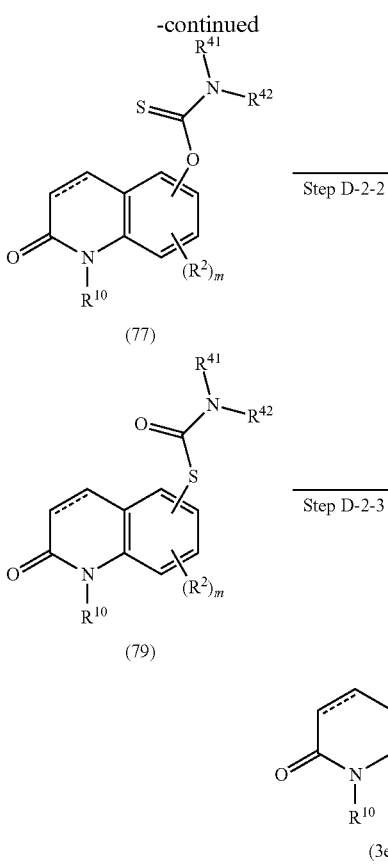

(77)

(79)

(3e)

wherein $R^{41}$ and $R^{42}$ each independently represents lower alkyl; $LG^{17}$ represents a leaving group; and other symbols are as defined above.

(Step D-2-1: (3a)+(78)→(77))

Compound (77) can be obtained, for example, by reacting compound (3a) with compound (78) in an inert solvent in the presence of a base.

The amount of compound (78) used is typically 1 to 10 molar equivalents, preferably 1 to 5 molar equivalents relative to compound (3a).

Examples of the base include, for example, alkali metal hydroxides, alkali metal hydrides, alkali metal carbonates, alkali metal hydrogen carbonates, alkali metal hydrogen phosphates, aromatic amines, tertiary amines, metal amides and metal alkoxides, and it is also possible to use any two or more of them in an appropriate ratio. The amount of the base used is typically 1 to 10 molar equivalents, preferably 1 to 5 molar equivalents relative to compound (3a).

Examples of the inert solvent include, for example, hydrocarbons, halogenated hydrocarbons, ethers, esters, ketones, alcohols, water, amides, nitriles and sulfoxides, and it is also possible to use any two or more of them in an appropriate ratio.

The reaction temperature is typically −80 to 150° C. The reaction time is typically 0.1 to 200 hours.

(Step D-2-2: (77)→(79))

Compound (79) can be obtained by heat treatment of compound (77) in an inert solvent.

Examples of the inert solvent include, for example, hydrocarbons, halogenated hydrocarbons, ethers, esters, ketones, alcohols, water, amides, nitriles and sulfoxides, and it is also possible to use any two or more of them in an appropriate ratio.

The reaction temperature is typically 100 to 300° C. The reaction time is typically 0.1 to 200 hours.

(Step D-2-3: (79)→(3e))

Among the compounds represented as formula (3), compound (3e) can be obtained, for example, by treating compound (79) with a base followed by hydrolysis.

Examples of the base include, for example, alkali metal hydroxides, alkali metal hydrides, alkali metal carbonates, alkali metal hydrogen carbonates, alkali metal hydrogen phosphates, aromatic amines, tertiary amines and metal amides, and it is also possible to use any two or more of them in an appropriate ratio. The amount of the base used is typically 1 to 10 molar equivalents, preferably 1 to 5 molar equivalents relative to compound (79).

Examples of the inert solvent include, for example, hydrocarbons, halogenated hydrocarbons, water, alcohols, ethers, esters, ketones, amides, nitriles and sulfoxides, and it is also possible to use any two or more of them in an appropriate ratio.

The reaction temperature is typically −80 to 150° C. The reaction time is typically 0.1 to 200 hours.

Scheme D-3

[Chem. 54]

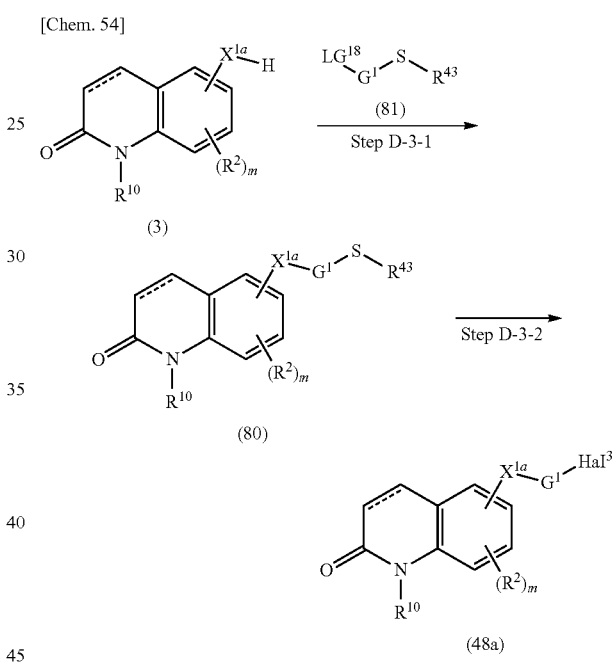

wherein $R^{43}$ represents lower alkyl; $LG^{18}$ represents a leaving group; $Hal^3$ represents halogen; and other symbols are as defined above.

(Step D-3-1: (3)+(81)→(80))

Compound (80) can be obtained, for example, by reacting compound (3) with compound (81) in an inert solvent in the presence of a base. Said reaction can be performed similar to the above step A-1-1.

(Step D-3-2: (80)→(48a))

Among the compounds represented as formula (48), compound (48a) can be obtained, for example, by reacting compound (80) with a halogenating agent in an inert solvent.

Examples of the halogenating agent include, For example, sulfuryl chloride, sulfuryl fluoride. The amount of the halogenating agent used is typically 1 to 10 molar equivalents relative to compound (80).

Examples of the inert solvent include, for example, hydrocarbons, halogenated hydrocarbons, ethers, ketones, amides, nitriles and sulfoxides, and it is also possible to use any two or more of them in an appropriate ratio.

The reaction temperature is typically −80 to 150° C. The reaction time is typically 0.1 to 200 hours.

Scheme D-4

[Chem. 55]

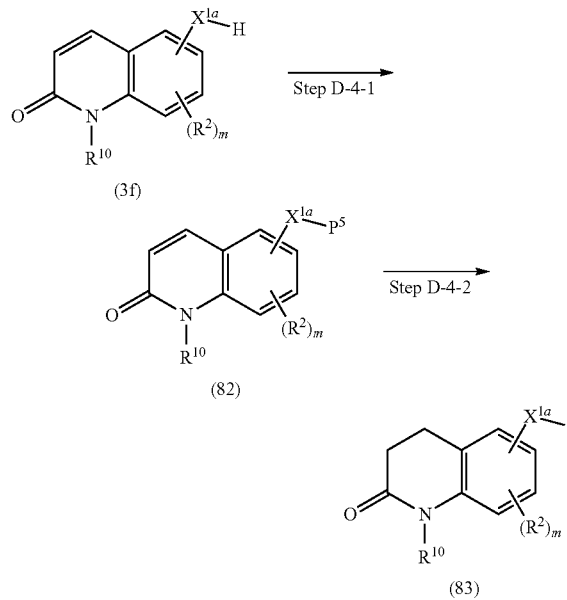

wherein $P^5$ represents a protecting group; and other symbols are as defined above.

(Step D-4-1: (3f)→(82))

Compound (82) can be obtained by subjecting compound (3f) to any of known reaction for introducing a protecting group.

(Step D-4-2: (82)→(83))

Compound (83) can be obtained, for example, by subjecting compound (82) to a reduction reaction in an inert solvent in the presence of a hydrogen source and a metal catalyst. Said reaction can be performed under the conditions similar to above step A-5-5.

wherein $R^{2a}$ and $R^{2b}$ each independently represents lower alkyl; $R^{44}$ and $R^{45}$ each independently represents hydrogen or lower alkyl, or $R^{44}$ and $R^{45}$ may unitedly form a ring; $LG^{19}$ represents a leaving group; $LG^{19}$ and $LG^{20}$ each independently represents a leaving group; ma is an integer of 0 to 2; and other symbols are as defined above.

(Step D-5-1: (84)→(85))

Compound (85) can be obtained by subjecting compound (84) to known reaction for introducing a protecting group.

(Step D-5-2: (85)+(87)→(86))

Compound (86) can be obtained, for example, by reacting compound (85) with compound (87) in an inert solvent in the presence of a base and a transition metal catalyst.

The amount of compound (87) used is typically 0.1 to 10 molar equivalents, preferably 0.2 to 5 molar equivalents relative to compound (85).

Examples of the base include, for example, alkali metal hydroxides, alkali metal hydrides, alkali metal carbonates, alkali metal hydrogen carbonates, alkali metal hydrogen phosphates, aromatic amines, tertiary amines, metal amides and metal alkoxides, and it is also possible to use any two or more of them in an appropriate ratio. The amount of the base used is typically 1 to 10 molar equivalents, preferably 1 to 5 molar equivalents relative to compound (85).

Examples of the transition metal catalyst include, for example, palladium catalysts such as palladium (II) acetate, palladium (II) chloride, tetrakis(triphenylphosphine)palladium (0), tris(dibenzylideneacetone)dipalladium (0), 1,1-bis(diphenylphosphino)ferrocene dichloropalladium (II), dichlorobis(triphenylphosphine)palladium (II), bis(tri-(tert-butylphosphine))palladium (0), phenylallylchloro[1,3-bis(diisopropylphenyl)-2-imidazol-2-ylidene]palladium (II) and phenylallylchloro-[1,3-bis(diisopropylphenyl)-2-imidazolidinylidene]palladium (II); copper catalysts such as copper (I) iodide and copper (I) oxide; rhodium catalysts such as tris(triphenylphosphine)rhodium (III) chloride; nickel catalysts such as tetrakis(triphenylphosphine)nickel (0), and it is also possible to use any two or more of them in an

Scheme D-5

[Chem. 56]

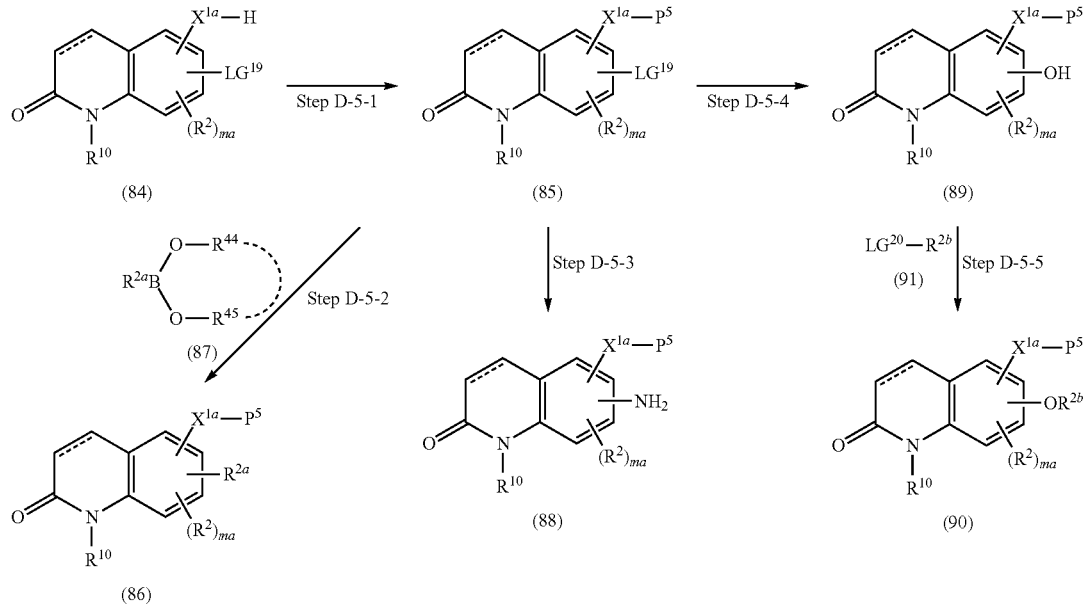

appropriate ratio. The amount of the transition metal catalyst used is typically 0.001 to 3 molar equivalents relative to compound (85).

In addition, a ligand can be added as necessary. Examples of the ligand include, for example, triphenylphosphine, tri(tert-butyl)phosphine, 2,2'-bis(diphenylphosphino)-1,1'-binaphthyl, 2-(dicyclohexylphosphino)-2',4',6'-triisopropyl-1,1'-biphenyl, 4,5'-bis(diphenylphosphino)-9,9'-dimethylxanthene. The amount of the ligand used is typically 0.001 to 3 molar equivalents relative to compound (85).

Examples of the inert solvent include, for example, hydrocarbons, halogenated hydrocarbons, ethers, esters, ketones, amides, nitriles and sulfoxides, and it is also possible to use any two or more of them in an appropriate ratio.

The reaction temperature is typically −80 to 150° C. The reaction time is typically 0.1 to 200 hours.

(Step D-5-3: (85)→(88))

Compound (88) can be obtained from compound (85) by using any known method for introducing amino, for example, by reacting compound (85) with benzophenone imine or hexamethyldisilazane in an inert solvent in the presence of base and transition metal catalyst followed by the hydrolysis of the obtained compound. Said reaction can be performed under the conditions similar to the above step D-1-1.

(Step D-5-4: (85)→(89))

Compound (89) can be obtained from compound (85) by using any known method for introducing hydroxy, for example, reacting compound (85) with a diboronic acid diester, which is $((R^{B1}O)_2B)_2$ wherein $R^{B1}$ each independently represents lower alkyl or may unitedly form a ring (such as bis(pinacolato)diboron), or a boronic acid ester, which is $B(OR^{B2})_3$ wherein $R^{B2}$ each independently represents hydrogen or lower alkyl, in an inert solvent, followed by the hydrolysis of the obtained compound.

The hydrolysis reaction can be done by using Oxone (registered trade name), hydroxyamine and a base.

The amount of the diboronic acid diester or boronic acid ester used is typically 1 to 10 molar equivalents, preferably 1 to 5 molar equivalents relative to compound (85).

When using the diboronic acid diester, it is preferred to react in the presence of base and transition metal catalyst.

Examples of the base include, for example, alkali metal hydroxides, alkali metal hydrides, alkali metal carbonates, alkali metal carboxylates, alkali metal hydrogen carbonates, alkali metal hydrogen phosphates, aromatic amines, tertiary amines, metal amides and metal alkoxides, and it is also possible to use any two or more of them in an appropriate ratio. The amount of the base used is typically 1 to 10 molar equivalents, preferably 1 to 5 molar equivalents relative to compound (85).

Examples of the transition metal catalyst include, for example, palladium catalysts such as palladium (II) acetate, palladium (II) chloride, tetrakis(triphenylphosphine)palladium (0), tris(dibenzylideneacetone)dipalladium (0), 1,1-bis(diphenylphosphino)ferrocene dichloropalladium (II), dichlorobis(triphenylphosphine)palladium (II), bis(tri-(tert-butylphosphine))palladium (0), phenylallylchloro[1,3-bis(diisopropylphenyl)-2-imidazol-2-ylidene]palladium (II) and phenylallylchloro-[1,3-bis(diisopropylphenyl)-2-imidazolidinylidene]palladium (II); copper catalysts such as copper (I) iodide and copper (I) oxide; rhodium catalysts such as tris(triphenylphosphine)rhodium (III) chloride; nickel catalysts such as tetrakis(triphenylphosphine)nickel (0), and it is also possible to use any two or more of them in an appropriate ratio. The amount of the transition metal catalyst used is typically 0.001 to 3 molar equivalents relative to compound (85).

In addition, a ligand can be added as necessary. Examples of the ligand include, for example, triphenylphosphine, tri(tert-butyl)phosphine, 2,2'-bis(diphenylphosphino)-1,1'-binaphthyl, 2-(dicyclohexylphosphino)-2',4',6'-triisopropyl-1,1'-biphenyl, 4,5'-bis(diphenylphosphino)-9,9'-dimethylxanthene. The amount of the ligand used is typically 0.001 to 3 molar equivalents relative to compound (85).

Examples of the inert solvent include, for example, hydrocarbons, halogenated hydrocarbons, ethers, esters, ketones, amides, nitriles and sulfoxides, and it is also possible to use any two or more of them in an appropriate ratio.

The reaction temperature is typically −80 to 150° C. The reaction time is typically 0.1 to 200 hours.

(Step D-5-5: (89)+(91)→(90))

Compound (90) can be obtained, for example, by reacting compound (89) with compound (91) in an inert solvent in the presence of a base. Said reaction can be performed under the conditions similar to above step C-4-5.

Scheme D-6

[Chem. 57]

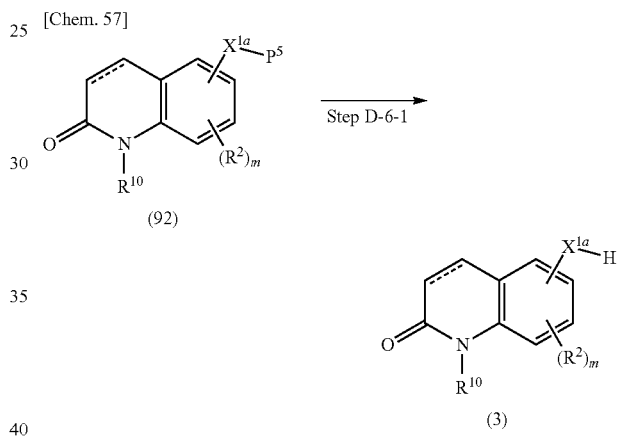

wherein each symbol is as defined above.

(Step D-6-1: (92)→(3))

Compound (3) can be obtained by subjecting compound (92) to any known deprotection reaction.

Scheme D-7

[Chem. 58]

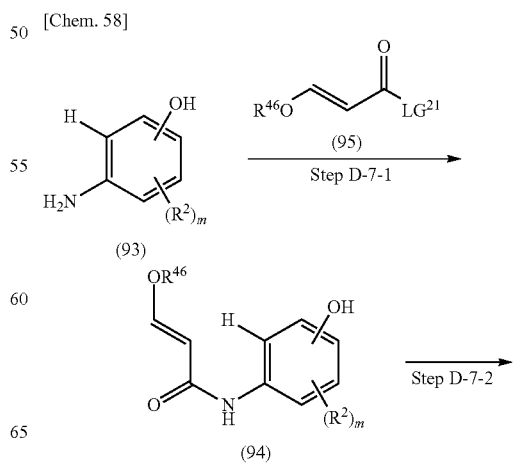

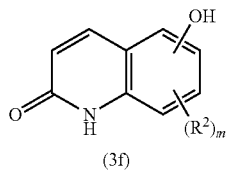

(3f)

wherein $R^{46}$ represents lower alkyl; $LG^{21}$ represents a leaving group; and other symbols are as defined above.

(Step D-7-1: (93)+(95)→(94))

Compound (94) can be obtained by a condensation reaction of compound (93) with compound (95) in an inert solvent. Said reaction can be performed under the conditions similar to above step C-4-8.

(Step D-7-2: (94)→(3f))

Among the compounds represented as formula (3), compound (3f) can be obtained, for example, by treating compound (94) with an acid.

Examples of the acid include, for example, inorganic acids such as hydrochloric acid, sulfuric acid, nitric acid and hydrobromic acid; and organic acids such as acetic acid, trifluoroacetic acid and trifluoromethanesulfonic acid, and it is also possible to use any two or more of them in an appropriate ratio. The amount of the acid used is typically 1 molar equivalent to excessive amounts relative to compound (94).

The acid can be used as a solvent, or an additional inert solvent can be used.

Examples of the inert solvent include, for example, hydrocarbons, halogenated hydrocarbons, ethers, water, alcohols, ketones, amides, nitriles and sulfoxides, and it is also possible to use any two or more of them in an appropriate ratio.

The reaction temperature is typically −80 to 150° C. The reaction time is typically 0.1 to 200 hours.

The compound (1) of the present invention can be prepared by any synthetic method including the above respective steps or a method analogous to those described above. Further, the intermediates and the starting materials in the respective steps can be prepared by considering any synthetic method including the above respective steps or a method analogous to those described above, or a method in Reference Examples and Examples disclosed herein or a method analogous to those described in Examples, and a method known or publicly known at the filing date of the present application. When an intermediate or a starting material is commercially available, such a compound may be used as it is.

In addition, in the preparation of the compound (1), it is possible to further derivatize the obtained compound optionally by subjecting the compound to any of the known reactions such as various alkylation reaction, acylation reaction, amidation reaction, esterification reaction, etherification reaction, halogenation reaction, hydroxylation reaction, amination reaction, aryl coupling reaction, condensation reaction such as carbon extension reaction, addition reaction, substitution reaction, oxidation reaction, reduction reaction, dehydration reaction and hydrolysis reaction in addition to the above steps.

If necessary, a functional group in the starting materials and the intermediates for the above respective steps can be protected with any protecting group by using any known method before subjecting a specific reaction, and after the completion of said specific reaction, the protecting group can be deprotected by using any known method.

Each intermediate and the final compound in the above respective steps can be used in the next step as it is, or it is possible to isolate and purify the compound after the completion of the reaction. For example, when the compound should be isolated and purified, the reaction mixture may be cooled and subjected to a procedure for isolating the crude reaction product such as filtration, condensation or extraction, and then, the crude reaction product may be subjected to a procedure of common purification such as column chromatography or recrystallization to isolate and purify the product from the reaction mixture.

The starting materials, the intermediates and the final compounds and the compound (1) of the present invention include their solvates in which a solvent is added to the compound (for example, hydrates and ethanol solvate etc.).

The starting materials, the intermediates and the final compounds and the compound (1) of the present invention include their geometric isomers, stereoisomers and optical isomers. These isomers can be separated by any known separation method. For example, a racemic compound can be separated to a sterically pure isomer by using common method for optical resolution (for example, optical resolution by crystallization, directly resolving by a chromatography etc.). In addition, it is possible to prepare an optically active compound by using an appropriate optically active starting material.

The starting materials and the final compounds in the above respective steps can be used in a form of an appropriate salt. Examples of such salts include those exemplified below as the salt of compound (1) of the present invention.

When a compound obtained in the respective steps or a commercially available product is in a free form, it is possible to convert the compound to a desired salt by using a method known per se. Alternatively, when a compound obtained in the respective steps or a commercially available product is in a salt form, it is possible to convert the compound to a desired free form or a desired another salt form by using a method known per se.

Compound (1) in the present invention includes a pharmaceutically acceptable salt form thereof.

Among Compound (1) in the present invention, the compound with one or more basic groups may form a salt with a pharmaceutically acceptable acid. An example of the acid includes, for example, an inorganic acid such as hydrochloric acid, hydrobromic acid, nitric acid, sulfuric acid, and phosphoric acid, and an organic acid such as methanesulfonic acid, p-toluenesulfonic acid, acetic acid, citric acid, tartaric acid, maleic acid, fumaric acid, malic acid, and lactic acid.

Among Compound (1) in the present invention, the compound with one or more acidic groups may form a salt with a pharmaceutically acceptable base. An example of the base includes, for example, an inorganic base such as sodium hydroxide, potassium hydroxide, calcium hydroxide, sodium carbonate, potassium carbonate, sodium hydrogencarbonate, and potassium hydrogencarbonate, and an organic base such as methylamine, diethylamine, trimethylamine, triethylamine, ethanolamine, diethanolamine, triethanolamine, ethylenediamine, tris(hydroxymethyl)methylamine, dicyclohexylamine, N,N′-dibenzylethylenediamine, guanidine, pyridine, picoline, and choline.

Compound (1) in the present invention includes the compound wherein one or more atoms are substituted with one or more isotopic atoms. An example of the isotopic atom includes, for example, deuterium ($^2$H), tritium ($^3$H), $^{13}$C, $^{14}$N, and $^{18}$O.

A medical formulation/pharmaceutical composition comprising as the active ingredient Compound (1) in the present invention is illustrated as below.

The medical formulation is what Compound (1) in the present invention is formulated into the form of the usual medical formulation, which is prepared with Compound (1) in the present invention and a pharmaceutically acceptable carrier. The carrier includes a diluent or an excipient such as a filler, a bulking agent, a binder, a humidity adding agent, a disintegrant, a surface active agent, and a lubricant as commonly used.

Such a medical formulation may be selected from various forms depending on therapeutic purposes, and a typical example of the formulation includes, for example, a tablet, a pill, a powder, a liquid, a suspension, an emulsion, a granule, a capsule, a suppository, and an injection (such as a liquid and a suspension).

Any known carriers may be widely used as a carrier used in preparing a tablet formulation, and include, for example, an excipient such as lactose, sucrose, sodium chloride, glucose, urea, starch, calcium carbonate, kaolin, and crystalline cellulose, a binder such as water, ethanol, propanol, simple syrup, glucose solution, starch solution, gelatin solution, carboxymethyl cellulose, shellac, methyl cellulose, potassium phosphate, and polyvinylpyrrolidone, a disintegrant such as dry starch, sodium alginate, agar powder, laminaran powder, sodium hydrogencarbonate, calcium carbonate, polyoxyethylene sorbitan fatty acid esters, sodium lauryl sulfate, monoglyceride stearate, and starch, lactose, a disintegration suppressant such as sucrose, stearin, cacao butter, and hydrogenated oil, an absorption promoter such as quaternary ammonium salt, and sodium lauryl sulfate, a humectant such as glycerin and starch, an adsorbent such as starch, lactose, kaolin, bentonite, and colloidal silica, a lubricant such as purified talc, stearate, boric acid powder, and polyethylene glycol.

The tablet may be also formulated, if needed, as a tablet with a common coating including, for example, a sugar-coated tablet, a gelatin-encapsulated tablet, an enteric coated tablet, a film coated tablet, a double tablet or a multi-layered tablet.

Any known carriers may be widely used as a carrier used in preparing a pill formulation, and include, for example, an excipient such as glucose, lactose, starch, cacao butter, hydrogenated vegetable oil, kaolin, and talc, a binder such as gum arabic powder, tragacanth powder, gelatin, and ethanol, and a disintegrant such as laminaran, and agar.

Any known carriers may be widely used as a carrier used in preparing a suppository formulation, and include, for example, polyethylene glycol, cacao butter, higher alcohol, esters of higher alcohol, gelatin, and semisynthetic glyceride.

It is preferable in the preparation of an injection that a liquid, an emulsion, and a suspension are sterilized and isotonic with blood. Any known diluents may be widely used as a diluent used in preparing the liquid, emulsion, and suspension, and include, for example, water, ethanol, propylene glycol, ethoxylated isostearyl alcohol, polyoxylated isostearyl alcohol, and polyoxyethylene sorbitan fatty acid esters. In this case, the medical formulation may comprise a sufficient amount of salt, glucose or glycerin to prepare the isotonic solution, and it may also comprise a common solubilizing agent, beffering agent, soothing agent, and the like as well as a colorant, preserving agent, perfume, flavoring agent, sweetening agent, and other medicinal products, if needed.

The amount of Compound (1) in the present invention contained in a medical formulation is not limited and may be optionally adjusted with a broad range; it is preferable that the medical formulation typically comprises 1 to 70% by weight of Compound (1) in the present invention.

A method of administering the medical formulation in the present invention is not limited and the medical formulation may be administered depending on various dosage forms, ages and genders of patients, disease states, and other conditions. For example, a tablet, pill, liquid, suspension, emulsion, granule, and capsule may be orally administered. An injection may be intravenously administered solely or in combination with a common replacement fluid such as glucose and amino acid, and if needed, may be solely administered intramuscularly, intradermally, subcutaneously or intraperitoneally. A suppository may be rectally administered.

A dosage amount of the medical formulation may be optionally adjusted depending on dosage regimens, ages and genders of patients, the extent of disease, and other conditions; it may be typically administered in 0.01 to 100 mg/kg, preferably 0.1 to 50 mg/kg, of body weight per day in a single dose or multiple doses.

The dosage amount may be varied on the basis of various conditions, and a lower dosage amount than the above may be sufficient in some cases and a higher dosage amount than the above may be necessary in other cases.

Compound (1) in the present invention has a specific efficacy in particular against tuberculosis bacteria such as mycobacteria, including tuberculosis bacteria genus, and non-tuberculous mycobacteria genus, and also has an excellent activity against multidrug-resistant tuberculosis bacteria. It not only shows an antibacterial activity in vitro but also expresses an antibacterial activity in oral administration in vivo due to its favorable distribution in lung tissues which are the primarily infected organ. Compound (1) in the present invention is thus useful as an agent for diagnosing, preventing and/or treating tuberculosis.

Compound (1) in the present invention does not induce diarrhea as seen in known antibacterial agents with a wide spectrum for common bacteria such as gram-positive bacteria and gram-negative bacteria, and may become a medicinal substance which allows for a long-term administration.

Compound (1) in the present invention is effective for intracellular parasitic bacteria such as human-origin tuberculosis bacteria which is parasitic in macrophage and has in a bactericidal test a stronger bactericidal activity in a low concentration than existing antitubercular agents. It can be thus expected that the relapse rate in tuberculosis will be reduced, which eventually allows for a short-term chemotherapy.

Due to a lower toxicity than existing drugs, Compound (1) in the present invention can be also expected for long-term use in the treatment for latent tuberculosis.

Compound (1) in the present invention shows a low inhibitory activity against a drug-metabolizing enzyme and a low possibility for an enzyme induction of CYP3A. Due to limited concerns about drug interaction, it can be expected for a combination use with other therapeutic agents. The agents capable of the combination use include, for example, a first antituberculosis drug, a secondary antituberculosis drug, a quinolone antimicrobial, a macrolide antimicrobial, an oxazolidinone antimicrobial, a sufa drug, an anti-HIV drug, delamanid, bedaquiline, or PA-824, Sutezolid currently under development.

EXAMPLES

Hereinafter, the present invention is described in more detail with reference to Reference Examples, Examples and Test Examples. These Examples are not intended to limit the present invention, and they can be modified within the scope of the present invention.

The term "room temperature" in the following Examples is usually referred to a temperature between about 10° C. to about 35° C. A ratio of mixed solvents is referred to a volume ratio, unless otherwise specified. % is referred to a weight %, unless otherwise specified.

$^1$HNMR (proton nuclear magnetic resonance spectrum) was determined at room temperature by using a Fourier transform NMR (any one of Bruker AVANCE 300 (300 M Hz), Bruker AVANCE 500 (500 M Hz), Bruker AVANCE III 400 (400 M Hz) and Bruker AVANCE III 500 (500 M Hz)). In a silica gel column chromatography, when it is described as a basic, an aminopropylsilane-bonded silica gel was used.

Reference Example 1

(2E)-N-(2-Chloro-5-hydroxyphenyl)-3-ethoxyprop-2-enamide

To a solution of 3-amino-4-chlorophenol (10.35 g), pyridine (6.41 mL) in N,N-dimethylacetamide (90 mL), a solution of (2E)-3-ethoxyprop-2-enoyl chloride (10.9 g) in N,N-dimethylacetamide (10 mL) was added dropwise under ice-cooling, and the reaction mixture was stirred at the same temperature for 1 h. The reaction solution was poured into water, and the precipitate was collected on a filter to provide the title compound (10.7 g).
$^1$HNMR (CDCl$_3$) δ ppm: 1.38 (3H, t, J=7.1 Hz), 4.01 (2H, q, J=7.1 Hz), 5.39 (1H, d, J=12.1 Hz), 6.58 (1H, dd, J=8.8 Hz, 2.9 Hz), 7.20 (1H, d, J=8.9 Hz), 7.52 (1H, brs), 7.68 (1H, d, J=12.1 Hz), 8.13 (1H, brs), 8.33 (1H, d, J=2.9 Hz).

Reference Example 2

(2E)-3-Ethoxy-N-(2-fluoro-5-hydroxyphenyl)prop-2-enamide

Synthesized analogous to Reference Example 1.
$^1$HNMR (CDCl$_3$) δ ppm: 1.38 (3H, t, J=7.0 Hz), 3.99 (2H, q, J=7.0 Hz), 5.36 (1H, d, J=12.1 Hz), 6.49-6.55 (1H, m), 6.94 (1H, dd, J=9.0 Hz, 8.9 Hz), 7.22 (1H, brs), 7.67 (1H, d, J=12.1 Hz), 8.08 (1H, brs), 8.23-8.29 (1H, m).

Reference Example 3

(2E)-N-(2,3-Difluoro-5-methoxyphenyl)-3-ethoxy-prop-2-enamide

Synthesized analogous to Reference Example 1.
$^1$HNMR (CDCl$_3$) δ ppm: 1.37 (3H, t, J=6.9 Hz), 3.78 (3H, s), 3.97 (2H, q, J=6.9 Hz), 5.35 (1H, d, J=12.0 Hz), 6.38-6.46 (1H, m), 7.13 (1H, s), 7.66 (1H, d, J=12.0 Hz), 7.82-7.87 (1H, m).

Reference Example 4

(2E)-N-(2,4-Dibromo-3-fluoro-5-methoxyphenyl)-3-ethoxyprop-2-enamide

Synthesized analogous to Reference Example 1.
$^1$HNMR (CDCl$_3$) δ ppm: 1.38 (3H, t, J=7.2 Hz), 3.93 (3H, s), 4.00 (2H, q, J=7.2 Hz), 5.36 (1H, d, J=12.0 Hz), 7.47 (1H, s), 7.67 (1H, d, J=12.0 Hz), 8.19 (1H, d, J=2.1 Hz).

Reference Example 5

8-Fluoro-5-hydroxyquinolin-2(1H)-one

To conc. hydrochloric acid (270 mL), a solution of (2E)-3-ethoxy-N-(2-fluoro-5-hydroxyphenyl)prop-2-enamide (27.0 g) in methanol (135 mL) was added dropwise at 65° C., then the reaction mixture was stirred at 85° C. for 30 min. The reaction solution was poured into water, and the precipitate was collected on a filter to provide the title compound (19.2 g).
$^1$HNMR (DMSO-d6) δ ppm: 6.46 (1H, d, J=9.8 Hz), 6.52 (1H, dd, J=8.8 Hz, 3.7 Hz), 7.21 (1H, dd, J=10.9 Hz, 8.8 Hz), 8.02 (1H, dd, J=9.8 Hz, 1.6 Hz), 10.33 (1H, brs), 11.60 (1H, brs).

Reference Example 6

8-Chloro-5-hydroxyquinolin-2(1H)-one

Synthesized analogous to Reference Example 5.
$^1$HNMR (DMSO-d6) δ ppm: 6.47 (1H, d, J=9.7 Hz), 6.62 (1H, d, J=8.6 Hz), 7.42 (1H, d, J=8.6 Hz), 8.05 (1H, d, J=9.8 Hz), 10.68 (1H, s), 10.75 (1H, brs).

Reference Example 7

7,8-Difluoro-5-methoxyquinolin-2(1H)-one

To conc. sulfuric acid (17 mL) was added (2E)-N-(2,3-difluoro-5-methoxyphenyl)-3-ethoxyprop-2-enamide (1.66 g) at 70-80° C., and the reaction mixture was stirred for 5 min. After the reaction solution was added to ice water, the precipitate was collected on a filter to provide the title compound (1.0 g).
$^1$HNMR (DMSO-d6) δ ppm: 3.90 (3H, s), 6.45 (1H, d, J=9.9 Hz), 6.90 (1H, dd, J=12.9 Hz, 6.0 Hz), 7.97 (1H, dd, J=9.9 Hz, 1.5 Hz), 12.00 (1H, s).

Reference Example 8

6,8-Dibromo-7-fluoro-5-methoxyquinolin-2(1H)-one

Synthesized analogous to Reference Example 7.
$^1$HNMR (DMSO-d6) δ ppm: 3.91 (3H, s), 6.61 (1H, d, J=9.5 Hz), 8.02 (1H, d, J=9.5 Hz), 10.96-11.10 (1H, brs).

Reference Example 9

7-Fluoro-5-methoxy-3,4-dihydroquinolin-2(1H)-one

Under hydrogen atmosphere, a suspension of 7-fluoro-5-methoxyquinolin-2(1H)-one (29.0 g) and 10% palladium on carbon (10 g) in acetic acid (600 mL) was stirred at 105° C. for 2.5 h. Insoluble materials were filtered off and the filtrate was concentrated. The residue was washed with water and dried to provide the title compound (25.7 g).
$^1$HNMR (CDCl$_3$) δ ppm: 2.56-2.62 (2H, m), 2.89 (2H, t, J=7.5 Hz), 3.82 (3H, s), 6.15 (1H, dd, J=9.0 Hz, 2.1 Hz), 6.32 (1H, dd, J=10.8 Hz, 2.1 Hz), 7.92 (1H, brs).

Reference Example 10

7,8-Difluoro-5-methoxy-3,4-dihydroquinolin-2(1H)-one

Synthesized analogous to Reference Example 9.
$^1$HNMR (CDCl$_3$) δ ppm: 2.58-2.64 (2H, m), 2.90-2.96 (2H, m), 3.79 (3H, s), 6.37 (1H, dd, J=12.0 Hz, 6.3 Hz), 7.51 (1H, brs).

Reference Example 11

7-Amino-8-fluoro-5-hydroxy-3,4-dihydroquinolin-2(1H)-one

A mixture of 7-amino-8-fluoro-5-methoxy-3,4-dihydroquinolin-2(1H)-one (0.90 g) and 48% hydrogen bromide in water (18 mL) was heated to reflux for 20 h. The precipitate was collected on a filter, and washed with 48% hydrogen bromide in water. The obtained solid was stirred in saturated aqueous sodium hydrogencarbonate, and the precipitated crystal was collected on a filter to provide the title compound (0.68 g).
$^1$HNMR (DMSO-d6) δ ppm: 2.30-2.36 (2H, m), 2.61-2.66 (2H, m), 4.90 (2H, brs), 5.90 (1H, d, J=7.5 Hz), 8.90 (1H, brs), 9.60 (1H, brs).

Reference Example 12

7-Fluoro-5-hydroxy-3,4-dihydroquinolin-2(1H)-one

Synthesized analogous to Reference Example 11.
$^1$HNMR (DMSO-d6) δ ppm: 2.37-2.42 (2H, m), 2.71 (2H, t, J=7.5 Hz), 6.14 (1H, dd, J=10.2 Hz, 2.4 Hz), 6.23 (1H, dd, J=10.8 Hz, 2.4 Hz), 9.01-11.2 (2H, m).

Reference Example 13

7,8-Difluoro-5-hydroxy-3,4-dihydroquinolin-2(1H)-one

Synthesized analogous to Reference Example 11.
$^1$HNMR (DMSO-d6) δ ppm: 2.39-2.44 (2H, m), 2.71-2.77 (2H, m), 6.37 (1H, dd, J=12.3 Hz, 6.6 Hz), 9.86 (1H, brs), 10.16 (1H, s).

Reference Example 14

8-Fluoro-5-hydroxy-7-methyl-3,4-dihydroquinolin-2(1H)-one

Synthesized analogous to Reference Example 11.
$^1$HNMR (DMSO-d6) δ ppm: 2.11 (3H, d, J=1.8 Hz), 2.36-2.44 (2H, m), 2.75 (2H, t, J=7.2 Hz), 6.28 (1H, d, J=6.3 Hz), 9.25 (1H, s), 9.77 (1H, s).

Reference Example 15

8-Chloro-7-fluoro-5-hydroxy-3,4-dihydroquinolin-2(1H)-one

Synthesized analogous to Reference Example 11.
$^1$HNMR (DMSO-d6) δ ppm: 2.41-2.50 (2H, m), 2.72-2.82 (2H, m), 6.47 (1H, d, J=11.1 Hz), 9.48 (1H, brs), 10.22 (1H, brs).

Reference Example 16

7-Fluoro-5-hydroxy-8-methyl-3,4-dihydroquinolin-2(1H)-one

Synthesized analogous to Reference Example 11.
$^1$HNMR (DMSO-d6) δ ppm: 1.99 (3H, d, J=1.8 Hz), 2.34-2.40 (2H, m), 2.68-2.74 (2H, m), 6.27 (1H, d, J=11.4 Hz), 9.45 (1H, s), 9.69 (1H, s).

Reference Example 17

8-Ethyl-7-fluoro-5-hydroxy-3,4-dihydroquinolin-2(1H)-one

To a solution of 8-ethyl-7-fluoro-5-methoxy-3,4-dihydroquinolin-2(1H)-one (150 mg) in dichloromethane (5 mL), a solution of 1 N boron tribromide in dichloromethane (2.02 mL) was added dropwise under ice-cooling, and the reaction mixture was stirred at room temperature overnight. Methanol (1 mL) was added to the reaction solution, and then the solvent was distilled off. The residue was purified by silica gel column chromatography (ethyl acetate) to provide the title compound (100 mg).
$^1$HNMR (DMSO-d6) δ ppm: 0.96 (3H, t, J=7.5 Hz), 2.34-2.39 (2H, m), 2.53-2.57 (2H, m), 2.67-2.73 (2H, m), 6.25 (1H, d, J=11.7 Hz), 9.50 (1H, s), 9.71 (1H, s).

Reference Example 18

6,8-Difluoro-5-hydroxy-3,4-dihydroquinolin-2(1H)-one

To a solution of 5-hydroxy-3,4-dihydroquinolin-2(1H)-one (0.50 g) in 1,2-dichloroethane (10 mL) was added fluoropyridinium triflate (2.27 g), and the reaction mixture was heated to reflux overnight. The reaction solution was concentrated, the water was added to the residue, and then extracted with ethyl acetate. The organic layer was washed with brine, dried over anhydrous sodium sulfate, and then the solvent was distilled off. The residue was purified by silica gel column chromatography (dichloromethane/ethyl acetate) to provide the title compound (38 mg).
$^1$HNMR (DMSO-d6) δ ppm: 2.44 (2H, t, J=8.0 Hz), 2.86 (2H, t, J=7.5 Hz), 7.10 (1H, t, J=10.7 Hz), 9.57 (1H, brs), 9.97 (1H, brs).

Reference Example 19

8-Chloro-5-(tetrahydro-2H-pyran-2-yloxy)-3,4-dihydroquinolin-2(1H)-one

A solution of 8-chloro-5-hydroxy-3,4-dihydroquinolin-2(1H)-one (2.00 g), 3,4-dihydro-2H-pyran (2.55 g) and pyridinium p-toluenesulfonate (0.51 g) in dichloromethane (40 mL) was stirred at room temperature overnight. The reaction solution was washed with brine, dried over sodium sulfate, and the solvent was distilled off. The residue was purified by silica gel column chromatography (hexane/ethyl acetate) to provide the title compound (2.74 g).
$^1$HNMR (CDCl$_3$) δ ppm: 1.48-1.78 (3H, m), 1.79-2.08 (3H, m), 2.62 (2H, t, J=7.7 Hz), 2.91-3.13 (2H, m), 3.56-3.67 (1H, m), 3.79-3.90 (1H, m), 5.34-5.45 (1H, m), 6.78 (1H, d, J=9.0 Hz), 7.15 (1H, d, J=9.0 Hz), 7.38 (1H, brs).

Reference Example 20

8-Fluoro-5-(tetrahydro-2H-pyran-2-yloxy)-3,4-dihydroquinolin-2(1H)-one

Synthesized analogous to Reference Example 19.
$^1$HNMR (CDCl$_3$) δ ppm: 1.57-1.75 (3H, m), 1.82-1.93 (2H, m), 1.93-2.03 (1H, m), 2.64 (2H, t, J=7.7 Hz), 2.96-3.10 (2H, m), 3.58-3.66 (1H, m), 3.82-3.90 (1H, m), 5.35 (1H, t, J=3.3 Hz), 6.74 (1H, dd, J=9.1 Hz, 4.2 Hz), 6.89 (1H, t, J=9.6 Hz), 7.90 (1H, brs).

Reference Example 21

7-Bromo-8-fluoro-5-methoxy-3,4-dihydroquinolin-2(1H)-one

To a solution of 8-fluoro-5-methoxy-7-(4,4,5,5-tetramethyl-1,3,2-dioxaborolan-2-yl)-3,4-dihydroquinolin-2(1H)-one (29.8 g) in methanol/water (3/1) (900 mL), copper (II) bromide (62.1 g) was added, and the reaction mixture was heated to reflux for 3 h. Water was added to the reaction solution, then which was ice-cooled to collect the precipitate on a filter. To the resultant precipitate was added ethyl acetate (1000 mL), and after refluxing for a while, insoluble materials were filtered off. The filtrate was concentrated and the precipitate was collected on a filter to provide the title compound (21.4 g).
$^1$HNMR (CDCl$_3$) δ ppm: 2.59-2.67 (2H, m), 2.90-2.95 (2H, m), 3.81 (3H, s), 6.67 (1H, d, J=5.1 Hz), 7.71 (1H, brs).

Reference Example 22

7-Amino-8-fluoro-5-methoxy-3,4-dihydroquinolin-2(1H)-one

Under nitrogen atmosphere, a solution of benzophenone imine (31.3 mL), 7-bromo-8-fluoro-5-methoxy-3,4-dihydroquinolin-2(1H)-one (21.4 g), 2,2'-bis(diphenylphosphino)-1,1'-binaphthyl (3.65 g), sodium tert-butoxide (19.5 g) and tris(dibenzylideneacetone)dipalladium (1.79 g) in toluene (250 mL) was heated to reflux for 2 h. The reaction solution was filtered over Celite, water (150 mL) and 6 N hydrochloric acid (75 mL) were added to the filtrate and the reaction mixture was stirred at 80° C. for 30 min. The reaction solution was cooled to room temperature, poured into aqueous sodium hydroxide, and the precipitate was collected on a filter to provide the title compound (13.0 g).
$^1$HNMR (DMSO-d6) δ ppm: 2.36 (2H, t, J=7.5 Hz), 2.67 (2H, t, J=7.5 Hz), 3.66 (3H, s), 5.04 (2H, brs), 6.05 (1H, d, J=6.9 Hz), 9.76 (1H, brs).

Reference Example 23

8-Fluoro-5-methoxy-7-methyl-3,4-dihydroquinolin-2(1H)-one

Under nitrogen atmosphere, a solution of 7-bromo-8-fluoro-5-methoxy-3,4-dihydroquinolin-2(1H)-one (50 mg), methylboronic acid (16.4 mg), 1,1'-bis(diphenylphosphino)ferrocene-palladium (II) dichloride dichloromethane adduct (14.9 mg) and tripotassium phosphate (77 mg) in 1,4-dioxane (2 mL) was stirred at 100° C. for 15 h. To the reaction solution was added ethyl acetate, and insoluble materials were filtered off. The filtrate was washed with water and brine, dried over anhydrous sodium sulfate, and then the solvent was distilled off. The residue was purified by silica gel column chromatography (dichloromethane→dichloromethane/methanol) to provide the title compound (34 mg).
$^1$HNMR (CDCl$_3$) δ ppm: 2.26 (3H, d, H=1.8 Hz), 2.55-2.65 (2H, m), 2.93 (2H, t, J=7.7 Hz), 3.79 (3H, s), 6.32 (1H, d, J=5.7 Hz), 8.14 (1H, brs).

Reference Example 24

8-Fluoro-7-hydroxy-5-methoxy-3,4-dihydroquinolin-2(1H)-one

To a solution of 8-fluoro-5-methoxy-7-(4,4,5,5-tetramethyl-1,3,2-dioxaborolan-2-yl)-3,4-dihydroquinolin-2(1H)-one (98 mg) in ethanol (7 mL), hydroxylamine hydrochloride (32.8 mg) and sodium hydroxide (24.4 mg) were added, and the reaction mixture was stirred at 40° C. for 72 h. After the solvent of the reaction solution was distilled off, to the residue was added aqueous saturated ammonium chloride, and the solution was extracted with ethyl acetate. The organic layer was washed with brine, dried over anhydrous sodium sulfate, and then the solvent was distilled off. The residue was purified by silica gel column chromatography (hexane/ethyl acetate) to provide the title compound (20 mg).
$^1$HNMR (DMSO-d6) δ ppm: 2.36-2.41 (2H, m), 2.68-2.73 (2H, m), 3.69 (3H, s), 6.20 (1H, d, J=6.6 Hz), 9.72 (1H, brs), 9.90 (1H, brs).

Reference Example 25

8-Fluoro-5-methoxy-7-(4,4,5,5-tetramethyl-1,3,2-dioxaborolan-2-yl)-3,4-dihydroquinolin-2(1H)-one Under nitrogen atmosphere, a solution of 8-fluoro-5-methoxy-3,4-dihydroquinolin-2(1H)-one (50 g), bis(pinacolato)diboron (98 g), 4,4'-di-tert-butyl-2,2'-dipyridyl (5.50 g) and di-µ-methoxobis(1,5-cyclooctadiene)diiridium (I) (6.79 g) in tetrahydrofuran (900 mL) was heated to reflux for 2.5 h. After cooling to room temperature, the reaction solution was concentrated, and the residue was purified by silica gel column chromatography (hexane/ethyl acetate) to provide the title compound (44.5 g).
$^1$HNMR (CDCl$_3$) δ ppm: 1.35 (12H, s), 2.57-2.63 (2H, m), 2.94-3.00 (2H, m), 3.84 (3H, s), 6.79 (1H, d, J=3.9 Hz), 7.50 (1H, brs).

Reference Example 26

7-Ethoxy-8-fluoro-5-methoxy-3,4-dihydroquinolin-2(1H)-one

To a solution of 8-fluoro-7-hydroxy-5-methoxy-3,4-dihydroquinolin-2(1H)-one (1.1 g) in N,N-dimethylformamide (20 mL) was added potassium carbonate (0.864 g) and ethyl iodide (0.505 mL), and the reaction mixture was stirred at room temperature for 3 h. The reaction solution was poured into water, and the solid was collected on a filter to provide the title compound (1.05 g).
$^1$HNMR (DMSO-d6) δ ppm: 1.33 (3H, t, J=6.9 Hz), 2.40 (2H, t, J=7.5 Hz), 2.75 (2H, t, J=7.5 Hz), 3.77 (3H, s), 4.10 (2H, q, J=6.9 Hz), 6.43 (1H, d, J=6.9 Hz), 10.00 (1H, brs).

Reference Example 27

7-Ethoxy-8-fluoro-5-hydroxy-3,4-dihydroquinolin-2(1H)-one

Synthesized analogous to Reference Example 17.
$^1$HNMR (DMSO-d6) δ ppm: 1.31 (3H, t, J=6.9 Hz), 2.37-2.42 (2H, m), 2.70-2.74 (2H, m), 3.98 (2H, q, J=6.9 Hz), 6.20 (1H, d, J=6.9 Hz), 9.34 (1H, s), 9.82 (1H, brs).

Reference Example 28

8-Bromo-7-fluoro-5-methoxy-3,4-dihydroquinolin-2(1H)-one

To a solution of 7-fluoro-5-methoxy-3,4-dihydroquinolin-2(1H)-one (10 g) in acetic acid (600 mL), bromine (2.76 mL) was added dropwise, and then the reaction mixture was stirred at room temperature for 20 min. The reaction solution was poured into water, and the precipitate was collected on a filter to provide the title compound (8.31 g).

$^1$HNMR (DMSO-d6) δ ppm: 2.42-2.53 (2H, m), 2.76-2.86 (2H, m), 3.81 (3H, s), 6.82 (1H, d, J=11.1 Hz), 9.17 (1H, brs).

Reference Example 29

8-Chloro-7-fluoro-5-methoxy-3,4-dihydroquinolin-2 (1H)-one

Under argon atmosphere, a solution of 8-bromo-7-fluoro-5-methoxy-3,4-dihydroquinolin-2(1H)-one (11.3 g) and copper (I) chloride (8.56 g) in N-methyl-2-pyrrolidone (300 mL) was stirred at 130° C. for 20 h. After cooling to room temperature, the reaction mixture was poured into 5% ammonium chloride aqueous solution, and the precipitate was collected on a filter. The obtained solid was purified by silica gel column chromatography (basic silica gel; dichloromethane) to provide the title compound (7.31 g).

$^1$HNMR (DMSO-d6) δ ppm: 2.41-2.53 (2H, m), 2.76-2.86 (2H, m), 3.80 (3H, s), 6.82 (1H, d, J=11.7 Hz), 9.60 (1H, brs).

Reference Example 30

7-Fluoro-5-methoxy-8-methyl-3,4-dihydroquinolin-2 (1H)-one

Under nitrogen atmosphere, a solution of 8-bromo-7-fluoro-5-methoxy-3,4-dihydroquinolin-2(1H)-one (1.23 g), methylboronic acid (0.81 g), potassium phosphate (2.86 g) and 1,1'-bis(diphenylphosphino)ferrocene-palladium (II) dichloride dichloromethane adduct (0.73 g) in 1,4-dioxane (25 mL) was stirred at 110° C. for 1 h. The reaction solution was cooled to room temperature, concentrated, and then purified by silica gel column chromatography (dichloromethane/methanol). The obtained material was treated with activated charcoal, filtrated and concentrated to provide the title compound (410 mg).

$^1$HNMR (CDCl$_3$) δ ppm: 2.06 (3H, d, J=1.5 Hz), 2.54-2.60 (2H, m), 2.87-2.93 (2H, m), 3.80 (3H, s), 6.34 (1H, d, J=11.4 Hz), 7.30-7.40 (1H, brs).

Reference Example 31

7-Fluoro-5-methoxyquinolin-2(1H)-one

Under hydrogen atmosphere, a suspension of 6,8-dibromo-7-fluoro-5-methoxyquinolin-2(1H)-one (40.6 g), sodium hydroxide (9.13 g) and 20% palladium hydroxide on carbon (4 g) in N,N-dimethylacetamide (800 mL) was stirred at 45° C. for 2 h. Insoluble materials were filtered off by using Celite, the filtrate was poured into water and neutralized with 6 N hydrochloric acid (57.1 mL). The precipitate was collected on a filter to provide the title compound (18.2 g).

$^1$HNMR (DMSO-d6) δ ppm: 3.92 (3H, s), 6.37 (1H, d, J=10.0 Hz), 6.63-6.72 (2H, m), 7.96 (1H, d, J=10.0 Hz), 11.81 (1H, s).

Reference Example 32

8-Ethenyl-7-fluoro-5-methoxy-3,4-dihydroquinolin-2(1H)-one

Under nitrogen atmosphere, a solution of 8-bromo-7-fluoro-5-methoxy-3,4-dihydroquinolin-2(1H)-one (100 mg), 4,4,5,5-tetramethyl-2-vinyl-1,3,3-dioxaborolane (112 mg), sodium carbonate (116 mg) and tetrakis(triphenylphosphine)palladium (42.2 mg) in 1,4-dioxane/water (5/1) (2 mL) was stirred at 100° C. overnight. The reaction solution was cooled to room temperature, concentrated, and then the residue was purified by silica gel chromatography (hexane/ethyl acetate) to provide the title compound (50 mg).

$^1$HNMR (CDCl$_3$) δ ppm: 2.55-2.61 (2H, m), 2.86-2.92 (2H, m), 3.82 (3H, s), 5.56-5.65 (2H, m), 6.36 (1H, d, J=12.0 Hz), 6.45-6.55 (1H, m), 7.66 (1H, s).

Reference Example 33

8-Ethyl-7-fluoro-5-methoxy-3,4-dihydroquinolin-2 (1H)-one

Under nitrogen atmosphere, to a solution of 8-ethenyl-7-fluoro-5-methoxy-3,4-dihydroquinolin-2(1H)-one (200 mg) in acetic acid (4 mL) was added 10% palladium on carbon (50 mg), and the reaction mixture was stirred at room temperature for 10 min under hydrogen atmosphere. The reaction solution was filtered over Celite and the solvents of the filtrate were distilled off. Water was added to the obtained residue, and the precipitate was collected on a filter to provide the title compound (150 mg).

$^1$HNMR (CDCl3) δ ppm: 1.13 (3H, t, J=7.6 Hz), 2.51-2.60 (4H, m), 2.87-2.92 (2H, m), 3.79 (3H, s), 6.34 (1H, d, J=11.6 Hz), 7.39 (1H, brs).

Reference Example 34

5-(Benzyloxy)-7-fluoro-3,4-dihydroquinolin-2(1H)-one

A solution of 7-fluoro-5-hydroxy-3,4-dihydroquinolin-2 (1H)-one (500 mg), potassium carbonate (496 mg) and benzyl bromide (0.39 mL) in N,N-dimethylformamide (5 mL) was stirred at room temperature for 1 h. The reaction solution was poured into cold-water, and the precipitate was collected on a filter, washed with water, ethanol and diethyl ether to provide the title compound (748 mg).

$^1$HNMR (CDCl$_3$) δ ppm: 2.56-2.62 (2H, m), 2.92-2.97 (2H, m), 5.05 (2H, s), 6.17 (1H, dd, J=9.0 Hz, 2.1 Hz), 6.39 (1H, dd, J=10.8 Hz, 2.1 Hz), 7.30-7.45 (5H, m), 7.99 (1H, s).

Reference Example 35

5-(Benzyloxy)-8-bromo-7-fluoro-3,4-dihydroquinolin-2(1H)-one

Synthesized analogous to Reference Example 28.

$^1$HNMR (CDCl$_3$) δ ppm: 2.55-2.61 (2H, m), 2.95-3.00 (2H, m), 5.04 (2H, s), 6.49 (1H, d, J=10.2 Hz), 7.30-7.45 (5H, m), 7.44 (1H, s).

Reference Example 36

5-[(3,5-Dimethylbenzyl)oxy]-8-fluoro-3,4-dihydroquinolin-2(1H)-one

Synthesized analogous to Reference Example 34.

$^1$HNMR (DMSO-d6) δ ppm: 2.28 (6H, s), 2.42-2.49 (2H, m), 2.85-2.91 (2H, m), 4.99 (2H, s), 6.66 (1H, dd, J=9.0 Hz, 3.9 Hz), 6.95-7.04 (4H, m), 10.01 (1H, s).

Reference Example 37

5-[(3,5-Dimethylbenzyl)oxy]-8-fluoro-7-hydroxy-3,4-dihydroquinolin-2(1H)-one

Under nitrogen atmosphere, a solution of 5-[(3,5-dimethylbenzyl)oxy]-8-fluoro-3,4-dihydroquinolin-2(1H)-one (1.0 g), bis(pinacolato)diboron (1.27 g), 4,4'-di-tert-butyl-2,2'-dipyridyl (0.07 g) and di-μ-methoxobis(1,5-cyclooctadiene) diiridium (I) (0.09 g) in tetrahydrofuran (20 mL) was heated to reflux for 10 h. After the reaction solution was allowed to cool to room temperature, methanol (20 mL) followed by Oxone (Registered trade mark) (2.46 g) in water (20 mL) were added, and the reaction mixture was stirred at room temperature for 10 min. To the reaction solution was added water, and the precipitated crystal was collected on a filter, then washed with water, ethanol and diethyl ether to provide the title compound (500 mg).

$^1$HNMR (DMSO-d6) δ ppm: 2.28 (6H, s), 2.38-2.43 (2H, m), 2.74-2.79 (2H, m), 4.91 (2H, s), 6.28 (1H, d, J=7.2 Hz), 6.96 (1H, s), 7.02 (2H, s), 9.72 (1H, s), 9.91 (1H, s).

Reference Example 38

5-[(3,5-Dimethylbenzyl)oxy]-8-fluoro-7-(tetrahydro-2H-pyran-2-yloxy)-3,4-dihydroquinolin-2(1H)-one A mixture of 5-[(3,5-dimethylbenzyl)oxy]-8-fluoro-7-hydroxy-3,4-dihydroquinolin-2(1H)-one (100 mg), 3,4-dihydro-2H-pyran (1 mL) and p-toluenesulfonic acid (10.9 mg) was stirred at room temperature for 30 min, and was extracted with saturated aqueous sodium hydrogencarbonate and ethyl acetate. The solvent of the organic layer was distilled off, and then the residue was purified by silica gel column chromatography (hexane/ethyl acetate) to provide the title compound (106 mg, 84%).

$^1$HNMR (DMSO-d6) δ ppm: 1.50-1.90 (6H, m), 2.27 (6H, s), 2.39-2.43 (2H, m), 2.77-2.82 (2H, m), 3.31-3.54 (1H, m), 3.75-3.83 (1H, m), 4.95 (2H, s), 5.48 (1H, s), m 6.65 (1H, d, J=6.7 Hz), 6.95 (1H, s), 7.03 (2H, s), 10.00 (1H, s).

Reference Example 39

5-(Benzyloxy)-7-fluoro-8-(4,4,5,5-tetramethyl-1,3,2-dioxaborolan-2-yl)-3,4-dihydroquinolin-2(1H)-one Under nitrogen atmosphere, a solution of 5-(benzyloxy)-8-bromo-7-fluoro-3,4-dihydroquinolin-2(1H)-one (1.0 g), bis(pinacolato)diboron (1.45 g), potassium acetate (0.84 g) and 1,1'-bis(diphenylphosphino)ferrocene-palladium (II) dichloride dichloromethane complex (0.12 g) in DMSO (10 mL) was stirred at 110° C. for 3.5 h. The reaction solution was allowed to cool to room temperature, and was extracted with ethyl acetate and water. The organic layer was washed with brine, dried over anhydrous sodium sulfate, and then the solvent was distilled off. The residue was purified by silica gel column chromatography (hexane/ethyl acetate) to provide the title compound (850 mg).

$^1$HNMR (DMSO-d6) δ ppm: 1.31 (12H, s), 2.41-2.50 (2H, m), 2.78-2.84 (2H, m), 5.18 (2H, s), 6.65 (1H, d, J=12.0 Hz), 7.33-7.46 (5H, m), 9.19 (1H, s).

Reference Example 40

5-(Benzyloxy)-7-fluoro-8-hydroxy-3,4-dihydroquinolin-2(1H)-one

To a solution of 5-(benzyloxy)-7-fluoro-8-(4,4,5,5-tetramethyl-1,3,2-dioxaborolan-2-yl)-3,4-dihydroquinolin-2(1H)-one (800 mg) in methanol (6 mL) was added Oxone (Registered trade mark) (1.86 g) in water (6 mL) under water-cooling and the reaction mixture was stirred at room temperature for 5 min. To the reaction solution was added water, the precipitate was collected on a filter, and washed with water. The obtained crude crystal was purified by silica gel column chromatography (hexane/ethyl acetate) to provide the title compound (300 mg).

$^1$HNMR (CD$_3$CN) δ ppm: 2.46-2.52 (2H, m), 2.87-2.93 (2H, m), 5.04 (2H, s), 6.49-6.56 (1H, m), 6.32 (1H, s), 7.34-7.46 (5H, m), 7.80 (1H, s).

Reference Example 41

5-(Benzyloxy)-7-fluoro-8-(tetrahydro-2H-pyran-2-yloxy)-3,4-dihydroquinolin-2(1H)-one Synthesized analogous to Reference Example 38.

$^1$HNMR (CDCl$_3$) δ ppm: 1.5-2.0 (4H, m), 2.45-2.55 (2H, m), 2.80-2.90 (1H, m), 2.95-3.05 (1H, m), 3.45-3.55 (2H, m), 4.00-4.10 (2H, m), 4.90-4.92 (1H, m), 5.00 (2H, s), 6.39 (1H, d, J=12.3 Hz), 7.40-7.45 (5H, m), 8.18 (1H, s).

Reference Example 42

8-Fluoro-5-hydroxy-1-(4-methoxybenzyl)-3,4-dihydroquinolin-2(1H)-one

To a solution of 8-fluoro-1-(4-methoxybenzyl)-5-[(4-methoxybenzyl)oxy]-3,4-dihydroquinolin-2(1H)-one (2.17 g) in ethanol/ethyl acetate (1:1) (40 mL) was added 20% palladium hydroxide on carbon (wetted with 50% water) (0.2 g) and stirred at room temperature for 1.5 h under hydrogen atmosphere. The reaction solution was filtered and the solvents of the filtrate were distilled off. The residue was washed with hexane to provide the title compound (1.39 g).

$^1$HNMR (CDCl$_3$) δ ppm: 2.61-2.69 (2H, m), 2.81-2.88 (2H, m), 3.74 (3H, s), 5.21 (2H, brs), 5.31 (1H, s), 6.43 (1H, dd, J=9.0 Hz, 3.5 Hz), 6.71-6.78 (3H, m), 7.09-7.14 (2H, m).

Reference Example 43

8-Fluoro-1-(4-methoxybenzyl)-5-(tetrahydro-2H-pyran-2-yloxy)-3,4-dihydroquinolin-2(1H)-one To a stirred solution of 8-fluoro-5-(tetrahydro-2H-pyran-2-yloxy)-3,4-dihydroquinolin-2(1H)-one (8.8 g) in N,N-dimethylformamide (100 mL) was added 60% sodium hydride (1.46 g) at 0° C. and stirred at the same temperature for 20 min. 4-Methoxybenzyl chloride (5.40 mL) was added at room temperature and stirred for 5 h. To the reaction solution was added aqueous saturated ammonium chloride, and the solution was extracted with ethyl acetate. The organic layer was washed with water and brine, dried over anhydrous sodium sulfate, and then the solvent was distilled off to provide the title compound (12.7 g).

$^1$HNMR (CDCl$_3$) δ ppm: 1.56-1.72 (3H, m), 1.80-1.91 (2H, m), 1.91-2.03 (1H, m), 2.64 (2H, t, J=7.2 Hz), 2.82-2.98 (2H, m), 3.57-3.63 (1H, m), 3.74 (3H, s), 3.80-3.88 (1H, m), 5.18 (1H, d, J=15.3 Hz), 5.26 (1H, d, J=15.3 Hz), 5.27-5.30 (1H, m), 6.73-6.84 (4H, m), 7.10-7.15 (2H, m).

Reference Example 44

8-Chloro-1-(4-methoxybenzyl)-5-(tetrahydro-2H-pyran-2-yloxy)-3,4-dihydroquinolin-2(1H)-one Synthesized analogous to Reference Example 43.
$^1$HNMR (CDCl$_3$) δ ppm: 1.52-2.03 (6H, m), 2.50-2.60 (2H, m), 2.67-2.87 (2H, m), 3.54-3.65 (1H, m), 3.73 (3H, s), 3.75-3.88 (1H, m), 5.30-5.44 (3H, m), 6.68-6.76 (2H, m), 6.82 (1H, d, J=9.0 Hz), 7.03-7.15 (3H, m).

Reference Example 45

8-Chloro-5-hydroxy-1-(4-methoxybenzyl)-3,4-dihydroquinolin-2(1H)-one

To a solution of 8-chloro-1-(4-methoxybenzyl)-5-(tetrahydro-2H-pyran-2-yloxy)-3,4-dihydroquinolin-2(1H)-one (43.7 g) in ethanol (450 mL) was added p-toluenesulfonic acid pyridinium (5.47 g) and the reaction mixture was stirred at 80° C. for 1 h. The reaction solution was poured into ice water, the solution was extracted with ethyl acetate, the organic layer was dried over anhydrous sodium sulfate, and then the solvent was distilled off to provide the title compound (33.75 g, quant.).
$^1$HNMR (DMSO-d6) δ ppm: 2.42-2.54 (2H, m), 2.62-2.72 (2H, m), 3.67 (3H, s), 5.26 (2H, brs), 6.58 (1H, d, J=8.7 Hz), 6.76 (2H, d, J=8.7 Hz), 6.98-7.05 (3H, m), 9.79 (1H, brs).

Reference Example 46

5-[(3,5-Dimethylbenzyl)oxy]-8-fluoro-1-(4-methoxybenzyl)-7-(tetrahydro-2H-pyran-2-yloxy)-3,4-dihydroquinolin-2(1H)-one Synthesized analogous to Reference Example 43.
$^1$HNMR (CDCl$_3$) δ ppm: 1.60-1.67 (4H, m), 1.81-1.88 (2H, m), 2.31 (6H, s), 2.56-2.61 (2H, m), 2.80-2.85 (2H, m), 3.54-3.59 (1H, m), 3.74 (3H, s), 3.84-3.92 (1H, m), 4.87 (2H, s), 5.20 (2H, s), 5.28-5.30 (1H, m), 6.60 (1H, d, J=6.3 Hz), 6.74-6.77 (2H, m), 6.95-6.99 (3H, m), 7.12 (2H, d, J=8.7 Hz).

Reference Example 47

2,8-Dichloroquinolin-5-ol

To a solution of 8-chloro-5-hydroxyquinolin-2(1H)-one (13.0 g) in N,N-dimethylformamide (150 mL), thionyl chloride (14.52 mL) was added dropwise, and the reaction mixture was stirred at 80° C. for 2 h. The reaction solution was allowed to cool to room temperature, poured into ice water, the precipitate was collected on a filter and washed with water. The obtained crystal was dissolved in ethyl acetate, dried over anhydrous sodium sulfate, and then the solvent was distilled of to provide the title compound (9.8 g).
$^1$HNMR (CDCl$_3$) δ ppm: 6.97 (1H, d, J=8.3 Hz), 7.60 (1H, d, J=8.8 Hz), 7.79 (1H, d, J=8.3 Hz), 8.57 (1H, d, J=8.8 Hz), 11.03 (1H, brs).

Reference Example 48

2-Chloro-8-fluoroquinolin-5-ol

Synthesized analogous to Reference Example 47.
$^1$HNMR (DMSO-d6) δ ppm: 6.88-6.94 (1H, m), 7.45-7.52 (1H, m), 7.56 (1H, d, J=8.5 Hz), 8.47-8.55 (1H, m), 10.74 (1H, brs).

Reference Example 49

2-Chloro-8-fluoro-5-(tetrahydro-2H-pyran-2-yloxy)quinoline

Synthesized analogous to Reference Example 19.
$^1$HNMR (CDCl$_3$) δ ppm: 1.60-1.83 (3H, m), 1.93-2.15 (3H, m), 3.64-3.69 (1H, m), 3.84-3.91 (1H, m), 5.57 (1H, t, J=3.1 Hz), 7.13 (1H, dd, J=8.7 Hz, 3.7 Hz), 7.33 (1H, dd, J=10.2 Hz, 8.7 Hz), 7.43 (1H, d, J=8.8 Hz), 8.53 (1H, dd, J=8.8 Hz, 1.6 Hz).

Reference Example 50

8-Fluoro-2-methoxyquinolin-5-ol

To a solution of 2-chloro-8-fluoro-5-(tetrahydro-2H-pyran-2-yloxy)quinoline (2.65 g) in N,N-dimethylformamide (25 mL), sodium methoxide (5M methanol solution) (5.6 mL) was added dropwise, and the reaction mixture was stirred at room temperature for 10 h. The reaction solution was poured into water, neutralized with acetic acid, and extracted with ethyl acetate. The organic layer was washed with water and brine, and dried over anhydrous sodium sulfate, and then the solvent was distilled off. The residue was dissolved into methanol (25 mL), 5 N hydrochloric acid (2 mL) was added thereto and the reaction mixture was stirred at room temperature for 5 h. To the mixture were added saturated aqueous sodium hydrogencarbonate (150 mL) and water (150 mL), the reaction mixture was stirred at room temperature for 1 h, and the precipitate was collected on a filter to provide the title compound (1.61 g).
$^1$HNMR (CDCl$_3$) δ ppm: 4.11 (3H, s), 5.38 (1H, brs), 6.60 (1H, dd, J=8.4 Hz, 3.5 Hz), 6.93 (1H, d, J=9.1 Hz), 7.16 (1H, dd, J=10.6 Hz, 8.4 Hz), 8.34 (1H, dd, J=9.1 Hz, 1.7 Hz).

Reference Example 51

2,8-Dichloro-5-(tetrahydro-2H-pyran-2-yloxy)quinoline

Synthesized analogous to Reference Example 19.
$^1$HNMR (CDCl$_3$) δ ppm: 1.72-1.81 (2H, m), 1.93-2.14 (4H, m), 3.63-3.68 (1H, m), 3.82-3.87 (1H, m), 5.62 (1H, t, J=3.0 Hz), 7.15 (1H, d, J=8.5 Hz), 7.43 (1H, d, J=8.7 Hz), 7.72 (1H, d, J=8.5 Hz), 8.56 (1H, d, J=8.7 Hz).

Reference Example 52

8-Chloro-2-methoxyquinolin-5-ol

Synthesized analogous to Reference Example 50.
$^1$HNMR (CDCl$_3$) δ ppm: 4.14 (3H, s), 5.70 (1H, brs), 6.65 (1H, d, J=8.2 Hz), 6.93 (1H, d, J=9.0 Hz), 7.54 (1H, d, J=8.2 Hz), 8.37 (1H, d, J=9.0 Hz).

Reference Example 53

8-Fluoro-1-(4-methoxybenzyl)-5-[(4-methoxybenzyl)oxy]-3,4-dihydroquinolin-2(1H)-one Under argon atmosphere, to a solution of 8-fluoro-5-hydroxy-3,4-dihydroquinolin-2(1H)-one (10.0 g) in N,N- dimethylformamide (100 mL) was added sodium hydride (55% in oil) (5.14 g) at 0° C., the reaction mixture was stirred at the same temperature for 30 min, and 4-methoxybenzyl chloride (16.0 mL) was added thereto dropwise. The reaction mixture was stirred at the same temperature for 1.5 h, then at room temperature for 7 h. To the reaction solution was added ammonium chloride aqueous solution, and the solution was extracted with ethyl acetate. The organic layer was washed with water and brine, dried over anhydrous sodium sulfate, and then the solvent was distilled of to provide the title compound (23.2 g, quant.).

$^1$HNMR (CDCl$_3$) δ ppm: 2.56-2.63 (2H, m), 2.82-2.89 (2H, m), 3.74 (3H, s), 3.82 (3H, s), 4.92 (2H, s), 5.22 (2H, brs), 6.59 (1H, dd, J=9.1 Hz, 3.4 Hz), 6.73-6.78 (2H, m), 6.82 (1H, dd, J=12.8 Hz, 9.1 Hz), 6.88-6.93 (2H, m), 7.09-7.14 (2H, m), 7.27-7.32 (2H, m).

Reference Example 54

7,8-Difluoro-1-(4-methoxybenzyl)-5-[(4-methoxybenzyl)oxy]-3,4-dihydroquinolin-2(1H)-one Synthesized analogous to Reference Example 53.
$^1$HNMR (CDCl$_3$) δ ppm: 2.57-2.63 (2H, m), 2.79-2.85 (2H, m), 3.75 (3H, s), 3.82 (3H, s), 4.88 (2H, s), 5.23 (2H, brs), 6.51 (1H, dd, J=11.7 Hz, 6.1 Hz), 6.75-6.80 (2H, m), 6.88-6.93 (2H, m), 7.09-7.15 (2H, m), 7.27-7.31 (2H, m).

Reference Example 55

7,8-Difluoro-5-hydroxy-1-(4-methoxybenzyl)-3,4-dihydroquinolin-2(1H)-one

Synthesized analogous to Reference Example 42.
$^1$HNMR (CDCl$_3$) δ ppm: 2.61-2.68 (2H, m), 2.78-2.83 (2H, m), 3.75 (3H, s), 5.22 (2H, brs), 5.40-6.20 (1H, broad signal), 6.34-6.42 (1H, m), 6.74-6.80 (2H, m), 7.08-7.14 (2H, m).

Reference Example 56

8-Fluoro-5-[(methylsulfanyl)methoxy]-3,4-dihydroquinolin-2(1H)-one

Under argon atmosphere, to a suspension of 8-fluoro-5-hydroxy-3,4-dihydroquinolin-2(1H)-one (5.0 g) and potassium carbonate (5.72 g) in N,N-dimethylformamide (50 mL), chloromethyl methyl sulfide (3.32 mL) was added dropwise at 0° C., and the reaction mixture was stirred at room temperature for 36 h. To the reaction solution was added water, and the precipitate was collected on a filter to provide the title compound (4.95 g).

$^1$HNMR (CDCl$_3$) δ ppm: 2.26 (3H, s), 2.60-2.25 (2H, m), 3.02 (2H, t, J=7.7 Hz), 5.15 (2H, s), 6.54 (1H, dd, J=9.1 Hz, 4.0 Hz), 6.93 (1H, dd, J=9.7 Hz, 9.2 Hz), 7.54 (1H, brs).

Reference Example 57

8-Fluoro-1-(4-methoxybenzyl)-5-[(methylsulfanyl)methoxy]-3,4-dihydroquinolin-2(1H)-one Synthesized analogous to Reference Example 43.
$^1$HNMR (CDCl$_3$) δ ppm: 2.22 (3H, s), 2.61-2.67 (2H, m), 2.86-2.92 (2H, m), 3.74 (3H, s), 5.10 (2H, s), 5.22 (2H, brs), 6.59 (1H, dd, J=9.1 Hz, 3.5 Hz), 6.73-6.78 (2H, m), 6.85 (1H, dd, J=12.7 Hz, 9.1 Hz), 7.10-7.15 (2H, m).

Reference Example 58

5-(Chloromethoxy)-8-fluoro-1-(4-methoxybenzyl)-3,4-dihydroquinolin-2(1H)-one

To a solution of 8-fluoro-1-(4-methoxybenzyl)-5-[(methylsulfanyl)methoxy]-3,4-dihydroquinolin-2(1H)-one (5.48 g) in dichloromethane (100 mL), sulfuryl chloride (1.22 mL) was added dropwise under ice-cooling, and the reaction mixture was stirred at the same temperature for 1 h. The solvent was distilled off to provide the title compound (5.3 g, quant.).

$^1$HNMR (CDCl$_3$) δ ppm: 2.60-2.66 (2H, m), 2.84-2.91 (2H, m), 3.74 (3H, s), 5.22 (2H, brs), 5.84 (2H, s), 6.74-6.78 (2H, m), 6.82 (1H, dd, J=9.2 Hz, 3.5 Hz), 6.90 (1H, dd, J=12.4 Hz, 9.2 Hz), 7.09-7.14 (2H, m).

Reference Example 59

1-tert-Butyl 4-ethyl 4-({[8-Fluoro-1-(4-methoxybenzyl)-2-oxo-1,2,3,4-tetrahydroquinolin-5-yl]oxy}methyl)piperidine-1,4-dicarboxylate Under argon atmosphere, to a solution of piperidine-1,4-dicarboxylic acid 4-ethyl 1-tert-butyl (9.75 g) in tetrahydrofuran (90 mL), lithium diisopropylamide (2 M heptane/tetrahydrofuran/ethylbenzene solution) (19.7 mL) was added dropwise at −70° C., the reaction mixture was stirred at the same temperature for 1 h, a solution of 5-(chloromethoxy)-8-fluoro-1-(4-methoxybenzyl)-3,4-dihydroquinolin-2(1H)-one (5.3 g) in tetrahydrofuran (50 mL) was added dropwise, and the reaction mixture was stirred at −40° C. for 7 h. To the reaction solution was added aqueous saturated ammonium chloride solution, the reaction was allowed to warm to room temperature, and extracted with ethyl acetate. The organic layer was washed with water and brine, and dried over anhydrous sodium sulfate, and then the solvent was distilled off. The residue was purified by silica gel column chromatography (hexane/ethyl acetate) to provide the title compound (6.31 g).

$^1$HNMR (CDCl$_3$) δ ppm: 1.21 (3H, t, J=7.1 Hz), 1.46 (9H, s), 1.48-1.58 (2H, m), 2.17-2.24 (2H, m), 2.57-2.63 (2H, m), 2.76-2.83 (2H, m), 2.83-3.15 (2H, m), 3.74 (3H, s), 3.79-4.04 (4H, m), 4.17 (2H, q, J=7.1 Hz), 5.21 (2H, brs), 6.45 (1H, dd, J=9.1 Hz, 3.3 Hz), 6.73-6.77 (2H, m), 6.81 (1H, dd, J=12.8 Hz, 9.1 Hz), 7.09-7.14 (2H, m).

Reference Example 60

Ethyl 4-({[8-fluoro-1-(4-methoxybenzyl)-2-oxo-1,2,3,4-tetrahydroquinolin-5-yl]oxy}methyl)piperidine-4-carboxylate To a solution of 4-({[8-fluoro-1-(4-methoxybenzyl)-2-oxo-1,2,3,4-tetrahydroquinolin-5-yl]oxy}methyl)piperidine-1,4-dicarboxylic acid 4-ethyl 1-tert-butyl (6.31 g) in ethyl acetate (60 mL) was added 4 N hydrochloric acid/ethyl acetate (60 mL), and the reaction mixture was stirred at room temperature for 3 h. The solvent was distilled off and to the residue was added ethyl acetate and water, the reaction mixture was made basic with aqueous sodium hydroxide, and then extracted with ethyl acetate. The organic layer was washed with water and brine, and dried over anhydrous sodium sulfate, and then the solvent was distilled off to provide the title compound (5.37 g, quant.).

$^1$HNMR (CDCl$_3$) δ ppm: 1.21 (3H, t, J=7.1 Hz), 1.51-1.59 (2H, m), 1.87 (1H, brs), 2.19-2.27 (2H, m), 2.57-2.63 (2H, m), 2.74-2.84 (4H, m), 2.96-3.03 (2H, m), 3.74 (3H, s), 3.90 (2H, s), 4.17 (2H, q, J=7.1 Hz), 5.21 (2H, brs), 6.45 (1H, dd, J=9.1 Hz, 3.3 Hz), 6.73-6.78 (2H, m), 6.81 (1H, dd, J=12.8 Hz, 9.1 Hz), 7.09-7.15 (2H, m).

Reference Example 61

8-Chloro-5-[(methylsulfanyl)methoxy]-3,4-dihydroquinolin-2(1H)-one

Synthesized analogous to Reference Example 56.
$^1$HNMR (CDCl$_3$) δ ppm: 2.26 (3H, s), 2.62 (2H, t, J=7.7 Hz), 3.01 (2H, t, J=7.7 Hz), 5.17 (2H, s), 6.59 (1H, d, J=8.9 Hz), 7.19 (1H, d, J=8.9 Hz), 7.74 (1H, brs).

Reference Example 62

8-Chloro-1-(4-methoxybenzyl)-5-[(methylsulfanyl)methoxy]-3,4-dihydroquinolin-2(1H)-one Synthesized analogous to Reference Example 43.
$^1$HNMR (CDCl$_3$) δ ppm: 2.21 (3H, s), 2.55 (2H, t, J=6.8 Hz), 2.77 (2H, t, J=6.8 Hz), 3.73 (3H, s), 5.12 (2H, s), 5.36 (2H, s), 6.64 (1H, d, J=9.0 Hz), 6.70-6.73 (2H, m), 7.05-7.08 (2H, m), 7.16 (1H, d, J=9.0 Hz).

Reference Example 63

8-Chloro-5-(chloromethoxy)-1-(4-methoxybenzyl)-3,4-dihydroquinolin-2(1H)-one

Synthesized analogous to Reference Example 58.
$^1$HNMR (CDCl$_3$) δ ppm: 2.55 (2H, t, J=6.8 Hz), 2.76 (2H, t, J=6.8 Hz), 3.73 (3H, s), 5.37 (2H, s), 5.85 (2H, s), 6.70-6.73 (2H, m), 6.87 (1H, d, J=9.0 Hz), 7.04-7.07 (2H, m), 7.22 (1H, d, J=9.0 Hz).

Reference Example 64

4-({[8-Chloro-1-(4-methoxybenzyl)-2-oxo-1,2,3,4-tetrahydroquinolin-5-yl]oxy}methyl)piperidine-1,4-dicarboxylic acid 4-ethyl 1-tert-butyl Synthesized analogous to Reference Example 59.
$^1$HNMR (CDCl$_3$) δ ppm: 1.20 (3H, t, J=7.1 Hz), 1.46 (9H, s), 1.52 (2H, br), 2.19-2.22 (2H, m), 2.52 (2H, t, J=6.8 Hz), 2.66-2.69 (2H, m), 3.00 (2H, brs), 3.73 (3H, s), 3.92 (4H, brs), 4.16 (2H, q, J=7.1 Hz), 5.36 (2H, s), 6.51 (1H, d, J=9.0 Hz), 6.70-6.73 (2H, m), 7.04-7.07 (2H, m), 7.12 (1H, d, J=8.9 Hz).

Reference Example 65

Ethyl 4-({[8-chloro-1-(4-methoxybenzyl)-2-oxo-1,2,3,4-tetrahydroquinolin-5-yl]oxy}methyl)piperidine-4-carboxylate Synthesized analogous to Reference Example 60.
$^1$HNMR (CDCl$_3$) δ ppm: 1.20 (3H, t, J=7.1 Hz), 1.64-1.69 (2H, m), 2.25-2.28 (2H, m), 2.52 (2H, t, J=6.7 Hz), 2.67-2.70 (2H, m), 2.81-2.86 (2H, m), 3.07-3.12 (2H, m), 3.73 (3H, s), 3.93 (2H, s), 4.17 (2H, q, J=7.1 Hz), 5.36 (2H, s), 6.51 (1H, d, J=9.0 Hz), 6.70-6.73 (2H, m), 7.04-7.07 (2H, m), 7.12 (1H, d, J=8.8 Hz).

Reference Example 66

Ethyl 1-(3,5-dichloropyridin-2-yl)-4-({[8-fluoro-1-(4-methoxybenzyl)-2-oxo-1,2,3,4-tetrahydroquinolin-5-yl]oxy}methyl)piperidine-4-carboxylate A solution of ethyl 4-({[8-fluoro-1-(4-methoxybenzyl)-2-oxo-1,2,3,4-tetrahydroquinolin-5-yl]oxy}methyl)piperidine-4-carboxylate (5.37 g), 2,3,5-trichloropyridine (2.50 g) and potassium carbonate (2.37 g) in N-methyl-2-pyrrolidone (50 mL) was stirred at 100° C. for 3 days. To the reaction solution was added ammonium chloride aqueous solution, and the reaction mixture was stirred and extracted with ethyl acetate. The organic layer was washed with water and brine, and dried over anhydrous sodium sulfate, and then the solvent was distilled off. The residue was purified by silica gel column chromatography (hexane/ethyl acetate) to provide the title compound (3.17 g).
$^1$HNMR (CDCl$_3$) δ ppm: 1.23 (3H, t, J=7.1 Hz), 1.74-1.83 (2H, m), 2.32-2.39 (2H, m), 2.58-2.64 (2H, m), 2.78-2.84 (2H, m), 3.02-3.10 (2H, m), 3.60-3.68 (2H, m), 3.74 (3H, s), 3.97 (2H, s), 4.18 (2H, q, J=7.1 Hz), 5.22 (2H, brs), 6.47 (1H, dd, J=9.1 Hz, 3.3 Hz), 6.73-6.78 (2H, m), 6.82 (1H, dd, J=12.8 Hz, 9.1 Hz), 7.09-7.15 (2H, m), 7.59 (1H, d, J=2.3 Hz), 8.11 (1H, d, J=2.3 Hz).

Reference Example 67

Ethyl 1-(3,5-difluoropyridin-2-yl)-4-({[8-fluoro-1-(4-methoxybenzyl)-2-oxo-1,2,3,4-tetrahydroquinolin-5-yl]oxy}methyl)piperidine-4-carboxylate Synthesized analogous to Reference Example 66.
$^1$HNMR (CDCl$_3$) δ ppm: 1.21 (3H, t, J=7.1 Hz), 1.72-1.80 (2H, m), 2.31-2.37 (2H, m), 2.60 (2H, t, J=7.1 Hz), 2.80 (2H, t, J=7.1 Hz), 3.05-3.12 (2H, m), 3.69-3.77 (2H, m), 3.75 (3H, s), 3.95 (2H, s), 4.16 (2H, q, J=7.1 Hz), 5.23 (2H, brs), 6.45 (1H, dd, J=9.1 Hz, 3.3 Hz), 6.73-6.78 (2H, m), 6.79 (1H, dd, J=12.7 Hz, 9.1 Hz), 7.08-7.14 (3H, m), 7.92 (1H, d, J=2.5 Hz).

Reference Example 68

Ethyl 4-({[8-fluoro-1-(4-methoxybenzyl)-2-oxo-1,2,3,4-tetrahydroquinolin-5-yl]oxy}methyl)-1-(5-fluoro-3-methylpyridin-2-yl)piperidine-4-carboxylate Under nitrogen atmosphere, a solution of ethyl 4-({[8-fluoro-1-(4-methoxybenzyl)-2-oxo-1,2,3,4-tetrahydroquinolin-5-yl]oxy}methyl)piperidine-4-carboxylate (2.69 g), 2-chloro-5-fluoro-3-methylpyridine (1 g), tris(dibenzylideneacetone)dipalladium (0) (0.105 g), 2,2'-bis(diphenylphosphino)-1,1'-binaphthyl (0.178 g) and sodium tert-butoxide (1.10 g) in toluene (20 mL) was stirred at 100° C. overnight. The reaction solution was poured into water, and the reaction mixture was extracted with ethyl acetate. The organic layer was washed with brine, dried over anhydrous sodium sulfate, and then the solvent was distilled off. The residue was purified by silica gel column chromatography (hexane/ethyl acetate) to provide the title compound (1.36 g).
$^1$HNMR (CDCl$_3$) δ ppm: 1.23 (3H, t, J=7.2 Hz), 1.77-1.82 (2H, m), 2.28 (3H, s), 2.34-2.37 (2H, m), 2.60-2.62 (2H, m), 2.81-2.83 (2H, m), 2.93-2.99 (2H, m), 3.19-3.23 (2H, m), 3.74 (3H, s), 4.00 (2H, s), 4.18 (2H, q, J=7.1 Hz), 5.22 (2H, s), 6.48 (1H, dd, J=9.1 Hz, 3.3 Hz), 6.74-6.77 (2H, m), 6.82 (1H, dd, J=12.7 Hz, 9.1 Hz), 7.11-7.14 (2H, m), 7.18 (1H, dd, J=8.6 Hz, 2.9 Hz), 7.99 (1H, d, J=3.0 Hz).

Reference Example 69

Ethyl 1-(2,4-dichlorophenyl)-4-({[8-fluoro-1-(4-methoxybenzyl)-2-oxo-1,2,3,4-tetrahydroquinolin-5-yl]oxy}methyl)piperidine-4-carboxylate Synthesized analogous to Reference Example 68.
$^1$HNMR (CDCl$_3$) δ ppm: 1.23 (3H, t, J=7.1 Hz), 1.80-1.85 (2H, m), 2.37-2.39 (2H, m), 2.60-2.63 (2H, m), 2.79-2.84 (4H, m), 3.20-3.24 (2H, m), 3.74 (3H, s), 3.98 (2H, s), 4.18 (2H, q, J=7.1 Hz), 5.22 (2H, s), 6.48 (1H, dd, J=9.1 Hz, 3.3 Hz), 6.74-6.77 (2H, m), 6.82 (1H, dd, J=12.7 Hz, 9.1 Hz), 6.94 (1H, d, J=8.6 Hz), 7.11-7.13 (2H, m), 7.17 (1H, dd, J=8.6 Hz, 2.5 Hz), 7.36 (1H, d, J=2.5 Hz).

Reference Example 70

Ethyl 1-(2,5-dichlorophenyl)-4-({[8-fluoro-1-(4-methoxybenzyl)-2-oxo-1,2,3,4-tetrahydroquinolin-5-yl]oxy}methyl)piperidine-4-carboxylate Under nitrogen atmosphere, a solution of ethyl 4-({[8-fluoro-1-(4-methoxybenzyl)-2-oxo-1,2,3,4-tetrahydroquinolin-5-yl]oxy}methyl)piperidine-4-carboxylate (300 mg), 1,4-dichloro-2-iodobenzene (0.103 mL), tris(dibenzylideneacetone)dipalladium (0) (11.7 mg), 2,2'-bis(diphenylphosphino)-1,1'-binaphthyl (19.85 mg) and cesium carbonate (415 mg) in toluene (6 mL) was stirred at 110° C. overnight. The reaction solution was poured into water, and the reaction mixture was extracted with ethyl acetate. The organic layer was washed with brine, and dried over anhydrous sodium sulfate, and then the solvent was distilled off. The residue was purified by silica gel column chromatography (hexane/ethyl acetate) to provide the title compound (240 mg).
$^1$HNMR (CDCl$_3$) δ ppm: 1.23 (3H, t, J=7.1 Hz), 1.80-1.86 (2H, m), 2.38-2.40 (2H, m), 2.60-2.63 (2H, m), 2.81-2.85 (4H, m), 3.24-3.28 (2H, m), 3.74 (3H, s), 3.98 (2H, s), 4.19 (2H, q, J=7.1 Hz), 5.22 (2H, s), 6.48 (1H, dd, J=9.1 Hz, 3.3 Hz), 6.74-6.77 (2H, m), 6.83 (1H, dd, J=12.8 Hz, 9.1 Hz), 6.94 (1H, dd, J=8.5 Hz, 2.4 Hz), 6.99 (1H, d, J=2.4 Hz), 7.11-7.13 (2H, m), 7.26-7.27 (1H, m).

Reference Example 71

Ethyl 4-({[8-fluoro-1-(4-methoxybenzyl)-2-oxo-1,2,3,4-tetrahydroquinolin-5-yl]oxy}methyl)-1-[4-(trifluoromethoxy)phenyl]piperidine-4-carboxylate Synthesized analogous to Reference Example 70.
$^1$HNMR (CDCl$_3$) δ ppm: 1.22 (3H, t, J=7.1 Hz), 1.74-1.80 (2H, m), 2.35-2.38 (2H, m), 2.60-2.62 (2H, m), 2.80-2.82 (2H, m), 2.92-2.98 (2H, m), 3.48-3.52 (2H, m), 3.74 (3H, s), 3.95 (2H, s), 4.18 (2H, q, J=7.1 Hz), 5.22 (2H, s), 6.46 (1H, dd, J=9.1 Hz, 3.3 Hz), 6.74-6.77 (2H, m), 6.82 (1H, dd, J=12.7 Hz, 9.1 Hz), 6.88-6.91 (2H, m), 7.09-7.13 (4H, m).

Reference Example 72

Ethyl 1-(2,4-dichloro-5-fluorophenyl)-4-({[8-fluoro-1-(4-methoxybenzyl)-2-oxo-1,2,3,4-tetrahydroquinolin-5-yl]oxy}methyl)piperidine-4-carboxylate Synthesized analogous to Reference Example 70.
$^1$HNMR (CDCl$_3$) δ ppm: 1.22 (3H, t, J=7.1 Hz), 1.79-1.85 (2H, m), 2.38-2.40 (2H, m), 2.60-2.63 (2H, m), 2.78-2.83 (4H, m), 3.23-3.26 (2H, m), 3.74 (3H, s), 3.97 (2H, s), 4.19 (2H, q, J=7.1 Hz), 5.22 (2H, s), 6.47 (1H, dd, J=9.1 Hz, 3.3 Hz), 6.74-6.77 (2H, m), 6.81-6.85 (2H, m), 7.12 (2H, d, J=8.6 Hz), 7.39 (1H, d, J=7.6 Hz).

Reference Example 73

Ethyl 1-(2,5-dichloro-4-fluorophenyl)-4-({[8-fluoro-1-(4-methoxybenzyl)-2-oxo-1,2,3,4-tetrahydroquinolin-5-yl]oxy}methyl)piperidine-4-carboxylate Synthesized analogous to Reference Example 70.
$^1$HNMR (CDCl$_3$) δ ppm: 1.23 (3H, t, J=7.1 Hz), 1.79-1.85 (2H, m), 2.37-2.40 (2H, m), 2.60-2.63 (2H, m), 2.77-2.84 (4H, m), 3.17-3.19 (2H, m), 3.74 (3H, s), 3.97 (2H, s), 4.19 (2H, q, J=7.1 Hz), 5.22 (2H, s), 6.47 (1H, dd, J=9.1 Hz, 3.3 Hz), 6.75-6.77 (2H, m), 6.83 (1H, dd, J=12.7 Hz, 9.1 Hz), 7.04 (1H, d, J=7.2 Hz), 7.12 (2H, d, J=8.6 Hz), 7.19 (1H, d, J=8.6 Hz).

Reference Example 74

Ethyl 4-({[8-fluoro-1-(4-methoxybenzyl)-2-oxo-1,2,3,4-tetrahydroquinolin-5-yl]oxy}methyl)-1-(2,4,5-trichlorophenyl)piperidine-4-carboxylate Synthesized analogous to Reference Example 70.
$^1$HNMR (CDCl$_3$) δ ppm: 1.23 (3H, t, J=7.1 Hz), 1.79-1.85 (2H, m), 2.37-2.40 (2H, m), 2.60-2.63 (2H, m), 2.79-2.83 (4H, m), 3.22-3.25 (2H, m), 3.74 (3H, s), 3.97 (2H, s), 4.19 (2H, q, J=7.1 Hz), 5.22 (2H, s), 6.47 (1H, dd, J=9.1 Hz, 3.2 Hz), 6.75-6.77 (2H, m), 6.82 (1H, dd, J=12.8 Hz, 8.9 Hz), 7.07 (1H, s), 7.12 (2H, d, J=8.6 Hz), 7.44 (1H, s).

Reference Example 75

Ethyl 4-({[8-fluoro-1-(4-methoxybenzyl)-2-oxo-1,2,3,4-tetrahydroquinolin-5-yl]oxy}methyl)-1-[5-fluoro-2-(trifluoromethyl)phenyl]piperidine-4-carboxylate Synthesized analogous to Reference Example 70.
$^1$HNMR (CDCl$_3$) δ ppm: 1.24 (3H, t, J=7.1 Hz), 1.77-1.83 (2H, m), 2.34-2.36 (2H, m), 2.60-2.63 (2H, m), 2.81-2.85 (4H, m), 3.01-3.03 (2H, m), 3.74 (3H, s), 3.97 (2H, s), 4.21 (2H, q, J=7.1 Hz), 5.22 (2H, s), 6.48 (1H, dd, J=9.1 Hz, 3.3 Hz), 6.75-6.77 (2H, m), 6.83 (1H, dd, J=12.7 Hz, 9.0 Hz), 6.87-6.91 (1H, m), 6.99 (1H, dd, J=10.1 Hz, 2.3 Hz), 7.12 (2H, d, J=8.6 Hz), 7.60 (1H, dd, J=8.7 Hz, 6.4 Hz).

Reference Example 76

Ethyl 1-(2,5-difluorophenyl)-4-({[8-fluoro-1-(4-methoxybenzyl)-2-oxo-1,2,3,4-tetrahydroquinolin-5-yl]oxy}methyl)piperidine-4-carboxylate Synthesized analogous to Reference Example 70.
$^1$HNMR (CDCl$_3$) δ ppm: 1.22 (3H, t, J=7.1 Hz), 1.79-1.84 (2H, m), 2.37-2.40 (2H, m), 2.60-2.63 (2H, m), 2.81-2.88 (4H, m), 3.32-3.35 (2H, m), 3.74 (3H, s), 3.96 (2H, s), 4.19 (2H, q, J=7.1 Hz), 5.22 (2H, s), 6.47 (1H, dd, J=9.1 Hz, 3.3 Hz), 6.56-6.66 (2H, m), 6.74-6.77 (2H, m), 6.82 (1H, dd, J=12.7 Hz, 9.1 Hz), 6.92-6.97 (1H, m), 7.12 (2H, d, J=8.6 Hz).

Reference Example 77

Ethyl 1-(4-chloro-2,6-difluorophenyl)-4-({[8-fluoro-1-(4-methoxybenzyl)-2-oxo-1,2,3,4-tetrahydroquinolin-5-yl]oxy}methyl)piperidine-4-carboxylate Synthesized analogous to Reference Example 68.
$^1$HNMR (CDCl$_3$) δ ppm: 1.23 (3H, t, J=7.1 Hz), 1.72-1.78 (2H, m), 2.30-2.32 (2H, m), 2.60-2.63 (2H, m), 2.80-2.83 (2H, m), 3.13-3.19 (4H, m), 3.74 (3H, s), 3.96 (2H, s), 4.20 (2H, q, J=7.1 Hz), 5.22 (2H, s), 6.47 (1H, dd, J=9.1 Hz, 3.3 Hz), 6.75-6.77 (2H, m), 6.80-6.88 (3H, m), 7.12 (2H, d, J=8.6 Hz).

Reference Example 78

Ethyl 4-({[8-fluoro-1-(4-methoxybenzyl)-2-oxo-1,2,3,4-tetrahydroquinolin-5-yl]oxy}methyl)-1-(2,4,6-trifluorophenyl)piperidine-4-carboxylate Synthesized analogous to Reference Example 70.
$^1$HNMR (CDCl$_3$) δ ppm: 1.23 (3H, t, J=7.1 Hz), 1.73-1.79 (2H, m), 2.30-2.33 (2H, m), 2.60-2.63 (2H, m), 2.80-2.83 (2H, m), 3.08-3.20 (4H, m), 3.74 (3H, s), 3.97 (2H, s), 4.20 (2H, q, J=7.1 Hz), 5.22 (2H, s), 6.48 (1H, dd, J=9.1 Hz, 3.3 Hz), 6.61 (2H, t, J=8.9 Hz), 6.74-6.77 (2H, m), 6.82 (1H, dd, J=12.8 Hz, 9.1 Hz), 7.12 (2H, d, J=8.6 Hz).

Reference Example 79

Ethyl 1-(4-chloro-2,5-difluorophenyl)-4-({[8-fluoro-1-(4-methoxybenzyl)-2-oxo-1,2,3,4-tetrahydroquinolin-5-yl]oxy}methyl)piperidine-4-carboxylate Under nitrogen atmosphere, a solution of ethyl 4-({[8-fluoro-1-(4-methoxybenzyl)-2-oxo-1,2,3,4-tetrahydroquinolin-5-yl]oxy}methyl)piperidine-4-carboxylate (0.85 g), 1-bromo-4-chloro-2,5-difluorobenzene (0.616 g), tris(dibenzylideneacetone)dipalladium (0) (0.033 g), 9,9-dimethyl-4,5-bis(diphenylphosphino)xanthene (Xantphos) (0.063 g) and cesium carbonate (1.177 g) in toluene (12 mL) was stirred at 110° C. overnight. The reaction solution was poured into water, and the solution was extracted with ethyl acetate. The organic layer was washed with brine, and dried over anhydrous sodium sulfate, and then the solvent was distilled off. The residue was purified by silica gel column chromatography (hexane/ethyl acetate) to provide the title compound (555 mg).
$^1$HNMR (CDCl$_3$) δ ppm: 1.22 (3H, t, J=7.1 Hz), 1.77-1.83 (2H, m), 2.37-2.39 (2H, m), 2.60-2.63 (2H, m), 2.80-2.87 (4H, m), 3.29-3.32 (2H, m), 3.74 (3H, s), 3.95 (2H, s), 4.19 (2H, q, J=7.1 Hz), 5.22 (2H, s), 6.47 (1H, dd, J=9.1 Hz, 3.3 Hz), 6.70-6.77 (3H, m), 6.82 (1H, dd, J=12.7 Hz, 9.0 Hz), 7.06 (1H, dd, J=11.6 Hz, 6.8 Hz), 7.12 (2H, d, J=8.6 Hz).

Reference Example 80

Ethyl 1-(4-chloro-2-fluorophenyl)-4-({[8-fluoro-1-(4-methoxybenzyl)-2-oxo-1,2,3,4-tetrahydroquinolin-5-yl]oxy}methyl)piperidine-4-carboxylate Synthesized analogous to Reference Example 79.
$^1$HNMR (CDCl$_3$) δ ppm: 1.22 (3H, t, J=7.1 Hz), 1.78-1.84 (2H, m), 2.37-2.39 (2H, m), 2.60-2.63 (2H, m), 2.80-2.87 (4H, m), 3.27-3.29 (2H, m), 3.74 (3H, s), 3.96 (2H, s), 4.18 (2H, q, J=7.1 Hz), 5.22 (2H, s), 6.47 (1H, dd, J=9.1 Hz, 3.3 Hz), 6.75-6.77 (2H, m), 6.80-6.88 (2H, m), 7.02-7.06 (2H, m), 7.12 (2H, d, J=8.6 Hz).

Reference Example 81

Ethyl 4-({[8-fluoro-1-(4-methoxybenzyl)-2-oxo-1,2,3,4-tetrahydroquinolin-5-yl]oxy}methyl)-1-(2,4,5-trifluorophenyl)piperidine-4-carboxylate Synthesized analogous to Reference Example 79.
$^1$HNMR (CDCl$_3$) δ ppm: 1.22 (3H, t, J=7.1 Hz), 1.78-1.84 (2H, m), 2.37-2.40 (2H, m), 2.60-2.63 (2H, m), 2.79-2.83 (4H, m), 3.23-3.25 (2H, m), 3.74 (3H, s), 3.95 (2H, s), 4.19 (2H, q, J=7.1 Hz), 5.22 (2H, s), 6.47 (1H, dd, J=9.1 Hz, 3.2 Hz), 6.74-6.93 (5H, m), 7.12 (2H, d, J=8.6 Hz).

Reference Example 82

Ethyl 4-({[8-fluoro-1-(4-methoxybenzyl)-2-oxo-1,2,3,4-tetrahydroquinolin-5-yl]oxy}methyl)-1-[2-fluoro-4-(trifluoromethyl)phenyl]piperidine-4-carboxylate Synthesized analogous to Reference Example 79.
$^1$HNMR (CDCl$_3$) δ ppm: 1.22 (3H, t, J=7.1 Hz), 1.79-1.84 (2H, m), 2.38-2.41 (2H, m), 2.60-2.63 (2H, m), 2.81-2.83 (2H, m), 2.91-2.97 (2H, m), 3.41-3.43 (2H, m), 3.74 (3H, s), 3.96 (2H, s), 4.19 (2H, q, J=7.1 Hz), 5.22 (2H, s), 6.47 (1H, dd, J=9.1 Hz, 3.2 Hz), 6.75-6.77 (2H, m), 6.82 (1H, dd, J=12.7 Hz, 9.1 Hz), 6.98 (1H, t, J=8.4 Hz), 7.12 (2H, d, J=8.6 Hz), 7.25-7.28 (1H, m), 7.31 (1H, d, J=8.5 Hz).

Reference Example 83

Ethyl 1-[2-chloro-4-(trifluoromethyl)phenyl]-4-({[8-fluoro-1-(4-methoxybenzyl)-2-oxo-1,2,3,4-tetrahydroquinolin-5-yl]oxy}methyl)piperidine-4-carboxylate Synthesized analogous to Reference Example 79.
$^1$HNMR (CDCl$_3$) δ ppm: 1.22 (3H, t, J=7.1 Hz), 1.81-1.87 (2H, m), 2.40-2.42 (2H, m), 2.60-2.63 (2H, m), 2.81-2.91 (4H, m), 3.33-3.35 (2H, m), 3.74 (3H, s), 3.99 (2H, s), 4.19 (2H, q, J=7.1 Hz), 5.22 (2H, s), 6.48 (1H, dd, J=9.1 Hz, 3.2 Hz), 6.74-6.77 (2H, m), 6.83 (1H, dd, J=12.7 Hz, 9.1 Hz), 7.07 (1H, t, J=8.4 Hz), 7.12 (2H, d, J=8.6 Hz), 7.45-7.46 (1H, m), 7.61 (1H, d, J=1.9 Hz).

Reference Example 84

Ethyl 1-(2,4-difluorophenyl)-4-({[8-fluoro-1-(4-methoxybenzyl)-2-oxo-1,2,3,4-tetrahydroquinolin-5-yl]oxy}methyl)piperidine-4-carboxylate Synthesized analogous to Reference Example 79.
$^1$HNMR (CDCl$_3$) δ ppm: 1.22 (3H, t, J=7.1 Hz), 1.79-1.85 (2H, m), 2.37-2.40 (2H, m), 2.60-2.63 (2H, m), 2.81-2.85 (4H, m), 3.22-3.24 (2H, m), 3.74 (3H, s), 3.96 (2H, s), 4.18 (2H, q, J=7.1 Hz), 5.22 (2H, s), 6.47 (1H, dd, J=9.1 Hz, 3.4 Hz), 6.75-6.84 (6H, m), 7.12 (2H, d, J=8.6 Hz).

Reference Example 85

Ethyl 4-({[8-fluoro-1-(4-methoxybenzyl)-2-oxo-1,2,3,4-tetrahydroquinolin-5-yl]oxy}methyl)-1-(2-fluoro-4-methylphenyl)piperidine-4-carboxylate Synthesized analogous to Reference Example 79.
$^1$HNMR (CDCl$_3$) δ ppm: 1.21 (3H, t, J=7.1 Hz), 1.79-1.85 (2H, m), 2.28 (3H, s), 2.37-2.39 (2H, m), 2.60-2.63 (2H, m), 2.81-2.85 (4H, m), 3.26-3.28 (2H, m), 3.74 (3H, s), 3.96 (2H, s), 4.18 (2H, q, J=7.1 Hz), 5.22 (2H, s), 6.47 (1H, dd, J=9.1 Hz, 3.3 Hz), 6.75-6.77 (2H, m), 6.80-6.86 (4H, m), 7.12 (2H, d, J=8.5 Hz).

Reference Example 86

Ethyl 1-[4-chloro-2-(trifluoromethyl)phenyl]-4-({[8-fluoro-1-(4-methoxybenzyl)-2-oxo-1,2,3,4-tetrahydroquinolin-5-yl]oxy}methyl)piperidine-4-carboxylate Synthesized analogous to Reference Example 79.
$^1$HNMR (CDCl$_3$) δ ppm: 1.23 (3H, t, J=7.1 Hz), 1.75-1.81 (2H, m), 2.33-2.35 (2H, m), 2.60-2.63 (2H, m), 2.81-2.86 (4H, m), 2.95-2.97 (2H, m), 3.74 (3H, s), 3.97 (2H, s), 4.20 (2H, q, J=7.1 Hz), 5.22 (2H, s), 6.48 (1H, dd, J=9.1 Hz, 3.3 Hz), 6.75-6.77 (2H, m), 6.82 (1H, dd, J=12.8 Hz, 9.0 Hz), 7.12 (2H, d, J=8.6 Hz), 7.26-7.28 (1H, m), 7.46 (1H, dd, J=8.6 Hz, 2.4 Hz), 7.59 (1H, d, J=2.4 Hz).

Reference Example 87

Ethyl 1-(4-bromo-2,5-difluorophenyl)-4-({[8-fluoro-1-(4-methoxybenzyl)-2-oxo-1,2,3,4-tetrahydroquinolin-5-yl]oxy}methyl)piperidine-4-carboxylate Synthesized analogous to Reference Example 79.
$^1$HNMR (CDCl$_3$) δ ppm: 1.22 (3H, t, J=7.1 Hz), 1.77-1.83 (2H, m), 2.36-2.39 (2H, m), 2.60-2.63 (2H, m), 2.80-2.87 (4H, m), 3.30-3.33 (2H, m), 3.74 (3H, s), 3.95 (2H, s), 4.19 (2H, q, J=7.1 Hz), 5.22 (2H, s), 6.46 (1H, dd, J=9.1 Hz, 3.2 Hz), 6.71 (1H, dd, J=10.2 Hz, 7.5 Hz), 6.74-6.77 (2H, m), 6.82 (1H, dd, J=12.7 Hz, 9.1 Hz), 7.12 (2H, d, J=8.6 Hz), 7.19 (1H, dd, J=11.4 Hz, 6.4 Hz).

Reference Example 88

Ethyl 1-(2',4'-dichloro-2,5-difluorobiphenyl-4-yl)-4-({[8-fluoro-1-(4-methoxybenzyl)-2-oxo-1,2,3,4-tetrahydroquinolin-5-yl]oxy}methyl)piperidine-4-carboxylate Under nitrogen atmosphere, to a solution of ethyl 1-(4-bromo-2,5-difluorophenyl)-4-({[8-fluoro-1-(4-methoxybenzyl)-2-oxo-1,2,3,4-tetrahydroquinolin-5-yl]oxy}methyl)piperidine-4-carboxylate (287 mg), 2,4-dichlorophenylboronic acid (108 mg) and 1,1'-bis(diphenylphosphino)ferrocene-palladium (II) dichloride dichloromethane adduct (17.7 mg) in 1,2-dimethoxyethane (4 mL) was added 2 M sodium carbonate aqueous solution (0.651 mL), and the reaction mixture was stirred under reflux for 20 h. The reaction solution was poured into water, and the solution was extracted with ethyl acetate. The organic layer was washed with brine, dried over anhydrous magnesium sulfate, and the solvent was distilled off. The residue was purified by silica gel column chromatography (hexane/ethyl acetate) to provide the title compound (213 mg).
$^1$HNMR (CDCl$_3$) δ ppm: 1.23 (3H, t, J=7.1 Hz), 1.80-1.86 (2H, m), 2.39-2.42 (2H, m), 2.61-2.64 (2H, m), 2.81-2.84 (2H, m), 2.90-2.95 (2H, m), 3.40-3.43 (2H, m), 3.74 (3H, s), 3.97 (2H, s), 4.20 (2H, q, J=7.1 Hz), 5.22 (2H, s), 6.48 (1H, dd, J=9.2 Hz, 3.2 Hz), 6.71 (1H, dd, J=12.7 Hz, 9.1 Hz), 6.75-6.77 (2H, m), 6.83 (1H, dd, J=12.7 Hz, 9.1 Hz), 6.96 (1H, dd, J=12.5 Hz, 6.7 Hz), 7.13 (2H, d, J=8.5 Hz), 7.23 (1H, d, J=8.3 Hz), 7.30 (1H, dd, J=8.3 Hz, 2.0 Hz), 7.49 (1H, d, J=2.1 Hz).

Reference Example 89

Ethyl 1-(4'-chloro-2,2',5-trifluorobiphenyl-4-yl)-4-({[8-fluoro-1-(4-methoxybenzyl)-2-oxo-1,2,3,4-tetrahydroquinolin-5-yl]oxy}methyl)piperidine-4-carboxylate Synthesized analogous to Reference Example 88.
$^1$HNMR (CDCl$_3$) δ ppm: 1.23 (3H, t, J=7.1 Hz), 1.80-1.86 (2H, m), 2.39-2.41 (2H, m), 2.60-2.63 (2H, m), 2.81-2.84 (2H, m), 2.90-2.94 (2H, m), 3.40-3.42 (2H, m), 3.74 (3H, s), 3.97 (2H, s), 4.20 (2H, q, J=7.1 Hz), 5.22 (2H, s), 6.48 (1H, dd, J=9.1 Hz, 3.3 Hz), 6.71-6.77 (3H, m), 6.83 (1H, dd, J=12.7 Hz, 9.1 Hz), 7.03 (1H, dd, J=12.7 Hz, 6.7 Hz), 7.13 (2H, d, J=8.6 Hz), 7.17-7.21 (2H, m), 7.26-7.31 (1H, m).

Reference Example 90

Ethyl 4-({[8-chloro-1-(4-methoxybenzyl)-2-oxo-1,2,3,4-tetrahydroquinolin-5-yl]oxy}methyl)-1-(2,4-dichlorophenyl)piperidine-4-carboxylate Synthesized analogous to Reference Example 79.
$^1$HNMR (CDCl$_3$) δ ppm: 1.20 (3H, t, J=7.1 Hz), 1.79-1.85 (2H, m), 2.37-2.39 (2H, m), 2.51-2.54 (2H, m), 2.69-2.72 (2H, m), 2.79-2.84 (2H, m), 3.21-3.23 (2H, m), 3.73 (3H, s), 4.00 (2H, s), 4.18 (2H, q, J=7.1 Hz), 5.37 (2H, s), 6.54 (1H, d, J=8.9 Hz), 6.71-6.73 (2H, m), 6.95 (1H, d, J=8.7 Hz), 7.05-7.07 (2H, m), 7.14 (1H, d, J=8.9 Hz), 7.18 (1H, dd, J=8.7 Hz, 2.4 Hz), 7.36 (1H, d, J=2.4 Hz).

Reference Example 91

Ethyl 1-(4-chloro-2-fluorophenyl)-4-({[8-chloro-1-(4-methoxybenzyl)-2-oxo-1,2,3,4-tetrahydroquinolin-5-yl]oxy}methyl)piperidine-4-carboxylate Synthesized analogous to Reference Example 79.
$^1$HNMR (CDCl$_3$) δ ppm: 1.20 (3H, t, J=7.1 Hz), 1.78-1.84 (2H, m), 2.36-2.39 (2H, m), 2.51-2.54 (2H, m), 2.69-2.71 (2H, m), 2.82-2.87 (2H, m), 3.26-3.29 (2H, m), 3.73 (3H, s), 3.98 (2H, s), 4.17 (2H, q, J=7.1 Hz), 5.37 (2H, s), 6.54 (1H, d, J=9.0 Hz), 6.70-6.73 (2H, m), 6.84-6.88 (1H, m), 7.02-7.07 (4H, m), 7.13 (1H, d, J=8.9 Hz).

Reference Example 92

Ethyl 1-(4-chloro-2,6-difluorophenyl)-4-({[8-chloro-1-(4-methoxybenzyl)-2-oxo-1,2,3,4-tetrahydroquinolin-5-yl]oxy}methyl)piperidine-4-carboxylate Synthesized analogous to Reference Example 79.
$^1$HNMR (CDCl$_3$) δ ppm: 1.21 (3H, t, J=7.1 Hz), 1.72-1.79 (2H, m), 2.29-2.32 (2H, m), 2.51-2.54 (2H, m), 2.69-2.71

(2H, m), 3.13-3.21 (4H, m), 3.73 (3H, s), 3.99 (2H, s), 4.19 (2H, q, J=7.1 Hz), 5.37 (2H, s), 6.54 (1H, d, J=9.0 Hz), 6.70-6.73 (2H, m), 6.84-6.89 (2H, m), 7.05-7.08 (2H, m), 7.13 (1H, d, J=8.9 Hz).

Reference Example 93

1-(3,5-Dichloropyridin-2-yl)-4-({[8-fluoro-1-(4-methoxybenzyl)-2-oxo-1,2,3,4-tetrahydroquinolin-5-yl]oxy}methyl)piperidine-4-carboxylic acid To a solution of ethyl 1-(3,5-dichloropyridin-2-yl)-4-({[8-fluoro-1-(4-methoxybenzyl)-2-oxo-1,2,3,4-tetrahydroquinolin-5-yl]oxy}methyl)piperidine-4-carboxylate (3.17 g) in methanol/tetrahydrofuran (1:1) (60 mL) was added 5 N aqueous sodium hydroxide (10.3 mL), and the reaction mixture was stirred at 60° C. for 5.5 h. The solvent was distilled off and to the residue were added water and 5 N hydrochloric acid to make the reaction residue acidic, and the solution was extracted with ethyl acetate. The organic layer was washed with water and brine, dried over anhydrous sodium sulfate, and then the solvent was distilled off to provide the title compound (3.15 g, quant.).
$^1$HNMR (CDCl$_3$) δ ppm: 1.75-1.84 (2H, m), 2.34-2.43 (2H, m), 2.58-2.66 (2H, m), 2.79-2.87 (2H, m), 3.09-3.18 (2H, m), 3.61-3.69 (2H, m), 3.72 (3H, s), 4.01 (2H, s), 5.22 (2H, brs), 6.50 (1H, dd, J=9.1 Hz, 3.2 Hz), 6.70-6.76 (2H, m), 6.83 (1H, dd, J=12.7 Hz, 9.1 Hz), 7.08-7.14 (2H, m), 7.60 (1H, d, J=2.3 Hz), 8.11 (1H, d, J=2.3 Hz).

Reference Example 94

1-(3,5-Difluoropyridin-2-yl)-4-({[8-fluoro-1-(4-methoxybenzyl)-2-oxo-1,2,3,4-tetrahydroquinolin-5-yl]oxy}methyl)piperidine-4-carboxylic acid Synthesized analogous to Reference Example 93.
$^1$HNMR (CDCl$_3$) δ ppm: 1.71-1.80 (2H, m), 2.33-2.40 (2H, m), 2.60 (2H, t, J=7.0 Hz), 2.81 (2H, t, J=7.0 Hz), 3.13-3.22 (2H, m), 3.71 (3H, s), 3.69-3.78 (2H, m), 3.99 (2H, s), 5.22 (2H, brs), 6.48 (1H, dd, J=9.0 Hz, 3.5 Hz), 6.70-6.74 (2H, m), 6.81 (1H, dd, J=13.0 Hz, 9.0 Hz), 7.08-7.14 (3H, m), 7.93 (1H, d J=2.5 Hz), 10.77 (1H, brs).

Reference Example 95

4-({[8-Fluoro-1-(4-methoxybenzyl)-2-oxo-1,2,3,4-tetrahydroquinolin-5-yl]oxy}methyl)-1-(5-fluoro-3-methylpyridin-2-yl)piperidine-4-carboxylic acid Synthesized analogous to Reference Example 93.
$^1$HNMR (CDCl$_3$) δ ppm: 1.70-2.00 (2H, br), 2.31-2.47 (2H, m), 2.59-2.62 (2H, m), 2.82-2.85 (2H, m), 3.10-3.47 (4H, br), 3.73 (3H, s), 4.02 (2H, s), 5.22 (2H, s), 6.51 (1H, dd, J=9.1 Hz, 3.2 Hz), 6.74-6.76 (2H, m), 6.84 (1H, dd, J=12.7 Hz, 9.1 Hz), 7.12 (2H, d, J=8.6 Hz), 7.31-7.37 (1H, m), 8.01 (1H, s).

Reference Example 96

1-(2,4-Dichlorophenyl)-4-({[8-fluoro-1-(4-methoxybenzyl)-2-oxo-1,2,3,4-tetrahydroquinolin-5-yl]oxy}methyl)piperidine-4-carboxylic acid Synthesized analogous to Reference Example 93.
$^1$HNMR (CDCl$_3$) δ ppm: 1.81-1.85 (2H, m), 2.40-2.42 (2H, m), 2.61-2.64 (2H, m), 2.82-2.91 (4H, m), 3.22-3.25 (2H, m), 3.72 (3H, s), 4.01 (2H, s), 5.22 (2H, s), 6.50 (1H, dd, J=9.1 Hz, 2.9 Hz), 6.73 (2H, d, J=8.7 Hz), 6.84 (1H, dd, J=12.6 Hz, 9.1 Hz), 6.95-6.97 (1H, m), 7.11 (2H, d, J=8.4 Hz), 7.17-7.19 (1H, m), 7.35-7.36 (1H, m).

Reference Example 97

1-(2,5-Dichlorophenyl)-4-({[8-fluoro-1-(4-methoxybenzyl)-2-oxo-1,2,3,4-tetrahydroquinolin-5-yl]oxy}methyl)piperidine-4-carboxylic acid Synthesized analogous to Reference Example 93.
$^1$HNMR (CDCl$_3$) δ ppm: 1.81-1.86 (2H, m), 2.40-2.43 (2H, m), 2.61-2.64 (2H, m), 2.83-2.92 (4H, m), 3.26-3.29 (2H, m), 3.72 (3H, s), 4.01 (2H, s), 5.23 (2H, s), 6.51 (1H, dd, J=9.1 Hz, 3.1 Hz), 6.74 (2H, d, J=8.6 Hz), 6.84 (1H, dd, J=12.6 Hz, 9.1 Hz), 6.94 (1H, dd, J=8.5 Hz, 2.4 Hz), 7.01 (1H, d, J=2.2 Hz), 7.12 (2H, d, J=8.6 Hz), 7.27 (1H, d, J=8.4 Hz).

Reference Example 98

4-({[8-Fluoro-1-(4-methoxybenzyl)-2-oxo-1,2,3,4-tetrahydroquinolin-5-yl]oxy}methyl)-1-[4-(trifluoromethoxy)phenyl]piperidine-4-carboxylic acid Synthesized analogous to Reference Example 93.
$^1$HNMR (CDCl$_3$) δ ppm: 1.70-1.85 (2H, br), 2.39-2.42 (2H, m), 2.61-2.64 (2H, m), 2.81-2.84 (2H, m), 2.98-3.09 (2H, br), 3.50-3.53 (2H, m), 3.71 (3H, s), 3.99 (2H, s), 5.22 (2H, s), 6.49 (1H, dd, J=9.1 Hz, 3.1 Hz), 6.71-6.74 (2H, m), 6.84 (1H, dd, J=12.7 Hz, 9.0 Hz), 6.87-6.94 (2H, m), 7.07-7.14 (4H, m).

Reference Example 99

1-(2,4-Dichloro-5-fluorophenyl)-4-({[8-fluoro-1-(4-methoxybenzyl)-2-oxo-1,2,3,4-tetrahydroquinolin-5-yl]oxy}methyl)piperidine-4-carboxylic acid Synthesized analogous to Reference Example 93.
$^1$HNMR (CDCl$_3$) δ ppm: 1.80-1.86 (2H, m), 2.41-2.43 (2H, m), 2.62-2.65 (2H, m), 2.83-2.89 (4H, m), 3.25-3.27 (2H, m), 3.73 (3H, s), 4.01 (2H, s), 5.22 (2H, s), 6.50 (1H, dd, J=9.2 Hz, 3.3 Hz), 6.73-6.75 (2H, m), 6.82-6.86 (2H, m), 7.12 (2H, d, J=8.6 Hz), 7.39 (1H, d, J=7.6 Hz).

Reference Example 100

1-(2,5-Dichloro-4-fluorophenyl)-4-({[8-fluoro-1-(4-methoxybenzyl)-2-oxo-1,2,3,4-tetrahydroquinolin-5-yl]oxy}methyl)piperidine-4-carboxylic acid Synthesized analogous to Reference Example 93.
$^1$HNMR (CDCl$_3$) δ ppm: 1.79-1.85 (2H, m), 2.41-2.44 (2H, m), 2.62-2.65 (2H, m), 2.83-2.90 (4H, m), 3.19-3.21 (2H, m), 3.72 (3H, s), 4.01 (2H, s), 5.23 (2H, s), 6.51 (1H, dd, J=9.2 Hz, 3.1 Hz), 6.72-6.74 (2H, m), 6.85 (1H, dd, J=12.6 Hz, 9.1 Hz), 7.06 (1H, d, J=7.2 Hz), 7.11 (2H, d, J=8.6 Hz), 7.20 (1H, d, J=8.6 Hz).

Reference Example 101

4-({[8-Fluoro-1-(4-methoxybenzyl)-2-oxo-1,2,3,4-tetrahydroquinolin-5-yl]oxy}methyl)-1-(2,4,5-trichlorophenyl)piperidine-4-carboxylic acid Synthesized analogous to Reference Example 93.
$^1$HNMR (CDCl$_3$) δ ppm: 1.79-1.84 (2H, m), 2.41-2.44 (2H, m), 2.62-2.65 (2H, m), 2.83-2.92 (4H, m), 3.24-3.26 (2H, m), 3.72 (3H, s), 4.02 (2H, s), 5.23 (2H, s), 6.50-6.52 (1H, m), 6.73 (2H, d, J=8.7 Hz), 6.84 (1H, dd, J=12.7 Hz, 9.1 Hz), 7.09-7.12 (3H, m), 7.44 (1H, s).

Reference Example 102

4-({[8-Fluoro-1-(4-methoxybenzyl)-2-oxo-1,2,3,4-tetrahydroquinolin-5-yl]oxy}methyl)-1-[5-fluoro-2-(trifluoromethyl)phenyl]piperidine-4-carboxylic acid Synthesized analogous to Reference Example 93.
$^1$HNMR (CDCl$_3$) δ ppm: 1.77-1.82 (2H, m), 2.38-2.41 (2H, m), 2.63-2.66 (2H, m), 2.83-2.86 (2H, m), 2.89-2.94 (2H, m), 3.03-3.05 (2H, m), 3.72 (3H, s), 4.02 (2H, s), 5.23 (2H, s), 6.52 (1H, dd, J=9.1 Hz, 3.2 Hz), 6.72-6.75 (2H, m), 6.83-6.91 (2H, m), 7.03 (1H, dd, J=10.1 Hz, 2.3 Hz), 7.11 (2H, d, J=8.6 Hz), 7.60 (1H, dd, J=8.8 Hz, 6.3 Hz).

Reference Example 103

1-(2,5-Difluorophenyl)-4-({[8-fluoro-1-(4-methoxybenzyl)-2-oxo-1,2,3,4-tetrahydroquinolin-5-yl]oxy}methyl)piperidine-4-carboxylic acid Synthesized analogous to Reference Example 93.
$^1$HNMR (CDCl$_3$) δ ppm: 1.80-1.85 (2H, m), 2.40-2.42 (2H, m), 2.61-2.64 (2H, m), 2.82-2.85 (2H, m), 2.91-2.96 (2H, m), 3.34-3.36 (2H, m), 3.72 (3H, s), 4.00 (2H, s), 5.22 (2H, s), 6.50 (1H, dd, J=9.0 Hz, 3.0 Hz), 6.57-6.62 (1H, m), 6.64-6.70 (1H, m), 6.74 (2H, d, J=8.5 Hz), 6.84 (1H, dd, J=12.6 Hz, 9.1 Hz), 6.92-6.98 (1H, m), 7.11 (2H, d, J=8.5 Hz).

Reference Example 104

1-(4-Chloro-2,6-difluorophenyl)-4-({[8-fluoro-1-(4-methoxybenzyl)-2-oxo-1,2,3,4-tetrahydroquinolin-5-yl]oxy}methyl)piperidine-4-carboxylic acid Synthesized analogous to Reference Example 93.
$^1$HNMR (CDCl$_3$) δ ppm: 1.74-1.80 (2H, m), 2.33-2.35 (2H, m), 2.61-2.64 (2H, m), 2.82-2.85 (2H, m), 3.15-3.18 (2H, m), 3.22-3.27 (2H, m), 3.73 (3H, s), 4.00 (2H, s), 5.22 (2H, s), 6.50 (1H, dd, J=9.1 Hz, 3.3 Hz), 6.73-6.75 (2H, m), 6.81-6.89 (3H, m), 7.12 (2H, d, J=8.6 Hz).

Reference Example 105

4-({[8-Fluoro-1-(4-methoxybenzyl)-2-oxo-1,2,3,4-tetrahydroquinolin-5-yl]oxy}methyl)-1-(2,4,6-trifluorophenyl)piperidine-4-carboxylic acid Synthesized analogous to Reference Example 93.
$^1$HNMR (CDCl$_3$) δ ppm: 1.75-1.80 (2H, m), 2.33-2.36 (2H, m), 2.61-2.64 (2H, m), 2.82-2.85 (2H, m), 3.10-3.13 (2H, m), 3.22-3.27 (2H, m), 3.73 (3H, s), 4.01 (2H, s), 5.22 (2H, s), 6.50 (1H, dd, J=9.1 Hz, 3.3 Hz), 6.62 (2H, t, J=8.9 Hz), 6.72-6.75 (2H, m), 6.84 (1H, dd, J=12.7 Hz, 9.1 Hz), 7.12 (2H, d, J=8.6 Hz).

Reference Example 106

1-(4-Chloro-2,5-difluorophenyl)-4-({[8-fluoro-1-(4-methoxybenzyl)-2-oxo-1,2,3,4-tetrahydroquinolin-5-yl]oxy}methyl)piperidine-4-carboxylic acid Synthesized analogous to Reference Example 93.
$^1$HNMR (CDCl$_3$) δ ppm: 1.77-1.83 (2H, m), 2.40-2.43 (2H, m), 2.62-2.65 (2H, m), 2.82-2.85 (2H, m), 2.90-2.95 (2H, m), 3.31-3.34 (2H, m), 3.72 (3H, s), 3.99 (2H, s), 5.23 (2H, s), 6.50 (1H, dd, J=9.1 Hz, 3.2 Hz), 6.71-6.77 (3H, m), 6.84 (1H, dd, J=12.7 Hz, 9.1 Hz), 7.07 (1H, dd, J=11.6 Hz, 6.9 Hz), 7.11 (2H, d, J=8.6 Hz).

Reference Example 107

1-(4-Chloro-2-fluorophenyl)-4-({[8-fluoro-1-(4-methoxybenzyl)-2-oxo-1,2,3,4-tetrahydroquinolin-5-yl]oxy}methyl)piperidine-4-carboxylic acid Synthesized analogous to Reference Example 93.
$^1$HNMR (CDCl$_3$) δ ppm: 1.78-1.84 (2H, m), 2.40-2.43 (2H, m), 2.62-2.65 (2H, m), 2.82-2.85 (2H, m), 2.90-2.94 (2H, m), 3.29-3.31 (2H, m), 3.72 (3H, s), 4.00 (2H, s), 5.22 (2H, s), 6.50 (1H, dd, J=9.1 Hz, 3.2 Hz), 6.71-6.73 (2H, m), 6.82-6.89 (2H, m), 7.02-7.06 (2H, m), 7.11 (2H, d, J=8.5 Hz).

Reference Example 108

4-({[8-Fluoro-1-(4-methoxybenzyl)-2-oxo-1,2,3,4-tetrahydroquinolin-5-yl]oxy}methyl)-1-(2,4,5-trifluorophenyl)piperidine-4-carboxylic acid Synthesized analogous to Reference Example 93.
$^1$HNMR (CDCl$_3$) δ ppm: 1.86-1.99 (2H, br), 2.43-2.46 (2H, m), 2.62-2.65 (2H, m), 2.82-2.84 (2H, m), 2.96-3.12 (2H, br), 3.31-3.34 (2H, m), 3.72 (3H, s), 4.01 (2H, s), 5.23 (2H, s), 6.52 (1H, dd, J=9.1 Hz, 3.1 Hz), 6.72-6.73 (2H, m), 6.85 (1H, dd, J=12.6 Hz, 9.1 Hz), 6.92-7.08 (2H, m), 7.11 (2H, d, J=8.6 Hz).

Reference Example 109

4-({[8-Fluoro-1-(4-methoxybenzyl)-2-oxo-1,2,3,4-tetrahydroquinolin-5-yl]oxy}methyl)-1-[2-fluoro-4-(trifluoromethyl)phenyl]piperidine-4-carboxylic acid Synthesized analogous to Reference Example 93.
$^1$HNMR (DMSO-d6) δ ppm: 1.72-1.78 (2H, m), 2.19-2.21 (2H, m), 2.57-2.60 (2H, m), 2.79-2.82 (2H, m), 2.92-2.96 (2H, m), 3.38-3.41 (2H, m), 3.68 (3H, s), 4.03 (2H, s), 5.09 (2H, s), 6.73 (1H, dd, J=9.2 Hz, 3.4 Hz), 6.79-6.82 (2H, m), 6.98 (1H, dd, J=13.1 Hz, 9.1 Hz), 7.06 (2H, d, J=8.7 Hz), 7.21 (1H, t, J=8.6 Hz), 7.44-7.46 (1H, m), 7.53 (1H, dd, J=13.2 Hz, 1.8 Hz).

Reference Example 110

1-[2-Chloro-4-(trifluoromethyl)phenyl]-4-({[8-fluoro-1-(4-methoxybenzyl)-2-oxo-1,2,3,4-tetrahydroquinolin-5-yl]oxy}methyl)piperidine-4-carboxylic acid Synthesized analogous to Reference Example 93.
$^1$HNMR (CDCl$_3$) δ ppm: 1.84-1.89 (2H, m), 2.43-2.46 (2H, m), 2.63-2.65 (2H, m), 2.83-2.86 (2H, m), 2.93-3.04 (2H, br), 3.35-3.38 (2H, m), 3.72 (3H, s), 4.03 (2H, s), 5.23 (2H, s), 6.51 (1H, dd, J=9.1 Hz, 3.3 Hz), 6.73-6.75 (2H, m), 6.85 (1H, dd, J=12.6 Hz, 9.0 Hz), 7.11-7.12 (3H, m), 7.45-7.48 (1H, m), 7.62 (1H, d, J=1.8 Hz).

Reference Example 111

1-(2,4-Difluorophenyl)-4-({[8-fluoro-1-(4-methoxybenzyl)-2-oxo-1,2,3,4-tetrahydroquinolin-5-yl]oxy}methyl)piperidine-4-carboxylic acid Synthesized analogous to Reference Example 93.
$^1$HNMR (CDCl$_3$) δ ppm: 2.40-2.84 (8H, m), 3.48-3.74 (7H, m), 4.08 (2H, s), 5.23 (2H, s), 6.52 (1H, dd, J=9.2 Hz, 3.21 Hz), 6.73-6.75 (2H, m), 6.84-6.99 (4H, m), 7.11 (2H, d, J=8.5 Hz).

Reference Example 112

4-({[8-Fluoro-1-(4-methoxybenzyl)-2-oxo-1,2,3,4-tetrahydroquinolin-5-yl]oxy}methyl)-1-(2-fluoro-4-methylphenyl)piperidine-4-carboxylic acid Synthesized analogous to Reference Example 93.
$^1$HNMR (CDCl$_3$) δ ppm: 1.74-1.97 (2H, br), 2.29 (3H, s), 2.40-2.44 (2H, m), 2.61-2.65 (2H, m), 2.81-3.05 (4H, m), 3.21-3.39 (2H, br), 3.71 (3H, s), 4.01 (2H, s), 5.22 (2H, s), 6.50 (1H, dd, J=9.1 Hz, 3.2 Hz), 6.72-6.73 (2H, m), 6.82-6.92 (4H, m), 7.11 (2H, d, J=8.5 Hz).

Reference Example 113

1-[4-Chloro-2-(trifluoromethyl)phenyl]-4-({[8-fluoro-1-(4-methoxybenzyl)-2-oxo-1,2,3,4-tetrahydroquinolin-5-yl]oxy}methyl)piperidine-4-carboxylic acid Synthesized analogous to Reference Example 93.
$^1$HNMR (CDCl$_3$) δ ppm: 1.74-1.97 (2H, m), 2.37-2.39 (2H, m), 2.62-2.65 (2H, m), 2.83-2.86 (2H, m), 2.89-2.99 (4H, m), 3.72 (3H, s), 4.01 (2H, s), 5.23 (2H, s), 6.51 (1H, dd, J=9.1 Hz, 3.3 Hz), 6.73-6.74 (2H, m), 6.84 (1H, dd, J=12.7 Hz, 9.1 Hz), 7.12 (2H, d, J=8.6 Hz), 7.29 (1H, d, J=8.6 Hz), 7.47 (1H, dd, J=8.6 Hz, 2.5 Hz), 7.60 (1H, d, J=2.5 Hz).

Reference Example 114

1-(2',4'-Dichloro-2,5-difluorobiphenyl-4-yl)-4-({[8-fluoro-1-(4-methoxybenzyl)-2-oxo-1,2,3,4-tetrahydroquinolin-5-yl]oxy}methyl)piperidine-4-carboxylic acid Synthesized analogous to Reference Example 93.
$^1$HNMR (CDCl$_3$) δ ppm: 1.95-2.08 (2H, br), 2.45-2.48 (2H, m), 2.63-2.66 (2H, m), 2.83-2.86 (2H, m), 3.10-3.24 (2H, br), 3.48-3.50 (2H, m), 3.72 (3H, s), 4.03 (2H, s), 5.23 (2H, s), 6.52 (1H, dd, J=9.1 Hz, 3.0 Hz), 6.73-6.74 (2H, m), 6.85 (1H, dd, J=12.5 Hz, 9.1 Hz), 6.99-7.08 (2H, m), 7.12 (2H, d, J=8.6 Hz), 7.23 (1H, d, J=8.3 Hz), 7.31 (1H, dd, J=8.3 Hz, 2.1 Hz), 7.50 (1H, d, J=2.1 Hz).

Reference Example 115

1-(4'-Chloro-2,2',5-trifluorobiphenyl-4-yl)-4-({[8-fluoro-1-(4-methoxybenzyl)-2-oxo-1,2,3,4-tetrahydroquinolin-5-yl]oxy}methyl)piperidine-4-carboxylic acid Synthesized analogous to Reference Example 93.
$^1$HNMR (CDCl$_3$) δ ppm: 1.82-1.88 (2H, m), 2.42-2.45 (2H, m), 2.63-2.65 (2H, m), 2.83-2.86 (2H, m), 2.99-3.04 (2H, m), 3.42-3.45 (2H, m), 3.72 (3H, s), 4.01 (2H, s), 5.23 (2H, s), 6.51 (1H, dd, J=9.1 Hz, 3.3 Hz), 6.73-6.80 (3H, m), 6.85 (1H, dd, J=12.7 Hz, 9.1 Hz), 7.04 (1H, dd, J=12.7 Hz, 6.7 Hz), 7.12 (2H, d, J=8.6 Hz), 7.17-7.21 (2H, m), 7.26-7.32 (1H, m).

Reference Example 116

4-({[8-Chloro-1-(4-methoxybenzyl)-2-oxo-1,2,3,4-tetrahydroquinolin-5-yl]oxy}methyl)-1-(2,4-dichlorophenyl)piperidine-4-carboxylic acid Synthesized analogous to Reference Example 93.
$^1$HNMR (CDCl$_3$) δ ppm: 1.79-1.85 (2H, m), 2.41-2.43 (2H, m), 2.51-2.54 (2H, m), 2.70-2.73 (2H, m), 2.87-2.91 (2H, m), 3.23-3.25 (2H, m), 3.70 (3H, s), 4.03 (2H, s), 5.39 (2H, s), 6.57 (1H, d, J=9.0 Hz), 6.67-6.68 (2H m), 6.96 (1H, d, J=8.6 Hz), 7.04-7.06 (2H, m), 7.15 (1H, d, J=8.9 Hz), 7.18 (1H, dd, J=8.7 Hz, 2.4 Hz), 7.36 (1H, d, J=2.4 Hz).

Reference Example 117

1-(4-Chloro-2-fluorophenyl)-4-({[8-chloro-1-(4-methoxybenzyl)-2-oxo-1,2,3,4-tetrahydroquinolin-5-yl]oxy}methyl)piperidine-4-carboxylic acid Synthesized analogous to Reference Example 93.
$^1$HNMR (CDCl$_3$) δ ppm: 1.78-1.84 (2H, m), 2.39-2.42 (2H, m), 2.51-2.54 (2H, m), 2.70-2.72 (2H, m), 2.89-2.94 (2H, m), 3.29-3.31 (2H, m), 3.70 (3H, s), 4.01 (2H, s), 5.38 (2H, s), 6.56 (1H, d, J=9.0 Hz), 6.67-6.69 (2H m), 6.86-6.89 (1H, m), 7.02-7.06 (4H, m), 7.15 (1H, d, J=8.9 Hz).

Reference Example 118

1-(4-Chloro-2,6-difluorophenyl)-4-({[8-chloro-1-(4-methoxybenzyl)-2-oxo-1,2,3,4-tetrahydroquinolin-5-yl]oxy}methyl)piperidine-4-carboxylic acid Synthesized analogous to Reference Example 93.
$^1$HNMR (CDCl$_3$) δ ppm: 1.75-1.82 (2H, m), 2.32-2.35 (2H, m), 2.51-2.54 (2H, m), 2.70-2.72 (2H, m), 3.14-3.28 (4H, m), 3.72 (3H, s), 4.03 (2H, s), 5.38 (2H, s), 6.56 (1H, d, J=8.9 Hz), 6.70 (2H, d, J=8.6 Hz), 6.84-6.90 (2H, m), 7.06 (2H, d, J=8.5 Hz), 7.14 (1H, d, J=8.9 Hz).

Reference Example 119

1-(5-Fluoro-3-methylpyridin-2-yl)-4-{[(8-fluoro-2-oxo-1,2,3,4-tetrahydroquinolin-5-yl)oxy]methyl}piperidine-4-carboxylic acid A solution of 4-({[8-fluoro-1-(4-methoxybenzyl)-2-oxo-1,2,3,4-tetrahydroquinolin-5-yl]oxy}methyl)-1-(5-fluoro-3- methylpyridin-2-yl)piperidine-4-carboxylic acid (1.33 g) and anisole (0.527 mL) in trifluoroacetic acid (10 mL) was stirred at 65° C. for 3 h. The reaction solution was concentrated, and the residue was purified by silica gel column chromatography (dichloromethane/ethyl acetate) to provide the title compound (1.00 g).

$^1$HNMR (DMSO-d6) δ ppm: 1.70-1.75 (2H, m), 2.18-2.21 (2H, m), 2.26 (3H, s), 2.43-2.46 (2H, m), 2.80-2.89 (4H, m), 3.17-3.20 (2H, m), 4.03 (2H, s), 6.62 (1H, dd, J=9.1 Hz, 3.8 Hz), 7.00-7.03 (1H, m), 7.05-7.52 (1H, m), 8.06-8.07 (1H, m), 10.03 (1H, s), 12.28-13.00 (1H, br).

Reference Example 120

1-(2,4-Dichlorophenyl)-4-{[(8-fluoro-2-oxo-1,2,3,4-tetrahydroquinolin-5-yl)oxy]methyl}piperidine-4-carboxylic acid Synthesized analogous to Reference Example 119.
$^1$HNMR (DMSO-d6) δ ppm: 1.73-1.78 (2H, m), 2.20-2.23 (2H, m), 2.43-2.46 (2H, m), 2.78-2.83 (4H, m), 3.15-3.17 (2H, m), 4.05 (2H, s), 6.62 (1H, dd, J=9.1 Hz, 3.8 Hz), 7.00-7.04 (1H, m), 7.17 (1H, d, J=8.8 Hz), 7.34 (1H, dd, J=8.7 Hz, 2.5 Hz), 7.53 (1H, d, J=2.5 Hz), 10.02 (1H, s), 12.59-12.79 (1H, br).

Reference Example 121

1-(2,5-Dichlorophenyl)-4-{[(8-fluoro-2-oxo-1,2,3,4-tetrahydroquinolin-5-yl)oxy]methyl}piperidine-4-carboxylic acid Synthesized analogous to Reference Example 119.
$^1$HNMR (DMSO-d6) δ ppm: 1.74-1.79 (2H, m), 2.19-2.22 (2H, m), 2.43-2.46 (2H, m), 2.80-2.86 (4H, m), 3.18-3.21 (2H, m), 4.07 (2H, s), 6.62 (1H, dd, J=9.1 Hz, 3.7 Hz), 7.00-7.04 (1H, m), 7.09 (1H, dd, J=8.5 Hz, 2.4 Hz), 7.17 (1H, d J=2.4 Hz), 7.43 (1H, d, J=8.5 Hz), 10.03 (1H, s), 12.54-12.81 (1H, br).

Reference Example 122

4-{[(8-Fluoro-2-oxo-1,2,3,4-tetrahydroquinolin-5-yl)oxy]methyl}-1-[4-(trifluoromethoxy)phenyl]piperidine-4-carboxylic acid Synthesized analogous to Reference Example 119.
$^1$HNMR (CDCl$_3$) δ ppm: 2.34-2.41 (2H, m), 2.51-2.58 (4H, m), 2.89-2.91 (2H, m), 3.46-3.51 (2H, m), 3.72-3.75 (2H, m), 3.86 (2H, s), 6.53 (1H, dd, J=9.2 Hz, 3.8 Hz), 6.90-6.96 (1H, m), 7.34-7.35 (2H, m), 7.57-7.59 (2H, m), 8.57-8.63 (1H, br).

Reference Example 123

1-(2,4-Dichloro-5-fluorophenyl)-4-{[(8-fluoro-2-oxo-1,2,3,4-tetrahydroquinolin-5-yl)oxy]methyl}piperidine-4-carboxylic acid Synthesized analogous to Reference Example 119.
$^1$HNMR (DMSO-d6) δ ppm: 1.73-1.78 (2H, m), 2.20-2.22 (2H, m), 2.43-2.46 (2H, m), 2.80-2.85 (4H, m), 3.19-3.23 (2H, m), 4.05 (2H, s), 6.62 (1H, dd, J=9.1 Hz, 3.8 Hz), 7.00-7.04 (1H, m), 7.24 (1H, d, J=11.2 Hz), 7.71 (1H, d, J=7.8 Hz), 10.03 (1H, s), 12.60-12.81 (1H, br).

Reference Example 124

4-{[(8-Fluoro-2-oxo-1,2,3,4-tetrahydroquinolin-5-yl)oxy]methyl}-1-[5-fluoro-2-(trifluoromethyl)phenyl]piperidine-4-carboxylic acid Synthesized analogous to Reference Example 119.
$^1$HNMR (DMSO-d6) δ ppm: 1.72-1.77 (2H, m), 2.15-2.18 (2H, m), 2.43-2.46 (2H, m), 2.80-2.84 (4H, m), 2.98-3.01 (2H, m), 4.09 (2H, s), 6.64 (1H, dd, J=9.1 Hz, 3.7 Hz), 7.03 (1H, t, J=9.7 Hz), 7.12-7.16 (1H, m), 7.38-7.41 (1H, m), 7.73 (1H, dd, J=8.7 Hz, 6.4 Hz), 10.03 (1H, s), 12.58-12.73 (1H, br).

Reference Example 125

1-(2,5-Difluorophenyl)-4-{[(8-fluoro-2-oxo-1,2,3,4-tetrahydroquinolin-5-yl)oxy]methyl}piperidine-4-carboxylic acid Synthesized analogous to Reference Example 119.
$^1$HNMR (DMSO-d6) δ ppm: 1.72-1.77 (2H, m), 2.18-2.20 (2H, m), 2.43-2.46 (2H, m), 2.80-2.87 (4H, m), 3.27-3.29 (2H, m), 4.04 (2H, s), 6.61 (1H, dd, J=9.1 Hz, 3.7 Hz), 6.71-6.76 (1H, m), 6.86-6.90 (1H, m), 7.02 (1H, t, J=9.7 Hz), 7.12-7.17 (1H, m), 10.03 (1H, s), 12.71 (1H, brs).

Reference Example 126

4-{[(8-Fluoro-2-oxo-1,2,3,4-tetrahydroquinolin-5-yl)oxy]methyl}-1-(2,4,5-trichlorophenyl)piperidine-4-carboxylic acid Synthesized analogous to Reference Example 119.
$^1$HNMR (DMSO-d6) δ ppm: 1.73-1.79 (2H, m), 2.18-2.22 (2H, m), 2.43-2.46 (2H, m), 2.80-2.87 (4H, m), 3.18-3.20 (2H, m), 4.06 (2H, s), 6.62 (1H, dd, J=9.2 Hz, 3.7 Hz), 7.02 (1H, t, J=9.7 Hz), 7.37 (1H, s), 7.76 (1H, s), 10.03 (1H, s), 12.70 (1H, brs).

Reference Example 127

1-(4-Chloro-2,6-difluorophenyl)-4-{[(8-fluoro-2-oxo-1,2,3,4-tetrahydroquinolin-5-yl)oxy]methyl}piperidine-4-carboxylic acid Synthesized analogous to Reference Example 119.
$^1$HNMR (DMSO-d6) δ ppm: 1.65-1.71 (2H, m), 2.14-2.17 (2H, m), 2.43-2.46 (2H, m), 2.79-2.82 (2H, m), 3.11-3.12 (4H, m), 4.02 (2H, s), 6.61 (1H, dd, J=9.1 Hz, 3.7 Hz), 7.01 (1H, t, J=9.7 Hz), 7.25-7.31 (2H, m), 10.03 (1H, s), 12.70 (1H, brs).

Reference Example 128

4-{[(8-Fluoro-2-oxo-1,2,3,4-tetrahydroquinolin-5-yl)oxy]methyl}-1-(2,4,6-trifluorophenyl)piperidine-4-carboxylic acid Synthesized analogous to Reference Example 119.
$^1$HNMR (DMSO-d6) δ ppm: 1.65-1.71 (2H, m), 2.14-2.17 (2H, m), 2.43-2.46 (2H, m), 2.79-2.82 (2H, m), 3.04-3.12 (4H, m), 4.02 (2H, s), 6.61 (1H, dd, J=9.1 Hz, 3.7 Hz), 7.00-7.03 (1H, m), 7.13 (2H, t, J=9.3 Hz), 10.03 (1H, s), 12.68 (1H, brs).

Reference Example 129

1-(2,5-Dichloro-4-fluorophenyl)-4-{[(8-fluoro-2-oxo-1,2,3,4-tetrahydroquinolin-5-yl)oxy]methyl}piperidine-4-carboxylic acid Synthesized analogous to Reference Example 119.
$^1$HNMR (DMSO-d6) δ ppm: 1.73-1.78 (2H, m), 2.19-2.21 (2H, m), 2.43-2.46 (2H, m), 2.79-2.83 (4H, m), 3.11-3.14 (2H, m), 4.06 (2H, s), 6.62 (1H, dd, J=9.1 Hz, 3.7 Hz), 7.02 (1H, t, J=9.7 Hz), 7.35 (1H, d, J=7.4 Hz), 7.66 (1H, d, J=9.1 Hz), 10.04 (1H, s), 12.69 (1H, brs).

Reference Example 130

1-(4-Chloro-2,5-difluorophenyl)-4-{[(8-fluoro-2-oxo-1,2,3,4-tetrahydroquinolin-5-yl)oxy]methyl}piperidine-4-carboxylic acid Synthesized analogous to Reference Example 119.
$^1$HNMR (DMSO-d6) δ ppm: 1.71-1.77 (2H, m), 2.17-2.20 (2H, m), 2.43-2.46 (2H, m), 2.80-2.88 (4H, m), 3.27-3.30 (2H, m), 4.03 (2H, s), 6.57-6.64 (1H, m), 7.02 (1H, t, J=9.7 Hz), 7.12 (1H, dd, J=11.3 Hz, 7.9 Hz), 7.50 (1H, dd, J=12.0 Hz, 7.1 Hz), 10.04 (1H, s), 12.72 (1H, brs).

Reference Example 131

1-(4-Chloro-2-fluorophenyl)-4-{[(8-fluoro-2-oxo-1,2,3,4-tetrahydroquinolin-5-yl)oxy]methyl}piperidine-4-carboxylic acid Synthesized analogous to Reference Example 119.
$^1$HNMR (DMSO-d6) δ ppm: 1.72-1.77 (2H, m), 2.18-2.21 (2H, m), 2.43-2.46 (2H, m), 2.80-2.84 (4H, m), 3.22-3.24 (2H, m), 4.03 (2H, s), 6.61 (1H, dd, J=9.1 Hz, 3.8 Hz), 7.00-7.03 (1H, m), 7.07 (1H, t, J=9.1 Hz), 7.16 (1H, dd, J=8.7 Hz, 2.0 Hz), 7.32 (1H, dd, J=12.4 Hz, 2.4 Hz), 10.03 (1H, s), 12.70 (1H, brs).

Reference Example 133

1-(3,5-Difluoropyridin-2-yl)-4-{[(8-fluoro-2-oxo-1,2,3,4-tetrahydroquinolin-5-yl)oxy]methyl}piperidine-4-carboxylic acid Synthesized analogous to Reference Example 119.
$^1$HNMR (CDCl$_3$) δ ppm: 1.67-1.75 (2H, m), 2.12-1.19 (2H, m), 2.42 (2H, t, J=7.5 Hz), 2.78 (2H, t, J=7.5 Hz), 3.02-3.10 (2H, m), 3.62-3.69 (2H, m), 4.02 (2H, s), 6.59 (1H, dd, J=9.0 Hz, 3.5 Hz), 6.99 (1H, t, J=9.5 Hz), 7.75-7.81 (1H, m), 8.09 (1H, d, J=2.5 Hz), 10.03 (1H, s), 12.72 (1H, brs).

Reference Example 134

5-{[1-(3,5-Dichloropyridin-2-yl)-4-isocyanatopiperidin-4-yl]methoxy}-8-fluoro-3,4-dihydroquinolin-2(1H)-one To a suspension of 1-(3,5-dichloropyridin-2-yl)-4-{[(8-fluoro-2-oxo-1,2,3,4-tetrahydroquinolin-5-yl)oxy]methyl}piperidine-4-carboxylic acid (1.46 g) in 1,4-dioxane (15 mL) were added triethylamine (0.456 mL) and diphenylphosphoryl azide (0.705 mL), and the reaction mixture was heated to reflux for 2 h. The solvent was distilled off and to the residue was added water, and insoluble materials were filtered off to provide the title compound (1.41 g).
$^1$HNMR (CDCl$_3$) δ ppm: 1.86-2.02 (4H, m), 2.62-2.69 (2H, m), 3.06 (2H, t, J=7.7 Hz), 3.17-3.26 (2H, m), 3.71-3.78 (2H, m), 3.95 (2H, s), 6.44 (1H, dd, J=9.1 Hz, 3.9 Hz), 6.93 (1H, t, J=9.4 Hz), 7.54 (1H, brs), 7.62 (1H, d, J=2.3 Hz), 8.14 (1H, d, J=2.3 Hz).

Reference Example 135

5-{[1-(3,5-Difluoropyridin-2-yl)-4-isocyanatopiperidin-4-yl]methoxy}-8-fluoro-3,4-dihydroquinolin-2(1H)-one Synthesized analogous to Reference Example 134.
$^1$HNMR (CDCl$_3$) δ ppm: 1.84-1.92 (2H, m), 1.92-1.98 (2H, m), 2.64 (2H, t, J=7.5 Hz), 3.04 (2H, t, J=7.5 Hz), 3.20-3.28 (2H, m), 3.82-3.88 (2H, m), 3.93 (2H, s), 6.42 (1H, dd, J=9.0 Hz, 4.0 Hz), 6.91 (1H, t, J=9.5 Hz), 7.11-7.17 (1H, m), 7.49 (1H, brs), 7.95 (1H, d, J=2.5 Hz).

Reference Example 136

8-Fluoro-5-{[1-(5-fluoro-3-methylpyridin-2-yl)-4-isocyanatopiperidin-4-yl]methoxy}-3,4-dihydroquinolin-2(1H)-one Synthesized analogous to Reference Example 134.
$^1$HNMR (CDCl$_3$) δ ppm: 1.88-1.98 (4H, m), 2.29 (3H, s), 2.65-2.68 (2H, m), 3.05-3.08 (2H, m), 3.15-3.20 (2H, m), 3.25-3.28 (2H, m), 3.96 (2H, s), 6.45 (1H, dd, J=9.1 Hz, 3.9 Hz), 6.93 (1H, t, J=9.4 Hz), 7.20 (1H, dd, J=8.5 Hz, 2.7 Hz), 7.51 (1H, brs), 8.02 (1H, d, J=2.9 Hz).

Reference Example 137

5-{[1-(2,4-Dichlorophenyl)-4-isocyanatopiperidin-4-yl]methoxy}-8-fluoro-3,4-dihydroquinolin-2(1H)-one Synthesized analogous to Reference Example 134.
$^1$HNMR (CDCl$_3$) δ ppm: 1.93-2.00 (4H, m), 2.64-2.68 (2H, m), 2.99-3.08 (4H, m), 3.26-3.28 (2H, m), 3.96 (2H, s), 6.45 (1H, dd, J=9.1 Hz, 3.9 Hz), 6.93 (1H, t, J=9.4 Hz), 7.03 (1H, d, J=8.7 Hz), 7.22 (1H, dd, J=8.6 Hz, 2.4 Hz), 7.38 (1H, d, J=2.5 Hz), 7.53 (1H, brs).

Reference Example 138

5-{[1-(2,5-Dichlorophenyl)-4-isocyanatopiperidin-4-yl]methoxy}-8-fluoro-3,4-dihydroquinolin-2(1H)-one Synthesized analogous to Reference Example 134.
$^1$HNMR (CDCl$_3$) δ ppm: 1.88-2.00 (4H, m), 2.65-2.68 (2H, m), 3.00-3.08 (4H, m), 3.31-3.33 (2H, m), 3.96 (2H, s), 6.45 (1H, dd, J=9.1 Hz, 3.8 Hz), 6.94 (1H, t, J=9.4 Hz), 7.08 (1H, d, J=2.3 Hz), 7.17-7.22 (1H, m), 7.28-7.30 (1H, m), 7.69 (1H, brs).

Reference Example 139

8-Fluoro-5-({4-isocyanato-1-[4-(trifluoromethoxy)phenyl]piperidin-4-yl}methoxy)-3,4-dihydroquinolin-2(1H)-one Synthesized analogous to Reference Example 134.

¹HNMR (CDCl₃) δ ppm: 1.98-2.08 (4H, m), 2.61-2.66 (2H, m), 2.94-2.98 (2H, m), 3.02-3.06 (2H, m), 3.54-3.57 (2H, m), 3.94 (2H, s), 6.41-6.44 (1H, m), 6.86-7.46 (5H, m), 7.56 (1H, brs).

Reference Example 140

5-{[1-(2,4-Dichloro-5-fluorophenyl)-4-isocyanatopiperidin-4-yl]methoxy}-8-fluoro-3,4-dihydroquinolin-2(1H)-one Synthesized analogous to Reference Example 134.
¹HNMR (CDCl₃) δ ppm: 1.92-2.01 (4H, m), 2.64-2.67 (2H, m), 2.97-3.02 (2H, m), 3.04-3.07 (2H, m), 3.29-3.31 (2H, m), 3.96 (2H, s), 6.45 (1H, dd, J=9.1 Hz, 3.8 Hz), 6.89-6.96 (2H, m), 7.41 (1H, d, J=7.6 Hz), 7.56 (1H, brs).

Reference Example 141

8-Fluoro-5-({1-[5-fluoro-2-(trifluoromethyl)phenyl]-4-isocyanatopiperidin-4-yl}methoxy)-3,4-dihydroquinolin-2(1H)-one Synthesized analogous to Reference Example 134.
¹HNMR (CDCl₃) δ ppm: 1.92-1.95 (4H, m), 2.64-2.67 (2H, m), 3.05-3.08 (6H, m), 3.96 (2H, s), 6.45 (1H, dd, J=9.1 Hz, 3.8 Hz), 6.92-6.96 (2H, m), 7.11 (1H, dd, J=9.9 Hz, 2.3 Hz), 7.51 (1H, brs), 7.63 (1H, dd, J=8.8 Hz, 6.1 Hz).

Reference Example 142 tert-Butyl (4-{[(8-fluoro-2-oxo-1,2,3,4-tetrahydroquinolin-5-yl)oxy]methyl}-1-[5-fluoro-2-(trifluoromethyl)phenyl]piperidin-4-yl)carbamate Synthesized analogous to Reference Example 134. In place of 1,4-dioxane, tert-butanol was used as the solvent.
¹HNMR (CDCl₃) δ ppm: 1.42 (9H, s), 1.92-1.98 (2H, m), 2.22-2.24 (2H, m), 2.63-2.66 (2H, m), 2.93-3.06 (6H, m), 4.13 (2H, s), 4.46 (1H, brs), 6.51 (1H, dd, J=9.1 Hz, 3.9 Hz), 6.89-6.93 (2H, m), 7.06 (1H, dd, J=10.1 Hz, 2.4 Hz), 7.54-7.63 (2H, m).

Reference Example 143

5-{[1-(2,5-Difluorophenyl)-4-isocyanatopiperidin-4-yl]methoxy}-8-fluoro-3,4-dihydroquinolin-2(1H)-one Synthesized analogous to Reference Example 134.
¹HNMR (CDCl₃) δ ppm: 1.92-2.00 (4H, m), 2.65-2.68 (2H, m), 3.02-3.07 (4H, m), 3.38-3.41 (2H, m), 3.95 (2H, s), 6.45 (1H, dd, J=9.1 Hz, 3.8 Hz), 6.61-6.65 (1H, m), 6.69-6.73 (1H, m), 6.92-7.00 (2H, m), 7.50 (1H, brs).

Reference Example 144

8-Fluoro-5-{[4-isocyanato-1-(2,4,5-trichlorophenyl)piperidin-4-yl]methoxy}-3,4-dihydroquinolin-2(1H)-one Synthesized analogous to Reference Example 134.
¹HNMR (CDCl₃) δ ppm: 1.92-2.01 (4H, m), 2.63-2.68 (2H, m), 2.97-3.07 (4H, m), 3.28-3.30 (2H, m), 3.96 (2H, s), 6.45 (1H, dd, J=9.1 Hz, 3.7 Hz), 6.94 (1H, t, J=9.5 Hz), 7.16 (1H, s), 7.47 (1H, s), 7.50 (1H, brs).

Reference Example 145

5-{[1-(4-Chloro-2,6-difluorophenyl)-4-isocyanatopiperidin-4-yl]methoxy}-8-fluoro-3,4-dihydroquinolin-2(1H)-one Synthesized analogous to Reference Example 134.
¹HNMR (CDCl₃) δ ppm: 1.85-1.93 (4H, m), 2.64-2.67 (2H, m), 3.04-3.07 (2H, m), 3.13-3.15 (2H, m), 3.40-3.45 (2H, m), 3.93 (2H, s), 6.44 (1H, dd, J=9.1 Hz, 3.9 Hz), 6.88-6.94 (2H, m), 7.39 (1H, t, J=7.9 Hz), 7.54 (1H, brs).

Reference Example 146

8-Fluoro-5-{[4-isocyanato-1-(2,4,6-trifluorophenyl)piperidin-4-yl]methoxy}-3,4-dihydroquinolin-2(1H)-one Synthesized analogous to Reference Example 134.
¹HNMR (CDCl₃) δ ppm: 1.85-1.94 (4H, m), 2.64-2.67 (2H, m), 3.00-3.09 (4H, m), 3.40-3.45 (2H, m), 3.93 (2H, s), 6.44 (1H, dd, J=9.1 Hz, 3.8 Hz), 6.63-6.66 (2H, m), 6.93 (1H, t, J=9.4 Hz), 7.52 (1H, brs).

Reference Example 147

5-{[1-(2,5-Dichloro-4-fluorophenyl)-4-isocyanatopiperidin-4-yl]methoxy}-8-fluoro-3,4-dihydroquinolin-2(1H)-one Synthesized analogous to Reference Example 134.
¹HNMR (CDCl₃) δ ppm: 1.92-2.00 (4H, m), 2.65-2.68 (2H, m), 2.98-3.03 (2H, m), 3.05-3.08 (2H, m), 3.22-3.24 (2H, m), 3.96 (2H, s), 6.45 (1H, dd, J=9.1 Hz, 3.9 Hz), 6.94 (1H, t, J=9.4 Hz), 7.13 (1H, d, J=7.2 Hz), 7.22 (1H, d, J=8.5 Hz), 7.53 (1H, brs).

Reference Example 148

5-{[1-(4-Chloro-2,5-difluorophenyl)-4-isocyanatopiperidin-4-yl]methoxy}-8-fluoro-3,4-dihydroquinolin-2(1H)-one Synthesized analogous to Reference Example 134.
¹HNMR (CDCl₃) δ ppm: 1.90-2.00 (4H, m), 2.64-2.68 (2H, m), 3.02-3.07 (4H, m), 3.35-3.37 (2H, m), 3.95 (2H, s), 6.44 (1H, dd, J=9.1 Hz, 3.9 Hz), 6.79 (1H, dd, J=10.5 Hz, 7.6 Hz), 6.94 (1H, d, J=9.4 Hz), 7.09 (1H, dd, J=11.5 Hz, 6.9 Hz), 7.58 (1H, brs).

Reference Example 149

5-{[1-(4-Chloro-2-fluorophenyl)-4-isocyanatopiperidin-4-yl]methoxy}-8-fluoro-3,4-dihydroquinolin-2(1H)-one Synthesized analogous to Reference Example 134.
¹HNMR (CDCl₃) δ ppm: 1.91-2.00 (4H, m), 2.64-2.68 (2H, m), 3.02-3.07 (4H, m), 3.32-3.34 (2H, m), 3.94 (2H, s), 6.44 (1H, dd, J=9.1 Hz, 3.9 Hz), 6.92-6.95 (2H, m), 7.05-7.08 (2H, m), 7.57 (1H, brs).

Reference Example 150

8-Fluoro-5-{[4-isocyanato-1-(2,4,5-trifluorophenyl)piperidin-4-yl]methoxy}-1-(4-methoxybenzyl)-3,4-dihydroquinolin-2(1H)-one Synthesized analogous to Reference Example 134.

¹HNMR (CDCl₃) δ ppm: 1.89-1.98 (4H, m), 2.65-2.68 (2H, m), 2.91-2.94 (2H, m), 2.98-3.03 (2H, m), 3.27-3.29 (2H, m), 3.74 (3H, s), 3.90 (2H, s), 5.24 (2H, s), 6.49 (1H, dd, J=9.1 Hz, 3.3 Hz), 6.76-6.78 (2H, m), 6.81-6.87 (2H, m), 6.90-6.95 (1H, m), 7.13 (2H, d, J=8.6 Hz).

Reference Example 151

8-Fluoro-5-({1-[2-fluoro-4-(trifluoromethyl)phenyl]-4-isocyanatopiperidin-4-yl}methoxy)-1-(4-methoxybenzyl)-3,4-dihydroquinolin-2(1H)-one Synthesized analogous to Reference Example 134.
¹HNMR (CDCl₃) δ ppm: 1.90-1.99 (4H, m), 2.65-2.68 (2H, m), 2.91-2.94 (2H, m), 3.09-3.14 (2H, m), 3.45-3.48 (2H, m), 3.74 (3H, s), 3.90 (2H, s), 5.24 (2H, s), 6.49 (1H, dd, J=9.1 Hz, 3.3 Hz), 6.76-6.78 (2H, m), 6.85 (1H, dd, J=12.6 Hz, 9.0 Hz), 7.04 (1H, t, J=8.5 Hz), 7.13 (2H, d, J=8.6 Hz), 7.27-7.30 (1H, m), 7.35 (1H, d, J=8.7 Hz).

Reference Example 152

5-({1-[2-Chloro-4-(trifluoromethyl)phenyl]-4-isocyanatopiperidin-4-yl}methoxy)-8-fluoro-1-(4-methoxybenzyl)-3,4-dihydroquinolin-2(1H)-one Synthesized analogous to Reference Example 134.
¹HNMR (CDCl₃) δ ppm: 1.92-2.01 (4H, m), 2.65-2.68 (2H, m), 2.92-2.95 (2H, m), 3.05-3.10 (2H, m), 3.37-3.40 (2H, m), 3.74 (3H, s), 3.92 (2H, s), 5.24 (2H, s), 6.50 (1H, dd, J=9.1 Hz, 3.2 Hz), 6.76-6.78 (2H, m), 6.85 (1H, dd, J=12.7 Hz, 9.0 Hz), 7.13-7.16 (3H, m), 7.48-7.51 (1H, m), 7.63 (1H, d, J=1.8 Hz).

Reference Example 153

5-{[1-(2,4-Difluorophenyl)-4-isocyanatopiperidin-4-yl]methoxy}-8-fluoro-1-(4-methoxybenzyl)-3,4-dihydroquinolin-2(1H)-one Synthesized analogous to Reference Example 134.
¹HNMR (CDCl₃) δ ppm: 1.90-1.95 (4H, m), 2.65-2.68 (2H, m), 2.92-2.94 (2H, m), 2.99-3.05 (2H, m), 3.26-3.28 (2H, m), 3.74 (3H, s), 3.90 (2H, s), 5.24 (2H, s), 6.49 (1H, dd, J=9.2 Hz, 3.2 Hz), 6.75-6.78 (2H, m), 6.80-6.87 (3H, m), 6.96-7.00 (1H, m), 7.13 (2H, d, J=8.6 Hz).

Reference Example 154

8-Fluoro-5-{[1-(2-fluoro-4-methylphenyl)-4-isocyanatopiperidin-4-yl]methoxy}-1-(4-methoxybenzyl)-3,4-dihydroquinolin-2(1H)-one Synthesized analogous to Reference Example 134.
¹HNMR (CDCl₃) δ ppm: 1.93-1.96 (4H, m), 2.65-2.68 (2H, m), 2.92-2.95 (2H, m), 2.98-3.04 (2H, m), 3.30-3.32 (2H, m), 3.74 (3H, s), 3.89 (2H, s), 5.24 (2H, s), 6.49 (1H, dd, J=9.2 Hz, 3.3 Hz), 6.75-6.78 (2H, m), 6.82-6.93 (4H, m), 7.13 (2H, d, J=8.6 Hz).

Reference Example 155

5-({1-[4-Chloro-2-(trifluoromethyl)phenyl]-4-isocyanatopiperidin-4-yl}methoxy)-8-fluoro-1-(4-methoxybenzyl)-3,4-dihydroquinolin-2(1H)-one Synthesized analogous to Reference Example 134.
¹HNMR (CDCl₃) δ ppm: 1.86-1.94 (4H, m), 2.65-2.68 (2H, m), 2.91-2.97 (4H, m), 3.04-3.09 (2H, m), 3.74 (3H, s), 3.90 (2H, s), 5.24 (2H, s), 6.49 (1H, dd, J=9.1 Hz, 3.3 Hz), 6.75-6.78 (2H, m), 6.85 (1H, dd, J=12.7 Hz, 9.1 Hz), 7.13 (2H, d, J=8.6 Hz), 7.38 (1H, d, J=8.6 Hz), 7.51 (1H, dd, J=8.5 Hz, 2.5 Hz), 7.61 (1H, d, J=2.5 Hz).

Reference Example 156

5-{[1-(2',4'-Dichloro-2,5-difluorobiphenyl-4-yl)-4-isocyanatopiperidin-4-yl]methoxy}-8-fluoro-1-(4-methoxybenzyl)-3,4-dihydroquinolin-2(1H)-one Synthesized analogous to Reference Example 134.
¹HNMR (CDCl₃) δ ppm: 1.91-2.00 (4H, m), 2.66-2.69 (2H, m), 2.92-2.95 (2H, m), 3.08-3.13 (2H, m), 3.45-3.48 (2H, m), 3.75 (3H, s), 3.91 (2H, s), 5.24 (2H, s), 6.50 (1H, dd, J=9.1 Hz, 3.3 Hz), 6.76-6.79 (3H, m), 6.85 (1H, dd, J=12.7 Hz, 9.1 Hz), 6.98 (1H, dd, J=12.4 Hz, 6.8 Hz), 7.14 (2H, d, J=8.6 Hz), 7.24 (1H, d, J=8.3 Hz), 7.31 (1H, dd, J=8.3 Hz, 2.2 Hz), 7.50 (1H, d, J=2.1 Hz).

Reference Example 157

5-{[1-(4'-Chloro-2,2',5-trifluorobiphenyl-4-yl)-4-isocyanatopiperidin-4-yl]methoxy}-8-fluoro-1-(4-methoxybenzyl)-3,4-dihydroquinolin-2(1H)-one Synthesized analogous to Reference Example 134.
¹HNMR (CDCl₃) δ ppm: 1.91-2.00 (4H, m), 2.66-2.68 (2H, m), 2.92-2.95 (2H, m), 3.07-3.12 (2H, m), 3.45-3.47 (2H, m), 3.75 (3H, s), 3.91 (2H, s), 5.24 (2H, s), 6.50 (1H, dd, J=9.2 Hz, 3.2 Hz), 6.76-6.87 (4H, m), 7.03-7.07 (1H, m), 7.14 (2H, d, J=8.6 Hz), 7.18-7.22 (2H, m), 7.28-7.32 (1H, m).

Reference Example 158

8-Chloro-5-{[1-(2,4-dichlorophenyl)-4-isocyanatopiperidin-4-yl]methoxy}-1-(4-methoxybenzyl)-3,4-dihydroquinolin-2(1H)-one Synthesized analogous to Reference Example 134.
¹HNMR (CDCl₃) δ ppm: 1.91-1.96 (4H, m), 2.57-2.59 (2H, m), 2.81-2.83 (2H, m), 2.97-3.02 (2H, m), 3.24-3.27 (2H, m), 3.73 (3H, s), 3.93 (2H, s), 5.39 (2H, s), 6.56 (1H, d, J=8.9 Hz), 6.73 (2H, d, J=8.6 Hz), 7.03 (1H, d, J=8.6 Hz), 7.08 (2H, d, J=8.6 Hz), 7.16 (1H, d, J=8.9 Hz), 7.22 (1H, dd, J=8.6 Hz, 2.4 Hz), 7.38 (1H, d, J=2.5 Hz).

Reference Example 159

8-Chloro-5-{[1-(4-chloro-2-fluorophenyl)-4-isocyanatopiperidin-4-yl]methoxy}-1-(4-methoxybenzyl)-3,4-dihydroquinolin-2(1H)-one Synthesized analogous to Reference Example 134.
¹HNMR (CDCl₃) δ ppm: 1.90-1.97 (4H, m), 2.57-2.59 (2H, m), 2.80-2.83 (2H, m), 3.00-3.05 (2H, m), 3.31-3.34 (2H, m), 3.73 (3H, s), 3.92 (2H, s), 5.39 (2H, s), 6.55 (1H, d, J=9.0 Hz), 6.72-6.74 (2H, m), 6.91-6.95 (1H, m), 7.05-7.08 (4H, m), 7.16 (1H, d, J=8.9 Hz).

Reference Example 160

8-Chloro-5-{[1-(4-chloro-2,6-difluorophenyl)-4-isocyanatopiperidin-4-yl]methoxy}-1-(4-methoxybenzyl)-3,4-dihydroquinolin-2(1H)-one Synthesized analogous to Reference Example 134.

¹HNMR (CDCl₃) δ ppm: 1.83-1.91 (4H, m), 2.56-2.59 (2H, m), 2.80-2.83 (2H, m), 3.12-3.14 (2H, m), 3.39-3.44 (2H, m), 3.73 (3H, s), 3.91 (2H, s), 5.38 (2H, s), 6.55 (1H, d, J=9.0 Hz), 6.71-6.75 (2H, m), 6.86-6.92 (2H, m), 7.06-7.09 (2H, m), 7.15 (1H, d, J=8.9 Hz).

Reference Example 161

5-{[4-Amino-1-(2,4,5-trifluorophenyl)piperidin-4-yl]methoxy}-8-fluoro-1-(4-methoxybenzyl)-3,4-dihydroquinolin-2(1H)-one To 8-fluoro-5-{[4-isocyanato-1-(2,4,5-trifluorophenyl)piperidin-4-yl]methoxy}-1-(4-methoxybenzyl)-3,4-dihydroquinolin-2(1H)-one (364 mg) were added acetic acid (4 mL) and 2 N hydrochloric acid (3.2 mL), and the reaction mixture was stirred at room temperature overnight. To the reaction solution, aqueous sodium hydroxide was added to make the reaction residue basic, and the solution was extracted with ethyl acetate. The organic layer was washed with brine and dried over anhydrous magnesium sulfate. The solvent was distilled off and the residue was purified by silica gel column chromatography (basic silica gel; dichloromethane/ethyl acetate) to provide the title compound (305 mg).
¹HNMR (CDCl₃) δ ppm: 1.65-1.68 (2H, m), 1.90-1.95 (2H, m), 2.64-2.67 (2H, m), 2.88-2.91 (2H, m), 3.06-3.16 (4H, m), 3.71 (2H, s), 3.74 (3H, s), 5.24 (2H, s), 6.51 (1H, dd, J=9.1 Hz, 3.3 Hz), 6.75-6.78 (2H, m), 6.80-6.94 (3H, m), 7.13 (2H, d, J=8.6 Hz).

Reference Example 162

5-({4-Amino-1-[2-chloro-4-(trifluoromethyl)phenyl]piperidin-4-yl}methoxy)-8-fluoro-1-(4-methoxybenzyl)-3,4-dihydroquinolin-2(1H)-one Synthesized analogous to Reference Example 161.
¹HNMR (CDCl₃) δ ppm: 1.68-1.71 (2H, m), 1.93-1.98 (2H, m), 2.65-2.67 (2H, m), 2.89-2.92 (2H, m), 3.14-3.18 (2H, m), 3.23-3.25 (2H, m), 3.73-3.75 (5H, m), 5.24 (2H, s), 6.52 (1H, dd, J=9.1 Hz, 3.3 Hz), 6.75-6.78 (2H, m), 6.84 (1H, dd, 12.7 Hz, 9.1 Hz), 7.13-7.15 (3H, m), 7.45-7.48 (1H, m), 7.61 (1H, d, J=1.8 Hz).

Reference Example 163

5-({4-Amino-1-[2-fluoro-4-(trifluoromethyl)phenyl]piperidin-4-yl}methoxy)-8-fluoro-1-(4-methoxybenzyl)-3,4-dihydroquinolin-2(1H)-one Synthesized analogous to Reference Example 161.
¹HNMR (CDCl₃) δ ppm: 1.67-1.69 (2H, m), 1.91-1.97 (2H, m), 2.64-2.67 (2H, m), 2.88-2.91 (2H, m), 3.19-3.24 (2H, m), 3.30-3.33 (2H, m), 3.72 (2H, s), 3.74 (3H, s), 5.24 (2H, s), 6.51 (1H, dd, J=9.1 Hz, 3.3 Hz), 6.75-6.78 (2H, m), 6.84 (1H, dd, 12.7 Hz, 9.1 Hz), 7.03 (1H, t, 8.5 Hz), 7.14 (2H, d, J=8.6 Hz), 7.25-7.28 (1H, m), 7.32 (1H, d, J=8.5 Hz).

Reference Example 164

5-{[4-Amino-1-(2,4-difluorophenyl)piperidin-4-yl]methoxy}-8-fluoro-1-(4-methoxybenzyl)-3,4-dihydroquinolin-2(1H)-one Synthesized analogous to Reference Example 161.
¹HNMR (CDCl₃) δ ppm: 1.66-1.69 (2H, m), 1.91-1.97 (2H, m), 2.64-2.67 (2H, m), 2.88-2.91 (2H, m), 3.06-3.15 (4H, m), 3.72 (2H, s), 3.74 (3H, s), 5.24 (2H, s), 6.51 (1H, dd, J=9.1 Hz, 3.3 Hz), 6.75-6.86 (5H, m), 6.94-6.99 (1H, m), 7.13 (2H, d, J=8.6 Hz).

Reference Example 165

5-{[4-Amino-1-(2-fluoro-4-methylphenyl)piperidin-4-yl]methoxy}-8-fluoro-1-(4-methoxybenzyl)-3,4-dihydroquinolin-2(1H)-one Synthesized analogous to Reference Example 161.
¹HNMR (CDCl₃) δ ppm: 1.67-1.70 (2H, m), 1.93-1.98 (2H, m), 2.28 (3H, s), 2.64-2.67 (2H, m), 2.88-2.91 (2H, m), 3.05-3.19 (4H, m), 3.73 (2H, s), 3.74 (3H, s), 5.23 (2H, s), 6.52 (1H, dd, J=9.1 Hz, 3.4 Hz), 6.75-6.77 (2H, m), 6.81-6.92 (4H, m), 7.13 (2H, d, J=8.6 Hz).

Reference Example 166

5-({4-Amino-1-[4-chloro-2-(trifluoromethyl)phenyl]piperidin-4-yl}methoxy)-8-fluoro-1-(4-methoxybenzyl)-3,4-dihydroquinolin-2(1H)-one Synthesized analogous to Reference Example 161.
¹HNMR (CDCl₃) δ ppm: 1.61-1.64 (2H, m), 1.88-1.93 (2H, m), 2.64-2.67 (2H, m), 2.86-2.91 (4H, m), 3.07-3.11 (2H, m), 3.73 (2H, s), 3.74 (3H, s), 5.24 (2H, s), 6.52 (1H, dd, J=9.1 Hz, 3.3 Hz), 6.75-6.77 (2H, m), 6.84 (1H, dd, J=12.7 Hz, 9.2 Hz), 7.13 (2H, d, J=8.6 Hz), 7.36 (1H, d, J=8.6 Hz), 7.47-7.49 (1H, m), 7.60 (1H, d, J=2.5 Hz).

Reference Example 167

5-{[4-Amino-1-(2',4'-dichloro-2,5-difluorobiphenyl-4-yl)piperidin-4-yl]methoxy}-8-fluoro-1-(4-methoxybenzyl)-3,4-dihydroquinolin-2(1H)-one Synthesized analogous to Reference Example 161.
¹HNMR (CDCl₃) δ ppm: 1.67-1.70 (2H, m), 1.93-1.98 (2H, m), 2.65-2.68 (2H, m), 2.89-2.92 (2H, m), 3.17-3.22 (2H, m), 3.30-3.33 (2H, m), 3.73 (2H, s), 3.74 (3H, s), 5.24 (2H, s), 6.52 (1H, dd, J=9.1 Hz, 3.3 Hz), 6.74-6.78 (3H, m), 6.84 (1H, dd, J=12.7 Hz, 9.0 Hz), 6.96 (1H, dd, J=12.5 Hz, 6.8 Hz), 7.14 (2H, d, J=8.6 Hz), 7.24 (1H, d, J=8.3 Hz), 7.30 (1H, dd, J=8.3 Hz, 2.1 Hz), 7.50 (1H, d, J=2.1 Hz).

Reference Example 168

5-{[4-Amino-1-(4'-chloro-2,2',5-trifluorobiphenyl-4-yl)piperidin-4-yl]methoxy}-8-fluoro-1-(4-methoxybenzyl)-3,4-dihydroquinolin-2(1H)-one Synthesized analogous to Reference Example 161.
¹HNMR (CDCl₃) δ ppm: 1.67-1.70 (2H, m), 1.92-1.98 (2H, m), 2.65-2.68 (2H, m), 2.89-2.91 (2H, m), 3.17-3.22 (2H, m), 3.30-3.32 (2H, m), 3.72 (2H, s), 3.74 (3H, s), 5.24 (2H, s), 6.52 (1H, dd, J=9.1 Hz, 3.3 Hz), 6.76-6.86 (4H, m), 7.04 (1H, dd, J=12.5 Hz, 6.9 Hz), 7.14 (2H, d, J=8.6 Hz), 7.18-7.22 (2H, m), 7.29-7.32 (1H, m).

Reference Example 169

5-{[4-Amino-1-(2,4-dichlorophenyl)piperidin-4-yl]methoxy}-8-chloro-1-(4-methoxybenzyl)-3,4-dihydroquinolin-2(1H)-one Synthesized analogous to Reference Example 161.

¹HNMR (CDCl₃) δ ppm: 1.66-1.69 (2H, m), 1.91-1.97 (2H, m), 2.56-2.58 (2H, m), 2.77-2.79 (2H, m), 3.06-3.14 (4H, m), 3.74 (3H, s), 3.76 (2H, s), 5.38 (2H, s), 6.58 (1H, d, J=9.0 Hz), 6.71-6.73 (2H, m), 7.01 (1H, d, J=8.6 Hz), 7.08 (2H, d, J=8.6 Hz), 7.15 (1H, d, J=8.9 Hz), 7.19 (1H, dd, J=8.7 Hz, 2.4 Hz), 7.37 (1H, d, J=2.4 Hz).

Reference Example 170

5-{[4-Amino-1-(4-chloro-2-fluorophenyl)piperidin-4-yl]methoxy}-8-chloro-1-(4-methoxybenzyl)-3,4-dihydroquinolin-2(1H)-one Synthesized analogous to Reference Example 161.
¹HNMR (CDCl₃) δ ppm: 1.65-1.68 (2H, m), 1.90-1.96 (2H, m), 2.55-2.58 (2H, m), 2.76-2.79 (2H, m), 3.08-3.13 (2H, m), 3.16-3.20 (2H, m), 3.74 (3H, s), 3.74 (2H, s), 5.38 (2H, s), 6.58 (1H, d, J=9.0 Hz), 6.71-6.74 (2H, m), 6.90-6.94 (1H, m), 7.03-7.09 (4H, m), 7.15 (1H, d, J=8.9 Hz).

Reference Example 171

5-{[4-Amino-1-(4-chloro-2,6-difluorophenyl)piperidin-4-yl]methoxy}-8-chloro-1-(4-methoxybenzyl)-3,4-dihydroquinolin-2(1H)-one Synthesized analogous to Reference Example 161.
¹HNMR (CDCl₃) δ ppm: 1.60-1.63 (2H, m), 1.84-1.90 (2H, m), 2.55-2.58 (2H, m), 2.76-2.79 (2H, m), 3.06-3.09 (2H, m), 3.36-3.41 (2H, m), 3.74 (3H, s), 3.75 (2H, s), 5.38 (2H, s), 6.58 (1H, d, J=9.0 Hz), 6.72-6.74 (2H, m), 6.85-6.90 (2H, m), 7.08 (2H, d, J=8.6 Hz), 7.15 (1H, d, J=8.9 Hz).

Reference Example 172

1-(tert-Butoxycarbonyl)-4-({[8-fluoro-1-(4-methoxybenzyl)-2-oxo-1,2,3,4-tetrahydroquinolin-5-yl]oxy}methyl)piperidine-4-carboxylic acid Synthesized analogous to Reference Example 93.
¹HNMR (CDCl₃) δ ppm: 1.42-1.47 (11H, m), 2.11-2.13 (2H, m), 2.53-2.56 (2H, m), 2.76-2.78 (2H, m), 3.02 (2H, brs), 3.69 (3H, s), 3.84 (4H, brs), 5.17 (2H, s), 6.41 (1H, dd, J=9.2 Hz, 2.7 Hz), 6.70-6.77 (3H, m), 7.07 (2H, d, J=8.5 Hz).

Reference Example 173 tert-Butyl 4-({[8-fluoro-1-(4-methoxybenzyl)-2-oxo-1,2,3,4-tetrahydroquinolin-5-yl]oxy}methyl)-4-isocyanatopiperidine-1-carboxylate Synthesized analogous to Reference Example 134.
¹HNMR (CDCl₃) δ ppm: 1.46 (9H, s), 1.57-1.64 (2H, m), 1.81-1.83 (2H, m), 2.64-2.67 (2H, m), 2.89-2.91 (2H, m), 2.99-3.14 (2H, br), 3.74 (3H, s), 3.84 (2H, s), 3.95-4.19 (2H, br), 5.23 (2H, s), 6.46 (1H, dd, J=9.1 Hz, 3.2 Hz), 6.75-6.78 (2H, m), 6.84 (1H, dd, J=12.6 Hz, 9.1 Hz), 7.13 (2H, d, J=8.6 Hz).

Reference Example 174

5-[(4-Aminopiperidin-4-yl)methoxy]-8-fluoro-1-(4-methoxybenzyl)-3,4-dihydroquinolin-2(1H)-one A mixture of tert-butyl 4-({[8-fluoro-1-(4-methoxybenzyl)-2-oxo-1,2,3,4-tetrahydroquinolin-5-yl]oxy}methyl)-4-isocyanatopiperidine-1-carboxylate (1.18 g), acetic acid (10 mL) and 2 N hydrochloric acid (10 mL) was stirred at room temperature overnight. The reaction solution was concentrated, water was added to the residue, and the reaction mixture was made basic with aqueous sodium hydroxide, and the solution was extracted with ethyl acetate. The organic layer was washed with brine, and dried over anhydrous sodium sulfate. The solvent was distilled off, and the residue was purified by silica gel column chromatography (basic silica gel; dichloromethane/methanol) to provide the title compound (683 mg).
¹HNMR (CDCl₃) δ ppm: 1.50-1.53 (2H, m), 1.69-1.77 (2H, m), 2.63-2.66 (2H, m), 2.87-2.92 (4H, m), 2.98-3.03 (2H, br), 3.67 (2H, s), 3.74 (3H, s), 5.23 (2H, s), 6.50 (1H, dd, J=9.1 Hz, 3.3 Hz), 6.74-6.77 (2H, m), 6.82 (1H, dd, J=12.8 Hz, 9.1 Hz), 7.13 (2H, d, J=8.5 Hz).

Reference Example 175

5-{[4-Amino-1-(2-chloro-4-fluorophenyl)piperidin-4-yl]methoxy}-8-fluoro-1-(4-methoxybenzyl)-3,4-dihydroquinolin-2(1H)-one Synthesized analogous to Reference Example 79.
¹HNMR (CDCl₃) δ ppm: 1.67-1.69 (2H, m), 1.92-1.98 (2H, m), 2.64-2.67 (2H, m), 2.89-2.92 (2H, m), 3.02-3.10 (4H, m), 3.74-3.74 (5H, m), 5.24 (2H, s), 6.52 (1H, dd, J=9.0 Hz, 3.3 Hz), 6.75-6.78 (2H, m), 6.84 (1H, dd, J=12.6 Hz, 9.1 Hz), 6.92-6.96 (1H, m), 7.04-7.07 (1H, m), 7.12-7.14 (3H, m).

Reference Example 176

Ethyl 1-(2,4-dichlorophenyl)piperidine-4-carboxylate

Synthesized analogous to Reference Example 79.
¹HNMR (CDCl₃) δ ppm: 1.28 (3H, t, J=7.1 Hz), 1.91-2.07 (4H, m), 2.04-2.46 (1H, m), 2.66-2.71 (2H, m), 3.30-3.33 (2H, m), 4.17 (2H, q, J=7.1 Hz), 6.94 (1H, d, J=8.7 Hz), 7.17 (1H, dd, J=8.6 Hz, 2.5 Hz), 7.36 (1H, d, J=2.5 Hz).

Reference Example 177

Ethyl 1-(4-chloro-2-fluorophenyl)piperidine-4-carboxylate

Synthesized analogous to Reference Example 79.
¹HNMR (CDCl₃) δ ppm: 1.28 (3H, t, J=7.1 Hz), 1.89-2.05 (4H, m), 2.39-2.45 (1H, m), 2.69-2.75 (2H, m), 3.36-3.39 (2H, m), 4.16 (2H, q, J=7.1 Hz), 6.84-6.88 (1H, m), 7.01-7.05 (2H, m).

Reference Example 178

8-Fluoro-2-methoxy-5-[(methylsulfanyl)methoxy]quinoline

Synthesized analogous to Reference Example 56.
¹HNMR (CDCl₃) δ ppm: 2.29 (3H, s), 4.11 (3H, s), 5.29 (2H, s), 6.71 (1H, dd, J=8.6 Hz, 3.4 Hz), 6.94 (1H, d, J=9.1 Hz), 7.23-7.27 (1H, m), 8.39 (1H, dd, J=9.1 Hz, 1.7 Hz).

Reference Example 179

8-Chloro-2-methoxy-5-[(methylsulfanyl)methoxy]quinoline

Synthesized analogous to Reference Example 56.

¹HNMR (CDCl₃) δ ppm: 2.29 (3H, s), 4.14 (3H, s), 5.30 (2H, s), 6.74 (1H, d, J=8.5 Hz), 6.93 (1H, d, J=9.0 Hz), 7.64 (1H, d, J=8.4 Hz), 8.41 (1H, d, J=9.0 Hz).

Reference Example 180

Ethyl 1-(2,4-dichlorophenyl)-4-{[(8-fluoro-2-methoxyquinolin-5-yl)oxy]methyl}piperidine-4-carboxylate Synthesized analogous to Reference Example 59.
¹HNMR (CDCl₃) δ ppm: 1.21 (3H, t, J=7.1 Hz), 1.89-1.94 (2H, m), 2.48-2.50 (2H, m), 2.84-2.89 (2H, m), 3.25-3.27 (2H, m), 4.10 (3H, s), 4.16 (2H, s), 4.21 (2H, q, J=7.1 Hz), 6.58 (1H, dd, J=8.6 Hz, 3.3 Hz), 6.92 (1H, d, J=9.1 Hz), 6.97 (1H, d, J=8.6 Hz), 7.18-7.24 (2H, m), 7.37 (1H, d, J=2.4 Hz), 8.32 (1H, d, J=9.1 Hz).

Reference Example 181

Ethyl 1-(4-chloro-2-fluorophenyl)-4-{[(8-fluoro-2-methoxyquinolin-5-yl)oxy]methyl}piperidine-4-carboxylate Synthesized analogous to Reference Example 59.
¹HNMR (CDCl₃) δ ppm: 1.20 (3H, t, J=7.1 Hz), 1.87-1.93 (2H, m), 2.47-2.50 (2H, m), 2.87-2.93 (2H, m), 3.30-3.34 (2H, m), 4.10 (3H, s), 4.14 (2H, s), 4.21 (2H, q, J=7.1 Hz), 6.58 (1H, dd, J=8.6 Hz, 3.3 Hz), 6.87-6.93 (2H, m), 7.03-7.07 (2H, m), 7.22 (1H, dd, J=10.6 Hz, 8.6 Hz), 8.32 (1H, dd, J=9.0 Hz, 1.6 Hz).

Reference Example 182

Ethyl 4-{[(8-chloro-2-methoxyquinolin-5-yl)oxy]methyl}-1-(2,4-dichlorophenyl)piperidine-4-carboxylate Synthesized analogous to Reference Example 79.
¹HNMR (CDCl₃) δ ppm: 1.20 (3H, t, J=7.1 Hz), 1.89-1.94 (2H, m), 2.48-2.50 (2H, m), 2.84-2.89 (2H, m), 3.25-3.27 (2H, m), 4.13 (3H, s), 4.17 (2H, s), 4.21 (2H, q, J=7.1 Hz), 6.64 (1H, d, J=8.5 Hz), 6.92 (1H, d, J=9.0 Hz), 6.97 (1H, d, J=8.7 Hz), 7.19 (1H, dd, J=8.6 Hz, 2.5 Hz), 7.37 (1H, d, J=2.5 Hz), 7.61 (1H, d, J=8.4 Hz), 8.34 (1H, d, J=9.1 Hz).

Reference Example 183

Ethyl 1-(4-chloro-2-fluorophenyl)-4-{[(8-chloro-2-methoxyquinolin-5-yl)oxy]methyl}piperidine-4-carboxylate Synthesized analogous to Reference Example 79.
¹HNMR (CDCl₃) δ ppm: 1.20 (3H, t, J=7.1 Hz), 1.87-1.93 (2H, m), 2.47-2.50 (2H, m), 2.88-2.93 (2H, m), 3.30-3.34 (2H, m), 4.13 (3H, s), 4.16 (2H, s), 4.21 (2H, q, J=7.1 Hz), 6.63 (1H, d, J=8.5 Hz), 6.87-6.93 (2H, m), 7.03-7.07 (2H, m), 7.61 (1H, d, J=8.4 Hz), 8.34 (1H, d, J=9.1 Hz).

Reference Example 184

1-(2,4-Dichlorophenyl)-4-{[(8-fluoro-2-methoxyquinolin-5-yl)oxy]methyl}piperidine-4-carboxylic acid Synthesized analogous to Reference Example 93.
¹HNMR (DMSO-d6) δ ppm: 1.80-1.86 (2H, m), 2.29-2.32 (2H, m), 2.88-2.86 (2H, m), 3.19-3.21 (2H, m), 4.00 (3H, s), 4.25 (2H, s), 6.90 (1H, dd, J=8.7 Hz, 3.3 Hz), 7.11 (1H, d, J=9.1 Hz), 7.19 (1H, d, J=8.7 Hz), 7.35 (1H, dd, J=8.7 Hz, 2.5 Hz), 7.44 (1H, dd, J=10.9 Hz, 8.7 Hz), 7.54 (1H, d, J=2.5 Hz), 8.31 (1H, dd, J=9.1 Hz, 1.5 Hz), 12.77 (1H, brs).

Reference Example 185

1-(4-Chloro-2-fluorophenyl)-4-{[(8-fluoro-2-methoxyquinolin-5-yl)oxy]methyl}piperidine-4-carboxylic acid Synthesized analogous to Reference Example 93.
¹HNMR (CDCl₃) δ ppm: 1.89-1.95 (2H, m), 2.47-2.50 (2H, m), 2.90-2.94 (2H, m), 3.31-3.33 (2H, m), 4.09 (3H, s), 4.16 (2H, s), 6.55 (1H, dd, J=8.6 Hz, 3.2 Hz), 6.78 (1H, d, J=9.1 Hz), 7.84-6.87 (1H, m), 7.03-7.06 (2H, m), 7.20 (1H, dd, J=10.5 Hz, 8.7 Hz), 8.22 (1H, d, J=9.1 Hz).

Reference Example 186

4-{[(8-Chloro-2-methoxyquinolin-5-yl)oxy]methyl}-1-(2,4-dichlorophenyl)piperidine-4-carboxylic acid Synthesized analogous to Reference Example 93.
¹HNMR (DMSO-d6) δ ppm: 1.81-1.86 (2H, m), 2.29-2.32 (2H, m), 2.82-2.86 (2H, m), 3.19-3.21 (2H, m), 4.04 (3H, s), 4.28 (2H, s), 6.98 (1H, dd, J=8.6 Hz), 7.12 (1H, d, J=9.0 Hz), 7.19 (1H, d, J=8.7 Hz), 7.35 (1H, dd, J=8.7 Hz, 2.5 Hz), 7.54 (1H, d, J=2.5 Hz), 7.76 (1H, d, J=8.5 Hz), 8.34 (1H, d, J=9.0 Hz), 12.79 (1H, brs).

Reference Example 187

1-(4-Chloro-2-fluorophenyl)-4-{[(8-chloro-2-methoxyquinolin-5-yl)oxy]methyl}piperidine-4-carboxylic acid Synthesized analogous to Reference Example 93.
¹HNMR (DMSO-d6) δ ppm: 1.80-1.85 (2H, m), 2.28-2.30 (2H, m), 2.84-2.88 (2H, m), 3.26-3.30 (2H, m), 4.04 (3H, s), 4.25 (2H, s), 6.97 (1H, d, J=8.6 Hz), 7.07-7.18 (3H, m), 7.33 (1H, dd, J=12.4 Hz, 2.4 Hz), 7.76 (1H, d, J=8.5 Hz), 8.34 (1H, d, J=9.0 Hz), 12.80 (1H, brs).

Reference Example 188

5-{[1-(2,4-Dichlorophenyl)-4-isocyanatopiperidin-4-yl]methoxy}-8-fluoro-2-methoxyquinoline Synthesized analogous to Reference Example 134.
¹HNMR (CDCl₃) δ ppm: 2.03-2.08 (4H, m), 3.03-3.08 (2H, m), 3.29-3.31 (2H, m), 4.10 (2H, s), 4.12 (3H, s), 6.62 (1H, dd, J=8.6 Hz, 3.3 Hz), 6.97 (1H, d, J=9.1 Hz), 7.05 (1H, d, J=8.6 Hz), 7.22-7.24 (2H, m), 7.39 (1H, d, J=2.5 Hz), 8.42 (1H, dd, J=9.1 Hz, 1.5 Hz).

Reference Example 189

5-{[1-(4-Chloro-2-fluorophenyl)-4-isocyanatopiperidin-4-yl]methoxy}-8-fluoro-2-methoxyquinoline Synthesized analogous to Reference Example 134.
¹HNMR (CDCl₃) δ ppm: 1.99-2.07 (4H, m), 3.06-3.11 (2H, m), 3.35-3.38 (2H, m), 4.09 (2H, s), 4.12 (3H, s), 6.61

(1H, dd, J=8.6 Hz, 3.3 Hz), 6.94-6.98 (2H, m), 7.06-7.09 (2H, m), 7.22-7.26 (1H, m), 8.41 (1H, dd, J=9.1 Hz, 1.6 Hz).

Reference Example 190

8-Chloro-5-{[1-(2,4-dichlorophenyl)-4-isocyanatopiperidin-4-yl]methoxy}-2-methoxyquinoline Synthesized analogous to Reference Example 134.
$^1$HNMR (CDCl$_3$) δ ppm: 2.00-2.08 (4H, m), 3.03-3.08 (2H, m), 3.29-3.31 (2H, m), 4.12 (2H, s), 4.15 (3H, s), 6.67 (1H, d, J=8.5 Hz), 6.97 (1H, d, J=9.0 Hz), 7.05 (1H, d, J=8.6 Hz), 7.23 (1H, dd, J=8.6 Hz, 2.4 Hz), 7.39 (1H, d, J=2.4 Hz), 7.64 (1H, d, J=8.4 Hz), 8.44 (1H, d, J=9.0 Hz).

Reference Example 191

8-Chloro-5-{[1-(4-chloro-2-fluorophenyl)-4-isocyanatopiperidin-4-yl]methoxy}-2-methoxyquinoline Synthesized analogous to Reference Example 134.
$^1$HNMR (CDCl$_3$) δ ppm: 1.99-2.07 (4H, m), 3.06-3.11 (2H, m), 3.35-3.38 (2H, m), 4.10 (2H, s), 4.15 (3H, s), 6.67 (1H, d, J=8.5 Hz), 6.94-6.98 (2H, m), 7.06-7.09 (2H, m), 7.64 (1H, d, J=8.4 Hz), 8.44 (1H, d, J=9.0 Hz).

Reference Example 192

4-{[(8-Chloro-2-methoxyquinolin-5-yl)oxy]methyl}-1-(2,4-dichlorophenyl)piperidine-4-amine Synthesized analogous to Reference Example 161.
$^1$HNMR (CDCl$_3$) δ ppm: 1.41 (2H, brs), 1.76-1.78 (2H, m), 2.02-2.08 (2H, m), 3.10-3.18 (4H, m), 3.94 (2H, s), 4.15 (3H, s), 6.69 (1H, d, J=8.5 Hz), 6.94 (1H, d, J=9.0 Hz), 7.04 (1H, d, J=8.7 Hz), 7.20 (1H, dd, J=8.6 Hz, 2.4 Hz), 7.38 (1H, d, J=2.4 Hz), 7.63 (1H, d, J=8.6 Hz), 8.42 (1H, d, J=9.0 Hz).

Reference Example 193

1-(4-Chloro-2-fluorophenyl)-4-{[(8-chloro-2-methoxyquinolin-5-yl)oxy]methyl}piperidine-4-amine Synthesized analogous to Reference Example 161.
$^1$HNMR (CDCl$_3$) δ ppm: 1.39 (2H, brs), 1.75-1.77 (2H, m), 2.02-2.07 (2H, m), 3.14-3.25 (4H, m), 3.92 (2H, s), 4.15 (3H, s), 6.68 (1H, d, J=8.5 Hz), 6.93-6.96 (2H, m), 7.04-7.07 (2H, m), 7.63 (1H, d, J=8.4 Hz), 8.41 (1H, d, J=9.0 Hz).

Reference Example 194

1-(2,4-Dichlorophenyl)-4-{[(8-fluoro-2-methoxyquinolin-5-yl)oxy]methyl}piperidine-4-amine Synthesized analogous to Reference Example 161.
$^1$HNMR (CDCl$_3$) δ ppm: 1.42 (2H, brs), 1.75-1.78 (2H, m), 2.02-2.08 (2H, m), 3.09-3.18 (4H, m), 3.93 (2H, s), 4.12 (3H, s), 6.63 (1H, dd, J=8.6 Hz, 3.3 Hz), 6.94 (1H, d, J=9.1 Hz), 7.03 (1H, d, J=8.6 Hz), 7.19-7.26 (2H, m), 7.38 (1H, d, J=2.4 Hz), 8.40 (1H, dd, J=9.0 Hz).

Reference Example 195

1-(4-Chloro-2-fluorophenyl)-4-{[(8-fluoro-2-methoxyquinolin-5-yl)oxy]methyl}piperidine-4-amine Synthesized analogous to Reference Example 161.
$^1$HNMR (CDCl$_3$) δ ppm: 1.39 (2H, brs), 1.75-1.77 (2H, m), 2.02-2.07 (2H, m), 3.14-3.25 (4H, m), 3.91 (2H, s), 4.12 (3H, s), 6.62 (1H, dd, J=8.6 Hz, 3.4 Hz), 6.93-6.96 (2H, m), 7.04-7.07 (2H, m), 7.23 (1H, dd, J=10.6 Hz, 8.6 Hz), 8.39 (1H, dd, J=9.1 Hz, 1.5 Hz).

Reference Example 196

8-(2,5-Dichloro-4-fluorophenyl)-1,4-dioxa-8-azaspiro[4.5]decane

To a microwave reaction tube were added 1-bromo-2,5-dichloro-4-fluorobenzene (1.00 g), sodium tert-butoxide (0.473 g), tris(dibenzylideneacetone)dipalladium (0.038 g), 2,2'-bis(diphenylphosphino)-1,1'-binaphthyl (0.077 g), 1,4-dioxa-8-azaspiro[4.5]decane (0.590 mL) and toluene (3 mL). The tube was sealed, and then irradiated with microwave at 130° C. for 1 h. To the reaction solution was added water, and the solution was extracted with ethyl acetate. The organic layer was washed with brine, dried over anhydrous sodium sulfate, and the solvent was distilled off. The residue was purified by silica gel column chromatography (hexane/ethyl acetate) to provide the title compound (845 mg).
$^1$HNMR (CDCl$_3$) δ ppm: 1.89 (4H, t, J=5.5 Hz), 3.05 (4H, t, J=5.5 Hz), 4.00 (4H, s), 7.07 (1H, d, J=7.5 Hz), 7.19 (1H, d, J=8.5 Hz).

Reference Example 197

8-(4-Chloro-2-fluorophenyl)-1,4-dioxa-8-azaspiro[4.5]decane

Synthesized analogous to Reference Example 196.
$^1$HNMR (CDCl$_3$) δ ppm: 1.88 (4H, t, J=5.5 Hz), 3.14 (4H, t, J=5.5 Hz), 4.00 (4H, s), 6.88 (1H, t, J=9.0 Hz), 7.01-7.05 (2H, m).

Reference Example 198

8-(2,4-Dichloro-5-fluorophenyl)-1,4-dioxa-8-azaspiro[4.5]decane

Synthesized analogous to Reference Example 196.
$^1$HNMR (CDCl$_3$) δ ppm: 1.89 (4H, t, J=6.0 Hz), 3.09 (4H, t, J=6.0 Hz), 4.00 (4H, s), 6.84 (1H, d, J=10.5 Hz), 7.38 (1H, d, J=8.0 Hz).

Reference Example 199

8-(4-Chloro-2,6-difluorophenyl)-1,4-dioxa-8-azaspiro[4.5]decane

Synthesized analogous to Reference Example 196.
$^1$HNMR (CDCl$_3$) δ ppm: 1.83 (4H, t, J=5.5 Hz), 3.23 (4H, t, J=5.5 Hz), 3.99 (4H, s), 6.83-6.89 (2H, m).

Reference Example 200

8-(2-Chloro-6-fluorophenyl)-1,4-dioxa-8-azaspiro[4.5]decane

Synthesized analogous to Reference Example 196.
$^1$HNMR (CDCl$_3$) δ ppm: 1.86 (4H, t, J=5.5 Hz), 3.24 (4H, t, J=5.5 Hz), 4.01 (4H, s), 6.91-6.95 (2H, m), 7.13-7.16 (1H, m).

Reference Example 201

8-(4-Chloro-2,5-difluorophenyl)-1,4-dioxa-8-azaspiro[4.5]decane

Synthesized analogous to Reference Example 196.
$^1$HNMR (CDCl$_3$) δ ppm: 1.87 (4H, t, J=6.0 Hz), 3.15 (4H, t, J=6.0 Hz), 4.00 (4H, s), 6.73 (1H, dd, J=10.5 Hz, 7.5 Hz), 7.06 (1H, dd, J=11.5 Hz, 7.0 Hz).

Reference Example 202

8-(2-Chloro-5-nitrophenyl)-1,4-dioxa-8-azaspiro[4.5]decane

Under nitrogen atmosphere, to a mixture of 3-bromo-4-chloronitrobenzene (3.05 g), sodium tert-butoxide (1.49 g), tris(dibenzylideneacetone)dipalladium (0.118 g), 2,2'-bis(diphenylphosphino)-1,1'-binaphthyl (0.241 g), and 1,4-dioxa-8-azaspiro[4.5]decane (1.86 mL) was added toluene (24 mL), and the reaction mixture was stirred at 90-110° C. for 18 h. To the reaction solution was added water, and the solution was extracted with ethyl acetate. The organic layer was washed with brine, dried over anhydrous sodium sulfate, and the solvent was distilled off. The residue was purified by silica gel column chromatography (hexane/ethyl acetate) to provide the title compound (346 mg).
$^1$HNMR (CDCl$_3$) δ ppm: 1.93 (4H, t, J=5.5 Hz), 3.20 (4H, t, J=5.5 Hz), 4.02 (4H, s), 7.50 (1H, d, J=8.5 Hz), 7.82 (1H, dd, J=8.5 Hz, 2.5 Hz), 7.91 (1H, d, J=2.5 Hz).

Reference Example 203

8-(2,4-Dichloro-6-methylphenyl)-1,4-dioxa-8-azaspiro[4.5]decane

Synthesized analogous to Reference Example 196.
$^1$HNMR (CDCl$_3$) δ ppm: 1.78-1.86 (4H, m), 2.31 (3H, s), 2.93-2.97 (2H, m), 3.41-3.46 (2H, m), 3.99-4.02 (4H, m), 7.05 (1H, d, J=2.5 Hz), 7.16 (1H, d, J=2.5 Hz).

Reference Example 204

8-[2-Chloro-5-(trifluoromethoxy)phenyl]-1,4-dioxa-8-azaspiro[4.5]decane

Synthesized analogous to Reference Example 196.
$^1$HNMR (CDCl$_3$) δ ppm: 1.91 (4H, t, J=5.5 Hz), 3.13 (4H, t, J=5.5 Hz), 4.01 (4H, s), 6.82 (1H, dd, J=9.0 Hz, 2.5 Hz), 6.89 (1H, d, J=2.5 Hz), 7.35 (1H, d, J=9.0 Hz).

Reference Example 205

8-(4-Chloro-3-methylphenyl)-1,4-dioxa-8-azaspiro[4.5]decane

Under nitrogen atmosphere, to a mixture of 5-bromo-2-chlorotoluene (2.19 mL), sodium tert-butoxide (1.85 g), tris(dibenzylideneacetone)dipalladium (0.147 g), 2,2'-bis(diphenylphosphino)-1,1'-binaphthyl (0.300 g) and 1,4-dioxa-8-azaspiro[4.5]decane (2.31 mL) was added toluene (24 mL), and the reaction mixture was heated to reflux for 3 h. After the reaction mixture was allowed to cool to room temperature, to the reaction solution was added water, and extracted with ethyl acetate. The organic layer was washed with brine, dried over anhydrous sodium sulfate, and the solvent was distilled off. The residue was purified by silica gel column chromatography (hexane/ethyl acetate) to provide the title compound (4.28 g).
$^1$HNMR (CDCl$_3$) δ ppm: 1.83 (4H, t, J=5.5 Hz), 2.32 (3H, s), 3.28 (4H, t, J=5.5 Hz), 3.99 (4H, s), 6.70 (1H, dd, J=8.5 Hz, 3.0 Hz), 6.80 (1H, d, J=3.0 Hz), 7.17 (1H, d, J=8.5 Hz).

Reference Example 206

Ethyl 2-chloro-5-(1,4-dioxa-8-azaspiro[4.5]dec-8-yl)benzoate

Under nitrogen atmosphere, to a mixture of ethyl 5-bromo-2-chlorobenzoate (2.12 mL), cesium carbonate (12.2 g), tris(dibenzylideneacetone)dipalladium (0.114 g), 2,2'-bis(diphenylphosphino)-1,1'-binaphthyl (0.233 g) and 1,4-dioxa-8-azaspiro[4.5]decane (1.79 mL) was added toluene (24 mL), and the reaction mixture was heated to reflux for 5 h. To the reaction solution was added aqueous saturated ammonium chloride solution, and the solution was extracted with ethyl acetate. The organic layer was washed with brine, dried over anhydrous sodium sulfate, and the solvent was distilled off. The residue was purified by silica gel column chromatography (hexane/ethyl acetate) to provide the title compound (852 mg).
$^1$HNMR (CDCl$_3$) δ ppm: 1.40 (3H, t, J=7.5 Hz), 1.83 (4H, t, J=5.5 Hz), 3.33 (4H, t, J=5.5 Hz), 3.99 (4H, s), 4.39 (2H, q, J=7.5 Hz), 6.95 (1H, dd, J=8.5 Hz, 3.5 Hz), 7.27 (1H, d, J=8.5 Hz), 7.32 (1H, d, J=3.5 Hz).

Reference Example 207

8-(4-Ethoxy-2-fluorophenyl)-1,4-dioxa-8-azaspiro[4.5]decane

Into an eggplant flask were added 1-bromo-4-ethoxy-2-fluorobenzene (758 mg), tris(dibenzylideneacetone)dipalladium (31.7 mg), 2',4',6'-triisopropyl-2-(dicyclohexylphosphino)-1,1'-biphenyl (X-PHOS) (39.6 mg), sodium tert-butoxide (499 mg) and 1,4-dioxa-8-azaspiro[4.5]decane (0.50 mL), the flask was purged with nitrogen, and then toluene (3.8 mL) was added thereto and the mixture was stirred at 100° C. for 3 h. To the reaction solution was added water, and the solution was extracted with ethyl acetate. The organic layer was washed with brine, dried over anhydrous sodium sulfate, and the solvent was distilled off. The residue was purified by silica gel column chromatography (hexane/ethyl acetate) to provide the title compound (310 mg).
$^1$HNMR (CDCl$_3$) δ ppm: 1.39 (3H, t, J=7.5 Hz), 1.89 (4H, t, J=5.5 Hz), 3.08 (4H, t, J=5.5 Hz), 3.97 (2H, q, J=7.5 Hz), 4.00 (4H, s), 6.59 (1H, ddd, J=9.0 Hz, 3.0 Hz, 1.0 Hz), 6.63 (1H, dd, J=13.5 Hz, 3.0 Hz), 6.92 (1H, t, J=9.0 Hz).

Reference Example 208

8-[2-Chloro-4-(propan-2-yl)phenyl]-1,4-dioxa-8-azaspiro[4.5]decane

To a solution of 8-[4-(propan-2-yl)phenyl]-1,4-dioxa-8-azaspiro[4.5]decane (803 mg) in N,N-dimethylformamide (6.5 mL) was added N-chlorosuccinimide (451 mg), and the reaction mixture was stirred at room temperature for 45 h. To the reaction solution was added water, and the solution was extracted with ethyl acetate. The organic layer was washed with brine, dried over anhydrous sodium sulfate, and the solvent was distilled off. The residue was purified by silica gel column chromatography (hexane/ethyl acetate) to provide the title compound (726 mg).

¹HNMR (CDCl₃) δ ppm: 1.22 (6H, d, J=7.0 Hz), 1.90 (4H, t, J=5.5 Hz), 2.83 (1H, sep, J=7.0 Hz), 3.09 (4H, t, J=5.5 Hz), 4.00 (4H, s), 6.99 (1H, d, J=8.5 Hz), 7.05 (1H, dd, J=8.5 Hz, 2.0 Hz), 7.22 (1H, d, J=2.0 Hz).

Reference Example 209

8-(2-Fluoro-4-propoxyphenyl)-1,4-dioxa-8-azaspiro[4.5]decane

Synthesized analogous to Reference Example 207.
¹HNMR (CDCl₃) δ ppm: 1.02 (3H, t, J=7.0 Hz), 1.74-1.81 (2H, m), 1.89 (4H, t, J=5.5 Hz), 3.08 (4H, t, J=5.5 Hz), 3.85 (2H, t, J=6.5 Hz), 3.99 (4H, s), 6.59 (1H, dd, J=9.0 Hz, 3.0 Hz), 6.64 (1H, dd, J=13.5 Hz, 3.0 Hz), 6.92 (1H, t, J=9.0 Hz).

Reference Example 210

8-(2-Chloro-4-ethylphenyl)-1,4-dioxa-8-azaspiro[4.5]decane

Synthesized analogous to Reference Example 208.
¹HNMR (CDCl₃) δ ppm: 1.21 (3H, t, J=7.5 Hz), 1.90 (4H, t, J=5.5 Hz), 2.57 (2H, q, J=7.5 Hz), 3.09 (4H, t, J=5.5 Hz), 4.00 (4H, s), 6.98 (1H, d, J=8.0 Hz), 7.03 (1H, dd, J=8.0 Hz, 2.0 Hz), 7.20 (1H, d, J=2.0 Hz).

Reference Example 211

8-(2-Chloro-4-propylphenyl)-1,4-dioxa-8-azaspiro[4.5]decane

Synthesized analogous to Reference Example 208.
¹HNMR (CDCl₃) δ ppm: 0.92 (3H, t, J=7.5 Hz), 1.60 (2H, sext, J=7.5 Hz), 1.90 (4H, t, J=5.5 Hz), 2.50 (2H, t, J=7.5 Hz), 3.09 (4H, t, J=5.5 Hz), 4.00 (4H, s), 6.97 (1H, d, J=8.0 Hz), 7.00 (1H, dd, J=8.0 Hz, 2.0 Hz), 7.18 (1H, d, J=2.0 Hz).

Reference Example 212

8-(2,4-Dichloro-6-fluorophenyl)-1,4-dioxa-8-azaspiro[4.5]decane

Synthesized analogous to Reference Example 208.
¹HNMR (CDCl₃) δ ppm: 1.84 (4H, t, J=5.5 Hz), 3.21 (4H, t, J=5.5 Hz), 4.00 (4H, s), 6.98 (1H, dd, J=11.0 Hz, 2.0 Hz), 7.18 (1H, dd, J=2.0 Hz, 1.5 Hz).

Reference Example 213

8-(4-Butoxy-2-fluorophenyl)-1,4-dioxa-8-azaspiro[4.5]decane

Synthesized analogous to Reference Example 207.
¹HNMR (CDCl₃) δ ppm: 0.96 (3H, t, J=7.5 Hz), 1.43-1.51 (2H, m), 1.71-1.76 (2H, m), 1.89 (4H, t, J=5.5 Hz), 3.08 (4H, t, J=5.5 Hz), 3.89 (2H, t, J=6.5 Hz), 4.00 (4H, s), 6.59 (1H, ddd, J=9.0 Hz, 3.0 Hz, 1.0 Hz), 6.64 (1H, dd, J=13.5 Hz, 3.0 Hz), 6.92 (1H, t, J=9.0 Hz).

Reference Example 214

8-[2-Fluoro-4-(propan-2-yloxy)phenyl]-1,4-dioxa-8-azaspiro[4.5]decane

Synthesized analogous to Reference Example 207.
¹HNMR (CDCl₃) δ ppm: 1.31 (6H, d, J=6.0 Hz), 1.89 (4H, t, J=5.5 Hz), 3.08 (4H, t, J=5.5 Hz), 3.99 (4H, s), 4.43 (1H, sep, J=6.0 Hz), 6.58 (1H, ddd, J=9.0 Hz, 3.0 Hz, 1.0 Hz), 6.62 (1H, dd, J=13.5 Hz, 3.0 Hz), 6.90 (1H, t, J=9.0 Hz).

Reference Example 215

8-[2-Chloro-4-(trifluoromethoxy)phenyl]-1,4-dioxa-8-azaspiro[4.5]decane

Synthesized analogous to Reference Example 208.
¹HNMR (CDCl₃) δ ppm: 1.90 (4H, t, J=5.5 Hz), 3.10 (4H, t, J=5.5 Hz), 4.01 (4H, s), 7.04 (1H, d, J=9.0 Hz), 7.07-7.09 (1H, m), 7.26 (1H, d, J=2.5 Hz).

Reference Example 216

8-[2-Fluoro-4-(trifluoromethoxy)phenyl]-1,4-dioxa-8-azaspiro[4.5]decane

Synthesized analogous to Reference Example 207.
¹HNMR (CDCl₃) δ ppm: 1.89 (4H, t, J=5.5 Hz), 3.16 (4H, t, J=5.5 Hz), 4.00 (4H, s), 6.92-6.97 (3H, m).

Reference Example 217

8-(2-Fluoro-4-methoxyphenyl)-1,4-dioxa-8-azaspiro[4.5]decane

Synthesized analogous to Reference Example 207.
¹HNMR (CDCl₃) δ ppm: 1.89 (4H, t, J=5.5 Hz), 3.08 (4H, t, J=5.5 Hz), 3.76 (3H, s), 4.00 (4H, s), 6.60 (1H, ddd, J=9.0 Hz, 2.5 Hz, 1.0 Hz), 6.65 (1H, dd, J=13.5 Hz, 2.5 Hz), 6.93 (1H, t, J=9.0 Hz).

Reference Example 218

8-[2,4-Dichloro-5-(trifluoromethoxy)phenyl]-1,4-dioxa-8-azaspiro[4.5]decane

Synthesized analogous to Reference Example 208.
¹HNMR (CDCl₃) δ ppm: 1.86-1.92 (4H, m), 3.09-3.12 (4H, m), 4.01 (4H, s), 6.98 (1H, d, J=1.0 Hz), 7.46 (1H, s).

Reference Example 219

8-[2-Fluoro-5-(trifluoromethoxy)phenyl]-1,4-dioxa-8-azaspiro[4.5]decane

Synthesized analogous to Reference Example 205.
¹HNMR (CDCl₃) δ ppm: 1.89 (4H, t, J=5.5 Hz), 3.19 (4H, t, J=5.5 Hz), 4.00 (4H, s), 6.75-6.80 (2H, m), 7.00 (1H, dd, J=12.0 Hz, 9.0 Hz).

Reference Example 220

8-[4-(Benzyloxy)-2-fluorophenyl]-1,4-dioxa-8-azaspiro[4.5]decane

Synthesized analogous to Reference Example 205.
¹HNMR (CDCl₃) δ ppm: 1.89 (4H, t, J=5.5 Hz), 3.08 (4H, t, J=5.5 Hz), 3.99 (4H, s), 5.00 (2H, s), 6.60 (1H, dd, J=9.0

Hz, 3.0 Hz), 6.72 (1H, dd, J=13.5 Hz, 3.0 Hz), 6.92 (1H, t, J=9.0 Hz), 7.31-7.34 (1H, m), 7.37-7.42 (4H, m).

Reference Example 221

8-[2-Fluoro-4-(2-methoxyethoxy)phenyl]-1,4-dioxa-8-azaspiro[4.5]decane

Synthesized analogous to Reference Example 205.
$^1$HNMR (CDCl$_3$) δ ppm: 1.89 (4H, t, J=5.5 Hz), 3.08 (4H, t, J=5.5 Hz), 3.44 (3H, s), 3.71-3.73 (2H, m), 3.99 (4H, s), 4.05-4.07 (2H, m), 6.63 (1H, ddd, J=9.0 Hz, 3.0 Hz, 1.0 Hz), 6.68 (1H, dd, J=13.5 Hz, 3.0 Hz), 6.91 (1H, t, J=9.0 Hz).

Reference Example 222

8-(2-Bromo-5-ethoxy-4-nitrophenyl)-1,4-dioxa-8-azaspiro[4.5]decane

Synthesized analogous to Reference Example 207.
$^1$HNMR (CDCl$_3$) δ ppm: 1.49 (3H, t, J=7.5 Hz), 1.92 (4H, t, J=5.5 Hz), 3.22 (4H, t, J=5.5 Hz), 4.02 (4H, s), 4.15 (2H, q, J=7.5 Hz), 6.61 (1H, s), 8.18 (1H, s).

Reference Example 223

8-[4-Chloro-2-fluoro-5-(trifluoromethoxy)phenyl]-1,4-dioxa-8-azaspiro[4.5]decane Synthesized analogous to Reference Example 208.
$^1$HNMR (CDCl$_3$) δ ppm: 1.85-1.89 (4H, m), 3.15-3.18 (4H, m), 4.01 (4H, s), 6.87 (1H, d, J=9.0 Hz), 7.13 (1H, d, J=11.5 Hz).

Reference Example 224

8-(4-Ethoxy-2,5-difluorophenyl)-1,4-dioxa-8-azaspiro[4.5]decane

Synthesized analogous to Reference Example 205.
$^1$HNMR (CDCl$_3$) δ ppm: 1.42 (3H, t, J=7.0 Hz), 1.88 (4H, t, J=5.5 Hz), 3.07 (4H, t, J=5.5 Hz), 3.99 (4H, s), 4.04 (2H, q, J=7.0 Hz), 6.71 (1H, dd, J=13.0 Hz, 7.5 Hz), 6.76 (1H, dd, J=13.0 Hz, 8.0 Hz).

Reference Example 225

8-[4-(Ethoxymethyl)-2-fluorophenyl]-1,4-dioxa-8-azaspiro[4.5]decane

Synthesized analogous to Reference Example 205.
$^1$HNMR (CDCl$_3$) δ ppm: 1.24 (3H, t, J=7.0 Hz), 1.89 (4H, t, J=5.5 Hz), 3.16 (4H, t, J=5.5 Hz), 3.52 (2H, q, J=7.0 Hz), 4.00 (4H, s), 4.41 (2H, s), 6.93 (1H, t, J=8.0 Hz), 7.00-7.05 (2H, m).

Reference Example 226

8-(2,6-Difluoro-4-methoxyphenyl)-1,4-dioxa-8-azaspiro[4.5]decane

Synthesized analogous to Reference Example 205.
$^1$HNMR (CDCl$_3$) δ ppm: 1.83 (4H, t, J=5.5 Hz), 3.18 (4H, t, J=5.5 Hz), 3.74 (3H, s), 3.99 (4H, s), 6.38-6.44 (2H, m).

Reference Example 227

2-[4-(1,4-Dioxa-8-azaspiro[4.5]dec-8-yl)-2,5-difluorophenoxy]-N,N-dimethylethaneamine Synthesized analogous to Reference Example 205.
$^1$HNMR (CDCl$_3$) δ ppm: 1.88 (4H, t, J=5.5 Hz), 2.33 (6H, s), 2.72 (2H, t, J=6.0 Hz), 3.08 (4H, t, J=5.5 Hz), 3.99 (4H, s), 4.06 (2H, t, J=6.0 Hz), 6.72-6.78 (2H, m).

Reference Example 228

8-(2-Fluoro-6-methylphenyl)-1,4-dioxa-8-azaspiro[4.5]decane

Synthesized analogous to Reference Example 196.
$^1$HNMR (CDCl$_3$) δ ppm: 1.82-1.84 (4H, m), 2.32 (3H, s), 3.14 (4H, brs), 4.00 (4H, s), 6.81-6.88 (1H, m), 6.93-6.98 (2H, m).

Reference Example 229

8-(4-Ethoxy-2,3,5,6-tetrafluorophenyl)-1,4-dioxa-8-azaspiro[4.5]decane

Synthesized analogous to Reference Example 205.
$^1$HNMR (CDCl$_3$) δ ppm: 1.39 (3H, t, J=7.0 Hz), 1.84 (4H, t, J=5.5 Hz), 3.26 (4H, t, J=5.5 Hz), 4.00 (4H, s), 4.19 (2H, q, J=7.0 Hz).

Reference Example 230

8-{2-Fluoro-4-[2-(2-methoxyethoxy)ethoxy]phenyl}-1,4-dioxa-8-azaspiro[4.5]decane Synthesized analogous to Reference Example 205.
$^1$HNMR (CDCl$_3$) δ ppm: 1.89 (4H, t, J=5.5 Hz), 3.08 (4H, t, J=5.5 Hz), 3.39 (3H, s), 3.56-3.58 (2H, m), 3.70-3.72 (2H, m), 3.83 (2H, t, J=5.0 Hz), 3.99 (4H, s), 4.08 (2H, t, J=5.0 Hz), 6.61 (1H, ddd, J=9.0 Hz, 3.0 Hz, 1.0 Hz), 6.67 (1H, dd, J=13.5 Hz, 3.0 Hz), 6.91 (1H, t, J=9.0 Hz).

Reference Example 231

8-(4-Chloro-2-fluoro-5-methylphenyl)-1,4-dioxa-8-azaspiro[4.5]decane

Synthesized analogous to Reference Example 205.
$^1$HNMR (CDCl$_3$) δ ppm: 1.88 (4H, t, J=5.5 Hz), 2.29 (3H, s), 3.13 (4H, t, J=5.5 Hz), 4.00 (4H, s), 6.80 (1H, d, J=9.0 Hz), 7.02 (1H, d, J=12.0 Hz).

Reference Example 232

8-(4-Ethoxy-2-fluoro-5-methoxyphenyl)-1,4-dioxa-8-azaspiro[4.5]decane

Synthesized analogous to Reference Example 205.
$^1$HNMR (CDCl$_3$) δ ppm: 1.43 (3H, t, J=7.0 Hz), 1.90 (4H, t, J=5.5 Hz), 3.11 (4H, t, J=5.5 Hz), 3.83 (3H, s), 4.00 (4H, s), 4.02 (2H, q, J=7.0 Hz), 6.61 (1H, d, J=8.5 Hz), 6.65 (1H, d, J=13.5 Hz).

Reference Example 233

8-(4-Ethoxy-2,6-difluorophenyl)-1,4-dioxa-8-azaspiro[4.5]decane

Synthesized analogous to Reference Example 205.
$^1$HNMR (CDCl$_3$) δ ppm: 1.38 (3H, t, J=7.0 Hz), 1.83 (4H, t, J=5.5 Hz), 3.17 (4H, t, J=5.5 Hz), 3.94 (2H, q, J=7.0 Hz), 3.99 (4H, s), 6.36-6.42 (2H, m).

Reference Example 234

8-[2-Fluoro-4-(2-fluoroethoxy)phenyl]-1,4-dioxa-8-azaspiro[4.5]decane

Synthesized analogous to Reference Example 205.
$^1$HNMR (CDCl$_3$) δ ppm: 1.89 (4H, t, J=5.5 Hz), 3.09 (4H, t, J=5.5 Hz), 4.00 (4H, s), 4.12-4.19 (2H, m), 4.67-4.78 (2H, m), 6.63 (1H, ddd, J=9.0 Hz, 3.0 Hz, 1.0 Hz), 6.68 (1H, dd, J=13.5 Hz, 3.0 Hz), 6.93 (1H, t, J=9.0 Hz).

Reference Example 235

2-[4-(1,4-Dioxa-8-azaspiro[4.5]dec-8-yl)-3-fluorophenoxy]-N,N-dimethylethaneamine Synthesized analogous to Reference Example 205.
$^1$HNMR (CDCl$_3$) δ ppm: 1.89 (4H, t, J=5.5 Hz), 2.32 (6H, s), 2.70 (2H, t, J=6.0 Hz), 3.08 (4H, t, J=5.5 Hz), 3.99 (4H, s), 4.00 (2H, t, J=6.0 Hz), 6.62 (1H, dd, J=9.0 Hz, 3.0 Hz), 6.67 (1H, dd, J=13.5 Hz, 3.0 Hz), 6.91 (1H, t, J=9.0 Hz).

Reference Example 236

8-[2-Fluoro-4-(2,2,2-trifluoroethoxy)phenyl]-1,4-dioxa-8-azaspiro[4.5]decane

Synthesized analogous to Reference Example 205.
$^1$HNMR (CDCl$_3$) δ ppm: 1.89 (4H, t, J=5.5 Hz), 3.10 (4H, t, J=5.5 Hz), 4.00 (4H, s), 4.29 (2H, q, J=8.0 Hz), 6.65 (1H, ddd, J=9.0 Hz, 3.0 Hz, 1.0 Hz), 6.71 (1H, dd, J=13.0 Hz, 3.0 Hz), 6.93 (1H, t, J=9.0 Hz).

Reference Example 237

8-(1-Benzofuran-5-yl)-1,4-dioxa-8-azaspiro[4.5]decane

Synthesized analogous to Reference Example 205.
$^1$HNMR (CDCl$_3$) δ ppm: 1.90 (4H, t, J=5.5 Hz), 3.27 (4H, t, J=5.5 Hz), 4.01 (4H, s), 6.68 (1H, d, J=2.0 Hz), 7.02 (1H, dd, J=9.0 Hz, 2.0 Hz), 7.14 (1H, d, J=2.0 Hz), 7.38 (1H, d, J=9.0 Hz), 7.56 (1H, d, J=2.0 Hz).

Reference Example 238

6-(1,4-Dioxa-8-azaspiro[4.5]dec-8-yl)quinoxaline

Synthesized analogous to Reference Example 205.
$^1$HNMR (CDCl$_3$) δ ppm: 1.89 (4H, t, J=5.5 Hz), 3.57 (4H, t, J=5.5 Hz), 4.02 (4H, s), 7.30 (1H, d, J=3.0 Hz), 7.55 (1H, dd, J=9.5 Hz, 3.0 Hz), 7.92 (1H, d, J=9.5 Hz), 8.58 (1H, d, J=2.0 Hz), 8.68 (1H, d, J=2.0 Hz).

Reference Example 239

8-[4-(Difluoromethoxy)-2-fluorophenyl]-1,4-dioxa-8-azaspiro[4.5]decane

Synthesized analogous to Reference Example 206.
$^1$HNMR (CDCl$_3$) δ ppm: 1.89 (4H, t, J=5.5 Hz), 3.13 (4H, t, J=5.5 Hz), 4.00 (4H, s), 6.43 (1H, t, J=74.0 Hz), 6.78-6.88 (2H, m), 6.94 (1H, t, J=9.0 Hz).

Reference Example 240

8-[4-(Difluoromethoxy)-2,6-difluorophenyl]-1,4-dioxa-8-azaspiro[4.5]decane

Synthesized analogous to Reference Example 206.
$^1$HNMR (CDCl$_3$) δ ppm: 1.83 (4H, t, J=5.5 Hz), 3.23 (4H, t, J=5.5 Hz), 4.00 (4H, s), 6.44 (1H, t, J=73.0 Hz), 6.64-6.70 (2H, m).

Reference Example 241

8-[2-Chloro-4-(methylsulfanyl)phenyl]-1,4-dioxa-8-azaspiro[4.5]decane

Synthesized analogous to Reference Example 208.
$^1$HNMR (CDCl$_3$) δ ppm: 1.90 (4H, t, J=5.5 Hz), 2.45 (3H, s), 3.09 (4H, t, J=5.5 Hz), 4.00 (4H, s), 6.99 (1H, d, J=8.5 Hz), 7.12 (1H, dd, J=8.5 Hz, 2.0 Hz), 7.20 (1H, d, J=2.0 Hz).

Reference Example 242

8-[4-(Ethylsulfanyl)-2,6-difluorophenyl]-1,4-dioxa-8-azaspiro[4.5]decane

Synthesized analogous to Reference Example 196.
$^1$HNMR (CDCl$_3$) δ ppm: 1.31 (3H, t, J=7.5 Hz), 1.83 (4H, t, J=5.5 Hz), 2.89 (2H, q, J=7.5 Hz), 3.24 (4H, t, J=5.5 Hz), 3.99 (4H, s), 6.77-6.83 (2H, m).

Reference Example 243

8-[2,6-Difluoro-4-(2,2,2-trifluoroethoxy)phenyl]-1,4-dioxa-8-azaspiro[4.5]decane Synthesized analogous to Reference Example 205.
$^1$HNMR (CDCl$_3$) δ ppm: 1.83 (4H, t, J=5.5 Hz), 3.19 (4H, t, J=5.5 Hz), 4.00 (4H, s), 4.27 (2H, q, J=8.0 Hz), 6.45-6.50 (2H, m).

Reference Example 244

1-(2,5-Dichloro-4-fluorophenyl)piperidin-4-one

To a solution of 8-(2,5-dichloro-4-fluorophenyl)-1,4-dioxa-8-azaspiro[4.5]decane (845 mg) in acetone (20 mL) was added 5 N hydrochloric acid (10 mL), and the reaction mixture was heated to reflux for 3 h. The reaction solution was concentrated, and the residue was purified by silica gel column chromatography (hexane/ethyl acetate) to provide the title compound (556 mg).
$^1$HNMR (CDCl$_3$) δ ppm: 2.64 (4H, t, J=6.0 Hz), 3.29 (4H, t, J=6.0 Hz), 7.08 (1H, d, J=7.0 Hz), 7.25 (1H, d, J=8.5 Hz).

Reference Example 245

1-(2,4-Dichloro-5-fluorophenyl)piperidin-4-one

Synthesized analogous to Reference Example 244.
$^1$HNMR (CDCl$_3$) δ ppm: 2.65 (4H, t, J=6.0 Hz), 3.32 (4H, t, J=6.0 Hz), 6.86 (1H, d, J=10.0 Hz), 7.44 (1H, d, J=7.5 Hz).

Reference Example 246

1-(4-Chloro-2,6-difluorophenyl)piperidin-4-one

Synthesized analogous to Reference Example 244.
$^1$HNMR (CDCl$_3$) δ ppm: 2.58 (4H, t, J=6.0 Hz), 3.46 (4H, t, J=6.0 Hz), 6.89-6.95 (2H, m).

Reference Example 247

1-(2-Chloro-6-fluorophenyl)piperidin-4-one

Synthesized analogous to Reference Example 244.
$^1$HNMR (CDCl$_3$) δ ppm: 2.61 (4H, t, J=6.0 Hz), 3.46 (4H, dt, J=1.5 Hz, 6.0 Hz), 6.92-7.04 (2H, m), 7.20-7.22 (1H, m).

Reference Example 248

1-(4-Chloro-2,5-difluorophenyl)piperidin-4-one

Synthesized analogous to Reference Example 244.
$^1$HNMR (CDCl$_3$) δ ppm: 2.62 (4H, t, J=6.0 Hz), 3.40 (4H, t, J=6.0 Hz), 6.77 (1H, dd, J=10.5 Hz, 7.5 Hz), 7.12 (1H, dd, J=11.5 Hz, 7.0 Hz).

Reference Example 249

1-[2-Chloro-5-(trifluoromethoxy)phenyl]piperidin-4-one

Synthesized analogous to Reference Example 244.
$^1$HNMR (CDCl$_3$) δ ppm: 2.66 (4H, t, J=6.0 Hz), 3.36 (4H, t, J=6.0 Hz), 6.89 (1H, d, J=1.0 Hz), 6.90 (1H, dd, J=9.0 Hz, 1.0 Hz), 7.41 (1H, d, J=9.0 Hz).

Reference Example 250

1-(2-Chloro-5-nitrophenyl)piperidin-4-one

To a solution of 8-(2-chloro-5-nitrophenyl)-1,4-dioxa-8-azaspiro[4.5]decane (346 mg) in tetrahydrofuran (4 mL) was added 5 N hydrochloric acid (2 mL), and the reaction mixture was stirred at room temperature for 13 h. The reaction solution was concentrated, neutralized with 5 N aqueous sodium hydroxide, and the solution was extracted with ethyl acetate. The organic layer was washed with brine, dried over anhydrous sodium sulfate, and the solvent was distilled off. The residue was purified by silica gel column chromatography (hexane/ethyl acetate) to provide the title compound (229 mg).
$^1$HNMR (CDCl$_3$) δ ppm: 2.69 (4H, t, J=6.0 Hz), 3.43 (4H, t, J=6.0 Hz), 7.57 (1H, d, J=9.0 Hz), 7.90 (1H, dd, J=9.0 Hz, 2.5 Hz), 7.92 (1H, d, J=2.5 Hz).

Reference Example 251

1-(4-Chloro-3-methylphenyl)piperidin-4-one

To a solution of 8-(4-chloro-3-methylphenyl)-1,4-dioxa-8-azaspiro[4.5]decane (2.26 g) in tetrahydrofuran (46 mL) was added 5 N hydrochloric acid (23 mL), and the reaction mixture was stirred at room temperature for 14 h, then at 70° C. for 3 h. The reaction solution was concentrated, neutralized with 5 N aqueous sodium hydroxide, and the solution was extracted with ethyl acetate. The organic layer was washed with brine, dried over anhydrous sodium sulfate, and the solvent was distilled off. The residue was purified by silica gel column chromatography (hexane/ethyl acetate) to provide the title compound (1.58 g).
$^1$HNMR (CDCl$_3$) δ ppm: 2.35 (3H, s), 2.55 (4H, t, J=6.0 Hz), 3.56 (4H, t, J=6.0 Hz), 6.74 (1H, dd, J=8.5 Hz, 3.0 Hz), 6.83 (1H, d, J=3.0 Hz), 7.23 (1H, d, J=8.5 Hz).

Reference Example 252

Ethyl 2-chloro-5-(4-oxopiperidin-1-yl)benzoate

Synthesized analogous to Reference Example 250.
$^1$HNMR (CDCl$_3$) δ ppm: 1.41 (3H, t, J=7.0 Hz), 2.57 (4H, t, J=6.0 Hz), 3.61 (4H, t, J=6.0 Hz), 4.41 (2H, q, J=7.0 Hz), 6.99 (1H, dd, J=9.0 Hz, 3.0 Hz), 7.33 (1H, d, J=9.0 Hz), 7.35 (1H, d, J=3.0 Hz).

Reference Example 253

1-[2-Chloro-4-(propan-2-yl)phenyl]piperidin-4-one

Synthesized analogous to Reference Example 251.
$^1$HNMR (CDCl$_3$) δ ppm: 1.23 (6H, d, J=7.0 Hz), 2.64 (4H, t, J=6.0 Hz), 2.86 (1H, sep, J=7.0 Hz), 3.31 (4H, t, J=6.0 Hz), 6.99 (1H, d, J=8.0 Hz), 7.09 (1H, dd, J=8.0 Hz, 2.0 Hz), 7.27 (1H, d, J=2.0 Hz).

Reference Example 254

1-(2,4-Dichloro-6-methylphenyl)piperidin-4-one

Synthesized analogous to Reference Example 251.
$^1$HNMR (CDCl$_3$) δ ppm: 2.37 (3H, s), 2.53-2.63 (4H, m), 3.22-3.27 (2H, m), 3.59-3.64 (2H, m), 7.10-7.12 (1H, m), 7.21 (1H, d, J=2.5 Hz).

Reference Example 255

1-(4-Ethoxy-2-fluorophenyl)piperidin-4-one

Synthesized analogous to Reference Example 244.
$^1$HNMR (CDCl$_3$) δ ppm: 1.40 (3H, t, J=7.0 Hz), 2.62 (4H, t, J=6.0 Hz), 3.31 (4H, t, J=6.0 Hz), 3.98 (2H, q, J=7.0 Hz), 6.62 (1H, ddd, J=9.0 Hz, 3.0 Hz, 1.0 Hz), 6.67 (1H, dd, J=13.5 Hz, 3.0 Hz), 6.93 (1H, t, J=9.0 Hz).

Reference Example 256

1-(2-Fluoro-4-propoxyphenyl)piperidin-4-one

Synthesized analogous to Reference Example 244.
$^1$HNMR (CDCl$_3$) δ ppm: 1.03 (3H, t, J=7.5 Hz), 1.76-1.83 (2H, m), 2.62 (4H, t, J=6.0 Hz), 3.31 (4H, t, J=6.0 Hz), 3.87 (2H, t, J=6.5 Hz), 6.62 (1H, ddd, J=8.5 Hz, 3.0 Hz, 1.0 Hz), 6.68 (1H, dd, J=13.5 Hz, 3.0 Hz), 6.93 (1H, t, J=8.5 Hz).

Reference Example 257

1-(2-Chloro-4-ethylphenyl)piperidin-4-one

Synthesized analogous to Reference Example 251.
$^1$HNMR (CDCl$_3$) δ ppm: 1.22 (3H, t, J=7.5 Hz), 2.59 (2H, q, J=7.5 Hz), 2.64 (4H, t, J=6.0 Hz), 3.31 (4H, t, J=6.0 Hz), 6.98 (1H, d, J=8.0 Hz), 7.06 (1H, dd, J=8.0 Hz, 2.0 Hz), 7.25 (1H, d, J=2.0 Hz).

Reference Example 258

1-(2-Chloro-4-propylphenyl)piperidin-4-one

Synthesized analogous to Reference Example 251.

¹HNMR (CDCl₃) δ ppm: 0.94 (3H, t, J=7.5 Hz), 1.62 (2H, sext, J=7.5 Hz), 2.52 (2H, t, J=7.5 Hz), 2.64 (4H, t, J=6.0 Hz), 3.32 (4H, t, J=6.0 Hz), 6.97 (1H, d, J=8.0 Hz), 7.03 (1H, dd, J=8.0 Hz, 2.0 Hz), 7.23 (1H, d, J=2.0 Hz).

Reference Example 259

1-(2,4-Dichloro-6-fluorophenyl)piperidin-4-one

Synthesized analogous to Reference Example 251.
¹HNMR (CDCl₃) δ ppm: 2.60 (4H, t, J=6.0 Hz), 3.43 (4H, dt, J=1.0 Hz, 6.0 Hz), 7.02 (1H, dd, J=11.0 Hz, 2.0 Hz), 7.24 (1H, t, J=2.0 Hz).

Reference Example 260

1-(4-Butoxy-2-fluorophenyl)piperidin-4-one

Synthesized analogous to Reference Example 244.
¹HNMR (CDCl₃) δ ppm: 0.97 (3H, t, J=7.5 Hz), 1.44-1.52 (2H, m), 1.72-1.78 (2H, m), 2.62 (4H, t, J=6.0 Hz), 3.31 (4H, t, J=6.0 Hz), 3.90 (2H, t, J=6.5 Hz), 6.62 (1H, ddd, J=9.0 Hz, 2.5 Hz, 1.0 Hz), 6.67 (1H, dd, J=13.5 Hz, 2.5 Hz), 6.93 (1H, t, J=9.0 Hz).

Reference Example 261

1-[2-Fluoro-4-(propan-2-yloxy)phenyl]piperidin-4-one

Synthesized analogous to Reference Example 244.
¹HNMR (CDCl₃) δ ppm: 1.32 (6H, d, J=6.0 Hz), 2.62 (4H, t, J=6.0 Hz), 3.31 (4H, t, J=6.0 Hz), 4.45 (1H, sep, J=6.0 Hz), 6.61 (1H, ddd, J=9.0 Hz, 3.0 Hz, 1.0 Hz), 6.66 (1H, dd, J=13.5 Hz, 3.0 Hz), 6.92 (1H, t, J=9.0 Hz).

Reference Example 262

1-[2-Chloro-4-(trifluoromethoxy)phenyl]piperidin-4-one

Synthesized analogous to Reference Example 251.
¹HNMR (CDCl₃) δ ppm: 2.65 (4H, t, J=6.0 Hz), 3.33 (4H, t, J=6.0 Hz), 7.06 (1H, d, J=9.0 Hz), 7.12 (1H, dd, J=9.0 Hz, 2.5 Hz), 7.32 (1H, d, J=2.5 Hz).

Reference Example 263

1-[2,4-Dichloro-5-(trifluoromethoxy)phenyl]piperidin-4-one

Synthesized analogous to Reference Example 251.
¹HNMR (CDCl₃) δ ppm: 2.65 (4H, t, J=6.0 Hz), 3.34 (4H, t, J=6.0 Hz), 6.98 (1H, d, J=1.0 Hz), 7.53 (1H, s).

Reference Example 264

1-[2-Fluoro-4-(trifluoromethoxy)phenyl]piperidin-4-one

Synthesized analogous to Reference Example 251.
¹HNMR (CDCl₃) δ ppm: 2.63 (4H, t, J=6.0 Hz), 3.40 (4H, t, J=6.0 Hz), 6.96-7.02 (3H, m).

Reference Example 265

1-(2-Fluoro-4-methoxyphenyl)piperidin-4-one

Synthesized analogous to Reference Example 244.
¹HNMR (CDCl₃) δ ppm: 2.62 (4H, t, J=6.0 Hz), 3.31 (4H, t, J=6.0 Hz), 3.77 (3H, s), 6.63 (1H, ddd, J=9.0 Hz, 3.0 Hz, 1.0 Hz), 6.68 (1H, dd, J=13.5 Hz, 3.0 Hz), 6.95 (1H, t, J=9.0 Hz).

Reference Example 266

1-[4-(Benzyloxy)-2-fluorophenyl]piperidin-4-one

Synthesized analogous to Reference Example 244.
¹HNMR (CDCl₃) δ ppm: 2.62 (4H, t, J=6.0 Hz), 3.31 (4H, t, J=6.0 Hz), 5.02 (2H, s), 6.70 (1H, ddd, J=9.0 Hz, 3.0 Hz, 1.0 Hz), 6.76 (1H, dd, J=13.5 Hz, 3.0 Hz), 6.93 (1H, t, J=9.0 Hz), 7.32-7.36 (1H, m), 7.37-7.43 (4H, m).

Reference Example 267

1-[2-Fluoro-4-(2-methoxyethoxy)phenyl]piperidin-4-one

Synthesized analogous to Reference Example 244.
¹HNMR (CDCl₃) δ ppm: 2.61 (4H, t, J=6.0 Hz), 3.31 (4H, t, J=6.0 Hz), 3.45 (3H, s), 3.73-3.74 (2H, m), 4.06-4.08 (2H, m), 6.66 (1H, ddd, J=9.0 Hz, 2.5 Hz, 1.0 Hz), 6.72 (1H, dd, J=13.5 Hz, 2.5 Hz), 6.93 (1H, t, J=9.0 Hz).

Reference Example 268

1-[4-Chloro-2-fluoro-5-(trifluoromethoxy)phenyl]piperidin-4-one

Synthesized analogous to Reference Example 251.
¹HNMR (CDCl₃) δ ppm: 2.63 (4H, t, J=6.0 Hz), 3.42 (4H, t, J=6.0 Hz), 6.91 (1H, dd, J=8.0 Hz, 1.0 Hz), 7.20 (1H, d, J=11.5 Hz).

Reference Example 269

1-(2-Bromo-5-ethoxy-4-nitrophenyl)piperidin-4-one

To a solution of 8-(2-bromo-5-ethoxy-4-nitrophenyl)-1,4-dioxa-8-azaspiro[4.5]decane (2.70 g) in tetrahydrofuran (54 mL) was added 2 N hydrochloric acid (54 mL), and the reaction mixture was stirred at room temperature for 64 h, then at 70° C. for 6 h. To the reaction mixture were added acetone (80 mL) and 5 N hydrochloric acid (40 mL), and the reaction mixture was heated to reflux for 5 h. The reaction solution was concentrated, neutralized with 5 N aqueous sodium hydroxide, and the solution was extracted with ethyl acetate. The organic layer was washed with brine, dried over anhydrous sodium sulfate, and the solvent was distilled off. The residue was purified by silica gel column chromatography (hexane/ethyl acetate) to provide the title compound (662 mg).
¹HNMR (CDCl₃) δ ppm: 1.50 (3H, t, J=7.0 Hz), 2.69 (4H, t, J=6.0 Hz), 3.44 (4H, t, J=6.0 Hz), 4.17 (2H, q, J=7.0 Hz), 6.63 (1H, s), 8.21 (1H, s).

Reference Example 270

1-(4-Ethoxy-2,5-difluorophenyl)piperidin-4-one

Synthesized analogous to Reference Example 244.
¹HNMR (CDCl₃) δ ppm: 1.43 (3H, t, J=7.0 Hz), 2.61 (4H, t, J=6.0 Hz), 3.31 (4H, t, J=6.0 Hz), 4.06 (2H, q, J=7.0 Hz), 6.75 (1H, dd, J=13.0 Hz, 8.0 Hz), 6.76 (1H, dd, J=12.5 Hz, 8.0 Hz).

Reference Example 271

1-[4-(Ethoxymethyl)-2-fluorophenyl]piperidin-4-one

To a solution of 8-[4-(ethoxymethyl)-2-fluorophenyl]-1,4-dioxa-8-azaspiro[4.5]decane (1.19 g) in ethanol/water (12-1.2 mL) was added oxalic acid (1.81 g), and the reaction mixture was heated to reflux for 6 h. To the reaction solution was added water, the mixture was neutralized with 5 N aqueous sodium hydroxide, and the solution was extracted with ethyl acetate. The organic layer was washed with brine, dried over anhydrous sodium sulfate, and the solvent was distilled off. The residue was purified by silica gel column chromatography (hexane/ethyl acetate) to provide the title compound (756 mg).
$^1$HNMR (CDCl$_3$) δ ppm: 1.25 (3H, t, J=7.0 Hz), 2.62 (4H, t, J=6.0 Hz), 3.40 (4H, t, J=6.0 Hz), 3.54 (2H, q, J=7.0 Hz), 4.43 (2H, s), 6.95 (1H, t, J=8.5 Hz), 7.05 (1H, dd, J=8.5 Hz, 2.0 Hz), 7.09 (1H, dd, J=13.0 Hz, 2.0 Hz).

Reference Example 272

1-(2,6-Difluoro-4-methoxyphenyl)piperidin-4-one

Synthesized analogous to Reference Example 244.
$^1$HNMR (CDCl$_3$) δ ppm: 2.57 (4H, t, J=6.0 Hz), 3.40 (4H, t, J=6.0 Hz), 3.76 (3H, s), 6.42-6.48 (2H, m).

Reference Example 273

1-{4-[2-(Dimethylamino)ethoxy]-2,5-difluorophenyl}piperidin-4-one

Synthesized analogous to Reference Example 244.
$^1$HNMR (CDCl$_3$) δ ppm: 2.34 (6H, s), 2.61 (4H, t, J=6.0 Hz), 2.74 (2H, t, J=5.5 Hz), 3.31 (4H, t, J=6.0 Hz), 4.08 (2H, t, J=5.5 Hz), 6.74-6.81 (2H, m).

Reference Example 274

1-(4-Ethoxy-2,3,5,6-tetrafluorophenyl)piperidin-4-one

Synthesized analogous to Reference Example 251.
$^1$HNMR (CDCl$_3$) δ ppm: 1.41 (3H, t, J=7.0 Hz), 2.59 (4H, t, J=6.0 Hz), 3.48 (4H, t, J=6.0 Hz), 4.23 (2H, q, J=7.0 Hz).

Reference Example 275

1-(4-Chloro-2-fluoro-6-methylphenyl)piperidin-4-one

To a solution of 8-(2-fluoro-6-methylphenyl)-1,4-dioxa-8-azaspiro[4.5]decane (3.46 g) in N,N-dimethylformamide (28 mL) was added N-chlorosuccinimide (2.57 g), and the reaction mixture was stirred at room temperature for 77 h. To the reaction solution was added water, and the solution was extracted with ethyl acetate. The organic layer was washed with brine, dried over anhydrous sodium sulfate, and the solvent was distilled off. The residue was purified by silica gel column chromatography (hexane/ethyl acetate) to give a mixture of 8-(2-fluoro-6-methylphenyl)-1,4-dioxa-8-azaspiro[4.5]decane and the title compound (1.9 g). To the mixture were added tetrahydrofuran (40 mL) and 2 N hydrochloric acid (20 L), and the reaction mixture was stirred at room temperature for 13 h, then at 70° C. for 6 h. The reaction solution was concentrated and neutralized with 5 N aqueous sodium hydroxide, and the solution was extracted with ethyl acetate. The organic layer was washed with brine, dried over anhydrous sodium sulfate, and the solvent was distilled off. The residue was purified by silica gel column chromatography (hexane/ethyl acetate) to provide the title compound (307 mg).
$^1$HNMR (CDCl$_3$) δ ppm: 2.38 (3H, s), 2.53-2.59 (4H, m), 3.32-3.37 (4H, m), 6.92 (1H, dd, J=11.5 Hz, 2.0 Hz), 7.00-7.02 (1H, m).

Reference Example 276

1-{2-Fluoro-4-[2-(2-methoxyethoxy)ethoxy]phenyl}piperidin-4-one

Synthesized analogous to Reference Example 244.
$^1$HNMR (CDCl$_3$) δ ppm: 2.61 (4H, t, J=6.0 Hz), 3.31 (4H, t, J=6.0 Hz), 3.40 (3H, s), 3.57-3.59 (2H, m), 3.71-3.72 (2H, m), 3.84 (2H, t, J=5.0 Hz), 4.10 (2H, t, J=5.0 Hz), 6.64 (1H, ddd, J=9.0 Hz, 3.0 Hz, 1.0 Hz), 6.71 (1H, dd, J=13.5 Hz, 3.0 Hz), 6.92 (1H, t, J=9.0 Hz).

Reference Example 277

1-(4-Chloro-2-fluoro-5-methylphenyl)piperidin-4-one

Synthesized analogous to Reference Example 251.
$^1$HNMR (CDCl$_3$) δ ppm: 2.31 (3H, s), 2.62 (4H, t, J=6.0 Hz), 3.37 (4H, t, J=6.0 Hz), 6.82 (1H, d, J=9.0 Hz), 7.08 (1H, d, J=12.0 Hz).

Reference Example 278

1-(4-Ethoxy-2-fluoro-5-methoxyphenyl)piperidin-4-one

Synthesized analogous to Reference Example 244.
$^1$HNMR (CDCl$_3$) δ ppm: 1.45 (3H, t, J=7.0 Hz), 2.62 (4H, t, J=6.0 Hz), 3.34 (4H, t, J=6.0 Hz), 3.85 (3H, s), 4.04 (2H, q, J=7.0 Hz), 6.60 (1H, d, J=8.5 Hz), 6.69 (1H, d, J=13.0 Hz).

Reference Example 279

1-(4-Ethoxy-2,6-difluorophenyl)piperidin-4-one

Synthesized analogous to Reference Example 244.
$^1$HNMR (CDCl$_3$) δ ppm: 1.40 (3H, t, J=7.0 Hz), 2.57 (4H, t, J=6.0 Hz), 3.39 (4H, t, J=6.0 Hz), 3.96 (2H, q, J=7.0 Hz), 6.40-6.46 (2H, m).

Reference Example 280

1-[2-Fluoro-4-(2-fluoroethoxy)phenyl]piperidin-4-one

Synthesized analogous to Reference Example 244.
$^1$HNMR (CDCl$_3$) δ ppm: 2.62 (4H, t, J=6.0 Hz), 3.32 (4H, t, J=6.0 Hz), 4.14-4.21 (2H, m), 4.68-4.79 (2H, m), 6.66 (1H, ddd, J=9.0 Hz, 3.0 Hz, 1.0 Hz), 6.72 (1H, dd, J=13.5 Hz, 3.0 Hz), 6.94 (1H, t, J=9.0 Hz).

Reference Example 281

1-{4-[2-(Dimethylamino)ethoxy]-2-fluorophenyl}piperidin-4-one

Synthesized analogous to Reference Example 244.

¹HNMR (CDCl₃) δ ppm: 2.33 (6H, s), 2.62 (4H, t, J=6.0 Hz), 2.71 (2H, t, J=5.5 Hz), 3.31 (4H, t, J=6.0 Hz), 4.01 (2H, t, J=5.5 Hz), 6.65 (1H, dd, J=9.0 Hz, 3.0 Hz), 6.71 (1H, dd, J=13.5 Hz, 3.0 Hz), 6.93 (1H, t, J=9.0 Hz).

Reference Example 282

1-[2-Fluoro-4-(2,2,2-trifluoroethoxy)phenyl]piperidin-4-one

Synthesized analogous to Reference Example 251.
¹HNMR (CDCl₃) δ ppm: 2.62 (4H, t, J=6.0 Hz), 3.33 (4H, t, J=6.0 Hz), 4.31 (2H, q, J=8.0 Hz), 6.68 (1H, ddd, J=9.0 Hz, 3.0 Hz, 1.0 Hz), 6.75 (1H, dd, J=13.0 Hz, 3.0 Hz), 6.96 (1H, t, J=9.0 Hz).

Reference Example 283

1-(Quinoxalin-6-yl)piperidin-4-one

Synthesized analogous to Reference Example 271.
¹HNMR (CDCl₃) δ ppm: 2.64 (4H, t, J=6.0 Hz), 3.84 (4H, t, J=6.0 Hz), 7.36 (1H, d, J=3.0 Hz), 7.57 (1H, dd, J=9.5 Hz, 3.0 Hz), 8.00 (1H, d, J=9.5 Hz), 8.63 (1H, d, J=2.0 Hz), 8.72 (1H, d, J=2.0 Hz).

Reference Example 284

1-(1-Benzofuran-5-yl)piperidin-4-one

Synthesized analogous to Reference Example 251.
¹HNMR (CDCl₃) δ ppm: 2.62 (4H, t, J=6.0 Hz), 3.54 (4H, t, J=6.0 Hz), 6.70 (1H, dd, J=2.5 Hz, 0.5 Hz), 7.05 (1H, dd, J=9.0 Hz, 2.5 Hz), 7.17 (1H, dd, J=2.5 Hz, 0.5 Hz), 7.43 (1H, d, J=9.0 Hz), 7.60 (1H, d, J=2.5 Hz).

Reference Example 285

1-[4-(Difluoromethoxy)-2-fluorophenyl]piperidin-4-one

Synthesized analogous to Reference Example 244.
¹HNMR (CDCl₃) δ ppm: 2.63 (4H, t, J=6.0 Hz), 3.37 (4H, t, J=6.0 Hz), 6.46 (1H, t, J=73.5 Hz), 6.88 (1H, dd, J=9.0 Hz, 2.5 Hz), 6.92 (1H, dd, J=12.5 Hz, 2.5 Hz), 6.97 (1H, t, J=9.0 Hz).

Reference Example 286

1-[4-(Difluoromethoxy)-2,6-difluorophenyl]piperidin-4-one

Synthesized analogous to Reference Example 244.
¹HNMR (CDCl₃) δ ppm: 2.59 (4H, t, J=6.0 Hz), 3.45 (4H, t, J=6.0 Hz), 6.47 (1H, t, J=72.5 Hz), 6.70-6.76 (2H, m).

Reference Example 287

1-[2-Chloro-4-(methylsulfanyl)phenyl]piperidin-4-one

Synthesized analogous to Reference Example 271.
¹HNMR (CDCl₃) δ ppm: 2.47 (3H, s), 2.64 (4H, t, J=6.0 Hz), 3.31 (4H, t, J=6.00 Hz), 6.99 (1H, d, J=8.5 Hz), 7.15 (1H, dd, J=8.5 Hz, 2.0 Hz), 7.32 (1H, d, J=2.0 Hz).

Reference Example 288

1-[4-(Ethylsulfanyl)-2,6-difluorophenyl]piperidin-4-one

Synthesized analogous to Reference Example 271.
¹HNMR (CDCl₃) δ ppm: 1.33 (3H, t, J=7.5 Hz), 2.58 (4H, t, J=6.0 Hz), 2.92 (2H, q, J=7.5 Hz), 3.45 (4H, t, J=6.0 Hz), 6.80-6.86 (2H, m).

Reference Example 289

1-[2,6-Difluoro-4-(2,2,2-trifluoroethoxy)phenyl]piperidin-4-one

Synthesized analogous to Reference Example 251.
¹HNMR (CDCl₃) δ ppm: 2.58 (4H, t, J=6.0 Hz), 3.41 (4H, t, J=6.0 Hz), 4.30 (2H, q, J=8.0 Hz), 6.49-6.55 (2H, m).

Reference Example 290

1-Bromo-4-ethoxy-2-fluoro-5-nitrobenzene

To a suspension of 4-bromo-5-fluoro-2-nitrophenol (5.14 g) and potassium carbonate (6.02 g) in acetonitrile (100 mL) was added ethyl iodide (2.29 mL), and the reaction mixture was heated to reflux for 4 h. To the reaction solution was added water, and the solution was extracted with ethyl acetate. The organic layer was washed with brine, dried over anhydrous sodium sulfate, and the solvent was distilled off. The residue was purified by silica gel column chromatography (hexane/ethyl acetate) to provide the title compound (4.73 g).
¹HNMR (CDCl₃) δ ppm: 1.50 (3H, t, J=7.0 Hz), 4.16 (2H, q, J=7.0 Hz), 6.86 (1H, d, J=10.0 Hz), 8.14 (1H, d, J=7.0 Hz).

Reference Example 291

4-Bromo-2,5-difluorophenyl ethyl ether

Synthesized analogous to Reference Example 290.
¹HNMR (CDCl₃) δ ppm: 1.46 (3H, t, J=7.0 Hz), 4.07 (2H, q, J=7.0 Hz), 6.76 (1H, dd, J=9.5 Hz, 7.0 Hz), 7.25 (1H, dd, J=10.5 Hz, 7.0 Hz).

Reference Example 292

1-Bromo-4-(ethoxymethyl)-2-fluorobenzene

To a solution of (4-bromo-3-fluorophenyl)methanol (2.19 g) in N,N-dimethylformamide (22 mL) was added sodium hydride (55% in oil) (0.282 g), and the reaction mixture was stirred at room temperature for 1.5 h. Then ethyl iodide (1.12 mL) was added thereto and the mixture was stirred at 60° C. for 5 h. To the reaction solution was added water, and the solution was extracted with ethyl acetate. The organic layer was washed with 5 N aqueous sodium hydroxide and brine, dried over anhydrous sodium sulfate, and the solvent was distilled off. The residue was purified by silica gel column chromatography (hexane/ethyl acetate) to provide the title compound (1.28 g).
¹HNMR (CDCl₃) δ ppm: 1.25 (3H, t, J=7.0 Hz), 3.54 (2H, q, J=7.0 Hz), 4.45 (2H, s), 7.00 (1H, dd, J=8.0 Hz, 1.5 Hz), 7.13 (1H, dd, J=9.5 Hz, 1.5 Hz), 7.50 (1H, dd, J=8.0 Hz, 7.0 Hz).

Reference Example 293

2-(4-Bromo-2,5-difluorophenoxy)-N,N-dimethyl-ethaneamine

To a suspension of 4-bromo-2,5-difluorophenol (4.44 g) and potassium carbonate (9.69 g) in acetonitrile (90 mL) were added sodium iodide (4.14 g) and 2-chloro-N,N-dimethylethylamine hydrochloride (3.98 g), and the reaction mixture was heated to reflux for 5 h. To the reaction solution was added water, and the solution was extracted with ethyl acetate. The organic layer was washed with 5 N aqueous sodium hydroxide and brine, dried over anhydrous sodium sulfate, and the solvent was distilled off. The residue was purified by silica gel column chromatography (ethyl acetate/methanol) to provide the title compound (2.11 g).
$^1$HNMR (CDCl$_3$) δ ppm: 2.39 (6H, s), 2.83 (2H, t, J=5.5 Hz), 4.13 (2H, t, J=5.5 Hz), 6.75-6.80 (1H, m), 7.21-7.27 (1H, m).

Reference Example 294

1-Bromo-4-ethoxy-2-fluoro-5-methoxybenzene

Synthesized analogous to Reference Example 290.
$^1$HNMR (CDCl$_3$) δ ppm: 1.47 (3H, t, J=7.0 Hz), 3.84 (3H, s), 4.05 (2H, q, J=7.0 Hz), 6.70 (1H, d, J=10.0 Hz), 6.96 (1H, d, J=6.5 Hz).

Reference Example 295

4-Bromo-3,5-difluorophenyl ethyl ether

Synthesized analogous to Reference Example 290.
$^1$HNMR (CDCl$_3$) δ ppm: 1.41 (3H, t, J=7.0 Hz), 3.99 (2H, q, J=7.0 Hz), 6.50-6.54 (2H, m).

Reference Example 296

4-Bromo-3,5-difluorophenyl ethyl sulfide

Synthesized analogous to Reference Example 290.
$^1$HNMR (CDCl$_3$) δ ppm: 1.35 (3H, t, J=7.5 Hz), 2.96 (2H, q, J=7.5 Hz), 6.84-6.87 (2H, m).

Reference Example 297

4-Bromo-3,5-difluorophenyl 2,2,2-trifluoroethyl ether

Synthesized analogous to Reference Example 290.
$^1$HNMR (CDCl$_3$) δ ppm: 4.33 (2H, q, J=8.0 Hz), 6.59-6.62 (2H, m).

Reference Example 298

4-Chloro-2-fluoro-5-(2-fluoroethoxy)aniline

Synthesized analogous to Reference Example 292.
$^1$HNMR (CDCl$_3$) δ ppm: 3.73 (2H, brs), 4.15-4.23 (2H, m), 4.69-4.81 (2H, m), 6.41 (1H, d, J=8.0 Hz), 7.02 (1H, d, J=10.5 Hz).

Reference Example 299

4-Chloro-2-fluoro-5-(2,2,2-trifluoroethoxy)aniline

Synthesized analogous to Reference Example 290.
$^1$HNMR (CDCl$_3$) δ ppm: 3.78 (2H, brs), 4.32 (2H, q, J=8.0 Hz), 6.46 (1H, d, J=8.0 Hz), 7.04 (1H, d, J=10.5 Hz).

Reference Example 300

4-Chloro-5-[2-(dimethylamino)ethoxy]-2-fluoroaniline

Synthesized analogous to Reference Example 292.
$^1$HNMR (CDCl$_3$) δ ppm: 2.36 (6H, s), 2.76 (2H, t, J=6.0 Hz), 3.72 (2H, brs), 4.03 (2H, t, J=6.0 Hz), 6.39 (1H, d, J=8.0 Hz), 7.01 (1H, d, J=10.5 Hz).

Reference Example 301

4-Chloro-5-[(4-chlorobenzyl)oxy]-2-fluoroaniline

Synthesized analogous to Reference Example 292.
$^1$HNMR (CDCl$_3$) δ ppm: 3.70 (2H, brs), 5.02 (2H, s), 6.37 (1H, d, J=8.0 Hz), 7.04 (1H, d, J=10.5 Hz), 7.34-7.39 (4H, m).

Reference Example 302

4-Chloro-2-fluoro-5-(2-methoxyethoxy)aniline

Synthesized analogous to Reference Example 292.
$^1$HNMR (CDCl$_3$) δ ppm: 3.47 (3H, s), 3.72 (2H, brs), 3.76 (2H, t, J=5.0 Hz), 4.09 (2H, t, J=5.0 Hz), 6.42 (1H, d, J=8.0 Hz), 7.01 (1H, d, J=10.0 Hz).

Reference Example 303

4-Chloro-2-fluoro-5-[2-(4-fluorophenoxy) ethoxy] aniline

Synthesized analogous to Reference Example 292.
$^1$HNMR (CDCl$_3$) δ ppm: 3.73 (2H, brs), 4.26-4.31 (4H, m), 6.45 (1H, d, J=8.0 Hz), 6.90-6.92 (2H, m), 6.96-7.01 (2H, m), 7.02 (1H, d, J=10.0 Hz).

Reference Example 304

4-Chloro-2-fluoro-5-propylaniline

Under nitrogen atmosphere, a solution of 1-bromo-2-chloro-4-fluoro-5-nitrobenzene (1.40 g), tetrakis(triphenylphosphine)palladium (0) (0.318 g), sodium carbonate (1.75 g) and trans-propenylboronic acid (0.945 g) in 1,4-dioxane-water (30-6 mL) was stirred at 100° C. for 5 h. To the reaction solution was added water, and the solution was extracted with ethyl acetate. The organic layer was washed with brine, dried over anhydrous sodium sulfate, and the solvent was distilled off. The residue was purified by silica gel column chromatography (hexane/ethyl acetate) to give (E)-4-chloro-2-fluoro-5-(1-propenyl)aniline. Under nitrogen atmosphere, to platinum on carbon (wetted with 56% water) (140 mg) was added a solution of the obtained compound in ethanol (14 mL) and the reaction mixture was stirred at room temperature for 5 h under hydrogen atmosphere. The reaction solution was filtrated with Celite, the filter was washed with ethanol, and the solvent of the filtrate was distilled off. The residue was purified by silica gel column chromatography (hexane/ethyl acetate) to provide the title compound (405 mg).

¹HNMR (CDCl₃) δ ppm: 0.95 (3H, t, J=7.0 Hz), 1.55-1.63 (2H, m), 2.56 (2H, t, J=7.5 Hz), 3.64 (2H, brs), 6.61 (1H, d, J=9.5 Hz), 6.98 (1H, d, J=11.0 Hz).

Reference Example 305

1-Chloro-2-ethenyl-5-fluoro-4-nitrobenzene

Under nitrogen atmosphere, a solution of 1-bromo-2-chloro-4-fluoro-5-nitrobenzene (4.14 g), tetrakis(triphenylphosphine)palladium (0) (0.941 g), sodium carbonate (5.18 g) and vinylboronic acid pinacol ester (5.95 mL) in 1,4-dioxane-water (80-16 mL) was stirred at 100° C. for 3 h. To the reaction solution was added water, and the solution was extracted with ethyl acetate. The organic layer was washed with brine, dried over anhydrous sodium sulfate, and the solvent was distilled off. The residue was purified by silica gel column chromatography (hexane/ethyl acetate) to provide the title compound (3.20 g).
¹HNMR (CDCl₃) δ ppm: 5.57 (1H, d, J=11.0 Hz), 5.85 (1H, d, J=17.0 Hz), 7.00 (1H, J=17.0 Hz, 11.0 Hz), 7.35 (1H, dd, J=10.0 Hz), 8.28 (1H, d, J=8.0 Hz).

Reference Example 306

4-Chloro-5-ethyl-2-fluoroaniline

Under nitrogen atmosphere, to a suspension of platinum on carbon (wetted with 56% water) (150 mg) in ethanol was added a solution of 1-chloro-2-ethenyl-5-fluoro-4-nitrobenzene (1.49 g) in ethanol, and the reaction mixture was stirred at room temperature for 5 h under hydrogen atmosphere. The reaction solution was filtered with Celite, the filtrate was washed with ethanol, and the solvent was distilled off. The residue was purified by silica gel column chromatography (hexane/ethyl acetate) to provide the title compound (929 mg).
¹HNMR (CDCl₃) δ ppm: 1.17 (3H, t, J=7.5 Hz), 2.62 (2H, q, J=7.5 Hz), 3.65 (2H, brs), 6.63 (1H, d, J=9.5 Hz), 6.98 (1H, d, J=10.5 Hz).

Reference Example 307

2-(2-Chloro-4-fluoro-5-nitrophenyl)ethanol

Under nitrogen atmosphere, to a solution of 1-chloro-2-ethenyl-5-fluoro-4-nitrobenzene (3.69 g) in tetrahydrofuran (70 mL) was added a solution of 1 M borane-tetrahydrofuran complex solution (18.3 mL), and the reaction mixture was stirred at room temperature for 10 h. To the reaction solution were added 10% aqueous sodium hydroxide (0.925 g) and 30% hydrogen peroxide water (2.26 mL), and the reaction mixture was stirred at room temperature for 14 h. To the reaction solution was added aqueous saturated ammonium chloride solution, and the solution was extracted with ethyl acetate. The organic layer was washed with brine, dried over anhydrous sodium sulfate, and the solvent was distilled off. The residue was purified by silica gel column chromatography (hexane/ethyl acetate) to provide the title compound (1.08 g).
¹HNMR (CDCl₃) δ ppm: 1.51 (1H, t, J=5.0 Hz), 3.05 (2H, t, J=6.5 Hz), 3.93-3.96 (2H, m), 7.36 (1H, J=10.0 Hz), 8.08 (1H, d, J=8.0 Hz).

Reference Example 308

5-Ethoxy-2,4-difluoroaniline

Synthesized analogous to Reference Example 292.
¹HNMR (CDCl₃) δ ppm: 1.41 (3H, t, J=7.0 Hz), 3.54 (2H, brs), 4.02 (2H, q, J=7.0 Hz), 6.41 (1H, t, J=8.5 Hz), 6.80 (1H, t, J=10.5 Hz).

Reference Example 309

4-Chloro-2-fluoro-5-[2-(4-fluorophenoxy) ethyl] aniline

Synthesized analogous to Reference Example 306.
¹HNMR (CDCl₃) δ ppm: 3.08 (2H, t, J=7.0 Hz), 3.70 (2H, brs), 4.10 (2H, t, J=7.0 Hz), 6.73 (1H, d, J=9.0 Hz), 6.83 (2H, dd, J=9.5 Hz, 4.0 Hz), 6.96 (2H, t, J=9.5 Hz), 7.03 (1H, d, J=10.5 Hz).

Reference Example 310

4-Chloro-2-fluoro-5-(2-methoxyethyl)aniline

Synthesized analogous to Reference Example 292.
¹HNMR (CDCl₃) δ ppm: 2.88 (2H, t, J=7.0 Hz), 3.36 (3H, s), 3.56 (2H, t, J=7.0 Hz), 3.67 (2H, brs), 6.68 (1H, d, J=9.5 Hz), 7.00 (1H, d, J=10.5 Hz).

Reference Example 311

1-Chloro-5-fluoro-2-[2-(4-fluorophenoxy) ethyl]-4-nitrobenzene

Under nitrogen atmosphere, to a solution of 2-(2-chloro-4-fluoro-5-nitrophenyl)ethanol (507 mg), 4-fluorophenol (259 mg) and triphenylphosphine (666 mg) in dichloromethane (10 mL) was added a solution of 2.2 M diethyl azodicarboxylate in toluene (1.26 mL) at 0° C., and the reaction mixture was stirred at room temperature for 20 h. To the reaction solution was added 1 N hydrochloric acid, and the solution was extracted with ethyl acetate. The organic layer was washed with saturated aqueous sodium hydrogencarbonate and brine, dried over anhydrous sodium sulfate, and the solvent was distilled off. The residue was purified by silica gel column chromatography (hexane/ethyl acetate) to provide the title compound (260 mg).
¹HNMR (CDCl₃) δ ppm: 3.25 (2H, t, J=6.5 Hz), 4.18 (2H, t, J=6.5 Hz), 6.82 (2H, dd, J=9.0 Hz, 4.5 Hz), 6.97 (2H, dd, J=9.0 Hz, 8.5 Hz), 7.37 (1H, J=10.0 Hz), 8.13 (1H, d, J=7.5 Hz).

Reference Example 312

5-Ethenyl-2,4-difluoroaniline

Under nitrogen atmosphere, a solution of 5-bromo-2,4-difluoroaniline (2.04 g), vinylboronic acid pinacol ester (3.44 mL), potassium fluoride (1.81 g), tri-tert-butylphosphine-tetrafluoroborate (0.137 g) and tris(dibenzylideneacetone)dipalladium (0.172 g) in tetrahydrofuran/water (4:1) (25 mL) was heated to reflux for 9 h. To the reaction solution was added water, and the solution was extracted with ethyl acetate. The organic layer was washed with brine, dried over anhydrous sodium sulfate, and the solvent was distilled off. The residue was purified by silica gel column chromatography (hexane/ethyl acetate) to provide the title compound (1.09 g).
¹HNMR (CDCl₃) δ ppm: 3.58 (2H, brs), 5.29 (1H, d, J=11.5 Hz), 5.67 (1H, d, J=17.5 Hz), 6.72-6.78 (2H, m), 6.87 (1H, dd, J=9.5 Hz, 7.5 Hz).

Reference Example 313

2,4-Difluoro-5-[(1E)-prop-1-en-1-yl]aniline

Synthesized analogous to Reference Example 312.
$^1$HNMR (CDCl$_3$) δ ppm: 1.87 (3H, dd, J=6.5 Hz, 1.0 Hz), 3.54 (2H, brs), 6.15 (1H, dq, J=16.0 Hz, 6.5 Hz), 6.42 (1H, dd, J=16.0 Hz, 1.0 Hz), 6.72 (1H, t, J=10.5 Hz), 6.79 (1H, dd, J=9.5 Hz, 7.5 Hz).

Reference Example 314

5-Ethyl-2,4-difluoroaniline

Under nitrogen atmosphere, to 10% palladium on carbon (wetted with 50% water) (110 mg) was added a solution of 5-ethenyl-2,4-difluoroaniline (1.09 g) in ethanol (11 mL), and the reaction mixture was stirred at room temperature for 5 h under hydrogen atmosphere. The reaction solution was filtrated with Celite, the filter was washed with ethanol, and the solvent of the filtrate was distilled off. The residue was purified by silica gel column chromatography (hexane/ethyl acetate) to provide the title compound (692 mg).
$^1$HNMR (CDCl$_3$) δ ppm: 1.17 (3H, t, J=7.5 Hz), 2.55 (2H, q, J=7.5 Hz), 3.51 (2H, brs), 6.59 (1H, dd, J=9.5 Hz, 7.5 Hz), 6.71 (1H, dd, J=11.0 Hz, 10.0 Hz).

Reference Example 315

2,4-Difluoro-5-propylaniline

Synthesized analogous to Reference Example 314.
$^1$HNMR (CDCl$_3$) δ ppm: 0.93 (3H, t, J=7.5 Hz), 1.58 (2H, sext, J=7.5 Hz), 2.49 (2H, t, J=7.5 Hz), 3.49 (2H, brs) 6.57 (1H, dd, J=10.0 Hz, 7.5 Hz), 6.71 (1H, dd, J=11.0 Hz, 9.5 Hz).

Reference Example 316

2-(5-Amino-2-chloro-4-fluorophenyl)ethanol

Synthesized analogous to Reference Example 306.
$^1$HNMR (CDCl$_3$) δ ppm: 1.43 (1H, brs), 2.88 (2H, t, J=6.5 Hz), 3.70 (2H, brs), 3.84 (2H, t, J=6.5 Hz), 6.69 (1H, d, J=9.5 Hz), 7.02 (1H, d, J=10.5 Hz).

Reference Example 317

1-Methyl-1-(2-nitrobenzyl)-4-oxopiperidinium bromide

To a solution of 1-methyl-4-piperidone (29.1 mL) in acetone (300 mL) was added 2-nitrobenzyl bromide (48.8 g), and the reaction mixture was stirred at room temperature. After 2 h, the precipitate was collected on a filter, and washed with acetone and ethanol to provide the title compound (63.2 g).
$^1$HNMR (DMSO-d6) δ ppm: 2.52-2.60 (2H, m), 2.81-2.96 (2H, m), 3.22 (3H, s), 3.63-3.72 (2H, m), 3.73-3.89 (2H, m), 5.11 (2H, s), 7.80-7.95 (3H, m), 8.18 (1H, d, J=7.2 Hz).

Reference Example 318

1-(4-Chloro-5-ethoxy-2-fluorophenyl)piperidin-4-one

To a solution of 4-chloro-5-ethoxy-2-fluoroaniline (2.60 g) in ethanol-water (27-18 mL) was added 1-benzyl-1-methyl-4-oxopiperidinium bromide (3.90 g), and the reaction mixture was stirred at 100° C. for 14 h. To the reaction solution was added water, and the solution was extracted with ethyl acetate. The organic layer was washed with brine, dried over anhydrous sodium sulfate, and the solvent was distilled off. The residue was purified by silica gel column chromatography (hexane/ethyl acetate) to provide the title compound (2.42 g).
$^1$HNMR (CDCl$_3$) δ ppm: 1.45 (3H, t, J=7.0 Hz), 2.62 (4H, t, J=6.0 Hz), 3.39 (4H, t, J=6.0 Hz), 4.06 (2H, q, J=7.0 Hz), 6.56 (1H, d, J=8.0 Hz), 7.11 (1H, d, J=11.5 Hz).

Reference Example 319

1-[4-Chloro-2-fluoro-5-(2-fluoroethoxy)phenyl]piperidin-4-one

Synthesized analogous to Reference Example 318.
$^1$HNMR (CDCl$_3$) δ ppm: 2.62 (4H, t, J=6.0 Hz), 3.39 (4H, t, J=6.0 Hz), 4.25 (2H, dt, J=28.0 Hz, 4.0 Hz), 4.77 (2H, dt, J=47.5 Hz, 4.0 Hz), 6.64 (1H, d, J=8.0 Hz), 7.12 (1H, d, J=11.5 Hz).

Reference Example 320

1-[4-Chloro-2-fluoro-5-(propan-2-yloxy)phenyl]piperidin-4-one

Synthesized analogous to Reference Example 318.
$^1$HNMR (CDCl$_3$) δ ppm: 1.35 (6H, d, J=6.0 Hz), 2.62 (4H, t, J=6.0 Hz), 3.38 (4H, t, J=6.0 Hz), 4.43 (1H, sep, J=6.0 Hz), 6.59 (1H, d, J=8.0 Hz), 7.10 (1H, d, J=11.5 Hz).

Reference Example 321

1-[4-Chloro-2-fluoro-5-(2,2,2-trifluoroethoxy)phenyl]piperidin-4-one

Synthesized analogous to Reference Example 318.
$^1$HNMR (CDCl$_3$) δ ppm: 2.63 (4H, t, J=6.0 Hz), 3.39 (4H, t, J=6.0 Hz), 4.37 (2H, q, J=8.0 Hz), 6.66 (1H, d, J=7.5 Hz), 7.14 (1H, d, J=11.5 Hz).

Reference Example 322

1-{4-Chloro-5-[(4-chlorobenzyl)oxy]-2-fluorophenyl}piperidin-4-one

Synthesized analogous to Reference Example 318.
$^1$HNMR (CDCl$_3$) δ ppm: 2.60 (4H, t, J=6.0 Hz), 3.35 (4H, t, J=6.0 Hz), 5.06 (2H, s), 6.55 (1H, d, J=7.5 Hz), 7.13 (1H, d, J=11.5 Hz), 7.36-7.40 (4H, m).

Reference Example 323

1-[4-Chloro-2-fluoro-5-(2-methoxyethoxy)phenyl]piperidin-4-one

Synthesized analogous to Reference Example 318.
$^1$HNMR (CDCl$_3$) δ ppm: 2.62 (4H, t, J=6.0 Hz), 3.39 (4H, t, J=6.0 Hz), 3.47 (3H, s), 3.76-3.78 (2H, m), 4.14-4.16 (2H, m), 6.66 (1H, d, J=7.5 Hz), 7.10 (1H, d, J=11.5 Hz).

Reference Example 324

1-{4-Chloro-2-fluoro-5-[2-(4-fluorophenoxy)ethoxy]phenyl}piperidin-4-one

Synthesized analogous to Reference Example 318.

¹HNMR (CDCl₃) δ ppm: 2.62 (4H, t, J=6.0 Hz), 3.37 (4H, t, J=6.0 Hz), 4.30-4.35 (4H, m), 6.66 (1H, d, J=7.5 Hz), 6.88-6.92 (2H, m), 6.97-7.01 (2H, m), 7.12 (1H, d, J=11.5 Hz).

Reference Example 325

1-(4-Chloro-2-fluoro-5-propoxyphenyl)piperidin-4-one

Synthesized analogous to Reference Example 318.
¹HNMR (CDCl₃) δ ppm: 1.07 (3H, t, J=7.5 Hz), 1.81-1.88 (2H, m), 2.62 (4H, t, J=6.0 Hz), 3.39 (4H, t, J=6.0 Hz), 3.94 (2H, t, J=6.5 Hz), 6.55 (1H, d, J=7.5 Hz), 7.10 (1H, d, J=11.5 Hz).

Reference Example 326

1-(5,6-Dimethylpyridin-2-yl)piperidin-4-one

Synthesized analogous to Reference Example 318.
¹HNMR (CDCl₃) δ ppm: 2.17 (3H, s), 2.38 (3H, s), 2.48 (4H, t, J=6.0 Hz), 3.87 (4H, t, J=6.0 Hz), 6.52 (1H, d, J=8.5 Hz), 7.26 (1H, d, J=8.5 Hz).

Reference Example 327

1-(4-Chloro-2-fluoro-5-propylphenyl)piperidin-4-one

Synthesized analogous to Reference Example 318.
¹HNMR (CDCl₃) δ ppm: 0.97 (3H, t, J=7.5 Hz), 1.57-1.65 (2H, m), 2.61-2.64 (2H, m), 2.62 (4H, t, J=6.0 Hz), 3.38 (4H, t, J=6.0 Hz), 6.79 (1H, d, J=9.0 Hz), 7.08 (1H, d, J=12.0 Hz).

Reference Example 328

1-[4-Chloro-2-fluoro-5-(propan-2-yl)phenyl]piperidin-4-one

Synthesized analogous to Reference Example 318.
¹HNMR (CDCl₃) δ ppm: 1.22 (6H, d, J=7.0 Hz), 2.62 (4H, t, J=6.0 Hz), 3.33 (1H, sep, J=7.0 Hz), 3.39 (4H, t, J=6.0 Hz), 6.86 (1H, d, J=9.5 Hz), 7.07 (1H, d, J=12.0 Hz).

Reference Example 329

1-(2,4-Difluoro-5-methylphenyl)piperidin-4-one

Synthesized analogous to Reference Example 318.
¹HNMR (CDCl₃) δ ppm: 2.22 (3H, s), 2.62 (4H, t, J=6.0 Hz), 3.33 (4H, t, J=6.0 Hz), 6.77-6.81 (2H, m).

Reference Example 330

1-(4-Chloro-5-ethyl-2-fluorophenyl)piperidin-4-one

Synthesized analogous to Reference Example 318.
¹HNMR (CDCl₃) δ ppm: 1.21 (3H, t, J=7.5 Hz), 2.62 (4H, t, J=6.0 Hz), 2.68 (2H, q, J=7.5 Hz), 3.38 (4H, t, J=6.0 Hz), 6.82 (1H, d, J=9.0 Hz), 7.08 (1H, d, J=11.5 Hz).

Reference Example 331

1-(4-Chloro-2-fluoro-5-methoxyphenyl)piperidin-4-one

Synthesized analogous to Reference Example 318.
¹HNMR (CDCl₃) δ ppm: 2.63 (4H, t, J=6.0 Hz), 3.41 (4H, t, J=6.0 Hz), 3.88 (3H, s), 6.55 (1H, d, J=8.0 Hz), 7.12 (1H, d, J=11.5 Hz).

Reference Example 332

1-(2,2,6-Trifluoro-1,3-benzodioxol-5-yl)piperidin-4-one

Synthesized analogous to Reference Example 318.
¹HNMR (CDCl₃) δ ppm: 2.63 (4H, t, J=6.0 Hz), 3.32 (4H, t, J=6.0 Hz), 6.80 (1H, d, J=7.0 Hz), 6.90 (1H, d, J=10.5 Hz).

Reference Example 333

1-(5-Ethoxy-2,4-difluorophenyl)piperidin-4-one

Synthesized analogous to Reference Example 318.
¹HNMR (CDCl₃) δ ppm: 1.42 (3H, t, J=7.0 Hz), 2.62 (4H, t, J=6.0 Hz), 3.34 (4H, t, J=6.0 Hz), 4.08 (2H, q, J=7.0 Hz), 6.63 (1H, t, J=8.0 Hz), 6.88 (1H, t, J=11.0 Hz).

Reference Example 334

1-(2,4-Difluoro-5-methoxyphenyl)piperidin-4-one

Synthesized analogous to Reference Example 318.
¹HNMR (CDCl₃) δ ppm: 2.63 (4H, t, J=6.0 Hz), 3.35 (4H, t, J=6.0 Hz), 3.87 (3H, s), 6.63 (1H, t, J=8.0 Hz), 6.89 (1H, t, J=11.5 Hz).

Reference Example 335

1-{4-Chloro-2-fluoro-5-[2-(4-fluorophenoxy) ethyl]phenyl}piperidin-4-one

Synthesized analogous to Reference Example 318.
¹HNMR (CDCl₃) δ ppm: 2.61 (4H, t, J=6.0 Hz), 3.14 (2H, t, J=6.5 Hz), 3.38 (4H, t, J=6.0 Hz), 4.12 (2H, t, J=6.5 Hz), 6.79-6.84 (1H, m), 6.91-6.98 (4H, m), 7.11 (1H, d, J=11.5 Hz).

Reference Example 336

1-(5-Ethyl-2,4-difluorophenyl)piperidin-4-one

Synthesized analogous to Reference Example 318.
¹HNMR (CDCl₃) δ ppm: 1.21 (3H, t, J=7.5 Hz), 2.62 (2H, q, J=7.5 Hz), 2.62 (4H, t, J=6.0 Hz), 3.34 (4H, t, J=6.0 Hz), 6.79 (1H, dd, J=11.5 Hz, 9.5 Hz), 6.81 (1H, dd, J=9.5 Hz, 8.0 Hz).

Reference Example 337

1-(2,4-Difluoro-5-propylphenyl)piperidin-4-one

Synthesized analogous to Reference Example 318.
¹HNMR (CDCl₃) δ ppm: 0.94 (3H, t, J=7.5 Hz), 1.60 (2H, sext, J=7.5 Hz), 2.55 (2H, t, J=7.5 Hz), 2.62 (4H, t, J=6.0 Hz), 3.33 (4H, t, J=6.0 Hz), 6.76-6.82 (2H, m).

Reference Example 338

1-[4-Chloro-2-fluoro-5-(2-methoxyethyl)phenyl]piperidin-4-one

Synthesized analogous to Reference Example 318.

¹HNMR (CDCl₃) δ ppm: 2.62 (4H, t, J=6.0 Hz), 2.94 (2H, t, J=7.0 Hz), 3.36 (3H, s), 3.39 (4H, t, J=6.0 Hz), 3.58 (2H, t, J=7.0 Hz), 6.88 (1H, d, J=9.0 Hz), 7.09 (1H, d, J=12.0 Hz).

Reference Example 339

1-(2-Bromo-4-chloro-6-fluorophenyl)piperidin-4-one

Synthesized analogous to Reference Example 318.
¹HNMR (CDCl₃) δ ppm: 2.61 (4H, brs), 3.34-3.51 (4H, m), 7.07 (1H, dd, J=11.2 Hz, 2.4 Hz), 7.43 (1H, t, 2.0 Hz).

Reference Example 340

6-(3,5-Dichloropyridin-2-yl)-1-oxa-6-azaspiro[2.5]octane

A solution of 1-(3,5-dichloropyridin-2-yl)piperidin-4-one (3.0 g), trimethylsulfoxonium iodide (2.69 g) and potassium tert-butoxide (1.37 g) in 1,2-dimethoxyethane (60 mL) was refluxed for 21 h. To the reaction solution was added water, and the solution was extracted with ethyl acetate. The organic layer was washed with water and brine, and dried over anhydrous sodium sulfate, and then the solvent was distilled off. The residue was purified by silica gel column chromatography (hexane/ethyl acetate) to provide the title compound (1.01 g).
¹HNMR (CDCl₃) δ ppm: 1.62-1.69 (2H, m), 1.96-2.04 (2H, m), 2.73 (2H, s), 3.38-3.46 (2H, m), 3.50-3.58 (2H, m), 7.60 (1H, d, J=2.2 Hz), 8.12 (1H, d, J=2.2 Hz).

Reference Example 341

6-(2,4-Dichlorophenyl)-1-oxa-6-azaspiro[2.5]octane

To a solution of trimethylsulfoxonium iodide (550 mg) in dimethyl sulfoxide (6.8 mL) was added sodium hydride (55% in oil) (109 mg), and the reaction mixture was stirred at room temperature for 30 min. To the reaction mixture was added a solution of 1-(2,4-dichlorophenyl)piperidin-4-one (555 mg) in dimethyl sulfoxide (3 mL), and the reaction mixture was stirred at room temperature for 2.5 h. Under ice-cooling, to the reaction solution was added water, and the solution was extracted with ethyl acetate. The organic layer was washed sequentially with water and brine, dried over anhydrous sodium sulfate, and the solvent was distilled off. The residue was purified by silica gel column chromatography (hexane/ethyl acetate) to provide the title compound (442 mg).
¹HNMR (CDCl₃) δ ppm: 1.60-1.64 (2H, m), 2.06-2.11 (2H, m), 2.73 (2H, s), 3.08-3.13 (2H, m), 3.15-3.20 (2H, m), 7.00 (1H, d, J=8.5 Hz), 7.19 (1H, dd, J=8.5 Hz, 2.5 Hz), 7.38 (1H, d, J=2.5 Hz).

Reference Example 342

6-(2,5-Dichlorophenyl)-1-oxa-6-azaspiro[2.5]octane

Synthesized analogous to Reference Example 341.
¹HNMR (CDCl₃) δ ppm: 1.61-1.67 (2H, m), 2.04-2.10 (2H, m), 2.73 (2H, s), 3.10-3.16 (2H, m), 3.18-3.22 (2H, m), 6.95 (1H, dd, J=8.5 Hz, 2.5 Hz), 7.03 (1H, d, J=2.5 Hz), 7.28 (1H, d, J=8.5 Hz).

Reference Example 343

6-(2,5-Dichloro-4-fluorophenyl)-1-oxa-6-azaspiro[2.5]octane

Synthesized analogous to Reference Example 341.
¹HNMR (CDCl₃) δ ppm: 1.60-1.65 (2H, m), 2.05-2.11 (2H, m), 2.73 (2H, s), 3.06-3.16 (4H, m), 7.09 (1H, d, J=7.0 Hz), 7.21 (1H, d, J=8.5 Hz).

Reference Example 344

6-(2-Chloro-4-fluorophenyl)-1-oxa-6-azaspiro[2.5]octane

Synthesized analogous to Reference Example 341.
¹HNMR (CDCl₃) δ ppm: 1.60-1.65 (2H, m), 2.06-2.11 (2H, m), 2.73 (2H, s), 3.05-3.16 (4H, m), 6.94 (1H, ddd, J=8.5 Hz, 8.0 Hz, 3.0 Hz), 7.04 (1H, dd, J=8.5 Hz, 5.5 Hz), 7.14 (1H, dd, J=8.0 Hz, 3.0 Hz).

Reference Example 345

6-Phenyl-1-oxa-6-azaspiro[2.5]octane

Synthesized analogous to Reference Example 341.
¹HNMR (CDCl₃) δ ppm: 1.61-1.66 (2H, m), 1.95-2.00 (2H, m), 2.72 (2H, s), 3.32-3.37 (2H, m), 3.40-3.44 (2H, m), 6.86 (1H, t, J=7.0 Hz), 6.97 (2H, d, J=8.0 Hz), 7.27 (2H, dd, J=8.0 Hz, 7.0 Hz).

Reference Example 346

N,N-Dimethyl-4-(1-oxa-6-azaspiro[2.5]oct-6-yl)aniline

Synthesized analogous to Reference Example 341.
¹HNMR (CDCl₃) δ ppm: 1.64-1.68 (2H, m), 1.95-2.00 (2H, m), 2.70 (2H, s), 2.87 (6H, s), 3.16-3.24 (4H, m), 6.74 (2H, d, J=9.5 Hz), 6.95 (2H, d, J=9.5 Hz).

Reference Example 347

6-(3-Chlorophenyl)-1-oxa-6-azaspiro[2.5]octane

Synthesized analogous to Reference Example 341.
¹HNMR (CDCl₃) δ ppm: 1.58-1.62 (2H, m), 1.94-1.99 (2H, m), 2.72 (2H, s), 3.32-3.37 (2H, m), 3.42-3.47 (2H, m), 6.79-6.83 (2H, m), 6.91 (1H, t, J=2.0 Hz), 7.16 (1H, t, J=8.5 Hz).

Reference Example 348

6-(Pyridin-3-yl)-1-oxa-6-azaspiro[2.5]octane

Synthesized analogous to Reference Example 341.
¹HNMR (CDCl₃) δ ppm: 1.61-1.65 (2H, m), 1.98-2.04 (2H, m), 2.74 (2H, s), 3.35-3.40 (2H, m), 3.45-3.50 (2H, m), 7.17 (1H, dd, J=8.5 Hz, 4.5 Hz), 7.23 (1H, ddd, J=8.5 Hz, 3.0 Hz, 1.5 Hz), 8.10 (1H, dd, J=4.5 Hz, 1.5 Hz), 8.35 (1H, d, J=3.0 Hz).

Reference Example 349

6-(Thiophen-3-yl)-1-oxa-6-azaspiro[2.5]octane

Synthesized analogous to Reference Example 341.

¹HNMR (CDCl₃) δ ppm: 1.62-1.67 (2H, m), 1.95-2.00 (2H, m), 2.72 (2H, s), 3.23-3.33 (4H, m), 6.22-6.24 (1H, m), 6.88-6.90 (1H, m), 7.23-7.26 (1H, m).

Reference Example 350

6-(4-Chloro-2-fluorophenyl)-1-oxa-6-azaspiro[2.5]octane

Synthesized analogous to Reference Example 341.
¹HNMR (CDCl₃) δ ppm: 1.61-1.65 (2H, m), 2.03-2.09 (2H, m), 2.73 (2H, s), 3.14-3.18 (2H, m), 3.21-3.25 (2H, m), 6.89-6.23 (1H, m), 7.03-7.07 (2H, m).

Reference Example 351

6-(2,4-Dichloro-5-fluorophenyl)-1-oxa-6-azaspiro[2.5]octane

Synthesized analogous to Reference Example 341.
¹HNMR (CDCl₃) δ ppm: 1.59-1.64 (2H, m), 2.07-2.12 (2H, m), 2.74 (2H, s), 3.08-3.13 (2H, m), 3.17-3.21 (2H, m), 6.86 (1H, d, J=10.5 Hz), 7.40 (1H, d, J=7.5 Hz).

Reference Example 352

6-(2,3-Dichlorophenyl)-1-oxa-6-azaspiro[2.5]octane

Synthesized analogous to Reference Example 341.
¹HNMR (CDCl₃) δ ppm: 1.61-1.65 (2H, m), 2.08-2.13 (2H, m), 2.74 (2H, s), 3.11-3.16 (2H, m), 3.18-3.22 (2H, m), 6.99 (1H, dd, J=7.0 Hz, 2.5 Hz), 7.13-7.17 (2H, m).

Reference Example 353

6-(4-Chloro-2,6-difluorophenyl)-1-oxa-6-azaspiro[2.5]octane

Synthesized analogous to Reference Example 341.
¹HNMR (CDCl₃) δ ppm: 1.60-1.65 (2H, m), 1.92-1.97 (2H, m), 2.71 (2H, s), 3.19-3.23 (2H, m), 3.34-3.39 (2H, m), 6.85-6.91 (2H, m).

Reference Example 354

6-[4-Chloro-2-(trifluoromethyl)phenyl]-1-oxa-6-azaspiro[2.5]octane

Synthesized analogous to Reference Example 341.
¹HNMR (CDCl₃) δ ppm: 1.53-1.57 (2H, m), 2.05-2.10 (2H, m), 2.72 (2H, s), 2.96-3.01 (2H, m), 3.05-3.09 (2H, m), 7.33 (1H, d, J=8.5 Hz), 7.48 (1H, dd, J=8.5 Hz, 2.5 Hz), 7.61 (1H, d, J=2.5 Hz).

Reference Example 355

6-(3,4-Dichlorophenyl)-1-oxa-6-azaspiro[2.5]octane

Synthesized analogous to Reference Example 341.
¹HNMR (CDCl₃) δ ppm: 1.57-1.61 (2H, m), 1.95-2.00 (2H, m), 2.73 (2H, s), 3.30-3.35 (2H, m), 3.40-3.45 (2H, m), 6.78 (1H, dd, J=9.0 Hz, 3.0 Hz), 7.00 (1H, d, J=3.0 Hz), 7.27 (1H, d, J=9.0 Hz).

Reference Example 356

6-(4-Chloro-2-methylphenyl)-1-oxa-6-azaspiro[2.5]octane

Synthesized analogous to Reference Example 341.
¹HNMR (CDCl₃) δ ppm: 1.62-1.68 (2H, m), 1.96-2.01 (2H, m), 2.30 (3H, s), 2.72 (2H, s), 2.94-2.99 (2H, m), 3.01-3.06 (2H, m), 6.97 (1H, d, J=8.0 Hz), 7.12 (1H, dd, J=8.0 Hz, 2.5 Hz), 7.16 (1H, d, J=2.5 Hz).

Reference Example 357

6-[2-(Trifluoromethoxy)phenyl]-1-oxa-6-azaspiro[2.5]octane

Synthesized analogous to Reference Example 341.
¹HNMR (CDCl₃) δ ppm: 1.60-1.64 (2H, m), 2.02-2.07 (2H, m), 2.72 (2H, s), 3.14-3.24 (4H, m), 6.99 (1H, ddd, J=8.0 Hz, 7.5 Hz, 1.5 Hz), 7.06 (1H, dd, J=8.0 Hz, 1.5 Hz), 7.19-7.26 (2H, m).

Reference Example 358

6-(2-Chloro-6-fluorophenyl)-1-oxa-6-azaspiro[2.5]octane

Synthesized analogous to Reference Example 341.
¹HNMR (CDCl₃) δ ppm: 1.67 (2H, brs), 1.94 (2H, brs), 2.71 (2H, s), 3.19-3.26 (2H, m), 3.36-3.41 (2H, m), 6.92-6.99 (2H, m), 7.14-7.19 (1H, m).

Reference Example 359

6-(4-Chloro-2,5-difluorophenyl)-1-oxa-6-azaspiro[2.5]octane

Synthesized analogous to Reference Example 341.
¹HNMR (CDCl₃) δ ppm: 1.60-1.64 (2H, m), 2.03-2.09 (2H, m), 2.74 (2H, s), 3.14-3.19 (2H, m), 3.23-3.27 (2H, m), 6.76 (1H, dd, J=11.0 Hz, 8.0 Hz), 7.08 (1H, dd, J=11.5 Hz, 7.0 Hz).

Reference Example 360

6-(2-Bromo-4-chlorophenyl)-1-oxa-6-azaspiro[2.5]octane

Synthesized analogous to Reference Example 341.
¹HNMR (CDCl₃) δ ppm: 1.60-1.64 (2H, m), 2.07-2.12 (2H, m), 2.73 (2H, s), 3.07-3.12 (2H, m), 3.14-3.18 (2H, m), 7.00 (1H, d, J=8.5 Hz), 7.24 (1H, dd, J=8.5 Hz, 2.5 Hz), 7.57 (1H, d, J=2.5 Hz).

Reference Example 361

6-(2,4,6-Trichlorophenyl)-1-oxa-6-azaspiro[2.5]octane

Synthesized analogous to Reference Example 341.
¹HNMR (CDCl₃) δ ppm: 1.63-1.68 (2H, m), 1.92-1.97 (2H, m), 2.71 (2H, s), 3.16-3.20 (2H, m), 3.41-3.46 (2H, m), 7.27-7.30 (2H, m).

Reference Example 362

6-(2,6-Dichlorophenyl)-1-oxa-6-azaspiro[2.5]octane

Synthesized analogous to Reference Example 341.
¹HNMR (CDCl₃) δ ppm: 1.66-1.71 (2H, m), 1.92-1.97 (2H, m), 2.71 (2H, s), 3.20-3.25 (2H, m), 3.43-3.48 (2H, m), 6.97 (1H, t, J=8.0 Hz), 7.25-7.29 (2H, m).

Reference Example 363

6-(4-Chloro-3-methoxyphenyl)-1-oxa-6-azaspiro[2.5]octane

Synthesized analogous to Reference Example 341.
$^1$HNMR (CDCl$_3$) δ ppm: 1.60-1.65 (2H, m), 1.97-2.02 (2H, m), 2.73 (2H, s), 3.29-3.34 (2H, m), 3.38-3.43 (2H, m), 3.89 (3H, s), 6.50 (1H, dd, J=9.0 Hz, 3.0 Hz), 6.54 (1H, d, J=3.0 Hz), 7.21 (1H, d, J=9.0 Hz).

Reference Example 364

6-(3-Ethoxyphenyl)-1-oxa-6-azaspiro[2.5]octane

Synthesized analogous to Reference Example 341.
$^1$HNMR (CDCl$_3$) δ ppm: 1.41 (3H, t, J=7.0 Hz), 1.59-1.64 (2H, m), 1.93-1.99 (2H, m), 2.71 (2H, s), 3.32-3.37 (2H, m), 3.40-3.45 (2H, m), 4.02 (2H, q, J=7.0 Hz), 6.41 (1H, dd, J=8.0 Hz, 2.5 Hz), 6.51 (1H, t, J=2.5 Hz), 6.57 (1H, dd, J=8.0 Hz, 2.5 Hz), 7.16 (1H, t, J=8.0 Hz).

Reference Example 365

6-(4-Ethoxyphenyl)-1-oxa-6-azaspiro[2.5]octane

Synthesized analogous to Reference Example 341.
$^1$HNMR (CDCl$_3$) δ ppm: 1.39 (3H, t, J=7.0 Hz), 1.64-1.68 (2H, m), 1.96-2.02 (2H, m), 2.72 (2H, s), 3.17-3.29 (4H, m), 3.99 (2H, q, J=7.0 Hz), 6.84 (2H, d, J=9.0 Hz), 6.94 (2H, d, J=9.0 Hz).

Reference Example 366

6-[3-(Propan-2-yl)phenyl]-1-oxa-6-azaspiro[2.5]octane

Synthesized analogous to Reference Example 341.
$^1$HNMR (CDCl$_3$) δ ppm: 1.25 (6H, d, J=7.0 Hz), 1.63-1.68 (2H, m), 1.95-2.01 (2H, m), 2.72 (2H, s), 2.86 (1H, sep, J=7.0 Hz), 3.30-3.34 (2H, m), 3.35-3.43 (2H, m), 6.76 (1H, dd, J=7.5 Hz, 1.0 Hz), 6.79 (1H, dd, J=7.5 Hz, 2.5 Hz), 6.85 (1H, dd, J=2.5 Hz, 1.0 Hz), 7.20 (1H, t, J=7.5 Hz).

Reference Example 367

6-[4-(Propan-2-yl)phenyl]-1-oxa-6-azaspiro[2.5]octane

Synthesized analogous to Reference Example 341.
$^1$HNMR (CDCl$_3$) δ ppm: 1.23 (6H, d, J=7.0 Hz), 1.62-1.67 (2H, m), 1.94-2.00 (2H, m), 2.71 (2H, s), 2.84 (1H, sep, J=7.0 Hz), 3.26-3.38 (4H, m), 6.92 (2H, d, J=8.5 Hz), 7.13 (2H, d, J=8.5 Hz).

Reference Example 368

6-(3,5-Dichloropyridin-4-yl)-1-oxa-6-azaspiro[2.5]octane

Synthesized analogous to Reference Example 341.
$^1$HNMR (CDCl$_3$) δ ppm: 1.61-1.66 (2H, m), 2.00-2.06 (2H, m), 2.74 (2H, s), 3.35-3.40 (2H, m), 3.54-3.59 (2H, m), 8.35 (2H, s).

Reference Example 369

4-(1-Oxa-6-azaspiro[2.5]oct-6-yl)benzonitrile

Synthesized analogous to Reference Example 341.
$^1$HNMR (CDCl$_3$) δ ppm: 1.54-1.59 (2H, m), 1.95-2.01 (2H, m), 2.74 (2H, s), 3.46-3.51 (2H, m), 3.63-3.68 (2H, m), 6.89 (2H, d, J=9.0 Hz), 7.50 (2H, d, J=9.0 Hz).

Reference Example 370

3-(1-Oxa-6-azaspiro[2.5]oct-6-yl)benzonitrile

Synthesized analogous to Reference Example 341.
$^1$HNMR (CDCl$_3$) δ ppm: 1.58-1.63 (2H, m), 1.97-2.02 (2H, m), 2.74 (2H, s), 3.35-3.40 (2H, m), 3.48-3.52 (2H, m), 7.09 (1H, dd, J=7.5 Hz, 1.0 Hz), 7.14-7.16 (2H, m), 7.32 (1H, dd, J=9.0 Hz, 7.5 Hz).

Reference Example 371

6-(4-Phenoxyphenyl)-1-oxa-6-azaspiro[2.5]octane

Synthesized analogous to Reference Example 341.
$^1$HNMR (CDCl$_3$) δ ppm: 1.64-1.68 (2H, m), 1.98-2.03 (2H, m), 2.73 (2H, s), 3.26-3.31 (2H, m), 3.34-3.38 (2H, m), 6.94-6.97 (6H, m), 7.04 (1H, t, J=7.5 Hz), 7.28-7.31 (2H, m).

Reference Example 372

6-(Biphenyl-2-yl)-1-oxa-6-azaspiro[2.5]octane

Synthesized analogous to Reference Example 341.
$^1$HNMR (CDCl$_3$) δ ppm: 1.39-1.44 (2H, m), 1.67-1.73 (2H, m), 2.61 (2H, s), 2.90-3.02 (4H, m), 7.08 (2H, t, J=7.5 Hz), 7.25-7.31 (3H, m), 7.40 (2H, t, J=7.5 Hz), 7.64-7.66 (2H, m).

Reference Example 373

6-[2-Chloro-5-(trifluoromethoxy)phenyl]-1-oxa-6-azaspiro[2.5]octane

Synthesized analogous to Reference Example 341.
$^1$HNMR (CDCl$_3$) δ ppm: 1.62-1.67 (2H, m), 2.07-2.12 (2H, m), 2.74 (2H, s), 3.12-3.17 (2H, m), 3.21-3.25 (2H, m), 6.85 (1H, ddd, J=8.5 Hz, 2.5 Hz, 1.0 Hz), 6.90 (1H, d, J=2.5 Hz), 7.37 (1H, d, J=8.5 Hz).

Reference Example 374

6-[2-(Propan-2-yl)phenyl]-1-oxa-6-azaspiro[2.5]octane

Synthesized analogous to Reference Example 341.
$^1$HNMR (CDCl$_3$) δ ppm: 1.23 (6H, d, J=7.0 Hz), 1.68 (2H, brs), 1.98 (2H, brs), 2.72 (2H, s), 2.93-2.98 (2H, m), 3.04-3.09 (2H, m), 3.52 (1H, sep J=7.0 Hz), 7.08-7.18 (3H, m), 7.24-7.28 (1H, m).

Reference Example 375

6-(2-Chloro-5-nitrophenyl)-1-oxa-6-azaspiro[2.5]octane

Synthesized analogous to Reference Example 341.
$^1$HNMR (CDCl$_3$) δ ppm: 1.66-1.70 (2H, m), 2.09-2.14 (2H, m), 2.76 (2H, s), 3.18-3.31 (4H, m), 7.52 (1H, d, J=8.5 Hz), 7.84 (1H, dd, J=8.5 Hz, 2.5 Hz), 7.92 (1H, d, J=2.5 Hz).

Reference Example 376

6-(2-Ethylphenyl)-1-oxa-6-azaspiro[2.5]octane

To a solution of trimethylsulfoxonium iodide (1.48 g) in dimethyl sulfoxide (10 mL) was added sodium tert-butoxide (0.65 g), and the reaction mixture was stirred at room temperature for 30 min. To the reaction solution was added a solution of 1-(2-ethylphenyl)-piperidin-4-one (1.24 g) in dimethyl sulfoxide (4 mL), and the reaction mixture was stirred at room temperature for 8.5 h. To the reaction solution was added water, and the solution was extracted with ethyl acetate. The organic layer was washed with brine, dried over anhydrous sodium sulfate, and the solvent was distilled off. The residue was purified by silica gel column chromatography (hexane/ethyl acetate) to provide the title compound (880 mg) as a colorless oil.
$^1$HNMR (CDCl$_3$) δ ppm: 1.26 (3H, t, J=7.5 Hz), 1.65-1.69 (2H, m), 1.96-1.99 (2H, m), 2.72 (2H, s), 2.73 (2H, q, J=7.5 Hz), 2.96-3.00 (2H, m), 3.05-3.10 (2H, m), 7.02-7.19 (3H, m), 7.21-7.28 (1H, m).

Reference Example 377

6-[3-(Trifluoromethyl)phenyl]-1-oxa-6-azaspiro[2.5]octane

Synthesized analogous to Reference Example 341.
$^1$HNMR (CDCl$_3$) δ ppm: 1.60-1.65 (2H, m), 1.97-2.02 (2H, m), 2.74 (2H, s), 3.36-3.41 (2H, m), 3.47-3.52 (2H, m), 7.08 (1H, d, J=8.0 Hz), 7.10 (1H, dd, J=8.0 Hz, 2.5 Hz), 7.15 (1H, d, J=2.5 Hz), 7.35 (1H, t, J=8.0 Hz).

Reference Example 378

6-(4-Chloro-3-methylphenyl)-1-oxa-6-azaspiro[2.5]octane

Synthesized analogous to Reference Example 341.
$^1$HNMR (CDCl$_3$) δ ppm: 1.59-1.64 (2H, m), 1.94-2.00 (2H, m), 2.33 (3H, s), 2.72 (2H, s), 3.27-3.32 (2H, m), 3.36-3.40 (2H, m), 6.73 (1H, dd, J=9.0 Hz, 3.0 Hz), 6.82 (1H, d, J=3.0 Hz), 7.19 (1H, d, J=9.0 Hz).

Reference Example 379

Ethyl 4-(1-oxa-6-azaspiro[2.5]oct-6-yl)benzoate

Synthesized analogous to Reference Example 341.
$^1$HNMR (CDCl$_3$) δ ppm: 1.37 (3H, t, J=7.0 Hz), 1.56-1.60 (2H, m), 1.95-2.00 (2H, m), 2.74 (2H, s), 3.46-3.51 (2H, m), 3.62-3.66 (2H, m), 4.33 (2H, q, J=7.0 Hz), 6.90 (2H, d, J=9.0 Hz), 6.93 (2H, d, J=9.0 Hz).

Reference Example 380

Ethyl 2-chloro-5-(1-oxa-6-azaspiro[2.5]oct-6-yl)benzoate

Synthesized analogous to Reference Example 341.
$^1$HNMR (CDCl$_3$) δ ppm: 1.41 (3H, t, J=7.0 Hz), 1.59-1.63 (2H, m), 1.96-2.01 (2H, m), 2.73 (2H, s), 3.32-3.37 (2H, m), 3.43-3.47 (2H, m), 4.40 (2H, q, J=7.0 Hz), 6.98 (1H, dd, J=9.0 Hz, 3.0 Hz), 7.29 (1H, d, J=9.0 Hz), 7.34 (1H, d, J=3.0 Hz).

Reference Example 381

6-(2-Chloro-4-methylphenyl)-1-oxa-6-azaspiro[2.5]octane

Synthesized analogous to Reference Example 341.
$^1$HNMR (CDCl$_3$) δ ppm: 1.61-1.65 (2H, m), 2.05-2.10 (2H, m), 2.28 (3H, s), 2.72 (2H, s), 3.07-3.17 (4H, m), 6.98 (1H, d, J=8.5 Hz), 7.02 (1H, dd, J=8.5 Hz, 1.5 Hz), 7.20 (1H, d, J=1.5 Hz).

Reference Example 382

6-(4-Methylphenyl)-1-oxa-6-azaspiro[2.5]octane

Synthesized analogous to Reference Example 341.
$^1$HNMR (CDCl$_3$) δ ppm: 1.62-1.67 (2H, m), 1.95-2.00 (2H, m), 2.28 (3H, s), 2.72 (2H, s), 3.26-3.31 (2H, m), 3.33-3.37 (2H, m), 6.89 (2H, d, J=8.5 Hz), 7.08 (2H, d, J=8.5 Hz).

Reference Example 383

6-(4-Chloro-2-nitrophenyl)-1-oxa-6-azaspiro[2.5]octane

Synthesized analogous to Reference Example 341.
$^1$HNMR (CDCl$_3$) δ ppm: 1.53-1.57 (2H, m), 2.10-2.15 (2H, m), 2.74 (2H, s), 3.17-3.23 (4H, m), 7.14 (1H, d, J=8.5 Hz), 7.45 (1H, dd, J=8.5 Hz, 2.5 Hz), 7.80 (1H, d, J=2.5 Hz).

Reference Example 384

6-[2-Chloro-4-(propan-2-yl)phenyl]-1-oxa-6-azaspiro[2.5]octane

Synthesized analogous to Reference Example 341.
$^1$HNMR (CDCl$_3$) δ ppm: 1.22 (6H, d, J=7.0 Hz), 1.62-1.65 (2H, m), 2.05-2.10 (2H, m), 2.72 (2H, s), 2.84 (1H, sep, J=7.0 Hz), 3.09-3.16 (4H, m), 7.00 (1H, d, J=8.5 Hz), 7.07 (1H, dd, J=8.5 Hz, 2.0 Hz), 7.24 (1H, d, J=2.0 Hz).

Reference Example 385

6-(4-Bromo-2-fluorophenyl)-1-oxa-6-azaspiro[2.5]octane

Synthesized analogous to Reference Example 341.
$^1$HNMR (CDCl$_3$) δ ppm: 1.61-1.65 (2H, m), 2.03-2.08 (2H, m), 2.73 (2H, s), 3.14-3.19 (2H, m), 3.21-3.25 (2H, m), 6.86 (1H, t, J=9.0 Hz), 7.17-7.21 (2H, m).

Reference Example 386

6-(4-Ethoxy-2-fluorophenyl)-1-oxa-6-azaspiro[2.5]octane

Synthesized analogous to Reference Example 341.
$^1$HNMR (CDCl$_3$) δ ppm: 1.39 (3H, t, J=7.0 Hz), 1.63-1.67 (2H, m), 2.02-2.07 (2H, m), 2.72 (2H, s), 3.08-3.17 (4H, m), 3.97 (2H, q, J=7.0 Hz), 6.61 (1H, ddd, J=9.0 Hz, 3.0 Hz, 1.0 Hz), 6.65 (1H, dd, J=13.5 Hz, 3.0 Hz), 6.94 (1H, t, J=9.0 Hz).

Reference Example 387

6-(2-Fluoro-4-propoxyphenyl)-1-oxa-6-azaspiro[2.5]octane

Synthesized analogous to Reference Example 341.

¹HNMR (CDCl₃) δ ppm: 1.02 (3H, t, J=7.5 Hz), 1.63-1.67 (2H, m), 1.75-1.82 (2H, m), 2.02-2.07 (2H, m), 2.72 (2H, s), 3.09-3.17 (4H, m), 3.86 (2H, t, J=6.5 Hz), 6.61 (1H, ddd, J=9.0 Hz, 2.5 Hz, 1.0 Hz), 6.65 (1H, dd, J=13.5 Hz, 2.5 Hz), 6.94 (1H, t, J=9.0 Hz).

Reference Example 388

6-(2,4-Dichloro-6-methylphenyl)-1-oxa-6-azaspiro[2.5]octane

Synthesized analogous to Reference Example 341.
¹HNMR (CDCl₃) δ ppm: 1.43-1.46 (1H, m), 1.67-1.71 (1H, m), 1.85-1.90 (1H, m), 2.05-2.11 (1H, m), 2.33 (1.5H, s), 2.34 (1.5H, s), 2.70 (1H, s), 2.72 (1H, s), 2.90-2.94 (1H, m), 3.10-3.15 (1H, m), 3.34-3.39 (1H, m), 3.58-3.63 (1H, m), 7.06-7.09 (1H, m), 7.17-7.19 (1H, m).

Reference Example 389

6-(2-Chloro-4-ethylphenyl)-1-oxa-6-azaspiro[2.5]octane

Synthesized analogous to Reference Example 341.
¹HNMR (CDCl₃) δ ppm: 1.21 (3H, t, J=7.5 Hz), 1.62-1.66 (2H, m), 2.05-2.10 (2H, m), 2.58 (2H, q, J=7.5 Hz), 2.72 (2H, s), 3.09-3.17 (4H, m), 7.00 (1H, d, J=8.5 Hz), 7.05 (1H, dd, J=8.5 Hz, 2.0 Hz), 7.22 (1H, d, J=2.0 Hz).

Reference Example 390

6-(2-Chloro-4-propylphenyl)-1-oxa-6-azaspiro[2.5]octane

Synthesized analogous to Reference Example 341.
¹HNMR (CDCl₃) δ ppm: 0.93 (3H, t, J=7.5 Hz), 1.57-1.65 (4H, m), 2.05-2.10 (2H, m), 2.51 (2H, t, J=7.5 Hz), 2.72 (2H, s), 3.09-3.20 (4H, m), 6.99 (1H, d, J=8.0 Hz), 7.02 (1H, dd, J=8.0 Hz, 2.0 Hz), 7.20 (1H, d, J=2.0 Hz).

Reference Example 391

6-(2,4-Dichloro-6-fluorophenyl)-1-oxa-6-azaspiro[2.5]octane

Synthesized analogous to Reference Example 341.
¹HNMR (CDCl₃) δ ppm: 1.65 (2H, brs), 1.95 (2H, brs), 2.71 (2H, s), 3.15-3.22 (2H, m), 3.33-3.38 (2H, m), 6.99 (1H, dd, J=11.5 Hz, 2.5 Hz), 7.20 (1H, dd, J=2.5 Hz, 2.0 Hz).

Reference Example 392

6-(2-Chloro-4,6-difluorophenyl)-1-oxa-6-azaspiro[2.5]octane

Synthesized analogous to Reference Example 341.
¹HNMR (CDCl₃) δ ppm: 1.64 (2H, brs), 1.95 (2H, brs), 2.71 (2H, s), 3.12-3.18 (2H, m), 3.30-3.38 (2H, m), 6.74 (1H, ddd, J=11.5 Hz, 8.5 Hz, 3.0 Hz), 6.96 (1H, ddd, J=8.0 Hz, 3.0 Hz, 2.0 Hz).

Reference Example 393

6-(4-Butoxy-2-fluorophenyl)-1-oxa-6-azaspiro[2.5]octane

Synthesized analogous to Reference Example 341.
¹HNMR (CDCl₃) δ ppm: 0.97 (3H, t, J=7.5 Hz), 1.44-1.51 (2H, m), 1.63-1.67 (2H, m), 1.71-1.77 (2H, m), 2.02-2.07 (2H, m), 2.72 (2H, s), 3.07-3.16 (4H, m), 3.90 (2H, t, J=6.5 Hz), 6.61 (1H, ddd, J=9.0 Hz, 3.0 Hz, 1.0 Hz), 6.65 (1H, dd, J=13.5 Hz, 3.0 Hz), 6.94 (1H, t, J=9.0 Hz).

Reference Example 394

6-[2-Fluoro-4-(propan-2-yloxy)phenyl]-1-oxa-6-azaspiro[2.5]octane

Synthesized analogous to Reference Example 341.
¹HNMR (CDCl₃) δ ppm: 1.31 (6H, d, J=6.0 Hz), 1.62-1.67 (2H, m), 2.02-2.07 (2H, m), 2.72 (2H, s), 3.07-3.18 (4H, m), 4.44 (1H, sep, J=6.0 Hz), 6.61 (1H, ddd, J=8.5 Hz, 3.0 Hz, 1.0 Hz), 6.64 (1H, dd, J=13.5 Hz, 3.0 Hz), 6.93 (1H, dd, J=9.5 Hz, 8.5 Hz).

Reference Example 395

6-[2-Chloro-4-(trifluoromethoxy)phenyl]-1-oxa-6-azaspiro[2.5]octane

Synthesized analogous to Reference Example 341.
¹HNMR (CDCl₃) δ ppm: 1.61-1.65 (2H, m), 2.08-2.13 (2H, m), 2.74 (2H, s), 3.10-3.15 (2H, m), 3.18-3.22 (2H, m), 7.07 (1H, d, J=8.5 Hz), 7.11 (1H, dd, J=8.5 Hz, 2.5 Hz), 7.28 (1H, d, J=2.5 Hz).

Reference Example 396

6-[2,4-Dichloro-5-(trifluoromethoxy)phenyl]-1-oxa-6-azaspiro[2.5]octane

Synthesized analogous to Reference Example 341.
¹HNMR (CDCl₃) δ ppm: 1.61-1.65 (2H, m), 2.07-2.12 (2H, m), 2.74 (2H, s), 3.10-3.15 (2H, m), 3.18-3.23 (2H, m), 7.00 (1H, d, J=1.0 Hz), 7.48 (1H, s).

Reference Example 397

6-(2-Fluoro-4-methoxyphenyl)-1-oxa-6-azaspiro[2.5]octane

Synthesized analogous to Reference Example 341.
¹HNMR (CDCl₃) δ ppm: 1.63-1.67 (2H, m), 2.03-2.08 (2H, m), 2.72 (2H, s), 3.07-3.17 (4H, m), 3.77 (3H, s), 6.62 (1H, ddd, J=9.0 Hz, 3.0 Hz, 1.0 Hz), 6.66 (1H, dd, J=13.5 Hz, 3.0 Hz), 6.96 (1H, t, J=9.0 Hz).

Reference Example 398

6-(2,4,6-Trifluorophenyl)-1-oxa-6-azaspiro[2.5]octane

To a solution of trimethylsulfoxonium iodide (4.89 g) in dimethyl sulfoxide (50 mL) was added sodium tert-butoxide (1.93 mL) at 0° C., and the reaction mixture was stirred at room temperature for 30 min. To the reaction mixture was added a solution of 1-(2,4,6-trifluorophenyl)piperidin-4-one (4.85 g) in dimethyl sulfoxide (10 mL) dropwise, and the reaction mixture was stirred at room temperature for 2 h. To the reaction solution was added water, and the solution was extracted with ethyl acetate. The organic layer was washed with water and brine, dried over anhydrous sodium sulfate, and then the solvent was distilled off. The residue was purified by silica gel column chromatography (hexane/ethyl acetate) to provide the title compound (4.3 g).
¹HNMR (CDCl₃) δ ppm: 1.60-1.68 (2H, m), 1.89-1.99 (2H, m), 2.71 (2H, s), 3.13-3.23 (2H, m), 3.30-3.38 (2H, m), 6.58-6.68 (2H, m).

Reference Example 399

6-[2-Fluoro-4-(trifluoromethoxy)phenyl]-1-oxa-6-azaspiro[2.5]octane

Synthesized analogous to Reference Example 341.
¹HNMR (CDCl₃) δ ppm: 1.61-1.66 (2H, m), 2.05-2.10 (2H, m), 2.74 (2H, s), 3.15-3.20 (2H, m), 3.23-3.27 (2H, m), 6.94-7.00 (3H, m).

Reference Example 400

6-[4-(Benzyloxy)-2-fluorophenyl]-1-oxa-6-azaspiro[2.5]octane

Synthesized analogous to Reference Example 341.
¹HNMR (CDCl₃) δ ppm: 1.62-1.67 (2H, m), 2.02-2.07 (2H, m), 2.72 (2H, s), 3.07-3.17 (4H, m), 5.01 (2H, s), 6.69 (1H, ddd, J=9.0 Hz, 3.0 Hz, 1.0 Hz), 6.73 (1H, dd, J=13.5 Hz, 3.0 Hz), 6.94 (1H, t, J=9.0 Hz), 7.31-7.35 (1H, m), 7.36-7.43 (4H, m).

Reference Example 401

6-[2-Fluoro-4-(2-methoxyethoxy)phenyl]-1-oxa-6-azaspiro[2.5]octane

Synthesized analogous to Reference Example 341.
¹HNMR (CDCl₃) δ ppm: 1.62-1.67 (2H, m), 2.02-2.07 (2H, m), 2.72 (2H, s), 3.07-3.18 (4H, m), 3.45 (3H, s), 3.72-3.74 (2H, m), 4.05-4.07 (2H, m), 6.65 (1H, ddd, J=9.0 Hz, 3.0 Hz, 1.0 Hz), 6.69 (1H, dd, J=13.5 Hz, 3.0 Hz), 6.94 (1H, t, J=9.0 Hz).

Reference Example 402

6-[4-Chloro-2-fluoro-5-(trifluoromethoxy)phenyl]-1-oxa-6-azaspiro[2.5]octane

Synthesized analogous to Reference Example 341.
¹HNMR (CDCl₃) δ ppm: 1.61-1.65 (2H, m), 2.03-2.09 (2H, m), 2.74 (2H, s), 3.16-3.21 (2H, m), 3.24-3.28 (2H, m), 6.90 (1H, dd, J=8.0 Hz, 1.0 Hz), 7.15 (1H, d, J=11.5 Hz).

Reference Example 403

6-(2-Bromo-5-ethoxy-4-nitrophenyl)-1-oxa-6-azaspiro[2.5]octane

Synthesized analogous to Reference Example 341.
¹HNMR (CDCl₃) δ ppm: 1.50 (3H, t, J=7.0 Hz), 1.58-1.63 (2H, m), 2.14-2.20 (2H, m), 2.76 (2H, s), 3.17-3.22 (2H, m), 3.34-3.38 (2H, m), 4.17 (2H, q, J=7.0 Hz), 6.63 (1H, s), 8.19 (1H, s).

Reference Example 404

6-(4-Ethoxy-2,5-difluorophenyl)-1-oxa-6-azaspiro[2.5]octane

Synthesized analogous to Reference Example 341.
¹HNMR (CDCl₃) δ ppm: 1.42 (3H, t, J=7.0 Hz), 1.62-1.66 (2H, m), 2.02-2.07 (2H, m), 2.72 (2H, s), 3.06-3.17 (4H, m), 4.04 (2H, q, J=7.0 Hz), 6.73 (1H, dd, J=13.0 Hz, 7.5 Hz), 6.79 (1H, dd, J=13.0 Hz, 8.0 Hz).

Reference Example 405

6-[4-(Ethoxymethyl)-2-fluorophenyl]-1-oxa-6-azaspiro[2.5]octane

Synthesized analogous to Reference Example 341.
¹HNMR (CDCl₃) δ ppm: 1.24 (3H, t, J=7.0 Hz), 1.63-1.67 (2H, m), 2.03-2.08 (2H, m), 2.73 (2H, s), 3.15-3.20 (2H, m), 3.22-3.26 (2H, m), 3.53 (2H, q, J=7.0 Hz), 4.42 (2H, s), 6.93-6.98 (1H, m), 7.02-7.07 (2H, m).

Reference Example 406

6-(2,6-Difluoro-4-methoxyphenyl)-1-oxa-6-azaspiro[2.5]octane

Synthesized analogous to Reference Example 341.
¹HNMR (CDCl₃) δ ppm: 1.63-1.68 (2H, m), 1.89-1.94 (2H, m), 2.70 (2H, s), 3.12-3.19 (2H, m), 3.29-3.34 (2H, m), 3.75 (3H, s), 6.39-6.45 (2H, m).

Reference Example 407

2-[2,5-Difluoro-4-(1-oxa-6-azaspiro[2.5]oct-6-yl)phenoxy]-N,N-dimethylethaneamine Synthesized analogous to Reference Example 341.
¹HNMR (CDCl₃) δ ppm: 1.61-1.66 (2H, m), 2.01-2.07 (2H, m), 2.34 (6H, s), 2.72 (2H, s), 2.73 (2H, t, J=6.0 Hz), 3.06-3.18 (4H, m), 4.07 (2H, t, J=6.0 Hz), 6.75 (1H, dd, J=13.0 Hz, 8.0 Hz), 6.78 (1H, dd, J=12.5 Hz, 8.0 Hz).

Reference Example 408

6-(4-Ethoxy-2,3,5,6-tetrafluorophenyl)-1-oxa-6-azaspiro[2.5]octane

Synthesized analogous to Reference Example 341.
¹HNMR (CDCl₃) δ ppm: 1.40 (3H, t, J=7.0 Hz), 1.60-1.65 (2H, m), 1.94-1.99 (2H, m), 2.72 (2H, s), 3.21-3.26 (2H, m), 3.37-3.42 (2H, m), 4.21 (2H, q, J=7.0 Hz), 6.73 (1H, dd, J=13.0 Hz, 7.5 Hz), 6.79 (1H, dd, J=13.0 Hz, 8.0 Hz).

Reference Example 409

6-(4-Chloro-5-ethoxy-2-fluorophenyl)-1-oxa-6-azaspiro[2.5]octane

Synthesized analogous to Reference Example 341.
¹HNMR (CDCl₃) δ ppm: 1.45 (3H, t, J=7.0 Hz), 1.60-1.64 (2H, m), 2.05-2.10 (2H, m), 2.73 (2H, s), 3.14-3.18 (2H, m), 3.22-3.26 (2H, m), 4.06 (2H, q, J=7.0 Hz), 6.57 (1H, d, J=8.0 Hz), 7.07 (1H, d, J=11.5 Hz).

Reference Example 410

6-{2-Fluoro-4-[2-(2-methoxyethoxy)ethoxy]phenyl}-1-oxa-6-azaspiro[2.5]octane

Synthesized analogous to Reference Example 341.
¹HNMR (CDCl₃) δ ppm: 1.62-1.67 (2H, m), 2.02-2.07 (2H, m), 2.72 (2H, s), 3.07-3.17 (4H, m), 3.39 (3H, s), 3.57-3.59 (2H, m), 3.70-3.72 (2H, m), 3.83-3.85 (2H, m), 4.08-4.10 (2H, m), 6.63 (1H, dd, J=9.0 Hz, 3.0 Hz), 6.68 (1H, dd, J=13.5 Hz, 3.0 Hz), 6.93 (1H, t, J=9.0 Hz).

Reference Example 411

6-(4-Chloro-2-fluoro-6-methylphenyl)-1-oxa-6-azaspiro[2.5]octane

Synthesized analogous to Reference Example 341.
$^1$HNMR (CDCl$_3$) δ ppm: 1.80 (4H, brs), 2.32 (3H, s), 2.71 (2H, s), 3.08 (2H, brs), 3.24 (2H, brs), 6.89 (1H, dd, J=11.5 Hz, 2.0 Hz), 6.96-6.98 (1H, m).

Reference Example 412

6-(4-Chloro-2-fluoro-5-methylphenyl)-1-oxa-6-azaspiro[2.5]octane

Synthesized analogous to Reference Example 341.
$^1$HNMR (CDCl$_3$) δ ppm: 1.60-1.65 (2H, m), 2.02-2.08 (2H, m), 2.30 (3H, s), 2.73 (2H, s), 3.13-3.17 (2H, m), 3.20-3.24 (2H, m), 6.82 (1H, d, J=9.5 Hz), 7.04 (1H, d, J=12.0 Hz).

Reference Example 413

6-(4-Ethoxy-2-fluoro-5-methoxyphenyl)-1-oxa-6-azaspiro[2.5]octane

Synthesized analogous to Reference Example 341.
$^1$HNMR (CDCl$_3$) δ ppm: 1.44 (3H, t, J=7.0 Hz), 1.62-1.67 (2H, m), 2.03-2.08 (2H, m), 2.73 (2H, s), 3.09-3.20 (4H, m), 3.85 (3H, s), 4.03 (2H, q, J=7.0 Hz), 6.62 (1H, d, J=8.0 Hz), 6.67 (1H, d, J=13.0 Hz).

Reference Example 414

6-[2-Fluoro-4-(2-fluoroethoxy)phenyl]-1-oxa-6-azaspiro[2.5]octane

Synthesized analogous to Reference Example 341.
$^1$HNMR (CDCl$_3$) δ ppm: 1.62-1.67 (2H, m), 2.03-2.08 (2H, m), 2.72 (2H, s), 3.08-3.18 (4H, m), 4.16 (2H, dt, J=28.0 Hz, 4.0 Hz), 4.73 (2H, dt, J=47.5 Hz, 4.0 Hz), 6.65 (1H, dd, J=9.0 Hz, 2.5 Hz), 6.70 (1H, dd, J=13.5 Hz, 2.5 Hz), 6.95 (1H, t, J=9.0 Hz).

Reference Example 415

6-(4-Ethoxy-2,6-difluorophenyl)-1-oxa-6-azaspiro[2.5]octane

Synthesized analogous to Reference Example 341.
$^1$HNMR (CDCl$_3$) δ ppm: 1.39 (3H, t, J=7.0 Hz), 1.63-1.68 (2H, m), 1.88-1.94 (2H, m), 2.70 (2H, s), 3.12-3.18 (2H, m), 3.28-3.33 (2H, m), 3.95 (2H, q, J=7.0 Hz), 6.38-6.43 (2H, m).

Reference Example 416

2-[3-Fluoro-4-(1-oxa-6-azaspiro[2.5]oct-6-yl)phenoxy]-N,N-dimethylethaneamine

Synthesized analogous to Reference Example 341.
$^1$HNMR (CDCl$_3$) δ ppm: 1.62-1.67 (2H, m), 2.02-2.07 (2H, m), 2.33 (6H, s), 2.68-2.72 (2H, m), 2.72 (2H, s), 3.07-3.17 (4H, m), 3.99-4.02 (2H, m), 6.64 (1H, ddd, J=9.0 Hz, 3.0 Hz, 1.0 Hz), 6.68 (1H, dd, J=13.5 Hz, 3.0 Hz), 6.94 (1H, t, J=9.0 Hz).

Reference Example 417

6-(1-Benzothiophen-5-yl)-1-oxa-6-azaspiro[2.5]octane

Synthesized analogous to Reference Example 341.
$^1$HNMR (CDCl$_3$) δ ppm: 1.67-1.71 (2H, m), 2.01-2.07 (2H, m), 2.74 (2H, s), 3.33-3.38 (2H, m), 3.42-3.46 (2H, m), 7.12 (1H, dd, J=9.0 Hz, 2.5 Hz), 7.23 (1H, d, J=5.0 Hz), 7.35 (1H, d, J=2.5 Hz), 7.41 (1H, d, J=5.0 Hz), 7.74 (1H, d, J=9.0 Hz).

Reference Example 418

6-[2-Fluoro-4-(2,2,2-trifluoroethoxy)phenyl]-1-oxa-6-azaspiro[2.5]octane

Synthesized analogous to Reference Example 341.
$^1$HNMR (CDCl$_3$) δ ppm: 1.63-1.66 (2H, m), 2.04-2.09 (2H, m), 2.73 (2H, s), 3.10-3.20 (4H, m), 4.30 (2H, q, J=8.0 Hz), 6.67 (1H, ddd, J=9.0 Hz, 2.5 Hz, 1.0 Hz), 6.72 (1H, dd, J=13.0 Hz, 2.5 Hz), 6.96 (1H, t, J=9.0 Hz).

Reference Example 419

6-(1-Oxa-6-azaspiro[2.5]oct-6-yl)quinoxaline

Synthesized analogous to Reference Example 341.
$^1$HNMR (CDCl$_3$) δ ppm: 1.64-1.68 (2H, m), 2.03-2.08 (2H, m), 2.77 (2H, s), 3.54-3.59 (2H, m), 3.69-3.74 (2H, m), 7.33 (1H, d, J=2.5 Hz), 7.56 (1H, dd, J=9.5 Hz, 2.5 Hz), 7.94 (1H, d, J=9.5 Hz), 8.60 (1H, d, J=2.0 Hz), 8.69 (1H, d, J=2.0 Hz).

Reference Example 420

6-(1-Benzofuran-5-yl)-1-oxa-6-azaspiro[2.5]octane

Synthesized analogous to Reference Example 341.
$^1$HNMR (CDCl$_3$) δ ppm: 1.67-1.71 (2H, m), 2.00-2.06 (2H, m), 2.73 (2H, s), 3.26-3.36 (4H, m), 6.69 (1H, d, J=2.0 Hz), 7.03 (1H, dd, J=9.0 Hz, 2.5 Hz), 7.16 (1H, d, J=2.5 Hz), 7.40 (1H, d, J=9.0 Hz), 7.57 (1H, d, J=2.0 Hz).

Reference Example 421

6-[4-(Difluoromethoxy)-2-fluorophenyl]-1-oxa-6-azaspiro[2.5]octane

Synthesized analogous to Reference Example 341.
$^1$HNMR (CDCl$_3$) δ ppm: 1.62-1.66 (2H, m), 2.04-2.09 (2H, m), 2.73 (2H, s), 3.13-3.18 (2H, m), 3.20-3.24 (2H, m), 6.44 (1H, t, J=73.5 Hz), 6.86 (1H, dd, J=9.0 Hz, 3.0 Hz), 6.89 (1H, dd, J=13.5 Hz, 3.0 Hz), 6.97 (1H, t, J=9.0 Hz).

Reference Example 422

6-(1-Oxa-6-azaspiro[2.5]oct-6-yl)quinoline

Synthesized analogous to Reference Example 341.
$^1$HNMR (CDCl$_3$) δ ppm: 1.66-1.71 (2H, m), 2.03-2.08 (2H, m), 2.76 (2H, s), 3.43-3.48 (2H, m), 3.57-3.61 (2H, m), 7.07-7.09 (1H, m), 7.30-7.32 (1H, m), 7.51-7.53 (1H, m), 7.94-8.00 (2H, m), 8.69-8.73 (1H, m).

Reference Example 423

6-(5-Chloro-3-fluoropyridin-2-yl)-1-oxa-6-azaspiro[2.5]octane

Synthesized analogous to Reference Example 398.
$^1$HNMR (CDCl$_3$) δ ppm: 1.56-1.65 (2H, m), 1.91-2.01 (2H, m), 2.73 (2H, s), 3.52-3.59 (2H, m), 3.70-3.77 (2H, m), 7.27 (1H, dd, J=12.2 Hz, 2.2 Hz), 7.95-7.99 (1H, m).

Reference Example 424

6-(2,4-Difluorophenyl)-1-oxa-6-azaspiro[2.5]octane

Synthesized analogous to Reference Example 341.
$^1$HNMR (CDCl$_3$) δ ppm: 1.61-1.66 (2H, m), 2.04-2.09 (2H, m), 2.73 (2H, s), 3.11-3.21 (4H, m), 6.78-6.84 (2H, m), 6.93-6.98 (1H, m).

Reference Example 425

6-[4-Chloro-2-fluoro-5-(2-fluoroethoxy)phenyl]-1-oxa-6-azaspiro[2.5]octane

Synthesized analogous to Reference Example 341.
$^1$HNMR (CDCl$_3$) δ ppm: 1.60-1.64 (2H, m), 2.04-2.10 (2H, m), 2.73 (2H, s), 3.14-3.19 (2H, m), 3.22-3.27 (2H, m), 4.25 (2H, dt, J=28.0 Hz, 4.5 Hz), 4.76 (2H, dt, J=47.5 Hz, 4.5 Hz), 6.64 (1H, d, J=8.0 Hz), 7.08 (1H, d, J=11.5 Hz).

Reference Example 426

6-[4-Chloro-2-fluoro-5-(2,2,2-trifluoroethoxy)phenyl]-1-oxa-6-azaspiro[2.5]octane Synthesized analogous to Reference Example 341.
$^1$HNMR (CDCl$_3$) δ ppm: 1.60-1.64 (2H, m), 2.04-2.09 (2H, m), 2.74 (2H, s), 3.14-3.19 (2H, m), 3.22-3.27 (2H, m), 4.36 (2H, q, J=8.5 Hz), 6.67 (1H, d, J=8.0 Hz), 7.09 (1H, d, J=11.5 Hz).

Reference Example 427

6-[4-Chloro-2-fluoro-5-(propan-2-yloxy)phenyl]-1-oxa-6-azaspiro[2.5]octane

Synthesized analogous to Reference Example 341.
$^1$HNMR (CDCl$_3$) δ ppm: 1.35 (6H, d, J=6.5 Hz), 1.60-1.64 (2H, m), 2.04-2.09 (2H, m), 2.73 (2H, s), 3.13-3.18 (2H, m), 3.21-3.25 (2H, m), 4.43 (1H, sep, J=6.5 Hz), 6.61 (1H, d, J=8.0 Hz), 7.06 (1H, d, J=12.0 Hz).

Reference Example 428

6-{4-Chloro-5-[(4-chlorobenzyl)oxy]-2-fluorophenyl}-1-oxa-6-azaspiro[2.5]octane

Synthesized analogous to Reference Example 341.
$^1$HNMR (CDCl$_3$) δ ppm: 1.57-1.62 (2H, m), 2.03-2.09 (2H, m), 2.73 (2H, s), 3.09-3.14 (2H, m), 3.18-3.22 (2H, m), 5.06 (2H, s), 6.57 (1H, d, J=7.5 Hz), 7.09 (1H, d, J=11.5 Hz), 7.36 (2H, d, J=8.5 Hz), 7.39 (2H, d, J=8.5 Hz).

Reference Example 429

6-[4-Chloro-2-fluoro-5-(2-methoxyethoxy)phenyl]-1-oxa-6-azaspiro[2.5]octane

Synthesized analogous to Reference Example 341.
$^1$HNMR (CDCl$_3$) δ ppm: 1.61-1.64 (2H, m), 2.04-2.09 (2H, m), 2.73 (2H, s), 3.13-3.18 (2H, m), 3.22-3.26 (2H, m), 3.47 (3H, s), 3.77 (2H, t, J=5.0 Hz), 4.14 (2H, t, J=5.0 Hz), 6.66 (1H, d, J=8.0 Hz), 7.06 (1H, d, J=11.5 Hz).

Reference Example 430

2-[2-Chloro-4-fluoro-5-(1-oxa-6-azaspiro[2.5]oct-6-yl)phenoxy]-N,N-dimethylethaneamine To a solution of 4-chloro-5-[2-(dimethylamino)ethoxy]-2-fluoroaniline (4.46 g) in ethanol-water (45-30 mL) was added 1-benzyl-1-methyl-4-oxopiperidinium bromide (5.45 g), and the reaction mixture was stirred at 100° C. for 23 h. To the reaction solution was added water, and the solution was extracted with ethyl acetate. The organic layer was washed with brine, dried over anhydrous sodium sulfate, and the solvent was distilled off to give 1-(4-chloro-5-(2-(dimethylamino)ethoxy)-2-fluorophenyl)piperidin-4-one (ketone compound). To a solution of trimethylsulfoxonium iodide (4.22 g) in dimethyl sulfoxide (55 mL) was added sodium hydride (55% in oil) (0.84 g), and the reaction mixture was stirred at room temperature for 30 min. The solution of the obtained ketone compound in dimethyl sulfoxide (8 mL) was added thereto, and the reaction mixture was stirred at room temperature for 2.5 h. To the reaction solution was added water, and the solution was extracted with ethyl acetate. The organic layer was washed with brine, dried over anhydrous sodium sulfate, and the solvent was distilled off. The residue was purified by silica gel column chromatography (NH silica gel; hexane/ethyl acetate) to provide the title compound (2.10 g).
$^1$HNMR (CDCl$_3$) δ ppm: 1.60-1.64 (2H, m), 2.04-2.09 (2H, m), 2.36 (6H, s), 2.73 (2H, s), 2.77 (2H, t, J=6.0 Hz), 3.13-3.18 (2H, m), 3.22-3.26 (2H, m), 4.08 (2H, t, J=6.0 Hz), 6.61 (1H, d, J=8.0 Hz), 7.06 (1H, d, J=11.5 Hz).

Reference Example 431

6-{4-Chloro-2-fluoro-5-[2-(4-fluorophenoxy)ethoxy]phenyl}-1-oxa-6-azaspiro[2.5]octane Synthesized analogous to Reference Example 341.
$^1$HNMR (CDCl$_3$) δ ppm: 1.59-1.63 (2H, m), 2.04-2.09 (2H, m), 2.73 (2H, s), 3.13-3.17 (2H, m), 3.21-3.25 (2H, m), 4.29-4.31 (2H, m), 4.33-4.35 (2H, m), 6.67 (1H, d, J=7.5 Hz), 6.90 (2H, dd, J=9.0 Hz, 2.5 Hz), 6.99 (2H, t, J=9.0 Hz), 7.08 (1H, d, J=11.5 Hz).

Reference Example 432

6-(4-Chloro-2-fluoro-5-propoxyphenyl)-1-oxa-6-azaspiro[2.5]octane

Synthesized analogous to Reference Example 341.
$^1$HNMR (CDCl$_3$) δ ppm: 1.06 (3H, t, J=7.5 Hz), 1.60-1.64 (2H, m), 1.81-1.88 (2H, m), 2.05-2.10 (2H, m), 2.73 (2H, s), 3.14-3.19 (2H, m), 3.22-3.26 (2H, m), 3.94 (2H, t, J=6.5 Hz), 6.57 (1H, d, J=7.5 Hz), 7.07 (1H, d, J=11.5 Hz).

Reference Example 433

6-[4-Chloro-2-fluoro-5-(propan-2-yl)phenyl]-1-oxa-6-azaspiro[2.5]octane

Synthesized analogous to Reference Example 341.
$^1$HNMR (CDCl$_3$) δ ppm: 1.22 (6H, d, J=6.5 Hz), 1.62-1.66 (2H, m), 2.03-2.08 (2H, m), 2.73 (2H, s), 3.16-3.26 (4H, m), 3.32 (1H, sep, J=6.5 Hz), 6.88 (1H, d, J=9.5 Hz), 7.04 (1H, d, J=11.5 Hz).

Reference Example 434

6-(4-Chloro-2-fluoro-5-propylphenyl)-1-oxa-6-azaspiro[2.5]octane

Synthesized analogous to Reference Example 341.
$^1$HNMR (CDCl$_3$) δ ppm: 0.96 (3H, t, J=7.5 Hz), 1.56-1.65 (4H, m), 2.03-2.08 (2H, m), 2.62 (2H, t, J=7.5 Hz), 2.73 (2H, s), 3.13-3.18 (2H, m), 3.20-3.25 (2H, m), 6.80 (1H, d, J=9.5 Hz), 7.04 (1H, d, J=12.0 Hz).

Reference Example 435

6-[4-(Difluoromethoxy)-2,6-difluorophenyl]-1-oxa-6-azaspiro[2.5]octane

Synthesized analogous to Reference Example 341.
$^1$HNMR (CDCl$_3$) δ ppm: 1.61-1.66 (2H, m), 1.92-1.97 (2H, m), 2.71 (2H, s), 3.17-3.24 (2H, m), 3.34-3.39 (2H, m), 6.45 (1H, t, J=73.5 Hz), 6.66-6.72 (2H, m).

Reference Example 436

6-(5,6-Dimethylpyridin-2-yl)-1-oxa-6-azaspiro[2.5]octane

Synthesized analogous to Reference Example 341.
$^1$HNMR (CDCl$_3$) δ ppm: 1.54-1.92 (2H, m), 1.85-1.93 (2H, m), 2.15 (3H, s), 2.37 (3H, s), 2.72 (2H, s), 3.55-3.62 (2H, m), 3.76-3.84 (2H, m), 6.45 (1H, d, J=8.5 Hz), 7.21 (1H, d, J=8.5 Hz).

Reference Example 437

6-(2,4-Difluoro-5-methylphenyl)-1-oxa-6-azaspiro[2.5]octane

Synthesized analogous to Reference Example 341.
$^1$HNMR (CDCl$_3$) δ ppm: 1.61-1.66 (2H, m), 2.03-2.08 (2H, m), 2.21 (3H, s), 2.72 (2H, s), 3.10-3.19 (4H, m), 6.76 (1H, dd, J=12.0 Hz, 9.5 Hz), 6.80 (1H, t, J=8.5 Hz).

Reference Example 438

6-(4-Chloro-2-fluoro-5-methoxyphenyl)-1-oxa-6-azaspiro[2.5]octane

Synthesized analogous to Reference Example 341.
$^1$HNMR (CDCl$_3$) δ ppm: 1.60-1.65 (2H, m), 2.05-2.11 (2H, m), 2.74 (2H, s), 3.15-3.20 (2H, m), 3.24-3.28 (2H, m), 3.87 (3H, s), 6.57 (1H, d, J=8.0 Hz), 7.08 (1H, d, J=11.5 Hz).

Reference Example 439

6-(4-Chloro-5-ethyl-2-fluorophenyl)-1-oxa-6-azaspiro[2.5]octane

Synthesized analogous to Reference Example 341.
$^1$HNMR (CDCl$_3$) δ ppm: 1.20 (3H, t, J=7.5 Hz), 1.61-1.66 (2H, m), 2.03-2.08 (2H, m), 2.68 (2H, q, J=7.5 Hz), 2.73 (2H, s), 3.14-3.19 (2H, m), 3.21-3.25 (2H, m), 6.83 (1H, d, J=9.0 Hz), 7.04 (1H, d, J=12.0 Hz).

Reference Example 440

6-(2,2,6-Trifluoro-1,3-benzodioxol-5-yl)-1-oxa-6-azaspiro[2.5]octane

Synthesized analogous to Reference Example 341.
$^1$HNMR (CDCl$_3$) δ ppm: 1.61-1.65 (2H, m), 2.05-2.10 (2H, m), 2.73 (2H, s), 3.09-3.18 (4H, m), 6.80 (1H, d, J=7.0 Hz), 6.86 (1H, d, J=10.0 Hz).

Reference Example 441

6-[2-Chloro-4-(methylsulfanyl)phenyl]-1-oxa-6-azaspiro[2.5]octane

Synthesized analogous to Reference Example 341.
$^1$HNMR (CDCl$_3$) δ ppm: 1.59-1.64 (2H, m), 2.04-2.10 (2H, m), 2.46 (3H, s), 2.73 (2H, s), 3.09-3.18 (4H, m), 6.99-7.01 (1H, m), 7.12-7.15 (1H, m), 7.26-7.30 (1H, m).

Reference Example 442

6-(5-Ethoxy-2,4-difluorophenyl)-1-oxa-6-azaspiro[2.5]octane

Synthesized analogous to Reference Example 341.
$^1$HNMR (CDCl$_3$) δ ppm: 1.42 (3H, t, J=7.0 Hz), 1.60-1.64 (2H, m), 2.04-2.09 (2H, m), 2.73 (2H, s), 3.10-3.15 (2H, m), 3.16-3.21 (2H, m), 4.07 (2H, q, J=7.0 Hz), 6.65 (1H, t, J=9.0 Hz), 6.85 (1H, t, J=11.5 Hz).

Reference Example 443

6-(2,4-Difluoro-5-methoxyphenyl)-1-oxa-6-azaspiro[2.5]octane

Synthesized analogous to Reference Example 341.
$^1$HNMR (CDCl$_3$) δ ppm: 1.61-1.65 (2H, m), 2.05-2.10 (2H, m), 2.73 (2H, s), 3.12-3.16 (2H, m), 3.18-3.22 (2H, m), 3.87 (3H, s), 6.65 (1H, t, J=8.5 Hz), 6.86 (1H, t, J=11.5 Hz).

Reference Example 444

6-(4-Bromo-2,6-difluorophenyl)-1-oxa-6-azaspiro[2.5]octane

Synthesized analogous to Reference Example 398.
$^1$HNMR (CDCl$_3$) δ ppm: 1.60-1.65 (2H, m), 1.91-1.97 (2H, m), 2.71 (2H, s), 3.19-3.23 (2H, m), 3.35-3.39 (2H, m), 7.00-7.05 (2H, m).

Reference Example 445

6-(5-Ethyl-2,4-difluorophenyl)-1-oxa-6-azaspiro[2.5]octane

Synthesized analogous to Reference Example 341.
$^1$HNMR (CDCl$_3$) δ ppm: 1.20 (3H, t, J=7.5 Hz), 1.62-1.66 (2H, m), 2.03-2.08 (2H, m), 2.60 (2H, q, J=7.5 Hz), 2.73 (2H, s), 3.11-3.20 (4H, m), 6.76 (1H, dd, J=12.0 Hz, 10.0 Hz), 6.82 (1H, t, J=9.0 Hz).

Reference Example 446

6-{4-Chloro-2-fluoro-5-[2-(4-fluorophenoxy)ethyl]phenyl}-1-oxa-6-azaspiro[2.5]octane Synthesized analogous to Reference Example 341.
$^1$HNMR (CDCl$_3$) δ ppm: 1.60-1.64 (2H, m), 2.03-2.08 (2H, m), 2.73 (2H, s), 3.11-3.18 (2H, m), 3.13 (2H, t, J=7.0 Hz), 3.21-3.25 (2H, m), 4.12 (2H, t, J=7.0 Hz), 6.80-6.84 (2H, m), 6.92 (1H, d, J=9.0 Hz), 6.96 (2H, t, J=8.5 Hz), 7.07 (1H, d, J=12.0 Hz).

Reference Example 447

6-(2,4-Difluoro-5-propylphenyl)-1-oxa-6-azaspiro[2.5]octane

Synthesized analogous to Reference Example 341.
$^1$HNMR (CDCl$_3$) δ ppm: 0.94 (3H, t, J=7.5 Hz), 1.55-1.66 (4H, m), 2.03-2.08 (2H, m), 2.55 (2H, t, J=7.5 Hz), 2.73 (2H, s), 3.11-3.19 (4H, m), 6.76 (1H, dd, J=11.5 Hz, 9.5 Hz), 6.79 (1H, dd, J=9.0 Hz, 8.0 Hz).

Reference Example 448

6-[4-(Ethylsulfanyl)-2,6-difluorophenyl]-1-oxa-6-azaspiro[2.5]octane

Synthesized analogous to Reference Example 341.
$^1$HNMR (CDCl$_3$) δ ppm: 1.31 (3H, t, J=7.5 Hz), 1.62-1.66 (2H, m), 1.90-1.96 (2H, m), 2.70 (2H, s), 2.90 (2H, q, J=7.5 Hz), 3.19-3.25 (2H, m), 3.34-3.38 (2H, m), 6.78-6.84 (2H, m).

Reference Example 449

6-[2,6-Difluoro-4-(2,2,2-trifluoroethoxy)phenyl]-1-oxa-6-azaspiro[2.5]octane

Synthesized analogous to Reference Example 398.
$^1$HNMR (CDCl$_3$) δ ppm: 1.62-1.66 (2H, m), 1.91-1.96 (2H, m), 2.71 (2H, s), 3.14-3.18 (2H, m), 3.31-3.35 (2H, m), 4.28 (2H, q, J=8.0 Hz), 6.46-6.52 (2H, m).

Reference Example 450

6-[4-Chloro-2-fluoro-5-(2-methoxyethyl)phenyl]-1-oxa-6-azaspiro[2.5]octane

Synthesized analogous to Reference Example 341.
$^1$HNMR (CDCl$_3$) δ ppm: 1.61-1.65 (2H, m), 2.02-2.08 (2H, m), 2.73 (2H, s), 2.94 (2H, t, J=7.0 Hz), 3.14-3.19 (2H, m), 3.21-3.25 (2H, m), 3.36 (3H, s), 3.58 (2H, t, J=7.0 Hz), 6.88 (1H, d, J=9.5 Hz), 7.05 (1H, d, J=12.0 Hz).

Reference Example 451

6-(2,2-Difluoro-1,3-benzodioxol-5-yl)-1-oxa-6-azaspiro[2.5]octane

Synthesized analogous to Reference Example 398.
$^1$HNMR (CDCl$_3$) δ ppm: 1.60-1.65 (2H, m), 1.98-2.03 (2H, m), 2.73 (2H, s), 3.22-3.27 (2H, m), 3.29-3.34 (2H, m), 6.62 (1H, dd, J=8.5 Hz, 2.0 Hz), 6.74 (1H, d, J=2.0 Hz), 6.93 (1H, d, J=8.5 Hz).

Reference Example 452

6-(2-Bromo-4-chloro-6-fluorophenyl)-1-oxa-6-azaspiro[2.5]octane

Synthesized analogous to Reference Example 398.
$^1$HNMR (DMSO-d6) δ ppm: 0.86-2.41 (4H, m), 2.71 (2H, s), 3.03 (2H, m), 3.27-3.44 (2H, m), 7.04 (1H, dd, J=11.3 Hz, 2.4 Hz), 7.39 (1H, t, J=2.0 Hz).

Reference Example 453 tert-Butyl 4-{[(8-fluoro-2-oxo-1,2,3,4-tetrahydroquinolin-5-yl)oxy]methyl}-4-hydroxypiperidine-1-carboxylate Under argon atmosphere, a solution of 8-fluoro-5-hydroxy-3,4-dihydroquinolin-2(1H)-one (1.0 g), tert-butyl 1-oxa-6-azaspiro[2.5]octane-6-carboxylate (1.30 g) and tripotassium phosphate (0.234 g) in N,N-dimethylformamide/2-propanol (1:1) (10 mL) was stirred at 70° C. for 48 h. To the reaction solution was added water, and the reaction mixture was extracted with ethyl acetate. The organic layer was washed with water and brine, and dried over anhydrous sodium sulfate, and then the solvent was distilled off. The residue was washed with diethyl ether to provide the title compound (1.15 g).
$^1$HNMR (CDCl$_3$) δ ppm: 1.47 (9H, s), 1.56-1.78 (4H, m), 1.99-2.08 (1H, m), 2.64 (2H, t, J=7.7 Hz), 2.99 (2H, t, J=7.7 Hz), 3.12-3.30 (2H, m), 3.79 (2H, s), 3.82-4.10 (2H, m), 6.46 (1H, dd, J=9.1 Hz, 4.0 Hz), 6.92 (1H, t, J=9.4 Hz), 7.56 (1H, brs).

Reference Example 454

8-Fluoro-5-[(4-hydroxypiperidin-4-yl)methoxy]-3,4-dihydroquinolin-2(1H)-one

Synthesized analogous to Reference Example 60.
$^1$HNMR (CDCl$_3$) δ ppm: 1.44-1.73 (5H, m), 2.02 (1H, brs), 2.61-2.68 (2H, m), 2.87-2.94 (2H, m), 2.97-3.09 (4H, m), 3.79 (2H, s), 6.47 (1H, dd, J=9.1 Hz, 4.0 Hz), 6.91 (1H, t, J=9.4 Hz), 7.59 (1H, brs).

Reference Example 455 tert-Butyl 4-({[8-fluoro-1-(4-methoxybenzyl)-2-oxo-1,2,3,4-tetrahydroquinolin-5-yl]oxy}methyl)-4-hydroxypiperidine-1-carboxylate Synthesized analogous to Reference Example 453.
$^1$HNMR (CDCl$_3$) δ ppm: 1.47 (9H, s), 1.58-1.67 (2H, m), 1.67-1.74 (2H, m), 1.99 (1H, brs), 2.61-2.67 (2H, m), 2.83-2.89 (2H, m), 3.11-3.30 (2H, m), 3.74 (3H, s), 3.75 (2H, s), 3.79-4.05 (2H, m), 5.23 (2H, brs), 6.50 (1H, dd, J=9.1 Hz, 3.3 Hz), 6.74-6.78 (2H, m), 6.83 (1H, dd, J=12.6 Hz, 9.1 Hz), 7.10-7.15 (2H, m).

Reference Example 456

8-Fluoro-5-[(4-hydroxypiperidin-4-yl)methoxy]-1-(4-methoxybenzyl)-3,4-dihydroquinolin-2(1H)-one hydrochloride To a solution of tert-Butyl 4-({[8-fluoro-1-(4-methoxybenzyl)-2-oxo-1,2,3,4-tetrahydroquinolin-5-yl]oxy}methyl)-4-hydroxypiperidine-1-carboxylate (6.35 g) in ethyl acetate (60 mL) was added 4 N hydrochloric acid/ethyl acetate (60 mL), and the reaction mixture was stirred at room temperature for 4 h. The solvent was distilled off, and the residue was crystallized from ethyl acetate/ethanol to provide the title compound (5.15 g).

$^1$HNMR (DMSO-d6) δ ppm: 1.64-1.73 (2H, m), 1.85-1.94 (2H, m), 2.57-2.66 (2H, m), 2.86-2.94 (2H, m), 3.04-3.13 (2H, m), 3.13-3.21 (2H, m), 3.68 (3H, s), 3.75 (2H, s), 5.10 (2H, brs), 5.14 (1H, s), 6.69 (1H, dd, J=9.2 Hz, 3.3 Hz), 6.78-6.83 (2H, m), 6.98 (1H, dd, J=13.1 Hz, 9.2 Hz), 7.04-7.09 (2H, m), 8.45-8.71 (2H, m).

Reference Example 457

8-Fluoro-5-[(4-hydroxypiperidin-4-yl)methoxy]-1-(4-methoxybenzyl)-3,4-dihydroquinolin-2(1H)-one To a suspension of 8-fluoro-5-[(4-hydroxypiperidin-4-yl)methoxy]-1-(4-methoxybenzyl)-3,4-dihydroquinolin-2(1H)-one hydrochloride (1.10 g) in ethyl acetate were added water and 5 N aqueous sodium hydroxide to make the reaction residue weakly basic, and the solution was extracted with ethyl acetate. The organic layer was washed with saturated brine, dried over anhydrous sodium sulfate, and the solvent was distilled of to provide the title compound (1.03 g).

$^1$HNMR (CDCl$_3$) δ ppm: 1.64-1.74 (4H, m), 1.95 (2H, brs), 2.62-2.67 (2H, m), 2.84-2.93 (4H, m), 3.00-3.07 (2H, m), 3.74 (3H, s), 3.75 (2H, s), 5.23 (2H, s), 6.51 (1H, dd, J=9.0 Hz, 2.5 Hz), 6.76 (2H, d, J=8.0 Hz), 6.83 (1H, dd, J=12.5 Hz, 9.0 Hz), 7.12 (2H, d, J=8.0 Hz).

Reference Example 458 tert-Butyl 4-{[(8-chloro-2-oxo-1,2,3,4-tetrahydroquinolin-5-yl)oxy]methyl}-4-hydroxypiperidine-1-carboxylate Synthesized analogous to Reference Example 453.

$^1$HNMR (CDCl$_3$) δ ppm: 1.47 (9H, s), 1.58-1.70 (2H, m), 1.70-1.76 (2H, m), 1.97 (1H, brs), 2.59-2.67 (2H, m), 2.99 (2H, t, J=7.7 Hz), 3.12-3.30 (2H, m), 3.81 (2H, s), 3.82-4.10 (2H, m), 6.52 (1H, d, J=8.9 Hz), 7.18 (1H, d, J=8.9 Hz), 7.74 (1H, brs).

Reference Example 459

8-Chloro-5-[(4-hydroxypiperidin-4-yl)methoxy]-3,4-dihydroquinolin-2(1H)-one

Synthesized analogous to Reference Example 60.

$^1$HNMR (CDCl$_3$) δ ppm: 1.55-2.20 (6H, m), 2.62 (2H, t, J=7.7 Hz), 2.84-2.96 (2H, m), 2.96-3.11 (4H, m), 3.81 (2H, s), 6.53 (1H, d, J=8.9 Hz), 7.18 (1H, d, J=8.9 Hz), 7.78 (1H, brs).

Reference Example 460

8-Fluoro-1-(4-methoxybenzyl)-2-oxo-1,2,3,4-tetrahydroquinolin-5-yl trifluoromethanesulfonate To a suspension of 8-fluoro-5-hydroxy-1-(4-methoxybenzyl)-3,4-dihydroquinolin-2(1H)-one (10 g) in dichloromethane (100 mL) was added pyridine (4.03 mL), and to the mixture trifluoromethanesulfonic anhydride (6.70 mL) was added dropwise under ice-cooling and then the reaction mixture was stirred at the same temperature for 4 h. To the reaction solution was added water, and the solution was extracted with dichloromethane. The organic layer was washed with water and brine, dried over anhydrous sodium sulfate, and then the solvent was distilled off. The residue was purified by silica gel column chromatography (hexane/ethyl acetate) to provide the title compound (12.8 g).

$^1$HNMR (CDCl$_3$) δ ppm: 2.68-2.73 (2H, m), 2.93-2.98 (2H, m), 3.75 (3H, s), 5.23 (2H, brs), 6.75-6.79 (2H, m), 6.92-7.00 (2H, m), 7.07-7.12 (2H, m).

Reference Example 461

5-Amino-8-fluoro-1-(4-methoxybenzyl)-3,4-dihydroquinolin-2(1H)-one

Under argon atmosphere, a solution of 8-fluoro-1-(4-methoxybenzyl)-2-oxo-1,2,3,4-tetrahydroquinolin-5-yl trifluoromethanesulfonate (17.5 g), benzophenone imine (9.44 mL), (±)-2,2'-bis(diphenylphosphino)-1,1'-binaphthyl (1.89 g), palladium (II) acetate (0.453 g) and cesium carbonate (13.16 g) in toluene (170 mL) was heated to reflux for 12 h. After the reaction mixture was allowed to cool to room temperature, to the reaction solution was added basic silica gel (80 g), and the reaction mixture was filtered. The filtrate was washed with water and brine, and dried over anhydrous sodium sulfate, and then the solvent was distilled off. The residue was dissolved in tetrahydrofuran (170 mL), and 1 N hydrochloric acid (80 mL) was added thereto. The mixture was stirred at room temperature for 1 h, 1 N aqueous sodium hydroxide (80 mL) and water was added thereto, and the solution was extracted with ethyl acetate. The organic layer was washed with brine, and dried over anhydrous sodium sulfate, and then the solvent was distilled off. The residue was purified by silica gel column chromatography (basic silica gel; dichloromethane/ethyl acetate) to provide the title compound (9.74 g).

$^1$HNMR (CDCl$_3$) δ ppm: 2.60-2.70 (4H, m), 3.44 (2H, brs), 3.74 (3H, s), 5.20 (2H, brs), 6.36 (1H, dd, J=8.8 Hz, 3.8 Hz), 6.70-6.78 (3H, m), 7.10-7.14 (2H, m).

Reference Example 462

N-[8-Fluoro-1-(4-methoxybenzyl)-2-oxo-1,2,3,4-tetrahydroquinolin-5-yl]acetamide

To acetic anhydride (7 mL) was added 5-amino-8-fluoro-1-(4-methoxybenzyl)-3,4-dihydroquinolin-2(1H)-one (782 mg), and the reaction mixture was stirred at room temperature for 15 min. To the reaction solution was added diethyl ether, and the precipitate was collected on a filter to provide the title compound (760 mg).

$^1$HNMR (DMSO-d6) δ ppm: 2.02 (3H, s), 2.47-2.62 (2H, m), 2.66-2.78 (2H, m), 3.68 (3H, s), 5.08 (2H, brs), 6.73-6.85 (2H, m), 6.95-7.13 (4H, m), 9.55 (1H, brs).

Reference Example 463

8-Chloro-1-(4-methoxybenzyl)-2-oxo-1,2,3,4-tetrahydroquinolin-5-yl trifluoromethanesulfonate Synthesized analogous to Reference Example 460.

$^1$HNMR (DMSO-d6) δ ppm: 2.58-2.68 (2H, m), 2.81-2.89 (2H, m), 3.66 (3H, s), 5.27 (2H, brs), 6.70-6.79 (2H, m), 6.98-7.08 (2H, m), 7.22 (1H, d, J=9.0 Hz), 7.46 (1H, d, J=9.0 Hz).

Reference Example 464

5-Amino-8-chloro-1-(4-methoxybenzyl)-3,4-dihydroquinolin-2(1H)-one

Synthesized analogous to Reference Example 461.
$^1$HNMR (CDCl$_3$) δ ppm: 2.47-2.63 (4H, m), 3.58 (2H, brs), 3.73 (3H, s), 5.34 (2H, brs), 6.41 (1H, d, J=8.7 Hz), 6.67-6.76 (2H, m), 7.01 (1H, d, J=8.7 Hz), 7.03-7.10 (2H, m).

Reference Example 465

N-[8-Chloro-1-(4-methoxybenzyl)-2-oxo-1,2,3,4-tetrahydroquinolin-5-yl]acetamide

Synthesized analogous to Reference Example 462.
$^1$HNMR (DMSO-d6) δ ppm: 2.02 (3H, brs), 2.42-2.54 (2H, m), 2.58-2.67 (2H, m), 3.67 (3H, s), 5.25 (2H, s), 6.71-6.79 (2H, m), 6.96-7.04 (2H, m), 7.15 (1H, d, J=8.9 Hz), 7.23 (1H, d, J=8.9 Hz), 9.58 (1H, brs).

Reference Example 466

7,8-Difluoro-1-(4-methoxybenzyl)-2-oxo-1,2,3,4-tetrahydroquinolin-5-yl trifluoromethanesulfonate Synthesized analogous to Reference Example 460.
$^1$HNMR (CDCl$_3$) δ ppm: 2.68-2.73 (2H, m), 2.89-2.97 (2H, m), 3.76 (3H, s), 5.24 (2H, brs), 6.76-6.81 (2H, m), 6.86 (1H, dd, J=9.3 Hz, 6.1 Hz), 7.07-7.12 (2H, m).

Reference Example 467

5-Amino-7,8-difluoro-1-(4-methoxybenzyl)-3,4-dihydroquinolin-2(1H)-one

Synthesized analogous to Reference Example 461.
$^1$HNMR (CDCl$_3$) δ ppm: 2.55-2.63 (2H, m), 2.63-2.71 (2H, m), 3.51 (2H, brs), 3.75 (3H, s), 5.21 (2H, brs), 6.24 (1H, dd, J=11.3 Hz, 6.4 Hz), 6.71-6.81 (2H, m), 7.07-7.16 (2H, m).

Reference Example 468

N-[7,8-Difluoro-1-(4-methoxybenzyl)-2-oxo-1,2,3,4-tetrahydroquinolin-5-yl]acetamide Synthesized analogous to Reference Example 462.
$^1$HNMR (CDCl$_3$) δ ppm: 2.18 (3H, s), 2.58-2.68 (2H, m), 2.68-2.76 (2H, m), 3.74 (3H, s), 5.22 (2H, s), 6.71-6.80 (2H, m), 6.90 (1H, brs), 7.07-7.14 (2H, m), 7.17 (1H, dd, J=11.0 Hz, 6.9 Hz).

Reference Example 469

2,2,2-Trifluoro-N-[8-fluoro-1-(4-methoxybenzyl)-2-oxo-1,2,3,4-tetrahydroquinolin-5-yl]acetamide To a solution of 5-amino-8-fluoro-1-(4-methoxybenzyl)-3,4-dihydroquinolin-2(1H)-one (0.7 g) in dichloromethane (7 mL), trifluoroacetic anhydride (0.389 mL) was added dropwise, and the reaction mixture was stirred at room temperature for 1.5 h. The solvent was distilled off, and the residue was washed with diisopropyl ether to provide the title compound (0.87 g).
$^1$HNMR (CDCl$_3$) δ ppm: 2.63-2.70 (2H, m), 2.70-2.76 (2H, m), 3.73 (3H, s), 5.23 (2H, brs), 6.73-6.78 (2H, m), 6.97 (1H, dd, J=12.3 Hz, 8.9 Hz), 7.08-7.12 (2H, m), 7.15 (1H, dd, J=8.9 Hz, 4.1 Hz), 7.69 (1H, brs).

Reference Example 470

8-Fluoro-1-(4-methoxybenzyl)-5-(methylamino)-3,4-dihydroquinolin-2(1H)-one

Under argon atmosphere, to a solution of 2,2,2-trifluoro-N-[8-fluoro-1-(4-methoxybenzyl)-2-oxo-1,2,3,4-tetrahydroquinolin-5-yl]acetamide (0.87 g) in N-methyl-2-pyrrolidone (8 mL) was added sodium hydride (55% in oil) (0.105 g) under ice-cooling. The reaction mixture was stirred at the same temperature for 15 min, and methyl iodide (0.273 mL) was added dropwise thereto. The reaction mixture was stirred at room temperature for 15 h. To the reaction solution was added aqueous saturated ammonium chloride solution, and the solution was extracted with ethyl acetate. The organic layer was washed with water and brine, and dried over anhydrous sodium sulfate, and then the solvent was distilled off. The residue was dissolved in methanol/tetrahydrofuran (1:1) (16 mL), 5 N aqueous sodium hydroxide (1.32 mL) was added to the reaction mixture, and the mixture was stirred at room temperature for 2 h. The solvent was distilled off, and to the residue was added aqueous saturated ammonium chloride solution, and then the solution was extracted with ethyl acetate. The organic layer was washed with water and brine, and dried over anhydrous sodium sulfate, and then the solvent was distilled off. The residue was purified by silica gel column chromatography (hexane/ethyl acetate) to provide the title compound (0.60 g).
$^1$HNMR (CDCl$_3$) δ ppm: 2.58-2.63 (2H, m), 2.63-2.68 (2H, m), 2.82 (3H, brs), 3.33 (1H, brs), 3.73 (3H, s), 5.21 (2H, brs), 6.32 (1H, dd, J=9.0 Hz, 3.4 Hz), 6.72-6.77 (2H, m), 6.83 (1H, dd, J=12.9 Hz, 9.0 Hz), 7.09-7.14 (2H, m).

Reference Example 471

5-[{[1-(2,4-Dichlorophenyl)-4-hydroxypiperidin-4-yl]methyl}(methyl)amino]-8-fluoro-1-(4-methoxybenzyl)-3,4-dihydroquinolin-2(1H)-one To a solution of 8-fluoro-1-(4-methoxybenzyl)-5-(methylamino)-3,4-dihydroquinolin-2(1H)-one (0.61 g) in acetic acid (3 mL) was added a solution of 6-(2,4-dichlorophenyl)-1-oxa-6-azaspiro[2.5]octane (3.00 g) in acetic acid (3 mL), and the reaction mixture was stirred at 60° C. for 13 h. The solvent was distilled off and to the residue was added saturated aqueous sodium hydrogencarbonate, and the solution was extracted with ethyl acetate. The organic layer was washed with water and brine, and dried over anhydrous sodium sulfate, and then the solvent was distilled off. The residue was purified by silica gel column chromatography (hexane/ethyl acetate) to provide the title compound (0.53 g).
$^1$HNMR (CDCl$_3$) δ ppm: 1.42-1.50 (2H, m), 1.60-1.69 (2H, m), 2.51 (1H, s), 2.60-2.67 (2H, m), 2.69 (3H, s), 2.87-2.95 (2H, m), 2.95-3.00 (2H, m), 3.00-3.06 (2H, m), 3.07 (1H, s), 3.69 (3H, s), 5.21 (2H, brs), 6.71-6.76 (2H, m), 6.84-6.95 (2H, m), 6.97 (1H, d, J=8.6 Hz), 7.03-7.13 (2H, m), 7.17 (1H, dd, J=8.6 Hz, 2.5 Hz), 7.34 (1H, d, J=2.5 Hz).

Reference Example 472

5-({[1-(2,4-Dichloro-5-fluorophenyl)-4-hydroxypiperidin-4-yl]methyl}amino)-8-fluoro-1-(4-methoxybenzyl)-3,4-dihydroquinolin-2(1H)-one Synthesized analogous to Reference Example 471.
¹HNMR (DMSO-d6) δ ppm: 1.71 (4H, brs), 2.58-2.61 (2H, m), 2.69-2.72 (2H, m), 2.90-3.10 (6H, m), 3.68 (3H, s), 4.50-4.60 (1H, m), 4.69 (1H, s), 5.08 (2H, brs), 6.41 (1H, dd, J=9.0 Hz, 3.6 Hz), 6.78-6.89 (3H, m), 7.06 (2H, d, J=8.7 Hz), 7.25 (1H, d, J=11.1 Hz), 7.70 (1H, d, J=7.8 Hz).

Reference Example 473

5-({[1-(4-Chloro-2,5-difluorophenyl)-4-hydroxypiperidin-4-yl]methyl}amino)-8-fluoro-1-(4-methoxybenzyl)-3,4-dihydroquinolin-2(1H)-one Synthesized analogous to Reference Example 471.
¹HNMR (CDCl₃) δ ppm: 1.68 (1H, s), 1.75-2.00 (4H, m), 2.68 (4H, s), 2.95-3.15 (4H, m), 3.15-3.30 (2H, m), 3.55-3.70 (1H, brs), 3.74 (3H, s), 5.22 (2H, brs), 6.40 (1H, dd, J=9.0 Hz, 3.6 Hz), 6.71-6.87 (4H, m), 7.03-7.18 (3H, m).

Reference Example 474

5-({[1-(4-Chloro-2,6-difluorophenyl)-4-hydroxypiperidin-4-yl]methyl}amino)-8-fluoro-1-(4-methoxybenzyl)-3,4-dihydroquinolin-2(1H)-one Synthesized analogous to Reference Example 471.
¹HNMR (CDCl₃) δ ppm: 1.65-1.95 (5H, m), 2.68 (4H, s), 3.00-3.15 (4H, m), 3.28-3.44 (2H, m), 3.60-3.71 (1H, brs), 3.74 (3H, s), 5.21 (2H, brs), 6.40 (1H, dd, J=9.0 Hz, 3.6 Hz), 6.71-6.94 (5H, m), 7.13 (2H, d, J=8.4 Hz).

Reference Example 475

5-({[1-(2,4-Dichloro-6-fluorophenyl)-4-hydroxypiperidin-4-yl]methyl}amino)-8-fluoro-1-(4-methoxybenzyl)-3,4-dihydroquinolin-2(1H)-one Synthesized analogous to Reference Example 471.
¹HNMR (CDCl₃) δ ppm: 1.68-1.94 (5H, m), 2.68 (4H, s), 2.95-3.15 (4H, m), 3.30-3.45 (2H, m), 3.60-3.70 (1H, brs), 3.74 (3H, s), 5.21 (2H, brs), 6.40 (1H, dd, J=9.0 Hz, 3.6 Hz), 6.72-6.88 (3H, m), 6.96-7.02 (1H, m), 7.10-7.21 (3H, m).

Reference Example 476

5-({[1-(2-Chloro-4,6-difluorophenyl)-4-hydroxypiperidin-4-yl]methyl}amino)-8-fluoro-1-(4-methoxybenzyl)-3,4-dihydroquinolin-2(1H)-one Synthesized analogous to Reference Example 471.
¹HNMR (DMSO-d6) δ ppm: 1.70-1.94 (5H, m), 2.68 (4H, m), 2.93-3.04 (2H, m), 3.11 (2H, brs), 3.29-3.43 (2H, m), 3.60-3.72 (1H, brs), 3.74 (3H, s), 5.21 (2H, brs), 6.41 (1H, dd, J=9.0 Hz, 3.6 Hz), 6.69-6.88 (4H, m), 6.91-7.00 (1H, m), 7.08-7.17 (2H, m).

Reference Example 477

5-[({1-[2-Chloro-4-(trifluoromethoxy)phenyl]-4-hydroxypiperidin-4-yl}methyl)amino)-8-fluoro-1-(4-methoxybenzyl)-3,4-dihydroquinolin-2(1H)-one Synthesized analogous to Reference Example 471.
¹HNMR (CDCl₃) δ ppm: 1.80-1.96 (4H, m), 2.68 (4H, s), 2.98-3.19 (7H, m), 3.73 (3H, s), 5.21 (2H, s), 6.40 (1H, dd, J=9.0 Hz, 3.6 Hz), 6.73-6.86 (3H, m), 7.04-7.11 (5H, m).

Reference Example 478

5-({[1-(4-Ethoxy-2-fluorophenyl)-4-hydroxypiperidin-4-yl]methyl}amino)-8-fluoro-1-(4-methoxybenzyl)-3,4-dihydroquinolin-2(1H)-one Synthesized analogous to Reference Example 471.
¹HNMR (CDCl₃) δ ppm: 1.39 (3H, t, J=6.9 Hz), 1.75-1.99 (5H, m), 2.60-2.75 (4H, m), 2.92-3.20 (6H, m), 3.60-3.80 (4H, m), 3.97 (2H, q, J=6.9 Hz), 5.21 (2H, brs), 6.36-6.43 (1H, m), 6.57-6.68 (2H, m), 6.70-6.87 (3H, m), 6.89-6.99 (1H, m), 7.08-7.17 (2H, m).

Reference Example 479

5-({[1-(2-Chloro-4-ethylphenyl)-4-hydroxypiperidin-4-yl]methyl}amino)-8-fluoro-1-(4-methoxybenzyl)-3,4-dihydroquinolin-2(1H)-one Synthesized analogous to Reference Example 471.
¹HNMR (CDCl₃) δ ppm: 1.21 (3H, t, J=7.8 Hz), 1.68-2.00 (5H, m), 2.58 (2H, q, H=7.8 Hz), 2.68 (4H, brs), 2.94-3.07 (2H, m), 3.08-3.12 (4H, m), 3.62-3.89 (4H, m), 5.21 (2H, brs), 6.41 (1H, dd, J=9.0 Hz, 3.6 Hz), 6.70-6.88 (3H, m), 6.96-7.25 (5H, m).

Reference Example 480

8-Fluoro-5-[({1-[2-fluoro-4-(propan-2-yloxy)phenyl]-4-hydroxypiperidin-4-yl}methyl)amino]-1-(4-methoxybenzyl)-3,4-dihydroquinolin-2(1H)-one Synthesized analogous to Reference Example 471.
¹HNMR (CDCl₃) δ ppm: 1.30 (6H, d, J=6 Hz), 1.75-1.98 (4H, m), 2.25-2.50 (1H, brs), 2.55-2.75 (4H, m), 2.90-3.18 (6H, m), 3.50-3.80 (4H, m), 4.36-4.50 (1H, m), 5.19 (2H, brs), 6.37 (1H, dd, J=9.0 Hz, 3.6 Hz), 6.54-6.98 (6H, m), 7.04-7.16 (2H, m).

Reference Example 481

5-({[1-(2-Chloro-4-propylphenyl)-4-hydroxypiperidin-4-yl]methyl}amino)-8-fluoro-1-(4-methoxybenzyl)-3,4-dihydroquinolin-2(1H)-one Synthesized analogous to Reference Example 471.
¹HNMR (CDCl₃) δ ppm: 0.92 (3H, t, J=7.4 Hz), 1.60 (2H, sex, J=7.4 Hz), 1.77-1.99 (4H, m), 2.22 (1H, brs), 2.50 (2H, t, J=7.4 Hz), 2.58-2.73 (4H, m), 2.92-3.20 (6H, m), 3.60-3.80 (4H, m), 5.20 (2H, brs), 6.39 (1H, dd, J=9.0 Hz, 3.6 Hz), 6.67-6.88 (3H, m), 6.94-7.05 (2H, m), 7.06-7.15 (2H, m), 7.16-7.20 (1H, m).

Reference Example 482

8-Fluoro-5-({[4-hydroxy-1-(2,4,6-trifluorophenyl)piperidin-4-yl]methyl}amino)-1-(4-methoxybenzyl)-3,4-dihydroquinolin-2(1H)-one Synthesized analogous to Reference Example 471.
¹HNMR (CDCl₃) δ ppm: 1.74-1.92 (4H, m), 2.60-2.76 (4H, m), 2.98-3.05 (4H, m), 3.31-3.42 (2H, m), 3.65-3.80 (1H, m), 3.73 (3H, s), 5.16-5.28 (2H, m), 6.40 (1H, dd, J=9.0

Hz, 3.6 Hz), 6.58-6.67 (2H, m), 6.72-6.78 (2H, m), 6.82 (1H, dd, J=12.8 Hz, 9.0 Hz), 7.10-7.16 (2H, m).

Reference Example 483

8-Chloro-5-({[1-(4-chloro-2-fluorophenyl)-4-hydroxypiperidin-4-yl]methyl}amino)-1-(4-methoxybenzyl)-3,4-dihydroquinolin-2(1H)-one To a solution of N-[8-chloro-1-(4-methoxybenzyl)-2-oxo-1,2,3,4-tetrahydroquinolin-5-yl]acetamide (200 mg) and 6-(4-chloro-2-fluorophenyl)-1-oxa-6-azaspiro[2.5]octane (202 mg) in N,N-dimethylformamide/2-propanol (1:1) (2 mL) was added tripotassium phosphate (59.2 mg), and the mixture was stirred at 90° C. for 18 h. To the mixture was added sodium hydroxide (11.2 mg), and the mixture was stirred at 90° C. for 18 h. The reaction solution was poured into water, and the reaction mixture was extracted with ethyl acetate. The organic layer was washed with brine, dried over anhydrous sodium sulfate, and then the solvent was distilled off. The residue was purified by silica gel column chromatography (hexane/ethyl acetate) to provide the title compound (279 mg).

$^1$HNMR (CDCl$_3$) δ ppm: 1.74-1.93 (4H, m), 2.33 (1H, brs), 2.53 (4H, brs), 2.97-3.25 (6H, m), 3.68 (3H, s), 3.92 (1H, brs), 5.31 (2H, brs), 6.43 (1H, d, J=8.7 Hz), 6.63-6.72 (2H, m), 6.83-6.93 (1H, m), 6.98-7.11 (5H, m).

Reference Example 484

8-Chloro-5-({[1-(4-chloro-2,6-difluorophenyl)-4-hydroxypiperidin-4-yl]methyl}amino)-1-(4-methoxybenzyl)-3,4-dihydroquinolin-2(1H)-one Synthesized analogous to Reference Example 483.

$^1$HNMR (CDCl$_3$) δ ppm: 1.70-1.89 (4H, m), 2.32 (1H, brs), 2.54 (4H, m), 3.00-3.16 (4H, m), 3.30-3.44 (2H, m), 3.69 (3H, s), 3.96 (1H, brs), 5.32 (2H, brs), 6.43 (1H, d, J=8.7 Hz), 6.65-6.72 (2H, m), 6.81-6.93 (2H, m), 7.01-7.13 (3H, m).

Reference Example 485

8-Chloro-5-({[1-(2,4-dichloro-5-fluorophenyl)-4-hydroxypiperidin-4-yl]methyl}amino)-1-(4-methoxybenzyl)-3,4-dihydroquinolin-2(1H)-one To a solution of N-[8-chloro-1-(4-methoxybenzyl)-2-oxo-1,2,3,4-tetrahydroquinolin-5-yl]acetamide (200 mg) and 6-(2,4-dichloro-5-fluorophenyl)-1-oxa-6-azaspiro[2.5]octane (200 mg) in N,N-dimethylformamide/2-propanol (1:1) (2 mL) was added tripotassium phosphate (59.2 mg), and the reaction mixture was stirred at 90° C. for 16 h. The reaction solution was poured into water, and the reaction mixture was extracted with ethyl acetate. The organic layer was washed with brine, dried over anhydrous sodium sulfate, and then the solvent was distilled off. The residue was purified by silica gel column chromatography (hexane/ethyl acetate) to provide the title compound (324 mg).

$^1$HNMR (CDCl$_3$) δ ppm: 1.76-1.94 (4H, m), 2.30 (1H, brs), 2.53 (4H, brs), 2.92-3.20 (6H, m), 3.68 (3H, s), 3.92 (1H, brs), 5.32 (2H, s), 6.44 (1H, d, J=9.0 Hz), 6.66-6.70 (2H, m), 6.85 (1H, d, J=10.5 Hz), 7.00-7.13 (3H, m), 7.37 (1H, d, J=7.8 Hz).

Reference Example 486

8-Chloro-5-({[1-(4-ethoxy-2-fluorophenyl)-4-hydroxypiperidin-4-yl]methyl}amino)-1-(4-methoxybenzyl)-3,4-dihydroquinolin-2(1H)-one Synthesized analogous to Reference Example 483.

$^1$HNMR (DMSO-d6) δ ppm: 1.29 (3H, t, J=6.9 Hz), 1.60-1.78 (4H, m), 2.55-2.65 (2H, m), 2.89-2.98 (4H, m), 3.04 (2H, d, J=5.7 Hz), 3.17-3.23 (2H, m), 3.67 (3H, s), 3.96 (2H, q, J=6.9 Hz), 4.50 (1H, brs), 4.72-4.75 (1H, m), 5.23 (2H, brs), 6.50 (1H, d, J=8.7 Hz), 6.62-6.71 (2H, m), 6.72-6.79 (2H, m), 6.94-7.08 (4H, m).

Reference Example 487

8-Chloro-5-({[4-hydroxy-1-(2,4,6-trifluorophenyl)piperidin-4-yl]methyl}amino)-1-(4-methoxybenzyl)-3,4-dihydroquinolin-2(1H)-one Synthesized analogous to Reference Example 483.

$^1$HNMR (CDCl$_3$) δ ppm: 1.71-1.89 (4H, m), 2.38 (1H, brs), 2.54 (4H, brs), 2.93-3.06 (2H, m), 3.11 (2H, brs), 3.30-3.44 (2H, m), 3.69 (3H, s), 3.97 (1H, brs), 5.32 (2H, s), 6.43 (1H, d, J=9.0 Hz), 6.55-6.72 (4H, m), 7.01-7.12 (3H, m).

Reference Example 488

8-Chloro-5-({[1-(4-chloro-2,5-difluorophenyl)-4-hydroxypiperidin-4-yl]methyl}amino)-1-(4-methoxybenzyl)-3,4-dihydroquinolin-2(1H)-one Synthesized analogous to Reference Example 485.

$^1$HNMR (CDCl$_3$) δ ppm: 1.72-1.92 (4H, m), 2.10 (1H, brs), 2.54 (4H, brs), 2.98-3.28 (6H, m), 3.70 (3H, s), 3.90 (1H, brs), 5.32 (2H, brs), 6.44 (1H, d, J=8.7 Hz), 6.66-6.80 (3H, m), 7.01-7.12 (4H, m).

Reference Example 489

5-({[1-(4-Chloro-2-fluorophenyl)-4-hydroxypiperidin-4-yl]methyl}amino)-7,8-difluoro-1-(4-methoxybenzyl)-3,4-dihydroquinolin-2(1H)-one Synthesized analogous to Reference Example 485.

$^1$HNMR (CDCl$_3$) δ ppm: 1.77-1.86 (2H, m), 1.86-1.97 (2H, m), 2.56-2.72 (4H, m), 2.98-3.10 (2H, m), 3.15-3.26 (2H, m), 3.75 (3H, s), 3.77-3.83 (1H, m), 5.22 (1H, brs), 6.27 (1H, dd, J=12.4 Hz, 6.3 Hz), 6.71-6.81 (2H, m), 6.87-6.95 (1H, m), 7.01-7.08 (2H, m), 7.09-7.17 (2H, m).

Reference Example 490

5-({[1-(4-Bromo-2-fluorophenyl)-4-hydroxypiperidin-4-yl]methyl}amino)-7,8-difluoro-1-(4-methoxybenzyl)-3,4-dihydroquinolin-2(1H)-one Synthesized analogous to Reference Example 485.

$^1$HNMR (CDCl$_3$) δ ppm: 1.74-1.95 (4H, m), 2.57-2.74 (4H, m), 2.97-3.09 (4H, m), 3.16-3.26 (2H, m), 3.75 (3H, s), 3.77-3.83 (1H, m), 5.22 (2H, brs), 6.27 (1H, dd, J=12.4 Hz, 6.3 Hz), 6.73-6.79 (2H, m), 6.86 (1H, t, J=8.6 Hz), 7.09-7.16 (2H, m), 7.17-7.22 (2H, m).

Reference Example 491

5-{[1-(2-Chlorophenyl)-4-hydroxypiperidin-4-yl]methoxy}-8-fluoro-1-(4-methoxybenzyl)-3,4-dihydroquinolin-2(1H)-one Synthesized analogous to Reference Example 70.
$^1$HNMR (CDCl$_3$) δ ppm: 1.85-1.88 (2H, m), 1.93-1.99 (2H, m), 2.06 (1H, brs), 2.65-2.68 (2H, m), 2.89-2.92 (2H, m), 3.07-3.12 (2H, m), 3.21-3.23 (2H, m), 3.74 (3H, s), 3.83 (2H, s), 5.24 (2H, brs), 6.54 (1H, dd, J=9.0, 3.0 Hz), 6.76 (2H, d, J=8.5 Hz), 6.85 (1H, dd, J=12.5H, 9.0 Hz), 6.97 (1H, dt, J=1.5 Hz, 8.0 Hz), 7.10 (1H, dd, J=8.0 Hz, 1.5 Hz), 7.13 (2H, d, J=8.5 Hz), 7.23 (1H, dt, J=1.5 Hz, 8.0 Hz), 7.37 (1H, dd, J=8.0 Hz, 1.5 Hz).

Reference Example 492

5-{[1-(4-Chloro-2-fluorophenyl)-4-hydroxypiperidin-4-yl]methoxy}-8-fluoro-1-(4-methoxybenzyl)-7-(tetrahydro-2H-pyran-2-yloxy)-3,4-dihydroquinolin-2(1H)-one A solution of 5-[(3,5-dimethylbenzyl)oxy]-8-fluoro-1-(4-methoxybenzyl)-7-(tetrahydro-2H-pyran-2-yloxy)-3,4-dihydroquinolin-2(1H)-one (630 mg), potassium carbonate (335 mg) and 10% palladium on carbon (300 mg) in 2-propanol (15 ml) was stirred at room temperature for 1 h under hydrogen atmosphere. The reaction solution was filtrated and to the filtrate were added sodium hydroxide (445 mg), N,N-dimethylformamide (15 mL) and 6-(4-chloro-2-fluorophenyl)-1-oxa-6-azaspiro[2.5]octane (740 mg), then the solution was stirred at 70° C. for 19.5 h. To the reaction solution was added water, and the solution was extracted with ethyl acetate. The organic layer was washed with brine, dried over anhydrous sodium sulfate, and then the solvent was distilled off. The residue was purified by silica gel column chromatography (hexane/ethyl acetate) to provide the title compound (370 mg).
$^1$HNMR (CDCl$_3$) δ ppm: 1.60-1.70 (4H, m), 1.80-2.00 (6H, m), 2.60-2.65 (2H, m), 2.79-2.84 (2H, m), 3.04-3.13 (2H, m), 3.20-3.24 (3H, m), 3.52-3.62 (1H, m), 3.70-3.90 (6H, m), 5.21 (2H, s), 5.33 (1H, s), 6.51 (1H, d, J=6.0 Hz), 6.74-6.79 (2H, m), 6.88-6.95 (1H, m), 7.01-7.07 (2H, m), 7.11-7.15 (2H, m).

Reference Example 493

1-(4-Chloro-2,6-difluorophenyl)-4-{[(8-fluoro-2-methoxyquinolin-5-yl)oxy]methyl}piperidin-4-ol Synthesized analogous to Reference Example 453.
$^1$HNMR (CDCl$_3$) δ ppm: 1.86-1.93 (2H, m), 1.93-2.02 (2H, m), 2.10 (1H, s), 3.07-3.15 (2H, m), 3.47-3.56 (2H, m), 4.00 (2H, s), 4.12 (3H, s), 6.65 (1H, dd, J=8.7 Hz, 3.4 Hz), 6.85-6.93 (2H, m), 6.95 (1H, d, J=9.1 Hz), 7.24 (1H, dd, J=10.6 Hz, 8.7 Hz), 8.37 (1H, dd, J=9.1 Hz, 1.6 Hz).

Reference Example 494

1-(4-Chloro-2-fluorophenyl)-4-{[(8-fluoro-2-methoxyquinolin-5-yl)oxy]methyl}piperidin-4-ol Synthesized analogous to Reference Example 453.
$^1$HNMR (CDCl$_3$) δ ppm: 1.92-1.98 (2H, m), 1.98-2.06 (2H, m), 2.08 (1H, s), 3.11-3.19 (2H, m), 3.23-3.31 (2H, m), 4.00 (2H, s), 4.12 (3H, s), 6.65 (1H, dd, J=8.6 Hz, 3.4 Hz), 6.92-6.98 (2H, m), 7.03-7.09 (2H, m), 7.24 (1H, dd, J=10.5 Hz, 8.6 Hz), 8.37 (1H, dd, J=9.1 Hz, 1.6 Hz).

Reference Example 495 tert-Butyl 4-{[(8-fluoro-2-oxo-1,2,3,4-tetrahydroquinolin-5-yl)oxy]methyl}-3,6-dihydropyridine-1(2H)-carboxylate A solution of 8-fluoro-5-hydroxy-3,4-dihydroquinolin-2(1H)-one (4.66 g), tert-butyl 4-(chloromethyl)-3,6-dihydropyridine-1(2H)-carboxylate (5.95 g) and potassium carbonate (3.55 g) in N-methyl-2-pyrrolidone (100 mL) was stirred at 80° C. for 4 h. To the reaction solution were added water (400 mL) and ethyl acetate (100 mL) and the solution was stirred at room temperature for 20 min. The precipitated crystal was collected on a filter and washed with ethyl acetate to provide the title compound (8.48 g).
$^1$HNMR (DMSO-d6) δ ppm: 1.41 (9H, s), 2.08-2.15 (2H, m), 2.42-2.48 (2H, m), 2.82-2.89 (2H, m), 3.40-3.48 (2H, m), 3.81-3.91 (2H), 4.41-4.47 (2H, m), 5.65-5.82 (1H, m), 6.60 (1H, dd, J=9.1 Hz, 3.8 Hz), 7.00 (1H, t, J=9.2 Hz), 10.01 (1H, brs).

Reference Example 496 tert-Butyl 4-{[(8-chloro-2-oxo-1,2,3,4-tetrahydroquinolin-5-yl)oxy]methyl}-3,6-dihydropyridine-1(2H)-carboxylate To a solution of tert-butyl 4-{[(8-chloro-2-oxo-1,2,3,4-tetrahydroquinolin-5-yl)oxy]methyl}-4-hydroxypiperidine-1-carboxylate (13.7 g) in acetonitrile (180 mL) were added N,N,N',N'-tetramethyl-1,3-diaminopropane (31.8 mL) and methanesulfonyl chloride (7.74 mL), and the solution was stirred at room temperature overnight. The reaction solution was poured into water, and the precipitate was collected on a filter. The residue was purified by silica gel column chromatography (dichloromethane/ethyl acetate) to provide the title compound (10.7 g).
$^1$HNMR (CDCl$_3$) δ ppm: 1.48 (9H, s), 2.14-2.24 (2H, m), 2.59-2.64 (2H, m), 2.97-3.02 (2H, m), 3.52-3.59 (2H, m), 3.92-3.98 (2H), 4.42-4.48 (2H, m), 5.76-5.84 (1H, m), 6.51 (1H, d, J=9.0 Hz), 7.16 (1H, d, J=9.0 Hz), 7.75 (1H, brs).

Reference Example 497 tert-Butyl 4-{[(8-chloro-7-fluoro-2-oxo-1,2,3,4-tetrahydroquinolin-5-yl)oxy]methyl}-3,6-dihydropyridine-1 (2H)-carboxylate Synthesized analogous to Reference Example 495.
$^1$HNMR (CDCl$_3$) δ ppm: 1.48 (9H, s), 2.15-2.22 (2H, m), 2.60-2.63 (2H, m), 2.93-2.97 (2H, m), 3.55-3.57 (2H, m), 3.93-3.99 (2H, m), 4.40 (2H, brs), 5.72-5.84 (1H, m), 6.43 (1H, d, J=10.9 Hz), 7.75 (1H, brs).

Reference Example 498 tert-Butyl 4-{[(7,8-difluoro-2-oxo-1,2,3,4-tetrahydroquinolin-5-yl)oxy]methyl}-3,6-dihydropyridine-1(2H)-carboxylate Synthesized analogous to Reference Example 495.
$^1$HNMR (CDCl$_3$) δ ppm: 1.48 (9H, s), 2.13-2.24 (2H, m), 2.60-2.64 (2H, m), 2.93-2.96 (2H, m), 3.52-3.60 (2H, m), 3.92-3.99 (2H, m), 4.37 (2H, brs), 5.71-5.87 (1H, m), 6.37 (1H, dd, J=12.0 Hz, 6.3 Hz), 7.58 (1H, brs).

Reference Example 499 tert-Butyl (3S*,4S*)-4-{[(8-fluoro-2-oxo-1,2,3,4-tetrahydroquinolin-5-yl)oxy]methyl}-3,4-dihydroxypiperidine-1-carboxylate To a solution of tert-butyl 4-{[(8-fluoro-2-oxo-1,2,3,4-tetrahydroquinolin-5-yl)oxy]methyl}-3,6-dihydropyridine-1(2H)-carboxylate (0.38 g) in acetone (3 mL)-water (1 mL) were added aqueous solution of 4.8 M N-methylmorpholine-N-oxide (0.42 mL) and aqueous solution of 4% osmium tetraoxide (0.01 mL) and the reaction mixture was stirred at room temperature for 6 days. The solvent was distilled off, and the obtained crude crystal was washed with ethyl acetate to provide the title compound (0.36 g).
$^1$HNMR (DMSO-d6) δ ppm: 1.40 (9H, s), 1.54-1.73 (2H, m), 2.44 (2H, t, J=7.6 Hz), 2.74-3.09 (4H, m), 3.46-3.55 (1H, m), 3.62 (1H, d, J=8.8 Hz), 3.66-3.85 (2H, m), 3.98 (1H, d, J=8.8 Hz), 4.58 (1H, brs), 4.92-5.01 (1H, m), 6.54 (1H, dd, J=9.1 Hz, 3.8 Hz), 7.01 (1H, t, J=9.4 Hz), 10.01 (1H, brs).

Reference Example 500 tert-Butyl (3R,4R)-4-{[(8-fluoro-2-oxo-1,2,3,4-tetrahydroquinolin-5-yl)oxy]methyl}-3,4-dihydroxypiperidine-1-carboxylate To a suspension of tert-butyl 4-{[(8-fluoro-2-oxo-1,2,3,4-tetrahydroquinolin-5-yl)oxy]methyl}-3,6-dihydropyridine-1(2H)-carboxylate (0.753 g) and AD-Mix-beta (2.8 g) in acetone (25 mL) was added water (15 mL), and the reaction mixture was stirred at room temperature overnight. To the reaction solution was added aqueous saturated sodium sulfite under ice-cooling, and the solution was stirred for 10 min. Then the solution was extracted with ethyl acetate, the organic layer was washed with brine, dried over anhydrous magnesium sulfate, and the solvent was distilled off. The residue was purified by silica gel column chromatography (dichloromethane/ethyl acetate), and recrystallized from ethanol to provide the title compound (347 mg, over 99% ee).
$^1$HNMR (CDCl$_3$) δ ppm: 1.47 (9H, s), 1.69-1.75 (1H, m), 1.83-1.86 (1H, m), 2.36-2.37 (1H, m), 2.51-2.60 (1H, m), 2.64 (2H, t, J=7.7 Hz), 2.91-3.00 (3H, m), 3.01-3.20 (1H, m), 3.68-4.17 (5H, m), 6.49 (1H, dd, J=9.1 Hz, 3.9 Hz), 6.93 (1H, t, J=9.4 Hz), 7.51 (1H, brs).

Reference Example 501 tert-Butyl (3S,4S)-4-{[(8-fluoro-2-oxo-1,2,3,4-tetrahydroquinolin-5-yl)oxy]methyl}-3,4-dihydroxypiperidine-1-carboxylate A solution of tert-butyl 4-{[(8-fluoro-2-oxo-1,2,3,4-tetrahydroquinolin-5-yl)oxy]methyl}-3,6-dihydropyridine-1(2H)-carboxylate (200 mg) and AD-Mix-alpha (743 mg) in acetone/water=(2:1) (10 mL) was stirred at room temperature overnight, and the reaction solution was treated in a manner analogous to Reference Example 500 to provide the title compound (131 mg, 90% ee).
$^1$HNMR (CDCl$_3$) δ ppm: 1.47 (9H, s), 1.69-1.75 (1H, m), 1.83-1.86 (1H, m), 2.26-2.39 (1H, m), 2.52-2.60 (1H, m), 2.64 (2H, t, J=7.6 Hz), 2.91-3.20 (4H, m), 3.71-4.19 (5H, m), 6.49 (1H, dd, J=9.1 Hz, 3.9 Hz), 6.93 (1H, t, J=9.4 Hz), 7.50 (1H, brs).

Reference Example 502 tert-Butyl (3R,4R)-4-{[(8-chloro-2-oxo-1,2,3,4-tetrahydroquinolin-5-yl)oxy]methyl}-3,4-dihydroxypiperidine-1-carboxylate Synthesized analogous to Reference Example 500.
$^1$HNMR (CDCl$_3$) δ ppm: 1.47 (9H, s), 1.71-1.77 (1H, m), 1.83-1.86 (1H, m), 2.37-2.69 (4H, m), 2.87-3.02 (3H, m), 3.03-3.20 (1H, m), 3.69-4.17 (5H, m), 6.55 (1H, d, J=8.9 Hz), 7.19 (1H, t, J=8.9 Hz), 7.76 (1H, brs).

Reference Example 503 tert-Butyl (3S,4S)-4-{[(8-chloro-2-oxo-1,2,3,4-tetrahydroquinolin-5-yl)oxy]methyl}-3,4-dihydroxypiperidine-1-carboxylate Synthesized analogous to Reference Example 501.
$^1$HNMR (CDCl$_3$) δ ppm: 1.47 (9H, s), 1.71-1.77 (1H, m), 1.83-1.86 (1H, m), 2.36-2.68 (4H, m), 2.86-3.02 (3H, m), 3.03-3.20 (1H, m), 3.67-4.19 (5H, m), 6.55 (1H, d, J=9.0 Hz), 7.18 (1H, t, J=8.9 Hz), 7.74 (1H, brs).

Reference Example 504 tert-Butyl (3R*,4R*)-4-{[(8-chloro-7-fluoro-2-oxo-1,2,3,4-tetrahydroquinolin-5-yl)oxy]methyl}-3,4-dihydroxypiperidine-1-carboxylate To a solution of tert-butyl 4-{[(8-chloro-7-fluoro-2-oxo-1,2,3,4-tetrahydroquinolin-5-yl)oxy]methyl}-3,6-dihydropyridine-1(2H)-carboxylate (250 mg) in tetrahydrofuran/water (3:1) (4 mL) were added Osmium Oxide, Immobilized Catalyst I (content: 7%) (110 mg) and N-methylmorpholine N-oxide (0.254 mL), and the reaction mixture was stirred at room temperature overnight. To the reaction solution was added aqueous saturated sodium sulfite under ice-cooling, insoluble materials were filtered off, and the filtrate was extracted with ethyl acetate. The organic layer was washed with brine, dried over anhydrous magnesium sulfate, and the solvent was distilled off. The residue was purified by silica gel column chromatography (dichloromethane/ethyl acetate) to provide the title compound (249 mg).
$^1$HNMR (CDCl$_3$) δ ppm: 1.47 (9H, s), 1.71-1.77 (1H, m), 1.83-1.85 (1H, m), 2.20-2.57 (2H, m), 2.62 (2H, t, J=7.7 Hz), 2.88-3.01 (3H, m), 3.02-3.19 (1H, m), 3.69-4.17 (5H, m), 6.47 (1H, d, J=10.6 Hz), 7.75 (1H, brs).

Reference Example 505 tert-Butyl (3R,4R)-4-{[(8-chloro-7-fluoro-2-oxo-1,2,3,4-tetrahydroquinolin-5-yl)oxy]methyl}-3,4-dihydroxypiperidine-1-carboxylate Synthesized analogous to Reference Example 500.
$^1$HNMR (CDCl$_3$) δ ppm: 1.47 (9H, s), 1.71-1.77 (1H, m), 1.83-1.85 (1H, m), 2.20-2.57 (2H, m), 2.60-2.63 (2H, m), 2.88-3.01 (3H, m), 3.02-3.19 (1H, m), 3.69-4.17 (5H, m), 6.47 (1H, d, J=10.6 Hz), 7.75 (1H, brs).

Reference Example 506 tert-Butyl (3R,4R)-4-{[(7,8-difluoro-2-oxo-1,2,3,4-tetrahydroquinolin-5-yl)oxy]methyl}-3,4-dihydroxypiperidine-1-carboxylate Synthesized analogous to Reference Example 500.
$^1$HNMR (CDCl$_3$) δ ppm: 1.47 (9H, s), 1.70-1.76 (1H, m), 1.82-1.85 (1H, m), 2.28-2.69 (4H, m), 2.85-3.21 (4H, m), 3.68-4.20 (5H, m), 6.41 (1H, dd, J=11.8 Hz, 6.3 Hz), 7.61 (1H, brs).

Reference Example 507 tert-Butyl (3R*,4R*)-4-{[(7,8-difluoro-2-oxo-1,2,3,4-tetrahydroquinolin-5-yl)oxy]methyl}-3,4-dihydroxypiperidine-1-carboxylate Synthesized analogous to Reference Example 504.
$^1$HNMR (CDCl$_3$) δ ppm: 1.47 (9H, s), 1.70-1.77 (1H, m), 1.82-1.85 (1H, m), 2.28-2.79 (4H, m), 2.83-3.21 (4H, m), 3.68-4.20 (5H, m), 6.41 (1H, dd, J=11.8 Hz, 6.3 Hz), 7.71 (1H, brs).

Reference Example 508

5-{[(3S*,4S*)-3,4-Dihydroxypiperidin-4-yl]methoxy}-8-fluoro-3,4-dihydroquinolin-2(1H)-one hydrochloride Synthesized analogous to Reference Example 456.
$^1$HNMR (DMSO-d6) δ ppm: 1.71-1.80 (1H, m), 1.95-2.07 (1H, m), 2.47 (2H, t, J=8.0 Hz), 2.83-3.16 (6H, m), 3.66 (1H, d, J=8.8 Hz), 3.85-3.95 (1H, m), 4.04 (1H, d, J=8.8 Hz), 5.07 (1H, brs), 5.34-5.44 (1H, m), 6.56 (1H, dd, J=9.1 Hz, 3.8 Hz), 7.02 (1H, t, J=9.5 Hz), 8.63-8.83 (2H, m), 10.04 (1H, brs).

Reference Example 509

5-{[(3R,4R)-3,4-Dihydroxypiperidin-4-yl]methoxy}-8-fluoro-3,4-dihydroquinolin-2(1H)-one hydrochloride Synthesized analogous to Reference Example 456.
$^1$HNMR (DMSO-d6) δ ppm: 1.74-1.77 (1H, m), 1.99-2.05 (1H, m), 2.45-2.48 (2H, m), 2.85-3.12 (6H, m), 3.66 (1H, d, J=8.8 Hz), 3.90-3.93 (1H, m), 4.04 (1H, d, J=8.8 Hz), 4.97-5.22 (1H, m), 5.28-5.51 (1H, m), 6.56 (1H, dd, J=9.1 Hz, 3.7 Hz), 7.03 (1H, t, J=9.7 Hz), 8.73-8.96 (2H, m), 10.06 (1H, brs).

Reference Example 510

5-{[(3R,4R)-3,4-Dihydroxypiperidin-4-yl]methoxy}-8-fluoro-3,4-dihydroquinolin-2(1H)-one Synthesized analogous to Reference Example 60.
$^1$HNMR (DMSO-d6) δ ppm: 1.49-1.55 (1H, m), 1.62-1.72 (1H, m), 1.80-2.10 (1H, broad signal), 2.43-2.49 (2H, m), 2.54-2.62 (2H, m), 2.62-2.75 (2H, m), 2.82-2.95 (2H, m), 3.47-3.54 (1H, m), 3.54 (1H, d, J=8.7 Hz), 3.96 (1H, d, J=8.7 Hz), 4.20 (1H, s), 4.50 (1H, d, J=6.5 Hz), 6.54 (1H, dd, J=9.2 Hz, 3.8 Hz), 7.00 (1H, t, J=9.7 Hz), 10.02 (1H, brs).

Reference Example 511

5-{[(3S,4S)-3,4-Dihydroxypiperidin-4-yl]methoxy}-8-fluoro-3,4-dihydroquinolin-2(1H)-one hydrochloride Synthesized analogous to Reference Example 456.
$^1$HNMR (DMSO-d6) δ ppm: 1.74-1.77 (1H, m), 1.99-2.05 (1H, m), 2.45-2.48 (2H, m), 2.85-3.12 (6H, m), 3.66 (1H, d, J=8.8 Hz), 3.90-3.93 (1H, m), 4.04 (1H, d, J=8.8 Hz), 4.41-5.77 (2H, m), 6.56 (1H, dd, J=9.1 Hz, 3.6 Hz), 7.02 (1H, t, J=9.7 Hz), 8.76-9.00 (2H, m), 10.05 (1H, brs).

Reference Example 512 tert-Butyl 4-({[8-fluoro-1-(4-methoxybenzyl)-2-oxo-1,2,3,4-tetrahydroquinolin-5-yl]oxy}methyl)-3,6-dihydropyridine-1(2H)-carboxylate Synthesized analogous to Reference Example 495.
$^1$HNMR (CDCl$_3$) δ ppm: 1.47 (9H, s), 2.13-2.23 (2H, m), 2.59-2.67 (2H, m), 2.83-2.92 (2H, m), 3.49-3.60 (2H, m), 3.74 (3H, s), 3.89-3.99 (2H, m), 4.32-4.39 (2H, m), 5.22 (2H, brs), 5.70-5.80 (1H, m), 6.49 (1H, dd, J=9.1 Hz, 3.4 Hz), 6.71-6.78 (2H, m), 6.81 (1H, dd, J=12.7 Hz, 9.1 Hz), 7.09-7.16 (2H, m).

Reference Example 513 tert-Butyl (3S*,4S*)-4-({[8-fluoro-1-(4-methoxybenzyl)-2-oxo-1,2,3,4-tetrahydroquinolin-5-yl]oxy}methyl)-3,4-dihydroxypiperidine-1-carboxylate Synthesized analogous to Reference Example 499.
$^1$HNMR (CDCl$_3$) δ ppm: 1.47 (9H, s), 1.64-1.75 (1H, m), 1.78-1.87 (1H, m), 2.26-2.35 (1H, m), 2.48-2.56 (1H, m), 2.61-2.68 (2H, m), 2.76-3.00 (3H, m), 3.01-3.18 (1H, m), 3.74 (3H, s), 3.75-3.83 (1H, m), 3.84-3.98 (3H, m), 3.99-4.16 (1H, m), 5.16-5.30 (2H, m), 6.52 (1H, dd, J=9.1 Hz, 3.4 Hz), 6.72-6.79 (2H, m), 6.84 (1H, dd, J=12.6 Hz, 9.2 Hz), 7.09-7.16 (2H, m).

Reference Example 514 tert-Butyl (3R,4R)-4-({[8-fluoro-1-(4-methoxybenzyl)-2-oxo-1,2,3,4-tetrahydroquinolin-5-yl]oxy}methyl)-3,4-dihydroxypiperidine-1-carboxylate Synthesized analogous to Reference Example 500.
$^1$HNMR (CDCl$_3$) δ ppm: 1.47 (9H, s), 1.67-1.73 (1H, m), 1.81-1.84 (1H, m), 2.38-2.39 (1H, m), 2.51-2.68 (3H, m), 2.78-3.18 (4H, m), 3.71-3.82 (4H, m), 3.85-4.18 (4H, m), 5.18-5.27 (2H, m), 6.53 (1H, dd, J=9.1 Hz, 3.3 Hz), 6.74-6.77 (2H, m), 6.84 (1H, dd, J=12.6 Hz, 9.1 Hz), 7.12 (2H, d, J=8.6 Hz).

Reference Example 515 tert-Butyl (3S,4S)-4-({[8-fluoro-1-(4-methoxybenzyl)-2-oxo-1,2,3,4-tetrahydroquinolin-5-yl]oxy}methyl)-3,4-dihydroxypiperidine-1-carboxylate Synthesized analogous to Reference Example 501.
$^1$HNMR (CDCl$_3$) δ ppm: 1.46 (9H, s), 1.67-1.74 (1H, m), 1.81-1.84 (1H, m), 2.35-2.68 (4H, m), 2.78-3.19 (4H, m), 3.71-4.18 (8H, m), 5.18-5.27 (2H, m), 6.53 (1H, dd, J=9.1 Hz, 3.3 Hz), 6.74-6.77 (2H, m), 6.84 (1H, dd, J=12.7 Hz, 9.1 Hz), 7.12 (2H, d, J=8.6 Hz).

Reference Example 516 tert-Butyl (3R,4R)-4-({[8-chloro-1-(4-methoxybenzyl)-2-oxo-1,2,3,4-tetrahydroquinolin-5-yl]oxy}methyl)-3,4-dihydroxypiperidine-1-carboxylate Synthesized analogous to Reference Example 43.
$^1$HNMR (CDCl$_3$) δ ppm: 1.46 (9H, s), 1.68-1.74 (1H, m), 1.81-1.84 (1H, m), 2.29 (1H, d, J=6.2 Hz), 2.46-2.78 (5H, m), 2.84-3.19 (2H, m), 3.65-4.17 (8H, m), 5.34-5.41 (2H, m), 6.59 (1H, d, J=9.0 Hz), 6.71-6.74 (2H, m), 7.07 (2H, d, J=8.6 Hz), 7.15 (1H, d, J=8.9 Hz).

Reference Example 517 tert-Butyl (3S,4S)-4-({[8-chloro-1-(4-methoxybenzyl)-2-oxo-1,2,3,4-tetrahydroquinolin-5-yl]oxy}methyl)-3,4-dihydroxypiperidine-1-carboxylate Synthesized analogous to Reference Example 43.
$^1$HNMR (CDCl$_3$) δ ppm: 1.46 (9H, s), 1.67-1.74 (1H, m), 1.81-1.84 (1H, m), 2.27 (1H, d, J=6.2 Hz), 2.46-2.78 (5H, m), 2.84-3.19 (2H, m), 3.65-4.17 (8H, m), 5.34-5.41 (2H, m), 6.59 (1H, d, J=9.0 Hz), 6.71-6.74 (2H, m), 7.05-7.08 (2H, m), 7.15 (1H, d, J=8.9 Hz).

Reference Example 518 tert-Butyl (3R,4R)-4-({[8-chloro-7-fluoro-1-(4-methoxybenzyl)-2-oxo-1,2,3,4-tetrahydroquinolin-5-yl]oxy}methyl)-3,4-dihydroxypiperidine-1-carboxylate Synthesized analogous to Reference Example 43.
$^1$HNMR (CDCl$_3$) δ ppm: 1.46 (9H, s), 1.69-1.75 (1H, m), 1.81-1.84 (1H, m), 2.19-2.74 (6H, m), 2.84-3.21 (2H, m), 3.63-4.19 (8H, m), 5.35-5.42 (2H, m), 6.53 (1H, d, J=10.5 Hz), 6.72-6.75 (2H, m), 7.06 (2H, d, J=8.6 Hz).

Reference Example 519 tert-Butyl (3R*,4R*)-4-({[8-chloro-7-fluoro-1-(4-methoxybenzyl)-2-oxo-1,2,3,4-tetrahydroquinolin-5-yl]oxy}methyl)-3,4-dihydroxypiperidine-1-carboxylate Synthesized analogous to Reference Example 43.
$^1$HNMR (CDCl$_3$) δ ppm: 1.46 (9H, s), 1.68-1.75 (1H, m), 1.81-1.83 (1H, m), 2.18-2.24 (1H, m), 2.40-2.73 (5H, m), 2.84-3.21 (2H, m), 3.63-4.19 (8H, m), 5.35-5.42 (2H, m), 6.53 (1H, d, J=10.5 Hz), 6.72-6.75 (2H, m), 7.05-7.07 (2H, m).

Reference Example 520 tert-Butyl (3R,4R)-4-({[7,8-difluoro-1-(4-methoxybenzyl)-2-oxo-1,2,3,4-tetrahydroquinolin-5-yl]oxy}methyl)-3,4-dihydroxypiperidine-1-carboxylate Synthesized analogous to Reference Example 43.
$^1$HNMR (CDCl$_3$) δ ppm: 1.46 (9H, s), 1.68-1.74 (1H, m), 1.80-1.83 (1H, m), 2.21-2.70 (4H, m), 2.73-2.86 (2H, m), 2.86-3.22 (2H, m), 3.63-4.19 (8H, m), 5.19-5.27 (2H, m), 6.46 (1H, dd, J=11.4 Hz, 5.9 Hz), 6.76-6.79 (2H, m), 7.12 (2H, d, J=8.6 Hz).

Reference Example 521 tert-Butyl (3R*,4R*)-4-({[7,8-difluoro-1-(4-methoxybenzyl)-2-oxo-1,2,3,4-tetrahydroquinolin-5-yl]oxy}methyl)-3,4-dihydroxypiperidine-1-carboxylate Synthesized analogous to Reference Example 43.
$^1$HNMR (CDCl$_3$) δ ppm: 1.46 (9H, s), 1.68-1.74 (1H, m), 1.80-1.83 (1H, m), 2.21-2.70 (4H, m), 2.73-2.86 (2H, m), 2.86-3.22 (2H, m), 3.63-4.19 (8H, m), 5.19-5.27 (2H, m), 6.46 (1H, dd, J=11.5 Hz, 5.9 Hz), 6.76-6.79 (2H, m), 7.12 (2H, d, J=8.6 Hz).

Reference Example 522

5-{[(3S*,4S*)-3,4-Dihydroxypiperidin-4-yl]methoxy}-8-fluoro-1-(4-methoxybenzyl)-3,4-dihydroquinolin-2(1H)-one hydrochloride Synthesized analogous to Reference Example 456.
$^1$HNMR (DMSO-d6) δ ppm: 1.70-1.80 (1H, m), 1.95-2.07 (1H, m), 2.56-2.65 (2H, m), 2.81-3.16 (6H, m), 3.65 (1H, d, J=8.8 Hz), 3.68 (3H, s), 3.86-3.95 (1H, m), 4.02 (1H, d, J=8.8 Hz), 5.00-5.20 (3H, m), 5.40 (1H, brs), 6.67 (1H, dd, J=9.2 Hz, 3.4 Hz), 6.77-6.84 (2H, m), 6.99 (1H, dd, J=13.1 Hz, 9.1 Hz), 7.04-7.11 (2H, m), 8.91 (2H, brs).

Reference Example 523

5-{[(3S*,4S*)-3,4-Dihydroxypiperidin-4-yl]methoxy}-8-fluoro-1-(4-methoxybenzyl)-3,4-dihydroquinolin-2(1H)-one Synthesized analogous to Reference Example 457.
$^1$HNMR (CDCl$_3$) δ ppm: 1.66-1.76 (1H, m), 1.78-1.87 (1H, m), 1.96-2.44 (2H, br), 2.59-2.68 (2H, m), 2.75-3.02 (6H, m), 3.73 (3H, s), 3.74-3.80 (1H, m), 3.85-3.93 (2H, m), 5.15-5.30 (2H, m), 6.52 (1H, dd, J=9.1 Hz, 3.4 Hz), 6.72-6.78 (2H, m), 6.83 (1H, dd, J=12.7 Hz, 9.1 Hz), 7.08-7.16 (2H, m).

Reference Example 524

5-{[(3R,4R)-3,4-Dihydroxypiperidin-4-yl]methoxy}-8-fluoro-1-(4-methoxybenzyl)-3,4-dihydroquinolin-2(1H)-one To a solution of tert-butyl (3R,4R)-4-({[8-fluoro-1-(4-methoxybenzyl)-2-oxo-1,2,3,4-tetrahydroquinolin-5-yl]

oxy}methyl)-3,4-dihydroxypiperidine-1-carboxylate (2.89 g) in dichloromethane (10 mL) was added trifluoroacetic acid (10 mL), and the reaction mixture was stirred at room temperature for 3 h. To the reaction solution was added 5 N aqueous sodium hydroxide, and the solution was extracted with ethyl acetate. The organic layer was washed with brine, dried over anhydrous magnesium sulfate, and the solvent was distilled off to provide the title compound (1.84 g).

$^1$HNMR (CDCl$_3$) δ ppm: 1.69-1.78 (1H, m), 1.82-1.86 (1H, m), 2.62-2.65 (2H, m), 2.80-3.02 (6H, m), 3.71-3.95 (6H, m), 5.17-5.26 (2H, m), 6.53 (1H, dd, J=9.1 Hz, 3.2 Hz), 6.74-6.76 (2H, m), 6.83 (1H, dd, J=12.6 Hz, 9.0 Hz), 7.12 (2H, d, J=8.5 Hz).

Reference Example 525

5-{[(3S,4S)-3,4-Dihydroxypiperidin-4-yl]methoxy}-8-fluoro-1-(4-methoxybenzyl)-3,4-dihydroquinolin-2(1H)-one Synthesized analogous to Reference Example 524.

$^1$HNMR (CDCl$_3$) δ ppm: 1.73-1.78 (1H, m), 1.82-1.86 (1H, m), 2.56-2.66 (2H, m), 2.79-3.06 (6H, m), 3.71-3.92 (6H, m), 5.17-5.26 (2H, m), 6.52 (1H, dd, J=9.2 Hz, 3.3 Hz), 6.74-6.76 (2H, m), 6.83 (1H, dd, J=12.7 Hz, 9.1 Hz), 7.11 (2H, d, J=8.5 Hz).

Reference Example 526

5-{[(3S*,4S*)-1-(2,4-Dichlorophenyl)-3,4-dihydroxypiperidin-4-yl]methoxy}-8-fluoro-1-(4-methoxybenzyl)-3,4-dihydroquinolin-2(1H)-one Under argon atmosphere, to a solution of 5-{[(3S*,4S*)-3,4-dihydroxypiperidin-4-yl]methoxy}-8-fluoro-1-(4-methoxybenzyl)-3,4-dihydroquinolin-2(1H)-one hydrochloride (0.37 g), 1-bromo-2,4-dichlorobenzene (0.20 g), triethylamine (0.27 mL) and sodium tert-butoxide (0.18 g) in toluene (3 mL) were added 2,2'-bis(diphenylphosphino)-1,1'-binaphthyl (15 mg) and tris(dibenzylideneacetone)dipalladium (0) (7 mg), and the reaction mixture was stirred while heating at 100° C. overnight. To the reaction solution was added water, and the solution was extracted with ethyl acetate. The organic layer was washed with water and brine, dried over anhydrous sodium sulfate, and then the solvent was distilled off. The residue was purified by silica gel column chromatography (hexane/ethyl acetate) to provide the title compound (40 mg).

$^1$HNMR (CDCl$_3$) δ ppm: 1.94-2.00 (2H, m), 2.44-2.51 (1H, m), 2.61-2.71 (3H, m), 2.80-2.96 (3H, m), 2.97-3.14 (2H, m), 3.24-3.33 (1H, m), 3.74 (3H, s), 3.94 (1H, d, J=9.2 Hz), 4.00-4.08 (2H, m), 5.15-5.34 (2H, m), 6.56 (1H, dd, J=9.2 Hz, 3.4 Hz), 6.67-6.80 (2H, m), 6.85 (1H, dd, J=12.6 Hz, 9.1 Hz), 7.00 (1H, d, J=8.6 Hz), 7.09-7.16 (2H, m), 7.20 (1H, dd, J=8.6 Hz, 2.4 Hz), 7.38 (1H, d, J=2.4 Hz).

Reference Example 527

5-{[(3S*,4S*)-1-(4-Chloro-2-fluorophenyl)-3,4-dihydroxypiperidin-4-yl]methoxy}-8-fluoro-1-(4-methoxybenzyl)-3,4-dihydroquinolin-2(1H)-one Synthesized analogous to Reference Example 70.

$^1$HNMR (CDCl$_3$) δ ppm: 1.93-2.00 (2H, m), 2.42-2.50 (1H, m), 2.58-2.70 (3H, m), 2.79-2.97 (3H, m), 3.00-3.10 (1H, m), 3.12-3.22 (1H, m), 3.30-3.39 (1H, m), 3.74 (3H, s), 3.94 (1H, d, J=9.1 Hz), 3.97-4.07 (2H, m), 5.14-5.32 (2H, m), 6.56 (1H, dd, J=9.1 Hz, 3.3 Hz), 6.73-6.79 (2H, m), 6.81-6.95 (2H, m), 7.02-7.09 (2H, m), 7.10-7.16 (2H, m).

Reference Example 528

2-[(3R,4R)-4-({[8-Fluoro-1-(4-methoxybenzyl)-2-oxo-1,2,3,4-tetrahydroquinolin-5-yl]oxy}methyl)-3,4-dihydroxypiperidin-1-yl]-5-iodopyridine-3-carbonitrile A solution of 2-chloro-5-iodopyridine-3-carbonitrile (0.675 g), 5-{[(3R,4R)-3,4-dihydroxypiperidin-4-yl]methoxy}-8-fluoro-1-(4-methoxybenzyl)-3,4-dihydroquinolin-2(1H)-one (1 g) and potassium carbonate (0.642 g) in N-methyl-2-pyrrolidone (20 mL) was stirred at 100° C. overnight. The reaction solution was poured into water, and the reaction mixture was extracted with ethyl acetate. The organic layer was washed with water and brine, dried over anhydrous magnesium sulfate, and the solvent was distilled off. The residue was purified by silica gel column chromatography (hexane/ethyl acetate) to provide the title compound (678 mg).

$^1$HNMR (CDCl$_3$) δ ppm: 1.85-1.92 (1H, m), 1.96-2.00 (1H, m), 2.62-2.65 (2H, m), 2.77-2.87 (2H, m), 2.89-3.04 (2H, m), 3.26-3.30 (1H, m), 3.43-3.48 (1H, m), 3.74 (3H, s), 3.90-4.00 (3H, m), 4.15-4.20 (1H, m), 4.25-4.29 (1H, m), 5.18-5.27 (2H, m), 6.53 (1H, dd, J=9.1 Hz, 3.3 Hz), 6.74-6.77 (2H, m), 6.84 (1H, dd, J=12.7 Hz, 9.1 Hz), 7.12 (2H, d, J=8.5 Hz), 7.98 (1H, d, J=2.4 Hz), 8.46 (1H, d, J=2.3 Hz).

Reference Example 529

2-[(3S,4S)-4-({[8-Fluoro-1-(4-methoxybenzyl)-2-oxo-1,2,3,4-tetrahydroquinolin-5-yl]oxy}methyl)-3,4-dihydroxypiperidin-1-yl]-5-iodopyridine-3-carbonitrile Synthesized analogous to Reference Example 528.

$^1$HNMR (CDCl$_3$) δ ppm: 1.85-1.91 (1H, m), 1.95-1.99 (1H, m), 2.62-2.65 (2H, m), 2.77-2.87 (2H, m), 2.89-3.04 (2H, m), 3.26-3.30 (1H, m), 3.42-3.48 (1H, m), 3.74 (3H, s), 3.90-4.00 (3H, m), 4.15-4.20 (1H, m), 4.25-4.29 (1H, m), 5.18-5.27 (2H, m), 6.53 (1H, dd, J=9.1 Hz, 3.3 Hz), 6.74-6.77 (2H, m), 6.84 (1H, dd, J=12.6 Hz, 9.1 Hz), 7.12 (2H, d, J=8.5 Hz), 7.98 (1H, d, J=2.3 Hz), 8.46 (1H, d, J=2.3 Hz).

Reference Example 530 tert-Butyl (3S*,4S*)-3-{[tert-butyl(dimethyl)silyl]oxy}-4-({[8-fluoro-1-(4-methoxybenzyl)-2-oxo-1,2,3,4-tetrahydroquinolin-5-yl]oxy}methyl)-4-hydroxypiperidine-1-carboxylate To a solution of tert-butyl (3S*,4S*)-4-({[8-fluoro-1-(4-methoxybenzyl)-2-oxo-1,2,3,4-tetrahydroquinolin-5-yl]oxy}methyl)-3,4-dihydroxypiperidine-1-carboxylate (5.31 g) in N,N-dimethylformamide (10 mL) were added imidazole (2.72 g) and tert-butyl dimethylchlorosilane (3.01 g) at 0° C., and the reaction mixture was stirred at room temperature overnight. To the reaction solution was added water, and the solution was extracted with ethyl acetate. The organic layer was washed with water, 2 M citric acid solution and brine, dried over anhydrous sodium sulfate, and then the solvent was distilled off. The residue was purified by silica gel column chromatography (hexane/ethyl acetate) to provide the title compound (5.5 g).

¹HNMR (CDCl₃) δ ppm: −0.15 (3H, s), 0.08 (3H, s), 0.83 (9H, s), 1.48 (9H, s), 1.67-1.75 (1H, m), 1.82-1.99 (1H, m), 2.42-2.68 (3H, m), 2.70-3.18 (4H, m), 3.55 (1H, d, J=8.6 Hz), 3.73 (3H, s), 3.77-4.15 (4H, m), 5.14-5.32 (2H, m), 6.45 (1H, dd, J=9.2 Hz, 3.3 Hz), 6.71-6.78 (2H, m), 6.82 (1H, dd, J=12.7 Hz, 9.0 Hz), 7.08-7.15 (2H, m).

Reference Example 531 tert-Butyl (3R,4R)-3-{[tert-butyl(dimethyl)silyl]oxy}-4-({[8-fluoro-1-(4-methoxybenzyl)-2-oxo-1,2,3,4-tetrahydroquinolin-5-yl]oxy}methyl)-4-hydroxypiperidine-1-carboxylate Synthesized analogous to Reference Example 530.
¹HNMR (CDCl₃) δ ppm: −0.14 (3H, s), 0.08 (3H, s), 0.83 (9H, s), 1.48 (9H, s), 1.67-1.76 (1H, m), 1.82-2.00 (1H, m), 2.42-2.68 (3H, m), 2.70-3.18 (4H, m), 3.55 (1H, d, J=8.5 Hz), 3.73 (3H, s), 3.78-4.16 (4H, m), 5.16-5.29 (2H, m), 6.45 (1H, dd, J=9.2 Hz, 3.3 Hz), 6.71-6.78 (2H, m), 6.82 (1H, dd, J=12.6 Hz, 9.0 Hz), 7.07-7.15 (2H, m).

Reference Example 532 tert-Butyl (3S,4S)-3-{[tert-butyl(dimethyl)silyl]oxy}-4-({[8-fluoro-1-(4-methoxybenzyl)-2-oxo-1,2,3,4-tetrahydroquinolin-5-yl]oxy}methyl)-4-hydroxypiperidine-1-carboxylate Synthesized analogous to Reference Example 530.
¹HNMR (CDCl₃) δ ppm: −0.14 (3H, s), 0.08 (3H, s), 0.83 (9H, s), 1.48 (9H, s), 1.67-1.76 (1H, m), 1.81-1.99 (1H, m), 2.42-2.69 (3H, m), 2.70-3.18 (4H, m), 3.55 (1H, d, J=8.5 Hz), 3.73 (3H, s), 3.77-4.16 (4H, m), 5.14-5.31 (2H, m), 6.45 (1H, dd, J=9.2 Hz, 3.3 Hz), 6.71-6.78 (2H, m), 6.82 (1H, dd, J=12.6 Hz, 9.0 Hz), 7.07-7.16 (2H, m).

Reference Example 533 tert-Butyl (3R,4R)-3-{[tert-butyl(dimethyl)silyl]oxy}-4-({[8-chloro-1-(4-methoxybenzyl)-2-oxo-1,2,3,4-tetrahydroquinolin-5-yl]oxy}methyl)-4-hydroxypiperidine-1-carboxylate Synthesized analogous to Reference Example 530.
¹HNMR (CDCl₃) δ ppm: −0.18 (3H, s), 0.07 (3H, brs), 0.83 (9H, s), 1.47 (9H, s), 1.69-1.72 (1H, m), 1.80-1.98 (1H, m), 2.42-3.15 (7H, m), 3.56 (1H, d, J=8.5 Hz), 3.72 (3H, s), 3.77-4.17 (4H, m), 5.32 (1H, d, J=15.3 Hz), 5.43 (1H, d, J=15.2 Hz), 6.52 (1H, d, J=9.0 Hz), 6.68-6.71 (2H, m), 7.05 (2H, d, J=8.6 Hz), 7.14 (1H, d, J=8.9 Hz).

Reference Example 534 tert-Butyl (3S,4S)-3-{[tert-butyl(dimethyl)silyl]oxy}-4-({[8-chloro-1-(4-methoxybenzyl)-2-oxo-1,2,3,4-tetrahydroquinolin-5-yl]oxy}methyl)-4-hydroxypiperidine-1-carboxylate Synthesized analogous to Reference Example 530.
¹HNMR (CDCl₃) δ ppm: −0.18 (3H, s), 0.07 (3H, brs), 0.83 (9H, s), 1.47 (9H, s), 1.69-1.72 (1H, m), 1.80-1.98 (1H, m), 2.42-3.15 (7H, m), 3.56 (1H, d, J=8.5 Hz), 3.72 (3H, s), 3.77-4.17 (4H, m), 5.32 (1H, d, J=14.7 Hz), 5.43 (1H, d, J=15.2 Hz), 6.52 (1H, d, J=9.0 Hz), 6.68-6.71 (2H, m), 7.05 (2H, d, J=8.7 Hz), 7.14 (1H, d, J=8.9 Hz).

Reference Example 535 tert-Butyl (3R,4R)-3-{[tert-butyl(dimethyl)silyl]oxy}-4-({[8-chloro-7-fluoro-1-(4-methoxybenzyl)-2-oxo-1,2,3,4-tetrahydroquinolin-5-yl]oxy}methyl)-4-hydroxypiperidine-1-carboxylate Synthesized analogous to Reference Example 530.
¹HNMR (CDCl₃) δ ppm: −0.17 (3H, s), 0.07 (3H, brs), 0.84 (9H, s), 1.47 (9H, s), 1.70-1.73 (1H, m), 1.78-1.97 (1H, m), 2.42-3.18 (7H, m), 3.54 (1H, d, J=8.5 Hz), 3.73 (3H, s), 3.76-4.16 (4H, m), 5.32 (1H, d, J=15.1 Hz), 5.44 (1H, d, J=15.2 Hz), 6.45 (1H, d, J=10.5 Hz), 6.71 (2H, d, J=8.6 Hz), 7.04 (2H, d, J=8.6 Hz).

Reference Example 536 tert-Butyl (3R*,4R*)-3-{[tert-butyl(dimethyl)silyl]oxy}-4-({[8-chloro-7-fluoro-1-(4-methoxybenzyl)-2-oxo-1,2,3,4-tetrahydroquinolin-5-yl]oxy}methyl)-4-hydroxypiperidine-1-carboxylate Synthesized analogous to Reference Example 530.
¹HNMR (CDCl₃) δ ppm: −0.17 (3H, s), 0.07 (3H, brs), 0.84 (9H, s), 1.47 (9H, s), 1.70-1.73 (1H, m), 1.77-1.95 (1H, m), 2.42-3.18 (7H, m), 3.54 (1H, d, J=8.4 Hz), 3.73 (3H, s), 3.76-4.16 (4H, m), 5.32 (1H, d, J=15.8 Hz), 5.44 (1H, d, J=15.1 Hz), 6.45 (1H, d, J=10.4 Hz), 6.71 (2H, d, J=8.7 Hz), 7.04 (2H, d, J=8.6 Hz).

Reference Example 537 tert-Butyl (3R,4R)-3-{[tert-butyl(dimethyl)silyl]oxy}-4-({[7,8-difluoro-1-(4-methoxybenzyl)-2-oxo-1,2,3,4-tetrahydroquinolin-5-yl]oxy}methyl)-4-hydroxypiperidine-1-carboxylate Synthesized analogous to Reference Example 530.
¹HNMR (CDCl₃) δ ppm: −0.13 (3H, s), 0.09 (3H, brs), 0.84 (9H, s), 1.48 (9H, s), 1.70-1.73 (1H, m), 1.77-1.97 (1H, m), 2.38-3.20 (7H, m), 3.51 (1H, d, J=8.4 Hz), 3.71-4.16 (7H, m), 5.23 (2H, brs), 6.38 (1H, dd, J=11.5 Hz, 5.8 Hz), 6.74-6.77 (2H, m), 7.11 (2H, d, J=8.6 Hz).

Reference Example 538 tert-Butyl (3R,4R)-3-{[tert-butyl(dimethyl)silyl]oxy}-4-({[7,8-difluoro-1-(4-methoxybenzyl)-2-oxo-1,2,3,4-tetrahydroquinolin-5-yl]oxy}methyl)-4-hydroxypiperidine-1-carboxylate Synthesized analogous to Reference Example 530.
¹HNMR (CDCl₃) δ ppm: −0.13 (3H, s), 0.09 (3H, brs), 0.84 (9H, s), 1.48 (9H, s), 1.70-1.73 (1H, m), 1.77-1.97 (1H, m), 2.41-3.18 (7H, m), 3.51 (1H, d, J=8.4 Hz), 3.71-4.16 (7H, m), 5.23 (2H, brs), 6.38 (1H, dd, J=11.5 Hz, 5.9 Hz), 6.74-6.77 (2H, m), 7.11 (2H, d, J=8.6 Hz).

Reference Example 539

5-({(3R*,4R*)-3-{[tert-Butyl(dimethyl) silyl]oxy}-4-[(trimethylsilyl)oxy]piperidin-4-yl}methoxy)-8-fluoro-1-(4-methoxybenzyl)-3,4-dihydroquinolin-2(1H)-one To a solution of tert-butyl (3S*,4S*)-3-{[tert-butyl(dimethyl)silyl]oxy}-4-({[8-fluoro-1-(4-methoxybenzyl)-2-oxo- 1,2,3,4-tetrahydroquinolin-5-yl]oxy}methyl)-4-hydroxypiperidine-1-carboxylate (1.82 g) and 2,6-lutidine (1.31 mL) in dichloromethane (1 mL), trimethylsilyl trifluoromethanesulfonate (2.04 mL) was added dropwise under cooling with water-bath, and the reaction mixture was stirred at room temperature for 4 h. To the reaction solution was added saturated aqueous sodium hydrogencarbonate, and the solution was extracted with dichloromethane. The organic layer was washed with brine, dried over anhydrous sodium sulfate, and then the solvent was distilled off to provide the title compound. The compound was used for the next step without further purification.

$^1$HNMR (CDCl$_3$) δ ppm: −0.12 (3H, s), 0.03 (3H, s), 0.14 (9H, s), 0.83 (9H, s), 1.68-1.88 (2H, m), 2.58-2.66 (2H, m), 2.77-3.04 (6H, m), 3.70 (1H, d, J=8.2 Hz), 3.73 (3H, s), 3.77-3.83 (1H, m), 3.97 (1H, d, J=8.2 Hz), 5.16-5.30 (2H, m), 6.40 (1H, d, J=9.0 Hz, 3.2 Hz), 6.71-6.78 (2H, m), 6.83 (1H, dd, J=12.6 Hz, 9.0 Hz), 7.08-7.15 (2H, m).

Reference Example 540

5-({(3R,4R)-3-{[tert-Butyl(dimethyl)silyl]oxy}-4-[(trimethylsilyl)oxy]piperidin-4-yl}methoxy)-8-fluoro-1-(4-methoxybenzyl)-3,4-dihydroquinolin-2 (1H)-one Synthesized analogous to Reference Example 539.

$^1$HNMR (CDCl$_3$) δ ppm: −0.12 (3H, s), 0.02 (3H, s), 0.13 (9H, s), 0.83 (9H, s), 1.68-1.88 (2H, m), 2.58-2.66 (2H, m), 2.77-3.02 (6H, m), 3.69 (1H, d, J=8.2 Hz), 3.73 (3H, s), 3.74-3.80 (1H, m), 3.97 (1H, d, J=8.2 Hz), 5.16-5.29 (2H, m), 6.41 (1H, d, J=9.0 Hz, 3.2 Hz), 6.71-6.78 (2H, m), 6.83 (1H, dd, J=12.6 Hz, 9.0 Hz), 7.08-7.15 (2H, m).

Reference Example 541

5-({(3S,4S)-3-{[tert-Butyl(dimethyl)silyl]oxy}-4-[(trimethylsilyl)oxy]piperidin-4-yl}methoxy)-8-fluoro-1-(4-methoxybenzyl)-3,4-dihydroquinolin-2 (1H)-one Synthesized analogous to Reference Example 539.

$^1$HNMR (CDCl$_3$) δ ppm: −0.12 (3H, s), 0.02 (3H, s), 0.13 (9H, s), 0.82 (9H, s), 1.68-1.86 (2H, m), 2.59-2.66 (2H, m), 2.76-3.01 (6H, m), 3.69 (1H, d, J=8.2 Hz), 3.73 (3H, s), 3.74-3.80 (1H, m), 3.97 (1H, d, J=8.2 Hz), 5.16-5.29 (2H, m), 6.41 (1H, d, J=9.0 Hz, 3.2 Hz), 6.71-6.78 (2H, m), 6.83 (1H, dd, J=12.6 Hz, 9.0 Hz), 7.08-7.16 (2H, m).

Reference Example 542

5-({(3R,4R)-3-{[tert-Butyl(dimethyl)silyl]oxy}-4-[(trimethylsilyl)oxy]piperidin-4-yl}methoxy)-8-chloro-1-(4-methoxybenzyl)-3,4-dihydroquinolin-2 (1H)-one Synthesized analogous to Reference Example 539.

$^1$HNMR (CDCl$_3$) δ ppm: −0.14 (3H, s), 0.00 (3H, s), 0.12 (9H, s), 0.83 (9H, s), 1.69-1.78 (2H, m), 2.54 (2H, t, J=6.7 Hz), 2.69-2.97 (6H, m), 3.69-3.71 (5H, m), 3.98 (1H, d, J=8.2 Hz), 5.34 (1H, d, J=15.3 Hz), 5.41 (1H, d, J=15.2 Hz), 6.48 (1H, d, J=8.9 Hz), 6.68-6.71 (2H, m), 7.04-7.07 (2H, m), 7.15 (1H, d, J=8.9 Hz).

Reference Example 543

5-({(3S,4S)-3-{[tert-Butyl(dimethyl)silyl]oxy}-4-[(trimethylsilyl)oxy]piperidin-4-yl}methoxy)-8-chloro-1-(4-methoxybenzyl)-3,4-dihydroquinolin-2 (1H)-one Synthesized analogous to Reference Example 539.

$^1$HNMR (CDCl$_3$) δ ppm: −0.14 (3H, s), 0.02 (3H, s), 0.13 (9H, s), 0.83 (9H, s), 1.75-1.78 (1H, m), 1.86-1.94 (1H, m), 2.52-2.55 (2H, m), 2.67-3.04 (6H, m), 3.54-3.56 (1H, m), 3.72 (3H, s), 3.83-3.85 (1H, m), 3.90-3.99 (2H, m), 5.34-5.41 (2H, m), 6.46 (1H, d, J=9.0 Hz), 6.68-6.70 (2H, m), 7.04-7.07 (2H, m), 7.13-7.15 (1H, m).

Reference Example 544

5-({(3R,4R)-3-{[tert-Butyl(dimethyl)silyl]oxy}-4-[(trimethylsilyl)oxy]piperidin-4-yl}methoxy)-8-chloro-7-fluoro-1-(4-methoxybenzyl)-3,4-dihydroquinolin-2(1H)-one Synthesized analogous to Reference Example 539.

$^1$HNMR (CDCl$_3$) δ ppm: −0.13 (3H, s), 0.03 (3H, s), 0.15 (9H, s), 0.84 (9H, s), 1.77-1.80 (1H, m), 1.92-1.98 (1H, m), 2.52-2.56 (2H, m), 2.65-2.78 (2H, m), 2.97-3.09 (4H, m), 3.15-3.56 (1H, m), 3.69-3.72 (4H, m), 3.87-3.90 (1H, m), 3.97 (1H, d, J=8.1 Hz), 5.35 (1H, d, J=15.1 Hz), 5.42 (1H, d, J=15.1 Hz), 6.37 (1H, d, J=10.4 Hz), 6.70 (2H, d, J=8.6 Hz), 7.04 (2H, d, J=8.6 Hz).

Reference Example 545

5-({(3R*,4R*)-3-{[tert-Butyl(dimethyl) silyl]oxy}-4-[(trimethylsilyl)oxy]piperidin-4-yl}methoxy)-8-chloro-7-fluoro-1-(4-methoxybenzyl)-3,4-dihydroquinolin-2(1H)-one Synthesized analogous to Reference Example 539.

$^1$HNMR (CDCl$_3$) δ ppm: −0.13 (3H, s), 0.01 (3H, s), 0.13 (9H, s), 0.84 (9H, s), 1.67-1.77 (1H, m), 2.52-2.55 (2H, m), 2.64-2.81 (4H, m), 2.86-2.96 (2H, m), 3.66-3.72 (5H, m), 3.95 (1H, d, J=8.1 Hz), 5.34 (1H, d, J=15.2 Hz), 5.42 (1H, d, J=15.2 Hz), 6.40 (1H, d, J=10.6 Hz), 6.69-6.72 (2H, m), 7.03-7.06 (2H, m).

Reference Example 546

5-({(3R,4R)-3-{[tert-Butyl(dimethyl)silyl]oxy}-4-[(trimethylsilyl)oxy]piperidin-4-yl}methoxy)-7,8-difluoro-1-(4-methoxybenzyl)-3,4-dihydroquinolin-2 (1H)-one Synthesized analogous to Reference Example 539.

$^1$HNMR (CDCl$_3$) δ ppm: −0.11 (3H, s), 0.06 (3H, s), 0.17 (9H, s), 0.84 (9H, s), 1.83-1.86 (1H, m), 2.08-2.15 (2H, m), 2.58-2.68 (2H, m), 2.82-2.84 (2H, m), 3.05-3.25 (4H, m), 3.69 (1H, d, J=8.1 Hz), 3.75 (3H, s), 3.97 (1H, d, J=8.1 Hz), 4.04 (1H, dd, J=10.7 Hz, 4.8 Hz), 5.23 (2H, s), 6.29 (1H, dd, J=11.4 Hz, 5.8 Hz), 6.74-6.77 (2H, m), 7.11 (2H, d, J=8.6 Hz).

Reference Example 547

5-({(3R*,4R*)-3-{[tert-Butyl(dimethyl) silyl]oxy}-4-[(trimethylsilyl)oxy]piperidin-4-yl}methoxy)-7,8-difluoro-1-(4-methoxybenzyl)-3,4-dihydroquinolin-2(1H)-one Synthesized analogous to Reference Example 539.
$^1$HNMR (CDCl$_3$) δ ppm: −0.11 (3H, s), 0.03 (3H, s), 0.14 (9H, s), 0.83 (9H, s), 1.81-1.87 (2H, m), 2.58-2.67 (2H, m), 2.82-3.02 (6H, m), 3.65 (1H, d, J=8.0 Hz), 3.74 (3H, s), 3.77-3.80 (1H, m), 3.94 (1H, d, J=8.0 Hz), 5.23 (2H, s), 6.32 (1H, dd, J=11.6 Hz, 5.7 Hz), 6.75-6.77 (2H, m), 7.11 (2H, d, J=8.6 Hz).

Reference Example 548

5-{[(3R*,4R*)-3-{[tert-Butyl(dimethyl)silyl]oxy}-4-hydroxypiperidin-4-yl]methoxy}-8-fluoro-1-(4-methoxybenzyl)-3,4-dihydroquinolin-2(1H)-one A solution of 5-({(3R*,4R*)-3-{[tert-butyl(dimethyl)silyl]oxy}-4-[(trimethylsilyl)oxy]piperidin-4-yl}methoxy)-8-fluoro-1-(4-methoxybenzyl)-3,4-dihydroquinolin-2(1H)-one (1.74 g) and potassium carbonate (1.95 g) in methanol (45 mL) was stirred at 50° C. for 18 h. To the reaction solution was added water and the solution was extracted with ethyl acetate. The organic layer was washed with water and brine, dried over anhydrous sodium sulfate, and then the solvent was distilled off. The residue was purified by silica gel column chromatography (hexane/ethyl acetate) to provide the title compound (1.17 g).
$^1$HNMR (CDCl$_3$) δ ppm: −0.16 (3H, s), 0.03 (3H, s), 0.82 (9H, s), 1.71-1.79 (1H, m), 1.84-1.95 (1H, m), 2.46-2.70 (3H, m), 2.74-3.02 (6H, m), 3.54 (1H, d, J=8.5 Hz), 3.73 (3H, s), 3.82 (1H, d, J=8.5 Hz), 3.87-3.94 (1H, m), 5.22 (2H, brs), 6.47 (1H, d, J=9.0 Hz, 3.3 Hz), 6.71-6.78 (2H, m), 6.82 (1H, dd, J=12.7 Hz, 9.1 Hz), 7.08-7.15 (2H, m).

Reference Example 549

5-{[(3R,4R)-3-{[tert-Butyl(dimethyl)silyl]oxy}-4-hydroxypiperidin-4-yl]methoxy}-8-fluoro-1-(4-methoxybenzyl)-3,4-dihydroquinolin-2(1H)-one Synthesized analogous to Reference Example 548.
$^1$HNMR (CDCl$_3$) δ ppm: −0.16 (3H, s), 0.03 (3H, s), 0.82 (9H, s), 1.71-1.79 (1H, m), 1.84-1.95 (1H, m), 2.44-2.70 (3H, m), 2.74-3.02 (6H, m), 3.54 (1H, d, J=8.5 Hz), 3.73 (3H, s), 3.83 (1H, d, J=8.5 Hz), 3.87-3.95 (1H, m), 5.22 (2H, brs), 6.47 (1H, d, J=9.1 Hz, 3.3 Hz), 6.71-6.78 (2H, m), 6.82 (1H, dd, J=12.7 Hz, 9.1 Hz), 7.08-7.15 (2H, m).

Reference Example 550

5-{[(3S,4S)-3-{[tert-Butyl(dimethyl)silyl]oxy}-4-hydroxypiperidin-4-yl]methoxy}-8-fluoro-1-(4-methoxybenzyl)-3,4-dihydroquinolin-2(1H)-one Synthesized analogous to Reference Example 548.
$^1$HNMR (CDCl$_3$) δ ppm: −0.16 (3H, s), 0.03 (3H, s), 0.82 (9H, s), 1.71-1.79 (1H, m), 1.85-1.95 (1H, m), 2.42-2.70 (3H, m), 2.74-3.02 (6H, m), 3.54 (1H, d, J=8.5 Hz), 3.73 (3H, s), 3.83 (1H, d, J=8.5 Hz), 3.88-3.95 (1H, m), 5.22 (2H, brs), 6.47 (1H, d, J=9.1 Hz, 3.3 Hz), 6.72-6.79 (2H, m), 6.82 (1H, dd, J=12.7 Hz, 9.1 Hz), 7.08-7.16 (2H, m).

Reference Example 551

5-{[(3R,4R)-3-{[tert-Butyl(dimethyl)silyl]oxy}-4-hydroxypiperidin-4-yl]methoxy}-8-chloro-1-(4-methoxybenzyl)-3,4-dihydroquinolin-2(1H)-one Synthesized analogous to Reference Example 548.
$^1$HNMR (CDCl$_3$) δ ppm: −0.19 (3H, s), 0.02 (3H, s), 0.82 (9H, s), 1.73-1.76 (1H, m), 1.85-1.90 (1H, m), 2.52-2.55 (3H, m), 2.63-2.85 (4H, m), 2.91-2.98 (2H, m), 3.55 (1H, d, J=8.5 Hz), 3.72 (3H, s), 3.84 (1H, d, J=8.5 Hz), 3.88 (1H, dd, J=10.3 Hz, 5.2 Hz), 5.33 (1H, d, J=15.1 Hz), 5.43 (1H, d, J=15.1 Hz), 6.54 (1H, d, J=8.9 Hz), 6.68-6.71 (2H, m), 7.06 (2H, d, J=8.6 Hz), 7.14 (1H, d, J=8.9 Hz).

Reference Example 552

5-{[(3S,4S)-3-{[tert-Butyl(dimethyl)silyl]oxy}-4-hydroxypiperidin-4-yl]methoxy}-8-chloro-1-(4-methoxybenzyl)-3,4-dihydroquinolin-2(1H)-one Synthesized analogous to Reference Example 548.
$^1$HNMR (CDCl$_3$) δ ppm: −0.19 (3H, s), 0.02 (3H, s), 0.82 (9H, s), 1.72-1.76 (1H, m), 1.85-1.92 (1H, m), 2.52-2.55 (3H, m), 2.63-2.85 (4H, m), 2.91-2.98 (2H, m), 3.55 (1H, d, J=8.5 Hz), 3.72 (3H, s), 3.84 (1H, d, J=8.5 Hz), 3.88 (1H, dd, J=10.3 Hz, 5.3 Hz), 5.33 (1H, d, J=15.1 Hz), 5.43 (1H, d, J=15.1 Hz), 6.54 (1H, d, J=9.0 Hz), 6.68-6.71 (2H, m), 7.04-7.07 (2H, m), 7.14 (1H, d, J=8.9 Hz).

Reference Example 553

5-{[(3R,4R)-3-{[tert-Butyl(dimethyl)silyl]oxy}-4-hydroxypiperidin-4-yl]methoxy}-8-chloro-7-fluoro-1-(4-methoxybenzyl)-3,4-dihydroquinolin-2(1H)-one Synthesized analogous to Reference Example 548.
$^1$HNMR (CDCl$_3$) δ ppm: −0.18 (3H, s), 0.03 (3H, s), 0.83 (9H, s), 1.74-1.77 (1H, m), 1.83-1.89 (1H, m), 2.53-2.55 (3H, m), 2.63-2.69 (1H, m), 2.76-2.82 (3H, m), 2.92-2.98 (2H, m), 3.53 (1H, d, J=8.4 Hz), 3.72 (3H, s), 3.81 (1H, d, J=8.4 Hz), 3.87 (1H, dd, J=10.3 Hz, 5.2 Hz), 5.33 (1H, d, J=15.2 Hz), 5.44 (1H, d, J=15.2 Hz), 6.47 (1H, d, J=10.6 Hz), 6.69-6.72 (2H, m), 7.03-7.06 (2H, m).

Reference Example 554

5-{[(3R*,4R*)-3-{[tert-Butyl(dimethyl)silyl]oxy}-4-hydroxypiperidin-4-yl]methoxy}-8-chloro-7-fluoro-1-(4-methoxybenzyl)-3,4-dihydroquinolin-2(1H)-one Synthesized analogous to Reference Example 548.
$^1$HNMR (CDCl$_3$) δ ppm: −0.18 (3H, s), 0.03 (3H, s), 0.83 (9H, s), 1.74-1.77 (1H, m), 1.83-1.89 (1H, m), 2.52-2.55 (3H, m), 2.63-2.69 (1H, m), 2.76-2.82 (3H, m), 2.92-2.98 (2H, m), 3.53 (1H, d, J=8.4 Hz), 3.72 (3H, s), 3.80 (1H, d, J=8.4 Hz), 3.86 (1H, dd, J=10.3 Hz, 5.2 Hz), 5.33 (1H, d, J=15.3 Hz), 5.44 (1H, d, J=15.4 Hz), 6.47 (1H, d, J=10.6 Hz), 6.69-6.72 (2H, m), 7.03-7.06 (2H, m).

Reference Example 555

5-{[(3R,4R)-3-{[tert-Butyl(dimethyl)silyl]oxy}-4-hydroxypiperidin-4-yl]methoxy}-7,8-difluoro-1-(4-methoxybenzyl)-3,4-dihydroquinolin-2(1H)-one Synthesized analogous to Reference Example 548.

$^1$HNMR (CDCl$_3$) δ ppm: −0.15 (3H, s), 0.04 (3H, s), 0.83 (9H, s), 1.73-1.76 (1H, m), 1.83-1.89 (1H, m), 2.53-2.67 (3H, m), 2.76-2.98 (6H, m), 3.50 (1H, d, J=8.4 Hz), 3.74 (3H, s), 3.78 (1H, d, J=8.5 Hz), 3.88 (1H, dd, J=10.3 Hz, 5.3 Hz), 5.23 (2H, s), 6.40 (1H, dd, J=11.6 Hz, 5.9 Hz), 6.74-6.77 (2H, m), 7.11 (2H, d, J=8.6 Hz).

Reference Example 556

5-{[(3R*,4R*)-3-{[tert-Butyl(dimethyl)silyl]oxy}-4-hydroxypiperidin-4-yl]methoxy}-7,8-difluoro-1-(4-methoxybenzyl)-3,4-dihydroquinolin-2(1H)-one Synthesized analogous to Reference Example 548.

$^1$HNMR (CDCl$_3$) δ ppm: −0.15 (3H, s), 0.04 (3H, s), 0.83 (9H, s), 1.73-1.77 (1H, m), 1.83-1.89 (1H, m), 2.53-2.67 (3H, m), 2.76-2.98 (6H, m), 3.50 (1H, d, J=8.5 Hz), 3.74 (3H, s), 3.78 (1H, d, J=8.4 Hz), 3.88 (1H, dd, J=10.3 Hz, 5.2 Hz), 5.23 (2H, s), 6.40 (1H, dd, J=11.6 Hz, 5.9 Hz), 6.74-6.77 (2H, m), 7.11 (2H, d, J=8.6 Hz).

Reference Example 557

5-{[(3R,4R)-3-{[tert-Butyl(dimethyl)silyl]oxy}-1-(4-chloro-2-fluorophenyl)-4-hydroxypiperidin-4-yl]methoxy}-8-fluoro-1-(4-methoxybenzyl)-3,4-dihydroquinolin-2(1H)-one Synthesized analogous to Reference Example 70.

$^1$HNMR (CDCl$_3$) δ ppm: −0.13 (3H, s), 0.07 (3H, s), 0.84 (9H, s), 1.83-1.91 (1H, m), 2.10-2.22 (1H, m), 2.50-2.54 (1H, m), 2.57-2.70 (2H, m), 2.80-2.96 (3H, m), 3.02-3.19 (2H, m), 3.26-3.34 (1H, m), 3.63 (1H, d, J=8.5 Hz), 3.73 (3H, s), 3.85 (1H, d, J=8.5 Hz), 4.12-4.18 (1H, m), 5.23 (2H, brs), 6.48 (1H, dd, J=9.2 Hz, 3.3 Hz), 6.72-6.78 (2H, m), 6.79-6.94 (2H, m), 7.03-7.09 (2H, m), 7.10-7.16 (2H, m).

Reference Example 558

5-{[(3S,4S)-3-{[tert-Butyl(dimethyl)silyl]oxy}-1-(4-chloro-2-fluorophenyl)-4-hydroxypiperidin-4-yl]methoxy}-8-fluoro-1-(4-methoxybenzyl)-3,4-dihydroquinolin-2(1H)-one Synthesized analogous to Reference Example 70.

$^1$HNMR (CDCl$_3$) δ ppm: −0.13 (3H, s), 0.07 (3H, s), 0.84 (9H, s), 1.82-1.91 (1H, m), 2.10-2.22 (1H, m), 2.50-2.56 (1H, m), 2.57-2.71 (2H, m), 2.79-2.96 (3H, m), 3.02-3.19 (2H, m), 3.26-3.34 (1H, m), 3.63 (1H, d, J=8.5 Hz), 3.73 (3H, s), 3.85 (1H, d, J=8.5 Hz), 4.12-4.18 (1H, m), 5.23 (2H, brs), 6.48 (1H, dd, J=9.2 Hz, 3.3 Hz), 6.71-6.78 (2H, m), 6.79-6.94 (2H, m), 7.02-7.09 (2H, m), 7.10-7.16 (2H, m).

Reference Example 559

5-{[(3R*,4R*)-3-{[tert-Butyl(dimethyl)silyl]oxy}-4-hydroxy-1-(2,2,6-trifluoro-1,3-benzodioxol-5-yl)piperidin-4-yl]methoxy}-8-fluoro-1-(4-methoxybenzyl)-3,4-dihydroquinolin-2(1H)-one Synthesized analogous to Reference Example 70.

$^1$HNMR (CDCl$_3$) δ ppm: −0.13 (3H, s), 0.06 (3H, s), 0.83 (9H, s), 1.85-1.88 (1H, m), 2.13-2.20 (1H, m), 2.52 (1H, d, J=2.5 Hz), 2.59-2.69 (2H, m), 2.80-2.96 (3H, m), 3.03-3.06 (2H, m), 3.17-3.20 (1H, m), 3.63 (1H, d, J=8.5 Hz), 3.73 (3H, s), 3.85 (1H, d, J=8.5 Hz), 4.12-4.16 (1H, m), 5.23 (2H, s), 6.48 (1H, dd, J=9.0 Hz, 3.0 Hz), 6.74 (2H, d, J=8.5 Hz), 6.79 (1H, d, J=7.0 Hz), 6.83 (1H, dd, J=12.5 Hz, 9.0 Hz), 6.87 (1H, d, J=10.0 Hz), 7.11 (2H, d, J=8.5 Hz).

Reference Example 560

5-{[(3R,4R)-3-{[tert-Butyl(dimethyl)silyl]oxy}-4-hydroxy-1-(2,2,6-trifluoro-1,3-benzodioxol-5-yl)piperidin-4-yl]methoxy}-8-fluoro-1-(4-methoxybenzyl)-3,4-dihydroquinolin-2(1H)-one Synthesized analogous to Reference Example 70.

$^1$HNMR (CDCl$_3$) δ ppm: −0.13 (3H, s), 0.06 (3H, s), 0.84 (9H, s), 1.85-1.89 (1H, m), 2.13-2.20 (1H, m), 2.51 (1H, d, J=2.3 Hz), 2.59-2.69 (2H, m), 2.81-2.95 (3H, m), 3.03-3.06 (2H, m), 3.18 (1H, dd, J=10.8 Hz, 5.2 Hz), 3.63 (1H, d, J=8.6 Hz), 3.73 (3H, s), 3.85 (1H, d, J=8.6 Hz), 4.12-4.16 (1H, m), 5.23 (2H, m), 6.48 (1H, dd, J=9.1 Hz, 3.3 Hz), 6.73-6.76 (2H, m), 6.79 (1H, d, J=7.0 Hz), 6.82-6.88 (2H, m), 7.12 (2H, d, J=8.6 Hz).

Reference Example 561

5-{[(3R,4R)-3-{[tert-Butyl(dimethyl)silyl]oxy}-1-(2-chloro-4-fluorophenyl)-4-hydroxypiperidin-4-yl]methoxy}-8-chloro-1-(4-methoxybenzyl)-3,4-dihydroquinolin-2(1H)-one Synthesized analogous to Reference Example 70.

$^1$HNMR (CDCl$_3$) δ ppm: −0.16 (3H, s), 0.05 (3H, s), 0.83 (9H, s), 1.85-1.88 (1H, m), 2.13-2.19 (1H, m), 2.55-2.59 (3H, m), 2.68-2.89 (3H, m), 2.99-3.22 (3H, m), 3.66 (1H, d, J=8.5 Hz), 3.72 (3H, s), 3.86 (1H, d, J=8.5 Hz), 4.17 (1H, dd, J=10.3 Hz, 5.3 Hz), 5.33 (1H, d, J=15.1 Hz), 5.44 (1H, d, J=15.1 Hz), 6.56 (1H, d, J=9.0 Hz), 6.70 (2H, d, J=8.6 Hz), 6.93-6.97 (1H, m), 7.02-708 (3H, m), 7.13-7.16 (2H, m).

Reference Example 562

5-{[(3S,4S)-3-{[tert-Butyl(dimethyl)silyl]oxy}-1-(2-chloro-4-fluorophenyl)-4-hydroxypiperidin-4-yl]methoxy}-8-chloro-1-(4-methoxybenzyl)-3,4-dihydroquinolin-2(1H)-one Synthesized analogous to Reference Example 70.

$^1$HNMR (CDCl$_3$) δ ppm: −0.16 (3H, s), 0.05 (3H, s), 0.83 (9H, s), 1.85-1.88 (1H, m), 2.14-2.20 (1H, m), 2.55-2.59 (3H, m), 2.68-2.89 (3H, m), 2.99-3.22 (3H, m), 3.66 (1H, d, J=8.6 Hz), 3.72 (3H, s), 3.86 (1H, d, J=8.6 Hz), 4.17 (1H, dd, J=10.2 Hz, 5.2 Hz), 5.33 (1H, d, J=15.0 Hz), 5.44 (1H, d, J=15.0 Hz), 6.56 (1H, d, J=9.0 Hz), 6.70 (2H, d, J=8.6 Hz), 6.93-6.97 (1H, m), 7.02-7.08 (3H, m), 7.13-7.16 (2H, m).

Reference Example 563

5-{[(3R,4R)-3-{[tert-Butyl(dimethyl)silyl]oxy}-1-(2-chloro-4-fluorophenyl)-4-hydroxypiperidin-4-yl]methoxy}-8-chloro-7-fluoro-1-(4-methoxybenzyl)-3,4-dihydroquinolin-2(1H)-one Synthesized analogous to Reference Example 70.
$^1$HNMR (CDCl$_3$) δ ppm: −0.15 (3H, s), 0.06 (3H, s), 0.84 (9H, s), 1.86-1.88 (1H, m), 2.11-2.17 (1H, m), 2.55-2.59 (3H, m), 2.63-2.85 (3H, m), 2.99-3.22 (3H, m), 3.63 (1H, d, J=8.5 Hz), 3.72 (3H, s), 3.83 (1H, d, J=8.5 Hz), 4.14 (1H, dd, J=10.2 Hz, 5.2 Hz), 5.33 (1H, d, J=15.2 Hz), 5.45 (1H, d, J=15.2 Hz), 6.49 (1H, d, J=10.5 Hz), 6.70-6.72 (2H, m), 6.93-6.97 (1H, m), 7.02-7.07 (3H, m), 7.15 (1H, dd, J=8.3 Hz, 2.9 Hz).

Reference Example 564

5-{[(3R*,4R*)-3-{[tert-Butyl(dimethyl) silyl]oxy}-1-(2-chloro-4-fluorophenyl)-4-hydroxypiperidin-4-yl]methoxy}-8-chloro-7-fluoro-1-(4-methoxybenzyl)-3,4-dihydroquinolin-2(1H)-one Synthesized analogous to Reference Example 70.
$^1$HNMR (CDCl$_3$) δ ppm: −0.15 (3H, s), 0.06 (3H, s), 0.84 (9H, s), 1.86-1.88 (1H, m), 2.11-2.18 (1H, m), 2.55-2.84 (6H, m), 2.99-3.22 (3H, m), 3.63 (1H, d, J=8.4 Hz), 3.72 (3H, s), 3.83 (1H, d, J=8.5 Hz), 4.14 (1H, dd, J=10.2 Hz, 5.3 Hz), 5.33 (1H, d, J=14.9 Hz), 5.45 (1H, d, J=14.6 Hz), 6.49 (1H, d, J=10.5 Hz), 6.70-6.72 (2H, m), 6.93-6.97 (1H, m), 7.02-7.07 (3H, m), 7.15 (1H, dd, J=8.3 Hz, 2.9 Hz).

Reference Example 565

5-{[(3R,4R)-3-{[tert-Butyl(dimethyl)silyl]oxy}-1-(4-chloro-2,5-difluorophenyl)-4-hydroxypiperidin-4-yl]methoxy}-8-fluoro-1-(4-methoxybenzyl)-3,4-dihydroquinolin-2(1H)-one Synthesized analogous to Reference Example 70.
$^1$HNMR (CDCl$_3$) δ ppm: −0.13 (3H, s), 0.07 (3H, s), 0.84 (9H, s), 1.85-1.88 (1H, m), 2.12-2.18 (1H, m), 2.51 (1H, d, J=2.3 Hz), 2.59-2.69 (2H, m), 2.81-2.93 (3H, m), 3.03-3.33 (3H, m), 3.62 (1H, d, J=8.6 Hz), 3.73 (3H, s), 3.85 (1H, d, J=8.6 Hz), 4.13 (1H, dd, J=10.4 Hz, 5.2 Hz), 5.23 (2H, brs), 6.48 (1H, dd, J=9.1 Hz, 3.2 Hz), 6.73-6.77 (3H, m), 6.84 (1H, dd, J=12.7 Hz, 9.1 Hz), 7.07-7.12 (3H, m).

Reference Example 566

5-{[(3R,4R)-3-{[tert-Butyl(dimethyl)silyl]oxy}-1-(2,4-dichlorophenyl)-4-hydroxypiperidin-4-yl]methoxy}-8-fluoro-1-(4-methoxybenzyl)-3,4-dihydroquinolin-2(1H)-one Synthesized analogous to Reference Example 70.
$^1$HNMR (CDCl$_3$) δ ppm: −0.13 (3H, s), 0.07 (3H, s), 0.83 (9H, s), 1.86-1.89 (1H, m), 2.14-2.20 (1H, m), 2.58 (1H, d, J=2.4 Hz), 2.61-2.70 (2H, m), 2.76 (1H, t, J=10.7 Hz), 2.84-2.97 (2H, m), 3.05-3.12 (2H, m), 3.25-3.28 (1H, m), 3.64 (1H, d, J=8.6 Hz), 3.73 (3H, s), 3.85 (1H, d, J=8.6 Hz), 4.17 (1H, dd, J=10.3 Hz, 5.3 Hz), 5.17-5.28 (2H, m), 6.47 (1H, dd, J=9.1 Hz, 3.3 Hz), 6.73-6.76 (2H, m), 6.84 (1H, dd, J=12.7 Hz, 9.1 Hz), 6.99 (1H, d, J=8.7 Hz), 7.12 (2H, d, J=8.5 Hz), 7.20 (1H, dd, J=8.6 Hz, 2.5 Hz), 7.39 (1H, d, J=2.5 Hz).

Reference Example 567

5-{[(3R,4R)-3-{[tert-Butyl(dimethyl)silyl]oxy}-1-(2,4-dichloro-5-fluorophenyl)-4-hydroxypiperidin-4-yl]methoxy}-8-fluoro-1-(4-methoxybenzyl)-3,4-dihydroquinolin-2(1H)-one Synthesized analogous to Reference Example 70.
$^1$HNMR (CDCl$_3$) δ ppm: −0.13 (3H, s), 0.07 (3H, s), 0.83 (9H, s), 1.86-1.90 (1H, m), 2.14-2.20 (1H, m), 2.57 (1H, d, J=2.4 Hz), 2.63-2.66 (2H, m), 2.75 (1H, t, J=10.7 Hz), 2.83-2.96 (2H, m), 3.06-3.08 (2H, m), 3.28 (1H, dd, J=11.1 Hz, 5.2 Hz), 3.64 (1H, d, J=8.6 Hz), 3.73 (3H, s), 3.85 (1H, d, J=8.6 Hz), 4.17 (1H, dd, J=10.3 Hz, 5.3 Hz), 5.19-5.27 (2H, m), 6.48 (1H, dd, J=9.1 Hz, 3.1 Hz), 6.73-6.76 (2H, m), 6.82-6.87 (2H, m), 7.12 (2H, d, J=8.5 Hz), 7.42 (1H, d, J=7.6 Hz).

Reference Example 568

5-{[(3R,4R)-3-{[tert-Butyl(dimethyl)silyl]oxy}-1-(2,5-dichloro-4-fluorophenyl)-4-hydroxypiperidin-4-yl]methoxy}-8-fluoro-1-(4-methoxybenzyl)-3,4-dihydroquinolin-2(1H)-one Synthesized analogous to Reference Example 70.
$^1$HNMR (CDCl$_3$) δ ppm: −0.13 (3H, s), 0.07 (3H, s), 0.83 (9H, s), 1.86-1.89 (1H, m), 2.14-2.20 (1H, m), 2.56 (1H, d, J=2.3 Hz), 2.62-2.66 (2H, m), 2.75 (1H, t, J=10.6 Hz), 2.83-3.11 (4H, m), 3.18-3.21 (1H, m), 3.64 (1H, d, J=8.5 Hz), 3.73 (3H, s), 3.85 (1H, d, J=8.6 Hz), 4.16 (1H, dd, J=10.3 Hz, 5.3 Hz), 5.19-5.27 (2H, m), 6.49 (1H, dd, J=9.1 Hz, 3.2 Hz), 6.73-6.76 (2H, m), 6.84 (1H, dd, J=12.7 Hz, 9.1 Hz), 7.08 (1H, d, J=7.1 Hz), 7.12 (2H, d, J=8.6 Hz), 7.21 (1H, d, J=4.4 Hz).

Reference Example 569

5-{[(3R,4R)-3-{[tert-Butyl(dimethyl)silyl]oxy}-1-(4-ethoxy-2-fluorophenyl)-4-hydroxypiperidin-4-yl]methoxy}-8-fluoro-1-(4-methoxybenzyl)-3,4-dihydroquinolin-2(1H)-one Synthesized analogous to Reference Example 70.
$^1$HNMR (CDCl$_3$) δ ppm: −0.13 (3H, s), 0.06 (3H, s), 0.83 (9H, s), 1.40 (3H, t, J=7.0 Hz), 1.84-1.88 (1H, m), 2.12-2.21 (1H, m), 2.53-3.23 (9H, m), 3.63 (1H, d, J=8.8 Hz), 3.73 (3H, s), 3.85 (1H, d, J=8.3 Hz), 3.98 (2H, q, J=7.1 Hz), 4.16 (1H, dd, J=10.0 Hz, 5.2 Hz), 5.23 (2H, brs), 6.47-6.50 (1H, m), 6.61-6.67 (2H, m), 6.74-6.76 (2H, m), 6.81-6.94 (2H, m), 7.11-7.13 (2H, m).

Reference Example 570

5-{[(3R,4R)-3-{[tert-Butyl(dimethyl)silyl]oxy}-1-(2-chloro-4-fluorophenyl)-4-hydroxypiperidin-4-yl]methoxy}-7,8-difluoro-1-(4-methoxybenzyl)-3,4-dihydroquinolin-2(1H)-one Synthesized analogous to Reference Example 70.
$^1$HNMR (CDCl$_3$) δ ppm: −0.11 (3H, s), 0.07 (3H, s), 0.84 (9H, s), 1.85-1.88 (1H, m), 2.12-2.17 (1H, m), 2.58-2.93 (6H, m), 2.99-3.23 (3H, m), 3.60 (1H, d, J=8.5 Hz), 3.74 (3H, s), 3.81 (1H, d, J=8.5 Hz), 4.15 (1H, dd, J=10.3 Hz, 5.3 Hz), 5.24 (2H, brs), 6.41 (1H, dd, J=11.5 Hz, 5.9 Hz), 6.75-6.78 (2H, m), 6.94-6.97 (1H, m), 7.03 (1H, dd, J=8.9 Hz, 5.5 Hz), 7.11-7.16 (3H, m).

Reference Example 571

5-{[(3R*,4R*)-3-{[tert-Butyl(dimethyl) silyl]oxy}-1-(2-chloro-4-fluorophenyl)-4-hydroxypiperidin-4-yl]methoxy}-7,8-difluoro-1-(4-methoxybenzyl)-3,4-dihydroquinolin-2(1H)-one Synthesized analogous to Reference Example 70.
$^1$HNMR (CDCl$_3$) δ ppm: −0.11 (3H, s), 0.07 (3H, s), 0.84 (9H, s), 1.85-1.88 (1H, m), 2.11-2.18 (1H, m), 2.58-2.92 (6H, m), 2.99-3.23 (3H, m), 3.60 (1H, d, J=8.5 Hz), 3.74 (3H, s), 3.81 (1H, d, J=8.5 Hz), 4.15 (1H, dd, J=10.3 Hz, 5.3 Hz), 5.24 (2H, brs), 6.41 (1H, dd, J=11.6 Hz, 5.9 Hz), 6.75-6.78 (2H, m), 6.94-6.97 (1H, m), 7.03 (1H, dd, J=9.0 Hz, 5.5 Hz), 7.11-7.16 (3H, m).

Reference Example 572

5-{[(3R,4R)-3-{[tert-Butyl(dimethyl)silyl]oxy}-1-(2,4-dichlorophenyl)-4-hydroxypiperidin-4-yl]methoxy}-8-chloro-1-(4-methoxybenzyl)-3,4-dihydroquinolin-2(1H)-one Synthesized analogous to Reference Example 70.
$^1$HNMR (CDCl$_3$) δ ppm: −0.16 (3H, s), 0.05 (3H, s), 0.83 (9H, s), 1.85-1.88 (1H, m), 2.13-2.19 (1H, m), 2.54-2.58 (3H, m), 2.69-2.86 (3H, m), 3.02-3.12 (2H, m), 3.24-3.27 (1H, m), 3.65 (1H, d, J=8.6 Hz), 3.72 (3H, s), 3.86 (1H, d, J=8.5 Hz), 4.14-4.18 (1H, m), 5.33 (1H, d, J=15.1 Hz), 5.44 (1H, d, J=14.8 Hz), 6.55 (1H, d, J=8.9 Hz), 6.68-6.71 (2H, m), 6.99 (1H, d, J=8.7 Hz), 7.07 (2H, d, J=8.6 Hz), 7.15 (1H, d, J=9.0 Hz), 7.20 (1H, dd, J=8.7 Hz, 2.4 Hz), 7.38 (1H, d, J=2.4 Hz).

Reference Example 573

5-{[(3R,4R)-3-{[tert-Butyl(dimethyl)silyl]oxy}-1-(2,5-dichloro-4-fluorophenyl)-4-hydroxypiperidin-4-yl]methoxy}-8-chloro-1-(4-methoxybenzyl)-3,4-dihydroquinolin-2(1H)-one Synthesized analogous to Reference Example 70.
$^1$HNMR (CDCl$_3$) δ ppm: −0.16 (3H, s), 0.05 (3H, s), 0.83 (9H, s), 1.85-1.88 (1H, m), 2.12-2.19 (1H, m), 2.55-2.57 (3H, m), 2.67-2.86 (3H, m), 2.98-3.20 (3H, m), 3.65 (1H, d, J=8.6 Hz), 3.72 (3H, s), 3.86 (1H, d, J=8.6 Hz), 4.14-4.17 (1H, m), 5.33 (1H, d, J=15.2 Hz), 5.44 (1H, d, J=15.2 Hz), 6.55 (1H, d, J=9.0 Hz), 6.68-6.71 (2H, m), 7.06-7.09 (3H, m), 7.16 (1H, d, J=8.9 Hz), 7.22 (1H, d, J=8.5 Hz).

Reference Example 574

5-{[(3R,4R)-3-{[tert-Butyl(dimethyl)silyl]oxy}-1-(2,4-dichloro-5-fluorophenyl)-4-hydroxypiperidin-4-yl]methoxy}-8-chloro-1-(4-methoxybenzyl)-3,4-dihydroquinolin-2(1H)-one Synthesized analogous to Reference Example 70.
$^1$HNMR (CDCl$_3$) δ ppm: −0.16 (3H, s), 0.06 (3H, s), 0.83 (9H, s), 1.86-1.89 (1H, m), 2.13-2.17 (1H, m), 2.54-2.57 (3H, m), 2.67-2.86 (3H, m), 3.05-3.07 (2H, m), 3.26-3.29 (1H, m), 3.65 (1H, d, J=8.6 Hz), 3.72 (3H, s), 3.86 (1H, d, J=8.6 Hz), 4.14-4.17 (1H, m), 5.33 (1H, d, J=15.1 Hz), 5.44 (1H, d, J=15.1 Hz), 6.55 (1H, d, J=9.0 Hz), 6.68-6.71 (2H, m), 6.86 (1H, d, J=10.5 Hz), 7.05-7.08 (2H, m), 7.16 (1H, d, J=8.9 Hz), 7.41 (1H, d, J=7.6 Hz).

Reference Example 575

5-{[(3R,4R)-3-{[tert-Butyl(dimethyl)silyl]oxy}-1-(2-chloro-4-fluorophenyl)-4-hydroxypiperidin-4-yl]methoxy}-8-fluoro-1-(4-methoxybenzyl)-3,4-dihydroquinolin-2(1H)-one Synthesized analogous to Reference Example 70.
$^1$HNMR (CDCl$_3$) δ ppm: −0.12 (3H, s), 0.07 (3H, s), 0.83 (9H, s), 1.86-1.89 (1H, m), 2.14-2.21 (1H, m), 2.58 (1H, d, J=2.2 Hz), 2.59-2.69 (2H, m), 2.76 (1H, t, J=10.6 Hz), 2.84-3.13 (4H, m), 3.18-3.25 (1H, m), 3.65 (1H, d, J=8.6 Hz), 3.73 (3H, s), 3.86 (1H, d, J=8.6 Hz), 4.18 (1H, dd, J=10.3 Hz, 5.3 Hz), 5.19-5.27 (2H, m), 6.49 (1H, dd, J=9.1 Hz, 3.2 Hz), 6.73-6.76 (2H, m), 6.84 (1H, dd, J=12.6 Hz, 9.0 Hz), 6.93-6.97 (1H, m), 7.04 (1H, dd, J=8.8 Hz, 5.4 Hz), 7.11-7.16 (3H, m).

Reference Example 576

5-{[(3R,4R)-3-{[tert-Butyl(dimethyl)silyl]oxy}-1-(4-chloro-2,5-difluorophenyl)-4-hydroxypiperidin-4-yl]methoxy}-8-chloro-1-(4-methoxybenzyl)-3,4-dihydroquinolin-2(1H)-one Synthesized analogous to Reference Example 70.
$^1$HNMR (CDCl$_3$) δ ppm: −0.17 (3H, s), 0.06 (3H, s), 0.84 (9H, s), 1.85-1.87 (1H, m), 2.12-2.17 (1H, m), 2.51-2.85 (6H, m), 3.03-3.17 (2H, m), 3.29-3.32 (1H, m), 3.63 (1H, d, J=8.5 Hz), 3.72 (3H, s), 3.86 (1H, d, J=8.6 Hz), 4.10-4.13 (1H, m), 5.33 (1H, d, J=15.2 Hz), 5.44 (1H, d, J=14.8 Hz), 6.55 (1H, d, J=9.0 Hz), 6.54-6.56 (2H, m), 6.74 (1H, dd, J=10.5 Hz, 7.6 Hz), 7.05-7.10 (3H, m), 7.15 (1H, d, J=8.7 Hz).

Reference Example 577

5-{[(3R,4R)-3-{[tert-Butyl(dimethyl)silyl]oxy}-1-(4-chloro-2,5-difluorophenyl)-4-hydroxypiperidin-4-yl]methoxy}-7,8-difluoro-1-(4-methoxybenzyl)-3,4-dihydroquinolin-2(1H)-one Synthesized analogous to Reference Example 70.
$^1$HNMR (CDCl$_3$) δ ppm: −0.12 (3H, s), 0.08 (3H, s), 0.84 (9H, s), 1.85-1.88 (1H, m), 2.08-2.15 (1H, m), 2.51 (1H, d, J=2.3 Hz), 2.58-2.69 (2H, m), 2.78-2.89 (3H, m), 3.03-3.33 (3H, m), 3.58 (1H, d, J=8.5 Hz), 3.74 (3H, s), 3.81 (1H, d, J=8.5 Hz), 4.10-4.14 (1H, m), 5.23 (2H, brs), 6.41 (1H, dd, J=11.5 Hz, 6.0 Hz), 6.73-6.77 (3H, m), 7.07-7.12 (3H, m).

Reference Example 578

5-{[(3R,4R)-3-{[tert-Butyl(dimethyl)silyl]oxy}-1-(4-chlorophenyl)-4-hydroxypiperidin-4-yl]methoxy}-8-fluoro-1-(4-methoxybenzyl)-3,4-dihydroquinolin-2(1H)-one Synthesized analogous to Reference Example 70.
$^1$HNMR (CDCl$_3$) δ ppm: −0.14 (3H, s), 0.10 (3H, s), 0.85 (9H, s), 1.81-1.85 (1H, m), 2.09-2.15 (1H, m), 2.53-2.64 (3H, m), 2.72-2.83 (2H, m), 2.89-2.93 (1H, m), 3.07-3.13 (1H, m), 3.39-3.48 (2H, m), 3.60 (1H, d, J=8.6 Hz), 3.73 (3H, s), 3.83 (1H, d, J=8.6 Hz), 4.07-4.10 (1H, m), 5.22 (2H, brs), 6.46 (1H, dd, J=9.1 Hz, 3.3 Hz), 6.73-6.75 (2H, m), 6.81-6.87 (3H, m), 7.11 (2H, d, J=8.5 Hz), 7.20-7.24 (2H, m).

Reference Example 579

5-({(3R,4R)-3-{[tert-Butyl(dimethyl)silyl]oxy}-1-[2-fluoro-4-(trifluoromethoxy)phenyl]-4-hydroxypiperidin-4-yl}methoxy)-8-fluoro-1-(4-methoxybenzyl)-3,4-dihydroquinolin-2(1H)-one Synthesized analogous to Reference Example 70.
$^1$HNMR (CDCl$_3$) δ ppm: −0.13 (3H, s), 0.07 (3H, s), 0.84 (9H, s), 1.86-1.89 (1H, m), 2.13-2.19 (1H, m), 2.53 (1H, d, J=2.3 Hz), 2.61-2.66 (2H, m), 2.84-2.91 (3H, m), 3.06-3.32 (3H, m), 3.63 (1H, d, J=8.6 Hz), 3.73 (3H, s), 3.86 (1H, d, J=8.6 Hz), 4.15 (1H, dd, J=10.4 Hz, 5.3 Hz), 5.23 (2H, brs), 6.48 (1H, dd, J=9.1 Hz, 3.2 Hz), 6.75 (2H, d, J=8.6 Hz), 6.84 (1H, dd, J=12.6 Hz, 9.1 Hz), 6.96-7.00 (3H, m), 7.12 (2H, d, J=8.6 Hz).

Reference Example 580

5-{[(3R,4R)-3-{[tert-Butyl(dimethyl)silyl]oxy}-1-(2-fluorophenyl)-4-hydroxypiperidin-4-yl]methoxy}-8-fluoro-1-(4-methoxybenzyl)-3,4-dihydroquinolin-2(1H)-one Synthesized analogous to Reference Example 70.
$^1$HNMR (CDCl$_3$) δ ppm: −0.12 (3H, s), 0.08 (3H, s), 0.84 (9H, s), 1.86-1.89 (1H, m), 2.15-2.20 (1H, m), 2.55 (1H, d, J=2.3 Hz), 2.59-2.69 (2H, m), 2.83-2.95 (3H, m), 3.06-3.38 (3H, m), 3.63 (1H, d, J=8.6 Hz), 3.73 (3H, s), 3.86 (1H, d, J=8.5 Hz), 4.17 (1H, dd, J=10.4 Hz, 5.3 Hz), 5.23 (2H, brs), 6.49 (1H, dd, J=9.1 Hz, 3.3 Hz), 6.73-6.76 (2H, m), 6.83 (1H, dd, J=12.7 Hz, 9.1 Hz), 6.93-7.09 (4H, m), 7.12 (2H, d, J=8.6 Hz).

Reference Example 581

5-{[(3R,4R)-3-{[tert-Butyl(dimethyl)silyl]oxy}-1-(2-chlorophenyl)-4-hydroxypiperidin-4-yl]methoxy}-8-fluoro-1-(4-methoxybenzyl)-3,4-dihydroquinolin-2(1H)-one Synthesized analogous to Reference Example 70.
$^1$HNMR (CDCl$_3$) δ ppm: −0.12 (3H, s), 0.07 (3H, s), 0.83 (9H, s), 1.87-1.90 (1H, m), 2.16-2.22 (1H, m), 2.60 (1H, d, J=2.4 Hz), 2.63-2.67 (2H, m), 2.79 (1H, t, J=10.7 Hz), 2.85-2.98 (2H, m), 3.10-3.13 (2H, m), 3.32-3.35 (1H, m), 3.65 (1H, d, J=8.6 Hz), 3.73 (3H, s), 3.86 (1H, d, J=8.6 Hz), 4.20 (1H, dd, J=10.3 Hz, 5.3 Hz), 5.19-5.27 (2H, m), 6.49 (1H, dd, J=9.1 Hz, 3.3 Hz), 6.73-6.76 (2H, m), 6.84 (1H, dd, J=12.7 Hz, 9.1 Hz), 6.99 (1H, dt, J=1.4 Hz, 7.6 Hz), 7.08 (1H, dd, J=8.0 Hz, 1.4 Hz), 7.12 (2H, d, J=8.7 Hz), 7.22-7.25 (1H, m), 7.38 (1H, dd, J=7.9 Hz, 1.5 Hz).

Reference Example 582

5-{[(3R,4R)-3-{[tert-Butyl(dimethyl)silyl]oxy}-1-(2,4-difluorophenyl)-4-hydroxypiperidin-4-yl]methoxy}-8-fluoro-1-(4-methoxybenzyl)-3,4-dihydroquinolin-2(1H)-one Synthesized analogous to Reference Example 70.
$^1$HNMR (CDCl$_3$) δ ppm: −0.13 (3H, s), 0.07 (3H, s), 0.84 (9H, s), 1.85-1.88 (1H, m), 2.13-2.20 (1H, m), 2.53 (1H, d, J=2.3 Hz), 2.59-3.25 (8H, m), 3.63 (1H, d, J=8.5 Hz), 3.73 (3H, s), 3.85 (1H, d, J=8.6 Hz), 4.14-4.17 (1H, m), 5.23 (2H, brs), 6.49 (1H, dd, J=9.1 Hz, 3.3 Hz), 6.73-6.76 (2H, m), 6.79-6.86 (3H, m), 6.94-6.97 (1H, m), 7.12 (2H, d, J=8.6 Hz).

Reference Example 583

5-{[(3R,4R)-3-{[tert-Butyl(dimethyl)silyl]oxy}-1-(2,6-difluorophenyl)-4-hydroxypiperidin-4-yl]methoxy}-8-fluoro-1-(4-methoxybenzyl)-3,4-dihydroquinolin-2(1H)-one Synthesized analogous to Reference Example 70.
$^1$HNMR (CDCl$_3$) δ ppm: −0.14 (3H, s), 0.05 (3H, s), 0.83 (9H, s), 1.78-1.81 (1H, m), 2.08-2.15 (1H, m), 2.58 (1H, d, J=2.3 Hz), 2.59-2.70 (2H, m), 2.84-3.05 (3H, m), 3.14 (1H, dd, 11.7 Hz, 5.3 Hz), 3.25-3.29 (1H, m), 3.46-3.50 (1H, m), 3.62 (1H, d, J=8.5 Hz), 3.73 (3H, s), 3.86 (1H, d, J=8.5 Hz), 4.10 (1H, dd, J=10.3 Hz, 5.5 Hz), 5.23 (2H, brs), 6.49 (1H, dd, J=9.1 Hz, 3.3 Hz), 6.73-6.76 (2H, m), 6.81-6.94 (4H, m), 7.12 (2H, d, J=8.6 Hz).

Reference Example 584

5-{[(3R,4R)-3-{[tert-Butyl(dimethyl)silyl]oxy}-4-hydroxy-1-phenylpiperidin-4-yl]methoxy}-8-fluoro-1-(4-methoxybenzyl)-3,4-dihydroquinolin-2(1H)-one Synthesized analogous to Reference Example 70.
$^1$HNMR (DMSO-d6) δ ppm: −0.17 (3H, s), 0.05 (3H, s), 0.80 (9H, s), 1.67-1.70 (1H, m), 1.93-1.99 (1H, m), 2.50-3.00 (6H, m), 3.40-3.50 (2H, m), 3.61 (1H, d, J=8.7 Hz), 3.67 (3H, s), 3.91-3.95 (2H, m), 4.43 (1H, s), 5.02-5.16 (2H, m), 6.60 (1H, dd, J=9.2 Hz, 3.3 Hz), 6.76-6.79 (3H, m), 6.92-704 (5H, m), 7.22-7.25 (2H, m).

Reference Example 585

5-({(3R,4R)-3-{[tert-Butyl(dimethyl)silyl]oxy}-4-hydroxy-1-[4-(trifluoromethoxy)phenyl]piperidin-4-yl}methoxy)-8-fluoro-1-(4-methoxybenzyl)-3,4-dihydroquinolin-2(1H)-one Synthesized analogous to Reference Example 70.
$^1$HNMR (DMSO-d6) δ ppm: −0.17 (3H, s), 0.06 (3H, s), 0.80 (9H, s), 1.68-1.70 (1H, m), 1.93-1.99 (1H, m), 2.45-3.03 (6H, m), 3.40-3.51 (2H, m), 3.61 (1H, d, J=8.7 Hz), 3.67 (3H, s), 3.91-3.94 (2H, m), 4.48 (1H, s), 5.02-5.16 (2H, m), 6.60 (1H, dd, J=9.2 Hz, 3.3 Hz), 6.76-6.78 (2H, m), 6.92-7.04 (5H, m), 7.21 (2H, d, J=8.9 Hz).

Reference Example 586

5-({(3R,4R)-3-{[tert-Butyl(dimethyl)silyl]oxy}-1-[4-(difluoromethoxy)phenyl]-4-hydroxypiperidin-4-yl}methoxy)-8-fluoro-1-(4-methoxybenzyl)-3,4-dihydroquinolin-2(1H)-one Synthesized analogous to Reference Example 70.
$^1$HNMR (DMSO-d6) δ ppm: −0.17 (3H, s), 0.05 (3H, s), 0.80 (9H, s), 1.67-1.70 (1H, m), 1.93-1.98 (1H, m), 2.50-3.00 (6H, m), 3.41-3.51 (2H, m), 3.61 (1H, d, J=8.7 Hz), 3.67 (3H, s), 3.91-3.95 (2H, m), 4.44 (1H, s), 5.01-5.17 (2H, m), 6.60 (1H, dd, J=9.4 Hz, 3.1 Hz), 6.78 (2H, d, J=8.7 Hz), 6.91-7.07 (7H, m).

Reference Example 587

5-{[(3R*,4R*)-3-{[tert-Butyl(dimethyl) silyl]oxy}-1-(4-chloro-2-fluorophenyl)-4-hydroxypiperidin-4-yl]methoxy}-7,8-difluoro-1-(4-methoxybenzyl)-3,4-dihydroquinolin-2(1H)-one Synthesized analogous to Reference Example 70.
$^1$HNMR (CDCl$_3$) δ ppm: −0.12 (3H, s), 0.08 (3H, s), 0.84 (9H, s), 1.82-1.89 (1H, m), 2.08-2.18 (1H, m), 2.53 (1H, d, J=2.5 Hz), 2.58-2.69 (2H, m), 2.78-2.91 (3H, m), 3.02-3.10 (1H, m), 3.11-3.17 (1H, m), 3.26-3.32 (1H, m), 3.58 (1H, d, J=8.5 Hz), 3.74 (3H, s), 3.80 (1H, d, J=8.5 Hz), 4.09-4.15 (1H, m), 5.24 (2H, brs), 6.39 (1H, dd, J=12.0 Hz, 6.0 Hz), 6.74-6.79 (2H, m), 6.87-6.92 (1H, m), 7.04-7.09 (2H, m), 7.09-7.14 (2H, m).

Reference Example 588

5-{[(3R,4R)-3-{[tert-Butyl(dimethyl)silyl]oxy}-1-(4-chloro-2-fluorophenyl)-4-hydroxypiperidin-4-yl]methoxy}-8-chloro-7-fluoro-1-(4-methoxybenzyl)-3,4-dihydroquinolin-2(1H)-one Synthesized analogous to Reference Example 70.
$^1$HNMR (CDCl$_3$) δ ppm: −0.16 (3H, s), 0.06 (3H, s), 0.84 (9H, s), 1.85-1.88 (1H, m), 2.09-2.16 (1H, m), 2.53-2.57 (3H, m), 2.63-2.86 (3H, m), 3.03-3.30 (3H, m), 3.61 (1H, d, J=8.5 Hz), 3.72 (3H, s), 3.83 (1H, d, J=8.5 Hz), 4.09-4.13 (1H, m), 5.33 (1H, d, J=15.2 Hz), 5.45 (1H, d, J=15.2 Hz), 6.48 (1H, d, J=10.5 Hz), 6.69-6.72 (2H, m), 6.87-6.91 (1H, m), 7.04-7.08 (4H, m).

Reference Example 589

5-{[(3R,4R)-3-{[tert-Butyl(dimethyl)silyl]oxy}-1-(4-chloro-2-fluorophenyl)-4-hydroxypiperidin-4-yl]methoxy}-8-chloro-1-(4-methoxybenzyl)-3,4-dihydroquinolin-2(1H)-one Synthesized analogous to Reference Example 70.
HNMR (CDCl$_3$) δ ppm: −0.17 (3H, s), 0.04 (3H, s), 0.84 (9H, s), 1.82-1.89 (1H, m), 2.10-2.20 (1H, m), 2.51-2.58 (3H, m), 2.65-2.64 (1H, m), 2.78-2.87 (2H, m), 3.03-3.09 (1H, m), 3.11-3.18 (1H, m), 3.25-3.31 (1H, m), 3.63 (1H, d, J=8.5 Hz), 3.72 (3H, s), 3.85 (1H, d, J=8.5 Hz), 4.10-4.16 (1H, m), 5.32 (1H, d, J=15.0 Hz), 5.43 (1H, d, J=15.0 Hz), 6.54 (1H, d, J=9.0 Hz), 6.68-6.72 (2H, m), 6.88 (1H, t, J=9.0 Hz), 7.03-7.09 (4H, m), 7.14 (1H, d, J=9.0 Hz).

Reference Example 590

5-{[(3R,4R)-3-{[tert-Butyl(dimethyl)silyl]oxy}-1-(4-chloro-2-fluoro-5-methoxyphenyl)-4-hydroxypiperidin-4-yl]methoxy}-8-fluoro-1-(4-methoxybenzyl)-3,4-dihydroquinolin-2(1H)-one Synthesized analogous to Reference Example 70.
$^1$HNMR (CDCl$_3$) δ ppm: −0.12 (3H, s), 0.072 (3H, s), 0.84 (9H, s), 1.86-1.90 (1H, m), 2.12-2.20 (1H, m), 2.52 (1H, d, J=2.3 Hz), 2.58-2.70 (2H, m), 2.82-2.96 (3H, m), 3.07-3.19 (2H, m), 3.31-3.36 (1H, m), 3.63 (1H, d, J=8.6 Hz), 3.73 (3H, s), 3.85 (1H, d, J=8.6 Hz), 3.87 (3H, s), 4.12-4.17 (1H, m), 5.23 (2H, s), 6.48 (1H, dd, J=9.2 Hz, 3.2 Hz), 6.55 (1H, d, J=7.7 Hz), 6.74 (2H, d, J=8.6 Hz), 6.84 (1H, dd, J=12.6 Hz, 9.2 Hz), 7.08 (1H, d, J=11.6 Hz), 7.12 (2H, d, J=8.6 Hz).

Reference Example 591

5-{[(3R,4R)-3-{[tert-Butyl(dimethyl)silyl]oxy}-1-(4-chloro-2-fluoro-5-methylphenyl)-4-hydroxypiperidin-4-yl]methoxy}-8-fluoro-1-(4-methoxybenzyl)-3,4-dihydroquinolin-2(1H)-one Synthesized analogous to Reference Example 70.
$^1$HNMR (CDCl$_3$) δ ppm: −0.13 (3H, s), 0.072 (3H, s), 0.84 (9H, s), 1.84-1.88 (1H, m), 2.11-2.20 (1H, m), 2.30 (3H, s), 2.53 (1H, d, J=2.4 Hz), 2.59-2.70 (2H, m), 2.80-2.96 (3H, m), 3.03-3.09 (1H, m), 3.12-3.17 (1H, m), 3.27-3.32 (1H, m), 3.62 (1H, d, J=8.6 Hz), 3.73 (3H, s), 3.85 (1H, d, J=8.6 Hz), 4.12-4.17 (1H, m), 5.23 (2H, s), 6.48 (1H, dd, J=9.2 Hz, 3.2 Hz), 6.74 (2H, d, J=8.8 Hz), 6.81 (1H, d, J=8.8 Hz), 6.83 (1H, dd, J=12.8 Hz, 9.2 Hz), 7.05 (1H, d, J=11.8 Hz), 7.12 (2H, d, J=8.8 Hz).

Reference Example 592

5-{[1-(4-Chloro-2,6-difluorophenyl)-1,2,3,6-tetrahydropyridin-4-yl]methoxy}-8-fluoro-3,4-dihydroquinolin-2(1H)-one Under nitrogen atmosphere, to a solution of 5-{[1-(4-chloro-2,6-difluorophenyl)-4-hydroxypiperidin-4-yl]methoxy}-8-fluoro-3,4-dihydroquinolin-2(1H)-one (441 mg) in tetrahydrofuran (8 mL), Burgess reagent (597 mg) was added under ice-cooling, and the reaction mixture was stirred at room temperature for 16.5 h, then at 60° C. for 2 h. To the reaction solution was added water, and the precipitate was collected on a filter to provide the title compound (380 mg). The compound was used for the next step without further purification.
$^1$HNMR (CDCl$_3$) δ ppm: 2.29-2.34 (2H, m), 2.63 (2H, t, J=8.0 Hz), 3.02 (2H, t, J=8.0 Hz), 3.32-3.35 (2H, m), 3.72 (2H, brs), 4.43 (2H, s), 5.85 (1H, brs), 6.48 (1H, dd, J=9.1 Hz, 4.0 Hz), 6.87-6.93 (3H, m), 7.49 (1H, brs).

Reference Example 593

8-Chloro-5-{[1-(4-chloro-2,6-difluorophenyl)-1,2,3,6-tetrahydropyridin-4-yl]methoxy}-3,4-dihydroquinolin-2(1H)-one Synthesized analogous to Reference Example 592.
$^1$HNMR (CDCl$_3$) δ ppm: 2.23-2.32 (2H, m), 2.60-2.66 (2H, m), 3.02 (2H, t, J=8.1 Hz), 3.32-3.35 (2H, m), 3.72 (2H, brs), 4.46 (2H, s), 5.85 (1H, brs), 6.54 (1H, d, J=8.9 Hz), 6.87-6.92 (2H, m), 7.16-7.19 (1H, m), 7.74 (1H, brs).

Reference Example 594

5-{[1-(4-Chloro-2,6-difluorophenyl)-1,2,3,6-tetrahydropyridin-4-yl]methoxy}-7,8-difluoro-3,4-dihydroquinolin-2(1H)-one Synthesized analogous to Reference Example 592.
$^1$HNMR (CDCl$_3$) δ ppm: 2.28-2.32 (2H, m), 2.60-2.65 (2H, m), 2.95-2.99 (2H, m), 3.33-3.35 (2H, m), 3.73 (2H, brs), 4.41 (2H, s), 5.86 (1H, brs), 6.40 (1H, dd, J=12.1 Hz, 6.3 Hz), 6.86-6.93 (2H, m), 7.67 (1H, brs).

Reference Example 595

5-{[1-(4-Bromo-2-fluorophenyl)-1,2,3,6-tetrahydropyridin-4-yl]methoxy}-8-fluoro-3,4-dihydroquinolin-2(1H)-one To a solution of 5-{[1-(4-bromo-2-fluorophenyl)-4-hydroxypiperidin-4-yl]methoxy}-8-fluoro-3,4-dihydroquinolin-2(1H)-one (8 g) in N-methyl-2-pyrrolidone (60 mL) was added N,N,N',N'-tetramethyl-1,3-diaminopropane (13.59 mL), then methanesulfonyl chloride (5.30 mL) was added dropwise under ice-cooling. The reaction mixture was stirred at room temperature for 16 h. To the reaction solution were added water and tert-butyl methyl ether, and the precipitate was collected on a filter. The obtained solid was washed with water and diisopropyl ether to provide the title compound (7.27 g).

$^1$HNMR (CDCl$_3$) δ ppm: 2.33-2.37 (2H, m), 2.61-2.65 (2H, m), 3.00-3.05 (2H, m), 3.29 (2H, t, J=5.6 Hz), 3.65 (2H, brs), 4.44 (2H, s), 5.88 (1H, brs), 6.47 (1H, dd, J=9.1 Hz, 3.9 Hz), 6.83 (1H, t, J=9.1 Hz), 6.90 (1H, t, J=9.4 Hz), 7.16-7.22 (2H, m), 7.49 (1H, brs).

Reference Example 596

5-{[1-(4-Bromo-2-fluorophenyl)-1,2,3,6-tetrahydropyridin-4-yl]methoxy}-8-chloro-3,4-dihydroquinolin-2(1H)-one Synthesized analogous to Reference Example 592.
$^1$HNMR (DMSO-d6) δ ppm: 2.25 (2H, brs), 2.44-2.48 (2H, m), 2.86-2.90 (2H, m), 3.20-3.22 (2H, m), 3.57-3.60 (2H, m), 4.52 (2H, s), 5.91 (1H, brs), 6.72 (1H, d, J=9.0 Hz), 6.98-7.02 (1H, m), 7.23-7.30 (2H, m), 7.42-7.45 (1H, m), 9.37 (1H, brs).

Reference Example 597

5-{[1-(4-Bromo-2-fluorophenyl)-1,2,3,6-tetrahydropyridin-4-yl]methoxy}-7,8-difluoro-3,4-dihydroquinolin-2(1H)-one Synthesized analogous to Reference Example 592.
$^1$HNMR (DMSO-d6) δ ppm: 2.25 (2H, brs), 2.42-2.47 (2H, m), 2.81-2.85 (2H, m), 3.21 (2H, t, J=5.6 Hz), 3.59 (2H, brs), 4.49 (2H, s), 5.92 (1H, brs), 6.79 (1H, dd, J=12.8 Hz, 6.3 Hz), 7.00 (1H, t, J=9.1 Hz), 7.27-7.30 (1H, m), 7.43 (1H, dd, J=12.2 Hz, 2.3 Hz), 10.31 (1H, brs).

Reference Example 598

8-Chloro-5-{[1-(4-chloro-2,6-difluorophenyl)-1,2,3,6-tetrahydropyridin-4-yl]methoxy}-7-fluoro-3,4-dihydroquinolin-2(1H)-one Synthesized analogous to Reference Example 595.
$^1$HNMR (DMSO-d6) δ ppm: 2.23 (2H, brs), 2.45-2.49 (2H, m), 2.83-2.87 (2H, m), 3.25-3.29 (2H, m), 3.64 (2H, brs), 4.53 (2H, s), 5.89 (1H, brs), 6.87 (1H, d, J=11.6 Hz), 7.23-7.33 (2H, m), 9.70 (1H, brs).

Reference Example 599

5-{[1-(4-Bromo-2-fluorophenyl)-1,2,3,6-tetrahydropyridin-4-yl]methoxy}-8-chloro-7-fluoro-3,4-dihydroquinolin-2(1H)-one Synthesized analogous to Reference Example 595.
$^1$HNMR (DMSO-d6) δ ppm: 2.25 (2H, brs), 2.45-2.49 (2H, m), 2.82-2.86 (2H, m), 3.21 (2H, t, J=5.6 Hz), 3.59 (2H, brs), 4.54 (2H, s), 5.93 (1H, brs), 6.87 (1H, d, J=11.6 Hz), 7.00 (1H, t, J=9.1 Hz), 7.27-7.30 (1H, m), 7.43 (1H, dd, J=12.3 Hz, 2.3 Hz), 9.69 (1H, brs).

Reference Example 600

5-{[1-(2-Chloro-4,6-difluorophenyl)-1,2,3,6-tetrahydropyridin-4-yl]methoxy}-8-fluoro-3,4-dihydroquinolin-2(1H)-one Synthesized analogous to Reference Example 595.
$^1$HNMR (CDCl$_3$) δ ppm: 2.32 (2H, brs), 2.62-2.66 (2H, m), 3.03 (2H, t, J=8.1 Hz), 3.27-3.29 (2H, m), 3.66 (2H, brs), 4.45 (2H, s), 5.86 (1H, brs), 6.49 (1H, dd, J=9.1 Hz, 4.0 Hz), 6.73-6.78 (1H, m), 6.89-6.98 (2H, m), 7.52 (1H, brs).

Reference Example 601

5-{[1-(4-Bromo-2,6-difluorophenyl)-1,2,3,6-tetrahydropyridin-4-yl]methoxy}-8-fluoro-3,4-dihydroquinolin-2(1H)-one Synthesized analogous to Reference Example 595.
$^1$HNMR (CDCl$_3$) δ ppm: 2.31 (2H, brs), 2.61-2.65 (2H, m), 3.02 (2H, t, J=7.7 Hz), 3.32-3.35 (2H, m), 3.72 (2H, brs), 4.43 (2H, s), 5.85 (1H, brs), 6.48 (1H, dd, J=9.1 Hz, 4.0 Hz), 6.91 (1H, t, J=9.3 Hz), 7.01-7.06 (2H, m), 7.51 (1H, brs).

Reference Example 602

8-Fluoro-5-{[1-(2,4,6-trifluorophenyl)-1,2,3,6-tetrahydropyridin-4-yl]methoxy}-3,4-dihydroquinolin-2(1H)-one Synthesized analogous to Reference Example 595.
$^1$HNMR (CDCl$_3$) δ ppm: 2.28-2.35 (2H, m), 2.60-2.66 (2H, m), 3.03 (2H, t, J=7.7 Hz), 3.31 (2H, t, J=5.5 Hz), 3.65-3.3.70 (2H, m), 4.44 (2H, brs), 5.83-5.88 (1H, m), 6.49 (1H, dd, J=9.1 Hz, 4.0 Hz), 6.60-6.69 (2H, m), 6.90 (1H, t, J=9.5 Hz), 7.49 (1H, brs).

Reference Example 603

5-{[1-(2,4-Dichloro-6-fluorophenyl)-1,2,3,6-tetrahydropyridin-4-yl]methoxy}-8-fluoro-3,4-dihydroquinolin-2(1H)-one Synthesized analogous to Reference Example 595.
$^1$HNMR (CDCl$_3$) δ ppm: 2.32 (2H, brs), 2.62-2.65 (2H, m), 3.03 (2H, t, J=7.7 Hz), 3.29-3.32 (2H, m), 3.69 (2H, brs), 4.44 (2H, s), 5.86 (1H, brs), 6.49 (1H, dd, J=9.3 Hz, 3.9 Hz), 6.91 (1H, t, J=9.3 Hz), 7.00 (1H, dd, J=11.3 Hz, 2.4 Hz), 7.20-7.21 (1H, m), 7.52 (1H, brs).

Reference Example 604

5-({1-[2,6-Difluoro-4-(2,2,2-trifluoroethoxy)phenyl]-1,2,3,6-tetrahydropyridin-4-yl}methoxy)-8-fluoro-3,4-dihydroquinolin-2(1H)-one Synthesized analogous to Reference Example 595.
$^1$HNMR (CDCl$_3$) δ ppm: 2.30-2.34 (2H, m), 2.62-2.65 (2H, m), 3.02 (2H, t, J=7.7 Hz), 3.28-3.31 (2H, m), 3.66 (2H, brs), 4.29 (2H, q, J=8.0 Hz), 4.43 (2H, s), 5.85 (1H, brs), 6.47-6.54 (3H, m), 6.91 (1H, t, J=9.5 Hz), 7.52 (1H, brs).

Reference Example 605

5-({1-[4-(Difluoromethoxy)-2,6-difluorophenyl]-1,2,3,6-tetrahydropyridin-4-yl}methoxy)-8-fluoro-3,4-dihydroquinolin-2(1H)-one Synthesized analogous to Reference Example 595.
¹HNMR (CDCl₃) δ ppm: 2.30-2.35 (2H, m), 2.62-2.65 (2H, m), 3.02 (2H, t, J=7.7 Hz), 3.31-3.34 (2H, m), 3.71 (2H, brs), 4.44 (2H, s), 5.86 (1H, brs), 6.46 (1H, t, J=73.2 Hz), 6.48 (1H, dd, J=9.1 Hz, 3.9 Hz), 6.68-6.73 (2H, m), 6.91 (1H, t, J=9.5 Hz), 7.57 (1H, brs).

Reference Example 606

5-{[1-(4-Ethoxy-2,6-difluorophenyl)-1,2,3,6-tetrahydropyridin-4-yl]methoxy}-8-fluoro-3,4-dihydroquinolin-2(1H)-one Synthesized analogous to Reference Example 595.
¹HNMR (CDCl₃) δ ppm: 1.39 (3H, t, J=6.8 Hz), 2.30-2.34 (2H, m), 2.60-2.65 (2H, m), 3.02 (2H, t, J=7.7 Hz), 3.26-3.29 (2H, m), 3.64 (2H, brs), 3.96 (2H, q, J=6.8 Hz), 4.43 (2H, s), 5.85 (1H, brs), 6.39-6.46 (2H, m), 6.49 (1H, dd, J=9.1 Hz, 4.0 Hz), 6.90 (1H, t, J=9.5 Hz), 7.56 (1H, brs).

Reference Example 607

5-{[1-(4-Chloro-2-fluorophenyl)-1,2,3,6-tetrahydropyridin-4-yl]methoxy}-7,8-difluoro-3,4-dihydroquinolin-2(1H)-one Synthesized analogous to Reference Example 595.
¹HNMR (CDCl₃) δ ppm: 2.31-2.38 (2H, m), 2.61 (2H, t, J=7.6 Hz), 2.95 (2H, t, J=7.6 Hz), 3.28 (2H, t, J=5.6 Hz), 3.63-3.68 (2H, m), 4.45 (2H, s), 5.90 (1H, brs), 6.38 (1H, dd, J=11.7 Hz, 6.3 Hz), 6.87 (1H, t, J=8.9 Hz), 7.02-7.09 (2H, m), 7.57 (1H, brs).

Reference Example 608

8-Chloro-5-{[1-(4-chloro-2-fluorophenyl)-1,2,3,6-tetrahydropyridin-4-yl]methoxy}-3,4-dihydroquinolin-2(1H)-one Synthesized analogous to Reference Example 595.
¹HNMR (CDCl₃) δ ppm: 2.32-2.39 (2H, m), 2.58 (2H, t, J=7.5 Hz), 3.00 (2H, t, J=7.5 Hz), 3.28 (2H, t, J=5.5 Hz), 3.66 (2H, s), 4.47 (2H, s), 5.90 (1H, s), 6.54 (1H, d, J=9.0 Hz), 6.86-6.91 (1H, m), 7.02-7.10 (2H, m), 7.16 (1H, d, J=9.0 Hz), 7.79 (1H, s).

Reference Example 609

5-{[1-(4-Bromo-2,6-difluorophenyl)-1,2,3,6-tetrahydropyridin-4-yl]methoxy}-8-chloro-3,4-dihydroquinolin-2(1H)-one Synthesized analogous to Reference Example 595.
¹HNMR (CDCl₃) δ ppm: 2.31 (2H, brs), 2.60-2.64 (2H, m), 3.02 (2H, t, J=7.7 Hz), 3.32-3.35 (2H, m), 3.72 (2H, brs), 4.46 (2H, s), 5.85 (1H, brs), 6.54 (1H, d, J=8.9 Hz), 7.01-7.06 (2H, m), 7.17 (1H, d, J=8.9 Hz), 7.73 (1H, brs).

Reference Example 610

5-{[1-(2-Bromo-4-chloro-6-fluorophenyl)-1,2,3,6-tetrahydropyridin-4-yl]methoxy}-8-fluoro-3,4-dihydroquinolin-2(1H)-one Synthesized analogous to Reference Example 595.
¹HNMR (DMSO-d6) δ ppm: 2.15-2.37 (2H, m), 2.42-2.49 (2H, m), 2.88 (2H, t, J=7.6 Hz), 3.17-3.29 (2H, m), 3.59 (2H, brs), 4.48 (2H, s), 5.89 (1H, brs), 6.63 (1H, dd, J=9.1 Hz, 3.8 Hz), 7.02 (1H, t, J=9.7 Hz), 7.52 (1H, dd, J=11.8 Hz, 2.4 Hz), 7.62-7.69 (1H, m), 10.03 (1H, brs).

Reference Example 611

5-{[1-(4-Chloro-2,5-difluorophenyl)-1,2,3,6-tetrahydropyridin-4-yl]methoxy}-8-fluoro-3,4-dihydroquinolin-2(1H)-one Synthesized analogous to Reference Example 592.
¹HNMR (CDCl₃) δ ppm: 2.29-2.40 (2H, m), 2.46-2.72 (2H, m), 3.01 (2H, t, J=7.6 Hz), 3.30 (2H, t, J=5.7 Hz), 3.60-3.72 (2H, m), 4.44 (2H, brs), 5.82-5.92 (1H, m), 6.47 (1H, dd, J=9.1 Hz, 4.0 Hz), 6.67-6.76 (1H, m), 6.91 (1H, t, J=9.4 Hz), 7.08 (1H, dd, J=11.7 Hz, 6.9 Hz), 7.52 (1H, brs).

Reference Example 612

5-{[1-(4-Chloro-2-fluorophenyl)-1,2,3,6-tetrahydropyridin-4-yl]methoxy}-8-fluoro-3,4-dihydroquinolin-2(1H)-one Synthesized analogous to Reference Example 592.
¹HNMR (CDCl₃) δ ppm: 2.32-2.38 (2H, m), 2.61-2.67 (2H, m), 3.00-3.05 (2H, m), 3.28-3.30 (2H, m), 3.65 (2H, brs), 4.44 (2H, s), 5.89 (1H, brs), 6.47 (1H, dd, J=9.1 Hz, 3.9 Hz), 6.86-6.93 (2H, m), 7.03-7.09 (2H, m), 7.52 (1H, brs).

Reference Example 613

4-{[tert-Butyl(dimethyl)silyl]oxy}-1-(4-chloro-2,6-difluorophenyl)-1,2,3,6-tetrahydropyridine Under nitrogen atmosphere, to a solution of potassium hexamethyldisilazide (2.05 g) in tetrahydrofuran (10 mL) was added a solution of 1-(4-chloro-2,6-difluorophenyl)piperidin-4-one (2.00 g) in tetrahydrofuran (10 mL) at −78° C., and the reaction mixture was stirred for 30 min. Then tert-butyldimethylsilyl chloride (1.35 g) was added to the reaction mixture, and the mixture was stirred at room temperature for 1.5 h. To the reaction solution were added hexane and water to extract the product. The organic layer was washed with water and brine, dried over anhydrous sodium sulfate, and the solvent was distilled of to provide the title compound (2.89 g).
¹HNMR (CDCl₃) δ ppm: 0.17 (6H, s), 0.93 (9H, s), 2.20-2.24 (2H, m), 3.29-3.32 (2H, m), 3.64-3.66 (2H, m), 4.87-4.89 (1H, m), 6.84-6.89 (2H, m).

Reference Example 614

1-(4-Bromo-2-fluorophenyl)-4-{[tert-butyl(dimethyl)silyl]oxy}-1,2,3,6-tetrahydropyridine To a solution of 1-(4-bromo-2-fluorophenyl)piperidin-4-one (20 g) in acetonitrile (60 mL), triethylamine (12.81 mL), tert-butyl dimethylchlorosilane (12.74 g) and sodium iodide (12.67 g) were added under ice-cooling. Under nitrogen atmosphere, the reaction mixture was stirred at reflux for 1 h. The reaction solution was allowed to cool to room temperature, and hexane was added thereto, filtered with Celite, and the filtrate was washed with water and brine. The organic layer was dried over anhydrous sodium sulfate, and the solvent was distilled off to provide the title compound (28.8 g).

$^1$HNMR (CDCl$_3$) δ ppm: 0.16 (6H, s), 0.93 (9H, s), 2.03-2.09 (2H, m), 3.11 (2H, t, J=5.7 Hz), 3.43 (2H, dd, J=5.7 Hz, 2.5 Hz), 4.73-4.76 (1H, m), 6.65 (1H, t, J=8.9 Hz), 6.97-7.05 (2H, m).

Reference Example 615

4-{[tert-Butyl(dimethyl)silyl]oxy}-1-(4-chloro-2-fluorophenyl)-1,2,3,6-tetrahydropyridine Synthesized analogous to Reference Example 614.
$^1$HNMR (CDCl$_3$) δ ppm: 0.16 (6H, s), 0.93 (9H, s), 2.19-2.26 (2H, m), 3.28 (2H, t, J=5.7 Hz), 3.60 (2H, dd, J=5.7 Hz, 2.5 Hz), 4.89-4.92 (1H, m), 6.88 (1H, t, J=8.9 Hz), 6.99-7.06 (2H, m).

Reference Example 616

1-(4-Bromo-2,6-difluorophenyl)-4-{[tert-butyl(dimethyl) silyl]oxy}-1,2,3,6-tetrahydropyridine Synthesized analogous to Reference Example 614.
$^1$HNMR (CDCl$_3$) δ ppm: 0.17 (6H, s), 0.93 (9H, s), 2.18-2.24 (2H, m), 3.27-3.33 (2H, m), 3.62-3.68 (2H, m), 4.86-4.89 (1H, m), 6.98-7.04 (2H, m).

Reference Example 617

(1R,6R)-3-(4-Bromo-2-fluorophenyl)-6-{[tert-butyl (dimethyl) silyl]oxy}-7-oxa-3-azabicyclo[4.1.0]heptane To a solution of potassium carbonate (9.44 g) in 32 mL of 4×10$^{-4}$ M aqueous ethylenediamine tetraacetic acid disodium salt was added a solution of 1-(4-bromo-2-fluorophenyl)-4-{[tert-butyl(dimethyl)silyl]oxy}-1,2,3,6-tetrahydropyridine (8.8 g) in acetonitrile/1-propanol/toluene (1:1:2) (95 mL). After the addition of Shi epoxidizing catalyst (1.765 g) under ice-cooling, 30% hydrogen peroxide aqueous solution (9.31 mL) was added dropwise thereto at an internal temperature of 2° C., and the reaction mixture was stirred at the same temperature for 12 h. To the reaction solution were added hexane and water to extract the product. The organic layer was washed with water, brine and sodium sulfite, dried over anhydrous sodium sulfate, and the solvent was distilled off to provide the title compound (8.79 g).

$^1$HNMR (CDCl$_3$) δ ppm: 0.14 (3H, s), 0.18 (3H, s), 0.90 (9H, s), 2.19-2.25 (1H, m), 2.29-2.36 (1H, m), 2.81-2.89 (1H, m), 3.08-3.14 (1H, m), 3.17 (1H, d, J=13.7 Hz), 3.37 (1H, d, J=4.5 Hz), 3.56-3.63 (1H, m), 6.72 (1H, t, J=9.0 Hz), 7.13-7.19 (2H, m).

Reference Example 618

(1R,6R)-6-{[tert-Butyl(dimethyl)silyl]oxy}-3-(4-chloro-2,6-difluorophenyl)-7-oxa-3-azabicyclo[4.1.0]heptane Synthesized analogous to Reference Example 617.
$^1$HNMR (CDCl$_3$) δ ppm: 0.14 (3H, s), 0.18 (3H, s), 0.90 (9H, s), 2.13-2.19 (1H, m), 2.23-2.31 (1H, m), 2.91-2.97 (1H, m), 3.07-3.14 (1H, m), 3.33-3.40 (2H, m), 3.51 (1H, dd, 13.7 Hz, 4.0 Hz), 6.83-6.90 (2H, m).

Reference Example 619

(1R*,6R*)-3-(4-Bromo-2,6-difluorophenyl)-6-{[tert-butyl(dimethyl)silyl]oxy}-7-oxa-3-azabicyclo[4.1.0]heptane To a solution of 1-(4-bromo-2,6-difluorophenyl)-4-{[tert-butyl(dimethyl)silyl]oxy}-1,2,3,6-tetrahydropyridine (7.0 g) and 1,1,1-trifluoroacetone (0.93 mL) in acetonitrile/toluene/1-propanol (1:2:1) (84 mL) was added a solution of potassium carbonate (7.18 g) and ethylenediamine tetraacetic acid disodium salt (3.9 mg) in water (26 mL) at 0° C. To the reaction mixture, 30% hydrogen peroxide aqueous solution (7.07 mL) was added dropwise at an internal temperature of 3-5° C., and the mixture was stirred at the same temperature for 9.5 h. To the reaction solution were added toluene and aqueous 1 M sodium thiosulfate to extract the product. The organic layer was washed with water and brine, and dried over anhydrous sodium sulfate, and then the solvent was distilled off to provide the title compound (6.58 g).

$^1$HNMR (CDCl$_3$) δ ppm: 0.14 (3H, s), 0.17 (3H, s), 0.90 (9H, s), 2.12-2.19 (1H, m), 2.22-2.30 (1H, m), 2.91-2.98 (1H, m), 3.06-3.14 (1H, m), 3.34 (1H, d, J=4.1 Hz), 3.37 (1H, d, J=14.1 Hz), 3.53 (1H, dd, J=14.1 Hz, 4.1 Hz), 6.97-7.03 (2H, m).

Reference Example 620

(1R,6R)-3-(4-Bromo-2,6-difluorophenyl)-6-{[tert-butyl(dimethyl)silyl]oxy}-7-oxa-3-azabicyclo[4.1.0]heptane Synthesized analogous to Reference Example 617.
$^1$HNMR (CDCl$_3$) δ ppm: 0.14 (3H, s), 0.18 (3H, s), 0.90 (9H, s), 2.14-2.18 (1H, m), 2.23-2.29 (1H, m), 2.92-2.97 (1H, m), 3.07-3.13 (1H, m), 3.35 (1H, d, J=4.0 Hz), 3.37 (1H, d, J=14.0 Hz), 3.53 (1H, dd, J=14.0 Hz, 4.0 Hz), 6.98-7.03 (2H, m).

Reference Example 621

(1R,6R)-6-{[tert-Butyl(dimethyl)silyl]oxy}-3-(4-chloro-2-fluorophenyl)-7-oxa-3-azabicyclo[4.1.0]heptane Synthesized analogous to Reference Example 617.
$^1$HNMR (CDCl$_3$) δ ppm: 0.14 (3H, s), 0.18 (3H, s), 0.90 (9H, s), 2.20-2.24 (1H, m), 2.29-2.34 (1H, m), 2.82-2.88 (1H, m), 3.07-3.11 (1H, m), 3.17 (1H, d, J=14.0 Hz), 3.37 (1H, d, J=4.3), 3.57-3.62 (1H, m), 6.79 (1H, t, J=9.2 Hz), 6.99-7.04 (2H, m).

Reference Example 622

(1R*,6R*)-6-{[tert-Butyl(dimethyl)silyl]oxy}-3-(4-chloro-2,6-difluorophenyl)-7-oxa-3-azabicyclo[4.1.0]heptane Synthesized analogous to Reference Example 619.
$^1$HNMR (CDCl$_3$) δ ppm: 0.14 (3H, s), 0.18 (3H, s), 0.90 (9H, s), 2.12-2.19 (1H, m), 2.22-2.31 (1H, m), 2.90-2.97

(1H, m), 3.06-3.15 (1H, m), 3.33-3.40 (2H, m), 3.53 (1H, dd, J=14.0 Hz, 3.2 Hz), 6.83-6.90 (2H, m).

Reference Example 623

(3R,4R)-6-(4-Chloro-2,6-difluorophenyl)-1-oxa-6-azaspiro[2.5]octan-4-ol

To a suspension of trimethylsulfoxonium iodide (3.44 g) in dimethyl sulfoxide (37 mL) was added sodium tert-butoxide (1.50 g), and the reaction mixture was stirred at room temperature for 30 min. Then a solution of (3R)-1-(4-chloro-2,6-difluorophenyl)-3-hydroxypiperidin-4-one (3.72 g, 81.7% ee) in dimethyl sulfoxide (37 mL) was added to the mixture, and the reaction mixture was stirred at room temperature for 10 min. To the reaction solution was added water, and the solution was extracted with ethyl acetate. The organic layer was washed with brine, dried over anhydrous sodium sulfate, and the solvent was distilled off. The residue was purified by silica gel column chromatography (hexane/ethyl acetate) and recrystallization from ethanol to provide the title compound (1.49 g, 98% ee).
$^1$HNMR (CDCl$_3$) δ ppm: 1.76 (1H, dt, J=14.0 Hz, 4.0 Hz), 2.05 (1H, d, J=11.0 Hz), 2.09 (1H, ddd, J=14.0 Hz, 9.5 Hz, 4.5 Hz), 2.69 (1H, d, J=4.5 Hz), 3.06 (1H, d, J=4.5 Hz), 3.06-3.10 (1H, m), 3.13-3.18 (1H, m), 3.26-3.32 (1H, m), 3.39-3.44 (1H, m), 3.85 (1H, ddd, J=11.0 Hz, 8.5 Hz, 4.5 Hz), 6.87-6.92 (2H, m).

Reference Example 624

(3R,4R)-6-(4-Chloro-2,6-difluorophenyl)-1-oxa-6-azaspiro[2.5]octan-4-ol

Synthesized analogous to Reference Example 623.
$^1$HNMR (CDCl$_3$) δ ppm: 1.76 (1H, dt, J=14.0 Hz, 4.0 Hz), 2.05 (1H, d, J=11.0 Hz), 2.09 (1H, ddd, J=14.0 Hz, 9.5 Hz, 4.5 Hz), 2.69 (1H, d, J=4.5 Hz), 3.06 (1H, d, J=4.5 Hz), 3.06-3.10 (1H, m), 3.13-3.18 (1H, m), 3.26-3.32 (1H, m), 3.39-3.44 (1H, m), 3.85 (1H, ddd, J=11.0 Hz, 8.5 Hz, 4.5 Hz), 6.87-6.92 (2H, m).

Reference Example 625

(3R,4R)-6-(4-Chloro-2-fluorophenyl)-1-oxa-6-azaspiro[2.5]octan-4-ol

To a suspension of 1-(4-chloro-2-fluorophenyl)piperidin-4-one (3.00 g) and DL-proline (0.455 g) in N,N-dimethylformamide (20 mL) was added a solution of nitrosobenzene (1.41 g) in N,N-dimethylformamide (40 mL) at 0° C. over 6 h, and the reaction mixture was stirred at the same temperature for 1 h. The reaction solution was poured into aqueous saturated ammonium chloride, and the reaction mixture was extracted with ethyl acetate. The organic layer was washed with brine, dried over anhydrous sodium sulfate, and the solvent was distilled off. The residue was dissolved in methanol (30 mL), copper (II) sulfate (0.631 g) was added to the solution and the mixture was stirred at 0° C. for 2 h. To the reaction solution was added brine and the solution was extracted with ethyl acetate. The organic layer was dried over anhydrous sodium sulfate and filtrated. To the filtrate was added dimethyl sulfoxide (30 mL) and the mixture was concentrated to give a solution of 1-(4-chloro-2-fluorophenyl)-3-hydroxypiperidin-4-one (α-hydroxyketone compound) in dimethyl sulfoxide. To a suspension of trimethylsulfoxonium iodide (3.19 g) in dimethyl sulfoxide (30 mL) was added sodium tert-butoxide (1.39 g), and the reaction mixture was stirred at room temperature for 30 min. To the obtained mixture a solution of α-hydroxyketone compound in dimethyl sulfoxide was added, and the mixture was stirred at room temperature for 30 min. To the reaction solution was added water, and the solution was extracted with ethyl acetate. The organic layer was washed with brine, dried over anhydrous sodium sulfate, and the solvent was distilled off. The residue was purified by silica gel column chromatography (hexane/ethyl acetate). The product was recrystallized from ethyl acetate/hexane to provide the title compound (647 mg).
$^1$HNMR (CDCl$_3$) δ ppm: 1.74 (1H, dt, J=14.0 Hz, 3.5 Hz), 1.97 (1H, d, J=11.0 Hz), 2.21 (1H, ddd, J=14.0 Hz, 10.5 Hz, 4.5 Hz), 2.72 (1H, d, J=4.5 Hz), 2.80 (1H, dd, J=11.0 Hz, 9.0 Hz), 2.99-3.04 (1H, m), 3.10 (1H, d, J=4.5 Hz), 3.24-3.29 (1H, m), 3.47-3.52 (1H, m), 3.96 (1H, ddd, J=11.0 Hz, 9.0 Hz, 4.5 Hz), 6.91 (1H, t, J=9.0 Hz), 7.04-7.08 (2H, m).

Reference Example 626

(3R,4R)-6-(4-Bromo-2-fluorophenyl)-1-oxa-6-azaspiro[2.5]octan-4-ol

Synthesized analogous to Reference Example 625.
$^1$HNMR (CDCl$_3$) δ ppm: 1.74 (1H, dt, J=14.0 Hz, 3.5 Hz), 1.96 (1H, d, J=11.0 Hz), 2.21 (1H, ddd, J=14.0 Hz, 11.0 Hz, 4.5 Hz), 2.72 (1H, d, J=4.5 Hz), 2.80 (1H, dd, J=11.0 Hz, 9.0 Hz), 2.98-3.04 (1H, m), 3.10 (1H, d, J=4.5 Hz), 3.24-3.29 (1H, m), 3.48-3.52 (1H, m), 3.96 (1H, ddd, J=11.0 Hz, 9.0 Hz, 4.5 Hz), 6.85 (1H, t, J=9.0 Hz), 7.18-7.20 (2H, m).

Reference Example 627

(3R,4R)-6-(4-Bromo-2-fluorophenyl)-1-oxa-6-azaspiro[2.5]octan-4-ol

To a solution of 1-(4-bromo-2-fluorophenyl)-4-{[tert-butyl(diphenyl) silyl]oxy}-1,2,3,6-tetrahydropyridine (34.2 g) in acetonitrile-dimethoxymethane (240-240 mL) were added at 0° C., 240 mL of buffer (0.05 M aqueous sodium tetraborate decahydrate in 4×10$^{-4}$ M aqueous ethylenediamine tetraacetic acid disodium salt), Shi epoxidizing catalyst (6.86 g), and tetrabutylammonium hydrogensulfate (0.910 g). Thereafter, a solution of Oxone (Registered trade mark) (56.8 g) in 300 mL of 4×10$^{-4}$ M aqueous ethylenediamine tetraacetic acid disodium salt and a solution of potassium carbonate (53.7 g) in water (300 mL) were added dropwise through two separate addition funnels over 2 h, and then the mixture was stirred at 0° C. for 2 h. To the reaction solution were added ice-cooled hexane and ice-cooled water to extract the product. The organic layer was washed with brine, dried over anhydrous sodium sulfate, and the solvent was distilled off. The residue was dissolved in tetrahydrofuran-water (175-140 mL), 5 N hydrochloric acid (35 mL) was added to the solution, and the mixture was stirred at room temperature for 1 h. To the reaction solution was added water, and the reaction mixture was extracted with ethyl acetate. The organic layer was washed with brine, dried over anhydrous sodium sulfate, and filtrated. To the filtrate was added dimethyl sulfoxide (160 mL) and the solution was concentrated to give a solution of (R)-1-(4-bromo-2-fluorophenyl)-3-hydroxypiperidin-4-one (α-hydroxyketone compound) in dimethyl sulfoxide. To a suspension of trimethylsulfonium iodide (16.2 g) in dimethyl sulfoxide (160 mL) was added sodium tert-butoxide (7.08 g), and the reaction mixture was stirred at room temperature for 30 min. The solution of α-hydroxyketone compound in dimethyl sulfoxide was added to the mixture, and the obtained mixture was stirred at room temperature for 15 min. To the reaction solution was added water, and the solution was extracted with ethyl acetate. The organic layer was washed with water and brine, dried over anhydrous sodium sulfate, and the solvent was distilled off. The residue was purified by silica gel column chromatography (hexane/ethyl acetate) and recrystallized from ethyl acetate/hexane to provide the title compound (3.27 g, 99% ee).

$^1$HNMR (CDCl$_3$) δ ppm: 1.74 (1H, dt, J=14.0 Hz, 3.5 Hz), 1.96 (1H, d, J=11.0 Hz), 2.21 (1H, ddd, J=14.0 Hz, 11.0 Hz, 4.5 Hz), 2.72 (1H, d, J=4.5 Hz), 2.80 (1H, dd, J=11.0 Hz, 9.0 Hz), 2.98-3.04 (1H, m), 3.10 (1H, d, J=4.5 Hz), 3.24-3.29 (1H, m), 3.48-3.52 (1H, m), 3.96 (1H, ddd, J=11.0 Hz, 9.0 Hz, 4.5 Hz), 6.85 (1H, t, J=9.0 Hz), 7.18-7.20 (2H, m).

Reference Example 628

(3R,4R)-6-(4-Bromo-2,6-difluorophenyl)-1-oxa-6-azaspiro[2.5]octan-4-ol

Synthesized analogous to Reference Example 625.
$^1$HNMR (CDCl$_3$) δ ppm: 1.76 (1H, dt, J=14.0 Hz, 4.0 Hz), 2.05 (1H, d, J=11.0 Hz), 2.09 (1H, ddd, J=14.0 Hz, 10.0 Hz, 4.5 Hz), 2.69 (1H, d, J=4.5 Hz), 3.06 (1H, d, J=4.5 Hz), 3.06-3.10 (1H, m), 3.14-3.19 (1H, m), 3.26-3.32 (1H, m), 3.40-3.44 (1H, m), 3.85 (1H, ddd, J=11.0 Hz, 8.5 Hz, 4.5 Hz), 7.02-7.07 (2H, m).

Reference Example 629

(3R,4R)-6-(4-Bromo-2,6-difluorophenyl)-1-oxa-6-azaspiro[2.5]octan-4-ol

Synthesized analogous to Reference Example 627.
$^1$HNMR (CDCl$_3$) δ ppm: 1.76 (1H, dt, J=14.0 Hz, 4.0 Hz), 2.05 (1H, d, J=11.0 Hz), 2.09 (1H, ddd, J=14.0 Hz, 10.0 Hz, 4.5 Hz), 2.69 (1H, d, J=4.5 Hz), 3.06 (1H, d, J=4.5 Hz), 3.06-3.10 (1H, m), 3.14-3.19 (1H, m), 3.26-3.32 (1H, m), 3.40-3.44 (1H, m), 3.85 (1H, ddd, J=11.0 Hz, 8.5 Hz, 4.5 Hz), 7.02-7.07 (2H, m).

Reference Example 630

(3R,4R)-6-(4-Chloro-2-fluorophenyl)-1-oxa-6-azaspiro[2.5]octan-4-ol

Synthesized analogous to Reference Example 627.
$^1$HNMR (CDCl$_3$) δ ppm: 1.74 (1H, dt, J=14.0 Hz, 3.5 Hz), 1.97 (1H, d, J=11.0 Hz), 2.21 (1H, ddd, J=14.0 Hz, 10.5 Hz, 4.5 Hz), 2.72 (1H, d, J=4.5 Hz), 2.80 (1H, dd, J=11.0 Hz, 9.0 Hz), 2.99-3.04 (1H, m), 3.10 (1H, d, J=4.5 Hz), 3.24-3.29 (1H, m), 3.47-3.52 (1H, m), 3.96 (1H, ddd, J=11.0 Hz, 9.0 Hz, 4.5 Hz), 6.91 (1H, t, J=9.0 Hz), 7.04-7.08 (2H, m).

Reference Example 631

(3R*,4R*)-6-(4-fluorophenyl)-1-oxa-6-azaspiro[2.5]octan-4-ol

Synthesized analogous to Reference Example 625.
$^1$HNMR (CDCl$_3$) δ ppm: 1.74 (1H, dt, J=14.0 Hz, 4.0 Hz), 1.94 (1H, d, J=11.0 Hz), 2.17 (1H, ddd, J=14.0 Hz, 10.5 Hz, 4.5 Hz), 2.71 (1H, d, J=4.5 Hz), 2.83 (1H, dd, J=11.5 Hz, 9.0 Hz), 3.04-3.09 (1H, m), 3.09 (1H, d, J=4.5 Hz), 3.34-3.38 (1H, m), 3.60-3.63 (1H, m), 3.96 (1H, ddd, J=11.0 Hz, 9.5 Hz, 4.5 Hz), 6.91-7.00 (4H, m).

Reference Example 632

(3R,4R)-6-(4-Fluorophenyl)-1-oxa-6-azaspiro[2.5]octan-4-ol

To a suspension of 1-(4-fluorophenyl)piperidin-4-one (10.3 g) and (S)-5-(pyrrolidin-2-yl)-1H-tetrazole (0.371 g) in N,N-dimethylformamide (100 mL) was added a solution of nitrosobenzene (5.71 g) in N,N-dimethylformamide (100 mL) over 6.5 h at −20° C., and the reaction mixture was stirred at the same temperature for 1 h. The reaction solution was poured into ice-cooled aqueous saturated ammonium chloride, and the reaction mixture was extracted with ethyl acetate. The organic layer was washed with brine, dried over anhydrous sodium sulfate, and the solvent was distilled off. The residue was dissolved in methanol (100 mL), copper (II) sulfate (2.55 g) was added to the solution and the mixture was stirred at 0° C. for 2 h. To the reaction solution was added brine, and the solution was extracted with ethyl acetate. The organic layer was dried over anhydrous sodium sulfate and filtrated. To the filtrate was added dimethyl sulfoxide (100 mL) and the mixture was concentrated to give a solution of (R)-1-(4-fluorophenyl)-3-hydroxypiperidin-4-one (α-hydroxyketone compound) in dimethyl sulfoxide. To a suspension of trimethylsulfonium iodide (12.9 g) in dimethyl sulfoxide (100 mL) was added sodium tert-butoxide (5.64 g), and the mixture was stirred at 1 h. To the mixture was added the solution of α-hydroxyketone compound in dimethyl sulfoxide and the reaction mixture was stirred at room temperature for 15 min. To the reaction solution was added water, and the solution was extracted with ethyl acetate. The organic layer was washed with brine, dried over anhydrous sodium sulfate, and the solvent was distilled off. The residue was purified by silica gel column chromatography (hexane/ethyl acetate) and recrystallized from ethyl acetate/hexane to provide the title compound (1.01 g, >99% ee).

$^1$HNMR (CDCl$_3$) δ ppm: 1.74 (1H, dt, J=14.0 Hz, 4.0 Hz), 1.94 (1H, d, J=11.0 Hz), 2.17 (1H, ddd, J=14.0 Hz, 10.5 Hz, 4.5 Hz), 2.71 (1H, d, J=4.5 Hz), 2.83 (1H, dd, J=11.5 Hz, 9.0 Hz), 3.04-3.09 (1H, m), 3.09 (1H, d, J=4.5 Hz), 3.34-3.38 (1H, m), 3.60-3.63 (1H, m), 3.96 (1H, ddd, J=11.0 Hz, 9.5 Hz, 4.5 Hz), 6.91-7.00 (4H, m).

Reference Example 633 tert-Butyl (1S*,6S*)-6-{[(8-fluoro-2-oxo-1,2,3,4-tetrahydroquinolin-5-yl)oxy]methyl}-7-oxa-3-azabicyclo[4.1.0]heptane-3-carboxylate To a solution of tert-butyl 4-{[(8-fluoro-2-oxo-1,2,3,4-tetrahydroquinolin-5-yl)oxy]methyl}-3,6-dihydropyridine-1(2H)-carboxylate (3.06 g) in chloroform (30 mL) was added 75% meta-chloroperoxybenzoic acid (2.81 g) and the reaction mixture was stirred at room temperature overnight. After insoluble materials were filtered off, the filtrate was concentrated, and the residue was purified by silica gel column chromatography (hexane/ethyl acetate) to provide the title compound (2.8 g).

$^1$HNMR (CDCl$_3$) δ ppm: 1.47 (9H, s), 1.96-2.06 (1H, m), 2.07-2.20 (1H, m), 2.59-2.67 (2H, m), 2.96-3.03 (2H, m), 3.06-3.22 (1H, m), 3.25-3.37 (1H, m), 3.51-3.80 (2H, m), 3.82-4.16 (3H, m), 6.42 (1H, dd, J=9.1 Hz, 3.9 Hz), 6.90 (1H, t, J=9.3 Hz), 7.59 (1H, brs).

Reference Example 634 tert-Butyl (1S*,6S*)-6-({[8-fluoro-1-(4-methoxybenzyl)-2-oxo-1,2,3,4-tetrahydroquinolin-5-yl]oxy}methyl)-7-oxa-3-azabicyclo[4.1.0]heptane-3-carboxylate Synthesized analogous to Reference Example 633.
$^1$HNMR (CDCl$_3$) δ ppm: 1.46 (9H, s), 1.94-2.04 (1H, m), 2.06-2.18 (1H, m), 2.58-2.68 (2H, m), 2.81-2.91 (2H, m), 3.06-3.20 (1H, m), 3.24-3.39 (1H, m), 3.51-3.79 (2H, m), 3.74 (3H, s), 3.82-4.18 (3H, m), 5.17-5.27 (2H, m), 6.47 (1H, dd, J=9.1 Hz, 3.3 Hz), 6.72-6.78 (2H, m), 6.82 (1H, dd, J=12.7 Hz, 9.1 Hz), 7.08-7.15 (2H, m).

Reference Example 635 tert-Butyl (3R*,4S*)-4-{[(8-fluoro-2-oxo-1,2,3,4-tetrahydroquinolin-5-yl)oxy]methyl}-3,4-dihydroxypiperidine-1-carboxylate To a solution of tert-butyl (1S*,6S*)-6-({[8-fluoro-1-(4-methoxybenzyl)-2-oxo-1,2,3,4-tetrahydroquinolin-5-yl]oxy}methyl)-7-oxa-3-azabicyclo[4.1.0]heptane-3-carboxylate (9.3 g) in anisole (0.4 mL) was added trifluoroacetic acid (40 mL) dropwise, the reaction mixture was stirred while heating at 60° C. for 3 h, and the solvent was distilled off. To the residue, methanol (40 mL) and triethylamine (7.6 mL) followed by di-tert-butyl dicarbonate (4.6 mL) were added, and the reaction mixture was stirred at room temperature overnight. To the reaction solution was added 5 N aqueous sodium hydroxide and the reaction mixture was stirred at 60° C. for 15 h. After the reaction mixture was allowed to cool to room temperature, the precipitate was collected on a filter and purified by silica gel column chromatography (dichloromethane/ethyl acetate) to provide the title compound (2.0 g).
$^1$HNMR (DMSO-d6) δ ppm: 1.32-1.39 (1H, m), 1.39 (9H, s), 1.66-1.79 (1H, m), 2.40-2.48 (2H, m), 2.86-3.00 (2H, m), 3.38-3.43 (1H, m), 3.52-3.82 (5H, m), 3.86-3.94 (1H, m), 4.82 (1H, brs), 4.86-4.96 (1H, m), 6.54 (1H, dd, J=9.1 Hz, 3.8 Hz), 6.98 (1H, t, J=9.2 Hz), 9.98 (1H, brs).

Reference Example 636 tert-Butyl (3R*,4S*)-4-({[8-fluoro-1-(4-methoxybenzyl)-2-oxo-1,2,3,4-tetrahydroquinolin-5-yl]oxy}methyl)-3,4-dihydroxypiperidine-1-carboxylate Synthesized analogous to Reference Example 43.
$^1$HNMR (CDCl$_3$) δ ppm: 1.47 (9H, s), 1.50-1.57 (1H, m), 1.83-1.92 (1H, m), 2.38 (1H, brs), 2.65 (2H, t, J=7.1 Hz), 2.80-2.91 (2H, m), 3.12-3.24 (1H, m), 3.34-3.51 (1H, m), 3.71-3.79 (2H, m), 3.74 (3H, s), 3.86-4.09 (3H, m), 5.23 (2H, brs), 6.55 (1H, dd, J=9.2 Hz, 3.4 Hz), 6.74-6.78 (2H, m), 6.83 (1H, dd, J=12.3 Hz, 9.2 Hz), 7.10-7.14 (2H, m).

Reference Example 637 tert-Butyl (3R*,4S*)-3-{[tert-butyl(dimethyl)silyl]oxy}-4-({[8-fluoro-1-(4-methoxybenzyl)-2-oxo-1,2,3,4-tetrahydroquinolin-5-yl]oxy}methyl)-4-hydroxypiperidine-1-carboxylate Synthesized analogous to Reference Example 530.
$^1$HNMR (CDCl$_3$) δ ppm: −0.15 (3H, s), 0.09-0.17 (3H, m), 0.76-0.86 (9H, m), 1.46 (9H, s), 1.47-1.55 (1H, m), 1.86-1.97 (1H, m), 2.28 (1H, brs), 2.57-2.70 (2H, m), 2.82-2.90 (2H, m), 3.07-3.39 (2H, m), 3.62-3.72 (2H, m), 3.73 (3H, s), 3.79-3.92 (1H, m), 3.93-4.08 (2H, m), 5.23 (2H, brs), 6.46 (1H, dd, J=9.1 Hz, 3.4 Hz), 6.72-6.78 (2H, m), 6.84 (1H, dd, J=12.6 Hz, 9.2 Hz), 7.09-7.14 (2H, m).

Reference Example 638

5-({(3R*,4S*)-3-{[tert-Butyl(dimethyl)silyl]oxy}-4-[(trimethylsilyl)oxy]piperidin-4-yl}methoxy)-8-fluoro-1-(4-methoxybenzyl)-3,4-dihydroquinolin-2(1H)-one Synthesized analogous to Reference Example 539.
$^1$HNMR (CDCl$_3$) δ ppm: −0.17 (3H, s), 0.04 (3H, s), 0.05 (9H, s), 0.81 (9H, s), 1.39-1.45 (1H, m), 1.69-1.77 (1H, m), 2.62 (2H, t. J=7.0 Hz), 2.65-2.71 (1H, m), 2.79-2.98 (4H, m), 3.12-3.17 (1H, m), 3.61-3.66 (2H, m), 3.73 (3H, s), 3.91 (1H, d, J=9.4 Hz), 5.12-5.32 (2H, m), 6.41 (1H, dd, J=9.2 Hz, 3.3 Hz), 6.71-6.76 (2H, m), 6.82 (1H, dd, J=12.6 Hz, 9.2 Hz), 7.08-7.13 (2H, m).

Reference Example 639

5-{[(3R*,4S*)-3-{[tert-Butyl(dimethyl)silyl]oxy}-1-(4-chloro-2-fluorophenyl)-4-hydroxypiperidin-4-yl]methoxy}-8-fluoro-1-(4-methoxybenzyl)-3,4-dihydroquinolin-2(1H)-one Synthesized analogous to Reference Example 70.
$^1$HNMR (CDCl$_3$) δ ppm: −0.11 (3H, s), 0.02 (3H, s), 0.78 (9H, s), 1.60-1.68 (1H, m), 2.19-2.27 (1H, m), 2.30 (1H, brs), 2.59-2.70 (2H, m), 2.83-2.92 (2H, m), 3.11-3.27 (3H, m), 3.32-3.37 (1H, m), 3.73 (3H, s), 3.77-3.81 (1H, m), 3.82-3.86 (1H, m), 4.03-4.09 (1H, m), 5.23 (2H, brs), 6.49 (1H, dd, J=9.2 Hz, 3.3 Hz), 6.73-6.78 (2H, m), 6.81-6.90 (2H, m), 6.98-7.05 (2H, m), 7.09-7.16 (2H, m).

Reference Example 640

5-{[(3R*,4S*)-3-{[tert-Butyl(dimethyl)silyl]oxy}-1-(2,4-dichlorophenyl)-4-hydroxypiperidin-4-yl]methoxy}-8-fluoro-1-(4-methoxybenzyl)-3,4-dihydroquinolin-2(1H)-one Synthesized analogous to Reference Example 70.
$^1$HNMR (CDCl$_3$) δ ppm: −0.06 (3H, s), 0.01 (3H, s), 0.81 (9H, s), 1.64-1.71 (1H, m), 2.26-2.32 (2H, m), 2.61-2.72 (2H, m), 2.87-2.92 (2H, m), 2.93-2.99 (1H, m), 3.03-3.10 (1H, m), 3.13-3.19 (1H, m), 3.40-3.46 (1H, m), 3.76 (3H, s), 3.89 (1H, d, J=9.0 Hz), 3.92-3.95 (1H, m), 4.10 (1H, d, =9.0 Hz), 5.26 (2H, brs), 6.53 (1H, dd, J=9.2 Hz, 3.2 Hz), 6.75-6.80 (2H, m), 6.87 (1H, dd, J=12.7 Hz, 9.1 Hz), 6.97 (1H, d, J=8.7 Hz), 7.12-7.16 (2H, m), 7.19 (1H, dd, J=8.7 Hz, 2.5 Hz), 7.37 (1H, d, J=2.5 Hz).

Reference Example 641

5-{[(3R*,4S*)-3-{[tert-Butyl(dimethyl)silyl]oxy}-1-(4-chloro-2,5-difluorophenyl)-4-hydroxypiperidin-4-yl]methoxy}-8-fluoro-1-(4-methoxybenzyl)-3,4-dihydroquinolin-2(1H)-one Synthesized analogous to Reference Example 70.
$^1$HNMR (CDCl$_3$) δ ppm: −0.13 (3H, s), 0.01 (3H, s), 0.75 (9H, s), 1.59-1.64 (1H, m), 2.16-2.24 (1H, m), 2.30 (1H, s), 2.59-2.70 (2H, m), 2.83-2.89 (2H, m), 3.17-3.31 (3H, m), 3.36 (1H, dd, J=12.7 Hz, 2.2 Hz), 3.73 (3H, s), 3.75 (1H, d, J=8.9 Hz), 3.79-3.83 (1H, m), 4.04 (1H, d, J=8.9 Hz), 5.23 (2H, brs), 6.48 (1H, dd, J=9.1 Hz, 3.3 Hz), 6.71 (1H, dd, J=10.9 Hz, 7.7 Hz), 6.73-6.77 (2H, m), 6.85 (1H, dd, J=12.7 Hz, 9.1 Hz), 7.03 (1H, dd, J=11.9 Hz, 7.0 Hz), 7.09-7.14 (2H, m).

Reference Example 642

8-Fluoro-1-(4-methoxybenzyl)-5-[(trimethylsilyl)ethinyl]-3,4-dihydroquinolin-2(1H)-one Under nitrogen atmosphere, to a solution of 8-fluoro-1-(4-methoxybenzyl)-2-oxo-1,2,3,4-tetrahydroquinolin-5-yl trifluoromethanesulfonate (433 mg), trimethylsilylacetylene (0.166 mL), bis(triphenylphosphine)palladium (II) dichloride (70 mg) and copper (I) iodide (38 mg) in N-methyl-2-pyrrolidone (3 mL) was added triethylamine (0.697 mL), and the mixture was stirred at 50° C. for 18 h. The reaction solution was poured into 1 N hydrochloric acid, and the solution was extracted with dichloromethane. The organic layer was washed with water and brine, and dried over anhydrous sodium sulfate, and then the solvent was distilled off. The residue was purified by silica gel column chromatography (hexane/ethyl acetate) to provide the title compound (222 mg).
$^1$HNMR (CDCl$_3$) δ ppm: 0.25 (9H, s), 2.66-2.69 (2H, m), 3.03-3.06 (2H, m), 3.74 (3H, s), 5.22 (2H, brs), 6.73-6.79 (2H, m), 6.80-6.85 (1H, m), 7.08-7.12 (3H, m).

Reference Example 643

5-Ethinyl-8-fluoro-1-(4-methoxybenzyl)-3,4-dihydroquinolin-2(1H)-one

To a solution of 8-fluoro-1-(4-methoxybenzyl)-5-[(trimethylsilyl)ethinyl]-3,4-dihydroquinolin-2(1H)-one (220 mg) in tetrahydrofuran (2 mL) was added tetrabutylammonium fluoride (1 M tetrahydrofuran solution) (0.692 mL), and the mixture was stirred at room temperature for 1 h. To the reaction solution was added water, and the solution was extracted with ethyl acetate. The organic layer was washed with water and brine, and dried over anhydrous sodium sulfate, and then the solvent was distilled off. The residue was purified by silica gel column chromatography (hexane/ethyl acetate) to provide the title compound (16 mg).
$^1$HNMR (CDCl$_3$) δ ppm: 2.66-2.70 (2H, m), 3.06-3.09 (2H, m), 3.24 (1H, s), 3.74 (3H, s), 5.22 (2H, brs), 6.74-6.76 (2H, m), 6.83-6.88 (1H, m), 7.09-7.15 (3H, m).

Reference Example 644

5-{[1-(4-Chloro-2,6-difluorophenyl)-4-hydroxypiperidin-4-yl]ethinyl}-8-fluoro-1-(4-methoxybenzyl)-3,4-dihydroquinolin-2(1H)-one To a solution of 5-ethinyl-8-fluoro-1-(4-methoxybenzyl)-3,4-dihydroquinolin-2(1H)-one (166 mg) in tetrahydrofuran (2 mL), n-butyllithium (1.6 M hexane solution) (0.351 mL) was added dropwise at −60° C., and the reaction mixture was stirred at the same temperature for 1 h. To the mixture was added a solution of 1-(4-chloro-2,6-difluorophenyl)piperidin-4-one (120 mg) in tetrahydrofuran (1 mL) dropwise, and the reaction mixture was stirred at −60° C. for 2 h, then at room temperature for 18 h. To the reaction solution was added aqueous saturated ammonium chloride, and the solution was extracted with ethyl acetate. The organic layer was washed with water and brine, dried over anhydrous sodium sulfate, and then the solvent was distilled off. The residue was purified by silica gel column chromatography (hexane/ethyl acetate) to provide the title compound (110 mg).
$^1$HNMR (CDCl$_3$) δ ppm: 1.97-2.04 (2H, m), 2.08-2.12 (3H, m), 2.67-2.71 (2H, m), 3.04-3.07 (2H, m), 3.21-3.31 (4H, m), 3.74 (3H, s), 5.23 (2H, brs), 6.72-6.77 (2H, m), 6.84-6.89 (3H, m), 7.08-7.12 (3H, m).

Reference Example 645

5-{2-[1-(4-Chloro-2,6-difluorophenyl)-4-hydroxypiperidin-4-yl]ethyl}-8-fluoro-1-(4-methoxybenzyl)-3,4-dihydroquinolin-2(1H)-one To a solution of 5-{[1-(4-chloro-2,6-difluorophenyl)-4-hydroxypiperidin-4-yl]ethinyl}-8-fluoro-1-(4-methoxybenzyl)-3,4-dihydroquinolin-2(1H)-one (0.105 g) in ethanol (2 mL) was added palladium-carbon ethylenediamine complex (palladium 3.5-6.5%) (50 mg), and the reaction mixture was stirred at room temperature for 1 h under hydrogen atmosphere. The catalyst was filtered off with Celite, and the filtrate was concentrated to provide the title compound (99 mg).
$^1$HNMR (CDCl$_3$) δ ppm: 1.64-1.69 (4H, m), 1.77-1.85 (2H, m), 2.63-2.70 (4H, m), 2.82-2.85 (2H, m), 3.02-3.06 (2H, m), 3.33-3.38 (2H, m), 3.74 (3H, s), 5.21 (2H, s), 6.74-6.77 (2H, m), 6.81-6.90 (4H, m), 7.12 (2H, d, J=8.5 Hz).

Reference Example 646

O-[8-Fluoro-1-(4-methoxybenzyl)-2-oxo-1,2,3,4-tetrahydroquinolin-5-yl]dimethylcarbamothioate Under argon atmosphere, to a solution of 8-fluoro-5-hydroxy-1-(4-methoxybenzyl)-3,4-dihydroquinolin-2(1H)-one (5.0 g) in N,N-dimethylformamide (50 mL) was added sodium hydride (55% in oil) (0.796 g) under ice-cooling, and the reaction mixture was stirred at room temperature for 45 min. To the reaction mixture, a solution of dimethylthiocarbamoyl chloride (3.28 g) in N,N-dimethylformamide (5 mL) was added dropwise, and the mixture was stirred at 60° C. for 2.5 h. The reaction solution was poured into cold ammonium chloride aqueous solution, and hexane was added to the mixture and the obtained solution was stirred. The precipitate was collected on a filter to provide the title compound (6.40 g).
$^1$HNMR (CDCl$_3$) δ ppm: 2.63-2.68 (2H, m), 2.68-2.73 (2H, m), 3.34 (3H, s), 3.45 (3H, s), 3.74 (3H, s), 5.22 (2H, brs), 6.67 (1H, dd, J=9.0 Hz, 3.9 Hz), 6.74-6.79 (2H, m), 6.91 (1H, dd, J=12.4 Hz, 9.0 Hz), 7.09-7.15 (2H, m).

Reference Example 647

S-[8-Fluoro-1-(4-methoxybenzyl)-2-oxo-1,2,3,4-tetrahydroquinolin-5-yl]dimethylcarbamothioate Under argon atmosphere, a suspension of O-[8-fluoro-1-(4-methoxybenzyl)-2-oxo-1,2,3,4-tetrahydroquinolin-5-yl]dimethylcarbamothioate (3.0 g) in diphenyl ether (15 mL) was stirred at 200° C. for 5 days. To the reaction solution was added hexane, and after stirring the mixture, the supernatant thereof was removed by decantation. The residue was purified by silica gel column chromatography (hexane/ethyl acetate) to provide the title compound (1.15 g).

¹HNMR (CDCl₃) δ ppm: 2.63-2.70 (2H, m), 2.93-3.06 (5H, m), 3.10 (3H, brs), 3.74 (3H, s), 5.20 (2H, brs), 6.75-6.79 (2H, m), 6.90 (1H, dd, J=12.6 Hz, 8.6 Hz), 7.10-7.14 (2H, m), 7.16 (1H, dd, J=8.6 Hz, 4.7 Hz).

Reference Example 648

8-Fluoro-1-(4-methoxybenzyl)-5-sulfanyl-3,4-dihydroquinolin-2(1H)-one

Under argon atmosphere, to a suspension of S-[8-fluoro-1-(4-methoxybenzyl)-2-oxo-1,2,3,4-tetrahydroquinolin-5-yl]dimethylcarbamothioate (1.15 g) in methanol/water (1:1) (20 mL) was added 5 N aqueous sodium hydroxide (2.96 mL) and the reaction mixture was heated to reflux for 3 h. The reaction solution was poured into ice water and was made weak acidic with 5 N hydrochloric acid, and the precipitate was collected on a filter. The obtained solid was dissolved into dichloromethane, dried over anhydrous sodium sulfate, and then the solvent was distilled off. The residue was washed with hexane/diisopropyl ether to provide the title compound (0.83 g).
¹HNMR (CDCl₃) δ ppm: 2.63-2.70 (2H, m), 2.90-2.97 (2H, m), 3.24 (1H, s), 3.74 (3H, s), 5.21 (2H, brs), 6.73-6.77 (2H, m), 6.80 (1H, dd, J=12.7 Hz, 8.7 Hz), 6.98 (1H, dd, J=8.7 Hz, 4.4 Hz), 7.07-7.12 (2H, m).

Reference Example 649

5-({[1-(4-Chloro-2-fluorophenyl)-4-hydroxypiperidin-4-yl]methyl}sulfanyl)-8-fluoro-1-(4-methoxybenzyl)-3,4-dihydroquinolin-2(1H)-one Synthesized analogous to Reference Example 453.
¹HNMR (CDCl₃) δ ppm: 1.67-1.81 (4H, m), 1.99 (1H, s), 2.63-2.69 (2H, m), 2.97-3.04 (4H, m), 3.06-3.11 (2H, m), 3.11-3.17 (2H, m), 3.71 (3H, s), 5.21 (2H, brs), 6.72-6.76 (2H, m), 6.84-6.91 (2H, m), 7.01-7.06 (2H, m), 7.07-7.12 (2H, m), 7.16 (1H, dd, J=8.7 Hz, 4.5 Hz).

Reference Example 650

5-({[1-(4-Chloro-2-fluorophenyl)-4-hydroxy-1-oxidepiperidin-4-yl]methyl}sulfonyl)-8-fluoro-3,4-dihydroquinolin-2(1H)-one To a suspension of 5-({[1-(4-chloro-2-fluorophenyl)-4-hydroxypiperidin-4-yl]methyl}sulfanyl)-8-fluoro-3,4-dihydroquinolin-2(1H)-one (0.25 g) in chloroform (10 mL) was added m-chloroperoxybenzoic acid (contain 25% water) (0.419 g) and the reaction mixture was stirred at room temperature for 7.5 h. The solvent was distilled off, the residue was washed with saturated aqueous sodium hydrogencarbonate and ethyl acetate, and crystallized from ethyl acetate to provide the title compound (0.25 g).
¹HNMR (DMSO-d6) δ ppm: 1.73-1.85 (2H, m), 2.51-2.60 (2H, m), 2.63-2.75 (2H, m), 2.76-2.86 (2H, m), 3.30-3.45 (2H, m), 3.57 (2H, s), 4.10-4.21 (2H, m), 4.70-5.50 (1H, broad signal), 7.37 (1H, t, J=9.4 Hz), 7.48 (1H, dd, J=8.9 Hz, 2.2 Hz), 7.58 (1H, dd, J=8.9 Hz, 5.1 Hz), 7.64 (1H, dd, J=12.4 Hz, 2.2 Hz), 8.71 (1H, t, J=9.2 Hz), 10.41 (1H, brs).

Reference Example 651 tert-Butyl (3R*,4R*)-4-{[(8-fluoro-2-oxo-1,2,3,4-tetrahydroquinolin-5-yl)oxy]methyl}-4-hydroxy-3-(methylamino) piperidine-1-carboxylate To tert-butyl (1S*,6S*)-6-{[(8-fluoro-2-oxo-1,2,3,4-tetrahydroquinolin-5-yl)oxy]methyl}-7-oxa-3-azabicyclo[4.1.0]heptane-3-carboxylate (0.39 g) was added 40% methylamine in methanol (30 mL) and the reaction mixture was heated to reflux for 6 h. The reaction solvent was distilled off to provide the title compound. The compound was used for the next step without further purification.
¹HNMR (CDCl₃) δ ppm: 1.47 (9H, s), 1.49-1.82 (4H, m), 2.42 (3H, s), 2.47-2.57 (1H, m), 2.64 (2H, t, J=7.9 Hz), 2.99 (2H, t, J=7.9 Hz), 3.13-3.52 (2H, m), 3.62-4.02 (3H, m), 4.06-4.18 (1H, m), 6.52 (1H, dd, J=9.1 Hz, 4.0 Hz), 6.91 (1H, t, J=9.3 Hz), 7.66 (1H, brs).

Reference Example 652

8-Fluoro-5-{[(3R*,4R*)-4-hydroxy-3-(methylamino) piperidin-4-yl]methoxy}-3,4-dihydroquinolin-2(1H)-one dihydrochloride Synthesized analogous to Reference Example 456.
¹HNMR (DMSO-d6) δ ppm: 1.81-1.93 (1H, m), 2.30-2.40 (1H, m), 2.42-2.49 (2H, m), 2.70 (3H, brs), 2.89-2.98 (2H, m), 3.10-3.30 (3H, m), 3.46-3.55 (1H, m), 3.56-3.68 (1H, m), 4.09-4.25 (3H, m), 6.63-6.72 (1H, m), 7.03-7.12 (1H, m), 8.91 (1H, brs), 9.51 (1H, brs), 9.59 (1H, brs), 9.83 (1H, brs), 10.05 (1H, brs).

Reference Example 653 tert-Butyl (3R*,4R*)-3-amino-4-{[(8-fluoro-2-oxo-1,2,3,4-tetrahydroquinolin-5-yl)oxy]methyl}-4-hydroxypiperidine-1-carboxylate Synthesized analogous to Reference Example 651.
¹HNMR (CDCl₃) δ ppm: 1.47 (9H, s), 1.49-1.74 (3H, m), 1.79-1.91 (1H, m), 2.26-2.42 (1H, m), 2.64 (2H, t, J=7.9 Hz), 2.93-3.06 (3H, m), 3.18-3.34 (1H, m), 3.47-3.79 (2H, m), 3.80-3.98 (2H, m), 4.09-4.19 (1H, m), 6.51 (1H, dd, J=9.1 Hz, 4.0 Hz), 6.92 (1H, t, J=9.4 Hz), 7.57 (1H, brs).

Reference Example 654

5-{[(3R*,4R*)-3-Amino-4-hydroxypiperidin-4-yl]methoxy}-8-fluoro-3,4-dihydroquinolin-2(1H)-one dihydrochloride Synthesized analogous to Reference Example 456.
¹HNMR (DMSO-d6) δ ppm: 1.79-1.89 (1H, m), 2.29-2.39 (1H, m), 2.41-2.49 (2H, m), 2.87-2.98 (2H, m), 3.09-3.29 (2H, m), 3.30-3.62 (3H, m), 3.90-3.90 (1H, m), 4.01-4.07 (1H, m), 4.11-4.18 (1H, m), 6.60-6.80 (1H, m), 7.01-7.11 (1H, m), 8.72 (3H, brs), 9.47 (1H, brs), 9.69 (1H, brs), 10.04 (1H, brs).

Reference Example 655 tert-Butyl (3S*,4S*)-4-{[(8-fluoro-2-oxo-1,2,3,4-tetrahydroquinolin-5-yl)oxy]methyl}-4-hydroxy-3-methylpiperidine-1-carboxylate Under argon atmosphere, to a suspension of tert-butyl (1S*,6S*)-6-{[(8-fluoro-2-oxo-1,2,3,4-tetrahydroquinolin- 5-yl)oxy]methyl}-7-oxa-3-azabicyclo[4.1.0]heptane-3-carboxylate (0.5 g) and copper (I) bromide-dimethylsulfide complex (0.026 g) in tetrahydrofuran (10 mL) was added dropwise methylmagnesium chloride (3M tetrahydrofuran solution) (1.27 mL) at 0° C., and the reaction mixture was heated to reflux for 3.5 h. To the reaction solution was added aqueous saturated ammonium chloride, and the solution was extracted with ethyl acetate. The organic layer was washed with water and brine, dried over anhydrous sodium sulfate, and then the solvent was distilled off. The residue was purified by silica gel column chromatography (hexane/ethyl acetate) to provide the title compound (0.25 g).

$^1$HNMR (CDCl$_3$) δ ppm: 0.99 (3H, d, J=7.1 Hz), 1.47 (9H, s), 1.50-1.57 (1H, m), 1.77-1.86 (1H, m), 1.86-2.01 (1H, m), 2.17 (1H, brs), 2.65 (2H, t, J=7.7 Hz), 2.95-3.03 (2H, m), 3.14-3.42 (1H, m), 3.45-3.53 (1H, m), 3.59-3.66 (1H, m), 3.68-4.02 (3H, m), 6.47 (1H, dd, J=9.1 Hz, 3.9 Hz), 6.92 (1H, t, J=9.5 Hz), 7.51 (1H, brs).

Reference Example 656

8-Fluoro-5-{[(3S*,4S*)-4-hydroxy-3-methylpiperidin-4-yl]methoxy}-3,4-dihydroquinolin-2(1H)-one Synthesized analogous to Reference Example 60.
$^1$HNMR (CDCl$_3$) δ ppm: 1.05 (3H, d, J=7.2 Hz), 1.48-1.56 (1H, m), 1.56-1.70 (1H, broad signal), 1.83-1.96 (2H, m), 2.20 (1H, brs), 2.60 (1H, dd, J=12.7 Hz, 5.6 Hz), 2.63-2.67 (2H, m), 2.79-2.86 (1H, m), 3.00 (2H, t, J=7.7 Hz), 3.03-3.10 (1H, m), 3.21 (1H, dd, J=12.7 Hz, 3.8 Hz), 3.84-3.93 (2H, m), 6.48 (1H, dd, J=9.1 Hz, 3.9 Hz), 6.92 (1H, t, J=9.4 Hz), 7.57 (1H, brs).

Reference Example 657 tert-Butyl (3S*,4R*)-4-({[8-fluoro-1-(4-methoxybenzyl)-2-oxo-1,2,3,4-tetrahydroquinolin-5-yl]oxy}methyl)-4-hydroxy-3-methoxypiperidine-1-carboxylate To a suspension of tert-butyl (1S*,6S*)-6-({[8-fluoro-1-(4-methoxybenzyl)-2-oxo-1,2,3,4-tetrahydroquinolin-5-yl]oxy}methyl)-7-oxa-3-azabicyclo[4.1.0]heptane-3-carboxylate (0.4 g) in methanol (5 mL) was added sodium methoxide (5M methanol solution) (1.56 mL), and the reaction mixture was stirred at 60° C. for 32 h. To the reaction solution was added acetic acid (0.45 mL) and the solvent was distilled off. Water was added to the residue, and the solution was extracted with ethyl acetate. The organic layer was washed with water and brine, dried over anhydrous sodium sulfate, and then the solvent was distilled off. The residue was purified by silica gel column chromatography (hexane/ethyl acetate) to provide the title compound (0.29 g).

$^1$HNMR (CDCl$_3$) δ ppm: 1.42-1.52 (10H, m), 1.77-1.86 (1H, m), 2.32 (1H, brs), 2.60-2.68 (2H, m), 2.79-2.89 (2H, m), 3.03-3.27 (3H, m), 3.33 (3H, brs), 3.69-4.07 (3H, m), 3.74 (3H, s), 4.08-4.32 (1H, m), 5.16-5.28 (2H, m), 6.55 (1H, dd, J=9.1 Hz, 3.4 Hz), 6.73-6.78 (2H, m), 6.84 (1H, dd, J=12.7 Hz, 9.1 Hz), 7.10-7.15 (2H, m).

Reference Example 658

8-Fluoro-5-{[(3S*,4R*)-4-hydroxy-3-methoxypiperidin-4-yl]methoxy}-1-(4-methoxybenzyl)-3,4-dihydroquinolin-2(1H)-one Synthesized analogous to Reference Example 60.
$^1$HNMR (CDCl$_3$) δ ppm: 1.44-1.51 (1H, m), 1.51-1.70 (1H, broad signal), 1.70-1.79 (1H, m), 2.27 (1H, brs), 2.62-2.67 (2H, m), 2.82-2.90 (3H, m), 2.94-3.02 (1H, m), 3.02-3.09 (2H, m), 3.09-3.14 (1H, m), 3.31 (3H, s), 3.73 (1H, d, J=9.0 Hz), 3.74 (3H, s), 4.03 (1H, d, J=9.0 Hz), 5.17-5.28 (2H, m), 6.56 (1H, dd, J=9.1 Hz, 3.4 Hz), 6.74-6.78 (2H, m), 6.84 (1H, dd, J=12.7 Hz, 9.1 Hz), 7.10-7.15 (2H, m).

Reference Example 659

5-{[(3S*,4R*)-1-(3,5-Dichloropyridin-2-yl)-4-hydroxy-3-methoxypiperidin-4-yl]methoxy}-8-fluoro-1-(4-methoxybenzyl)-3,4-dihydroquinolin-2(1H)-one Synthesized analogous to Reference Example 66.
$^1$HNMR (CDCl$_3$) δ ppm: 1.62-1.68 (1H, m), 2.16-2.25 (1H, m), 2.37 (1H, s), 2.62-2.69 (2H, m), 2.85-2.91 (2H, m), 3.28 (3H, s), 3.31-3.40 (2H, m), 3.42-3.48 (1H, m), 3.60-3.67 (1H, m), 3.74 (3H, s), 3.85 (1H, d, J=9.1 Hz), 3.89-3.97 (1H, m), 4.10 (1H, d, J=9.1 Hz), 5.16-5.28 (2H, m), 6.57 (1H, dd, J=9.1 Hz, 3.4 Hz), 6.73-6.78 (2H, m), 6.84 (1H, dd, J=12.7 Hz, 9.1 Hz), 7.10-7.16 (2H, m), 7.58 (1H, d, J=2.3 Hz), 8.10 (1H, d, J=2.3 Hz).

Reference Example 660 tert-Butyl (3R*,4S*)-3-cyano-4-({[8-fluoro-1-(4-methoxybenzyl)-2-oxo-1,2,3,4-tetrahydroquinolin-5-yl]oxy}methyl)-4-hydroxypiperidine-1-carboxylate Under argon atmosphere, to a solution of acetonecyanohydrin (0.342 mL) in tetrahydrofuran (4 mL) was added lithium hydride (0.028 g) and the reaction mixture was stirred at room temperature for 2 h. Then, to the mixture was added tert-butyl (1S*,6S*)-6-({[8-fluoro-1-(4-methoxybenzyl)-2-oxo-1,2,3,4-tetrahydroquinolin-5-yl]oxy}methyl)-7-oxa-3-azabicyclo[4.1.0]heptane-3-carboxylate (0.6 g) and the reaction mixture was heated to reflux for 7 h. After the reaction solution was allowed to cool to room temperature, water was added thereto, and the solution was extracted with ethyl acetate. The organic layer was washed with water and brine, and dried over anhydrous sodium sulfate, and then the solvent was distilled off. The residue was purified by silica gel column chromatography (hexane/ethyl acetate) to provide the title compound (0.53 g).

$^1$HNMR (CDCl$_3$) δ ppm: 1.50 (9H, s), 1.62-1.70 (1H, m), 1.86-1.95 (1H, m), 2.50 (1H, s), 2.62-2.69 (2H, m), 2.77-3.03 (3H, m), 3.03-3.31 (1H, m), 3.31-3.60 (1H, m), 3.74 (3H, s), 3.90 (1H, d, J=9.4 Hz), 3.93-4.49 (3H, m), 5.14-5.31 (2H, m), 6.56 (1H, dd, J=9.1 Hz, 3.3 Hz), 6.74-6.79 (2H, m), 6.87 (1H, dd, J=12.5 Hz, 9.1 Hz), 7.10-7.15 (2H, m).

Reference Example 661

(3R*,4S*)-4-({[8-Fluoro-1-(4-methoxybenzyl)-2-oxo-1,2,3,4-tetrahydroquinolin-5-yl]oxy}methyl)-4-hydroxypiperidine-3-carbonitrile Synthesized analogous to Reference Example 60.
$^1$HNMR (CDCl$_3$) δ ppm: 1.54-1.68 (2H, m), 1.79-1.88 (1H, m), 2.42 (1H, brs), 2.66 (2H, t, J=7.0 Hz), 2.79-2.92 (3H, m), 2.95-3.02 (1H, m), 3.02-3.11 (1H, m), 3.17 (1H, dd, J=13.1 Hz, 2.2 Hz), 3.34 (1H, dd, J=13.1 Hz, 3.1 Hz), 3.74 (3H, s), 3.88 (1H, d, J=9.4 Hz), 4.10 (1H, d, J=9.4 Hz), 5.17-5.29 (2H, m), 6.57 (1H, dd, J=9.1 Hz, 3.3 Hz), 6.74-6.79 (2H, m), 6.86 (1H, dd, J=12.6 Hz, 9.1 Hz), 7.09-7.16 (2H, m).

Reference Example 662

(3R*,4S*)-1-(3,5-Dichloropyridin-2-yl)-4-({[8-fluoro-1-(4-methoxybenzyl)-2-oxo-1,2,3,4-tetrahydroquinolin-5-yl]oxy}methyl)-4-hydroxypiperidine-3-carbonitrile Synthesized analogous to Reference Example 66.
$^1$HNMR (CDCl$_3$) δ ppm: 1.79-1.85 (1H, m), 2.19-2.26 (1H, m), 2.48 (1H, s), 2.68 (2H, t, J=7.1 Hz), 2.82-2.94 (2H, m), 3.09-3.12 (1H, m), 3.25-3.33 (1H, m), 3.52 (1H, dd, J=12.9 Hz, 2.8 Hz), 3.65-3.72 (1H, m), 3.74 (3H, s), 3.91-3.97 (1H, m), 3.98 (1H, d, J=9.4 Hz), 4.20 (1H, d, J=9.4 Hz), 5.16-5.30 (2H, m), 6.60 (1H, dd, J=9.1 Hz, 3.3 Hz), 6.74-6.80 (2H, m), 6.88 (1H, dd, J=12.5 Hz, 9.1 Hz), 7.10-7.15 (2H, m), 7.65 (1H, d, J=2.3 Hz), 8.15 (1H, d, J=2.3 Hz).

Reference Example 663 tert-Butyl (3R*,4S*)-3-fluoro-4-({[8-fluoro-1-(4-methoxybenzyl)-2-oxo-1,2,3,4-tetrahydroquinolin-5-yl]oxy}methyl)-4-hydroxypiperidine-1-carboxylate To tert-butyl (1S*,6S*)-6-({[8-fluoro-1-(4-methoxybenzyl)-2-oxo-1,2,3,4-tetrahydroquinolin-5-yl]oxy}methyl)-7-oxa-3-azabicyclo[4.1.0]heptane-3-carboxylate (0.51 g) was added tetrabutylammonium dihydrogen trifluoride (2.0 g, excess), and the reaction mixture was stirred at 120° C. for 2 days. To the reaction solution was added water and the solution was extracted with ethyl acetate. The organic layer was washed with water and brine, dried over anhydrous sodium sulfate, and then the solvent was distilled off. The residue was purified by silica gel column chromatography (hexane/ethyl acetate) to provide the title compound (0.36 g).
$^1$HNMR (CDCl$_3$) δ ppm: 1.47 (9H, s), 1.57-1.62 (1H, m), 1.78-1.91 (1H, m), 2.42-2.48 (1H, m), 2.61-2.69 (2H, m), 2.79-2.93 (2H, m), 3.03-3.49 (2H, m), 3.75 (3H, m), 3.75-3.79 (1H, m), 3.90-4.06 (2H, m), 4.21-4.79 (2H, m), 5.16-5.29 (2H, m), 6.54 (1H, dd, J=9.0 Hz, 3.3 Hz), 6.72-6.79 (2H, m), 6.85 (1H, dd, J=12.6 Hz, 9.1 Hz), 7.05-7.16 (2H, m).

Reference Example 664

8-Fluoro-5-{[(3R*,4S*)-3-fluoro-4-hydroxypiperidin-4-yl]methoxy}-1-(4-methoxybenzyl)-3,4-dihydroquinolin-2(1H)-one hydrochloride Synthesized analogous to Reference Example 456.
$^1$HNMR (DMSO-d6) δ ppm: 1.72-1.80 (1H, m), 1.83-1.92 (1H, m), 2.56-2.65 (2H, m), 2.81-3.02 (2H, m), 3.06-3.20 (2H, m), 3.44-3.56 (1H, m), 3.68 (3H, s), 3.81-3.90 (1H, m), 3.92-4.00 (1H, m), 4.77-4.83 (1H, m), 4.88-4.94 (1H, m), 5.05-5.16 (2H, m), 5.81 (1H, brs), 6.72 (1H, dd, J=9.2 Hz, 3.4 Hz), 6.77-6.85 (2H, m), 6.99 (1H, dd, J=9.1 Hz, 4.2 Hz), 7.03-7.11 (2H, m), 8.66 (1H, brs), 9.27 (1H, brs).

Reference Example 665

5-{[(3R*,4S*)-1-(3,5-Dichloropyridin-2-yl)-3-fluoro-4-hydroxypiperidin-4-yl]methoxy}-8-fluoro-1-(4-methoxybenzyl)-3,4-dihydroquinolin-2(1H)-one Synthesized analogous to Reference Example 66.
$^1$HNMR (CDCl$_3$) δ ppm: 1.68-1.77 (1H, m), 2.17-2.28 (1H, m), 2.48-2.58 (1H, m), 2.61-2.70 (2H, m), 2.81-2.94 (2H, m), 3.21-3.31 (1H, m), 3.44-3.61 (1H, m), 3.74 (3H, s), 3.75-3.86 (2H, m), 4.02-4.13 (2H, m), 4.56-4.72 (1H, m), 5.16-5.30 (2H, m), 6.56 (1H, dd, J=9.1 Hz, 3.4 Hz), 6.72-6.80 (2H, m), 6.85 (1H, dd, J=12.6 Hz. 9.1 Hz), 7.09-7.16 (2H, m), 7.60 (1H, d, J=2.3 Hz), 8.10 (1H, d, J=2.3 Hz).

Reference Example 666

4-[(Acetyloxy)methyl]-1-(4-methoxybenzyl)-3-methylpyridinium chloride

A solution of (3-methylpyridin-4-yl)methyl acetate (20.4 g) and 4-methoxybenzyl chloride (15.6 mL) in acetonitrile (120 mL) was stirred at 100° C. for 8 h. The reaction solution was allowed to cool to room temperature, and the precipitate was collected on a filter which was washed with ethyl acetate to provide the title compound (23.1 g).
$^1$HNMR (DMSO-d6) δ ppm: 2.20 (3H, s), 2.43 (3H, s), 3.75 (3H, s), 5.36 (2H, s), 5.73 (2H, s), 6.96-7.02 (2H, m), 7.52-7.58 (2H, m), 8.01 (1H, d, J=8.0 Hz), 9.08 (1H, d, J=8.0 Hz), 9.16 (1H, s).

Reference Example 667

[1-(4-Methoxybenzyl)-5-methyl-1,2,3,6-tetrahydropyridin-4-yl]methyl acetate

To a solution of 4-[(acetyloxy)methyl]-1-(4-methoxybenzyl)-3-methylpyridinium chloride (23.1 g) in methanol (200 mL) was added at −20° C. sodium borohydride (8.86 g), and the reaction mixture was stirred at the same temperature for 30 min. To the reaction solution was added water, the mixture was stirred overnight, the solvent was distilled off, ethyl acetate was added to the residue, and insoluble materials were filtered off. The organic layer was washed with water and brine, dried over anhydrous sodium sulfate, and then the solvent was distilled off. The residue was purified by silica gel column chromatography (hexane/ethyl acetate) to provide the title compound (6.8 g).
$^1$HNMR (CDCl$_3$) δ ppm: 1.66 (3H, s), 2.05 (3H, s), 2.13-2.22 (2H, m), 2.53 (2H, t, J=7.2 Hz), 2.84-2.90 (2H, m), 3.49-3.54 (2H, m), 3.81 (3H, s), 4.57-4.61 (2H, m), 6.83-6.89 (2H, m), 7.22-7.29 (2H, m).

Reference Example 668 tert-Butyl 4-(hydroxymethyl)-5-methyl-3,6-dihydropyridine-1(2H)-carboxylate

To a solution of [1-(4-methoxybenzyl)-5-methyl-1,2,3,6-tetrahydropyridin-4-yl]methyl acetate (0.33 g) in dichloromethane (10 mL) was added 2-chloroethyl chloroformate (0.19 mL) and the reaction mixture was stirred at 50° C. for 5 h. The solvent was distilled off and to the residue was added methanol (10 mL) and the reaction mixture was stirred at 70° C. for 2 h. After the reaction was completed, the solvent was distilled off, and the residue was dissolved in methanol (10 mL). To the solution were added triethylamine (0.48 mL) and di-tert-butyl dicarbonate (0.39 mL), and the reaction mixture was stirred at room temperature overnight. To the reaction solution was added 2 N aqueous sodium hydroxide (10 mL), the reaction mixture was stirred at 1 h, to which an aqueous solution of 2 M citric acid was added and the solution was extracted with ethyl acetate. The organic layer was washed with water and brine, dried over anhydrous sodium sulfate, and then the solvent was distilled off. The residue was purified by silica gel column chromatography (hexane/ethyl acetate) to provide the title compound (0.20 g).

$^1$HNMR (CDCl$_3$) δ ppm: 1.47 (9H, s), 1.50-1.65 (2H, m), 1.71 (3H, s), 2.20-2.30 (2H, m), 3.45-3.55 (2H, m), 4.16 (2H, brs).

Reference Example 669 tert-Butyl 4-(chloromethyl)-5-methyl-3,6-dihydropyridine-1 (2H)-carboxylate

To a solution of tert-butyl 4-(hydroxymethyl)-5-methyl-3,6-dihydropyridine-1(2H)-carboxylate (3.57 g) in acetonitrile (50 mL) were added triethylamine (3.06 mL) and methanesulfonyl chloride (1.46 mL) at 0° C., and the reaction mixture was stirred at room temperature overnight. To the reaction solution was added water, and the solution was extracted with ethyl acetate. The organic layer was washed with water and brine, dried over anhydrous sodium sulfate, and then the solvent was distilled off. The residue was purified by silica gel column chromatography (hexane/ethyl acetate) to provide the title compound (2.53 g).

$^1$HNMR (CDCl$_3$) δ ppm: 1.47 (9H, s), 1.74 (3H, s), 2.15-2.28 (2H, m), 3.45-3.55 (2H, m), 3.73-3.86 (2H, m), 4.07-4.12 (2H, m).

Reference Example 670 tert-Butyl 4-({[8-fluoro-1-(4-methoxybenzyl)-2-oxo-1,2,3,4-tetrahydroquinolin-5-yl]oxy}methyl)-5-methyl-3,6-dihydropyridine-1(2H)-carboxylate Synthesized analogous to Reference Example 495.

$^1$HNMR (CDCl$_3$) δ ppm: 1.47 (9H, s), 1.69 (3H, brs), 2.16-2.26 (2H, m), 2.58-2.66 (2H, m), 2.81-2.89 (2H, m), 2.44-2.54 (2H, m), 3.74 (3H, s), 3.76-3.84 (2H, m), 4.42-4.47 (2H, m), 5.18-5.26 (2H, m), 6.51 (1H, dd, J=9.1 Hz, 3.4 Hz), 6.73-6.78 (2H, m), 6.82 (1H, dd, J=12.8 Hz, 9.1 Hz), 7.09-7.16 (2H, m).

Reference Example 671 tert-Butyl (1S*,6S*)-6-({[8-fluoro-1-(4-methoxybenzyl)-2-oxo-1,2,3,4-tetrahydroquinolin-5-yl]oxy}methyl)-1-methyl-7-oxa-3-azabicyclo[4.1.0]heptane-3-carboxylate Synthesized analogous to Reference Example 633.

$^1$HNMR (CDCl$_3$) δ ppm: 1.37 (3H, s), 1.46 (9H, s), 2.02-2.20 (2H, m), 2.60-2.69 (2H, m), 2.81-2.95 (2H, m), 3.14-3.47 (1H, m), 3.48-3.76 (2H, m), 3.74 (3H, s), 3.93-4.08 (2H, m), 5.17-5.29 (2H, brs), 6.50 (1H, dd, J=9.1 Hz, 3.3 Hz), 6.73-6.79 (2H, m), 6.82 (1H, dd, J=12.4 Hz, 9.1 Hz), 7.09-7.16 (2H, m).

Reference Example 672 tert-Butyl (3S*,4S*)-4-({[8-fluoro-1-(4-methoxybenzyl)-2-oxo-1,2,3,4-tetrahydroquinolin-5-yl]oxy}methyl)-3,4-dihydroxy-3-methylpiperidine-1-carboxylate Synthesized analogous to Reference Example 499.

$^1$HNMR (CDCl$_3$) δ ppm: 1.47 (9H, s), 1.64 (3H, s), 1.66-1.75 (1H, m), 1.77-1.85 (1H, m), 2.58-2.71 (2H, m), 2.73-2.92 (3H, m), 2.93-3.00 (1H, m), 3.02-3.26 (2H, m), 3.65-3.84 (2H, m), 3.74 (3H, s), 3.96-4.09 (1H, m), 4.13-4.18 (1H, m), 5.12-5.33 (2H, m), 6.55 (1H, dd, J=9.1 Hz, 3.4 Hz), 6.73-6.80 (2H, m), 6.85 (1H, dd, J=12.6 Hz, 9.1 Hz), 7.09-7.16 (2H, m).

Reference Example 673

5-{[(3S*,4S*)-3,4-Dihydroxy-3-methylpiperidin-4-yl]methoxy}-8-fluoro-1-(4-methoxybenzyl)-3,4-dihydroquinolin-2(1H)-one hydrochloride Synthesized analogous to Reference Example 456.

$^1$HNMR (DMSO-d6) δ ppm: 1.22 (3H, s), 1.93-2.08 (2H, m), 2.55-2.65 (2H, m), 2.77-3.12 (6H, m), 3.38-3.50 (2H, m), 3.68 (3H, s), 3.78-3.85 (1H, m), 4.11-4.19 (1H, m), 5.10 (2H, brs), 6.77 (1H, dd, J=9.4 Hz, 3.3 Hz), 6.78-6.86 (2H, m), 6.99 (1H, dd, J=13.1 Hz, 9.1 Hz), 7.04-7.12 (2H, m), 8.81 (1H, brs), 8.95 (1H, brs).

Reference Example 674

5-{[(3S*,4S*)-1-(3,5-Dichloropyridin-2-yl)-3,4-dihydroxy-3-methylpiperidin-4-yl]methoxy}-8-fluoro-1-(4-methoxybenzyl)-3,4-dihydroquinolin-2(1H)-one Synthesized analogous to Reference Example 66.

$^1$HNMR (CDCl$_3$) δ ppm: 1.37 (3H, s), 1.86-1.96 (1H, m), 2.02-2.12 (1H, m), 2.61-2.69 (2H, m), 2.84-2.93 (2H, m), 3.05 (1H, brs), 3.31-3.51 (4H, m), 3.60-3.74 (1H, m), 3.75 (3H, s), 3.93 (1H, d, J=9.4 Hz), 4.14 (1H, d, J=9.4 Hz), 5.14-5.32 (2H, m), 6.58 (1H, dd, J=9.2 Hz, 3.4 Hz), 6.73-6.80 (2H, m), 6.86 (1H, dd, J=12.6 Hz, 9.1 Hz), 7.09-7.17 (2H, m), 7.63 (1H, d, J=2.3 Hz), 8.12 (1H, d, J=2.3 Hz).

Reference Example 675

5-{[(3S*,4S*)-1-(4-Chloro-2-fluorophenyl)-3,4-dihydroxy-3-methylpiperidin-4-yl]methoxy}-8-fluoro-1-(4-methoxybenzyl)-3,4-dihydroquinolin-2(1H)-one Under nitrogen atmosphere, to a solution of 5-{[(3S*,4S*)-3,4-dihydroxy-3-methylpiperidin-4-yl]methoxy}-8-fluoro-1-(4-methoxybenzyl)-3,4-dihydroquinolin-2(1H)-one hydrochloride (0.36 g), 1-bromo-4-chloro-2-fluorobenzene (0.19 g), triethylamine (0.16 mL) and cesium carbonate (0.72 g) in toluene (6 mL) were added 2,2'-bis(diphenylphosphino)-1,1'-binaphthyl (41 mg) and tris(dibenzylideneacetone)dipalladium (0) (20 mg), and the reaction mixture was stirred at 100° C. overnight. To the reaction solution was added water, and the solution was extracted with ethyl acetate. The organic layer was washed with water and brine, dried over anhydrous sodium sulfate, and then the solvent was distilled off. The residue was purified by silica gel column chromatography (hexane/ethyl acetate) to provide the title compound (42 mg).
$^1$HNMR (CDCl$_3$) δ ppm: 1.45 (3H, s), 1.89-2.05 (2H, m), 2.59-2.72 (2H, m), 2.79-3.08 (6H, m), 3.09-3.15 (2H, m), 3.74 (3H, s), 3.89 (1H, d, J=9.2 Hz), 4.17 (1H, d, J=9.2 Hz), 5.14-5.32 (2H, m), 6.58 (1H, dd, J=9.1 Hz, 3.4 Hz), 6.73-6.80 (2H, m), 6.82-6.93 (2H, m), 7.01-7.08 (2H, m), 7.09-7.17 (2H, m).

Reference Example 676

1-(2-Chloro-4-fluorophenyl)-3-fluoro-4,4-dimethoxypiperidine

Synthesized analogous to Reference Example 205.
$^1$HNMR (CDCl$_3$) δ ppm: 1.91-1.98 (1H, m), 2.10-2.18 (1H, m), 2.80-2.88 (1H, m), 3.06-3.22 (2H, m), 3.30 (3H, s), 3.34 (3H, s), 3.39-3.49 (1H, m), 4.57-4.71 (1H, m), 6.90-6.95 (1H, m), 7.02 (1H, dd, J=8.9 Hz, 5.5 Hz), 7.12 (1H, dd, J=8.3 Hz, 2.9 Hz).

Reference Example 677

1-(2-Chloro-4-fluorophenyl)-3-fluoropiperidin-4-one

Synthesized analogous to Reference Example 251.
$^1$HNMR (CDCl$_3$) δ ppm: 2.58-2.66 (1H, m), 2.81-2.91 (1H, m), 3.03-3.16 (2H, m), 3.49-3.56 (1H, m), 3.85-3.92 (1H, m), 5.18 (1H, ddd, J=48.0 Hz, 10.3 Hz, 6.9 Hz), 6.95-7.01 (1H, m), 7.05 (1H, dd, J=8.9 Hz, 5.4 Hz), 7.19 (1H, dd, J=8.2 Hz, 2.9 Hz).

Reference Example 678

1-(4-Chloro-2-fluorophenyl)-3-fluoro-4,4-dimethoxypiperidine

Synthesized analogous to Reference Example 205.
$^1$HNMR (CDCl$_3$) δ ppm: 1.92-1.98 (1H, m), 2.06-2.15 (1H, m), 2.86-2.93 (1H, m), 3.11-3.26 (2H, m), 3.28 (3H, s), 3.33 (3H, s), 3.55-3.63 (1H, m), 4.56-4.69 (1H, m), 6.84-6.90 (1H, m), 7.00-7.07 (2H, m).

Reference Example 679

1-(4-Chloro-2-fluorophenyl)-3-fluoropiperidin-4-one

Synthesized analogous to Reference Example 251.
$^1$HNMR (CDCl$_3$) δ ppm: 2.61-2.68 (1H, m), 2.77-2.86 (1H, m), 3.09-3.22 (2H, m), 3.60-3.67 (1H, m), 3.93-4.01 (1H, m), 5.05-5.20 (1H, m), 6.90-6.95 (1H, m), 7.06-7.14 (2H, m).

Reference Example 680

(3R*,4S*)-6-(4-Chloro-2-fluorophenyl)-4-fluoro-1-oxa-6-azaspiro[2.5]octane

Under argon atmosphere, to a solution of trimethylsulfoxonium iodide (2.00 g) in dimethyl sulfoxide (20 mL) was added sodium tert-butoxide (0.834 g), and the reaction mixture was stirred at room temperature for 30 min. To the mixture was added a solution of 1-(4-chloro-2-fluorophenyl)-3-fluoropiperidin-4-one (2.03 g) in dimethyl sulfoxide (10 mL), and the mixture was stirred at room temperature for 1 h. To the reaction solution was added water, and the solution was extracted with ethyl acetate. The organic layer was washed with water and brine, and dried over anhydrous sodium sulfate, and then the solvent was distilled off. The residue was purified by silica gel column chromatography (hexane/ethyl acetate) and the title compound (1.03 g) was obtained from lower polarity fractions.
$^1$HNMR (CDCl$_3$) δ ppm: 1.64-1.71 (1H, m), 2.26-2.35 (1H, m), 2.80 (1H, dd, J=4.6 Hz, 1.9 Hz), 3.00 (1H, d, J=4.6 Hz), 3.16-3.29 (2H, m), 3.31-3.50 (2H, m), 4.32 (1H, ddd, J=48.0 Hz, 5.1 Hz, 3.1 Hz), 6.88-6.94 (1H, m), 7.03-7.10 (2H, m).

Reference Example 681

(3R,4R)-6-(4-Chloro-2-fluorophenyl)-4-fluoro-1-oxa-6-azaspiro[2.5]octane

From higher polarity fractions of Reference Example 680, the title compound (0.48 g) was obtained.
$^1$HNMR (CDCl$_3$) δ ppm: 1.90-2.03 (2H, m), 2.78 (1H, dd, J=4.6 Hz, 3.4 Hz), 3.03 (1H, d, J=4.6 Hz), 3.16-3.28 (2H, m), 3.32-3.47 (2H, m), 4.65 (1H, ddd, J=48.0 Hz, 7.3 Hz, 3.9 Hz), 6.89-6.94 (1H, m), 7.04-7.10 (2H, m).

Reference Example 682

(3R*,4S*)-6-(2-Chloro-4-fluorophenyl)-4-fluoro-1-oxa-6-azaspiro[2.5]octane

The reaction and purification analogous to Reference Example 680 and 681 gave the title compound from lower polarity fractions.
$^1$HNMR (CDCl$_3$) δ ppm: 1.74-1.83 (1H, m), 2.16-2.26 (1H, m), 2.78 (1H, dd, J=4.7 Hz, 2.1 Hz), 3.03 (1H, d, J=4.7 Hz), 3.08-3.19 (2H, m), 3.24-3.43 (2H, m), 4.41 (1H, ddd, J=48.5 Hz, 5.7 Hz, 3.4 Hz), 6.93-6.98 (1H, m), 7.04 (1H, dd, J=8.9 Hz, 5.5 Hz), 7.15 (1H, dd, J=8.3 Hz, 2.9 Hz).

Reference Example 683

(3R,4R)-6-(2-Chloro-4-fluorophenyl)-4-fluoro-1-oxa-6-azaspiro[2.5]octane

The reaction and purification analogous to Reference Example 680 and 681 gave the title compound from higher polarity fractions.
$^1$HNMR (CDCl$_3$) δ ppm: 1.80-1.90 (1H, m), 2.02-2.13 (1H, m), 2.78 (1H, dd, J=4.8 Hz, 2.6 Hz), 3.07 (1H, d, J=4.8 Hz), 3.08-3.17 (2H, m), 3.18-3.27 (1H, m), 3.37-3.46 (1H, m), 4.75 (1H, ddd, J=47.9 Hz, 8.3 Hz, 4.1 Hz), 6.93-6.99 (1H, m), 7.05 (1H, dd, J=8.9 Hz, 5.5 Hz), 7.15 (1H, dd, J=8.3 Hz, 2.9 Hz).

Reference Example 684

1-(4-Chloro-2,6-difluorophenyl)-4-[(trimethylsilyl)oxy]-1,2,3,6-tetrahydropyridine Under argon atmosphere, a solution of 1-(4-chloro-2,6-difluorophenyl)piperidin-4-one (1 g), chlorotrimethylsilane (1.55 mL) and triethylamine (2.84 mL) in N,N-dimethylformamide (5 mL) was stirred at 70° C. for 15 h, and the solvent was distilled off. To the residue was added water, and the solution was extracted with ethyl acetate. The organic layer was washed with water, dried over anhydrous sodium sulfate, and then the solvent was distilled off to provide the title compound (1.28 g).

¹HNMR (CDCl₃) δ ppm: 0.21 (9H, s), 2.18-2.25 (2H, m), 3.27-3.34 (2H, m), 3.62-3.68 (2H, m), 4.86-4.90 (1H, m), 6.83-6.91 (2H, m).

Reference Example 685

1-(4-Chloro-2,6-difluorophenyl)-3-fluoropiperidin-4-one

Under argon atmosphere, to a solution of 1-(4-chloro-2,6-difluorophenyl)-4-[(trimethylsilyl)oxy]-1,2,3,6-tetrahydropyridine (1.28 g) in acetonitrile (15 mL) was added 1-chloromethyl-4-fluoro-1,4-diazoniabicyclo[2.2.2]octane bis(tetrafluoroborate) (1.57 g) under ice-cooling, and the mixture was stirred at the same temperature for 1 h, then at room temperature for 1.5 h. To the reaction solution was added saturated aqueous sodium hydrogencarbonate, and the solution was extracted with ethyl acetate. The organic layer was washed with brine, dried over anhydrous magnesium sulfate, and the solvent was distilled off. The residue was purified by silica gel column chromatography (hexane/ethyl acetate) to provide the title compound (0.76 g).
¹HNMR (CDCl₃) δ ppm: 2.55-2.65 (1H, m), 2.74-2.84 (1H, m), 3.38-3.50 (3H, m), 3.78-3.86 (1H, m), 5.08 (1H, ddd, J=48.3 Hz, 10.1 Hz, 6.8 Hz), 6.90-6.99 (2H, m).

Reference Example 686

(3R*,4S*)-6-(4-Chloro-2,6-difluorophenyl)-4-fluoro-1-oxa-6-azaspiro[2.5]octane

The reaction and purification analogous to Reference Example 680 and 681 gave the title compound from lower polarity fractions.
¹HNMR (CDCl₃) δ ppm: 1.64-1.72 (1H, m), 2.18-2.26 (1H, m), 2.77 (1H, dd, J=4.7 Hz, 2.0 Hz), 2.99 (1H, d, J=4.7 Hz), 3.20-3.28 (1H, m), 3.30-3.44 (2H, m), 3.52-3.63 (1H, m), 4.29 (1H, ddd, J=48.5 Hz, 5.6 Hz, 3.2 Hz), 6.86-6.93 (2H, m).

Reference Example 687

(3R,4R)-6-(4-Chloro-2,6-difluorophenyl)-4-fluoro-1-oxa-6-azaspiro[2.5]octane

The reaction and purification analogous to Reference Example 680 and 681 gave the title compound from higher polarity fractions.
¹HNMR (CDCl₃) δ ppm: 1.82-1.90 (1H, m), 1.97-2.05 (1H, m), 2.76 (1H, dd, J=4.7 Hz, 3.7 Hz), 3.00 (1H, d, J=4.7 Hz), 3.15-3.22 (1H, m), 3.34-3.54 (3H, m), 4.56 (1H, ddd, J=48.3 Hz, 6.9 Hz, 3.9 Hz), 6.86-6.94 (2H, m).

Reference Example 688

(3R)-1-(4-Chloro-2,6-difluorophenyl)-3-fluoropiperidin-4-one

Under argon atmosphere, to a suspension of N-fluorobenzenesulfonimide (2.0 g) and sodium carbonate (1.01 g) in tetrahydrofuran (10 mL) was added a solution of 9-epi-9-amino-9-deoxydihydroquinidine (9-epi-DHQDA) (0.413 g), trichloroacetic acid (0.218 g) and water (0.023 mL) in tetrahydrofuran (15 mL) at −20° C., and the mixture was stirred for 10 min. To the mixture was added 1-(4-chloro-2,6-difluorophenyl)piperidin-4-one (3.12 g), and the reaction mixture was stirred at the same temperature for 16 h, then at −10° C. for 24 h. To the reaction solution was added water, and the solution was extracted with ethyl acetate. The organic layer was washed with water and brine, and dried over anhydrous sodium sulfate, and then the solvent was distilled off. The residue was purified by silica gel column chromatography (hexane/ethyl acetate) to provide the title compound (1.26 g).
¹HNMR (CDCl₃) δ ppm: 2.57-2.65 (1H, m), 2.75-2.84 (1H, m), 3.38-3.50 (3H, m), 3.78-3.86 (1H, m), 5.00-5.16 (1H, m), 6.92-6.98 (2H, m).

Reference Example 689

(3S)-1-(4-Chloro-2,6-difluorophenyl)-3-fluoropiperidin-4-one

By the procedure analogous to Reference Example 688, with 9-epi-9-amino-9-deoxydihydroquinine (9-epi-DHQA) as catalyst, the title compound was obtained.
¹HNMR (CDCl₃) δ ppm: 2.57-2.65 (1H, m), 2.75-2.84 (1H, m), 3.38-3.50 (3H, m), 3.78-3.86 (1H, m), 5.00-5.16 (1H, m), 6.92-6.98 (2H, m).

Reference Example 690

(3S,4R)-6-(4-Chloro-2,6-difluorophenyl)-4-fluoro-1-oxa-6-azaspiro[2.5]octane

The reaction and purification analogous to Reference Examples 680 and 681 with (3R)-1-(4-chloro-2,6-difluorophenyl)-3-fluoropiperidin-4-one (1.20 g) were done. The material obtained from lower polarity fractions was recrystallized from ethanol/water to provide the title compound (0.47 g, 97% ee).
¹HNMR (CDCl₃) δ ppm: 1.64-1.72 (1H, m), 2.18-2.26 (1H, m), 2.77 (1H, dd, J=4.7 Hz, 2.0 Hz), 2.99 (1H, d, J=4.7 Hz), 3.20-3.28 (1H, m), 3.30-3.44 (2H, m), 3.52-3.63 (1H, m), 4.29 (1H, ddd, J=48.5 Hz, 5.6 Hz, 3.2 Hz), 6.86-6.93 (2H, m).

Reference Example 691

(3R,4R)-6-(4-Chloro-2,6-difluorophenyl)-4-fluoro-1-oxa-6-azaspiro[2.5]octane

The material obtained from higher polarity fractions of Reference Example 690 was recrystallized from hexane to provide the title compound (0.24 g, 91% ee).
¹HNMR (CDCl₃) δ ppm: 1.82-1.90 (1H, m), 1.97-2.05 (1H, m), 2.76 (1H, dd, J=4.7 Hz, 3.7 Hz), 3.00 (1H, d, J=4.7 Hz), 3.15-3.22 (1H, m), 3.34-3.54 (3H, m), 4.56 (1H, ddd, J=48.3 Hz, 6.9 Hz, 3.9 Hz), 6.86-6.94 (2H, m).

Reference Example 692

(3R,4S)-6-(4-Chloro-2,6-difluorophenyl)-4-fluoro-1-oxa-6-azaspiro[2.5]octane

The reaction and purification analogous to Reference Example 680 and 681 with (3S)-1-(4-chloro-2,6-difluorophenyl)-3-fluoropiperidin-4-one (1.19 g) were done. The material obtained from lower polarity fractions was recrystallized from ethanol/water to provide the title compound (0.43 g, 96% ee).
¹HNMR (CDCl₃) δ ppm: 1.64-1.72 (1H, m), 2.18-2.26 (1H, m), 2.77 (1H, dd, J=4.7 Hz, 2.0 Hz), 2.99 (1H, d, J=4.7

Hz), 3.20-3.28 (1H, m), 3.30-3.44 (2H, m), 3.52-3.63 (1H, m), 4.29 (1H, ddd, J=48.5 Hz, 5.6 Hz, 3.2 Hz), 6.86-6.93 (2H, m).

Reference Example 693

(3S,4S)-6-(4-Chloro-2,6-difluorophenyl)-4-fluoro-1-oxa-6-azaspiro[2.5]octane

The material obtained from higher polarity fractions of Reference Example 692 was recrystallized from ethanol/water to provide the title compound (0.22 g, 86% ee).
$^1$HNMR (CDCl$_3$) δ ppm: 1.82-1.90 (1H, m), 1.97-2.05 (1H, m), 2.76 (1H, dd, J=4.7 Hz, 3.7 Hz), 3.00 (1H, d, J=4.7 Hz), 3.15-3.22 (1H, m), 3.34-3.54 (3H, m), 4.56 (1H, ddd, J=48.3 Hz, 6.9 Hz, 3.9 Hz), 6.86-6.94 (2H, m).

Reference Example 694

(3R*,4R*)-4-({[tert-Butyl(dimethyl)silyl]oxy}methyl)piperidin-3-ol

To a solution of (3R*,4R*)-1-benzyl-4-({[tert-butyl(dimethyl) silyl]oxy}methyl)-piperidin-3-ol (11.6 g) in ethanol (100 mL) was added 20% palladium hydroxide on carbon (1.16 g, 10 wt %), and the reaction mixture was stirred under hydrogen atmosphere at 50° C. for 2 h. After the reaction solution was allowed to cool to room temperature, palladium hydroxide was filtered off with Celite, and the solvent of the filtrate was distilled off to provide the title compound (8.66 g).
$^1$HNMR (CDCl$_3$) δ ppm: 0.09 (3H, s), 0.10 (3H, s), 0.91 (9H, s), 1.00-1.13 (1H, m), 1.45-1.72 (3H, m), 2.42 (1H, dd, J=11.7 Hz, 10.0 Hz), 2.56 (1H, dt, J=2.8 Hz, 12.3 Hz), 2.97-3.04 (1H, m), 3.17-3.24 (1H, m), 3.50-3.58 (1H, m), 3.62 (1H, t, J=9.6 Hz), 3.69-3.77 (1H, m), 3.94-4.30 (1H, m).

Reference Example 695

(3R*,4R*)-4-({[tert-Butyl(dimethyl)silyl]oxy}methyl)-1-(2,4-dichlorophenyl)piperidin-3-ol Synthesized analogous to Reference Example 68.
$^1$HNMR (CDCl$_3$) δ ppm: 0.11 (3H, s), 0.12 (3H, s), 0.92 (9H, s), 1.35-1.48 (1H, m), 1.59-1.76 (2H, m), 2.50 (1H, dd, J=10.8 Hz, 9.8 Hz), 2.59 (1H, dt, J=2.6 Hz, 11.8 Hz), 3.26-3.35 (1H, m), 3.43-3.51 (1H, m), 3.71 (1H, t, J=9.6 Hz), 3.79-3.90 (2H, m), 4.16-4.20 (1H, m), 6.96 (1H, d, J=8.6 Hz), 7.18 (1H, dd, J=8.6 Hz, 2.3 Hz), 7.35 (1H, d, J=2.3 Hz).

Reference Example 696

(3R*,4R*)-1-(2,4-Dichlorophenyl)-4-(hydroxymethyl)piperidin-3-ol

To a solution of (3R*,4R*)-4-({[tert-butyl(dimethyl)silyl]oxy}methyl)-1-(2,4-dichlorophenyl)piperidin-3-ol (1.67 g) in tetrahydrofuran (12 mL) was added a solution of 1 M tetrabutylammonium fluoride in tetrahydrofuran (5.1 mL), and the reaction mixture was stirred at room temperature overnight. After the solvent was distilled off, water was added to the residue and the solution was extracted with ethyl acetate. The organic layer was washed with water and brine, dried over anhydrous sodium sulfate, and then the solvent was distilled off. The residue was purified by silica gel column chromatography (hexane/ethyl acetate) to provide the title compound (1.11 g).
$^1$HNMR (CDCl$_3$) δ ppm: 1.40-1.54 (1H, m), 1.66-1.79 (2H, m), 2.36-2.34 (1H, m), 2.53 (1H, dd, J=10.8 Hz, 9.7 Hz), 2.62 (1H, dt, J=2.5 Hz, 11.7 Hz), 3.12-3.19 (1H, m), 3.26-3.34 (1H, m), 3.42-3.49 (1H, m), 3.75-3.93 (3H, m), 6.96 (1H, d, J=8.6 Hz), 7.18 (1H, dd, J=8.6 Hz, 2.5 Hz), 7.36 (1H, d, J=2.5 Hz).

Reference Example 697

[(3R*,4R*)-1-(2,4-Dichlorophenyl)-3-hydroxypiperidin-4-yl]methyl 4-methylbenzenesulfonate To a solution of (3R*,4R*)-1-(2,4-dichlorophenyl)-4-(hydroxymethyl)piperidin-3-ol (1.11 g) in dichloromethane (12 mL) were added para-toluenesulfonyl chloride (0.84 g) and N,N,N',N'-tetramethyl-1,3-diaminopropane (0.94 mL) at 0° C., and the reaction mixture was stirred at room temperature for 4 h. To the reaction solution was added water and the solution was extracted with ethyl acetate. The organic layer was washed with water and brine, dried over anhydrous sodium sulfate, and then the solvent was distilled off. The residue was purified by silica gel column chromatography (hexane/ethyl acetate) to provide the title compound (1.0 g).
$^1$HNMR (CDCl$_3$) δ ppm: 1.60-1.77 (2H, m), 1.81-1.87 (1H, m), 2.05-2.10 (1H, m), 2.46 (3H, m), 2.48-2.64 (2H, m), 3.21-3.29 (1H, m), 3.40-3.48 (1H, m), 3.71-3.81 (1H, m), 4.14-4.20 (1H, m), 4.23-4.30 (1H, m), 6.92 (1H, d, J=8.6 Hz), 7.17 (1H, dd, J=8.6 Hz, 2.4 Hz), 7.35 (1H, d, J=2.4 Hz), 7.36-7.40 (2H, m), 7.80-7.85 (2H, m).

Reference Example 698

(3R*,4R*)-4-({[tert-Butyl(dimethyl)silyl]oxy}methyl)-1-(4-chloro-2-fluorophenyl)piperidin-3-ol Synthesized analogous to Reference Example 68.
$^1$HNMR (CDCl$_3$) δ ppm: 0.11 (3H, s), 0.12 (3H, s), 0.92 (9H, s), 1.33-1.45 (1H, m), 1.58-1.75 (2H, m), 2.52 (1H, t, J=10.5 Hz), 2.63 (1H, dt, J=2.5 Hz, 12.0 Hz), 3.34-3.41 (1H, m), 3.49-3.56 (1H, m), 3.69 (1H, t, J=9.7 Hz), 3.78-3.87 (2H, m), 4.17-4.20 (1H, m), 6.83-6.91 (1H, m), 7.00-7.07 (2H, m).

Reference Example 699

(3R*,4R*)-1-(4-Chloro-2-fluorophenyl)-4-(hydroxymethyl)piperidin-3-ol

Synthesized analogous to Reference Example 696.
$^1$HNMR (CDCl$_3$) δ ppm: 1.37-1.51 (1H, m), 1.65-1.77 (2H, m), 2.18-2.29 (1H, m), 2.55 (1H, t, J=10.5 Hz), 2.65 (1H, dt, J=2.6 Hz, 12.0 Hz), 3.05-3.08 (1H, m), 3.33-3.40 (1H, m), 3.48-3.56 (1H, m), 3.73-3.91 (3H, m), 6.84-6.91 (1H, m), 7.05-7.08 (2H, m).

Reference Example 700

4-methylbenzenesulfonic acid [(3R*,4R*)-1-(4-Chloro-2-fluorophenyl)-3-hydroxypiperidin-4-yl]methyl ester Synthesized analogous to Reference Example 697.
$^1$HNMR (CDCl$_3$) δ ppm: 1.57-1.75 (2H, m), 1.78-1.85 (1H, m), 2.06-2.11 (1H, m), 2.46 (3H, m), 2.47-2.66 (2H, m), 3.28-3.36 (1H, m), 3.47-3.53 (1H, m), 3.69-3.79 (1H, m), 4.13-4.19 (1H, m), 4.24-4.30 (1H, m), 6.80-6.87 (1H, m), 7.00-7.07 (2H, m), 7.34-7.39 (2H, m), 7.78-7.84 (2H, m).

Reference Example 701

(3R*,4R*)-4-({[tert-Butyl(dimethyl)silyl]oxy}methyl)-1-(4-chloro-2,5-difluorophenyl)piperidin-3-ol Synthesized analogous to Reference Example 68.
$^1$HNMR (CDCl$_3$) δ ppm: 0.11 (3H, s), 0.12 (3H, s), 0.92 (9H, s), 1.31-1.44 (1H, m), 1.58-1.75 (2H, m), 2.50 (1H, t, J=10.6 Hz), 2.64 (1H, dt, J=2.5 Hz, 12.0 Hz), 3.35-3.43 (1H, m), 3.52-3.59 (1H, m), 3.68 (1H, t, J=9.6 Hz), 3.77-3.85 (2H, m), 4.16-4.19 (1H, m), 6.73 (1H, dd, J=10.7 Hz, 7.6 Hz), 7.05 (1H, dd, J=11.6 Hz, 6.9 Hz).

Reference Example 702

(3R*,4R*)-1-(4-Chloro-2,5-difluorophenyl)-4-(hydroxymethyl)piperidin-3-ol

Synthesized analogous to Reference Example 696.
$^1$HNMR (CDCl$_3$) δ ppm: 1.37-1.50 (1H, m), 1.66-1.78 (2H, m), 2.15-2.24 (1H, m), 2.53 (1H, t, J=10.5 Hz), 2.65 (1H, dt, J=2.6 Hz, 12.1 Hz), 3.16-3.23 (1H, m), 3.35-3.43 (1H, m), 3.51-3.59 (1H, m), 3.73-3.90 (3H, m), 6.73 (1H, dd, J=10.6 Hz, 7.6 Hz), 7.06 (1H, d, J=11.6 Hz, 6.9 Hz).

Reference Example 703

[(3R*,4R*)-1-(4-Chloro-2,5-difluorophenyl)-3-hydroxypiperidin-4-yl]methyl 4-methylbenzenesulfonate Synthesized analogous to Reference Example 697.
$^1$HNMR (CDCl$_3$) δ ppm: 1.59-1.75 (2H, m), 1.78-1.86 (1H, m), 2.04-2.08 (1H, m), 2.46 (3H, m), 2.47-2.64 (2H, m), 3.31-3.39 (1H, m), 3.50-3.57 (1H, m), 3.69-3.78 (1H, m), 4.11-4.18 (1H, m), 4.26-4.32 (1H, m), 6.70 (1H, dd, J=10.6 Hz, 7.6 Hz), 7.06 (1H, dd, J=11.5 Hz, 6.8 Hz), 7.33-7.40 (2H, m), 7.78-7.84 (2H, m).

Reference Example 704 tert-Butyl 4-{[(8-fluoro-2-oxo-1,2,3,4-tetrahydroquinolin-5-yl)oxy]methyl}piperidine-1-carboxylate Synthesized analogous to Reference Example 495.
$^1$HNMR (CDCl$_3$) δ ppm: 1.23-1.35 (2H, m), 1.47 (9H, s), 1.75-1.83 (2H, m), 1.90-2.03 (1H, m), 2.59-2.66 (2H, m), 2.69-2.83 (2H, m), 2.98 (2H, t, J=7.7 Hz), 3.78 (2H, d, J=6.3 Hz), 4.05-4.28 (2H, m), 6.43 (1H, dd, J=9.1 Hz, 4.0 Hz), 6.90 (1H, t, J=9.5 Hz), 7.51 (1H, brs).

Reference Example 705

8-Fluoro-5-(piperidin-4-ylmethoxy)-3,4-dihydroquinolin-2(1H)-one

Synthesized analogous to Reference Example 60.
$^1$HNMR (CDCl$_3$) δ ppm: 1.24-1.36 (2H, m), 1.49-1.77 (1H, broad signal), 1.77-1.84 (2H, m), 1.87-1.99 (1H, m), 2.58-2.70 (4H, m), 2.99 (2H, t, J=7.7 Hz), 3.09-3.17 (2H, m), 3.77 (2H, d, J=6.3 Hz), 6.43 (1H, dd, J=9.1 Hz, 3.9 Hz), 6.89 (1H, t, J=9.5 Hz), 7.53 (1H, brs).

Reference Example 706 tert-Butyl (3S*,4S*)-4-{[(8-fluoro-2-oxo-1,2,3,4-tetrahydroquinolin-5-yl)oxy]methyl}-3-hydroxypiperidine-1-carboxylate Synthesized analogous to Reference Example 495.
$^1$HNMR (CDCl$_3$) δ ppm: 1.42-1.46 (1H, m), 1.47 (9H, s), 1.77-1.85 (1H, m), 1.86-1.95 (1H, m), 2.41-2.52 (1H, m), 2.53-2.83 (4H, m), 2.89-3.03 (2H, m), 3.57-3.67 (1H, m), 4.00-4.42 (4H, m), 6.49 (1H, dd, J=9.1 Hz, 3.9 Hz), 6.91 (1H, t, J=9.4 Hz), 7.59 (1H, brs).

Reference Example 707

8-Fluoro-5-{[(3S*,4S*)-3-hydroxypiperidin-4-yl]methoxy}-3,4-dihydroquinolin-2(1H)-one hydrochloride Synthesized analogous to Reference Example 456.
$^1$HNMR (DMSO-d6) δ ppm: 1.68-1.79 (1H, m), 1.83-1.91 (1H, m), 1.92-1.99 (1H, m), 2.42-2.49 (2H, m), 2.58-2.69 (1H, m), 2.81-2.94 (3H, m), 3.19-3.30 (2H, m), 3.42-3.46 (1H, m), 3.72-3.80 (1H, m), 4.00-4.07 (2H, m), 6.60 (1H, dd, J=9.2 Hz, 3.8 Hz), 7.03 (1H, t, J=9.4 Hz), 8.83-8.95 (1H, m), 8.97-9.08 (1H, m), 10.04 (1H, brs).

Reference Example 708

(3R*,4S*)-1-(3,5-Dichloropyridin-2-yl)-4-{[(8-fluoro-2-oxo-1,2,3,4-tetrahydroquinolin-5-yl)oxy]methyl}piperidin-3-yl 4-nitrobenzoate To a solution of 5-{[(3S*,4S*)-1-(3,5-dichloropyridin-2-yl)-3-hydroxypiperidin-4-yl]methoxy}-8-fluoro-3,4-dihydroquinolin-2(1H)-one (1.0 g) in tetrahydrofuran (20 mL) were added 4-nitrobenzoic acid (0.49 g), triphenylphosphine (0.89 g) and diethyl azodicarboxylate (1.55 mL), and the reaction mixture was stirred at room temperature overnight. The solvent was distilled off, and the residue was purified by silica gel column chromatography (hexane/ethyl acetate) and further purified by basic silica gel column chromatography (hexane/ethyl acetate) to provide the title compound (1.0 g).
$^1$HNMR (CDCl$_3$) δ ppm: 1.85-1.92 (1H, m), 2.12-2.22 (1H, m), 2.41-2.50 (1H, m), 2.61 (2H, d, J=7.7 Hz), 2.92-3.03 (2H, m), 3.05-3.12 (1H, m), 3.13-3.18 (1H, m), 3.91-3.96 (2H, m), 4.00-4.07 (1H, m), 4.32-4.39 (1H, m), 5.53-5.56 (1H, m), 6.39 (1H, dd, J=9.1 Hz, 3.9 Hz), 6.84 (1H, t, J=9.5 Hz), 7.46 (1H, d, J=2.3 Hz), 7.59 (1H, brs), 8.04-8.08 (3H, m), 8.22-8.26 (2H, m).

Reference Example 709 tert-Butyl (3R*,4R*)-4-({[8-fluoro-1-(4-methoxybenzyl)-2-oxo-1,2,3,4-tetrahydroquinolin-5-yl]oxy}methyl)-3-hydroxypiperidine-1-carboxylate Synthesized analogous to Reference Example 495.
$^1$HNMR (CDCl$_3$) δ ppm: 1.36-1.45 (1H, m), 1.46 (9H, s), 1.74-1.93 (2H, m), 2.36-2.48 (1H, m), 2.50-2.92 (6H, m), 3.55-3.66 (1H, m), 3.74 (3H, s), 3.96-4.39 (4H, m), 5.15-

5.31 (2H, m), 6.53 (1H, dd, J=9.2 Hz, 3.4 Hz), 6.73-6.79 (2H, m), 6.83 (1H, dd, J=12.7 Hz, 9.2 Hz), 7.09-7.16 (2H, m).

Reference Example 710

8-Fluoro-5-{[(3R*,4R*)-3-hydroxypiperidin-4-yl]methoxy}-1-(4-methoxybenzyl)-3,4-dihydroquinolin-2(1H)-one hydrochloride Synthesized analogous to Reference Example 456.
$^1$HNMR (DMSO-d6) δ ppm: 1.66-1.98 (3H, m), 2.55-2.69 (3H, m), 2.79-2.93 (3H, m), 3.18-3.28 (2H, m), 3.68 (3H, s), 3.70-3.81 (1H, m), 3.97-4.03 (2H, m), 5.04-5.16 (2H, m), 5.45-5.55 (1H, m), 6.71 (1H, dd, J=9.2 Hz, 3.3 Hz), 6.78-6.84 (2H, m), 6.98 (1H, dd, J=13.1 Hz, 9.1 Hz), 7.03-7.10 (2H, m), 8.86-9.26 (2H, m).

Reference Example 711

5-{[(3R*,4R*)-1-(2,4-Dichlorophenyl)-3-hydroxypiperidin-4-yl]methoxy}-8-fluoro-1-(4-methoxybenzyl)-3,4-dihydroquinolin-2(1H)-one Synthesized analogous to Reference Example 526.
$^1$HNMR (CDCl$_3$) δ ppm: 1.65-1.78 (1H, m), 1.87-1.98 (2H, m), 2.41-2.45 (1H, m), 2.54-2.73 (4H, m), 2.79-2.95 (2H, m), 3.28-3.36 (1H, m), 3.47-3.54 (1H, m), 3.74 (3H, s), 3.86-3.95 (1H, m), 4.01-4.16 (2H, m), 5.15-5.32 (2H, m), 6.56 (1H, dd, J=9.2 Hz, 3.4H), 6.73-6.80 (2H, m), 6.85 (1H, dd, J=12.7 Hz, 9.1 Hz), 6.94 (1H, d, J=8.6 Hz), 7.10-7.16 (2H, m), 7.19 (1H, dd, J=8.6 Hz, 2.4 Hz), 7.37 (1H, d, J=2.4 Hz).

Reference Example 712

5-{[(3R*,4R*)-1-(4-Chloro-2-fluorophenyl)-3-hydroxypiperidin-4-yl]methoxy}-8-fluoro-1-(4-methoxybenzyl)-3,4-dihydroquinolin-2(1H)-one Synthesized analogous to Reference Example 526.
$^1$HNMR (CDCl$_3$) δ ppm: 1.65-1.77 (1H, m), 1.85-1.96 (2H, m), 2.31-2.35 (1H, m), 2.55-2.75 (4H, m), 2.81-2.93 (2H, m), 3.36-3.43 (1H, m), 3.53-3.60 (1H, m), 3.74 (3H, s), 3.84-3.94 (1H, m), 4.02-4.12 (2H, m), 5.18-5.30 (2H, m), 6.56 (1H, dd, J=9.1 Hz, 3.4H), 6.73-6.79 (2H, m), 6.80-6.92 (2H, m), 7.02-7.09 (2H, m), 7.10-7.16 (2H, m).

Reference Example 713

5-{[(3R*,4R*)-1-(4-Chloro-2,5-difluorophenyl)-3-hydroxypiperidin-4-yl]methoxy}-8-fluoro-1-(4-methoxybenzyl)-3,4-dihydroquinolin-2(1H)-one Synthesized analogous to Reference Example 526.
$^1$HNMR (CDCl$_3$) δ ppm: 1.55-1.76 (2H, m), 1.86-1.95 (1H, m), 2.41-2.49 (1H, m), 2.56-2.73 (3H, m), 2.80-2.89 (2H, m), 3.33-3.39 (1H, m), 3.46-3.62 (2H, m), 3.68 (3H, s), 3.96-4.04 (1H, m), 4.06-4.13 (1H, m), 5.04-5.16 (3H, m), 6.70 (1H, dd, J=9.2 Hz, 3.4H), 6.77-6.84 (2H, m), 6.98 (1H, dd, J=13.2 Hz, 9.1 Hz), 7.02-7.13 (3H, m), 7.50 (1H, dd, J=12.1 Hz, 7.1 Hz).

Reference Example 714

5-{[1-(3,5-Dichloropyridin-2-yl)-4-methoxypiperidin-4-yl]methoxy}-8-fluoro-1-(4-methoxybenzyl)-3,4-dihydroquinolin-2(1H)-one Under argon atmosphere, to a solution of 5-{[1-(3,5-dichloropyridin-2-yl)-4-hydroxypiperidin-4-yl]methoxy}-8-fluoro-1-(4-methoxybenzyl)-3,4-dihydroquinolin-2(1H)-one (0.35 g) and methyl iodide (0.078 mL) in N,N-dimethylformamide (7 mL) was added sodium hydride (55% in oil) (0.030 g) under ice-cooling, and the reaction mixture was stirred at the same temperature for 2 h. To the reaction solution was added water, and the solution was extracted with ethyl acetate, the organic layer was washed with water and brine, and dried over anhydrous sodium sulfate, and then the solvent was distilled off. The residue was purified by silica gel column chromatography (hexane/ethyl acetate) to provide the title compound (0.33 g).
$^1$HNMR (CDCl$_3$) δ ppm: 1.80-1.89 (2H, m), 1.98-2.04 (2H, m), 2.61-2.68 (2H, m), 2.87-2.94 (2H, m), 3.16-3.26 (2H, m), 3.32 (3H, s), 3.54-3.61 (2H, m), 3.74 (3H, s), 3.87 (2H, s), 5.23 (2H, brs), 6.52 (1H, dd, J=9.1 Hz, 3.3 Hz), 6.73-6.79 (2H, m), 6.83 (1H, dd, J=12.7 Hz, 9.1 Hz), 7.10-7.17 (2H, m), 7.59 (1H, d, J=2.3 Hz), 8.12 (1H, d, J=2.3 Hz).

Reference Example 715

8-Fluoro-5-{[4-(hydroxymethyl)piperidin-4-yl]methoxy}-1-(4-methoxybenzyl)-3,4-dihydroquinolin-2(1H)-one Under argon atmosphere at −70° C., to a solution of 1-tert-butyl 4-ethyl 4-({[8-fluoro-1-(4-methoxybenzyl)-2-oxo-1,2,3,4-tetrahydroquinolin-5-yl]oxy}methyl)piperidine-1,4-dicarboxylate (1.50 g) in tetrahydrofuran (15 mL) was added sodium triethylborohydride (1 M tetrahydrofuran solution) (6.05 mL) dropwise, and the reaction mixture was stirred for 9 h while allowing to warm to room temperature slowly. Then, brine was added to the mixture, and the solution was extracted with ethyl acetate. The organic layer was washed with water and brine, and dried over anhydrous sodium sulfate, and then the solvent was distilled off. The residue was purified by silica gel column chromatography (hexane/ethyl acetate) to give 1-tert-butyl 4-({[8-fluoro-1-(4-methoxybenzyl)-2-oxo-1,2,3,4-tetrahydroquinolin-5-yl]oxy}methyl)-4-(hydroxymethyl)piperidine-1-carboxylate (alcohol compound). The obtained alcohol compound was dissolved into ethyl acetate (4 mL), and 4 N hydrochloric acid/ethyl acetate (4 mL) was added to the mixture. After stirring the mixture at room temperature for 2 h, the solvent was distilled off. The residue was dissolved into water, the reaction mixture was made basic with aqueous sodium hydroxide, and the solution was extracted with dichloromethane. The organic layer was washed with water and brine, and dried over anhydrous sodium sulfate, and then the solvent was distilled off, the residue was purified by silica gel column chromatography (basic silica gel: dichloromethane/methanol) to provide the title compound (0.15 g).
$^1$HNMR (CDCl$_3$) δ ppm: 1.54-1.63 (4H, m), 1.63-1.74 (2H, m), 2.61-2.67 (2H, m), 2.81-2.91 (6H, m), 3.71 (2H, s), 3.74 (3H, s), 3.84 (2H, s), 5.23 (2H, brs), 6.55 (1H, dd, J=9.1 Hz, 3.3 Hz), 6.74-6.78 (2H, m), 6.83 (1H, dd, J=12.7 Hz, 9.1 Hz), 7.11-7.15 (2H, m).

Reference Example 716

5-{[1-(3,5-Dichloropyridin-2-yl)-4-(hydroxymethyl) piperidin-4-yl]methoxy}-8-fluoro-1-(4-methoxybenzyl)-3,4-dihydroquinolin-2(1H)-one Synthesized analogous to Reference Example 66.
$^1$HNMR (CDCl$_3$) δ ppm: 1.65-1.73 (1H, m), 1.75-1.82 (4H, m), 2.60-2.68 (2H, m), 2.82-2.89 (2H, m), 3.28-3.35 (4H, s), 3.74 (3H, s), 3.77 (2H, brs), 3.91 (2H, s), 5.23 (2H, brs), 6.56 (1H, dd, J=9.1 Hz, 3.4 Hz), 6.74-6.79 (2H, m), 6.84 (1H, dd, J=12.7 Hz, 9.1 Hz), 7.11-7.16 (2H, m), 7.60 (1H, d, J=2.3 Hz), 8.11 (1H, d, J=2.3 Hz).

Reference Example 717

Methyl [1-(3,5-Dichloropyridin-2-yl)-4-({[8-fluoro-1-(4-methoxybenzyl)-2-oxo-1,2,3,4-tetrahydroquinolin-5-yl]oxy}methyl)piperidin-4-yl]carbamate To a solution of 1-(3,5-dichloropyridin-2-yl)-4-({[8-fluoro-1-(4-methoxybenzyl)-2-oxo-1,2,3,4-tetrahydroquinolin-5-yl]oxy}methyl)piperidine-4-carboxylic acid (0.86 g) in 1,4-dioxane (8 mL) were added triethylamine (0.214 mL) and diphenylphosphoryl azide (0.331 mL), and the mixture was refluxed for 2 h. The solvent was distilled off and to the residue was added methanol (20 mL), and the reaction mixture was refluxed for 15 h. The solvent was distilled off, the residue was purified by silica gel column chromatography (hexane/ethyl acetate) to provide the title compound (0.82 g).
$^1$HNMR (CDCl$_3$) δ ppm: 1.91-2.00 (2H, m), 2.22-2.30 (2H, m), 2.61-2.67 (2H, m), 2.83-2.89 (2H, m), 3.09-3.17 (2H, m), 3.56-3.60 (2H, m), 3.61 (3H, s), 3.74 (3H, s), 4.08 (2H, s), 4.64 (1H, s), 5.22 (2H, brs), 6.53 (1H, dd, J=9.1 Hz, 3.3 Hz), 6.74-6.79 (2H, m), 6.82 (1H, dd, J=12.7 Hz, 9.1 Hz), 7.10-7.16 (2H, m), 7.61 (1H, d, J=2.3 Hz), 8.12 (1H, d, J=2.3 Hz).

Reference Example 718

Methyl [1-(3,5-dichloropyridin-2-yl)-4-({[8-fluoro-1-(4-methoxybenzyl)-2-oxo-1,2,3,4-tetrahydroquinolin-5-yl]oxy}methyl)piperidin-4-yl]methylcarbamate To a solution of methyl [1-(3,5-dichloropyridin-2-yl)-4-({[8-fluoro-1-(4-methoxybenzyl)-2-oxo-1,2,3,4-tetrahydroquinolin-5-yl]oxy}methyl)piperidin-4-yl]carbamate (0.3 g) in N,N-dimethylformamide (3 mL) was added methyl iodide (0.061 mL), then sodium hydride (55% in oil) (0.032 g) was added under ice-cooling, and the reaction mixture was stirred at room temperature for 4 h. To the reaction solution was added ammonium chloride aqueous solution, and the solution was extracted with ethyl acetate. The organic layer was washed with water and brine, and dried over anhydrous sodium sulfate, and then the solvent was distilled off. The residue was purified by silica gel column chromatography (hexane/ethyl acetate) to provide the title compound (0.31 g).
$^1$HNMR (CDCl$_3$) δ ppm: 2.08-2.18 (2H, m), 2.60-2.68 (4H, m), 2.81-2.87 (2H, m), 3.07 (3H, s), 3.18-3.26 (2H, m), 3.44-3.51 (2H, m), 3.64 (3H, s), 3.74 (3H, s), 4.18 (2H, s), 5.22 (2H, brs), 6.51 (1H, dd, J=9.1 Hz, 3.3 Hz), 6.74-6.79 (2H, m), 6.82 (1H, dd, J=12.7 Hz, 9.1 Hz), 7.10-7.16 (2H, m), 7.60 (1H, d, J=2.3 Hz), 8.12 (1H, d, J=2.3 Hz).

Reference Example 719

Methyl [1-(3,5-Dichloropyridin-2-yl)-4-{[(8-fluoro-2-oxo-1,2,3,4-tetrahydroquinolin-5-yl)oxy]methyl}piperidin-4-yl]methylcarbamate Synthesized analogous to Reference Example 119.
$^1$HNMR (CDCl$_3$) δ ppm: 2.10-2.19 (2H, m), 2.61-2.71 (4H, m), 2.97 (2H, t, J=7.7 Hz), 3.10 (3H, s), 3.18-3.27 (2H, m), 3.46-3.53 (2H, m), 3.66 (3H, s), 4.23 (2H, s), 6.46 (1H, dd, J=9.1 Hz, 4.0 Hz), 6.90 (1H, t, J=9.5 Hz), 7.48 (1H, brs), 7.61 (1H, d, J=2.3 Hz), 8.12 (1H, d, J=2.3 Hz).

Reference Example 720

5-{[4-(Aminooxy)-1-(3,5-dichloropyridin-2-yl)piperidin-4-yl]methoxy}-8-fluoro-1-(4-methoxybenzyl)-3,4-dihydroquinolin-2(1H)-one Under argon atmosphere, to a solution of 5-{[1-(3,5-dichloropyridin-2-yl)-4-hydroxypiperidin-4-yl]methoxy}-8-fluoro-1-(4-methoxybenzyl)-3,4-dihydroquinolin-2(1H)-one (0.694 g) in N,N-dimethylformamide (7 mL) was added sodium hydride (55% in oil) (0.059 g) under ice-cooling, and the mixture was stirred at room temperature for 30 min. To the reaction solution was added O-mesitylenesulfonylhydroxylamine (0.32 g) under ice-cooling, and the mixture was stirred at the same temperature for 30 min, and then at room temperature for 18 h. To the reaction solution was added ammonium chloride aqueous solution, and the solution was extracted with ethyl acetate. The organic layer was washed with water and brine, and dried over anhydrous sodium sulfate, and then the solvent was distilled off. The residue was purified by silica gel column chromatography (hexane/ethyl acetate) to provide the title compound (0.30 g).
$^1$HNMR (CDCl$_3$) δ ppm: 1.78-1.87 (2H, m), 2.06-2.13 (2H, m), 2.61-2.68 (2H, m), 2.88-2.94 (2H, m), 3.11-3.19 (2H, m), 3.53-3.61 (2H, m), 3.74 (3H, s), 3.95 (2H, s), 4.95 (2H, s), 5.23 (2H, brs), 6.56 (1H, dd, J=9.1 Hz, 3.3 Hz), 6.73-6.78 (2H, m), 6.83 (1H, dd, J=12.8 Hz, 9.1 Hz), 7.10-7.16 (2H, m), 7.59 (1H, d, J=2.3 Hz), 8.12 (1H, d, J=2.3 Hz).

Reference Example 721

5-Fluoro-2-[4-({[8-fluoro-1-(4-methoxybenzyl)-2-oxo-1,2,3,4-tetrahydroquinolin-5-yl]oxy}methyl)-4-hydroxypiperidin-1-yl]benzonitrile To a solution of 8-fluoro-5-[(4-hydroxypiperidin-4-yl)methoxy]-1-(4-methoxybenzyl)-3,4-dihydroquinolin-2(1H)-one hydrochloride (1.0 g) in water (10 mL) was added 5 N aqueous sodium hydroxide (1 mL) to make the reaction residue basic, and the solution was extracted with dichloromethane. The organic layer was washed with brine, and dried over anhydrous sodium sulfate, and then the solvent was distilled off. To the residue were added 2,5-difluorobenzonitrile (0.463 g), potassium carbonate (0.460 g) and N-methyl-2-pyrrolidone (5 mL), and the mixture was stirred at 100° C. for 24 h. To the reaction solution was added ammonium chloride aqueous solution and the solution was extracted with ethyl acetate. The organic layer was washed with water and brine, and dried over anhydrous sodium sulfate, and then the solvent was distilled off. The residue was purified by silica gel column chromatography (hexane/ethyl acetate) to provide the title compound (0.83 g).

¹HNMR (CDCl₃) δ ppm: 1.87-2.01 (4H, m), 2.02 (1H, s), 2.63-2.69 (2H, m), 2.86-2.92 (2H, m), 3.16-3.25 (2H, m), 3.28-3.34 (2H, m), 3.74 (3H, s), 3.82 (2H, s), 5.24 (2H, brs), 6.53 (1H, dd, J=9.1 Hz, 3.3 Hz), 6.74-6.79 (2H, m), 6.85 (1H, dd, J=12.7 Hz, 9.1 Hz), 7.06 (1H, dd, J=9.1 Hz, 4.6 Hz), 7.11-7.16 (2H, m), 7.20-7.25 (1H, m), 7.28 (1H, dd, J=7.8 Hz, 3.0 Hz).

Reference Example 722

5-Fluoro-2-[4-({[8-fluoro-1-(4-methoxybenzyl)-2-oxo-1,2,3,4-tetrahydroquinolin-5-yl]oxy}methyl)-4-hydroxypiperidin-1-yl]pyridine-3-carbonitrile Synthesized analogous to Reference Example 721.
¹HNMR (CDCl₃) δ ppm: 1.82-1.91 (4H, m), 2.05 (1H, s), 2.63-2.69 (2H, m), 2.84-2.91 (2H, m), 3.42-3.51 (2H, m), 3.74 (3H, s), 3.80 (2H, s), 3.99-4.07 (2H, m), 5.23 (2H, brs), 6.51 (1H, dd, J=9.1 Hz, 3.3 Hz), 6.74-6.78 (2H, m), 6.84 (1H, dd, J=12.7 Hz, 9.1 Hz), 7.10-7.15 (2H, m), 7.54 (1H, dd, J=7.3 Hz, 3.1 Hz), 8.24 (1H, d, J=3.1 Hz).

Reference Example 723

2-[4-(Aminooxy)-4-({[8-fluoro-1-(4-methoxybenzyl)-2-oxo-1,2,3,4-tetrahydroquinolin-5-yl]oxy}methyl)piperidin-1-yl]-5-fluorobenzonitrile Synthesized analogous to Reference Example 720.
¹HNMR (CDCl₃) δ ppm: 1.84-1.94 (2H, m), 2.13-2.20 (2H, m), 2.62-2.68 (2H, m), 2.88-2.95 (2H, m), 3.02-3.10 (2H, m), 3.24-3.30 (2H, m), 3.74 (3H, s), 3.96 (2H, s), 4.95 (2H, s), 5.24 (2H, brs), 6.56 (1H, dd, J=9.1 Hz, 3.4 Hz), 6.74-6.79 (2H, m), 6.84 (1H, dd, J=12.7 Hz, 9.1 Hz), 7.03 (1H, dd, J=9.1 Hz, 4.6 Hz), 7.11-7.16 (2H, m), 7.19-7.24 (1H, m), 7.28 (1H, dd, J=7.8 Hz, 3.0 Hz).

Reference Example 724

2-[4-(Aminooxy)-4-({[8-fluoro-1-(4-methoxybenzyl)-2-oxo-1,2,3,4-tetrahydroquinolin-5-yl]oxy}methyl)piperidin-1-yl]-5-fluoropyridine-3-carbonitrile Synthesized analogous to Reference Example 720.
¹HNMR (CDCl₃) δ ppm: 1.74-1.84 (2H, m), 2.09-2.17 (2H, m), 2.61-2.67 (2H, m), 2.86-2.93 (2H, m), 3.28-3.38 (2H, m), 3.74 (3H, s), 3.94 (2H, s), 3.94-4.01 (2H, m), 4.97 (2H, s), 5.23 (2H, brs), 6.54 (1H, dd, J=9.1 Hz, 3.3 Hz), 6.73-6.79 (2H, m), 6.83 (1H, dd, J=12.7 Hz, 9.1 Hz), 7.10-7.16 (2H, m), 7.53 (1H, dd, J=7.3 Hz, 3.1 Hz), 8.24 (1H, d, J=3.1 Hz).

Reference Example 725 tert-Butyl 4-cyano-4-({[8-fluoro-1-(4-methoxybenzyl)-2-oxo-1,2,3,4-tetrahydroquinolin-5-yl]oxy}methyl)piperidine-1-carboxylate Synthesized analogous to Reference Example 59.
¹HNMR (CDCl₃) δ ppm: 1.47 (9H, s), 1.55-1.63 (2H, m), 2.04-2.09 (2H, m), 2.63-2.69 (2H, m), 2.86-2.94 (2H, m), 3.00-3.20 (2H, m), 3.74 (3H, s), 3.90 (2H, s), 4.05-4.40 (2H, m), 5.23 (2H, brs), 6.45 (1H, dd, J=9.1 Hz, 3.3 Hz), 6.74-6.79 (2H, m), 6.84 (1H, dd, J=12.6 Hz, 9.1 Hz), 7.10-7.15 (2H, m).

Reference Example 726

4-{[(8-Fluoro-2-oxo-1,2,3,4-tetrahydroquinolin-5-yl)oxy]methyl}piperidine-4-carbonitrile To a mixture of tert-butyl 4-cyano-4-({[8-fluoro-1-(4-methoxybenzyl)-2-oxo-1,2,3,4-tetrahydroquinolin-5-yl]oxy}methyl)piperidine-1-carboxylate (0.92 g) and anisole (0.382 mL) was added trifluoroacetic acid (10 mL), and the mixture was stirred at 65-70° C. for 2 h, and then the solvent was distilled off. To the residue was added ethyl acetate, and the insoluble precipitate was collected on a filter. The obtained solid was suspended in water (20 mL), to which 5 N aqueous sodium hydroxide (0.35 mL) was added and insoluble crystal was collected on a filter to provide the title compound (0.46 g).
¹HNMR (CDCl₃) δ ppm: 1.55-1.69 (3H, m), 2.06-2.12 (2H, m), 2.65 (2H, t, J=7.7 Hz), 2.99-3.08 (4H, m), 3.11-3.18 (2H, m), 3.94 (2H, s), 6.42 (1H, dd, J=9.1 Hz, 3.9 Hz), 6.92 (1H, t, J=9.4 Hz), 7.51 (1H, brs).

Reference Example 727

5-{[1-(2,4-Dichlorophenyl)-4-(hydroxymethyl)piperidin-4-yl]methoxy}-8-fluoro-1-(4-methoxybenzyl)-3,4-dihydroquinolin-2(1H)-one To a suspension of 1-(2,4-dichlorophenyl)-4-({[8-fluoro-1-(4-methoxybenzyl)-2-oxo-1,2,3,4-tetrahydroquinolin-5-yl]oxy}methyl)piperidine-4-carboxylic acid (397 mg) in tetrahydrofuran (8 mL) was added triethylamine (0.104 mL), then ethyl chlorocarbonate (0.068 mL) was added dropwise under ice-cooling, and the reaction mixture was stirred for 1 h. The precipitate was filtered off, and to the filtrate was added a solution of sodium borohydride (77 mg) in water (3 mL), and the solution was stirred at room temperature for 1 h. To the reaction solution was added water, and the solution was extracted with ethyl acetate. The organic layer was washed with brine, dried over anhydrous magnesium sulfate, and the solvent was distilled off to provide the title compound (304 mg).
¹HNMR (CDCl₃) δ ppm: 1.70 (1H, t, J=5.6 Hz), 1.77-1.86 (4H, m), 2.63-2.66 (2H, m), 2.84-2.87 (2H, m), 3.01 (4H, t, J=5.5 Hz), 3.74 (3H, s), 3.77 (2H, d, J=5.5 Hz), 3.91 (2H, s), 5.23 (2H, brs), 6.57 (1H, dd, 9.2 Hz, 3.2 Hz), 6.77 (2H, d, 8.7 Hz), 6.85 (1H, dd, J=12.7 Hz, 9.1 Hz), 6.96 (1H, d, J=8.6 Hz), 7.13 (2H, d, J=8.6 Hz), 7.18 (1H, dd, J=8.6 Hz, 2.5 Hz), 7.36 (1H, d, J=2.5 Hz).

Reference Example 728 tert-Butyl (3S*,4S*)-4-({[8-fluoro-1-(4-methoxybenzyl)-2-oxo-1,2,3,4-tetrahydroquinolin-5-yl]oxy}methyl)-4-hydroxy-3-methoxypiperidine-1-carboxylate To a solution of tert-butyl (3S*,4S*)-4-({[8-fluoro-1-(4-methoxybenzyl)-2-oxo-1,2,3,4-tetrahydroquinolin-5-yl]oxy}methyl)-3,4-dihydroxypiperidine-1-carboxylate (1.06 g) in tetrahydrofuran (10 mL) was added sodium tert-butoxide (0.23 g) and the mixture was stirred at room temperature for 30 min. At the same temperature methyl iodide (0.15 mL) and N-methyl-2-pyrrolidone (2 mL) were added to the mixture and the solution was stirred at room temperature overnight. The solvent was distilled off, and the residue was purified by silica gel column chromatography (hexane/ethyl acetate) to provide the title compound (0.40 g).

$^1$HNMR (CDCl$_3$) δ ppm: 1.48 (9H, s), 1.68-1.76 (1H, m), 1.77-1.89 (1H, m), 2.36-2.42 (1H, m), 2.60-2.68 (2H, m), 2.78-3.02 (3H, m), 3.08-3.19 (1H, m), 3.33-3.40 (1H, m), 3.38 (3H, m), 3.64-3.71 (1H, m), 3.74 (3H, s), 3.78-3.90 (1H, m), 3.91-3.96 (1H, m), 4.16-4.40 (1H, m), 5.16-5.28 (2H, m), 6.52 (1H, dd, J=9.1 Hz, 3.4 Hz), 6.73-6.79 (2H, m), 6.83 (1H, dd, J=12.7 Hz, 9.0 Hz), 7.09-7.16 (2H, m).

Reference Example 729

8-Fluoro-5-{[(3S*,4S*)-4-hydroxy-3-methoxypiperidin-4-yl]methoxy}-1-(4-methoxybenzyl)-3,4-dihydroquinolin-2(1H)-one hydrochloride Synthesized analogous to Reference Example 456.
$^1$HNMR (DMSO-d6) δ ppm: 1.71-1.79 (1H, m), 1.93-2.06 (1H, m), 2.59-2.60 (2H, m), 2.83-3.06 (4H, m), 3.09-3.19 (1H, m), 3.25 (3H, s), 3.56-3.61 (1H, m), 3.68 (3H, s), 3.70-3.76 (1H, m), 3.99-4.20 (2H, m), 5.04-5.15 (2H, m), 5.22 (1H, brs), 6.70 (1H, dd, J=9.2 Hz, 3.4 Hz), 6.77-6.84 (2H, m), 7.00 (1H, dd, J=13.0 Hz, 9.1 Hz), 7.04-7.10 (2H, m), 8.76 (1H, brs), 8.93 (1H, brs).

Reference Example 730

5-{[(3S*,4S*)-1-(3,5-Dichloropyridin-2-yl)-4-hydroxy-3-methoxypiperidin-4-yl]methoxy}-8-fluoro-1-(4-methoxybenzyl)-3,4-dihydroquinolin-2(1H)-one Synthesized analogous to Reference Example 66.
$^1$HNMR (CDCl$_3$) δ ppm: 1.81-1.87 (1H, m), 2.03-2.12 (1H, m), 2.42-2.46 (1H, m), 2.61-2.68 (2H, m), 2.81-2.94 (2H, m), 2.98-3.05 (1H, m), 3.15-3.23 (1H, m), 3.39 (3H, s), 3.62-3.69 (2H, m), 3.72-3.77 (1H, m), 3.74 (3H, s), 3.91-4.02 (2H, m), 5.18-5.28 (2H, m), 6.55 (1H, dd, J=9.1 Hz, 3.3 Hz), 6.73-6.79 (2H, m), 6.84 (1H, dd, J=12.8 Hz, 9.0 Hz), 7.10-7.17 (2H, m), 7.62 (1H, d, J=2.3 Hz), 8.13 (1H, d, J=2.3 Hz).

Reference Example 731

1-(4-Chloro-2,6-difluorophenyl)-4-ethylidenepiperidine

To a solution of ethyltriphenylphosphonium bromide (1.81 g) in tetrahydrofuran (12 mL), n-butyllithium (1.6 M hexane solution) (3.05 mL) was added dropwise at 0° C., and the reaction mixture was stirred for 10 min. To the mixture was added a solution of 1-(4-chloro-2,6-difluorophenyl)piperidin-4-one (1 g) in tetrahydrofuran (4 mL), and the mixture was stirred at room temperature for 1 h. To the reaction solution was added aqueous saturated ammonium chloride, and the solution was extracted with ethyl acetate. The organic layer was washed with water and brine, and dried over anhydrous sodium sulfate, and then the solvent was distilled off. The residue was purified by silica gel column chromatography (hexane/ethyl acetate) to provide the title compound (852 mg).

$^1$HNMR (CDCl$_3$) δ ppm: 1.61 (3H, d, J=6.9 Hz), 2.26-2.36 (4H, m), 3.09-3.21 (4H, m), 5.25-5.30 (1H, m), 6.82-6.89 (2H, m).

Reference Example 732

1-(4-Chloro-2,6-difluorophenyl)-4-[1-hydroxyethyl]piperidin-4-ol

Synthesized analogous to Reference Example 504.
$^1$HNMR (CDCl$_3$) δ ppm: 1.22 (3H, d, J=6.6 Hz), 1.57-1.62 (1H, m), 1.67-1.81 (3H, m), 1.86-1.89 (2H, m), 3.06 (2H, d, J=11.8 Hz), 3.36-3.44 (2H, m), 3.60-3.66 (1H, m), 6.83-6.90 (2H, m).

Reference Example 733

1-[1-(4-Chloro-2,6-difluorophenyl)-4-hydroxypiperidin-4-yl]ethyl 4-methylbenzenesulfonate Synthesized analogous to Reference Example 697.
$^1$HNMR (CDCl$_3$) δ ppm: 1.26 (3H, d, J=6.4 Hz), 1.50-1.57 (1H, m), 1.62-1.67 (4H, m), 2.46 (3H, s), 2.95-3.03 (2H, m), 3.31-3.39 (2H, m), 4.51 (1H, q, J=6.4 Hz), 6.82-6.89 (2H, m), 7.36 (2H, d, J=8.0 Hz), 7.81 (2H, d, J=8.0 Hz).

Reference Example 734

(3R*,5R*)-1-(4-Chloro-2,6-difluorophenyl)-3,5-dihydroxypiperidin-4-one

To a suspension of 1-(4-chloro-2,6-difluorophenyl)piperidin-4-one (5.00 g) and DL-proline (0.703 g) in N,N-dimethylformamide (50 mL), a solution of nitrosobenzene (2.18 g) in N,N-dimethylformamide (50 mL) was added over 5 h at 0° C., and the mixture was stirred at the same temperature for 2 h. The reaction solution was poured into ice-cooled aqueous saturated ammonium chloride, and the reaction mixture was extracted with ethyl acetate. The organic layer was washed with brine, dried over anhydrous sodium sulfate, and the solvent was distilled off. The residue was dissolved into methanol (50 mL), and copper (II) sulfate (0.975 g) was added to the solution at 0° C., and the mixture was stirred at the same temperature for 2 h. To the reaction solution was added brine, and the solution was extracted with ethyl acetate. The organic layer was dried over anhydrous sodium sulfate, and the solvent was distilled off. The residue was purified by silica gel column chromatography (hexane/ethyl acetate) to provide the title compound. The compound was used for the next step without further purification.

$^1$HNMR (CDCl$_3$) δ ppm: 3.26-3.30 (2H, m), 3.59-3.63 (2H, m), 4.57-4.59 (2H, m), 6.95-7.00 (2H, m).

Reference Example 735

(4R,8R)-6-(4-Chloro-2,6-difluorophenyl)-1-oxa-6-azaspiro[2.5]octane-4,8-diol

Synthesized analogous to Reference Example 623.
$^1$HNMR (CDCl$_3$) δ ppm: 2.01 (1H, d, J=10.5 Hz), 2.74 (1H, d, J=8.0 Hz), 2.94 (1H, d, J=4.5 Hz), 3.06 (1H, d, J=4.5 Hz), 3.08-3.16 (2H, m), 3.38-3.43 (1H, m), 3.50-3.52 (1H, m), 3.65-3.70 (1H, m), 4.12-4.17 (1H, m), 6.90-6.98 (2H, m).

Reference Example 736

8-(4-Chloro-2-fluorophenyl)-1,4-dioxaspiro[4.5]decan-8-ol

To a solution of 4-chloro-2-fluoro-1-iodobenzene (1.01 mL) in tetrahydrofuran (20 ml), a solution of 2 M isopropylmagnesium chloride tetrahydrofuran (4.29 mL) was added dropwise under argon atmosphere at −30° C., and the mixture was stirred at from −30 to −20° C. for 5 min, then at room temperature for 2 h. To the reaction solution at −5° C. was added 1,4-dioxaspiro[4.5]decan-8-one (1.47 g), and the reaction mixture was stirred at room temperature overnight. The reaction solution was poured into aqueous saturated ammonium chloride, and the reaction mixture was extracted with ethyl acetate. The organic layer was washed with brine, and dried over anhydrous sodium sulfate, and then the solvent was distilled off. The residue was purified by silica gel column chromatography (hexane/ethyl acetate) to provide the title compound (1.16 g).

$^1$HNMR (CDCl$_3$) δ ppm: 1.63-1.74 (2H, m,), 1.80-1.91 (2H, m), 1.97 (1H, d, J=4.2 Hz), 2.04-2.16 (2H, m), 2.26-2.39 (2H, m), 3.99 (4H, t, J=2.3 Hz), 7.07 (1H, dd, J=12.0 Hz, 2.1 Hz), 7.12 (1H, dd, J=8.5 Hz, 2.2 Hz), 7.48 (1H, t, J=8.7 Hz).

Reference Example 737

4-(4-Chloro-2-fluorophenyl)-4-[(4-methoxybenzyl) oxy]cyclohexanone

Under argon atmosphere, to a solution of 8-(4-chloro-2-fluorophenyl)-1,4-dioxaspiro[4.5]decan-8-ol (6.51 g) in N,N-dimethylformamide (65 ml) was added sodium hydride (50% in oil) (2.18 g) under ice-cooling, and the mixture was stirred at the same temperature for 30 min. To the mixture was added α-chloro-4-methoxytoluene (6.16 mL) and the solution was stirred at room temperature for 3 h. The reaction solution was poured into water, and the solution was extracted with ethyl acetate. The organic layer was washed with brine, and dried over anhydrous sodium sulfate, and then the solvent was distilled off. The residue was purified by silica gel column chromatography to provide 8-(4-chloro-2-fluorophenyl)-8-[(4-methoxybenzyl)oxy]-1,4-dioxaspiro [4.5]decane as oil (9.06 g). The oil was dissolved into tetrahydrofuran (130 mL), and to the solution was added 5 N hydrochloric acid (33 mL), and the mixture was stirred at room temperature for 5 h. The reaction solution was poured into potassium carbonate aqueous solution, and the solution was extracted with ethyl acetate. The organic layer was washed with brine, and dried over anhydrous sodium sulfate, and then the solvent was distilled off. The residue was purified by silica gel column chromatography (hexane/ethyl acetate) to provide the title compound (7.64 g).

$^1$HNMR (CDCl$_3$) δ ppm: 2.21-2.42 (4H, m), 2.55-2.66 (2H, m), 2.76-2.90 (2H, m), 3.81 (3H, s), 4.23 (2H, s), 6.85-6.93 (2H, m), 7.13 (1H, dd, J=11.7 Hz, 2.1 Hz), 7.17 (1H, m), 7.22-7.29 (2H, m), 7.40 (1H, t, J=8.5 Hz).

Reference Example 738

6-(4-Chloro-2-fluorophenyl)-6-[(4-methoxybenzyl) oxy]-1-oxaspiro[2.5]octane

Synthesized analogous to Reference Example 623.

$^1$HNMR (CDCl$_3$) δ ppm: 1.15-1.23 (2H, m), 2.15-2.26 (2H, m), 2.29-2.38 (2H, m), 2.38-2.50 (2H, m), 2.71 (2H, s), 3.81 (3H, s), 4.12 (2H, s), 6.84-6.93 (2H, m), 7.05-7.13 (1H, dd, J=11.7 Hz, 2.1 Hz), 7.13-7.18 (1H, dd, J=8.4 Hz, 2.1 Hz), 7.22-7.30 (2H, m), 7.38 (1H, t, J=8.5 Hz).

Reference Example 739

4-Chloro-2-fluoro-1-{1-[(4-methoxybenzyl)oxy]-4-methylidenecyclohexyl}benzene

To a suspension of methyltriphenylphosphonium bromide (5.59 g) in tetrahydrofuran (42 mL) was added potassium tert-butoxide (1.55 g) under argon atmosphere, and the mixture was stirred at room temperature for 1 h. To the mixture was added a solution of 4-(4-chloro-2-fluorophenyl)-4-[(4-methoxybenzyl)oxy]cyclohexanone (4.36 g) in tetrahydrofuran (10 mL), and the reaction mixture was stirred at room temperature overnight. The reaction solution was poured into water, and the solution was extracted with ethyl acetate. The organic layer was washed with brine, and dried over anhydrous sodium sulfate, and then the solvent was distilled off. The residue was purified by silica gel column chromatography (hexane/ethyl acetate) to provide the title compound (3.90 g).

$^1$HNMR (CDCl$_3$) δ ppm: 1.86-2.00 (2H, m), 2.17-2.27 (2H, m), 2.30-2.40 (2H, m), 2.52-2.64 (2H, m), 3.80 (3H, s), 4.16 (2H, s), 4.65-4.71 (2H, m), 6.83-6.90 (2H, m), 7.08 (1H, dd, J=11.8 Hz, 2.1 Hz), 7.10-7.16 (1H, m), 7.21-7.28 (2H, m), 7.36 (1H, t, J=8.5 Hz).

Reference Example 740

4-(4-Chloro-2-fluorophenyl)-1-(hydroxymethyl)-4-[(4-methoxybenzyl)oxy]cyclohexanol To a solution of 4-chloro-2-fluoro-1-{1-[(4-methoxybenzyl)oxy]-4-methylidenecyclohexyl}benzene (0.30 g) in acetone/water (6 mL/1.5 mL) were added N-methylmorpholine (0.24 g) and Osmium Oxide, Immobilized Catalyst I (content: 7%) (0.030 g, 8.31 μM), and the reaction mixture was stirred at room temperature overnight. Insoluble materials were filtered off, and the filtrate was concentrated. Water was added to the residue, and the solution was extracted with ethyl acetate. The organic layer was washed with brine, and dried over anhydrous sodium sulfate, and then the solvent was distilled off. The residue was purified by silica gel column chromatography (hexane/ethyl acetate) to provide the title compound (0.28 g).

$^1$HNMR (CDCl$_3$) δ ppm: 1.51-1.68 (2H, m), 1.69-1.86 (2H, m), 1.86-2.30 (6H, m), 3.49 (0.6H, d, J=5.1 Hz), 3.63 (1.4H, d, J=5.4 Hz), 3.80 (3H, s), 4.09 (0.6H, s), 4.14 (1.4H, s), 6.83 (2H, m), 7.09 (1H, dd, J=11.9 Hz, 2.1 Hz), 7.13 (1H, dd, J=8.4 Hz, 2.1 Hz), 7.17-7.28 (2H, m), 7.32-7.42 (1H, m).

Reference Example 741

{cis-4-(4-Chloro-2-fluorophenyl)-1-hydroxy-4-[(4-methoxybenzyl)oxy]cyclohexyl}methyl 4-methyl-benzenesulfonate Synthesized analogous to Reference Example 697.

$^1$HNMR (CDCl$_3$) δ ppm: 1.61-1.71 (2H, m), 1.80-2.00 (4H, m), 2.11 (1H, s), 2.12-2.23 (2H, m), 2.45 (3H, s), 3.80 (3H, s), 4.04 (2H, s), 4.10 (2H, s), 6.82-6.89 (2H, m), 7.05-7.15 (2H, m), 7.18-7.22 (2H, m), 7.31 (1H, t, J=8.5 Hz), 7.36 (2H, d, J=8.0 Hz), 7.76-7.84 (2H, m).

Reference Example 742

(3s,6s)-6-(4-Chloro-2-fluorophenyl)-6-[(4-methoxybenzyl)oxy]-1-oxaspiro[2.5]octane A solution of {cis-4-(4-chloro-2-fluorophenyl)-1-hydroxy-4-[(4-methoxybenzyl)-oxy]cyclohexyl}methyl 4-methylbenzenesulfonate (1.09 g) and 1,8-diazabicyclo[5.4.0]undecene (0.36 mL) in ethyl acetate (11 mL) was stirred at room temperature overnight. The reaction solution was poured into water, and the solution was extracted with ethyl acetate. The organic layer was washed with brine, and dried over anhydrous sodium sulfate, and then the solvent was distilled off. The residue was purified by silica gel column chromatography (hexane/ethyl acetate) to provide the title compound (0.68 g).
$^1$HNMR (CDCl$_3$) δ ppm: 1.21-1.34 (2H, m), 2.07-2.19 (2H, m), 2.32-2.47 (4H, m), 2.67 (2H, s), 3.81 (3H, s), 4.16 (2H, s), 6.83-6.92 (2H, m), 7.11 (1H, dd, J=11.8 Hz, 2.1 Hz), 7.13-7.20 (1H, m), 7.22-7.30 (2H, m), 7.40 (1H, t, J=8.5 Hz).

Reference Example 743

8-(4-Chloro-2-fluorophenyl)-1,4-dioxaspiro[4.5]dec-7-ene

A solution of 8-(4-chloro-2-fluorophenyl)-1,4-dioxaspiro[4.5]decan-8-ol (0.30 g) and (methoxycarbonylsulfamoyl)triethylammonium hydroxide (0.50 g) in tetrahydrofuran (6 mL) was stirred, under argon atmosphere, at room temperature for 1 h. The reaction solution was poured into water, and the solution was extracted with ethyl acetate. The organic layer was washed with brine, and dried over anhydrous sodium sulfate, and then the solvent was distilled off. The residue was purified by silica gel column chromatography (hexane/ethyl acetate) to provide the title compound (0.25 g).
$^1$HNMR (CDCl$_3$) δ ppm: 1.90 (2H, t, J=6.5 Hz), 2.44-2.49 (2H, m), 2.57-2.63 (2H, m), 3.99-4.05 (4H, m), 5.83-5.87 (1H, m), 7.03-7.09 (2H, m), 7.19 (1H, t, J=8.4 Hz).

Reference Example 744

8-(4-Chloro-2-fluorophenyl)-1,4-dioxaspiro[4.5]decane

To a solution of 8-(4-chloro-2-fluorophenyl)-1,4-dioxaspiro[4.5]dec-7-ene (1.18 g) in ethyl acetate (12 mL) was added platinum oxide (60 mg) under argon atmosphere, and the reaction mixture was stirred at room temperature for 7 h under hydrogen atmosphere. Insoluble materials were filtered off, and the filtrate was concentrated. The residue was purified by silica gel column chromatography (hexane/ethyl acetate) to provide the title compound (0.60 g).
$^1$HNMR (CDCl$_3$) δ ppm: 1.63-1.92 (8H, m), 2.82-2.94 (1H, m), 3.98 (4H, s), 7.04 (1H, dd, J=10.1 Hz, 2.1 Hz), 7.07 (1H, dd, J=8.3 Hz, 2.0 Hz), 7.19 (1H, t, J=8.2 Hz).

Reference Example 745

4-(4-Chloro-2-fluorophenyl)cyclohexanone

A solution of 8-(4-chloro-2-fluorophenyl)-1,4-dioxaspiro[4.5]decane (2.95 g) and 5 N hydrochloric acid (15 mL) in tetrahydrofuran (59 mL) was stirred at room temperature for 5 h, then under heated to reflux for 5 h. The reaction solution was concentrated, and potassium carbonate aqueous solution was added to the residue, and the solution was extracted with ethyl acetate. The organic layer was washed with brine, and dried over anhydrous sodium sulfate, and then the solvent was distilled off. The residue was purified by silica gel column chromatography (hexane/ethyl acetate) to provide the title compound (1.95 g).
$^1$HNMR (CDCl$_3$) δ ppm: 1.81-2.02 (2H, m), 2.13-2.27 (2H, m), 2.45-2.60 (4H, m), 3.26-3.39 (1H, m), 7.02-7.20 (3H, m).

Reference Example 746

4-Chloro-2-fluoro-1-(4-methylidenecyclohexyl)benzene

Synthesized analogous to Reference Example 739.
$^1$HNMR (CDCl$_3$) δ ppm: 1.44-1.59 (2H, m), 1.83-1.99 (2H, m), 2.09-2.24 (2H, m), 2.38-2.47 (2H, m), 2.94-3.05 (1H, m), 4.68 (2H, t, J=1.7 Hz), 7.03 (1H, dd, J=10.1 Hz, 2.1 Hz), 7.06 (1H, dd, J=8.3 Hz, 2.1 Hz), 7.12 (1H, t, J=8.1 Hz).

Reference Example 747

4-(4-Chloro-2-fluorophenyl)-1-(hydroxymethyl)cyclohexanol

Synthesized analogous to Reference Example 740.
$^1$HNMR (CDCl$_3$) δ ppm: 1.40-1.65 (4H, m), 1.68-1.78 (0.5H, m), 1.78-1.91 (2.5H, m), 1.91-1.99 (1.5H, m), 1.99-2.11 (1.5H, m), 2.76-2.99 (1H, m), 3.48 (0.5H, d, J=5.9 Hz), 3.70 (1.5H, d, J=5.9 Hz), 7.00-7.25 (3H, m).

Reference Example 748

[cis-4-(4-Chloro-2-fluorophenyl)-1-hydroxycyclohexyl]methyl 4-methylbenzenesulfonate To a solution of 4-(4-chloro-2-fluorophenyl)-1-(hydroxymethyl)cyclohexanol (1.96 g) in dichloromethane (20 mL) were added p-toluenesulfonyl chloride (1.74 g) and N,N,N',N'-tetramethyl-1,3-propanediamine (2.52 mL) under ice-cooling, and the mixture was stirred at the same temperature for 3 h. To the reaction solution was added water, and the solution was extracted with dichloromethane. The organic layer was dried over anhydrous sodium sulfate, and then the solvent was distilled off. The residue was purified by silica gel column chromatography (hexane/ethyl acetate) to provide the title compound (0.45 g).
$^1$HNMR (CDCl$_3$) δ ppm: 1.39-1.52 (2H, m), 1.63-1.73 (2H, m), 1.75-1.92 (5H, m), 2.46 (3H, s), 2.71-2.87 (1H, m), 3.87 (2H, s), 7.02 (1H, dd, J=10.1 Hz, 2.1 Hz), 7.07 (1H, dd, J=8.4 Hz, 1.9 Hz), 7.18 (1H, t, J=8.2 Hz), 7.37 (2H, d, J=8.1 Hz), 7.77-7.85 (2H, m).

Reference Example 749

[trans-4-(4-Chloro-2-fluorophenyl)-1-hydroxycyclohexyl]methyl 4-methylbenzenesulfonate To a solution of 4-(4-chloro-2-fluorophenyl)-1-(hydroxymethyl)cyclohexanol (1.96 g) in dichloromethane (20 mL) were added p-toluenesulfonyl chloride (1.74 g) and N,N,N',N'-tetramethyl-1,3-propanediamine (2.52 mL) under ice-cooling, and the reaction mixture was stirred at the same temperature for 3 h. To the reaction solution was added water, and the solution was extracted with dichloromethane. The organic layer was dried over anhydrous sodium sulfate, and then the solvent was distilled off. The residue was purified by silica gel column chromatography (hexane/ethyl acetate) to provide the title compound (1.97 g).

$^1$HNMR (CDCl$_3$) δ ppm: 1.29-1.44 (2H, m), 1.51-1.68 (2H, m), 1.71-1.85 (2H, m), 1.88-2.02 (2H, m), 2.17 (1H, s), 2.46 (3H, s), 2.72-2.83 (1H, m), 4.12 (2H, s), 6.96-7.11 (3H, m), 7.38 (2H, d, J=8.0 Hz), 7.79-7.89 (2H, m).

Reference Example 750

(3r,6r)-6-(4-Chloro-2-fluorophenyl)-1-oxaspiro[2.5]octane

Synthesized analogous to Reference Example 742.
$^1$HNMR (CDCl$_3$) δ ppm: 1.33-1.48 (2H, m), 1.62-1.77 (2H, m), 1.94-2.15 (4H, m), 2.66 (2H, s), 2.85-2.97 (1H, m), 7.03 (1H, dd, J=10.1 Hz, 2.1 Hz), 7.07 (1H, dd, J=8.4 Hz, 1.9 Hz), 7.16 (1H, t, J=8.1 Hz).

Reference Example 751

(3 s,6s)-6-(4-Chloro-2-fluorophenyl)-1-oxaspiro[2.5]octane

Synthesized analogous to Reference Example 742.
$^1$HNMR (CDCl$_3$) δ ppm: 1.32-1.43 (2H, m), 1.77-1.95 (4H, m), 2.01-2.16 (2H, m), 2.71 (2H, s), 2.88-3.00 (1H, m), 7.05 (1H, dd, J=10.1 Hz, 2.1 Hz), 7.10 (1H, dd, J=8.4 Hz, 2.3 Hz), 7.21 (1H, t, J=8.2 Hz).

Reference Example 752

5-{[cis-4-(4-Chloro-2-fluorophenyl)-1-hydroxycyclohexyl]methoxy}-8-fluoro-1-(4-methoxybenzyl)-3,4-dihydroquinolin-2(1H)-one Synthesized analogous to Reference Example 453.
$^1$HNMR (CDCl$_3$) δ ppm: 1.56-1.66 (2H, m), 1.70-1.79 (2H, m), 1.85-1.99 (5H, m), 2.62-2.70 (2H, m), 2.81-2.93 (3H, m), 3.74 (3H, s), 3.77 (2H, s), 5.24 (2H, brs), 6.52 (1H, dd, J=7.3 Hz, 3.4 Hz), 6.73-6.79 (2H, m), 6.84 (1H, dd, J=12.7 Hz, 9.1 Hz), 7.05 (1H, dd, J=10.1 Hz, 2.1 Hz), 7.10 (1H, dd, J=8.5 Hz, 1.9 Hz), 7.12-7.15 (2H, m), 7.23 (1H, t, J=8.0 Hz).

Reference Example 753

5-{[4-(4-Chloro-2-fluorophenyl)cyclohex-1-en-1-yl]methoxy}-8-fluoro-1-(4-methoxybenzyl)-3,4-dihydroquinolin-2(1H)-one Synthesized analogous to Reference Example 595.
$^1$HNMR (CDCl$_3$) δ ppm: 1.76-1.90 (1H, m), 1.90-2.00 (1H, m), 2.10-2.31 (3H, m), 2.31-2.41 (1H, m), 2.60-2.69 (2H, m), 2.83-2.97 (2H, m), 3.05-3.19 (1H, m), 3.73 (3H, s), 4.35 (2H, s), 5.23 (2H, brs), 5.82-5.90 (1H, m), 6.52 (1H, dd, J=9.1 Hz, 3.4 Hz), 6.71-6.79 (2H, m), 6.82 (1H, dd, J=12.8 Hz, 9.1 Hz), 7.00-7.11 (2H, m), 7.10-7.18 (3H, m).

Reference Example 754

5-{[(1R*,2R*,4R*)-4-(4-Chloro-2-fluorophenyl)-1,2-dihydroxycyclohexyl]methoxy}-8-fluoro-1-(4-methoxybenzyl)-3,4-dihydroquinolin-2(1H)-one Synthesized analogous to Reference Example 740.
$^1$HNMR (CDCl$_3$) δ ppm: 1.62-1.74 (2H, m), 1.77-1.93 (2H, m), 1.93-2.08 (2H, m), 2.20 (1H, d, J=5.8 Hz), 2.48 (1H, d, J=0.7 Hz), 2.61-2.71 (2H, m), 2.81-3.00 (3H, m), 3.74 (3H, s), 3.88-3.93 (1H, m), 3.94 (2H, s), 5.14-5.34 (2H, m), 6.56 (1H, dd, J=9.1 Hz, 3.4 Hz), 6.73-6.79 (2H, m), 6.85 (1H, dd, J=12.7 Hz, 9.1 Hz), 7.06 (1H, dd, J=10.1 Hz, 2.1 Hz), 7.09-7.16 (3H, m), 7.21 (1H, t, J=8.1 Hz).

Reference Example 755

5-{[(1R*,2R*,4S*)-4-(4-Chloro-2-fluorophenyl)-1,2-dihydroxycyclohexyl]methoxy}-8-fluoro-1-(4-methoxybenzyl)-3,4-dihydroquinolin-2(1H)-one Synthesized analogous to Reference Example 740.
$^1$HNMR (CDCl$_3$) δ ppm: 1.58-1.67 (1H, m), 1.78-1.94 (3H, m), 1.98-2.15 (2H, m), 2.56-2.69 (4H, m), 2.83-2.92 (2H, m), 3.31-3.42 (1H, m), 3.74 (3H, s), 4.04 (2H, s), 4.08 (1H, brs), 5.24 (2H, brs), 6.56 (1H, dd, J=9.1 Hz, 3.4 Hz), 6.73-6.80 (2H, m), 6.86 (1H, dd, J=12.6 Hz, 9.1 Hz), 7.00-7.09 (2H, m), 7.09-7.17 (3H, m).

Reference Example 756

5-({4-(4-Chloro-2-fluorophenyl)-4-[(4-methoxybenzyl)oxy]cyclohex-1-en-1-yl}methoxy)-8-fluoro-3,4-dihydroquinolin-2(1H)-one Synthesized analogous to Reference Example 595.
$^1$HNMR (CDCl$_3$) δ ppm: 1.86-2.01 (1H, m), 2.25-2.44 (3H, m), 2.54-2.62 (2H, m), 2.63-2.82 (2H, m), 2.96 (2H, t, J=7.7 Hz), 3.79 (3H, s), 4.17 (2H, s), 4.39 (2H, brs), 5.78 (1H, brs), 6.42 (1H, dd, J=9.1 Hz, 4.0 Hz), 6.77-6.94 (3H, m), 7.05-7.15 (2H, m), 7.15-7.20 (2H, m), 7.29 (1H, t, J=8.6 Hz), 7.51 (1H, brs).

Reference Example 757

5-({(1R*,2R*)-4-(4-Chloro-2-fluorophenyl)-1,2-dihydroxy-4-[(4-methoxybenzyl)oxy]cyclohexyl}methoxy)-8-fluoro-3,4-dihydroquinolin-2(1H)-one Synthesized analogous to Reference Example 740.
$^1$HNMR (CDCl$_3$) δ ppm: 1.77-2.46 (6H, m), 2.48-2.69 (4H, m), 2.78-2.95 (2H, m), 3.81 (3H, s), 3.93 (1H, d, J=8.9 Hz), 4.00 (1H, d, J=8.9 Hz), 4.10 (2H, s), 4.19-4.33 (1H, m), 6.49 (1H, dd, J=9.0 Hz, 3.9 Hz), 6.80-6.95 (3H, m), 7.09-7.24 (4H, m), 7.33-7.42 (1H, m), 7.51 (1H, brs).

Reference Example 758

(1R*,2R*,5S*)-5-(4-Chloro-2-fluorophenyl)-2-{[(8-fluoro-2-oxo-1,2,3,4-tetrahydroquinolin-5-yl)oxy]methyl}-2-hydroxy-5-[(4-methoxybenzyl)oxy]cyclohexyl acetate To a solution of 5-({(1R,2R)-4-(4-chloro-2-fluorophenyl)-1,2-dihydroxy-4-[(4-methoxybenzyl)oxy]cyclohexyl}methoxy)-8-fluoro-3,4-dihydroquinolin-2(1H)-one (1.39 g) in pyridine (14 mL) was added acetic anhydride (0.28 mL), and the reaction mixture was stirred at 50-60° C. for 4 h. The reaction solution was poured into water, and the solution was extracted with ethyl acetate. The organic layer was washed with brine, and dried over anhydrous sodium sulfate, and then the solvent was distilled off. The residue was purified by silica gel column chromatography (dichloromethane/ethyl acetate) to provide the title compound (0.67 g).

$^1$HNMR (CDCl$_3$) δ ppm: 1.70-1.80 (1H, m), 2.07 (3H, s), 2.14-2.22 (2H, m), 2.23-2.25 (1H, m), 2.27-2.37 (1H, m), 2.38-2.52 (3H, m), 2.58 (1H, dd, J=12.9 Hz, 4.3 Hz), 2.72-2.91 (2H, m), 3.73-3.88 (5H, m), 4.06 (1H, d, J=10.3 Hz), 4.39 (1H, d, J=10.3 Hz), 5.49 (1H, dd, J=11.6 Hz, 4.4 Hz), 6.41 (1H, dd, J=9.1 Hz, 3.9 Hz), 6.81-6.92 (3H, m), 7.12 (1H, dd, J=11.6 Hz, 2.0 Hz), 7.15 (1H, dd, J=8.4 Hz, 2.1 Hz), 7.27-7.32 (2H, m), 7.38 (1H, t, J=8.4 Hz), 7.54 (1H, brs).

Reference Example 759

(1R*,2R*,5R*)-5-(4-Chloro-2-fluorophenyl)-2-{[(8-fluoro-2-oxo-1,2,3,4-tetrahydroquinolin-5-yl)oxy]methyl}-2-hydroxy-5-[(4-methoxybenzyl)oxy]cyclohexyl acetate To a solution of 5-({(1R,2R)-4-(4-chloro-2-fluorophenyl)-1,2-dihydroxy-4-[(4-methoxybenzyl)oxy]cyclohexyl}methoxy)-8-fluoro-3,4-dihydroquinolin-2(1H)-one (1.39 g) in pyridine (14 mL) was added acetic anhydride (0.28 mL), and the reaction mixture was stirred at 50-60° C. for 4 h. The reaction solution was poured into water, and the solution was extracted with ethyl acetate. The organic layer was washed with brine, and dried over anhydrous sodium sulfate, and then the solvent was distilled off. The residue was purified by silica gel column chromatography (dichloromethane/ethyl acetate) to provide the title compound (0.29 g).

$^1$HNMR (CDCl$_3$) δ ppm: 1.50-1.64 (1H, m), 1.81-1.92 (1H, m), 2.08 (3H, s), 2.15-2.34 (3H, m), 2.48-2.73 (5H, m), 2.84-2.94 (1H, m), 3.73 (2H, s), 3.78 (3H, s), 4.04 (1H, d, J=10.4 Hz), 4.19 (1H, d, J=10.4 Hz), 5.10 (1H, dd, J=12.0 Hz, 4.4 Hz), 6.34 (1H, dd, J=9.1 Hz, 3.9 Hz), 6.79 (3H, m), 7.08-7.15 (2H, m), 7.17 (1H, dd, J=11.9 Hz, 2.1 Hz), 7.24 (1H, dd, J=8.5 Hz, 2.1 Hz), 7.48 (1H, brs), 7.71 (1H, t, J=8.5 Hz).

Reference Example 760

Dimethyl 4-(4-chloro-2-fluorophenyl)-4-cyanoheptanedioate

A solution of 4-chloro-2-fluorophenylacetonitrile (10.00 g), methyl acrylate (53.1 mL) and Triton B (2.68 mL) in acetonitrile (200 mL) was heated to reflux for 8 h. The reaction solution was concentrated, and 2 N hydrochloric acid was added to the residue. The solution was extracted with diethyl ether, the organic layer was washed with water and potassium carbonate aqueous solution, and dried over anhydrous sodium sulfate, and then the solvent was distilled off to provide the title compound (20.2 g).

$^1$HNMR (CDCl$_3$) δ ppm: 2.10-2.23 (2H, m), 2.29-2.43 (2H, m), 2.46-2.66 (4H, m), 3.62 (6H, s), 7.06-7.30 (2H, m), 7.50 (1H, t, J=8.5 Hz).

Reference Example 761

Methyl 5-(4-chloro-2-fluorophenyl)-5-cyano-2-oxocyclohexanecarboxylate

To a solution of dimethyl 4-(4-chloro-2-fluorophenyl)-4-cyanoheptanedioate (20.15 g) in 1,2-dimethoxyethane (202 mL) was added sodium hydride (50% in oil) (8.49 g) under argon atmosphere at 0° C., and the mixture was stirred at the same temperature for 5 min, then at room temperature for 10 min, and then heated to reflux for 1 h. The reaction solution was poured into aqueous saturated ammonium chloride, and the reaction mixture was extracted with ethyl acetate. The organic layer was washed with brine, and dried over anhydrous sodium sulfate, and then the solvent was distilled off. The residue was purified by silica gel column chromatography (hexane/ethyl acetate) to provide the title compound (14.04 g).

$^1$HNMR (CDCl$_3$) δ ppm: 2.23-2.54 (3H, m), 2.66-2.89 (2H, m), 3.01-3.17 (1H, m), 3.79 (3H, s), 7.15-7.26 (2H, m), 7.38-7.50 (1H, m), 12.25 (1H, s).

Reference Example 762

1-(4-Chloro-2-fluorophenyl)-4-oxocyclohexanecarbonitrile

To a solution of methyl 5-(4-chloro-2-fluorophenyl)-5-cyano-2-oxocyclohexanecarboxylate (14.04 g) in dimethyl sulfoxide (112 mL) were added sodium chloride (14.04 g) and water (18 mL), and the reaction mixture was stirred at 140-150° C. for 8 h. To the reaction solution was added water, and the solution was extracted with ethyl acetate. The organic layer was washed with brine, and dried over anhydrous sodium sulfate, and then the solvent was distilled off. The residue was purified by silica gel column chromatography (hexane/ethyl acetate) to provide the title compound (10.2 g).

$^1$HNMR (CDCl$_3$) δ ppm: 2.34-2.45 (2H, m), 2.51-2.65 (4H, m), 2.84-2.98 (2H, m), 7.18-7.25 (2H, m), 7.48 (1H, t, J=8.5 Hz).

Reference Example 763

(3r,6r)-6-(4-Chloro-2-fluorophenyl)-1-oxaspiro[2.5]octane-6-carbonitrile

Synthesized analogous to Reference Example 623.
$^1$HNMR (CDCl$_3$) δ ppm: 1.35-1.49 (2H, m), 2.23-2.34 (4H, m), 2.45-2.60 (2H, m), 2.78 (2H, s), 7.13-7.24 (2H, m), 7.41 (1H, t, J=8.6 Hz).

Reference Example 764

8-(4-Chloro-2-fluorophenyl)-8-methoxy-1,4-dioxaspiro[4.5]decane

To a solution of 8-(4-chloro-2-fluorophenyl)-1,4-dioxaspiro[4.5]decan-8-ol (2.00 g) in N,N-dimethylformamide (20 mL) was added sodium hydride (50% in oil) (0.670 g) under argon atmosphere at 0° C., and the reaction mixture was stirred at the same temperature for 30 min. Then to the mixture was added iodomethane (0.868 mL) and the solution was stirred at room temperature for 1 h. The reaction solution was poured into water, and the solution was extracted with ethyl acetate. The organic layer was washed with brine, and dried over anhydrous sodium sulfate, and then the solvent was distilled off. The residue was purified by silica gel column chromatography (hexane/ethyl acetate) to provide the title compound (1.98 g).

$^1$HNMR (CDCl$_3$) δ ppm: 1.60-1.70 (2H, m), 1.93-2.05 (2H, m), 2.05-2.21 (4H, m), 3.07 (3H, s), 3.88-4.04 (4H, m), 7.00-7.09 (1H, dd, J=11.8 Hz, 2.2 Hz), 7.11 (1H, m), 7.31 (1H, t, J=8.5 Hz).

Reference Example 765

4-(4-Chloro-2-fluorophenyl)-4-methoxycyclohexanone

Synthesized analogous to Reference Example 745.
$^1$HNMR (CDCl$_3$) δ ppm: 2.20-2.39 (4H, m), 2.42-2.55 (2H, m), 2.70-2.84 (2H, m), 3.19 (3H, s), 7.11 (1H, dd, J=11.8 Hz, 2.1 Hz), 7.15-7.20 (1H, m), 7.34 (1H, t, J=8.5 Hz).

Reference Example 766

4-Chloro-2-fluoro-1-(1-methoxy-4-methylidenecyclohexyl)benzene

Synthesized analogous to Reference Example 739.
$^1$HNMR (CDCl$_3$) δ ppm: 1.83-1.99 (2H, m), 2.12-2.28 (4H, m), 2.41-2.56 (2H, m), 3.11 (3H, s), 4.68 (2H, t, J=1.7 Hz), 7.06 (1H, dd, J=11.8 Hz, 2.1 Hz), 7.09-7.15 (1H, m), 7.30 (1H, t, J=8.5 Hz).

Reference Example 767

4-(4-Chloro-2-fluorophenyl)-1-(hydroxymethyl)-4-methoxycyclohexanol

Synthesized analogous to Reference Example 740.
$^1$HNMR (CDCl$_3$) δ ppm: 1.46-1.64 (1H, m), 1.67-2.25 (9H, m), 3.05 (1H, s), 3.10 (2H, s), 3.51 (0.6H, d, J=5.2 Hz), 3.63 (1.4H, d, J=5.6 Hz), 7.00-7.17 (2H, m), 7.28-7.36 (1H, m).

Reference Example 768

[trans-4-(4-Chloro-2-fluorophenyl)-1-hydroxy-4-methoxycyclohexyl]methyl 4-methylbenzenesulfonate To a solution of 4-(4-chloro-2-fluorophenyl)-1-(hydroxymethyl)-4-methoxycyclohexanol (1.48 g) in dichloromethane (15 mL) were added N,N,N',N'-tetramethyl-1,3-propanediamine (1.704 mL) and p-toluenesulfonyl chloride (1.17 g), and the reaction mixture was stirred at room temperature for 1 h. To the reaction solution was added brine, and the solution was extracted with dichloromethane. The organic layer was dried over anhydrous sodium sulfate, and then the solvent was distilled off. The residue was purified by silica gel column chromatography (hexane/ethyl acetate) to provide the title compound (0.53 g).
$^1$HNMR (CDCl$_3$) δ ppm: 1.49-1.62 (2H, m), 1.65-1.78 (2H, m), 1.80 (1H, s), 1.97-2.03 (2H, m), 2.09-2.22 (2H, m), 2.46 (3H, s), 3.00 (3H, s), 3.89 (2H, s), 7.06 (1H, dd, J=11.8 Hz, 2.1 Hz), 7.09-7.15 (1H, m), 7.28 (1H, t, J=7.9 Hz), 7.37 (2H, d, J=8.0 Hz), 7.77-7.85 (2H, m).

Reference Example 769

[cis-4-(4-Chloro-2-fluorophenyl)-1-hydroxy-4-methoxycyclohexyl]methyl 4-methylbenzenesulfonate To a solution of 4-(4-chloro-2-fluorophenyl)-1-(hydroxymethyl)-4-methoxycyclohexanol (1.48 g) in dichloromethane (15 mL) were added N,N,N',N'-tetramethyl-1,3-propanediamine (1.704 mL) and p-toluenesulfonyl chloride (1.173 g), and the reaction mixture was stirred at room temperature for 1 h. To the reaction solution was added brine, and the solution was extracted with dichloromethane. The organic layer was dried over anhydrous sodium sulfate, and then the solvent was distilled off. The residue was purified by silica gel column chromatography (hexane/ethyl acetate) to provide the title compound (1.41 g).
$^1$HNMR (CDCl$_3$) δ ppm: 1.60-1.69 (2H, m), 1.73-1.93 (4H, m), 1.98-2.08 (2H, m), 2.11 (1H, s), 2.45 (3H, s), 3.06 (3H, s), 4.04 (2H, s), 7.06 (1H, dd, J=12.2 Hz, 2.2 Hz), 7.12 (1H, dd, J=8.5 Hz, 2.2 Hz), 7.25 (1H, t, J=8.5 Hz), 7.33-7.40 (2H, m), 7.76-7.85 (2H, m).

Reference Example 770

(3r,6r)-6-(4-Chloro-2-fluorophenyl)-6-methoxy-1-oxaspiro[2.5]octane

Synthesized analogous to Reference Example 742.
$^1$HNMR (CDCl$_3$) δ ppm: 1.11-1.22 (2H, m), 2.09-2.26 (4H, m), 2.31-2.43 (2H, m), 2.72 (2H, s), 3.09 (3H, s), 7.09 (1H, dd, J=11.8 Hz, 2.1 Hz), 7.13 (1H, dd, J=8.5 Hz, 2.2 Hz), 7.31 (1H, t, J=8.5 Hz).

Reference Example 771

(3s,6s)-6-(4-Chloro-2-fluorophenyl)-6-methoxy-1-oxaspiro[2.5]octane

Synthesized analogous to Reference Example 742.
$^1$HNMR (CDCl$_3$) δ ppm: 1.12-1.30 (2H, m), 1.97-2.13 (2H, m), 2.18-2.35 (4H, m), 2.66 (2H, s), 3.12 (3H, s), 7.08 (1H, dd, J=11.8 Hz, 2.1 Hz), 7.14 (1H, dd, J=8.5 Hz, 2.1 Hz), 7.34 (1H, t, J=8.5 Hz).

Reference Example 772

8-(4-Chloro-2,6-difluorophenyl)-1,4-dioxaspiro[4.5]decan-8-ol

Synthesized analogous to Reference Example 736.
$^1$HNMR (CDCl$_3$) δ ppm: 1.61-1.70 (2H, m), 2.08-2.14 (4H, m), 2.29-2.43 (2H, m), 2.53 (1H, t, J=5.5 Hz), 3.93-4.01 (4H, m), 6.86-6.95 (2H, m).

Reference Example 773

4-(4-Chloro-2,6-difluorophenyl)-4-hydroxycyclohexanone

Synthesized analogous to Reference Example 745.
$^1$HNMR (CDCl$_3$) δ ppm: 2.27-2.40 (2H, m), 2.40-2.55 (4H, m), 2.86-2.98 (3H, m), 6.94-7.00 (2H, m).

Reference Example 774

1-(4-Chloro-2,6-difluorophenyl)-4-methylidenecyclohexanol

Synthesized analogous to Reference Example 739.
$^1$HNMR (CDCl$_3$) δ ppm: 2.02-2.25 (6H, m), 2.54-2.70 (3H, m), 4.68 (2H, t, J=1.7 Hz), 6.81-6.96 (2H, m).

Reference Example 775

1-(4-Chloro-2,6-difluorophenyl)-4-(hydroxymethyl) cyclohexane-1,4-diol

Synthesized analogous to Reference Example 740.
$^1$HNMR (DMSO-d6) δ ppm: 1.22-1.31 (0.5H, m), 1.40-1.52 (1.5H, m), 1.56-1.72 (1.5H, m), 1.75-1.96 (2.5H, m), 2.01-2.11 (1.5H, m), 2.17-2.33 (0.5H, m), 3.15 (0.5H, d, J=5.6 Hz), 3.28 (1.5H, d, J=5.9 Hz), 3.86 (0.25H, s), 4.06 (0.75H, s), 4.38 (0.75H, t, J=5.9 Hz), 4.47 (0.25H, t, J=5.6 Hz), 5.00 (0.25H, s), 5.20 (0.75H, s), 7.15-7.29 (2H, m).

Reference Example 776

[trans-4-(4-Chloro-2,6-difluorophenyl)-1,4-dihydroxycyclohexyl]methyl 4-methylbenzenesulfonate To a solution of 1-(4-chloro-2,6-difluorophenyl)-4-(hydroxymethyl)cyclohexane-1,4-diol (1.59 g) in dichloromethane (32 mL) were added N,N,N',N'-tetramethyl-1,3-propanediamine (1.81 mL) and p-toluenesulfonyl chloride (1.24 g), and the reaction mixture was stirred at room temperature for 3 h. To the reaction solution was added water, and the solution was extracted with dichloromethane. The organic layer was dried over anhydrous sodium sulfate, and then the solvent was distilled off. The residue was purified by silica gel column chromatography (hexane/ethyl acetate) to provide the title compound (0.72 g).
$^1$HNMR (CDCl$_3$) δ ppm: 1.52-1.63 (2H, m), 1.79 (1H, s), 1.81-1.92 (2H, m), 1.92-2.00 (2H, m), 2.22-2.32 (1H, m), 2.35-2.50 (5H, m), 3.88 (2H, s), 6.84-6.97 (2H, m), 7.37 (2H, d, J=8.0 Hz), 7.81 (2H, m).

Reference Example 777

[cis-4-(4-Chloro-2,6-difluorophenyl)-1,4-dihydroxycyclohexyl]methyl 4-methylbenzenesulfonate To a solution of 1-(4-chloro-2,6-difluorophenyl)-4-(hydroxymethyl)cyclohexane-1,4-diol (1.59 g) in dichloromethane (32 mL) were added N,N,N',N'-tetramethyl-1,3-propanediamine (1.81 mL) and p-toluenesulfonyl chloride (1.24 g), and the reaction mixture was stirred at room temperature for 3 h. To the reaction solution was added water, and the solution was extracted with dichloromethane. The organic layer was dried over anhydrous sodium sulfate, and then the solvent was distilled off. The residue was purified by silica gel column chromatography (hexane/ethyl acetate) to provide the title compound (1.35 g).
$^1$HNMR (CDCl$_3$) δ ppm: 1.62-1.74 (2H, m), 1.94-2.04 (6H, m), 2.14 (1H, s), 2.45 (3H, s), 2.51 (1H, t, J=4.9 Hz), 4.06 (2H, s), 6.83-6.97 (2H, m), 7.36 (2H, d, J=8.0 Hz), 7.76-7.86 (2H, m).

Reference Example 778

(3r,6r)-6-(4-Chloro-2,6-difluorophenyl)-1-oxaspiro[2.5]octan-6-ol

Synthesized analogous to Reference Example 742.
$^1$HNMR (CDCl$_3$) δ ppm: 1.14-1.22 (1.6H, m), 1.22-1.28 (0.4H, m), 2.11-2.19 (1.6H, m), 2.23-2.33 (0.4H, m), 2.35-2.55 (4H, m), 2.57-2.64 (1H, m), 2.67 (0.4H, s), 2.72 (1.6H, s), 6.85-6.99 (2H, m).

Reference Example 779

(3s,6s)-6-(4-Chloro-2,6-difluorophenyl)-1-oxaspiro[2.5]octan-6-ol

Synthesized analogous to Reference Example 742.
$^1$HNMR (CDCl$_3$) δ ppm: 1.17-1.32 (2H, m), 2.16-2.34 (4H, m), 2.40-2.53 (2H, m), 2.61 (1H, t, J=5.5 Hz), 2.66 (2H, s), 6.87-6.99 (2H, m).

Reference Example 780

1-(4-Chloro-2,6-difluorophenyl)-3-[(phenylamino) oxy]piperidin-4-one

Under nitrogen atmosphere, to a suspension of 1-(4-chloro-2,6-difluorophenyl)piperidin-4-one (3.00 g) and DL-proline (0.070 g) in dimethyl sulfoxide (8 mL) was added a solution of nitrosobenzene (0.436 g) in dimethyl sulfoxide (8 mL), and the reaction mixture was stirred at room temperature for 1.5 h. The reaction solution was poured into ice-cooled aqueous saturated ammonium chloride, and the reaction mixture was extracted with ethyl acetate. The organic layer was washed with brine, dried over anhydrous sodium sulfate, and the solvent was distilled off. The residue was purified by silica gel column chromatography (hexane/ethyl acetate) to provide the title compound (807 mg).
$^1$HNMR (CDCl$_3$) δ ppm: 2.57-2.59 (1H, m), 2.77-2.83 (1H, m), 3.43-3.47 (2H, m), 3.49-3.54 (1H, m), 3.81-3.85 (1H, m), 4.63-4.67 (1H, m), 6.91-6.98 (5H, m), 7.24-7.27 (2H, m), 7.76 (1H, brs).

Reference Example 781

1-(4-Chloro-2,6-difluorophenyl)-3-hydroxypiperidin-4-one

To a solution of 1-(4-chloro-2,6-difluorophenyl)-3-[(phenylamino)oxy]piperidin-4-one (807 mg) in methanol (8 mL) was added copper (II) sulfate (110 mg) at 0° C., and the reaction mixture was stirred for 4 h. To the reaction solution was added brine, and the solution was extracted with ethyl acetate. The organic layer was washed with brine, dried over anhydrous sodium sulfate, and the solvent was distilled off. The residue was purified by silica gel column chromatography (hexane/ethyl acetate) to provide the title compound (342 mg).
$^1$HNMR (CDCl$_3$) δ ppm: 2.56-2.60 (1H, m), 2.84-2.90 (1H, m), 3.09-3.14 (1H, m), 3.37-3.43 (1H, m), 3.49-3.54 (1H, m), 3.63 (1H, d, J=4.0 Hz), 3.76-3.81 (1H, m), 4.38-4.43 (1H, m), 6.91-6.96 (2H, m).

Reference Example 782

(3R)-1-(4-Chloro-2,6-difluorophenyl)-3-hydroxypiperidin-4-one

To a suspension of 1-(4-chloro-2,6-difluorophenyl)piperidin-4-one (2.00 g) and L-proline (0.187 g) in N,N-dimethylformamide (8 mL) was added a solution of nitrosobenzene (0.581 g) in N,N-dimethylformamide (8 mL), and the reaction mixture was stirred at room temperature for 1 h. The reaction solution was poured into ice-cooled aqueous saturated ammonium chloride, and the reaction mixture was extracted with ethyl acetate. The organic layer was washed with brine, dried over anhydrous sodium sulfate, and the solvent was distilled off. The residue was dissolved into methanol (16 mL), to the obtained solution copper (II) sulfate (0.260 g) was added at 0° C., and the mixture was stirred for 4 h. To the reaction solution was added brine, and the solution was extracted with ethyl acetate. The organic layer was washed with brine, dried over anhydrous sodium sulfate, and the solvent was distilled off. The residue was purified by silica gel column chromatography (hexane/ethyl acetate) to provide the title compound (545 mg).

$^1$HNMR (CDCl$_3$) δ ppm: 2.56-2.60 (1H, m), 2.84-2.90 (1H, m), 3.09-3.14 (1H, m), 3.37-3.43 (1H, m), 3.49-3.54 (1H, m), 3.63 (1H, d, J=3.5 Hz), 3.76-3.81 (1H, m), 4.38-4.43 (1H, m), 6.91-6.96 (2H, m).

Reference Example 783

(3R)-1-(4-Chloro-2-fluorophenyl)-3-hydroxypiperidin-4-one

To a suspension of 1-(4-chloro-2-fluorophenyl)piperidin-4-one (3.00 g) and (S)-5-(pyrrolidin-2-yl)-1H-tetrazole (0.183 g) in N,N-dimethylformamide (20 mL), ¾ of a solution of nitrosobenzene (1.41 g) in N,N-dimethylformamide (40 mL) was added dropwise at −40° C. After stirring the mixture at −30° C. for 4 h, the remaining ¼ of the solution was added dropwise, and the reaction mixture was stirred for 12 h. The reaction solution was poured into ice-cooled aqueous saturated ammonium chloride, and the reaction mixture was extracted with ethyl acetate. The organic layer was washed with brine, dried over anhydrous sodium sulfate, and the solvent was distilled off. The residue was dissolved into methanol (30 mL), copper (II) sulfate (0.631 g) was added to the solution at 0° C., and the mixture was stirred for 2 h. To the reaction solution was added brine, and the solution was extracted with ethyl acetate. The organic layer was washed with brine, dried over anhydrous sodium sulfate, and the solvent was distilled off. The residue was purified by silica gel column chromatography (hexane/ethyl acetate) to provide the title compound (1.25 g).

$^1$HNMR (CDCl$_3$) δ ppm: 2.59-2.63 (1H, m), 2.81 (1H, t, J=11.0 Hz), 2.85-2.92 (1H, m), 3.04-3.09 (1H, m), 3.62 (1H, d, J=3.5 Hz), 3.71-3.76 (1H, m), 3.95-3.99 (1H, m), 4.43-4.47 (1H, m), 6.91 (1H, t, J=9.0 Hz), 7.07 (1H, ddd, J=9.0 Hz, 2.5 Hz, 1.0 Hz), 7.10 (1H, dd, J=11.5 Hz, 2.5 Hz).

Reference Example 784

(3S)-1-(4-Chloro-2,6-difluorophenyl)-3-hydroxypiperidin-4-one

To a suspension of 1-(4-chloro-2,6-difluorophenyl)piperidin-4-one (31.6 g) and D-proline (4.44 g) in N,N-dimethylformamide (300 mL), a solution of nitrosobenzene (14.06 g) in N,N-dimethylformamide (300 mL) was added dropwise at 0° C. over 10 h. The reaction solution was poured into ice-cooled aqueous saturated ammonium chloride, and the reaction mixture was extracted with ethyl acetate. The organic layer was washed with brine, dried over anhydrous sodium sulfate, and the solvent was distilled off. The residue was dissolved into methanol (300 mL), copper (II) sulfate (6.16 g) was added to the solution at 0° C., and the mixture was stirred for 2 h. To the reaction solution was added brine, and the solution was extracted with ethyl acetate. The organic layer was washed with brine, dried over anhydrous sodium sulfate, and the solvent was distilled off. The residue was purified by silica gel column chromatography (hexane/ethyl acetate) to provide the title compound (11.5 g).

$^1$HNMR (CDCl$_3$) δ ppm: 2.56-2.60 (1H, m), 2.84-2.90 (1H, m), 3.09-3.14 (1H, m), 3.37-3.43 (1H, m), 3.49-3.54 (1H, m), 3.63 (1H, d, J=3.5 Hz), 3.76-3.81 (1H, m), 4.38-4.43 (1H, m), 6.91-6.96 (2H, m).

Reference Example 785

(3S)-1-(4-Chloro-2-fluorophenyl)-3-hydroxypiperidin-4-one

Synthesized analogous to Reference Example 784.

$^1$HNMR (CDCl$_3$) δ ppm: 2.59-2.63 (1H, m), 2.81 (1H, t, J=11.0 Hz), 2.85-2.92 (1H, m), 3.04-3.09 (1H, m), 3.62 (1H, d, J=3.5 Hz), 3.71-3.76 (1H, m), 3.95-3.99 (1H, m), 4.43-4.47 (1H, m), 6.91 (1H, t, J=9.0 Hz), 7.07 (1H, ddd, J=9.0 Hz, 2.5 Hz, 1.0 Hz), 7.10 (1H, dd, J=11.5 Hz, 2.5 Hz).

Reference Example 786

(3R)-1-(4-Bromo-2-fluorophenyl)-3-hydroxypiperidin-4-one

To a solution of (1R,6R)-3-(4-bromo-2-fluorophenyl)-6-{[tert-butyl(dimethyl)silyl]oxy}-7-oxa-3-azabicyclo[4.1.0]heptane (0.28 g) in tetrahydrofuran/water (15:1) (3 mL) was added p-toluenesulfonic acid monohydrate (13.2 mg), and the reaction mixture was stirred at room temperature for 1 h. To the reaction solution was added water, and the solution was extracted with ethyl acetate. The organic layer was washed with brine, dried over anhydrous sodium sulfate, and the solvent was distilled off to provide the title compound (0.3 g).

$^1$HNMR (CDCl$_3$) δ ppm: 2.59-2.65 (1H, m), 2.79 (1H, t, J=11.1 Hz), 2.84-2.93 (1H, m), 3.04 (1H, dt, J=12.2 Hz, 9.4 Hz), 3.61 (1H, d, J=3.8 Hz), 3.73-3.78 (1H, m), 3.95-4.01 (1H, m), 4.41-4.48 (1H, m), 6.84 (1H, t, J=8.8 Hz), 7.13-7.27 (2H, m).

Reference Example 787

1-(4-Bromo-2,6-difluorophenyl)-3-hydroxypiperidin-4-one

To a solution of (1R*,6R*)-3-(4-bromo-2,6-difluorophenyl)-6-{[tert-butyl(dimethyl)silyl]oxy}-7-oxa-3-azabicyclo[4.1.0]heptane (6.58 g) in dichloromethane (65 mL) was added 5 N hydrochloric acid (15.65 mL), and the reaction mixture was stirred at room temperature for 30 min. To the reaction solution was added water, and the solution was extracted with dichloromethane. The organic layer was washed with water and brine, and dried over anhydrous sodium sulfate, and then the solvent was distilled off. The residue was purified by silica gel column chromatography (hexane/ethyl acetate) to provide the title compound (3.90 g).

$^1$HNMR (CDCl$_3$) δ ppm: 2.55-2.61 (1H, m), 2.82-2.91 (1H, m), 3.07-3.14 (1H, m), 3.35-3.43 (1H, m), 3.48-3.56 (1H, m), 3.61-3.66 (1H, m), 3.75-3.83 (1H, m), 4.37-4.44 (1H, m), 7.04-7.11 (2H, m).

Reference Example 788

(3R)-1-(4-Chloro-2,6-difluorophenyl)-3-[(4-methoxybenzyl)oxy]piperidin-4-one

To a solution of 4-methoxybenzyl2,2,2-trichloroethaneimidate (1.58 g) in hexane (9.4 mL) was added a solution of (3R)-1-(4-chloro-2,6-difluorophenyl)-3-hydroxypiperidin-4-one (976 mg) in dichloromethane (4.7 mL), then boron trifluoride-diethylether complex (0.014 mL) was added to the mixture at 0° C., and the reaction mixture was stirred for 14 h. The reaction solution was filtered with Celite, the filtrate was washed with hexane/dichloromethane (2/1), then the organic layer was washed with aqueous saturated sodium bicarbonate, dried over anhydrous sodium sulfate, and the solvent was distilled off. The residue was purified by silica gel column chromatography (hexane/ethyl acetate) to provide the title compound (663 mg).
$^1$HNMR (CDCl$_3$) δ ppm: 2.53-2.57 (1H, m), 2.68-2.75 (1H, m), 3.31-3.45 (3H, m), 3.60-3.64 (1H, m), 3.80 (3H, s), 4.12-4.15 (1H, m), 4.50 (1H, d, J=11.5 Hz), 4.78 (1H, d, J=11.5 Hz), 6.88 (2H, d, J=8.5 Hz), 6.88-6.94 (2H, m), 7.30 (2H, d, J=8.5 Hz).

Reference Example 789

1-(4-Chloro-2,6-difluorophenyl)-3-[(4-methoxybenzyl)oxy]piperidin-4-one

Synthesized analogous to Reference Example 788.
$^1$HNMR (CDCl$_3$) δ ppm: 2.53-2.57 (1H, m), 2.68-2.75 (1H, m), 3.31-3.45 (3H, m), 3.60-3.64 (1H, m), 3.80 (3H, s), 4.12-4.15 (1H, m), 4.50 (1H, d, J=11.5 Hz), 4.78 (1H, d, J=11.5 Hz), 6.88 (2H, d, J=8.5 Hz), 6.88-6.94 (2H, m), 7.30 (2H, d, J=8.5 Hz).

Reference Example 790

(3S)-1-(4-Chloro-2,6-difluorophenyl)-3-[(4-methoxybenzyl)oxy]piperidin-4-one

Synthesized analogous to Reference Example 788.
$^1$HNMR (CDCl$_3$) δ ppm: 2.53-2.57 (1H, m), 2.68-2.75 (1H, m), 3.31-3.45 (3H, m), 3.60-3.64 (1H, m), 3.80 (3H, s), 4.12-4.15 (1H, m), 4.50 (1H, d, J=11.5 Hz), 4.78 (1H, d, J=11.5 Hz), 6.88 (2H, d, J=8.5 Hz), 6.88-6.94 (2H, m), 7.30 (2H, d, J=8.5 Hz).

Reference Example 791

(3S)-1-(4-Chloro-2-fluorophenyl)-3-[(4-methoxybenzyl)oxy]piperidin-4-one

Synthesized analogous to Reference Example 788.
$^1$HNMR (CDCl$_3$) δ ppm: 2.56-2.60 (1H, m), 2.69-2.75 (1H, m), 3.02-3.13 (2H, m), 3.57-3.62 (1H, m), 3.70-3.79 (1H, m), 3.80 (3H, s), 4.14-4.18 (1H, m), 4.51 (1H, d, J=11.5 Hz), 4.80 (1H, d, J=11.5 Hz), 6.84 (1H, t, J=9.0 Hz), 6.88 (2H, d, J=8.5 Hz), 7.03 (1H, ddd, J=9.0 Hz, 2.5 Hz, 1.0 Hz), 7.07 (1H, dd, J=11.5 Hz, 2.5 Hz), 7.30 (2H, d, J=8.5 Hz).

Reference Example 792

(3S,4R)-6-(4-Chloro-2,6-difluorophenyl)-4-[(4-methoxybenzyl)oxy]-1-oxa-6-azaspiro[2.5]octane Synthesized analogous to Reference Example 398.
$^1$HNMR (CDCl$_3$) δ ppm: 1.84-1.94 (2H, m), 2.65 (1H, d, J=5.0 Hz), 3.04 (1H, d, J=5.0 Hz), 3.16-3.23 (2H, m), 3.27-3.32 (1H, m), 3.40-3.43 (1H, m), 3.49-3.51 (1H, m), 3.79 (3H, s), 4.50 (1H, d, J=11.5 Hz), 4.58 (1H, d, J=11.5 Hz), 6.86 (2H, d, J=8.5 Hz), 6.85-6.90 (2H, m), 7.23 (2H, d, J=8.5 Hz).

Reference Example 793

(3S*,4R*)-6-(4-Chloro-2,6-difluorophenyl)-4-[(4-methoxybenzyl)oxy]-1-oxa-6-azaspiro[2.5]octane Synthesized analogous to Reference Example 398.
$^1$HNMR (CDCl$_3$) δ ppm: 1.84-1.94 (2H, m), 2.65 (1H, d, J=5.0 Hz), 3.04 (1H, d, J=5.0 Hz), 3.16-3.23 (2H, m), 3.27-3.32 (1H, m), 3.40-3.43 (1H, m), 3.49-3.51 (1H, m), 3.79 (3H, s), 4.50 (1H, d, J=11.5 Hz), 4.58 (1H, d, J=11.5 Hz), 6.86 (2H, d, J=8.5 Hz), 6.85-6.90 (2H, m), 7.23 (2H, d, J=8.5 Hz).

Reference Example 794

(3R,4S)-6-(4-Chloro-2,6-difluorophenyl)-4-[(4-methoxybenzyl)oxy]-1-oxa-6-azaspiro[2.5]octane Synthesized analogous to Reference Example 340.
$^1$HNMR (CDCl$_3$) δ ppm: 1.84-1.94 (2H, m), 2.65 (1H, d, J=5.0 Hz), 3.04 (1H, d, J=5.0 Hz), 3.16-3.23 (2H, m), 3.27-3.32 (1H, m), 3.40-3.43 (1H, m), 3.49-3.51 (1H, m), 3.79 (3H, s), 4.50 (1H, d, J=11.5 Hz), 4.58 (1H, d, J=11.5 Hz), 6.86 (2H, d, J=8.5 Hz), 6.85-6.90 (2H, m), 7.23 (2H, d, J=8.5 Hz).

Reference Example 795

(3R,4S)-6-(4-Chloro-2-fluorophenyl)-4-[(4-methoxybenzyl)oxy]-1-oxa-6-azaspiro[2.5]octane Synthesized analogous to Reference Example 340.
$^1$HNMR (CDCl$_3$) δ ppm: 1.84-1.89 (1H, m), 1.98-2.02 (1H, m), 2.68 (1H, d, J=5.0 Hz), 3.00 (1H, d, J=5.0 Hz), 3.03-3.08 (1H, m), 3.10-3.14 (1H, m), 3.24-3.34 (2H, m), 3.47-3.49 (1H, m), 3.80 (3H, s), 4.54 (1H, d, J=11.5 Hz), 4.60 (1H, d, J=11.5 Hz), 6.84-6.91 (3H, m), 7.00-7.07 (2H, m), 7.24 (2H, d, J=8.5 Hz).

Reference Example 796

(3R*,4S*)-6-(4-Bromo-2,6-difluorophenyl)-4-[(4-methoxybenzyl)oxy]-1-oxa-6-azaspiro[2.5]octane A solution of 1-(4-bromo-2,6-difluorophenyl)-3-hydroxypiperidin-4-one (2 g), 4-methoxybenzyl 2,2,2-trichloroacetimidate (5.16 g) and lanthanum (III) trifluoromethanesulfonate (0.191 g) in toluene (25 mL) was stirred at room temperature for 16.5 h. After insoluble materials were filtered off, the solvent was distilled off, and the residue was purified by silica gel column chromatography (dichloromethane) to give the mixture of 1-(4-bromo-2,6-difluorophenyl)-3-hydroxypiperidin-4-one and 1-(4-bromo-2,6-difluorophenyl)-3-[(4-methoxybenzyl)oxy]piperidin-4-one. To a suspension of trimethylsulfoxonium iodide (0.898 g) in dimethyl sulfoxide (7.5 mL) was added sodium t-butoxide (0.392 g), the mixture was stirred at room temperature for 30 min, to which the solution of the mixture in dimethyl sulfoxide (7.5 mL) was added, and the reaction mixture was stirred at room temperature for 1 h. To the reaction mixture was added water, and the solution was extracted with ethyl acetate. The organic layer was washed with water and brine, and dried over anhydrous sodium sulfate, and then the solvent was distilled off. The residue was purified by silica gel column chromatography (hexane/ethyl acetate) to provide the title compound (0.44 g).

¹HNMR (CDCl₃) δ ppm: 1.81-1.94 (2H, m), 2.65 (1H, d, J=5.2 Hz), 3.03 (1H, d, J=5.2 Hz), 3.15-3.24 (2H, m), 3.26-3.33 (1H, m), 3.39-3.45 (1H, m), 3.50 (1H, dd, J=7.6 Hz, 4.0 Hz), 3.80 (3H, s), 4.50 (1H, d, J=11.5 Hz), 4.58 (1H, d, J=11.5 Hz), 6.83-6.88 (2H, m), 6.98-7.05 (2H, m), 7.21-7.25 (2H, m).

Reference Example 797

5-({(3R,4S)-1-(4-Chloro-2,6-difluorophenyl)-4-hydroxy-3-[(4-methoxybenzyl)oxy]piperidin-4-yl}methoxy)-8-fluoro-3,4-dihydroquinolin-2(1H)-one Synthesized analogous to Reference Example 453.
¹HNMR (CDCl₃) δ ppm: 1.62-1.65 (1H, m), 2.15-2.21 (1H, m), 2.41 (1H, brs), 2.59 (2H, t, J=7.5 Hz), 2.74-2.80 (1H, m), 2.87-2.93 (1H, m), 3.08-3.12 (1H, m), 3.33-3.36 (1H, m), 3.47-3.55 (3H, m), 3.73 (3H, s), 3.79 (1H, d, J=9.0 Hz), 4.15 (1H, d, J=9.0 Hz), 4.33 (1H, d, J=11.5 Hz), 4.62 (1H, d, J=11.5 Hz), 6.44 (1H, dd, J=9.0 Hz, 4.0 Hz), 6.70 (2H, d, J=8.5 Hz), 6.86-6.91 (2H, m), 6.92 (1H, t, J=9.0 Hz), 7.11 (2H, d, J=8.5 Hz), 7.75 (1H, brs).

Reference Example 798

5-({(3R*,4S*)-1-(4-Chloro-2,6-difluorophenyl)-4-hydroxy-3-[(4-methoxybenzyl)oxy]piperidin-4-yl}methoxy)-8-fluoro-3,4-dihydroquinolin-2(1H)-one Synthesized analogous to Reference Example 453.
¹HNMR (CDCl₃) δ ppm: 1.62-1.65 (1H, m), 2.15-2.21 (1H, m), 2.35 (1H, brs), 2.59 (2H, t, J=7.5 Hz), 2.74-2.80 (1H, m), 2.87-2.93 (1H, m), 3.08-3.12 (1H, m), 3.33-3.36 (1H, m), 3.47-3.55 (3H, m), 3.73 (3H, s), 3.79 (1H, d, J=9.0 Hz), 4.15 (1H, d, J=9.0 Hz), 4.33 (1H, d, J=11.5 Hz), 4.62 (1H, d, J=11.5 Hz), 6.44 (1H, dd, J=9.0 Hz, 4.0 Hz), 6.70 (2H, d, J=8.5 Hz), 6.86-6.91 (2H, m), 6.92 (1H, t, J=9.0 Hz), 7.11 (2H, d, J=8.5 Hz), 7.60 (1H, brs).

Reference Example 799

5-({(3S,4R)-1-(4-Chloro-2,6-difluorophenyl)-4-hydroxy-3-[(4-methoxybenzyl)oxy]piperidin-4-yl}methoxy)-8-fluoro-3,4-dihydroquinolin-2(1H)-one Synthesized analogous to Reference Example 453.
¹HNMR (CDCl₃) δ ppm: 1.62-1.65 (1H, m), 2.15-2.21 (1H, m), 2.45 (1H, brs), 2.59 (2H, t, J=7.5 Hz), 2.74-2.80 (1H, m), 2.87-2.93 (1H, m), 3.08-3.12 (1H, m), 3.33-3.36 (1H, m), 3.47-3.55 (3H, m), 3.73 (3H, s), 3.79 (1H, d, J=9.0 Hz), 4.15 (1H, d, J=9.0 Hz), 4.33 (1H, d, J=11.5 Hz), 4.62 (1H, d, J=11.5 Hz), 6.44 (1H, dd, J=9.0 Hz, 4.0 Hz), 6.70 (2H, d, J=8.5 Hz), 6.86-6.91 (2H, m), 6.92 (1H, t, J=9.0 Hz), 7.11 (2H, d, J=8.5 Hz), 7.82 (1H, brs).

Reference Example 800

5-({(3S,4R)-1-(4-Chloro-2-fluorophenyl)-4-hydroxy-3-[(4-methoxybenzyl)oxy]piperidin-4-yl}methoxy)-8-fluoro-3,4-dihydroquinolin-2(1H)-one Synthesized analogous to Reference Example 453.
¹HNMR (CDCl₃) δ ppm: 1.68-1.72 (1H, m), 2.17-2.23 (1H, m), 2.37 (1H, brs), 2.59 (2H, t, J=7.5 Hz), 2.71-2.77 (1H, m), 2.85-2.91 (1H, m), 3.10-3.17 (2H, m), 3.22-3.27 (1H, m), 3.50-3.52 (1H, m), 3.52-3.63 (1H, m), 3.73 (3H, s), 3.76 (1H, d, J=9.0 Hz), 4.16 (1H, d, J=9.0 Hz), 4.39 (1H, d, J=11.5 Hz), 4.70 (1H, d, J=11.5 Hz), 6.43 (1H, dd, J=9.0 Hz, 4.0 Hz), 6.69 (2H, d, J=8.5 Hz), 6.90-6.94 (2H, m), 7.02-7.08 (2H, m), 7.11 (2H, d, J=8.5 Hz), 7.67 (1H, brs).

Reference Example 801

5-({(3S*,4R*)-1-(4-Bromo-2,6-difluorophenyl)-4-hydroxy-3-[(4-methoxybenzyl)oxy]piperidin-4-yl}methoxy)-8-fluoro-3,4-dihydroquinolin-2(1H)-one Synthesized analogous to Reference Example 453.
¹HNMR (CDCl₃) δ ppm: 1.59-1.67 (1H, m), 2.13-2.22 (1H, m), 2.34 (1H, s), 2.60 (2H, t, J=7.7 Hz), 2.73-2.81 (1H, m), 2.85-2.94 (1H, m), 3.07-3.14 (1H, m), 3.31-3.38 (1H, m), 3.44-3.56 (3H, m), 3.74 (3H, s), 3.78 (1H, d, J=8.9 Hz), 4.15 (1H, d, J=8.9 Hz), 4.33 (1H, d, J=11.7 Hz), 4.61 (1H, d, J=11.7 Hz), 6.44 (1H, dd, J=9.1 Hz, 4.0 Hz), 6.68-6.73 (2H, m), 6.92 (1H, t, J=9.5 Hz), 6.99-7.07 (2H, m), 7.09-7.13 (2H, m), 7.55 (1H, brs).

Reference Example 802

5-(Chloromethoxy)-8-fluoro-2-methoxyquinoline

Synthesized analogous to Reference Example 58.
¹HNMR (CDCl₃) δ ppm: 4.11 (3H, s), 6.03 (2H, s), 6.96 (1H, d, J=9.1 Hz), 7.01 (1H, dd, J=8.7 Hz, 3.5 Hz), 7.30 (1H, dd, J=10.3 Hz, 8.7 Hz), 8.32 (1H, dd, J=9.1 Hz, 1.6 Hz).

Reference Example 803

8-Chloro-5-(chloromethoxy)-2-methoxyquinoline

Synthesized analogous to Reference Example 58.
¹HNMR (CDCl₃) δ ppm: 4.14 (3H, s), 6.04 (2H, s), 6.96 (1H, d, J=9.1 Hz), 7.03 (1H, d, J=8.5 Hz), 7.70 (1H, d, J=8.5 Hz), 8.35 (1H, d, J=9.1 Hz).

Reference Example 804

1-tert-butyl 4-ethyl 4-{[(8-Chloro-2-methoxyquinolin-5-yl)oxy]methyl}piperidine-1,4-dicarboxylate Synthesized analogous to Reference Example 59.
¹HNMR (CDCl₃) δ ppm: 1.19 (3H, t, J=7.1 Hz), 1.47 (9H, s), 1.57-1.64 (2H, m), 2.30-2.33 (2H, m), 2.94-3.16 (2H, br), 3.85-4.06 (2H, br), 4.10 (2H, brs), 4.13 (3H, s), 4.20 (2H, q, J=7.1 Hz), 6.61 (1H, d, J=8.4 Hz), 6.91 (1H, d, J=8.9 Hz), 7.60 (1H, d, J=8.4 Hz), 8.30 (1H, d, J=8.9 Hz).

Reference Example 805

Ethyl 4-{[(8-chloro-2-methoxyquinolin-5-yl)oxy]methyl}piperidine-4-carboxylate

Synthesized analogous to Reference Example 60.
¹HNMR (CDCl₃) δ ppm: 1.19 (3H, t, J=7.2 Hz), 1.65-1.70 (2H, m), 2.33-2.36 (2H, m), 2.82-2.88 (2H, m), 3.05-3.08 (2H, m), 4.10 (2H, s), 4.13 (3H, s), 4.19 (2H, q, J=7.1 Hz), 6.62 (1H, d, J=8.6 Hz), 6.91 (1H, d, J=9.0 Hz), 7.60 (1H, d, J=8.4 Hz), 8.33 (1H, d, J=9.0 Hz).

Reference Example 806

2,4-Dibromo-3-fluoro-5-methoxyaniline

To a solution of 4-bromo-3-fluoro-5-methoxyaniline (456 mg) in acetonitrile (5 mL) was added N-bromosuccinimide (369 mg) under ice-cooling, and the mixture was stirred at the same temperature for 3 min. To the reaction solution was added water, the precipitate was collected on a filter, and washed with water to give the title compound (530 mg).
$^1$HNMR (CDCl$_3$) δ ppm: 3.83 (3H, s), 4.26 (2H, brs), 6.15 (1H, d, J=1.8 Hz).

Reference Example 807

5-Bromo-2,2,6-trifluoro-1,3-benzodioxole

To a solution of 2,2,6-trifluoro-1,3-benzodioxol-5-amine (5.38 g) in acetonitrile (90 mL) was added tert-butyl nitrite (5.02 mL) at 0° C., and the mixture was stirred at the same temperature for 15 min. To the mixture was added copper (II) bromide (9.43 g), and the reaction mixture was stirred at room temperature for 3 h. To the reaction solution were added water, hexane and ethyl acetate, and the precipitate was filtered off by using Celite. The organic layer of the filtrate was washed with brine, dried over anhydrous sodium sulfate, and the solvent was distilled off. The residue was purified by silica gel column chromatography (hexane/ethyl acetate) to provide the title compound (4.89 g).
$^1$HNMR (CDCl$_3$) δ ppm: 6.95 (1H, d, J=7.0 Hz), 7.27 (1H, d, J=5.5 Hz).

Reference Example 808

1-(4-Bromo-2-fluorophenyl)-4-{[tert-butyl(diphenyl)silyl]oxy}-1,2,3,6-tetrahydropyridine Synthesized analogous to Reference Example 613.
$^1$HNMR (CDCl$_3$) δ ppm: 1.04 (9H, s), 2.21-2.25 (2H, m), 3.23-3.25 (2H, m), 3.42-3.43 (2H, m), 4.64-4.69 (1H, m), 6.62 (1H, t, J=9.0 Hz), 7.07 (1H, ddd, J=9.0 Hz, 2.0 Hz, 1.0 Hz), 7.14 (1H, dd, J=12.0 Hz, 2.0 Hz), 7.37-7.40 (4H, m), 7.43-7.46 (2H, m), 7.71-7.73 (4H, m).

Reference Example 809

5-{[1-(3,5-Dichloropyridin-2-yl)-4-hydroxypiperidin-4-yl]methoxy}-8-fluoro-1-(4-methoxybenzyl)-3,4-dihydroquinolin-2(1H)-one Synthesized analogous to Reference Example 66.
$^1$HNMR (CDCl$_3$) δ ppm: 1.80-1.95 (4H, m), 2.01 (1H, s), 2.62-2.69 (2H, m), 2.85-2.92 (2H, m), 3.23-3.34 (2H, m), 3.59-3.67 (2H, m), 3.74 (3H, s), 3.81 (2H, s), 5.23 (2H, brs), 6.53 (1H, dd, J=9.1 Hz, 3.3 Hz), 6.73-6.79 (2H, m), 6.84 (1H, dd, J=12.7 Hz, 9.1 Hz), 7.10-7.16 (2H, m), 7.60 (1H, d, J=2.3 Hz), 8.12 (1H, d, J=2.3 Hz).

Example 1

5-{[4-Amino-1-(3,5-dichloropyridin-2-yl)piperidin-4-yl]methoxy}-8-fluoro-3,4-dihydroquinolin-2(1H)-one To a suspension of 5-{[1-(3,5-dichloropyridin-2-yl)-4-isocyanatopiperidin-4-yl]methoxy}-8-fluoro-3,4-dihydroquinolin-2(1H)-one (0.44 g) in acetic acid (4 mL) was added conc. hydrochloric acid (3 mL), and the reaction mixture was stirred at 80° C. for 2 h. The solvent was distilled off, aqueous sodium hydroxide was added to the residue, and the insoluble precipitate was collected on a filter. The obtained solid was dissolved into dichloromethane, the solution was washed with 1 N aqueous sodium hydroxide and brine, and the organic layer was dried over anhydrous sodium sulfate. After the solvent was distilled off, the residue was purified by silica gel column chromatography (basic silica gel: dichloromethane→dichloromethane/ethyl acetate), and the obtained product was recrystallized from ethanol. The crystal was collected on a filter and air-dried (60° C.) to provide the title compound (0.32 g).
m.p. 173-174° C.
$^1$HNMR (CDCl$_3$) δ ppm: 1.38 (2H, brs), 1.62-1.71 (2H, m), 1.88-1.98 (2H, m), 2.65 (2H, t, J=8.0 Hz)), 3.02 (2H, t, J=8.0 Hz), 3.24-3.36 (2H, m), 3.49-3.60 (2H, m), 3.78 (2H, s), 6.47 (1H, dd, J=9.1 Hz, 4.0 Hz), 6.91 (1H, t, J=9.4 Hz), 7.52 (1H, brs), 7.60 (1H, d, J=2.3 Hz), 8.12 (1H, d, J=2.3 Hz).

Example 2

2-(4-Amino-4-{[(8-fluoro-2-oxo-1,2,3,4-tetrahydroquinolin-5-yl)oxy]methyl}piperidin-1-yl)-5-fluorobenzonitrile To N-[1-(2-cyano-4-fluorophenyl)-4-{[(8-fluoro-2-oxo-1,2,3,4-tetrahydroquinolin-5-yl)oxy]methyl}piperidin-4-yl]acetamide (68.0 mg) were added acetic acid (2 mL) and 6 N hydrochloric acid (12 mL) and the mixture was refluxed for 36 h. After the reaction mixture was allowed to cool to room temperature, 3 N aqueous sodium hydroxide was added to make the reaction solution alkaline, and the solution was extracted with ethyl acetate. The organic layer was dried over anhydrous sodium sulfate, and then the solvent was distilled off. The residue was purified by silica gel column chromatography (dichloromethane/methanol), and the obtained solid was recrystallized from hexane/ethyl acetate to provide the title compound (30 mg).
m.p. 223.9-225.1° C.
$^1$HNMR (CDCl$_3$) δ ppm: 1.20-1.70 (2H, brs), 1.68-1.75 (2H, m), 1.95-2.04 (2H, m), 2.64 (2H, t, J=7.5 Hz), 3.02 (2H, t, J=7.5 Hz), 3.20-3.30 (4H), 3.77 (2H, s), 6.45 (1H, dd, J=9.0 Hz, 4.0 Hz), 6.90 (1H, t, J=9.5 Hz), 7.05 (1H, dd, J=9.0 Hz, 4.5 Hz), 7.19-7.25 (1H, m), 7.25-7.31 (1H, m), 7.50 (1H, brs).

Example 3

5-{[4-Amino-1-(2,5-difluorophenyl)piperidin-4-yl]methoxy}-8-fluoro-3,4-dihydroquinolin-2(1H)-one Synthesized analogous to Example 1.
$^1$HNMR (DMSO-d6) δ ppm: 1.51-1.54 (2H, m), 1.79-1.84 (2H, m), 2.46 (2H, t, J=7.7 Hz), 2.90 (2H, t, J=7.7 Hz), 3.11-3.14 (4H, m), 3.71 (2H, s), 6.57 (1H, dd, J=9.1 Hz, 3.6 Hz), 6.69-6.74 (1H, m), 6.88 (1H, ddd, J=10.7 Hz, 7.4 Hz, 3.2 Hz), 7.01 (1H, t, J=9.7 Hz), 7.13 (1H, ddd, J=12.6 Hz, 8.9 Hz, 5.4 Hz), 10.02 (1H, s).

Example 4

5-{[4-Amino-1-(2,4,5-trichlorophenyl)piperidin-4-yl]methoxy}-8-fluoro-3,4-dihydroquinolin-2(1H)-one Synthesized analogous to Example 1.
$^1$HNMR (DMSO-d6) δ ppm: 1.53-1.58 (4H, m), 1.79-1.85 (2H, m), 2.47 (2H, t, J=7.6 Hz), 2.92 (2H, t, J=7.6 Hz), 3.04-3.14 (4H, m), 3.74 (2H, s), 6.58 (1H, dd, J=9.1 Hz, 3.8 Hz), 7.02 (1H, t, J=9.7 Hz), 7.37 (1H, s), 7.75 (1H, s), 10.02 (1H, s).

Example 5

5-{[4-Amino-1-(4-chloro-2,6-difluorophenyl)piperidin-4-yl]methoxy}-8-fluoro-3,4-dihydroquinolin-2(1H)-one Synthesized analogous to Example 1.
$^1$HNMR (DMSO-d6) δ ppm: 1.47-1.65 (4H, m), 1.73-1.79 (2H, m), 2.47 (2H, t, J=7.7 Hz), 2.91 (2H, t, J=7.7 Hz), 2.95-2.97 (2H, m), 3.38-3.47 (2H, m), 3.71 (2H, s), 6.58 (1H, dd, J=9.1 Hz, 3.7 Hz), 7.01 (1H, t, J=9.7 Hz), 7.22-7.30 (2H, m), 10.01 (1H, s).

Example 6

5-{[4-Amino-1-(2,4,5-trifluorophenyl)piperidin-4-yl]methoxy}-8-fluoro-3,4-dihydroquinolin-2(1H)-one A solution of 5-{[4-amino-1-(2,4,5-trifluorophenyl)piperidin-4-yl]methoxy}-8-fluoro-1-(4-methoxybenzyl)-3,4-dihydroquinolin-2(1H)-one (305 mg) and anisole (0.123 mL) in trifluoroacetic acid (3 mL) was stirred at 65° C. for 1 h. The reaction solution was concentrated, 5 N aqueous sodium hydroxide was added to the residue, and the solution was extracted with dichloromethane. The organic layer was dried over anhydrous magnesium sulfate. After the solvent was distilled off, the residue was purified by silica gel column chromatography (dichloromethane/methanol). The obtained product was crystallized from ethanol, the precipitate was collected on a filter and dried under reduced pressure to provide the title compound (195 mg).
$^1$HNMR (DMSO-d6) δ ppm: 1.40-1.62 (4H, m), 1.78-1.84 (2H, m), 2.46 (2H, t, J=7.6 Hz), 2.91 (2H, t, J=7.6 Hz), 3.04-3.12 (4H, m), 3.72 (2H, s), 6.57 (1H, dd, J=9.1 Hz, 3.7 Hz), 7.01 (1H, t, J=9.7 Hz), 7.16 (1H, dt, J=12.7 Hz, 8.4 Hz), 7.45 (1H, dt, J=7.7 Hz, 11.4 Hz), 10.02 (1H, s).

Example 7

5-({4-Amino-1-[2-fluoro-4-(trifluoromethyl)phenyl]piperidin-4-yl}methoxy)-8-fluoro-3,4-dihydroquinolin-2(1H)-one Synthesized analogous to Example 6.
$^1$HNMR (DMSO-d6) δ ppm: 1.52-1.57 (4H, m), 1.80-1.86 (2H, m), 2.45 (2H, t, J=7.6 Hz), 2.89 (2H, t, J=7.6 Hz), 3.22-3.29 (4H, m), 3.72 (2H, s), 6.57 (1H, dd, J=9.1 Hz, 3.7 Hz), 7.01 (1H, t, J=9.7 Hz), 7.22 (1H, t, J=8.7 Hz), 7.45 (1H, d, J=8.6 Hz), 7.51 (1H, dd, J=13.3 Hz, 1.7 Hz), 10.02 (1H, s).

Example 8

5-({4-Amino-1-[2-chloro-4-(trifluoromethyl)phenyl]piperidin-4-yl}methoxy)-8-fluoro-3,4-dihydroquinolin-2(1H)-one Synthesized analogous to Example 6.
$^1$HNMR (DMSO-d6) δ ppm: 1.56-1.58 (4H, m), 1.81-1.87 (2H, m), 2.47 (2H, t, J=7.7 Hz), 2.92 (2H, t, J=7.6 Hz), 3.17-3.21 (4H, m), 3.74 (2H, s), 6.59 (1H, dd, J=9.1 Hz, 3.8 Hz), 7.01 (1H, t, J=9.7 Hz), 7.34 (1H, d, J=8.5 Hz), 7.63 (1H, dd, J=8.6 Hz, 1.8 Hz), 7.75 (1H, d, J=1.9 Hz), 10.02 (1H, s).

Example 9

5-{[4-Amino-1-(2,4-dichlorophenyl)piperidin-4-yl]methoxy}-8-fluoroquinolin-2(1H)-one A solution of 1-(2,4-dichlorophenyl)-4-{[(8-fluoro-2-methoxyquinolin-5-yl)oxy]methyl}piperidine-4-amine (144 mg) in 1 M hydrogen chloride/ethanol (4 mL) was stirred under reflux for 6 h. The reaction solution was concentrated, aqueous sodium hydroxide was added to the residue, and the solution was extracted with ethyl acetate. The organic layer was washed with brine, dried over anhydrous magnesium sulfate, and the solvent was distilled off. The residue was crystallized from ethanol, and the precipitate was collected on a filter and dried under reduced pressure to provide the title compound (40 mg).
$^1$HNMR (DMSO-d6) δ ppm: 1.61-1.64 (2H, m), 1.80-1.85 (2H, m), 3.01-3.04 (2H, m), 3.09-3.14 (2H, m), 3.86 (2H, s), 6.52 (1H, d, J=9.8 Hz), 6.68 (1H, dd, J=8.9 Hz, 3.3 Hz), 7.22 (1H, d, J=8.7 Hz), 7.32-7.37 (2H, m), 7.53 (1H, d, J=2.5 Hz), 8.22 (1H, dd, J=9.8 Hz, 1.5 Hz).

Example 10

5-{[4-Amino-1-(2',4'-dichloro-2,5-difluorobiphenyl-4-yl)piperidin-4-yl]methoxy}-8-fluoro-3,4-dihydroquinolin-2(1H)-one Synthesized analogous to Example 6.
$^1$HNMR (DMSO-d6) δ ppm: 1.53-1.56 (4H, m), 1.81-1.87 (2H, m), 2.46 (2H, t, J=7.6 Hz), 2.91 (2H, t, J=7.6 Hz), 3.18-3.26 (4H, m), 3.73 (2H, s), 6.58 (1H, dd, J=9.1 Hz, 3.8 Hz), 6.98-7.04 (2H, m), 7.19 (1H, dd, J=13.0 Hz, 7.0 Hz), 7.44 (1H, d, J=8.3 Hz), 7.52 (1H, dd, J=8.3 Hz, 2.1 Hz), 7.76 (1H, d, J=2.1 Hz), 10.02 (1H, s).

Example 11

5-{[4-amino-1-(4'-chloro-2,2',5-trifluorobiphenyl-4-yl)piperidin-4-yl]methoxy}-8-fluoro-3,4-dihydroquinolin-2(1H)-one Synthesized analogous to Example 6.
$^1$HNMR (DMSO-d6) δ ppm: 1.56-1.58 (2H, m), 1.82-1.88 (2H, m), 2.46 (2H, t, J=7.6 Hz), 2.91 (2H, t, J=7.6 Hz), 3.22-3.27 (4H, m), 3.76 (2H, s), 6.59 (1H, dd, J=9.1 Hz, 3.7 Hz), 7.00-7.04 (2H, m), 7.27 (1H, dd, J=13.1 Hz, 7.0 Hz), 7.40 (1H, dd, J=8.3 Hz, 2.0 Hz), 7.49 (1H, t, J=8.2 Hz), 7.57 (1H, dd, J=10.0 Hz, 2.0 Hz), 10.02 (1H, s).

Example 12

5-{[4-Amino-1-(4-chloro-2-fluorophenyl)piperidin-4-yl]methoxy}-8-fluoroquinolin-2(1H)-one Synthesized analogous to Example 9.
$^1$HNMR (DMSO-d6) δ ppm: 1.78-1.87 (2H, m), 1.91-1.96 (2H, m), 3.08-3.11 (2H, m), 3.19-3.23 (2H, m), 4.07 (2H, s), 6.53 (1H, d, J=9.8 Hz), 6.73 (1H, dd, J=9.0 Hz, 3.3 Hz), 7.10 (1H, t, J=9.1 Hz), 7.19 (1H, dd, J=8.6 Hz, 2.0 Hz), 7.31-7.38 (2H, m), 8.36 (1H, d, J=9.8 Hz).

Example 13

5-{[4-Amino-1-(2,4-dichlorophenyl)piperidin-4-yl]methoxy}-8-chloro-3,4-dihydroquinolin-2(1H)-one Synthesized analogous to Example 6.
$^1$HNMR (DMSO-d6) δ ppm: 1.54-1.56 (4H, m), 1.79-1.84 (2H, m), 2.48 (2H, t, J=7.6 Hz), 2.93 (2H, J=7.6 Hz), 3.00-3.03 (2H, m), 3.07-3.11 (2H, m), 3.77 (2H, s), 6.69 (1H, d, J=9.0 Hz), 7.20 (1H, d, J=8.7 Hz), 7.24 (1H, d, J=8.9 Hz), 7.35 (1H, dd, J=8.6 Hz, 2.5 Hz), 7.52 (1H, d, J=2.5 Hz), 9.36 (1H, s).

Example 14

5-{[4-Amino-1-(4-chloro-2-fluorophenyl)piperidin-4-yl]methoxy}-8-chloro-3,4-dihydroquinolin-2(1H)-one Synthesized analogous to Example 6.
$^1$HNMR (DMSO-d6) δ ppm: 1.52-1.55 (4H, m), 1.79-1.84 (2H, m), 2.47 (2H, t, J=7.7 Hz), 2.91 (2H, t, J=7.6 Hz), 3.08-3.15 (4H, m), 3.75 (2H, s), 6.68 (1H, d, J=9.0 Hz), 7.09 (1H, t, J=9.1 Hz), 7.17 (1H, dd, J=8.7 Hz, 2.2 Hz), 7.24 (1H, d, J=8.9 Hz), 7.30 (1H, dd, J=12.5 Hz, 2.4 Hz), 9.36 (1H, s).

Example 15

5-{[4-Amino-1-(4-chloro-2,6-difluorophenyl)piperidin-4-yl]methoxy}-8-chloro-3,4-dihydroquinolin-2(1H)-one Synthesized analogous to Example 6.
$^1$HNMR (DMSO-d6) δ ppm: 1.48-1.53 (4H, m), 1.73-1.78 (2H, m), 2.48 (2H, t, J=7.3 Hz), 2.91-2.97 (4H, m), 3.40-3.45 (2H, m), 3.74 (2H, s), 6.68 (1H, d, J=9.0 Hz), 7.23-7.28 (3H, m), 9.36 (1H, s).

Example 16

5-{[4-Amino-1-(2,4-dichlorophenyl)piperidin-4-yl]methoxy}-8-chloroquinolin-2(1H)-one Synthesized analogous to Example 9.
$^1$HNMR (DMSO-d6) δ ppm: 1.62-1.65 (2H, m), 1.79-1.85 (2H, m), 3.02-3.14 (4H, m), 3.90 (2H, s), 6.55 (1H, d, J=9.8 Hz), 6.80 (1H, d, J=8.9 Hz), 7.22 (1H, d, J=8.8 Hz), 7.36 (1H, dd, J=8.7 Hz, 2.5 Hz), 7.53 (1H, d, J=2.5 Hz), 7.58 (1H, d, J=8.7 Hz), 8.28 (1H, d, J=9.8 Hz).

Example 17

5-{[4-Amino-1-(4-chloro-2-fluorophenyl)piperidin-4-yl]methoxy}-8-chloroquinolin-2(1H)-one Synthesized analogous to Example 9.
$^1$HNMR (DMSO-d6) δ ppm: 1.60-1.62 (2H, m), 1.79-1.85 (2H, m), 3.10-3.17 (4H, m), 3.88 (2H, s), 6.54 (1H, d, J=9.7 Hz), 6.79 (1H, d, J=8.8 Hz), 7.10 (1H, t, J=9.1 Hz), 7.18 (1H, dd, J=8.7 Hz, 2.2 Hz), 7.31 (1H, dd, J=12.5 Hz, 2.4 Hz), 7.58 (1H, d, J=8.7 Hz), 8.25 (1H, d, J=9.8 Hz).

Example 18

5-{[4-Amino-1-(3,5-difluoropyridin-2-yl)piperidin-4-yl]methoxy}-8-fluoro-3,4-dihydroquinolin-2(1H)-one Synthesized analogous to Example 1.
(Ethanol) m.p. 160.9-163.1° C.
$^1$HNMR (DMSO-d6) δ ppm: 1.43-1.50 (2H, m), 1.57 (2H, brs), 1.71-1.82 (2H, m), 2.43 (2H, t, J=7.5 Hz), 2.84 (2H, t, J=7.5 Hz), 3.27-3.37 (2H, m), 3.53-3.61 (2H, m), 3.69 (2H, s), 6.54 (1H, dd, J=9.0 Hz, 4.0 Hz), 6.98 (1H, t, J=9.8 Hz), 7.71-7.78 (1H, m), 8.08 (1H, d, J=2.5 Hz), 10.01 (1H, s).

Example 19

5-{[4-Amino-1-(5-fluoro-3-methylpyridin-2-yl)piperidin-4-yl]methoxy}-8-fluoro-3,4-dihydroquinolin-2(1H)-one Synthesized analogous to Example 1.
$^1$HNMR (CDCl$_3$) δ ppm: 1.46 (2H, brs), 1.68-1.72 (2H, m), 1.90-1.96 (2H, m), 2.30 (3H, s), 2.65 (2H, t, J=7.7 Hz), 3.03 (2H, t, J=7.7 Hz), 3.10-3.19 (4H, m), 3.82 (2H, s), 6.48 (1H, dd, J=9.1 Hz, 3.9 Hz), 6.92 (1H, t, J=9.5 Hz), 7.19-7.21 (1H, m), 7.65 (1H, brs), 8.01 (1H, d, J=2.9 Hz).

Example 20

5-{[4-Amino-1-(2,4-dichlorophenyl)piperidin-4-yl]methoxy}-8-fluoro-3,4-dihydroquinolin-2(1H)-one Synthesized analogous to Example 1.
$^1$HNMR (CDCl$_3$) δ ppm: 1.34 (2H, brs), 1.68-1.70 (2H, m), 1.94-1.99 (2H, m), 2.65 (2H, t, J=7.7 Hz), 3.02-3.15 (6H, m), 3.78 (2H, s), 6.47 (1H, dd, J=9.1 Hz, 3.9 Hz), 6.92 (1H, t, J=9.4 Hz), 7.02 (1H, d, J=8.7 Hz), 7.19 (1H, dd, J=8.6 Hz, 2.4 Hz), 7.37 (1H, d, J=2.4 Hz), 7.55 (1H, brs).

Example 21

5-{[4-Amino-1-(2,5-dichlorophenyl)piperidin-4-yl]methoxy}-8-fluoro-3,4-dihydroquinolin-2(1H)-one Synthesized analogous to Example 1.
$^1$HNMR (CDCl$_3$) δ ppm: 1.68-1.71 (2H, m), 1.94-2.00 (2H, m), 2.67 (2H, dd, J=7.1 Hz, 8.3 Hz), 3.03 (2H, t, J=7.7 Hz), 3.08-3.19 (4H, m), 3.78 (2H, s), 6.47 (1H, dd, J=9.1 Hz, 3.9 Hz), 6.91 (1H, d, J=9.6 Hz), 6.95 (1H, dd, J=8.5 Hz, 2.5 Hz), 7.07 (1H, d, J=2.4 Hz), 7.28 (1H, d, J=8.5 Hz), 7.61 (1H, brs).

Example 22

5-({4-Amino-1-[4-(trifluoromethoxy)phenyl]piperidin-4-yl}methoxy)-8-fluoro-3,4-dihydroquinolin-2(1H)-one Synthesized analogous to Example 1.
$^1$HNMR (CDCl$_3$) δ ppm: 1.66-1.69 (2H, m), 1.89-1.95 (2H, m), 2.64 (2H, t, J=7.7 Hz), 3.01 (2H, t, J=7.7 Hz), 3.19-3.24 (2H, m), 3.39-3.43 (2H, m), 3.76 (2H, s), 6.46 (1H, dd, J=9.1 Hz, 3.9 Hz), 6.89-6.95 (3H, m), 7.11 (2H, d, J=9.1 Hz), 7.55 (1H, brs).

Example 23

5-{[4-Amino-1-(2,4-dichloro-5-fluorophenyl)piperidin-4-yl]methoxy}-8-fluoro-3,4-dihydroquinolin-2(1H)-one Synthesized analogous to Example 1.
$^1$HNMR (DMSO-d6) δ ppm: 1.54-1.56 (4H, m), 1.79-1.85 (2H, m), 2.47 (2H, t, J=7.7 Hz), 2.92 (2H, t, J=7.6 Hz), 3.04-3.13 (4H, m), 3.74 (2H, s), 6.58 (1H, dd, J=9.1 Hz, 3.8 Hz), 7.02 (1H, t, J=9.7 Hz), 7.24 (1H, d, J=11.3 Hz), 7.70 (1H, d, J=7.9 Hz), 10.02 (1H, s).

Example 24

5-({4-Amino-1-[5-fluoro-2-(trifluoromethyl)phenyl]piperidin-4-yl}methoxy)-8-fluoro-3,4-dihydroquinolin-2(1H)-one Synthesized analogous to Example 1.
$^1$HNMR (DMSO-d6) δ ppm: 1.51-1.54 (2H, m), 1.63 (2H, brs), 1.77-1.83 (2H, m), 2.47 (2H, t, J=7.7 Hz), 2.81-2.83 (2H, m), 2.92 (2H, t, J=7.6 Hz), 3.12 (2H, t, J=10.0 Hz), 3.75 (2H, s), 6.60 (1H, dd, J=9.1 Hz, 3.8 Hz), 7.02 (1H, t, J=9.7 Hz), 7.13 (1H, dt, J=2.4 Hz, 8.3 Hz), 7.44 (1H, dd, J=10.8 Hz, 2.3 Hz), 7.72 (1H, dd, J=8.8 Hz, 6.4 Hz), 10.02 (1H, s).

Example 25

5-{[4-Amino-1-(2,4,6-trifluorophenyl)piperidin-4-yl]methoxy}-8-fluoro-3,4-dihydroquinolin-2(1H)-one Synthesized analogous to Example 1.
$^1$HNMR (DMSO-d6) δ ppm: 1.48-1.50 (4H, m), 1.73-1.79 (2H, m), 2.47 (2H, t, J=7.7 Hz), 2.87-2.93 (4H, m), 3.38-3.43 (2H, m), 3.71 (2H, s), 6.58 (1H, dd, J=9.1 Hz, 3.8 Hz), 7.01 (1H, t, J=9.7 Hz), 7.11 (2H, t, J=9.4 Hz), 10.01 (1H, s).

Example 26

5-{[4-Amino-1-(2,5-dichloro-4-fluorophenyl)piperidin-4-yl]methoxy}-8-fluoro-3,4-dihydroquinolin-2(1H)-one To a solution of 5-{[1-(2,5-dichloro-4-fluorophenyl)-4-isocyanatopiperidin-4-yl]methoxy}-8-fluoro-3,4-dihydroquinolin-2(1H)-one (144 mg) in acetic acid (4 mL) was added 2 N hydrochloric acid (1.5 mL), and the reaction mixture was stirred at room temperature for 3 h. The solvent was distilled off, aqueous sodium hydroxide was added to the residue, and the solution was extracted with dichloromethane. The organic layer was washed with brine, dried over anhydrous sodium sulfate, and the solvent was distilled off. The residue was purified by silica gel column chromatography (basic silica gel: dichloromethane→dichloromethane/ethyl acetate), and the obtained product was recrystallized from dichloromethane/ethanol. The crystal was collected on a filter, and air-dried (60° C.) to provide the title compound (60 mg).
$^1$HNMR (DMSO-d6) δ ppm: 1.53-1.56 (4H, m), 1.79-1.84 (2H, m), 2.47 (2H, t, J=7.7 Hz), 2.92 (2H, t, J=7.6 Hz), 2.97-3.11 (4H, m), 3.74 (2H, s), 6.58 (1H, dd, J=9.1 Hz, 3.7 Hz), 7.01 (1H, t, J=9.7 Hz), 7.36 (1H, d, J=7.4 Hz), 7.65 (1H, d, J=9.1 Hz), 10.01 (1H, s).

Example 27

5-{[4-Amino-1-(4-chloro-2,5-difluorophenyl)piperidin-4-yl]methoxy}-8-fluoro-3,4-dihydroquinolin-2(1H)-one Synthesized analogous to Example 26.
$^1$HNMR (DMSO-d6) δ ppm: 1.50-1.55 (4H, m), 1.78-1.84 (2H, m), 2.46 (2H, t, J=7.6 Hz), 2.90 (2H, t, J=7.6 Hz), 3.15-3.16 (4H, m), 3.71 (2H, s), 6.56 (1H, dd, J=9.1 Hz, 3.7 Hz), 7.01 (1H, t, J=9.7 Hz), 7.11 (1H, dd, J=11.4 Hz, 7.9 Hz), 7.48 (1H, dd, J=12.2 Hz, 7.1 Hz), 10.01 (1H, s).

Example 28

5-{[4-Amino-1-(4-chloro-2-fluorophenyl)piperidin-4-yl]methoxy}-8-fluoro-3,4-dihydroquinolin-2(1H)-one Synthesized analogous to Example 26.
$^1$HNMR (DMSO-d6) δ ppm: 1.51-1.54 (4H, m), 1.79-1.84 (2H, m), 2.46 (2H, t, J=7.6 Hz), 2.90 (2H, t, J=7.6 Hz), 3.08-3.14 (4H, m), 3.71 (2H, s), 6.57 (1H, dd, J=9.1 Hz, 3.7 Hz), 7.01 (1H, t, J=9.7 Hz), 7.09 (1H, t, J=9.1 Hz), 7.17 (1H, dd, J=8.8 Hz, 2.2 Hz), 7.30 (1H, dd, J=12.5 Hz, 2.4 Hz), 10.01 (1H, s).

Example 29

5-{[4-Amino-1-(2-chloro-4-fluorophenyl)piperidin-4-yl]methoxy}-8-fluoro-3,4-dihydroquinolin-2(1H)-one Synthesized analogous to Example 6.
$^1$HNMR (DMSO-d6) δ ppm: 1.54-1.56 (4H, m), 1.79-1.85 (2H, m), 2.47 (2H, t, J=7.6 Hz), 2.92-2.97 (4H, m), 3.05-3.08 (2H, m), 3.74 (2H, s), 6.59 (1H, dd, J=9.1 Hz, 3.8 Hz), 7.02 (1H, t, J=9.7 Hz), 7.17 (1H, dt, J=2.9 Hz, 8.5 Hz), 7.24 (1H, dd, J=9.0 Hz, 5.7 Hz), 7.38 (1H, dd, J=8.6 Hz, 3.0 Hz), 10.02 (1H, s).

Example 30

5-{[4-Amino-1-(2,4-difluorophenyl)piperidin-4-yl]methoxy}-8-fluoro-3,4-dihydroquinolin-2(1H)-one Synthesized analogous to Example 6.
$^1$HNMR (DMSO-d6) δ ppm: 1.52-1.54 (4H, m), 1.79-1.85 (2H, m), 2.46 (2H, t, J=7.7 Hz), 2.91 (2H, t, J=7.6 Hz), 3.01-3.11 (4H, m), 3.72 (2H, s), 6.57 (1H, dd, J=9.1 Hz, 3.8 Hz), 6.96-7.03 (2H, m), 7.09-7.19 (2H, m), 10.01 (1H, s).

Example 31

5-{[4-Amino-1-(2-fluoro-4-methylphenyl)piperidin-4-yl]methoxy}-8-fluoro-3,4-dihydroquinolin-2(1H)-one Synthesized analogous to Example 6.
$^1$HNMR (DMSO-d6) δ ppm: 1.52-1.53 (4H, m), 1.79-1.84 (2H, m), 2.23 (3H, s), 2.46 (2H, t, J=7.7 Hz), 2.91 (2H, t, J=7.6 Hz), 3.02-3.09 (4H, m), 3.71 (2H, s), 6.57 (1H, dd, J=9.1 Hz, 3.7 Hz), 6.89-7.03 (4H, m), 10.01 (1H, s).

Example 32

5-({4-Amino-1-[4-chloro-2-(trifluoromethyl)phenyl]piperidin-4-yl}methoxy)-8-fluoro-3,4-dihydroquinolin-2(1H)-one Synthesized analogous to Example 6.
$^1$HNMR (DMSO-d6) δ ppm: 1.51-1.59 (4H, m), 1.76-1.82 (2H, m), 2.47 (2H, t, J=7.7 Hz), 2.75-2.77 (2H, m), 2.92 (2H, t, J=7.6 Hz), 3.10-3.15 (2H, m), 3.74 (2H, s), 6.59 (1H, dd, J=9.0 Hz, 3.7 Hz), 7.02 (1H, t, J=9.7 Hz), 7.64 (1H, d, J=8.6 Hz), 7.68 (1H, d, J=2.4 Hz), 7.72 (1H, dd, J=8.6 Hz, 2.4 Hz), 10.02 (1H, s).

Example 33

5-{[1-(3,5-Dichloropyridin-2-yl)-4-hydroxypiperidin-4-yl]methoxy}-8-fluoro-3,4-dihydroquinolin-2(1H)-one A solution of 8-fluoro-5-[(4-hydroxypiperidin-4-yl)methoxy]-3,4-dihydroquinolin-2(1H)-one (0.25 g), 2,3,5-trichloropyridine (0.186 g) and potassium carbonate (0.176 g) in N-methyl-2-pyrrolidone (NMP) (3 mL) was stirred at 100° C. for 12 h. To a solution were added ammonium chloride aqueous solution and diethyl ether, and the insoluble precipitate was collected on a filter. The obtained solid was purified by silica gel column chromatography (dichloromethane→dichloromethane/methanol) and recrystallized from ethanol/water. The precipitate was collected on a filter, and air-dried (60° C.) to provide the title compound (0.29 g).
m.p. 176-178° C.
$^1$HNMR (CDCl$_3$) δ ppm: 1.82-1.97 (4H, m), 2.05 (1H, s), 2.62-2.69 (2H, m), 3.02 (2H, t, J=8.0 Hz), 3.24-3.35 (2H, m), 3.61-3.68 (2H, m), 3.86 (2H, s), 6.48 (1H, dd, J=9.1 Hz, 3.9 Hz), 6.92 (1H, t, J=9.4 Hz), 7.52 (1H, brs), 7.60 (1H, d, J=2.3 Hz), 8.13 (1H, d, J=2.3 Hz).

Example 34

5-Fluoro-2-(4-{[(8-fluoro-2-oxo-1,2,3,4-tetrahydroquinolin-5-yl)oxy]methyl}-4-hydroxypiperidin-1-yl)pyridine-3-carbonitrile Synthesized analogous to Example 33.
$^1$HNMR (CDCl$_3$) δ ppm: 1.83-1.93 (4H, m), 2.07 (1H, s), 2.65 (2H, t, J=7.7 Hz), 3.01 (2H, t, J=7.7 Hz), 3.41-3.3.52 (2H, m), 3.85 (2H, s), 4.00-4.08 (2H, m), 6.48 (1H, dd, J=9.1 Hz, 3.9 Hz), 6.92 (1H, t, J=9.4 Hz), 7.50 (1H, brs), 7.54 (1H, dd, J=7.3 Hz, 3.1 Hz), 8.25 (1H, d, J=3.1 Hz).

Example 35

5-{[1-(2,5-Difluoropyridin-3-yl)-4-hydroxypiperidin-4-yl]methoxy}-8-fluoro-3,4-dihydroquinolin-2(1H)-one A solution of 8-fluoro-5-[(4-hydroxypiperidin-4-yl)methoxy]-3,4-dihydroquinolin-2(1H)-one (0.2 g), 2,3,5-trifluoropyridine (0.078 mL) and potassium carbonate (0.141 g) in N-methyl-2-pyrrolidone (NMP) (3 mL) was stirred at room temperature for 12 h, then at 60° C. for 8 h. To a solution was added ammonium chloride aqueous solution, and insoluble precipitate was collected on a filter. The crude product was purified by silica gel column chromatography (dichloromethane/ethyl acetate), and further purified by thin layer chromatography (dichloromethane/ethyl acetate). The product obtained from lower polarity fractions was washed with diethyl ether to provide the title compound (60 mg).
$^1$HNMR (CDCl$_3$) δ ppm: 1.86-1.98 (4H, m), 2.05 (1H, s), 2.64-2.69 (2H, m), 3.02 (2H, t, J=7.7 Hz), 3.12-3.21 (2H, m), 3.35-3.42 (2H, m), 3.86 (2H, s), 6.48 (1H, dd, J=9.1 Hz, 3.9 Hz), 6.93 (1H, t, J=9.5 Hz), 7.02-7.08 (1H, m), 7.52-7.58 (2H, m).

Example 36

5-{[1-(3,5-Difluoropyridin-2-yl)-4-hydroxypiperidin-4-yl]methoxy}-8-fluoro-3,4-dihydroquinolin-2(1H)-one The product obtained from higher polarity fractions of Example 35 was washed with diethyl ether to provide the title compound (68 mg).
$^1$HNMR (CDCl$_3$) δ ppm: 1.79-1.93 (4H, m), 2.04 (1H, s), 2.62-2.69 (2H, m), 3.02 (2H, t, J=7.7 Hz), 3.30-3.39 (2H, m), 3.71-3.79 (2H, m), 3.84 (2H, s), 6.47 (1H, dd, J=9.1 Hz, 4.0 Hz), 6.92 (1H, t, J=9.5 Hz), 7.09-7.15 (1H, m), 7.52 (1H, s), 7.94 (1H, d, J=2.5 Hz).

Example 37

5-Fluoro-2-(4-{[(8-fluoro-2-oxo-1,2,3,4-tetrahydroquinolin-5-yl)oxy]methyl}-4-hydroxypiperidin-1-yl)benzonitrile Synthesized analogous to Example 33.
(Ethanol/diethyl ether) m.p. 206.0-206.9° C.
$^1$HNMR (DMSO-d6) δ ppm: 1.69-1.76 (2H, m), 1.83-1.92 (2H, m), 2.46 (2H, t, J=7.5 Hz), 2.93 (2H, t, J=7.5 Hz), 3.08-3.17 (2H, m), 3.18-3.25 (2H, m), 3.81 (2H, s), 4.76 (1H, s), 6.59 (1H, dd, J=9.0 Hz, 3.5 Hz), 6.99 (1H, t, J=9.8 Hz), 7.24 (1H, dd, J=9.3 Hz, 4.8 Hz), 7.47 (1H, dt, J=3.0 Hz, 8.8 Hz), 7.69 (1H, dd, J=8.5 Hz, 3.0 Hz), 10.02 (1H, s).

Example 38

8-Fluoro-5-{[4-hydroxy-1-(quinolin-2-yl)piperidin-4-yl]methoxy}-3,4-dihydroquinolin-2(1H)-one Synthesized analogous to Example 33.
(Ethanol/ethyl acetate) m.p. 198-199° C.
$^1$HNMR (CDCl$_3$) δ ppm: 1.79-1.90 (4H, m), 2.09 (1H, s), 2.60-2.65 (2H, m), 2.98 (2H, t, J=7.7 Hz), 3.47-3.55 (2H, m), 3.82 (2H, s), 4.33-4.41 (2H, m), 6.45 (1H, dd, J=9.1 Hz, 3.9 Hz), 6.91 (1H, t, J=9.4 Hz), 7.04 (1H, d, J=9.2 Hz), 7.20-7.25 (1H, m), 7.50-7.56 (2H, m), 7.60 (1H, dd, J=8.0 Hz, 1.2 Hz), 7.69 (1H, d, J=8.1 Hz), 7.89 (1H, d, J=9.1 Hz).

Example 39

8-Fluoro-5-{[4-hydroxy-1-(isoquinolin-1-yl)piperidin-4-yl]methoxy}-3,4-dihydroquinolin-2(1H)-one Synthesized analogous to Example 33.
(Ethanol/ethyl acetate) m.p. 198-199° C.
$^1$HNMR (CDCl$_3$) δ ppm: 1.92-1.99 (2H, m), 2.05-2.14 (3H, m), 2.64-2.69 (2H, m), 3.05 (2H, t, J=7.7 Hz), 3.44-3.51 (2H, m), 3.64-3.71 (2H, m), 3.93 (2H, s), 6.52 (1H, dd, J=9.1 Hz, 4.0 Hz), 6.94 (1H, t, J=9.4 Hz), 7.23-7.27 (1H, overlapping with solvent signal), 7.49-7.54 (1H, m), 7.55 (1H, brs), 7.59-7.64 (1H, m), 7.76 (1H, d, J=8.1 Hz), 8.08 (1H, d, J=8.5 Hz), 8.15 (1H, d, J=5.8 Hz).

Example 40

1-Amino-5-{[1-(3,5-dichloropyridin-2-yl)-4-hydroxypiperidin-4-yl]methoxy}-8-fluoro-3,4-dihydroquinolin-2(1H)-one Under argon atmosphere, to a suspension of 5-{[1-(3,5-dichloropyridin-2-yl)-4-hydroxypiperidin-4-yl]methoxy}-8-fluoro-3,4-dihydroquinolin-2(1H)-one (0.5 g) in N,N-dimethylformamide (5 mL) was added sodium hydride (55% in oil) (0.050 g), and the mixture was stirred at room temperature for 15 min. To the mixture was added 2-[(aminooxy)sulfonyl]-1,3,5-trimethylbenzene (0.293 g) at 0° C., and the reaction mixture was stirred at the same temperature for 1 h. To the reaction solution was added water, the precipitate was collected on a filter and purified by silica gel column chromatography (dichloromethane/ethyl acetate→dichloromethane/methanol), and recrystallized from ethanol/ethyl acetate. The precipitate was collected on a filter, and air-dried (60° C.) to provide the title compound (0.3 g).
(Ethyl acetate/ethanol) m.p. 187-189° C.
$^1$HNMR (CDCl$_3$) δ ppm: 1.81-1.96 (4H, m), 2.02 (1H, s), 2.66-2.71 (2H, m), 2.91-2.97 (2H, m), 3.26-3.34 (2H, m), 3.61-3.68 (2H, m), 3.86 (2H, s), 5.00 (2H, d, J=2.3 Hz), 6.61 (1H, dd, J=9.1 Hz, 3.4 Hz), 6.98 (1H, dd, J=12.1 Hz, 9.1 Hz), 7.60 (1H, d, J=2.3 Hz), 8.12 (1H, d, J=2.3 Hz).

Example 41

5-{[1-(2,5-Dichlorophenyl)-4-hydroxypiperidin-4-yl]methoxy}-8-fluoro-3,4-dihydroquinolin-2(1H)-one To a microwave reaction tube were added 8-fluoro-5-[(4-hydroxypiperidin-4-yl)methoxy]-3,4-dihydroquinolin-2(1H)-one (384 mg), 1-bromo-2,5-dichlorobenzene (295 mg), sodium tert-butoxide (151 mg), tris(dibenzylideneacetone)dipalladium (0) (11.96 mg), 2,2'-bis(diphenylphosphino)-1,1'-binaphthyl (BINAP) (24.39 mg) and toluene (3 mL) and the tube was sealed. Then the tube was irradiated with microwave at 130° C. for 1 h. To the reaction solution was added water, and the solution was extracted with ethyl acetate, the organic layer was washed with brine, dried over anhydrous sodium sulfate, and the solvent was distilled off. The residue was purified by silica gel column chromatography (hexane/ethyl acetate) and recrystallized form methanol/ethyl acetate to provide the title compound (7.5 mg).
(Ethyl acetate/methanol) m.p. 191.5° C.
$^1$HNMR (CDCl$_3$) δ ppm: 1.87-1.90 (2H, m), 1.93-1.99 (2H, m), 2.03 (1H, brs), 2.66 (2H, t, J=7.5 Hz), 3.03 (2H, t, J=7.5 Hz), 3.07-3.12 (2H, m), 3.22-3.24 (2H, m), 3.87 (2H, s), 6.49 (1H, dd, J=9.0 Hz, 4.0 Hz), 6.93 (1H, t, J=9.0 Hz), 6.95 (1H, dd, J=8.5 Hz, 2.5 Hz), 7.07 (1H, d, J=2.5 Hz), 7.28 (1H, d, J=8.5 Hz), 7.54 (1H, brs).

Example 42

5-{[1-(2,4-Dichlorophenyl)-4-hydroxypiperidin-4-yl]methoxy}-8-fluoro-3,4-dihydroquinolin-2(1H)-one Under argon atmosphere, a solution of 8-fluoro-5-hydroxy-3,4-dihydroquinolin-2(1H)-one (355 mg), 6-(2,4-dichlorophenyl)-1-oxa-6-azaspiro[2.5]octane (442 mg) and tripotassium phosphate (72.7 mg) in N,N-dimethylformamide:2-propanol (1:1) (3.6 mL) was stirred ad 70° C. for 22 h. To the reaction solution was added water, and the solution was extracted with ethyl acetate, the organic layer was washed with brine, dried over anhydrous sodium sulfate, and the solvent was distilled off. The residue was recrystallized form ethyl acetate, and the precipitate was collected on a filter and dried to provide the title compound (427 mg).
(Ethyl acetate) m.p. 209.1° C.
$^1$HNMR (DMSO-d6) δ ppm: 1.69-1.71 (2H, m), 1.84-1.89 (2H, m), 2.47 (2H, t, J=7.5 Hz), 2.93 (2H, t, J=7.5 Hz), 2.99-3.08 (4H, m), 3.80 (2H, s), 4.74 (1H, brs), 6.60 (1H, dd, J=9.0 Hz, 3.5 Hz), 7.01 (1H, t, J=9.0 Hz), 7.21 (1H, d, J=8.5 Hz), 7.35 (1H, dd, J=8.5 Hz, 2.5 Hz), 7.52 (1H, d, J=2.5 Hz), 10.01 (1H, brs).

Example 43

5-{[1-(2-Chlorophenyl)-4-hydroxypiperidin-4-yl]methoxy}-8-fluoro-3,4-dihydroquinolin-2(1H)-one Synthesized analogous to Example 6.
$^1$HNMR (CDCl$_3$) δ ppm: 1.88-1.90 (2H, m), 1.95-2.01 (2H, m), 2.05 (1H, brs), 2.66 (2H, t, J=7.5 Hz), 3.03 (2H, t, J=7.5 Hz), 3.08-3.13 (2H, m), 3.22-3.25 (2H, m), 3.88 (2H, s), 6.50 (1H, dd, J=9.0 Hz, 3.5 Hz), 6.93 (1H, t, J=9.0 Hz), 6.98 (1H, t, J=8.0 Hz), 7.11 (1H, d, J=8.0 Hz), 7.23 (1H, t, J=8.0 Hz), 7.37 (1H, d, J=8.0 Hz), 7.56 (1H, brs).

Example 44

5-{[1-(2,5-Dichloro-4-fluorophenyl)-4-hydroxypiperidin-4-yl]methoxy}-8-fluoro-3,4-dihydroquinolin-2(1H)-one Synthesized analogous to Example 42.
(Ethyl acetate/methanol) m.p. 207.9° C.
$^1$HNMR (CDCl$_3$) δ ppm: 1.87-1.89 (2H, m), 1.92-1.98 (2H, m), 2.03 (1H, brs), 2.66 (2H, t, J=7.5 Hz), 3.03 (2H, t, J=7.5 Hz), 3.06-3.09 (2H, m), 3.13-3.15 (2H, m), 3.87 (2H, s), 6.49 (1H, dd, J=9.5 Hz, 4.0 Hz), 6.93 (1H, t, J=9.5 Hz), 7.12 (1H, d, J=7.5 Hz), 7.21 (1H, d, J=9.0 Hz), 7.54 (1H, brs).

Example 45

5-{[1-(2-Chloro-4-fluorophenyl)-4-hydroxypiperidin-4-yl]methoxy}-8-fluoro-3,4-dihydroquinolin-2(1H)-one Synthesized analogous to Example 42.
(Ethyl acetate/methanol) m.p. 208° C.
$^1$HNMR (CDCl$_3$) δ ppm: 1.87-1.89 (2H, m), 1.93-1.99 (2H, m), 2.04 (1H, brs), 2.66 (2H, t, J=7.5 Hz), 3.03 (2H, t, J=7.5 Hz), 3.07-3.09 (2H, m), 3.13-3.15 (2H, m), 3.87 (2H, s), 6.49 (1H, dd, J=9.5 Hz, 4.0 Hz), 6.91-6.97 (2H, m), 7.07 (1H, dd, J=9.0 Hz, 5.5 Hz), 7.14 (1H, dd, J=8.0 Hz, 2.5 Hz), 7.56 (1H, brs).

Example 46

8-Fluoro-5-[(4-hydroxy-1-phenylpiperidin-4-yl)methoxy]-3,4-dihydroquinolin-2(1H)-one

Synthesized analogous to Example 42.
(Ethyl acetate/methanol) m.p. 177.0-177.4° C.
$^1$HNMR (CDCl$_3$) δ ppm: 1.84-1.94 (4H, m), 2.05 (1H, brs), 2.65 (2H, t, J=7.5 Hz), 3.01 (2H, t, J=7.5 Hz), 3.19-3.24 (2H, m), 3.49-3.53 (2H, m), 3.84 (2H, s), 6.47 (1H, dd, J=9.0 Hz, 4.0 Hz), 6.85-6.89 (1H, m), 6.92 (1H, t, J=9.0 Hz), 6.98-6.99 (2H, m), 7.25-7.29 (2H, m), 7.58 (1H, brs).

Example 47

8-Fluoro-5-({4-hydroxy-1-[4-(trifluoromethoxy)phenyl]piperidin-4-yl}methoxy)-3,4-dihydroquinolin-2(1H)-one

Synthesized analogous to Example 42.
(Ethyl acetate/methanol) m.p. 200.7° C.
$^1$HNMR (CDCl$_3$) δ ppm: 1.85-1.93 (4H, m), 2.06 (1H, brs), 2.65 (2H, t, J=8.0 Hz), 3.01 (2H, t, J=8.0 Hz), 3.19-3.24 (2H, m), 3.46-3.49 (2H, m), 3.84 (2H, s), 6.47 (1H, dd, J=9.0 Hz, 4.0 Hz), 6.92 (1H, dd, J=9.0 Hz, 1.0 Hz), 6.94 (2H, d, J=9.0 Hz), 7.12 (2H, d, J=9.0 Hz), 7.60 (1H, brs).

Example 48

8-Fluoro-5-({4-hydroxy-1-[4-(trifluoromethyl)phenyl]piperidin-4-yl}methoxy)-3,4-dihydroquinolin-2(1H)-one

Synthesized analogous to Example 42.
(Ethyl acetate/methanol) m.p. 216.1° C.
$^1$HNMR (CDCl$_3$) δ ppm: 1.85-1.87 (4H, m), 2.09 (1H, brs), 2.65 (2H, t, J=7.5 Hz), 3.00 (2H, t, J=7.5 Hz), 3.29-3.35 (2H, m), 3.63-3.66 (2H, m), 3.83 (2H, s), 6.47 (1H, dd, J=9.0 Hz, 4.0 Hz), 6.92 (1H, dd, J=9.0 Hz, 1.0 Hz), 6.97 (2H, d, J=9.0 Hz), 7.48 (2H, d, J=9.0 Hz), 7.56 (1H, brs).

Example 49

5-{[1-(4-Chlorophenyl)-4-hydroxypiperidin-4-yl]methoxy}-8-fluoro-3,4-dihydroquinolin-2(1H)-one

Synthesized analogous to Example 42.
$^1$HNMR (CDCl$_3$) δ ppm: 1.84-1.92 (4H, m), 2.05 (1H, brs), 2.65 (2H, t, J=7.5 Hz), 3.01 (2H, t, J=7.5 Hz), 3.17-3.22 (2H, m), 3.45-3.47 (2H, m), 3.84 (2H, s), 6.47 (1H, dd, J=9.0 Hz, 4.0 Hz), 6.89 (2H, d, J=9.0 Hz), 6.92 (1H, dd, J=9.0 Hz, 1.0 Hz), 7.21 (2H, d, J=9.0 Hz), 7.57 (1H, brs).

Example 50

5-{[1-(3-Chlorophenyl)-4-hydroxypiperidin-4-yl]methoxy}-8-fluoro-3,4-dihydroquinolin-2(1H)-one

Synthesized analogous to Example 42.
(Ethyl acetate) m.p. 169-170° C.
$^1$HNMR (CDCl$_3$) δ ppm: 1.83-1.91 (4H, m), 2.05 (1H, brs), 2.65 (2H, t, J=7.5 Hz), 3.00 (2H, t, J=7.5 Hz), 3.21-3.27 (2H, m), 3.50-3.53 (2H, m), 3.84 (2H, s), 6.47 (1H, dd, J=9.0 Hz, 4.0 Hz), 6.79-6.84 (2H, m), 6.90-6.93 (2H, m), 7.17 (1H, t, J=8.5 Hz), 7.56 (1H, brs).

Example 51

8-Fluoro-5-{[4-hydroxy-1-(pyridin-3-yl)piperidin-4-yl]methoxy}-3,4-dihydroquinolin-2(1H)-one

Synthesized analogous to Example 42.
(Ethyl acetate/methanol) m.p. 178.2-178.8° C.
$^1$HNMR (CDCl$_3$) δ ppm: 1.88-1.91 (4H, m), 2.11 (1H, brs), 2.65 (2H, t, J=8.0 Hz), 3.01 (2H, t, J=8.0 Hz), 3.24-3.29 (2H, m), 3.52-3.56 (2H, m), 3.85 (2H, s), 6.47 (1H, dd, J=9.0 Hz, 4.0 Hz), 6.93 (1H, t, J=9.0 Hz), 7.16-7.18 (1H, m), 7.23-7.25 (1H, m), 7.56 (1H, brs), 8.09-8.10 (1H, m), 8.36-8.37 (1H, m).

Example 52

5-{[1-(4-Chloro-2-fluorophenyl)-4-hydroxypiperidin-4-yl]methoxy}-8-fluoro-3,4-dihydroquinolin-2(1H)-one

Synthesized analogous to Example 42.
(Methanol/dichloromethane) m.p. 190.6-190.7° C.
$^1$HNMR (CDCl$_3$) δ ppm: 1.86-1.89 (2H, m), 1.92-1.98 (2H, m), 2.03 (1H, brs), 2.66 (2H, t, J=7.5 Hz), 3.02 (2H, t, J=7.5 Hz), 3.09-3.14 (2H, m), 3.23-3.26 (2H, m), 3.85 (2H, s), 6.48 (1H, dd, J=9.5 Hz, 4.0 Hz), 6.91-6.95 (2H, m), 7.05-7.07 (2H, m), 7.56 (1H, brs).

Example 53

5-{[1-(2,4-Dichloro-5-fluorophenyl)-4-hydroxypiperidin-4-yl]methoxy}-8-fluoro-3,4-dihydroquinolin-2(1H)-one

Synthesized analogous to Example 42.
(Ethyl acetate/methanol) m.p. 198.7-198.9° C.
$^1$HNMR (CDCl$_3$) δ ppm: 1.87-1.90 (2H, m), 1.92-1.98 (2H, m), 2.03 (1H, brs), 2.66 (2H, t, J=7.5 Hz), 3.03 (2H, t, J=7.5 Hz), 3.06-3.09 (2H, m), 3.20-3.22 (2H, m), 3.87 (2H, s), 6.49 (1H, dd, J=9.0 Hz, 4.0 Hz), 6.89 (1H, d, J=10.5 Hz), 6.93 (1H, t, J=9.0 Hz), 7.40 (1H, d, J=7.5 Hz), 7.52 (1H, brs).

Example 54

5-{[1-(2,3-Dichlorophenyl)-4-hydroxypiperidin-4-yl]methoxy}-8-fluoro-3,4-dihydroquinolin-2(1H)-one

Synthesized analogous to Example 42.
(Ethyl acetate/methanol) m.p. 228.7° C.
$^1$HNMR (CDCl$_3$) δ ppm: 1.88-1.90 (2H, m), 1.94-2.00 (2H, m), 2.04 (1H, brs), 2.66 (2H, t, J=7.5 Hz), 3.03 (2H, t, J=7.5 Hz), 3.08-3.13 (2H, m), 3.20-3.23 (2H, m), 3.88 (2H, s), 6.50 (1H, dd, J=9.0 Hz, 4.0 Hz), 6.94 (1H, t, J=9.0 Hz), 7.01-7.03 (1H, m), 7.16-7.17 (2H, m), 7.53 (1H, brs).

Example 55

5-{[1-(4-Chloro-2,6-difluorophenyl)-4-hydroxypiperidin-4-yl]methoxy}-8-fluoro-3,4-dihydroquinolin-2(1H)-one

Synthesized analogous to Example 42.
(Ethyl acetate/methanol) m.p. 225.5-225.6° C.
$^1$HNMR (DMSO-d6) δ ppm: 1.63-1.65 (2H, m), 1.78-1.81 (2H, m), 2.47 (2H, t, J=7.5 Hz), 2.92 (2H, t, J=7.5 Hz), 2.96-2.99 (2H, m), 3.35-3.40 (2H, m), 3.77 (2H, s), 4.81 (1H, brs), 6.59 (1H, dd, J=9.0 Hz, 4.0 Hz), 7.02 (1H, dd, J=9.0 Hz, 1.0 Hz), 7.23-7.29 (2H, m), 10.03 (1H, brs).

Example 56

5-({1-[4-Chloro-2-(trifluoromethyl)phenyl]-4-hydroxypiperidin-4-yl}methoxy)-8-fluoro-3,4-dihydroquinolin-2(1H)-one Synthesized analogous to Example 42.

(Ethyl acetate/methanol) m.p. 211.3-211.5° C.

$^1$HNMR (CDCl$_3$) δ ppm: 1.82-1.85 (2H, m), 1.88-1.94 (2H, m), 2.03 (1H, brs), 2.66 (2H, t, J=7.5 Hz), 2.89-2.91 (2H, m), 3.02 (2H, t, J=7.5 Hz), 3.11-3.14 (2H, m), 3.86 (2H, s), 6.49 (1H, dd, J=9.5 Hz, 4.0 Hz), 6.93 (1H, t, J=9.5 Hz), 7.37 (1H, d, J=8.5 Hz), 7.49 (1H, dd, J=8.5 Hz, 2.5 Hz), 7.56 (1H, brs), 7.61 (1H, d, J=2.5 Hz).

Example 57

5-{[1-(3,4-Dichlorophenyl)-4-hydroxypiperidin-4-yl]methoxy}-8-fluoro-3,4-dihydroquinolin-2(1H)-one Synthesized analogous to Example 42.

(Acetic acid-dimethyl sulfoxide) m.p. 230.9-231.2° C.

$^1$HNMR (DMSO-d6) δ ppm: 1.60-1.62 (2H, m), 1.77-1.81 (2H, m), 2.43 (2H, t, J=7.5 Hz), 2.82 (2H, t, J=7.5 Hz), 3.09-3.14 (2H, m), 3.47-3.68 (2H, m), 3.75 (2H, s), 4.89 (1H, brs), 6.57 (1H, dd, J=9.0 Hz, 4.0 Hz), 6.96 (1H, dd, J=9.0 Hz, 2.5 Hz), 7.01 (1H, dd, J=9.0 Hz, 1.0 Hz), 7.14 (1H, d, J=2.5 Hz), 7.38 (1H, d, J=9.0 Hz), 10.02 (1H, brs).

Example 58

8-Fluoro-5-{[4-hydroxy-1-(thiophen-3-yl)piperidin-4-yl]methoxy}-3,4-dihydroquinolin-2(1H)-one Synthesized analogous to Example 42.

(Ethyl acetate/methanol) m.p. 200.4-200.5° C.

$^1$HNMR (CDCl$_3$) δ ppm: 1.84-1.87 (2H, m), 1.90-1.95 (2H, m), 2.03 (1H, brs), 2.65 (2H, t, J=7.5 Hz), 3.01 (2H, t, J=7.5 Hz), 3.12-3.17 (2H, m), 3.37-3.40 (2H, m), 3.84 (2H, s), 6.25 (1H, dd, J=3.0 Hz, 1.5 Hz), 6.47 (1H, dd, J=9.5 Hz, 4.0 Hz), 6.90 (1H, dd, 5.0 Hz, 1.5 Hz), 6.92 (1H, t, J=9.5 Hz), 7.24 (1H, dd, J=5.0 Hz, 3.0 Hz), 7.57 (1H, brs).

Example 59

5-{[1-(4-Chloro-2-methylphenyl)-4-hydroxypiperidin-4-yl]methoxy}-8-fluoro-3,4-dihydroquinolin-2(1H)-one Synthesized analogous to Example 42.

(Ethyl acetate/methanol) m.p. 214-215° C.

$^1$HNMR (CDCl$_3$) δ ppm: 1.86-1.94 (4H, m), 2.02 (1H, brs), 2.28 (3H, s), 2.66 (2H, t, J=7.5 Hz), 2.90-2.93 (2H, m), 3.03 (2H, t, J=7.5 Hz), 3.01-3.07 (2H, m), 3.87 (2H, s), 6.49 (1H, dd, J=9.5 Hz, 4.0 Hz), 6.93 (1H, t, J=9.5 Hz), 7.00 (1H, d, J=8.5 Hz), 7.13 (1H, dd, J=8.5 Hz, 2.5 Hz), 7.16 (1H, d, J=2.5 Hz), 7.53 (1H, brs).

Example 60

8-Fluoro-5-({4-hydroxy-1-[2-(trifluoromethoxy)phenyl]piperidin-4-yl}methoxy)-3,4-dihydroquinolin-2(1H)-one Synthesized analogous to Example 42.

(Ethyl acetate/hexane) m.p. 168° C.

$^1$HNMR (CDCl$_3$) δ ppm: 1.85-1.88 (2H, m), 1.90-1.96 (2H, m), 2.01 (1H, brs), 2.66 (2H, t, J=7.5 Hz), 3.03 (2H, t, J=7.5 Hz), 3.10-3.15 (2H, m), 3.23-3.25 (2H, m), 3.86 (2H, s), 6.49 (1H, dd, J=9.0 Hz, 4.0 Hz), 6.93 (1H, t, J=9.0 Hz), 6.99 (1H, dt, J=1.5 Hz, 8.0 Hz), 7.08 (1H, dd, J=8.0 Hz, 1.5 Hz), 7.19-7.24 (2H, m), 7.55 (1H, brs).

Example 61

5-{[1-(2-Chloro-6-fluorophenyl)-4-hydroxypiperidin-4-yl]methoxy}-8-fluoro-3,4-dihydroquinolin-2(1H)-one Synthesized analogous to Example 42.

(Ethyl acetate/methanol) m.p. 212-213° C.

$^1$HNMR (CDCl$_3$) δ ppm: 1.82-1.84 (2H, m), 1.90-1.96 (2H, m), 2.06 (1H, brs), 2.66 (2H, t, J=7.5 Hz), 3.03 (2H, t, J=7.5 Hz), 3.05-3.09 (2H, m), 3.47-3.52 (2H, m), 3.88 (2H, s), 6.50 (1H, dd, J=9.0 Hz, 4.0 Hz), 6.93 (1H, t, J=9.0 Hz), 6.95-6.97 (2H, m), 7.16-7.18 (1H, m), 7.53 (1H, brs).

Example 62

5-{[1-(4-Chloro-2,5-difluorophenyl)-4-hydroxypiperidin-4-yl]methoxy}-8-fluoro-3,4-dihydroquinolin-2(1H)-one Synthesized analogous to Example 42.

(Ethyl acetate/methanol) m.p. 185.1-185.2° C.

$^1$HNMR (CDCl$_3$) δ ppm: 1.86-1.89 (2H, m), 1.90-1.96 (2H, m), 2.03 (1H, brs), 2.66 (2H, t, J=7.5 Hz), 3.02 (2H, t, J=7.5 Hz), 3.09-3.14 (2H, m), 3.26-3.28 (2H, m), 3.85 (2H, s), 6.48 (1H, dd, J=9.0 Hz, 4.0 Hz), 6.79 (1H, dd, J=10.5 Hz, 7.5 Hz), 6.93 (1H, t, J=9.0 Hz), 7.08 (1H, dd, J=11.5 Hz, 7.0 Hz), 7.54 (1H, brs).

Example 63

5-{[1-(2-Bromo-4-chlorophenyl)-4-hydroxypiperidin-4-yl]methoxy}-8-fluoro-3,4-dihydroquinolin-2(1H)-one Synthesized analogous to Example 42.

(Ethyl acetate/methanol) m.p. 204.9° C.

$^1$HNMR (CDCl$_3$) δ ppm: 1.87-1.89 (2H, m), 1.93-1.99 (2H, m), 2.04 (1H, brs), 2.66 (2H, t, J=7.5 Hz), 3.03 (2H, t, J=7.5 Hz), 3.05-3.10 (2H, m), 3.15-3.17 (2H, m), 3.87 (2H, s), 6.49 (1H, dd, J=9.0 Hz, 4.0 Hz), 6.93 (1H, t, J=9.0 Hz), 7.03 (1H, d, J=8.5 Hz), 7.25 (1H, dd, J=8.5 Hz, 2.5 Hz), 7.55 (1H, brs), 7.57 (1H, d, J=2.5 Hz).

Example 64

5-{[1-(4-Chloro-3-methoxyphenyl)-4-hydroxypiperidin-4-yl]methoxy}-8-fluoro-3,4-dihydroquinolin-2(1H)-one Synthesized analogous to Example 42.
(Ethyl acetate/methanol) m.p. 222.6-222.7° C.
$^1$HNMR (DMSO-d6) δ ppm: 1.61-1.63 (2H, m), 1.79-1.85 (2H, m), 2.43 (2H, t, J=7.5 Hz), 2.85 (2H, t, J=7.5 Hz), 3.07-3.12 (2H, m), 3.51-3.53 (2H, m), 3.75 (2H, s), 3.82 (3H, s), 4.74 (1H, brs), 6.52 (1H, dd, J=8.5 Hz, 2.5 Hz), 6.57 (1H, dd, J=9.0 Hz, 4.0 Hz), 6.66 (1H, d, J=2.5 Hz), 7.00 (1H, t, J=9.0 Hz), 7.16 (1H, d, J=8.5 Hz), 10.01 (1H, brs).

Example 65

5-{[1-(2,6-Dichlorophenyl)-4-hydroxypiperidin-4-yl]methoxy}-8-fluoro-3,4-dihydroquinolin-2(1H)-one Synthesized analogous to Example 42.
(Ethyl acetate/methanol) m.p. 203.6-203.8° C. $^1$HNMR (CDCl$_3$) δ ppm: 1.81-1.83 (2H, m), 1.93-1.99 (2H, m), 2.06 (1H, brs), 2.66 (2H, t, J=7.5 Hz), 2.97-3.02 (2H, m), 3.04 (2H, t, J=7.5 Hz), 3.63-3.68 (2H, m), 3.89 (2H, s), 6.50 (1H, dd, J=9.0 Hz, 4.0 Hz), 6.93 (1H, t, J=9.0 Hz), 6.97 (1H, t, J=8.0 Hz), 7.24 (1H, d, J=8.0 Hz), 7.30 (1H, d, J=8.0 Hz), 7.53 (1H, brs).

Example 66

5-{[1-(3-Ethoxyphenyl)-4-hydroxypiperidin-4-yl]methoxy}-8-fluoro-3,4-dihydroquinolin-2(1H)-one Synthesized analogous to Example 42.
(ethyl acetate/hexane) m.p. 128.1° C.
$^1$HNMR (CDCl$_3$) δ ppm: 1.41 (3H, t, J=7.0 Hz), 1.82-1.84 (2H, m), 1.86-1.92 (2H, m), 2.01 (1H, brs), 2.65 (2H, t, J=7.5 Hz), 3.01 (2H, t, J=7.5 Hz), 3.19-3.24 (2H, m), 3.50-3.52 (2H, m), 3.83 (2H, s), 4.02 (2H, q, J=7.0 Hz), 6.41 (1H, dd, J=8.0 Hz, 2.0 Hz), 6.47 (1H, dd, J=9.0 Hz, 4.0 Hz), 6.52 (1H, t, J=2.0 Hz), 6.58 (1H, dd, J=8.0 Hz, 2.0 Hz), 6.92 (1H, dd, J=9.0 Hz, 1.0 Hz), 7.16 (1H, t, J=8.0 Hz), 7.51 (1H, brs).

Example 67

5-{[1-(4-Ethoxyphenyl)-4-hydroxypiperidin-4-yl]methoxy}-8-fluoro-3,4-dihydroquinolin-2(1H)-one Synthesized analogous to Example 42.
(Ethyl acetate/methanol) m.p. 198.8-199.1° C.
$^1$HNMR (CDCl$_3$) δ ppm: 1.39 (3H, t, J=7.0 Hz), 1.85-1.88 (2H, m), 1.90-1.96 (2H, m), 2.02 (1H, brs), 2.65 (2H, t, J=7.5 Hz), 3.02 (2H, t, J=7.5 Hz), 3.08-3.14 (2H, m), 3.31-3.34 (2H, m), 3.85 (2H, s), 3.99 (2H, q, J=7.0 Hz), 6.48 (1H, dd, J=9.0 Hz, 4.0 Hz), 6.84 (2H, d, J=9.0 Hz), 6.92 (1H, t, J=9.0 Hz), 6.96 (2H, d, J=9.0 Hz), 7.57 (1H, brs).

Example 68

8-Fluoro-5-{[4-hydroxy-1-(2,4,6-trichlorophenyl)piperidin-4-yl]methoxy}-3,4-dihydroquinolin-2(1H)-one Synthesized analogous to Example 42.
(Ethyl acetate/methanol) m.p. 239.4-239.8° C.
$^1$HNMR (CDCl$_3$) δ ppm: 1.80-1.83 (2H, m), 1.90-1.96 (2H, m), 2.06 (1H, brs), 2.66 (2H, t, J=7.5 Hz), 2.93-2.96 (2H, m), 3.03 (2H, t, J=7.5 Hz), 3.61-3.66 (2H, m), 3.87 (2H, s), 6.50 (1H, dd, J=9.0 Hz, 4.0 Hz), 6.93 (1H, t, J=9.0 Hz), 7.26 (1H, s), 7.32 (1H, s), 7.56 (1H, brs).

Example 69

8-Fluoro-5-({4-hydroxy-1-[3-(propan-2-yl)phenyl]piperidin-4-yl}methoxy)-3,4-dihydroquinolin-2(1H)-one Synthesized analogous to Example 42.
(Ethyl acetate/hexane) m.p. 131.1-131.3° C.
$^1$HNMR (CDCl$_3$) δ ppm: 1.25 (6H, d, J=7.0 Hz), 1.85-1.87 (2H, m), 1.89-1.95 (2H, m), 2.01 (1H, brs), 2.65 (2H, t, J=7.5 Hz), 2.86 (1H, sep, J=7.0 Hz), 3.01 (2H, t, J=7.5 Hz), 3.18-3.23 (2H, m), 3.48-3.51 (2H, m), 3.85 (2H, s), 6.48 (1H, dd, J=9.0 Hz, 4.0 Hz), 6.75 (1H, dd, J=8.0 Hz, 1.0 Hz), 6.81 (1H, dd, 8.0 Hz, 2.0 Hz), 6.86 (1H, dd, J=2.0 Hz, 1.0 Hz), 6.92 (1H, t, J=9.0 Hz), 7.20 (1H, t, J=8.0 Hz), 7.52 (1H, brs).

Example 70

8-Fluoro-5-({4-hydroxy-1-[4-(propan-2-yl)phenyl]piperidin-4-yl}methoxy)-3,4-dihydroquinolin-2(1H)-one Synthesized analogous to Example 42.
(Ethyl acetate/methanol) m.p. 194.9-195.0° C.
$^1$HNMR (CDCl$_3$) δ ppm: 1.23 (6H, d, J=7.0 Hz), 1.84-1.87 (2H, m), 1.88-1.94 (2H, m), 2.00 (1H, brs), 2.65 (2H, t, J=7.5 Hz), 2.85 (1H, sep, J=7.0 Hz), 3.02 (2H, t, J=7.5 Hz), 3.14-3.20 (2H, m), 3.43-3.47 (2H, m), 3.84 (2H, s), 6.47 (1H, dd, J=9.0 Hz, 4.0 Hz), 6.92 (1H, t, J=9.0 Hz), 6.93 (2H, d, J=8.5 Hz), 7.14 (2H, d, J=8.5 Hz), 7.52 (1H, brs).

Example 71

5-{[1-(3,5-Dichloropyridin-4-yl)-4-hydroxypiperidin-4-yl]methoxy}-8-fluoro-3,4-dihydroquinolin-2(1H)-one Synthesized analogous to Example 42.
(Ethyl acetate/methanol) m.p. 225.8-225.9° C.
$^1$HNMR (CDCl$_3$) δ ppm: 1.84-1.86 (2H, m), 1.91-1.97 (2H, m), 2.07 (1H, brs), 2.66 (2H, t, J=7.5 Hz), 3.03 (2H, t, J=7.5 Hz), 3.23-3.25 (2H, m), 3.67-3.72 (2H, m), 3.88 (2H, s), 6.49 (1H, dd, J=9.0 Hz, 4.0 Hz), 6.93 (1H, t, J=9.0 Hz), 7.51 (1H, brs), 8.34 (2H, s).

Example 72

4-(4-{[(8-Fluoro-2-oxo-1,2,3,4-tetrahydroquinolin-5-yl)oxy]methyl}-4-hydroxypiperidin-1-yl)benzonitrile Synthesized analogous to Example 42.
(Ethyl acetate/methanol) m.p. 216° C.
$^1$HNMR (CDCl$_3$) δ ppm: 1.78-1.84 (2H, m), 1.86-1.88 (2H, m), 2.12 (1H, brs), 2.65 (2H, t, J=7.5 Hz), 3.00 (2H, t, J=7.5 Hz), 3.35-3.40 (2H, m), 3.69-3.72 (2H, m), 3.83 (2H, s), 6.46 (1H, dd, J=9.0 Hz, 4.0 Hz), 6.90 (2H, d, J=9.5 Hz), 6.92 (1H, t, J=9.0 Hz), 7.50 (2H, d, J=9.5 Hz), 7.57 (1H, brs).

Example 73

3-(4-{[(8-Fluoro-2-oxo-1,2,3,4-tetrahydroquinolin-5-yl)oxy]methyl}-4-hydroxypiperidin-1-yl)benzonitrile Synthesized analogous to Example 42.
(Ethyl acetate/methanol) m.p. 175-177° C.
$^1$HNMR (CDCl$_3$) δ ppm: 1.85-1.88 (4H, m), 2.07 (1H, brs), 2.66 (2H, t, J=7.5 Hz), 3.01 (2H, t, J=7.5 Hz), 3.25-3.30 (2H, m), 3.54-3.56 (2H, m), 3.84 (2H, s), 6.47 (1H, dd, J=9.0 Hz, 4.0 Hz), 6.93 (1H, t, J=9.0 Hz), 7.08-7.10 (1H, m), 7.15-7.17 (2H, m), 7.31-7.34 (1H, m), 7.55 (1H, brs).

Example 74

8-Fluoro-5-{[4-hydroxy-1-(4-phenoxyphenyl)piperidin-4-yl]methoxy}-3,4-dihydroquinolin-2(1H)-one Synthesized analogous to Example 42.
(Ethyl acetate/methanol) m.p. 186.9-187.2° C.
$^1$HNMR (CDCl$_3$) δ ppm: 1.87-1.96 (4H, m), 2.02 (1H, brs), 2.66 (2H, t, J=7.5 Hz), 3.02 (2H, t, J=7.5 Hz), 3.15-3.21 (2H, m), 3.41-3.44 (2H, m), 3.86 (2H, s), 6.48 (1H, dd, J=9.0 Hz, 4.0 Hz), 6.93 (1H, t, J=9.0 Hz), 6.95-6.98 (6H, m), 7.04 (1H, t, J=7.5 Hz), 7.28-7.31 (2H, m), 7.53 (1H, brs).

Example 75

5-({1-[2-Chloro-5-(trifluoromethoxy)phenyl]-4-hydroxypiperidin-4-yl}methoxy)-8-fluoro-3,4-dihydroquinolin-2(1H)-one Synthesized analogous to Example 42.
(Ethyl acetate/methanol) m.p. 190.4-190.5° C.
$^1$HNMR (CDCl$_3$) δ ppm: 1.88-1.91 (2H, m), 1.94-2.00 (2H, m), 2.04 (1H, brs), 2.66 (2H, t, J=7.5 Hz), 3.03 (2H, t, J=7.5 Hz), 3.08-3.13 (2H, m), 3.24-3.26 (2H, m), 3.88 (2H, s), 6.49 (1H, dd, J=9.0 Hz, 4.0 Hz), 6.85 (1H, dd, J=8.5 Hz, 1.0 Hz), 6.94 (1H, t, J=9.0 Hz), 6.94 (1H, d, J=1.0 Hz), 7.37 (1H, d, J=8.5 Hz), 7.52 (1H, brs).

Example 76

8-Fluoro-5-({4-hydroxy-1-[2-(propan-2-yl)phenyl]piperidin-4-yl}methoxy)-3,4-dihydroquinolin-2(1H)-one Synthesized analogous to Example 42.
(Ethyl acetate/methanol) m.p. 163.0-163.3° C.
$^1$HNMR (CDCl$_3$) δ ppm: 1.22 (6H, d, J=7.0 Hz), 1.86-1.95 (4H, m), 2.03 (1H, brs), 2.66 (2H, t, J=7.5 Hz), 2.86-2.89 (2H, m), 3.04 (2H, t, J=7.5 Hz), 3.10-3.13 (2H, m), 3.48 (1H, sep, J=7.0 Hz), 3.89 (2H, s), 6.50 (1H, dd, J=9.0 Hz, 4.0 Hz), 6.94 (1H, t, J=9.0 Hz), 7.09-7.12 (1H, m), 7.15-7.19 (2H, m), 7.26-7.28 (1H, m), 7.51 (1H, brs).

Example 77

5-{[1-(2-Chloro-5-nitrophenyl)-4-hydroxypiperidin-4-yl]methoxy}-8-fluoro-3,4-dihydroquinolin-2(1H)-one Synthesized analogous to Example 42.
(Ethyl acetate) m.p. 204.8-205.4° C.
$^1$HNMR (CDCl$_3$) δ ppm: 1.91-1.94 (2H, m), 1.95-2.01 (2H, m), 2.06 (1H, brs), 2.67 (2H, t, J=7.5 Hz), 3.04 (2H, t, J=7.5 Hz), 3.17-3.23 (2H, m), 3.29-3.31 (2H, m), 3.89 (2H, s), 6.50 (1H, dd, J=9.0 Hz, 4.0 Hz), 6.94 (1H, t, J=9.0 Hz), 7.52 (1H, d, J=9.0 Hz), 7.53 (1H, brs), 7.84 (1H, dd, J=9.0 Hz, 2.5 Hz), 7.95 (1H, d, J=2.5 Hz).

Example 78

5-{[1-(2-Ethylphenyl)-4-hydroxypiperidin-4-yl]methoxy}-8-fluoro-3,4-dihydroquinolin-2(1H)-one Synthesized analogous to Example 42.
(Ethyl acetate/methanol) m.p. 178.6-179.3° C.
$^1$HNMR (CDCl$_3$) δ ppm: 1.25 (3H, t, J=7.5 Hz), 1.86-1.95 (4H, m), 2.05 (1H, brs), 2.66 (2H, t, J=7.5 Hz), 2.71 (2H, q, J=7.5 Hz), 2.91-2.93 (2H, m), 3.04 (2H, t, J=7.5 Hz), 3.07-3.12 (2H, m), 3.88 (2H, s), 6.50 (1H, dd, J=9.0 Hz, 4.0 Hz), 6.93 (1H, t, J=9.0 Hz), 7.05-7.13 (1H, m), 7.13-7.18 (2H, m), 7.23-7.25 (1H, m), 7.61 (1H, brs).

Example 79

8-Fluoro-5-({4-hydroxy-1-[3-(trifluoromethyl)phenyl]piperidin-4-yl}methoxy)-3,4-dihydroquinolin-2(1H)-one Synthesized analogous to Example 42.
(Ethyl acetate/hexane) m.p. 159.4-159.5° C.
$^1$HNMR (CDCl$_3$) δ ppm: 1.87-1.90 (4H, m), 2.06 (1H, brs), 2.65 (2H, t, J=7.5 Hz), 3.00 (2H, t, J=7.5 Hz), 3.25-3.31 (2H, m), 3.55-3.58 (2H, m), 3.84 (2H, s), 6.47 (1H, dd, J=9.0 Hz, 4.0 Hz), 6.92 (1H, t, J=9.0 Hz), 7.07 (1H, d, J=8.0 Hz), 7.11 (1H, d, J=8.0 Hz), 7.16 (1H, s), 7.35 (1H, t, J=8.0 Hz), 7.57 (1H, brs).

Example 80

5-{[1-(4-Chloro-3-methylphenyl)-4-hydroxypiperidin-4-yl]methoxy}-8-fluoro-3,4-dihydroquinolin-2(1H)-one Synthesized analogous to Example 42.
(Ethyl acetate/methanol) m.p. 216.1-216.3° C.
$^1$HNMR (DMSO-d$_6$) δ ppm: 1.59-1.61 (2H, m), 1.77-1.83 (2H, m), 2.26 (3H, s), 2.42 (2H, t, J=7.5 Hz), 2.83 (2H, t, J=7.5 Hz), 3.04-3.09 (2H, m), 3.47-3.49 (2H, m), 3.74 (2H, s), 4.72 (1H, brs), 6.56 (1H, dd, J=9.0 Hz, 3.5 Hz), 6.80 (1H, dd, J=9.0 Hz, 2.5 Hz), 6.94 (1H, d, J=2.5 Hz), 7.00 (1H, t, J=9.0 Hz), 7.17 (1H, d, J=9.0 Hz), 10.01 (1H, brs).

Example 81

Ethyl 2-chloro-5-(4-{[(8-fluoro-2-oxo-1,2,3,4-tetrahydroquinolin-5-yl)oxy]methyl}-4-hydroxypiperidin-1-yl)benzoate Synthesized analogous to Example 42.
(Ethyl acetate) m.p. 148° C.
$^1$HNMR (CDCl$_3$) δ ppm: 1.41 (3H, t, J=7.0 Hz), 1.86-1.88 (4H, m), 2.04 (1H, brs), 2.65 (2H, t, J=7.5 Hz), 3.01 (2H, t, J=7.5 Hz), 3.21-3.27 (2H, m), 3.50-3.52 (2H, m), 3.84 (2H, s), 4.40 (2H, q, J=7.0 Hz), 6.47 (1H, dd, J=9.0 Hz, 4.0 Hz), 6.92 (1H, t, J=9.0 Hz), 6.99 (1H, dd, J=9.0 Hz, 3.0 Hz), 7.29 (1H, d, J=9.0 Hz), 7.32 (1H, d, J=3.0 Hz), 7.53 (1H, brs).

Example 82

5-{[1-(2-Chloro-4-methylphenyl)-4-hydroxypiperidin-4-yl]methoxy}-8-fluoro-3,4-dihydroquinolin-2(1H)-one Synthesized analogous to Example 42.
$^1$HNMR (CDCl$_3$) δ ppm: 1.86-1.89 (2H, m), 1.94-2.00 (2H, m), 2.03 (1H, brs), 2.28 (3H, s), 2.66 (2H, t, J=7.5 Hz), 3.03 (2H, t, J=7.5 Hz), 3.04-3.09 (2H, m), 3.17-3.19 (2H, m), 3.87 (2H, s), 6.49 (1H, dd, J=9.0 Hz, 3.5 Hz), 6.93 (1H, t, J=9.0 Hz), 7.01 (1H, d, J=8.5 Hz), 7.03 (1H, dd, J=8.5 Hz, 1.5 Hz), 7.20 (1H, d, J=1.5 Hz), 7.54 (1H, brs).

Example 83

8-Fluoro-5-{[4-hydroxy-1-(4-methylphenyl)piperidin-4-yl]methoxy}-3,4-dihydroquinolin-2(1H)-one Synthesized analogous to Example 42.
(Ethyl acetate/methanol) m.p. 181° C.
$^1$HNMR (CDCl$_3$) δ ppm: 1.84-1.87 (2H, m), 1.89-1.95 (2H, m), 2.00 (1H, brs), 2.28 (3H, s), 2.65 (2H, t, J=7.5 Hz), 3.01 (2H, t, J=7.5 Hz), 3.13-3.19 (2H, m), 3.42-3.45 (2H, m), 3.84 (2H, s), 6.47 (1H, dd, J=9.0 Hz, 4.0 Hz), 6.90 (1H, d, J=8.5 Hz), 6.92 (2H, t, J=9.0 Hz), 7.08 (2H, d, J=8.5 Hz), 7.51 (1H, brs).

Example 84

5-{[1-(4-Chloro-2-nitrophenyl)-4-hydroxypiperidin-4-yl]methoxy}-8-fluoro-3,4-dihydroquinolin-2(1H)-one Synthesized analogous to Example 42.
(Methanol/dichloromethane) m.p. 188-189° C.
$^1$HNMR (CDCl$_3$) δ ppm: 1.84-1.86 (2H, m), 1.91-1.97 (2H, m), 2.02 (1H, brs), 2.66 (2H, t, J=7.5 Hz), 3.02 (2H, t, J=7.5 Hz), 3.09-3.12 (2H, m), 3.23-3.28 (2H, m), 3.86 (2H, s), 6.48 (1H, dd, J=9.0 Hz, 3.5 Hz), 6.93 (1H, t, J=9.0 Hz), 7.15 (1H, d, J=8.5 Hz), 7.45 (1H, dd, J=8.5 Hz, 2.5 Hz), 7.51 (1H, brs), 7.80 (1H, d, J=2.5 Hz).

Example 85

5-{[1-(4-Ethoxy-2-fluorophenyl)-4-hydroxypiperidin-4-yl]methoxy}-8-fluoro-3,4-dihydroquinolin-2(1H)-one Synthesized analogous to Example 42.
(Ethyl acetate/methanol) m.p. 196.0-196.1° C.
$^1$HNMR (CDCl$_3$) δ ppm: 1.40 (3H, t, J=7.0 Hz), 1.86-1.88 (2H, m), 1.93-1.99 (2H, m), 2.00 (1H, brs), 2.66 (2H, t, J=7.5 Hz), 3.03 (2H, t, J=7.5 Hz), 3.04-3.10 (2H, m), 3.15-3.17 (2H, m), 3.85 (2H, s), 3.98 (2H, q, J=7.0 Hz), 6.49 (1H, dd, J=9.0 Hz, 4.0 Hz), 6.61-6.67 (2H, m), 6.91-6.99 (2H, m), 7.52 (1H, brs).

Example 86

8-Fluoro-5-{[1-(2-fluoro-4-propoxyphenyl)-4-hydroxypiperidin-4-yl]methoxy}-3,4-dihydroquinolin-2(1H)-one Synthesized analogous to Example 42.
(Ethyl acetate) m.p. 185.1-185.9° C.
$^1$HNMR (CDCl$_3$) δ ppm: 1.40 (3H, t, J=7.5 Hz), 1.75-1.82 (2H, m), 1.86-1.88 (2H, m), 1.93-1.99 (2H, m), 2.00 (1H, brs), 2.66 (2H, t, J=7.5 Hz), 3.03 (2H, t, J=7.5 Hz), 3.04-3.10 (2H, m), 3.15-3.17 (2H, m), 3.85 (2H, s), 3.85-3.88 (2H, m), 6.49 (1H, dd, J=9.0 Hz, 4.0 Hz), 6.62-6.67 (2H, m), 6.91-6.99 (2H, m), 7.52 (1H, brs).

Example 87

5-{[1-(4-Bromo-2-fluorophenyl)-4-hydroxypiperidin-4-yl]methoxy}-8-fluoro-3,4-dihydroquinolin-2(1H)-one Synthesized analogous to Example 42.
(Ethyl acetate/methanol) m.p. 204.8-205.0° C.
$^1$HNMR (CDCl$_3$) δ ppm: 1.86-1.89 (2H, m), 1.92-1.97 (2H, m), 2.03 (1H, brs), 2.66 (2H, t, J=7.5 Hz), 3.02 (2H, t, J=7.5 Hz), 3.09-3.14 (2H, m), 3.24-3.26 (2H, m), 3.85 (2H, s), 6.48 (1H, dd, J=9.0 Hz, 4.0 Hz), 6.87-6.95 (2H, m), 7.18-7.20 (2H, m), 7.57 (1H, brs).

Example 88

5-({1-[2-Chloro-4-(propan-2-yl)phenyl]-4-hydroxypiperidin-4-yl}methoxy)-8-fluoro-3,4-dihydroquinolin-2(1H)-one Synthesized analogous to Example 42.
(Ethyl acetate) m.p. 176.5-176.9° C.
$^1$HNMR (CDCl$_3$) δ ppm: 1.23 (6H, d, J=6.5 Hz), 1.86-1.89 (2H, m), 1.94-2.00 (2H, m), 2.02 (1H, brs), 2.66 (2H, t, J=7.5 Hz), 2.84 (1H, sep, J=6.5 Hz), 3.03 (2H, t, J=7.5 Hz), 3.05-3.10 (2H, m), 3.18-3.21 (2H, m), 3.87 (2H, s), 6.49 (1H, dd, J=9.0 Hz, 4.0 Hz), 6.93 (1H, t, J=9.0 Hz), 7.04 (1H, d, J=8.5 Hz), 7.09 (1H, dd, J=8.5 Hz, 2.0 Hz), 7.24 (1H, d, J=2.0 Hz), 7.51 (1H, brs).

Example 89

5-{[1-(2,4-Dichloro-6-methylphenyl)-4-hydroxypiperidin-4-yl]methoxy}-8-fluoro-3,4-dihydroquinolin-2(1H)-one Synthesized analogous to Example 42.
(Ethyl acetate/methanol) m.p. 251.6-251.9° C.
$^1$HNMR (CDCl$_3$) δ ppm: 1.82-1.86 (3.2H, m), 1.94-2.00 (0.8H, m), 2.02 (0.6H, brs), 2.15 (0.4H, brs), 2.31 (1.8H, s), 2.35 (1.2H, s), 2.65 (2H, t, J=7.5 Hz), 2.72-2.74 (1.2H, m), 3.03 (2H, t, J=7.5 Hz), 3.07-3.10 (0.8H, m), 3.28-3.33 (0.8H, m), 3.75-3.80 (1.2H, m), 3.85 (1.2H, s), 3.93 (0.8H, s), 6.48-6.52 (1H, m), 6.91-6.95 (1H, m), 7.05 (0.4H, d, J=2.5

Hz), 7.10 (0.6H, d, J=2.5 Hz), 7.17 (0.6H, d, J=2.5 Hz), 7.21 (0.4H, d, J=2.5 Hz), 7.58 (1H, brs).

Example 90

5-{[1-(2-Chloro-4-propylphenyl)-4-hydroxypiperidin-4-yl]methoxy}-8-fluoro-3,4-dihydroquinolin-2(1H)-one Synthesized analogous to Example 42.
(Ethyl acetate/methanol) m.p. 197.5-197.6° C.
$^1$HNMR (CDCl$_3$) δ ppm: 0.93 (3H, t, J=7.5 Hz), 1.59-1.64 (2H, m), 1.86-1.89 (2H, m), 1.94-2.00 (2H, m), 2.04 (1H, brs), 2.51 (2H, t, J=7.5 Hz), 2.66 (2H, t, J=7.5 Hz), 3.03 (2H, t, J=7.5 Hz), 3.05-3.10 (2H, m), 3.18-3.20 (2H, m), 3.87 (2H, s), 6.49 (1H, dd, J=9.0 Hz, 3.5 Hz), 6.93 (1H, t, J=9.0 Hz), 7.01-7.05 (2H, m), 7.20 (1H, s), 7.57 (1H, brs).

Example 91

5-{[1-(2-Chloro-4-ethylphenyl)-4-hydroxypiperidin-4-yl]methoxy}-8-fluoro-3,4-dihydroquinolin-2(1H)-one Synthesized analogous to Example 42.
(Ethyl acetate) m.p. 167.8-168.0° C.
$^1$HNMR (CDCl$_3$) δ ppm: 1.22 (3H, t, J=7.5 Hz), 1.87-1.89 (2H, m), 1.94-2.00 (2H, m), 2.03 (1H, brs), 2.58 (2H, q, J=7.5 Hz), 2.66 (2H, t, J=7.5 Hz), 3.03 (2H, t, J=7.5 Hz), 3.05-3.10 (2H, m), 3.18-3.20 (2H, m), 3.87 (2H, s), 6.49 (1H, dd, J=9.0 Hz, 3.5 Hz), 6.93 (1H, t, J=9.0 Hz), 7.03 (1H, d, J=8.0 Hz), 7.06 (1H, dd, J=8.0 Hz, 2.0 Hz), 7.22 (1H, d, J=2.0 Hz), 7.54 (1H, brs).

Example 92

5-{[1-(4-Butoxy-2-fluorophenyl)-4-hydroxypiperidin-4-yl]methoxy}-8-fluoro-3,4-dihydroquinolin-2(1H)-one Synthesized analogous to Example 42.
(Ethyl acetate/methanol) m.p. 193.2-193.5° C.
$^1$HNMR (CDCl$_3$) δ ppm: 0.97 (3H, t, J=7.5 Hz), 1.44-1.50 (2H, m), 1.72-1.77 (2H, m), 1.86-1.88 (2H, m), 1.93-1.99 (2H, m), 2.02 (1H, brs), 2.66 (2H, t, J=7.5 Hz), 3.03 (2H, t, J=7.5 Hz), 3.04-3.10 (2H, m), 3.15-3.17 (2H, m), 3.85 (2H, s), 3.90 (2H, t, J=6.5 Hz), 6.49 (1H, dd, J=9.0 Hz, 4.0 Hz), 6.61-6.67 (2H, m), 6.91-6.98 (2H, m), 7.57 (1H, brs).

Example 93

8-Fluoro-5-({1-[2-fluoro-4-(propan-2-yloxy)phenyl]-4-hydroxypiperidin-4-yl}methoxy)-3,4-dihydroquinolin-2(1H)-one Synthesized analogous to Example 42.
(Ethyl acetate/methanol) m.p. 191.9-192.2° C.
$^1$HNMR (CDCl$_3$) δ ppm: 1.32 (6H, d, J=6.0 Hz), 1.86-1.89 (2H, m), 1.93-1.99 (2H, m), 2.01 (1H, brs), 2.66 (2H, t, J=7.5 Hz), 3.03 (2H, t, J=7.5 Hz), 3.04-3.10 (2H, m), 3.15-3.18 (2H, m), 3.85 (2H, s), 4.44 (1H, sep, J=6.0 Hz), 6.49 (1H, dd, J=9.0 Hz, 4.0 Hz), 6.60-6.66 (2H, m), 6.91-6.96 (2H, m), 7.54 (1H, brs).

Example 94

5-{[1-(2,4-Dichloro-6-fluorophenyl)-4-hydroxypiperidin-4-yl]methoxy}-8-fluoro-3,4-dihydroquinolin-2(1H)-one Synthesized analogous to Example 42.
(Ethyl acetate/methanol) m.p. 238.8-239.1° C.
$^1$HNMR (CDCl$_3$) δ ppm: 1.81-1.84 (2H, m), 1.88-1.94 (2H, m), 2.06 (1H, brs), 2.66 (2H, t, J=7.5 Hz), 3.01-3.04 (2H, m), 3.02 (2H, t, J=7.5 Hz), 3.45-3.50 (2H, m), 3.87 (2H, s), 6.49 (1H, dd, J=9.0 Hz, 4.0 Hz), 6.93 (1H, t, J=9.0 Hz), 7.00 (1H, dd, J=11.5 Hz, 2.0 Hz), 7.20 (1H, dd, J=2.0 Hz, 0.5 Hz), 7.56 (1H, brs).

Example 95

5-{[1-(2-Chloro-4,6-difluorophenyl)-4-hydroxypiperidin-4-yl]methoxy}-8-fluoro-3,4-dihydroquinolin-2(1H)-one Synthesized analogous to Example 42.
(Ethyl acetate/methanol) m.p. 239.3-239.6° C.
$^1$HNMR (CDCl$_3$) δ ppm: 1.81-1.84 (2H, m), 1.88-1.94 (2H, m), 2.05 (1H, brs), 2.66 (2H, t, J=7.5 Hz), 2.97-3.01 (2H, m), 3.03 (2H, t, J=7.5 Hz), 3.44-3.49 (2H, m), 3.87 (2H, s), 6.49 (1H, dd, J=9.0 Hz, 4.0 Hz), 6.75 (1H, ddd, J=11.5 Hz, 8.5 Hz, 3.0 Hz), 6.93 (1H, t, J=9.0 Hz), 6.96 (1H, ddd, J=8.5 Hz, 5.0 Hz, 3.0 Hz), 7.55 (1H, brs).

Example 96

5-({1-[2-Chloro-4-(trifluoromethoxy)phenyl]-4-hydroxypiperidin-4-yl}methoxy)-8-fluoro-3,4-dihydroquinolin-2(1H)-one Synthesized analogous to Example 42.
(Ethyl acetate/hexane) m.p. 181.8-181.9° C.
$^1$HNMR (CDCl$_3$) δ ppm: 1.88-1.90 (2H, m), 1.93-1.99 (2H, m), 2.05 (1H, brs), 2.66 (2H, t, J=7.5 Hz), 3.03 (2H, t, J=7.5 Hz), 3.08-3.13 (2H, m), 3.19-3.21 (2H, m), 3.87 (2H, s), 6.49 (1H, dd, J=9.0 Hz, 4.0 Hz), 6.93 (1H, t, J=9.0 Hz), 7.03-7.13 (2H, m), 7.28 (1H, s), 7.58 (1H, brs).

Example 97

5-({1-[2,4-Dichloro-5-(trifluoromethoxy)phenyl]-4-hydroxypiperidin-4-yl}methoxy)-8-fluoro-3,4-dihydroquinolin-2(1H)-one Synthesized analogous to Example 42.
(Ethyl acetate/methanol) m.p. 254.8-254.9° C.
$^1$HNMR (DMSO-d6) δ ppm: 1.69-1.71 (2H, m), 1.84-1.90 (2H, m), 2.46 (2H, t, J=7.5 Hz), 2.92 (2H, t, J=7.5 Hz), 3.02-3.07 (2H, m), 3.12-3.15 (2H, m), 3.80 (2H, s), 4.76 (1H, brs), 6.59 (1H, dd, J=9.5 Hz, 4.0 Hz), 7.01 (1H, t, J=9.5 Hz), 7.26 (1H, s), 7.84 (1H, s), 10.02 (1H, brs).

Example 98

8-Fluoro-5-({1-[2-fluoro-4-(trifluoromethoxy)phenyl]-4-hydroxypiperidin-4-yl}methoxy)-3,4-dihydroquinolin-2(1H)-one Synthesized analogous to Example 42.
(Ethyl acetate/hexane) m.p. 174.2-174.3° C.
$^1$HNMR (CDCl$_3$) δ ppm: 1.87-1.90 (2H, m), 1.92-1.98 (2H, m), 2.02 (1H, brs), 2.66 (2H, t, J=7.5 Hz), 3.03 (2H, t, J=7.5 Hz), 3.11-3.16 (2H, m), 3.25-3.27 (2H, m), 3.86 (2H, s), 6.49 (1H, dd, J=9.0 Hz, 4.0 Hz), 6.91-7.02 (4H, m), 7.53 (1H, brs).

Example 99

8-Fluoro-5-{[1-(2-fluoro-4-methoxyphenyl)-4-hydroxypiperidin-4-yl]methoxy}-3,4-dihydroquinolin-2(1H)-one Synthesized analogous to Example 42.
(Ethyl acetate/methanol) m.p. 201.3-201.9° C.
$^1$HNMR (CDCl$_3$) δ ppm: 1.86-1.89 (2H, m), 1.93-1.99 (2H, m), 2.00 (1H, brs), 2.66 (2H, t, J=7.5 Hz), 3.03 (2H, t, J=7.5 Hz), 3.04-3.10 (2H, m), 3.15-3.18 (2H, m), 3.77 (3H, s), 3.85 (2H, s), 6.49 (1H, dd, J=9.0 Hz, 4.0 Hz), 6.62-6.68 (2H, m), 6.91-7.00 (2H, m), 7.53 (1H, brs).

Example 100

8-Fluoro-5-{[4-hydroxy-1-(2,4,6-trifluorophenyl)piperidin-4-yl]methoxy}-3,4-dihydroquinolin-2(1H)-one Synthesized analogous to Example 42.
$^1$HNMR (CDCl$_3$) δ ppm: 1.79-1.85 (2H, m), 1.86-1.94 (2H, m), 2.07 (1H, brs), 2.66 (2H, t, J=8.0 Hz), 2.99-3.06 (4H, m), 3.42-3.50 (2H, m), 3.85 (2H, s), 6.49 (1H, dd, J=9.1 Hz, 3.9 Hz), 6.59-6.67 (2H, m), 6.93 (1H, t, J=9.4 Hz), 7.64 (1H, brs).

Example 101

8-Chloro-5-{[1-(4-chloro-2-fluorophenyl)-4-hydroxypiperidin-4-yl]methoxy}-3,4-dihydroquinolin-2(1H)-one Synthesized analogous to Example 42.
(Ethyl acetate/methanol) m.p. 222.9-223.0° C.
$^1$HNMR (CDCl$_3$) δ ppm: 1.86-1.89 (2H, m), 1.92-1.98 (2H, m), 2.00 (1H, brs), 2.64 (2H, t, J=7.5 Hz), 3.02 (2H, t, J=7.5 Hz), 3.09-3.14 (2H, m), 3.24-3.26 (2H, m), 3.88 (2H, s), 6.55 (1H, d, J=9.0 Hz), 6.94 (1H, t, J=9.0 Hz), 7.05-7.07 (2H, m), 7.20 (1H, d, J=9.0 Hz), 7.75 (1H, brs).

Example 102

8-Chloro-5-{[1-(4-chloro-2,6-difluorophenyl)-4-hydroxypiperidin-4-yl]methoxy}-3,4-dihydroquinolin-2(1H)-one Synthesized analogous to Example 42.
(Ethyl acetate/methanol) m.p. 181.0-181.2° C.
$^1$HNMR (CDCl$_3$) δ ppm: 1.81-1.83 (2H, m), 1.86-1.92 (2H, m), 1.99 (1H, brs), 2.64 (2H, t, J=7.5 Hz), 3.02 (2H, t, J=7.5 Hz), 3.07-3.09 (2H, m), 3.45-3.49 (2H, m), 3.87 (2H, s), 6.55 (1H, d, J=9.0 Hz), 6.85-6.91 (2H, m), 7.19 (1H, d, J=9.0 Hz), 7.74 (1H, brs).

Example 103

5-({1-[4-(Benzyloxy)-2-fluorophenyl]-4-hydroxypiperidin-4-yl}methoxy)-8-fluoro-3,4-dihydroquinolin-2(1H)-one Synthesized analogous to Example 42.
(Ethyl acetate/methanol) m.p. 193° C.
$^1$HNMR (CDCl$_3$) δ ppm: 1.86-1.88 (2H, m), 1.93-1.99 (2H, m), 2.01 (1H, brs), 2.66 (2H, t, J=7.5 Hz), 3.03 (2H, t, J=7.5 Hz), 3.05-3.10 (2H, m), 3.15-3.17 (2H, m), 3.85 (2H, s), 5.01 (2H, s), 6.49 (1H, dd, J=9.0 Hz, 4.0 Hz), 6.69-6.75 (2H, m), 6.91-6.99 (2H, m), 7.31-7.43 (5H, m), 7.54 (1H, brs).

Example 104

8-Fluoro-5-({1-[2-fluoro-4-(2-methoxyethoxy)phenyl]-4-hydroxypiperidin-4-yl}methoxy)-3,4-dihydroquinolin-2(1H)-one Synthesized analogous to Example 42.
(Ethyl acetate) m.p. 174° C.
$^1$HNMR (CDCl$_3$) δ ppm: 1.86-1.88 (2H, m), 1.93-1.99 (2H, m), 2.01 (1H, brs), 2.66 (2H, t, J=7.5 Hz), 3.03 (2H, t, J=7.5 Hz), 3.04-3.10 (2H, m), 3.15-3.18 (2H, m), 3.45 (3H, s), 3.72-3.74 (2H, m), 3.85 (2H, s), 4.06-4.08 (2H, m), 6.49 (1H, dd, J=9.0 Hz, 4.0 Hz), 6.65-6.71 (2H, m), 6.91-6.98 (2H, m), 7.56 (1H, brs).

Example 105

5-({1-[4-Chloro-2-fluoro-5-(trifluoromethoxy)phenyl]-4-hydroxypiperidin-4-yl}methoxy)-8-fluoro-3,4-dihydroquinolin-2(1H)-one Synthesized analogous to Example 42.
(Ethyl acetate/hexane) m.p. 208° C.
$^1$HNMR (CDCl$_3$) δ ppm: 1.87-1.97 (4H, m), 2.04 (1H, brs), 2.66 (2H, t, J=7.5 Hz), 3.02 (2H, t, J=7.5 Hz), 3.12-3.17 (2H, m), 3.27-3.29 (2H, m), 3.86 (2H, s), 6.48 (1H, dd, J=9.0 Hz, 4.0 Hz), 6.91-6.95 (2H, m), 7.15 (1H, d, J=11.5 Hz), 7.55 (1H, brs).

Example 106

5-{[1-(4-Ethoxy-2,5-difluorophenyl)-4-hydroxypiperidin-4-yl]methoxy}-8-fluoro-3,4-dihydroquinolin-2(1H)-one Synthesized analogous to Example 42.
(Ethyl acetate/hexane) m.p. 174.1-174.5° C.
$^1$HNMR (CDCl$_3$) δ ppm: 1.43 (3H, t, J=7.0 Hz), 1.86-1.88 (2H, m), 1.92-1.98 (2H, m), 2.01 (1H, brs), 2.66 (2H, t, J=7.5 Hz), 3.03 (2H, t, J=7.5 Hz), 3.03-3.09 (2H, m), 3.14-3.19 (2H, m), 3.85 (2H, s), 4.05 (2H, q, J=7.0 Hz), 6.48 (1H, dd, J=9.5 Hz, 3.5 Hz), 6.73 (1H, dd, J=13.0 Hz, 8.0 Hz), 6.82 (1H, dd, J=13.0 Hz, 8.0 Hz), 6.93 (1H, t, J=9.5 Hz), 7.56 (1H, brs).

Example 107

5-{[1-(2-Bromo-5-ethoxy-4-nitrophenyl)-4-hydroxypiperidin-4-yl]methoxy}-8-fluoro-3,4-dihydroquinolin-2(1H)-one Synthesized analogous to Example 42.
$^1$HNMR (DMSO-d6) δ ppm: 1.36 (3H, t, J=7.0 Hz), 1.71-1.73 (2H, m), 1.87-1.92 (2H, m), 2.47 (2H, t, J=7.5 Hz), 2.93 (2H, t, J=7.5 Hz), 3.14-3.18 (2H, m), 3.29-3.37 (2H, m), 3.82 (2H, s), 4.27 (2H, q, J=7.0 Hz), 4.80 (1H, brs), 6.60 (1H, dd, J=9.0 Hz, 4.0 Hz), 6.87 (1H, s), 7.01 (1H, t, J=9.0 Hz), 8.14 (1H, s), 10.02 (1H, brs).

Example 108

5-{[1-(4-Chloro-2-fluorophenyl)-4-hydroxypiperidin-4-yl]methoxy}-7,8-difluoro-3,4-dihydroquinolin-2(1H)-one Synthesized analogous to Example 42.
¹HNMR (DMSO-d6) δ ppm: 1.65-1.70 (2H, m), 1.79-1.87 (2H, m), 2.44-2.50 (2H, m), 2.88 (2H, t, J=7.2 Hz), 2.98-3.22 (4H, m), 3.79 (2H, s), 4.77 (1H, s), 6.75 (1H, dd, J=12.9 Hz, 6.3 Hz), 7.07-7.20 (2H, m), 7.32 (1H, dd, J=12.6 Hz, 2.4 Hz), 10.31 (1H, s).

Example 109

5-({1-[4-(Ethoxymethyl)-2-fluorophenyl]-4-hydroxypiperidin-4-yl}methoxy)-8-fluoro-3,4-dihydroquinolin-2(1H)-one Synthesized analogous to Example 42.
(Ethyl acetate/hexane) m.p. 154.2-154.5° C.
¹HNMR (CDCl₃) δ ppm: 1.24 (3H, t, J=7.0 Hz), 1.86-1.89 (2H, m), 1.93-1.99 (2H, m), 2.06 (1H, brs), 2.66 (2H, t, J=7.5 Hz), 3.03 (2H, t, J=7.5 Hz), 3.09-3.14 (2H, m), 3.26-3.28 (2H, m), 3.53 (2H, q, J=7.0 Hz), 3.85 (2H, s), 4.42 (2H, s), 6.49 (1H, dd, J=9.0 Hz, 4.0 Hz), 6.93 (1H, t, J=9.0 Hz), 6.99-7.07 (3H, m), 7.63 (1H, brs).

Example 110

5-{[1-(2,6-Difluoro-4-methoxyphenyl)-4-hydroxypiperidin-4-yl]methoxy}-8-fluoro-3,4-dihydroquinolin-2(1H)-one Synthesized analogous to Example 42.
(Ethyl acetate/methanol) m.p. 195.7-196.4° C.
¹HNMR (CDCl₃) δ ppm: 1.81-1.83 (2H, m), 1.87-1.93 (2H, m), 2.02 (1H, brs), 2.66 (2H, t, J=7.5 Hz), 2.98-3.01 (2H, m), 3.03 (2H, t, J=7.5 Hz), 3.41-3.45 (2H, m), 3.75 (3H, s), 3.85 (2H, s), 6.40-6.46 (2H, m), 6.49 (1H, dd, J=9.0 Hz, 4.0 Hz), 6.93 (1H, t, J=9.0 Hz), 7.51 (1H, brs).

Example 111

5-{[1-(4-Chloro-2-fluorophenyl)-4-hydroxypiperidin-4-yl]methoxy}-3,4-dihydroquinolin-2(1H)-one Synthesized analogous to Example 42.
(Methanol/ethyl acetate) m.p. 231.6-232.9° C.
¹HNMR (DMSO-d6) δ ppm: 1.68-1.75 (2H, m), 1.84-1.93 (2H, m), 1.41 (2H, t, J=7.7 Hz), 2.87 (2H, t, J=7.7 Hz), 3.00-3.70 (2H, m), 3.08-3.15 (2H, m), 3.75 (2H, s), 4.06 (1H, s), 6.41-6.46 (2H, m), 6.84-6.89 (1H, m), 6.91-6.99 (3H, m), 9.54 (1H, s).

Example 112

7-{[1-(4-Chloro-2-fluorophenyl)-4-hydroxypiperidin-4-yl]methoxy}-3,4-dihydroquinolin-2(1H)-one Synthesized analogous to Example 42.
(Methanol/ethyl acetate) m.p. 207.8-208.7° C.
¹HNMR (DMSO-d6) δ ppm: 1.60-1.67 (2H, m), 1.79-1.88 (2H, m), 2.40 (2H, t, J=7.5 Hz), 2.77 (2H, t, J=7.5 Hz), 2.98-3.05 (2H, m), 3.09-3.15 (2H, m), 3.73 (2H, s), 4.73 (1H, s), 6.47 (1H, d, J=2.5 Hz), 6.50 (1H, dd, J=8.5 Hz, 2.5 Hz), 7.04-7.12 (2H, m), 7.16 (1H, dd, J=9.0, 2.0 Hz), 7.29 (1H, dd, J=12.5 Hz, 2.5 Hz), 10.01 (1H, s).

Example 113

8-Fluoro-5-({1-[2-fluoro-4-(hydroxymethyl)phenyl]-4-hydroxypiperidin-4-yl}methoxy)-3,4-dihydroquinolin-2(1H)-one To a solution of 5-({1-[4-(ethoxymethyl)-2-fluorophenyl]-4-hydroxypiperidin-4-yl}methoxy)-8-fluoro-3,4-dihydroquinolin-2(1H)-one (591 mg) in tetrahydrofuran (THF) (12 mL) was added 5 N hydrochloric acid (6 mL) and the reaction mixture was stirred at 70° C. for 16 h. Then, to the reaction solution were added water and ethyl acetate, the mixture was stirred, and the precipitate was collected on a filter. The obtained solid was recrystallized from ethyl acetate. The precipitate was collected on a filter and dried to provide the title compound (165 mg).
(Ethyl acetate) m.p. 202.4-202.6° C.
¹HNMR (DMSO-d6) δ ppm: 1.66-1.68 (2H, m), 1.84-1.90 (2H, m), 2.46 (2H, t, J=7.5 Hz), 2.92 (2H, t, J=7.5 Hz), 2.99-3.03 (2H, m), 3.11-3.14 (2H, m), 3.78 (2H, s), 4.41 (2H, d, J=5.5 Hz), 4.69 (1H, brs), 5.15 (1H, t, J=5.5 Hz), 6.58 (1H, dd, J=9.0 Hz, 4.0 Hz), 6.99-7.04 (4H, m), 10.02 (1H, brs).

Example 114

8-Chloro-5-{[1-(4-ethoxy-2,5-difluorophenyl)-4-hydroxypiperidin-4-yl]methoxy}-3,4-dihydroquinolin-2(1H)-one Synthesized analogous to Example 42.
(Ethyl acetate/hexane) m.p. 169.0-169.2° C.
¹HNMR (CDCl₃) δ ppm: 1.43 (3H, t, J=7.0 Hz), 1.86-1.88 (2H, m), 1.92-1.99 (2H, m), 1.99 (1H, brs), 2.64 (2H, t, J=7.5 Hz), 3.02 (2H, t, J=7.5 Hz), 3.04-3.09 (2H, m), 3.16-3.18 (2H, m), 3.87 (2H, s), 4.05 (2H, q, J=7.0 Hz), 6.55 (1H, d, J=9.0 Hz), 6.73 (1H, dd, J=13.0 Hz, 8.0 Hz), 6.82 (1H, dd, J=13.0 Hz, 8.0 Hz), 7.19 (1H, d, J=9.0 Hz), 7.75 (1H, brs).

Example 115

8-Chloro-5-({1-[2-fluoro-4-(trifluoromethoxy)phenyl]-4-hydroxypiperidin-4-yl}methoxy)-3,4-dihydroquinolin-2(1H)-one Synthesized analogous to Example 42.
(Ethyl acetate/hexane) m.p. 149.7-149.9° C.
¹HNMR (CDCl₃) δ ppm: 1.87-1.90 (2H, m), 1.93-1.98 (2H, m), 1.99 (1H, brs), 2.65 (2H, t, J=7.5 Hz), 3.02 (2H, t, J=7.5 Hz), 3.11-3.16 (2H, m), 3.25-3.28 (2H, m), 3.88 (2H, s), 6.55 (1H, d, J=9.0 Hz), 6.95-7.02 (3H, m), 7.20 (1H, d, J=9.0 Hz), 7.75 (1H, brs).

Example 116

8-{[1-(4-Chloro-2-fluorophenyl)-4-hydroxypiperidin-4-yl]methoxy}-3,4-dihydroquinolin-2(1H)-one Synthesized analogous to Example 42.
¹HNMR (DMSO-d6) δ ppm: 1.67-1.77 (2H, m), 1.77-1.85 (2H, m), 2.42-2.52 (2H, m), 2.86 (2H, t, J=7.3 Hz), 3.00-3.09 (2H, m), 3.11-3.19 (2H, m), 3.80 (2H, s), 5.18

(1H, brs), 6.75-6.85 (2H, m), 6.85-6.91 (1H, m), 7.09 (1H, t, J=9.3 Hz), 7.16-7.20 (1H, m), 7.28-7.35 (1H, m), 9.71 (1H, brs).

Example 117

8-Chloro-5-{[1-(4-chloro-2,5-difluorophenyl)-4-hydroxypiperidin-4-yl]methoxy}-3,4-dihydroquinolin-2(1H)-one Synthesized analogous to Example 42.
(Ethyl acetate) m.p. 190.3-190.4° C.
$^1$HNMR (CDCl$_3$) δ ppm: 1.86-1.89 (2H, m), 1.91-1.97 (2H, m), 1.99 (1H, brs), 2.65 (2H, t, J=7.5 Hz), 3.02 (2H, t, J=7.5 Hz), 3.09-3.14 (2H, m), 3.26-3.29 (2H, m), 3.87 (2H, s), 6.54 (1H, d, J=9.0 Hz), 6.79 (1H, dd, J=11.0 Hz, 7.5 Hz), 7.08 (1H, dd, J=12.0 Hz, 7.0 Hz), 7.20 (1H, d, J=9.0 Hz), 7.75 (1H, brs).

Example 118

8-Chloro-5-{[1-(2,6-difluoro-4-methoxyphenyl)-4-hydroxypiperidin-4-yl]methoxy}-3,4-dihydroquinolin-2(1H)-one Synthesized analogous to Example 42.
(Ethyl acetate) m.p. 171.1-171.3° C.
$^1$HNMR (CDCl$_3$) δ ppm: 1.80-1.83 (2H, m), 1.87-1.93 (2H, m), 2.00 (1H, brs), 2.64 (2H, t, J=7.5 Hz), 2.98-3.02 (2H, m), 3.02 (2H, t, J=7.5 Hz), 3.41-3.45 (2H, m), 3.75 (3H, s), 3.88 (2H, s), 6.43 (2H, d, J=11.0 Hz), 6.55 (1H, d, J=9.0 Hz), 7.19 (1H, d, J=9.0 Hz), 7.74 (1H, brs).

Example 119

6-{[1-(4-Chloro-2-fluorophenyl)-4-hydroxypiperidin-4-yl]methoxy}-3,4-dihydroquinolin-2(1H)-one Synthesized analogous to Example 42.
(Methanol/ethyl acetate) m.p. 219.1-220.0° C.
$^1$HNMR (DMSO-d6) δ ppm: 1.60-1.66 (2H, m), 1.81-1.89 (2H, m), 2.37-2.42 (2H, m), 2.82 (2H, t, J=7.5 Hz), 2.98-3.05 (2H, m), 3.09-3.15 (2H, m), 3.74 (2H, s), 4.68 (1H, s), 6.72-6.78 (2H, m), 6.80-6.83 (1H, m), 7.07 (1H, t, J=9.0 Hz), 7.15 (1H, dd, J=9.0 Hz, 2.0 Hz), 7.29 (1H, dd, J=12.5 Hz, 2.5 Hz), 9.92 (1H, s).

Example 120

5-{[1-(4-Ethoxy-2,3,5,6-tetrafluorophenyl)-4-hydroxypiperidin-4-yl]methoxy}-8-fluoro-3,4-dihydroquinolin-2(1H)-one Synthesized analogous to Example 42.
(Ethyl acetate/methanol) m.p. 208.9-209.3° C.
$^1$HNMR (CDCl$_3$) δ ppm: 1.40 (3H, t, J=7.0 Hz), 1.82-1.84 (2H, m), 1.86-1.92 (2H, m), 2.03 (1H, brs), 2.66 (2H, t, J=7.5 Hz), 3.02 (2H, t, J=7.5 Hz), 3.09-3.12 (2H, m), 3.49-3.53 (2H, m), 3.85 (2H, s), 4.21 (2H, q, J=7.0 Hz), 6.48 (1H, dd, J=9.0 Hz, 4.0 Hz), 6.93 (1H, t, J=9.0 Hz), 7.54 (1H, brs).

Example 121

8-Chloro-5-{[1-(4-ethoxy-2,3,5,6-tetrafluorophenyl)-4-hydroxypiperidin-4-yl]methoxy}-3,4-dihydroquinolin-2(1H)-one Synthesized analogous to Example 42.
(Ethyl acetate) m.p. 174.4-174.5° C.
$^1$HNMR (CDCl$_3$) δ ppm: 1.40 (3H, t, J=7.0 Hz), 1.82-1.84 (2H, m), 1.87-1.93 (2H, m), 2.01 (1H, brs), 2.65 (2H, t, J=7.5 Hz), 3.02 (2H, t, J=7.5 Hz), 3.09-3.12 (2H, m), 3.49-3.53 (2H, m), 3.87 (2H, s), 4.21 (2H, q, J=7.0 Hz), 6.55 (1H, d, J=9.0 Hz), 7.20 (1H, d, J=9.0 Hz), 7.75 (1H, brs).

Example 122

5-{[1-(4-Chloro-5-ethoxy-2-fluorophenyl)-4-hydroxypiperidin-4-yl]methoxy}-8-fluoro-3,4-dihydroquinolin-2(1H)-one Synthesized analogous to Example 42.
(Ethyl acetate/methanol) m.p. 239.8-239.9° C.
$^1$HNMR (CDCl$_3$) δ ppm: 1.45 (3H, t, J=7.0 Hz), 1.87-1.89 (2H, m), 1.92-1.98 (2H, m), 2.02 (1H, brs), 2.66 (2H, t, J=7.5 Hz), 3.02 (2H, t, J=7.5 Hz), 3.09-3.14 (2H, m), 3.25-3.27 (2H, m), 3.86 (2H, s), 4.07 (2H, q, J=7.0 Hz), 6.49 (1H, dd, J=9.0 Hz, 4.0 Hz), 6.61 (1H, d, J=8.0 Hz), 6.93 (1H, t, J=9.0 Hz), 7.06 (1H, d, J=11.5 Hz), 7.54 (1H, brs).

Example 123

8-Fluoro-5-[(1-{2-fluoro-4-[2-(2-methoxyethoxy)ethoxy]phenyl}-4-hydroxypiperidin-4-yl)methoxy]-3,4-dihydroquinolin-2(1H)-one Synthesized analogous to Example 42.
(Ethyl acetate/hexane) m.p. 128.7-130.7° C.
$^1$HNMR (CDCl$_3$) δ ppm: 1.86-1.88 (2H, m), 1.93-1.99 (2H, m), 2.01 (1H, brs), 2.66 (2H, t, J=7.5 Hz), 3.03 (2H, t, J=7.5 Hz), 3.04-3.10 (2H, m), 3.15-3.17 (2H, m), 3.40 (3H, s), 3.57-3.59 (2H, m), 3.71-3.72 (2H, m), 3.83-3.85 (2H, m), 3.85 (2H, s), 4.08-4.10 (2H, m), 6.49 (1H, dd, J=9.0 Hz, 4.0 Hz), 6.64-6.70 (2H, m), 6.91-6.98 (2H, m), 7.53 (1H, brs).

Example 124

8-Chloro-5-{[1-(4-chloro-5-ethoxy-2-fluorophenyl)-4-hydroxypiperidin-4-yl]methoxy}-3,4-dihydroquinolin-2(1H)-one Synthesized analogous to Example 42.
(Ethyl acetate/methanol) m.p. 228.1-229.0° C.
$^1$HNMR (CDCl$_3$) δ ppm: 1.45 (3H, t, J=7.0 Hz), 1.86-1.89 (2H, m), 1.93-1.99 (2H, m), 1.99 (1H, brs), 2.64 (2H, t, J=7.5 Hz), 3.02 (2H, t, J=7.5 Hz), 3.09-3.14 (2H, m), 3.25-3.27 (2H, m), 3.88 (2H, s), 4.07 (2H, q, J=7.0 Hz), 6.55 (1H, d, J=9.0 Hz), 6.60 (1H, d, J=8.0 Hz), 7.07 (1H, d, J=11.5 Hz), 7.20 (1H, d, J=9.0 Hz), 7.75 (1H, brs).

Example 125

5-{[1-(4-Chloro-2-fluoro-5-methylphenyl)-4-hydroxypiperidin-4-yl]methoxy}-8-fluoro-3,4-dihydroquinolin-2(1H)-one Synthesized analogous to Example 42.
(dichloromethane) m.p. 208.6-208.8° C.
$^1$HNMR (CDCl$_3$) δ ppm: 1.86-1.88 (2H, m), 1.92-1.98 (2H, m), 2.01 (1H, brs), 2.31 (3H, s), 2.66 (2H, t, J=7.5 Hz), 3.02 (2H, t, J=7.5 Hz), 3.08-3.13 (2H, m), 3.23-3.25 (2H, m), 3.85 (2H, s), 6.48 (1H, dd, J=9.0 Hz, 4.0 Hz), 6.85 (1H, d, J=9.0 Hz), 6.93 (1H, t, J=9.0 Hz), 7.04 (1H, d, J=12.0 Hz), 7.55 (1H, brs).

Example 126

8-Chloro-5-{[1-(4-chloro-2-fluoro-5-methylphenyl)-4-hydroxypiperidin-4-yl]methoxy}-3,4-dihydroquinolin-2(1H)-one Synthesized analogous to Example 42.
(dichloromethane/methanol) m.p. 212.2-213.1° C.
$^1$HNMR (CDCl$_3$) δ ppm: 1.86-1.88 (2H, m), 1.92-1.98 (2H, m), 1.98 (1H, brs), 2.31 (3H, s), 2.65 (2H, t, J=7.5 Hz), 3.02 (2H, t, J=7.5 Hz), 3.08-3.13 (2H, m), 3.23-3.25 (2H, m), 3.87 (2H, s), 6.55 (1H, d, J=9.0 Hz), 6.85 (1H, d, J=9.0 Hz), 7.04 (1H, d, J=12.0), 7.19 (1H, d, J=9.0 Hz), 7.75 (1H, brs).

Example 127

5-{[1-(4-Chloro-2-fluoro-6-methylphenyl)-4-hydroxypiperidin-4-yl]methoxy}-8-fluoro-3,4-dihydroquinolin-2(1H)-one Synthesized analogous to Example 42.
(Ethyl acetate/methanol) m.p. 258.8-259.0° C.
$^1$HNMR (CDCl$_3$) δ ppm: 1.81-1.88 (4H, m), 2.06 (1H, brs), 2.29 (3H, s), 2.66 (2H, t, J=7.5 Hz), 2.86-2.87 (2H, m), 3.03 (2H, t, J=7.5 Hz), 3.36-3.47 (2H, m), 3.88 (2H, s), 6.50 (1H, dd, J=9.0 Hz, 4.0 Hz), 6.90 (1H, dd, J=11.5 Hz, 2.5 Hz), 6.93 (1H, t, J=9.0 Hz), 6.97 (1H, d, J=2.5 Hz), 7.53 (1H, brs).

Example 128

5-{[1-(4-Ethoxy-2-fluoro-5-methoxyphenyl)-4-hydroxypiperidin-4-yl]methoxy}-8-fluoro-3,4-dihydroquinolin-2(1H)-one Synthesized analogous to Example 42.
(Ethyl acetate) m.p. 190.8-191.1° C.
$^1$HNMR (CDCl$_3$) δ ppm: 1.44 (3H, t, J=7.0 Hz), 1.86-1.89 (2H, m), 1.94-1.99 (2H, m), 2.01 (1H, brs), 2.66 (2H, t, J=7.5 Hz), 3.03 (2H, t, J=7.5 Hz), 3.08-3.13 (2H, m), 3.17-3.19 (2H, m), 3.85 (3H, s), 3.86 (2H, s), 4.03 (2H, q, J=7.0 Hz), 6.49 (1H, dd, J=9.0 Hz, 4.0 Hz), 6.65 (1H, d, J=7.5 Hz), 6.67 (1H, d, J=13.0 Hz), 6.93 (1H, t, J=9.0 Hz), 7.52 (1H, brs).

Example 129

5-{[1-(4-Chloro-2,6-difluorophenyl)-4-hydroxypiperidin-4-yl]methoxy}-8-fluoroquinolin-2(1H)-one A solution of 1-(4-chloro-2,6-difluorophenyl)-4-{[(8-fluoro-2-methoxyquinolin-5-yl)oxy]methyl}piperidin-4-ol (0.34 g) in 1 N hydrogen chloride/ethanol (14 mL) was refluxed for 9 h. After the reaction mixture was allowed to cool to room temperature, the solvent was distilled off and to the residue was added ethanol-water, the insoluble precipitate was collected on a filter, and the obtained solid was recrystallized form acetic acid/water. The precipitate was collected on a filter, dried (60° C. air) to provide the title compound (0.27 g).
m.p. 297° C.
$^1$HNMR (DMSO-d6) δ ppm: 1.67-1.75 (2H, m), 1.75-1.85 (2H, m), 2.95-3.04 (2H, m), 3.35-3.44 (2H, m), 3.90 (2H, s), 4.86 (1H, s), 6.54 (1H, d, J=9.8 Hz), 6.68 (1H, dd, J=9.0 Hz, 3.4 Hz), 7.23-7.31 (2H, m), 7.33 (1H, dd, J=10.8 Hz, 9.0 Hz), 8.23 (1H, dd, J=9.8 Hz, 1.5 Hz), 11.73 (1H, s).

Example 130

5-{[1-(4-Bromo-2-fluorophenyl)-4-hydroxypiperidin-4-yl]methoxy}-7,8-difluoro-3,4-dihydroquinolin-2(1H)-one Synthesized analogous to Example 42.
$^1$HNMR (DMSO-d6) δ ppm: 1.63-1.67 (2H, m), 1.77-1.84 (2H, m), 2.42-2.49 (2H, m), 2.86 (2H, t, J=7.8 Hz), 2.96-3.03 (2H, m), 3.10-3.14 (2H, m), 3.78 (2H, s), 4.75 (1H, s), 6.75 (1H, dd, J=12.9 Hz, 6.3 Hz), 6.99-7.05 (1H, m), 7.25-7.29 (1H, m), 7.40 (1H, m), 10.30 (1H, s).

Example 131

5-{[1-(2,4-Dichloro-5-fluorophenyl)-4-hydroxypiperidin-4-yl]methoxy}-7,8-difluoro-3,4-dihydroquinolin-2(1H)-one Synthesized analogous to Example 42.
$^1$HNMR (DMSO-d6) δ ppm: 1.66-1.71 (2H, m), 1.78-1.82 (2H, m), 2.42-2.49 (2H, m), 2.88-2.92 (2H, m), 2.96-3.12 (4H, m), 3.80 (2H, s), 4.78 (1H, s), 6.76 (1H, dd, J=12.6 Hz, 6.3 Hz), 7.25 (1H, d, J=11.4 Hz), 7.71 (1H, d, J=6.9 Hz), 10.32 (1H, s).

Example 132

5-{[1-(4-Ethoxy-2-fluorophenyl)-4-hydroxypiperidin-4-yl]methoxy}-7,8-difluoro-3,4-dihydroquinolin-2(1H)-one Synthesized analogous to Example 42.
$^1$HNMR (DMSO-d6) δ ppm: 1.28 (3H, t, J=7.2 Hz), 1.63-1.67 (2H, m), 1.76-1.83 (2H, m), 2.42-2.49 (2H, m), 2.84-2.98 (6H, m), 3.78 (2H, s), 3.96 (2H, q, J=7.2 Hz), 4.62 (1H, s), 6.65-6.77 (3H, m), 6.96-7.03 (1H, m), 10.21 (1H, s).

Example 133

8-Fluoro-5-{[1-(2-fluoro-4-hydroxyphenyl)-4-hydroxypiperidin-4-yl]methoxy}-3,4-dihydroquinolin-2(1H)-one A solution of 5-({1-[4-(benzyloxy)-2-fluorophenyl]-4-hydroxypiperidin-4-yl}methoxy)-8-fluoro-3,4-dihydroquinolin-2(1H)-one (5.14 g) and 10% palladium on carbon (containing water) (1 g) in ethanol (100 mL) was stirred at room temperature for 1.5 h under hydrogen atmosphere. Insoluble materials were filtered off with Celite, and the solvent of the filtrate was distilled off. The residue was washed with ethyl acetate/methanol and dried to provide the title compound (590 mg).
$^1$HNMR (DMSO-d6) δ ppm: 1.62-1.65 (2H, m), 1.80-1.86 (2H, m), 2.45 (2H, t, J=7.5 Hz), 2.91 (2H, t, J=7.5 Hz), 2.92-2.94 (4H, m), 3.75 (2H, s), 4.62 (1H, brs), 6.49-6.53 (2H, m), 6.57 (1H, dd, J=9.0 Hz, 3.5 Hz), 6.89-6.93 (1H, m), 6.99 (1H, t, J=9.0 Hz), 9.36 (1H, brs), 10.00 (1H, brs).

Example 134

4-{[1-(4-Chloro-2-fluorophenyl)-4-hydroxypiperidin-4-yl]methoxy}quinolin-2(1H)-one Synthesized analogous to Example 42.
$^1$HNMR (DMSO-d6) δ ppm: 1.73-1.82 (2H, m), 1.82-1.92 (2H, m), 3.02-3.20 (4H, m), 3.96 (2H, s), 4.92 (1H, brs), 7.08-7.14 (2H, m), 7.16-7.21 (2H, m), 7.26-7.30 (1H, m), 7.30-7.34 (1H, m), 7.49-7.54 (1H, m), 7.93-7.97 (1H, m), 11.35 (1H, brs).

Example 135

5-{[1-(4-Ethoxy-2,6-difluorophenyl)-4-hydroxypiperidin-4-yl]methoxy}-8-fluoro-3,4-dihydroquinolin-2(1H)-one Synthesized analogous to Example 42.
(Ethyl acetate) m.p. 207.9-208.8° C.
$^1$HNMR (CDCl$_3$) δ ppm: 1.39 (3H, t, J=7.0 Hz), 1.80-1.83 (2H, m), 1.87-1.93 (2H, m), 2.02 (1H, brs), 2.65 (2H, t, J=7.5 Hz), 2.98-3.03 (2H, m), 3.03 (2H, t, J=7.5 Hz), 3.41-3.45 (2H, m), 3.85 (2H, s), 3.95 (2H, q, J=7.0 Hz), 6.38-6.44 (2H, m), 6.49 (1H, dd, J=9.0 Hz, 4.0 Hz), 6.93 (1H, t, J=9.0 Hz), 7.52 (1H, brs).

Example 136

8-Fluoro-5-({1-[2-fluoro-4-(2-fluoroethoxy)phenyl]-4-hydroxypiperidin-4-yl}methoxy)-3,4-dihydroquinolin-2(1H)-one Synthesized analogous to Example 42.
(Ethyl acetate/hexane) m.p. 186.5-186.7° C.
$^1$HNMR (CDCl$_3$) δ ppm: 1.86-1.89 (2H, m), 1.93-1.99 (2H, m), 2.01 (1H, brs), 2.66 (2H, t, J=7.5 Hz), 3.03 (2H, t, J=7.5 Hz), 3.05-3.11 (2H, m), 3.16-3.18 (2H, m), 3.85 (2H, s), 4.13-4.20 (2H, m), 4.68-4.79 (2H, m), 6.49 (1H, dd, J=9.0 Hz, 4.0 Hz), 6.65-6.71 (2H, m), 6.93 (1H, t, J=9.0 Hz), 6.98 (1H, t, J=9.0 Hz), 7.55 (1H, brs).

Example 137

8-Chloro-5-{[1-(4-ethoxy-2,6-difluorophenyl)-4-hydroxypiperidin-4-yl]methoxy}-3,4-dihydroquinolin-2(1H)-one Synthesized analogous to Example 42.
(Ethyl acetate/hexane) m.p. 180.6-181.0° C.
$^1$HNMR (CDCl$_3$) δ ppm: 1.39 (3H, t, J=7.0 Hz), 1.80-1.83 (2H, m), 1.87-1.93 (2H, m), 2.00 (1H, brs), 2.64 (2H, t, J=7.5 Hz), 2.97-3.01 (2H, m), 3.02 (2H, t, J=7.5 Hz), 3.41-3.45 (2H, m), 3.87 (2H, s), 3.95 (2H, q, J=7.0 Hz), 6.38-6.44 (2H, m), 6.55 (1H, d, J=9.0 Hz), 7.19 (1H, d, J=9.0 Hz), 7.74 (1H, brs).

Example 138

5-{[1-(4-Chloro-2-fluorophenyl)-4-hydroxypiperidin-4-yl]methoxy}quinolin-2(1H)-one Synthesized analogous to Example 42.
(Methanol/ethyl acetate) m.p. 275.7-277.0° C.
$^1$HNMR (DMSO-d6) δ ppm: 1.73-1.79 (2H, m), 1.82-1.91 (2H, m), 3.02-3.10 (2H, m), 3.13-3.21 (2H, m), 3.92 (2H, s), 4.87 (1H, s), 6.44 (1H, d, J=9.5 Hz), 6.71 (1H, d, J=8.5 Hz), 6.87 (1H, d, J=8.5 Hz), 7.10 (1H, t, J=8.5 Hz), 7.17 (1H, dd, J=8.5 Hz, 2.0 Hz), 7.31 (1H, dd, J=12.5 Hz, 2.0 Hz), 7.39 (1H, t, J=8.5 Hz), 8.20 (1H, d, J=10.0 Hz), 11.72 (1H, s).

Example 139

8-Chloro-5-{[1-(3,5-dichloropyridin-2-yl)-4-hydroxypiperidin-4-yl]methoxy}-3,4-dihydroquinolin-2(1H)-one Synthesized analogous to Example 33.
(Acetic acid/water) m.p. 218° C.
$^1$HNMR (CDCl$_3$) δ ppm: 1.82-1.89 (2H, m), 1.89-1.97 (2H, m), 2.02 (1H, brs), 2.61-2.67 (2H, m), 3.02 (2H, t, J=7.7 Hz), 3.26-3.35 (2H, m), 3.61-3.68 (2H, m), 3.88 (2H, s), 6.54 (1H, d, J=8.9 Hz), 7.19 (1H, d, J=8.9 Hz), 7.60 (1H, d, J=2.3 Hz), 7.75 (1H, brs), 8.13 (1H, d, J=2.3 Hz).

Example 140

5-{[1-(4-Chloro-2-fluorophenyl)-4-hydroxypiperidin-4-yl]methoxy}-8-fluoroquinolin-2(1H)-one Synthesized analogous to Example 129.
(Acetic acid/water) m.p. 255-256° C.
$^1$HNMR (DMSO-d6) δ ppm: 1.71-1.80 (2H, m), 1.80-1.91 (2H, m), 3.01-3.10 (2H, m), 3.12-3.20 (2H, m), 3.91 (2H, s), 4.87 (1H, s), 6.54 (1H, d, J=9.8 Hz), 6.67 (1H, dd, J=9.0 Hz, 3.4 Hz), 7.11 (1H, t, J=9.1 Hz), 7.18 (1H, dd, J=8.6 Hz, 2.1 Hz), 7.29-7.36 (2H, m), 8.22 (1H, dd, J=1.5 Hz, 9.8 Hz), 11.73 (1H, s).

Example 141

5-{[1-(1-Benzothiophen-5-yl)-4-hydroxypiperidin-4-yl]methoxy}-8-fluoro-3,4-dihydroquinolin-2(1H)-one Synthesized analogous to Example 42.
(Ethyl acetate/methanol/dichloromethane) m.p. 209.5-210.2° C.
$^1$HNMR (CDCl$_3$) δ ppm: 1.88-1.91 (2H, m), 1.94-2.00 (2H, m), 2.04 (1H, brs), 2.65 (2H, t, J=7.5 Hz), 3.02 (2H, t, J=7.5 Hz), 3.22-3.27 (2H, m), 3.50-3.53 (2H, m), 3.86 (2H, s), 6.48 (1H, dd, J=9.0 Hz, 4.0 Hz), 6.93 (1H, t, J=9.0 Hz), 7.13 (1H, dd, J=8.5 Hz, 2.5 Hz), 7.23 (1H, d, J=5.5 Hz), 7.36 (1H, d, J=2.5 Hz), 7.41 (1H, d, J=5.5 Hz), 7.54 (1H, brs), 7.74 (1H, d, J=8.5 Hz).

Example 142

5-{[1-(1-Benzothiophen-5-yl)-4-hydroxypiperidin-4-yl]methoxy}-8-chloro-3,4-dihydroquinolin-2(1H)-one Synthesized analogous to Example 42.
(Ethyl acetate/dichloromethane) m.p. 193.8-194.5° C.
$^1$HNMR (CDCl$_3$) δ ppm: 1.88-1.91 (2H, m), 1.95-2.00 (2H, m), 2.00 (1H, brs), 2.64 (2H, t, J=7.5 Hz), 3.01 (2H, t, J=7.5 Hz), 3.22-3.27 (2H, m), 3.51-3.53 (2H, m), 3.88 (2H, s), 6.54 (1H, d, J=9.0 Hz), 7.13 (1H, dd, J=8.5 Hz, 2.5 Hz), 7.19 (1H, d, J=9.0 Hz), 7.24 (1H, d, J=5.5 Hz), 7.36 (1H, d, J=2.5 Hz), 7.41 (1H, d, J=5.5 Hz), 7.74 (1H, d, J=8.5 Hz), 7.75 (1H, brs).

Example 143

8-Fluoro-5-({1-[2-fluoro-4-(2,2,2-trifluoroethoxy)phenyl]-4-hydroxypiperidin-4-yl}methoxy)-3,4-dihydroquinolin-2(1H)-one Synthesized analogous to Example 42.
$^1$HNMR (CDCl$_3$) δ ppm: 1.87-1.89 (2H, m), 1.93-1.99 (2H, m), 2.00 (1H, brs), 2.66 (2H, t, J=7.5 Hz), 3.03 (2H, t, J=7.5 Hz), 3.06-3.11 (2H, m), 3.18-3.20 (2H, m), 3.86 (2H, s), 4.28-4.33 (2H, m), 6.49 (1H, dd, J=9.0 Hz, 4.0 Hz), 6.66-6.69 (1H, m), 6.73 (1H, dd, J=13.0 Hz, 3.0 Hz), 6.93 (1H, t, J=9.0 Hz), 6.99 (1H, t, J=9.0 Hz), 7.51 (1H, brs).

Example 144

8-Fluoro-5-{[4-hydroxy-1-(quinoxalin-6-yl)piperidin-4-yl]methoxy}-3,4-dihydroquinolin-2(1H)-one Synthesized analogous to Example 42.
$^1$HNMR (CDCl$_3$) δ ppm: 1.92-1.94 (4H, m), 2.13 (1H, brs), 2.64 (2H, t, J=7.5 Hz), 3.01 (2H, t, J=7.5 Hz), 3.41-3.47 (2H, m), 3.79-3.81 (2H, m), 3.86 (2H, s), 6.47 (1H, dd, J=9.0 Hz, 4.0 Hz), 6.92 (1H, t, J=9.0 Hz), 7.34 (1H, d, J=2.5 Hz), 7.53 (1H, brs), 7.57 (1H, dd, J=9.5 Hz, 2.5 Hz), 7.94 (1H, d, J=9.5 Hz), 8.60 (1H, d, J=2.0 Hz), 8.69 (1H, d, J=2.0 Hz).

Example 145

7-Amino-5-{[1-(4-chloro-2-fluorophenyl)-4-hydroxypiperidin-4-yl]methoxy}-8-fluoro-3,4-dihydroquinolin-2(1H)-one hydrochloride A solution of 7-amino-8-fluoro-5-hydroxy-3,4-dihydroquinolin-2(1H)-one (310 mg), 6-(4-chloro-2-fluorophenyl)-1-oxa-6-azaspiro[2.5]octane (764 mg) and sodium hydroxide (63.2 mg) in N,N-dimethylformamide/2-propanol (1:1) (4 mL) was stirred at 70° C.-80° C. for 30 min. After the reaction mixture was allowed to cool to room temperature, water and ethyl acetate were added to the mixture, and the insoluble precipitate was collected on a filter. The obtained solid was dissolved in ethanol/6 N hydrochloric acid. The solution was treated with activated charcoal, insoluble materials were filtered off, and the solvent in the filtrate was distilled off. The residue was washed with ethanol and dried under reduced pressure to provide the title compound (120 mg).
$^1$HNMR (DMSO-d6) δ ppm: 1.61-1.66 (2H, m), 1.82-1.91 (2H, m), 2.39 (2H, t, J=6.9 Hz), 2.78 (2H, t, J=6.9 Hz), 2.99-3.16 (4H, m), 3.67 (2H, s), 4.16-4.22 (4H, brs), 6.19 (1H, d, J=6.3 Hz), 7.06-7.18 (2H, m), 7.30 (1H, dd, J=12.6 Hz, 2.4 Hz), 9.84 (1H, s).

Example 146

5-{[1-(1-Benzofuran-5-yl)-4-hydroxypiperidin-4-yl]methoxy}-8-fluoro-3,4-dihydroquinolin-2(1H)-one Synthesized analogous to Example 42.
(Ethyl acetate/dichloromethane) m.p. 215.7-216.0° C.
$^1$HNMR (DMSO-d6) δ ppm: 1.65-1.68 (2H, m), 1.85-1.91 (2H, m), 2.42 (2H, t, J=7.5 Hz), 2.87 (2H, t, J=7.5 Hz), 3.04-3.08 (2H, m), 3.37-3.39 (2H, m), 3.77 (2H, s), 4.69 (1H, brs), 6.58 (1H, dd, J=9.0 Hz, 3.5 Hz), 6.82 (1H, d, J=2.0 Hz), 7.00 (1H, t, J=9.0 Hz), 7.03 (1H, dd, J=9.0 Hz, 2.0 Hz), 7.15 (1H, d, J=2.0 Hz), 7.42 (1H, d, J=9.0 Hz), 7.87 (1H, d, J=2.0 Hz), 10.01 (1H, brs).

Example 147

5-({1-[4-(Difluoromethoxy)-2-fluorophenyl]-4-hydroxypiperidin-4-yl}methoxy)-8-fluoro-3,4-dihydroquinolin-2(1H)-one Synthesized analogous to Example 42.
(Ethyl acetate/dichloromethane) m.p. 201.6-202.0° C.
$^1$HNMR (CDCl$_3$) δ ppm: 1.87-1.90 (2H, m), 1.93-1.98 (2H, m), 2.01 (1H, brs), 2.66 (2H, t, J=7.5 Hz), 3.03 (2H, t, J=7.5 Hz), 3.09-3.14 (2H, m), 3.22-3.25 (2H, m), 3.86 (2H, s), 6.45 (1H, t, J=73.8 Hz), 6.49 (1H, dd, J=9.0 Hz, 4.0 Hz), 6.86-6.90 (2H, m), 6.93 (1H, t, J=9.0 Hz), 6.99 (1H, t, J=9.0 Hz), 7.51 (1H, brs).

Example 148

5-[(1-{4-[(4-Chlorobenzyl)oxy]-2-fluorophenyl}-4-hydroxypiperidin-4-yl)methoxy]-8-fluoro-3,4-dihydroquinolin-2(1H)-one Under nitrogen atmosphere, a suspension of 8-fluoro-5-{[1-(2-fluoro-4-hydroxyphenyl)-4-hydroxypiperidin-4-yl]methoxy}-3,4-dihydroquinolin-2(1H)-one (182 mg), potassium carbonate (124 mg) and 4-chlorobenzyl bromide (120 mg) in N,N-dimethylformamide (2.7 mL) was stirred at room temperature for 3 h, then at 60° C. for 1.5 h. To the reaction solution were added water and ethyl acetate, the precipitate was collected on a filter, and the obtained solid was recrystallized from ethyl acetate. The precipitate was collected on a filter, and dried to provide the title compound (126 mg).
(Ethyl acetate) m.p. 200.0-200.1° C.
$^1$HNMR (CDCl$_3$) δ ppm: 1.86-1.88 (2H, m), 1.93-1.99 (2H, m), 1.99 (1H, brs), 2.66 (2H, t, J=7.5 Hz), 3.03 (2H, t, J=7.5 Hz), 3.05-3.10 (2H, m), 3.16-3.18 (2H, m), 3.85 (2H, s), 4.98 (2H, s), 6.49 (1H, dd, J=9.0 Hz, 4.0 Hz), 6.66-6.69 (1H, m), 6.71 (1H, dd, J=13.5 Hz, 3.0 Hz), 6.93 (1H, t, J=9.0 Hz), 6.99 (1H, t, J=9.0 Hz), 7.33-7.37 (4H, m), 7.49 (1H, brs).

Example 149

8-Chloro-5-{[4-hydroxy-1-(2,4,6-trifluorophenyl)piperidin-4-yl]methoxy}-3,4-dihydroquinolin-2(1H)-one Synthesized analogous to Example 42.
(Ethyl acetate/hexane) m.p. 175.6-176.1° C.
$^1$HNMR (CDCl$_3$) δ ppm: 1.81-1.83 (2H, m), 1.87-1.93 (2H, m), 1.99 (1H, brs), 2.64 (2H, t, J=7.5 Hz), 3.00-3.04 (2H, m), 3.02 (2H, t, J=7.5 Hz), 3.44-3.48 (2H, m), 3.87 (2H, s), 6.55 (1H, d, J=9.0 Hz), 6.60-6.66 (2H, m), 7.19 (1H, d, J=9.0 Hz), 7.74 (1H, brs).

Example 150

8-Fluoro-5-[(1-{2-fluoro-4-[(4-fluorobenzyl)oxy]phenyl}-4-hydroxypiperidin-4-yl)methoxy]-3,4-dihydroquinolin-2(1H)-one Synthesized analogous to Example 148.
$^1$HNMR (CDCl$_3$) δ ppm: 1.86-1.89 (2H, m), 1.93-1.99 (2H, m), 2.00 (1H, brs), 2.66 (2H, t, J=7.5 Hz), 3.03 (2H, t, J=7.5 Hz), 3.06-3.10 (2H, m), 3.16-3.18 (2H, m), 3.85 (2H, s), 4.97 (2H, s), 6.49 (1H, dd, J=9.5 Hz, 4.0 Hz), 6.67-6.70 (1H, m), 6.72 (1H, dd, J=13.5 Hz, 2.5 Hz), 6.93 (1H, t, J=9.5

Hz), 6.97 (1H, t, J=9.5 Hz), 7.07 (2H, t, J=8.5 Hz), 7.39 (2H, dd, J=8.5 Hz, 5.5 Hz), 7.52 (1H, brs).

Example 151

8-Chloro-5-({1-[3-chloro-5-(trifluoromethyl)pyridin-2-yl]-4-hydroxypiperidin-4-yl}methoxy)-3,4-dihydroquinolin-2(1H)-one Synthesized analogous to Example 33.
(Ethyl acetate/hexane) m.p. 193.0-194.7° C.
$^1$HNMR (DMSO-d6) δ ppm: 1.66-1.72 (2H, m), 1.80-1.88 (2H, m), 2.44 (2H, t, J=7.5 Hz), 2.88 (2H, t, J=7.5 Hz), 3.27-3.34 (2H, m), 3.78-3.90 (2H, m), 3.82 (2H, s), 4.85 (1H, s), 6.68 (1H, d, J=9.0 Hz), 7.22 (1H, d, J=9.0 Hz), 8.15 (1H, d, J=2.0 Hz), 8.43-8.46 (1H, m), 9.36 (1H, s).

Example 152

8-Fluoro-5-{[1-(2-fluoro-4-{[4-(trifluoromethoxy)benzyl]oxy}phenyl)-4-hydroxypiperidin-4-yl]methoxy}-3,4-dihydroquinolin-2(1H)-one Synthesized analogous to Example 148.
(Ethyl acetate/hexane) m.p. 199.9-200.5° C.
$^1$HNMR (CDCl$_3$) δ ppm: 1.86-1.89 (2H, m), 1.93-1.99 (2H, m), 1.99 (1H, brs), 2.66 (2H, t, J=7.5 Hz), 3.03 (2H, t, J=7.5 Hz), 3.04-3.11 (2H, m), 3.16-3.18 (2H, m), 3.85 (2H, s), 5.01 (2H, s), 6.49 (1H, dd, J=9.0 Hz, 4.0 Hz), 6.68-6.70 (1H, m), 6.73 (1H, dd, J=13.5 Hz, 3.0 Hz), 6.93 (1H, t, J=9.0 Hz), 6.98 (1H, t, J=9.0 Hz), 7.24 (2H, d, J=8.5 Hz), 7.45 (2H, d, J=8.5 Hz), 7.49 (1H, brs).

Example 153

8-Chloro-5-{[1-(5-chloro-3-fluoropyridin-2-yl)-4-hydroxypiperidin-4-yl]methoxy}-3,4-dihydroquinolin-2(1H)-one Synthesized analogous to Example 33.
(Ethyl acetate) m.p. 174.4-175.8° C.
$^1$HNMR (DMSO-d6) δ ppm: 1.60-1.67 (2H, m), 1.75-1.85 (2H, m), 2.43 (2H, t, J=7.5 Hz), 2.85 (2H, t, J=7.5 Hz), 3.22-3.31 (2H, m), 3.73-3.82 (2H, m), 3.78 (2H, s), 4.82 (1H, s), 6.66 (1H, d, J=8.5 Hz), 7.21 (1H, d, J=8.5 Hz), 7.77 (1H, dd, J=12.5 Hz, 2.0 Hz), 8.07 (1H, d, J=2.0 Hz), 9.35 (1H, s).

Example 154

8-Fluoro-5-{[1-(2-fluoro-4-{[4-(trifluoromethyl)benzyl]oxy}phenyl)-4-hydroxypiperidin-4-yl]methoxy}-3,4-dihydroquinolin-2(1H)-one Synthesized analogous to Example 148.
(Ethyl acetate/hexane) m.p. 207.4-210.3° C.
$^1$HNMR (CDCl$_3$) δ ppm: 1.86-1.89 (2H, m), 1.93-1.99 (2H, m), 2.00 (1H, brs), 2.66 (2H, t, J=7.5 Hz), 3.03 (2H, t, J=7.5 Hz), 3.05-3.11 (2H, m), 3.16-3.18 (2H, m), 3.85 (2H, s), 5.08 (2H, s), 6.49 (1H, dd, J=9.0 Hz, 4.0 Hz), 6.67-6.70 (1H, m), 6.73 (1H, dd, J=13.5 Hz, 3.0 Hz), 6.93 (1H, t, J=9.0 Hz), 6.98 (1H, t, J=9.0 Hz), 7.53 (1H, brs), 7.53 (2H, d, J=8.0 Hz), 7.65 (2H, d, J=8.0 Hz).

Example 155

5-[(1-{4-[(2,4-Dichlorobenzyl)oxy]-2-fluorophenyl}-4-hydroxypiperidin-4-yl)methoxy]-8-fluoro-3,4-dihydroquinolin-2(1H)-one Synthesized analogous to Example 148.
(Ethyl acetate/hexane) m.p. 175.9-177.1° C.
$^1$HNMR (CDCl$_3$) δ ppm: 1.86-1.89 (2H, m), 1.93-1.99 (2H, m), 2.00 (1H, brs), 2.66 (2H, t, J=7.5 Hz), 3.03 (2H, t, J=7.5 Hz), 3.06-3.11 (2H, m), 3.16-3.19 (2H, m), 3.85 (2H, s), 5.07 (2H, s), 6.49 (1H, dd, J=9.0 Hz, 4.0 Hz), 6.68-6.70 (1H, m), 6.74 (1H, dd, J=13.5 Hz, 3.0 Hz), 6.93 (1H, t, J=9.0 Hz), 6.98 (1H, t, J=9.0 Hz), 7.28 (1H, dd, J=8.5 Hz, 2.0 Hz), 7.42 (1H, d, J=2.0 Hz), 7.47 (1H, d, J=8.5 Hz), 7.52 (1H, brs).

Example 156

8-Fluoro-5-{[4-hydroxy-1-(quinolin-6-yl)piperidin-4-yl]methoxy}-3,4-dihydroquinolin-2(1H)-one Synthesized analogous to Example 42.
$^1$HNMR (CDCl$_3$) δ ppm: 1.91-1.99 (4H, m), 2.05 (1H, brs), 2.65 (2H, t, J=7.5 Hz), 3.02 (2H, t, J=7.5 Hz), 3.31-3.36 (2H, m), 3.67-3.69 (2H, m), 3.87 (2H, s), 6.48 (1H, dd, J=9.0 Hz, 4.0 Hz), 6.93 (1H, t, J=9.0 Hz), 7.09 (1H, d, J=2.5 Hz), 7.31 (1H, dd, J=8.5 Hz, 4.5 Hz), 7.52-7.54 (2H, m), 7.97-8.00 (2H, m), 8.71-8.72 (1H, m).

Example 157

5-{[1-(2,4-Difluorophenyl)-4-hydroxypiperidin-4-yl]methoxy}-8-fluoro-3,4-dihydroquinolin-2(1H)-one Synthesized analogous to Example 42.
(Ethyl acetate/hexane) m.p. 201.7-201.9° C.
$^1$HNMR (CDCl$_3$) δ ppm: 1.87-1.89 (2H, m), 1.93-1.99 (2H, m), 2.02 (1H, brs), 2.66 (2H, t, J=7.5 Hz), 3.03 (2H, t, J=7.5 Hz), 3.07-3.12 (2H, m), 3.18-3.20 (2H, m), 3.86 (2H, s), 6.49 (1H, dd, J=9.0 Hz, 4.0 Hz), 6.79-6.84 (2H, m), 6.93 (1H, t, J=9.0 Hz), 6.96-7.01 (1H, m), 7.57 (1H, brs).

Example 158

8-Chloro-5-{[1-(2,4-difluorophenyl)-4-hydroxypiperidin-4-yl]methoxy}-3,4-dihydroquinolin-2(1H)-one Synthesized analogous to Example 42.
(Ethyl acetate/methanol) m.p. 200.0-200.3° C.
$^1$HNMR (DMSO-d6) δ ppm: 1.67-1.69 (2H, m), 1.83-1.89 (2H, m), 2.48 (2H, t, J=7.5 Hz), 2.93 (2H, t, J=7.5 Hz), 2.97-3.03 (2H, m), 3.06-3.08 (2H, m), 3.81 (2H, s), 4.73 (1H, brs), 6.69 (1H, d, J=9.0 Hz), 6.98-7.00 (1H, m), 7.09-7.19 (2H, m), 7.23 (1H, d, J=9.0 Hz), 9.36 (1H, brs).

Example 159

5-({1-[3-Chloro-5-(trifluoromethyl)pyridin-2-yl]-4-hydroxypiperidin-4-yl}methoxy)-8-fluoro-3,4-dihydroquinolin-2(1H)-one Synthesized analogous to Example 33.
(Ethyl acetate) m.p. 172.5-172.7° C.
$^1$HNMR (DMSO-d6) δ ppm: 1.64-1.71 (2H, m), 1.80-1.99 (2H, m), 2.43 (2H, t, J=7.5 Hz), 2.86 (2H, t, J=7.5 Hz), 3.25-3.34 (2H, m), 3.78 (2H, s), 3.80-3.87 (2H, m), 4.00 (1H, s), 6.57 (1H, dd, J=9.5 Hz, 4.0 Hz), 6.98 (1H, t, J=9.9 Hz), 8.15 (1H, d, J=2.5 Hz), 8.54 (1H, d, J=1.0 Hz), 10.01 (1H, s).

Example 160

5-({1-[4-Chloro-2-fluoro-5-(2-fluoroethoxy)phenyl]-4-hydroxypiperidin-4-yl}methoxy)-8-fluoro-3,4-dihydroquinolin-2(1H)-one Synthesized analogous to Example 42.
$^1$HNMR (DMSO-d6) δ ppm: 1.66-1.68 (2H, m), 1.83-1.89 (2H, m), 2.46 (2H, t, J=7.5 Hz), 2.91 (2H, t, J=7.5 Hz), 3.05-3.10 (2H, m), 3.18-3.20 (2H, m), 3.78 (2H, s), 4.30-4.38 (2H, m), 4.68-4.80 (2H, m), 4.74 (1H, brs), 6.58 (1H, dd, J=9.5 Hz, 4.0 Hz), 6.80 (1H, d, J=8.0 Hz), 7.01 (1H, t, J=9.5 Hz), 7.31 (1H, d, J=12.5 Hz), 10.02 (1H, brs).

Example 161

8-Chloro-5-({1-[4-chloro-2-fluoro-5-(2-fluoroethoxy)phenyl]-4-hydroxypiperidin-4-yl}methoxy)-3,4-dihydroquinolin-2(1H)-one Synthesized analogous to Example 42.
(Ethyl acetate/methanol) m.p. 223.0-223.3° C.
$^1$HNMR (DMSO-d6) δ ppm: 1.66-1.69 (2H, m), 1.83-1.89 (2H, m), 2.47 (2H, t, J=7.5 Hz), 2.93 (2H, t, J=7.5 Hz), 3.05-3.10 (2H, m), 3.18-3.20 (2H, m), 3.82 (2H, s), 4.30-4.38 (2H, m), 4.68-4.80 (2H, m), 4.76 (1H, brs), 6.69 (1H, d, J=9.0 Hz), 6.80 (1H, d, J=8.0 Hz), 7.24 (1H, d, J=9.0 Hz), 7.31 (1H, d, J=12.0 Hz), 9.36 (1H, brs).

Example 162

5-{[1-(4-Chloro-2-fluorophenyl)-4-hydroxypiperidin-4-yl]methoxy}-8-fluoro-7-methyl-3,4-dihydroquinolin-2(1H)-one Synthesized analogous to Example 42.
$^1$HNMR (DMSO-d6) δ ppm: 1.60-1.72 (2H, m), 1.78-1.93 (2H, m), 2.19 (3H, d, J=1.8 Hz), 2.43 (2H, t, J=7.6 Hz), 2.86 (2H, t, J=7.6 Hz), 2.97-3.20 (4H, m), 3.76 (2H, s), 4.66 (1H, s), 6.50 (1H, d, J=5.7 Hz), 7.06-7.18 (2H, m), 7.26-7.31 (1H, m), 9.89 (1H, s).

Example 163

5-{[1-(4-Chloro-2-fluorophenyl)-4-hydroxypiperidin-4-yl]methoxy}-7-ethoxy-8-fluoro-3,4-dihydroquinolin-2(1H)-one Synthesized analogous to Example 42.
$^1$HNMR (DMSO-d6) δ ppm: 1.32 (3H, t, J=7.0 Hz), 1.61-1.73 (2H, m), 1.78-1.92 (2H, m), 2.39-2.47 (2H, m), 2.79-2.88 (2H, m), 2.98-3.20 (4H, m), 3.80 (2H, s), 4.10 (2H, q, J=7.0 Hz), 4.67 (1H, s), 6.42 (1H, d, J=6.6 Hz), 7.06-7.18 (2H, m), 7.27-7.32 (1H, m), 9.93 (1H, s).

Example 164

5-({1-[4-Chloro-2-fluoro-5-(propan-2-yloxy)phenyl]-4-hydroxypiperidin-4-yl}methoxy)-8-fluoro-3,4-dihydroquinolin-2(1H)-one Synthesized analogous to Example 42.
(Ethyl acetate/methanol) m.p. 216.7-217.0° C.
$^1$HNMR (CDCl$_3$) δ ppm: 1.36 (6H, d, J=6.0 Hz), 1.87-1.89 (2H, m), 1.92-1.98 (2H, m), 2.02 (1H, brs), 2.66 (2H, t, J=7.5 Hz), 3.02 (2H, t, J=7.5 Hz), 3.08-3.13 (2H, m), 3.24-3.26 (2H, m), 3.85 (2H, s), 4.43 (1H, sep, J=6.0 Hz), 6.49 (1H, dd, J=9.0 Hz, 4.0 Hz), 6.64 (1H, d, J=8.0 Hz), 6.93 (1H, t, J=9.0 Hz), 7.06 (1H, d, J=11.5 Hz), 7.53 (1H, brs).

Example 165

5-[(1-{4-Chloro-5-[(4-chlorobenzyl)oxy]-2-fluorophenyl}-4-hydroxypiperidin-4-yl)methoxy]-8-fluoro-3,4-dihydroquinolin-2(1H)-one Synthesized analogous to Example 42.
(Ethyl acetate/hexane) m.p. 205.1-205.7° C.
$^1$HNMR (CDCl$_3$) δ ppm: 1.85-1.88 (2H, m), 1.89-1.95 (2H, m), 2.01 (1H, brs), 2.66 (2H, t, J=7.5 Hz), 3.02 (2H, t, J=7.5 Hz), 3.06-3.11 (2H, m), 3.20-3.22 (2H, m), 3.84 (2H, s), 5.06 (2H, s), 6.48 (1H, dd, J=9.0 Hz, 4.0 Hz), 6.60 (1H, d, J=8.0 Hz), 6.93 (1H, t, J=9.0 Hz), 7.09 (1H, d, J=11.5 Hz), 7.36 (2H, d, J=8.5 Hz), 7.39 (2H, d, J=8.5 Hz), 7.52 (1H, brs).

Example 166

8-Chloro-5-({1-[4-chloro-2-fluoro-5-(propan-2-yloxy)phenyl]-4-hydroxypiperidin-4-yl}methoxy)-3,4-dihydroquinolin-2(1H)-one Synthesized analogous to Example 42.
(Ethyl acetate/hexane) m.p. 173.3-173.5° C.
$^1$HNMR (CDCl$_3$) δ ppm: 1.36 (6H, d, J=6.0 Hz), 1.86-1.89 (2H, m), 1.92-1.99 (2H, m), 1.99 (1H, brs), 2.64 (2H, t, J=7.5 Hz), 3.02 (2H, t, J=7.5 Hz), 3.07-3.13 (2H, m), 3.24-3.26 (2H, m), 3.88 (2H, s), 4.43 (1H, sep, J=6.0 Hz), 6.55 (1H, d, J=9.0 Hz), 6.64 (1H, d, J=8.0 Hz), 7.06 (1H, d, J=12.0 Hz), 7.20 (1H, d, J=9.0 Hz), 7.75 (1H, brs).

Example 167

5-({1-[4-Chloro-2-fluoro-5-(2,2,2-trifluoroethoxy)phenyl]-4-hydroxypiperidin-4-yl}methoxy)-8-fluoro-3,4-dihydroquinolin-2(1H)-one Synthesized analogous to Example 42.
(Ethyl acetate/hexane) m.p. 200.6-201.0° C.
$^1$HNMR (CDCl$_3$) δ ppm: 1.87-1.89 (2H, m), 1.91-1.97 (2H, m), 2.03 (1H, brs), 2.66 (2H, t, J=7.5 Hz), 3.02 (2H, t, J=7.5 Hz), 3.10-3.15 (2H, m), 3.25-3.27 (2H, m), 3.85 (2H, s), 4.34-4.39 (2H, m), 6.48 (1H, dd, J=9.0 Hz, 4.0 Hz), 6.70 (1H, d, J=8.0 Hz), 6.93 (1H, t, J=9.0 Hz), 7.09 (1H, d, J=12.0 Hz), 7.55 (1H, brs).

Example 168

7-Chloro-5-{[1-(4-chloro-2-fluorophenyl)-4-hydroxypiperidin-4-yl]methoxy}-8-fluoro-3,4-dihydroquinolin-2(1H)-one Synthesized analogous to Example 42.
$^1$HNMR (DMSO-d6) δ ppm: 1.60-1.90 (4H, m), 2.41-2.55 (2H, m), 2.93 (2H, t, J=7.7 Hz), 2.98-3.20 (4H, m), 3.82 (2H, s), 4.70 (1H, s), 6.80 (1H, d, J=5.7 Hz), 7.05-7.20 (2H, m), 7.29 (1H, dd, J=12.6 Hz, 2.4 Hz), 10.19 (1H, s).

Example 169

5-{[1-(5-Chloro-3-fluoropyridin-2-yl)-4-hydroxypiperidin-4-yl]methoxy}-8-fluoro-3,4-dihydroquinolin-2(1H)-one Synthesized analogous to Example 42.
$^1$HNMR (DMSO-d6) δ ppm: 1.59-1.66 (1H, m), 1.75-1.85 (1H, m), 2.43 (2H, t, J=7.8 Hz), 2.85 (2H, t, J=7.8 Hz), 3.23-3.31 (2H, m), 3.34 (2H, s), 3.73-3.81 (4H, m), 4.80 (1H, brs), 6.56 (1H, dd, J=9.2 Hz, 3.5 Hz), 6.99 (1H, t, J=9.6 Hz), 7.76-7.81 (1H, m), 8.05-8.08 (1H, m), 10.01 (1H, brs).

Example 170

5-{[1-(3,5-Dichloro-1-oxidopyridin-2-yl)-4-hydroxypiperidin-4-yl]methoxy}-8-fluoro-3,4-dihydroquinolin-2(1H)-one To a solution of 5-{[1-(3,5-dichloropyridin-2-yl)-4-hydroxypiperidin-4-yl]methoxy}-8-fluoro-3,4-dihydroquinolin-2(1H)-one (403 mg) in chloroform (30 mL) was added m-chloroperoxybenzoic acid (75%) (660 mg), and the reaction mixture was stirred at room temperature for 3 days. To the reaction solution was added sodium hydrogen carbonate aqueous solution, and the solution was extracted with dichloromethane. The organic layer was dried over anhydrous sodium sulfate, and the solvent was distilled off. The residue was recrystallized from dichloromethane/methanol, the precipitate was collected on a filter and dried under reduced pressure to provide the title compound (120 mg).
m.p. 141.0-141.7° C.
$^1$HNMR (DMSO-d6) δ ppm: 1.70-1.79 (2H, m), 1.80-1.95 (2H, m), 2.40-2.57 (2H, m), 2.83-2.95 (2H, m), 3.05-3.20 (3H, m), 3.74 (2H, s), 4.82 (2H, s), 6.50-6.63 (1H, m), 6.92-7.01 (1H, m), 8.16 (1H, s), 8.22 (1H, s), 10.01 (1H, s).

Example 171

5-({1-[4-Chloro-2-fluoro-5-(2-methoxyethoxy)phenyl]-4-hydroxypiperidin-4-yl}methoxy)-8-fluoro-3,4-dihydroquinolin-2(1H)-one Synthesized analogous to Example 42.
(Ethyl acetate/hexane) m.p. 170.6-170.8° C.
$^1$HNMR (CDCl$_3$) δ ppm: 1.86-1.89 (2H, m), 1.91-1.97 (2H, m), 2.03 (1H, brs), 2.66 (2H, t, J=7.5 Hz), 3.02 (2H, t, J=7.5 Hz), 3.09-3.14 (2H, m), 3.24-3.27 (2H, m), 3.47 (3H, s), 3.76-3.78 (2H, m), 3.85 (2H, s), 4.13-4.14 (2H, m), 6.48 (1H, dd, J=9.0 Hz, 4.0 Hz), 6.68 (1H, d, J=7.5 Hz), 6.93 (1H, t, J=9.0 Hz), 7.06 (1H, d, J=12.0 Hz), 7.54 (1H, brs).

Example 172

5-[(1-{4-Chloro-5-[2-(dimethylamino)ethoxy]-2-fluorophenyl}-4-hydroxypiperidin-4-yl)methoxy]-8-fluoro-3,4-dihydroquinolin-2(1H)-one Synthesized analogous to Example 42.
(Ethyl acetate/hexane) m.p. 162.9-164.1° C.
$^1$HNMR (CDCl$_3$) δ ppm: 1.86-1.89 (2H, m), 1.92-1.97 (2H, m), 2.02 (1H, brs), 2.37 (6H, s), 2.66 (2H, t, J=7.5 Hz), 2.77 (2H, t, J=6.0 Hz), 3.03 (2H, t, J=7.5 Hz), 3.09-3.14 (2H, m), 3.24-3.27 (2H, m), 3.85 (2H, s), 4.09 (2H, t, J=6.0 Hz), 6.49 (1H, dd, J=9.0 Hz, 4.0 Hz), 6.64 (1H, d, J=8.0 Hz), 6.93 (1H, t, J=9.0 Hz), 7.06 (1H, d, J=11.5 Hz), 7.51 (1H, brs).

Example 173

5-{[1-(4-Chloro-2-fluoro-5-propoxyphenyl)-4-hydroxypiperidin-4-yl]methoxy}-8-fluoro-3,4-dihydroquinolin-2(1H)-one Synthesized analogous to Example 42.
(Ethyl acetate/hexane) m.p. 200.7-201.4° C.
$^1$HNMR (CDCl$_3$) δ ppm: 1.07 (3H, t, J=7.0 Hz), 1.81-1.89 (4H, m), 1.92-1.98 (2H, m), 2.03 (1H, brs), 2.66 (2H, t, J=7.5 Hz), 3.02 (2H, t, J=7.5 Hz), 3.09-3.14 (2H, m), 3.25-3.27 (2H, m), 3.86 (2H, s), 3.95 (2H, t, J=6.5 Hz), 6.49 (1H, dd, J=9.0 Hz, 4.0 Hz), 6.60 (1H, d, J=8.0 Hz), 6.93 (1H, t, J=9.0 Hz), 7.07 (1H, d, J=12.0 Hz), 7.56 (1H, brs).

Example 174

5-[(1-{4-Chloro-2-fluoro-5-[2-(4-fluorophenoxy)ethoxy]phenyl}-4-hydroxypiperidin-4-yl)methoxy]-8-fluoro-3,4-dihydroquinolin-2(1H)-one Synthesized analogous to Example 42.
(Ethyl acetate/hexane) m.p. 159.2-160.0° C.
$^1$HNMR (CDCl$_3$) δ ppm: 1.86-1.88 (2H, m), 1.91-1.97 (2H, m), 2.02 (1H, brs), 2.66 (2H, t, J=7.5 Hz), 3.02 (2H, t, J=7.5 Hz), 3.08-3.13 (2H, m), 3.23-3.25 (2H, m), 3.85 (2H, s), 4.30-4.36 (4H, m), 6.48 (1H, dd, J=9.0 Hz, 3.5 Hz), 6.70 (1H, d, J=8.0 Hz), 6.90-6.95 (3H, m), 6.97-7.01 (2H, m), 7.08 (1H, d, J=11.5 Hz), 7.53 (1H, brs).

Example 175

8-Chloro-5-({1-[4-chloro-2-fluoro-5-(2-methoxyethoxy)phenyl]-4-hydroxypiperidin-4-yl}methoxy)-3,4-dihydroquinolin-2(1H)-one Synthesized analogous to Example 42.
(Ethyl acetate/hexane) m.p. 143.5-145.1° C.
$^1$HNMR (CDCl$_3$) δ ppm: 1.86-1.89 (2H, m), 1.92-1.98 (2H, m), 1.98 (1H, brs), 2.65 (2H, t, J=7.5 Hz), 3.02 (2H, t, J=7.5 Hz), 3.09-3.14 (2H, m), 3.25-3.27 (2H, m), 3.48 (3H, s), 3.76-3.78 (2H, m), 3.87 (2H, s), 4.13-4.15 (2H, m), 6.55 (1H, d, J=9.0 Hz), 6.68 (1H, d, J=7.5 Hz), 7.06 (1H, d, J=11.5 Hz), 7.20 (1H, d, J=9.0 Hz), 7.75 (1H, brs).

Example 176

8-Fluoro-5-[(1-{2-fluoro-4-[2-(4-fluorophenoxy)ethoxy]phenyl}-4-hydroxypiperidin-4-yl)methoxy]-3,4-dihydroquinolin-2(1H)-one Under nitrogen atmosphere, a suspension of 8-fluoro-5-{[1-(2-fluoro-4-hydroxyphenyl)-4-hydroxypiperidin-4-yl]methoxy}-3,4-dihydroquinolin-2(1H)-one (185 mg), potassium carbonate (126 mg), 1-(2-bromoethoxy)-4-fluorobenzene (110 mg) and sodium iodide (75 mg) in N,N-dimethylformamide (1.9 mL) was stirred at room temperature for 3 h, then at 60° C. for 10 h. To the reaction solution was added water and the solution was extracted with ethyl acetate/methanol, the organic layer was washed with brine, and dried over anhydrous sodium sulfate, and then the solvent was distilled off. The residue was purified by silica gel column chromatography (dichloromethane/methanol), and the obtained product was recrystallized form ethyl acetate. The precipitate was collected on a filter and dried to provide the title compound (99 mg).
m.p. 199.3-199.5° C.

¹HNMR (CDCl₃) δ ppm: 1.86-1.89 (2H, m), 1.93-1.99 (2H, m), 1.99 (1H, brs), 2.66 (2H, t, J=7.5 Hz), 3.03 (2H, t, J=7.5 Hz), 3.06-3.11 (2H, m), 3.16-3.19 (2H, m), 3.86 (2H, s), 4.26 (4H, s), 6.49 (1H, dd, J=9.0 Hz, 3.5 Hz), 6.67-6.69 (1H, m), 6.72 (1H, dd, J=13.5 Hz, 3.0 Hz), 6.88-6.90 (2H, m), 6.93 (1H, t, J=9.0 Hz), 6.96-7.00 (3H, m), 7.49 (1H, brs).

Example 177

5-{[1-(4-Chloro-2,5-difluorophenyl)-4-hydroxypiperidin-4-yl]methoxy}-7,8-difluoro-3,4-dihydroquinolin-2(1H)-one Synthesized analogous to Example 42.
¹HNMR (DMSO-d6) δ ppm: 1.64-1.69 (2H, m), 1.78-1.82 (2H, m), 2.43-2.49 (2H, m), 2.84-2.89 (2H, m), 3.05-3.11 (2H, m), 3.18-3.22 (2H, m), 3.79 (2H, s), 4.75 (1H, s), 6.74 (1H, dd, J=12.6 Hz, 6.3 Hz), 7.11 (1H, dd, J=11.1 Hz, 7.5 Hz), 7.46 (1H, dd, J=12.0 Hz, 6.9 Hz), 10.24 (1H, s).

Example 178

5-{[1-(4-Chloro-2,6-difluorophenyl)-4-hydroxypiperidin-4-yl]methoxy}-7,8-difluoro-3,4-dihydroquinolin-2(1H)-one Synthesized analogous to Example 42.
¹HNMR (DMSO-d6) δ ppm: 1.61-1.65 (2H, m), 1.72-1.78 (2H, m), 2.43-2.49 (2H, m), 2.85-2.90 (2H, m), 2.94-2.99 (2H, m), 3.18-3.25 (2H, m), 3.78 (2H, s), 4.70 (1H, s), 6.74 (1H, dd, J=12.6 Hz, 6.3 Hz), 7.25 (2H, dd, J=15 Hz, 5.4 Hz), 10.24 (1H, s).

Example 179

5-{[1-(4-Chloro-2-fluoro-5-propylphenyl)-4-hydroxypiperidin-4-yl]methoxy}-8-fluoro-3,4-dihydroquinolin-2(1H)-one Synthesized analogous to Example 42.
(Ethyl acetate) m.p. 196.5-196.6° C.
¹HNMR (CDCl₃) δ ppm: 0.97 (3H, t, J=7.5 Hz), 1.58-1.66 (2H, m), 1.86-1.89 (2H, m), 1.92-1.98 (2H, m), 2.00 (1H, brs), 2.61-2.67 (4H, m), 3.02 (2H, t, J=7.5 Hz), 3.08-3.13 (2H, m), 3.23-3.25 (2H, m), 3.85 (2H, s), 6.49 (1H, dd, J=9.0 Hz, 4.0 Hz), 6.83 (1H, d, J=9.5 Hz), 6.93 (1H, t, J=9.0 Hz), 7.04 (1H, d, J=11.5 Hz), 7.50 (1H, brs).

Example 180

5-({1-[4-Chloro-2-fluoro-5-(propan-2-yl)phenyl]-4-hydroxypiperidin-4-yl}methoxy)-8-fluoro-3,4-dihydroquinolin-2(1H)-one Synthesized analogous to Example 42.
(Ethyl acetate/methanol/dichloromethane) m.p. 225.3-225.7° C.
¹HNMR (CDCl₃) δ ppm: 1.22 (6H, d, J=7.0 Hz), 1.87-1.90 (2H, m), 1.92-1.98 (2H, m), 2.04 (1H, brs), 2.66 (2H, t, J=7.5 Hz), 3.03 (2H, t, J=7.5 Hz), 3.10-3.16 (2H, m), 3.24-3.26 (2H, m), 3.33 (1H, sep, J=7.0 Hz), 3.86 (2H, s), 6.49 (1H, dd, J=9.0 Hz, 4.0 Hz), 6.90 (1H, d, J=9.0 Hz), 6.93 (1H, t, J=9.0 Hz), 7.04 (1H, d, J=12.0 Hz), 7.55 (1H, brs).

Example 181

5-({1-[4-(Difluoromethoxy)-2,6-difluorophenyl]-4-hydroxypiperidin-4-yl}methoxy)-8-fluoro-3,4-dihydroquinolin-2(1H)-one Synthesized analogous to Example 42.
(Ethyl acetate/hexane) m.p. 172.6-172.7° C.
¹HNMR (CDCl₃) δ ppm: 1.81-1.84 (2H, m), 1.86-1.92 (2H, m), 2.02 (1H, brs), 2.66 (2H, t, J=7.5 Hz), 3.02 (2H, t, J=7.5 Hz), 3.04-3.07 (2H, m), 3.45-3.50 (2H, m), 3.85 (2H, s), 6.45 (1H, t, J=73.0 Hz), 6.49 (1H, dd, J=9.0 Hz, 4.0 Hz), 6.66-6.72 (2H, m), 6.93 (1H, t, J=9.0 Hz), 7.52 (1H, brs).

Example 182

5-{[1-(2,4-Difluoro-5-methylphenyl)-4-hydroxypiperidin-4-yl]methoxy}-8-fluoro-3,4-dihydroquinolin-2(1H)-one Synthesized analogous to Example 42.
¹HNMR (CDCl₃) δ ppm: 1.86-1.89 (2H, m), 1.92-1.98 (2H, m), 2.01 (1H, brs), 2.22 (3H, s), 2.66 (2H, t, J=7.5 Hz), 3.03 (2H, t, J=7.5 Hz), 3.06-3.10 (2H, m), 3.17-3.19 (2H, m), 3.85 (2H, s), 6.49 (1H, dd, J=9.0 Hz, 4.0 Hz), 6.76 (1H, dd, J=12.0 Hz, 9.5 Hz), 6.82 (1H, t, J=9.0 Hz), 6.93 (1H, t, J=9.0 Hz), 7.54 (1H, brs).

Example 183

8-Chloro-5-{[1-(2,4-difluoro-5-methylphenyl)-4-hydroxypiperidin-4-yl]methoxy}-3,4-dihydroquinolin-2(1H)-one Synthesized analogous to Example 42.
(Ethyl acetate) m.p. 195.0-195.2° C.
¹HNMR (CDCl₃) δ ppm: 1.86-1.88 (2H, m), 1.93-1.99 (2H, m), 1.98 (1H, brs), 2.22 (3H, s), 2.64 (2H, t, J=7.5 Hz), 3.02 (2H, t, J=7.5 Hz), 3.06-3.11 (2H, m), 3.17-3.19 (2H, m), 3.87 (2H, s), 6.55 (1H, d, J=9.0 Hz), 6.76 (1H, dd, J=12.0 Hz, 9.5 Hz), 6.82 (1H, t, J=9.0 Hz), 7.19 (1H, d, J=9.0 Hz), 7.75 (1H, brs).

Example 184

8-Chloro-5-({1-[4-(difluoromethoxy)-2,6-difluorophenyl]-4-hydroxypiperidin-4-yl}methoxy)-3,4-dihydroquinolin-2(1H)-one Synthesized analogous to Example 42.
(Ethyl acetate/hexane) m.p. 143.6-143.7° C.
¹HNMR (CDCl₃) δ ppm: 1.81-1.84 (2H, m), 1.87-1.93 (2H, m), 2.01 (1H, brs), 2.64 (2H, t, J=7.5 Hz), 3.02 (2H, t, J=7.5 Hz), 3.05-3.07 (2H, m), 3.45-3.49 (2H, m), 3.87 (2H, s), 6.45 (1H, t, J=73.0 Hz), 6.55 (1H, d, J=9.0 Hz), 6.66-6.72 (2H, m), 7.19 (1H, d, J=9.0 Hz), 7.75 (1H, brs).

Example 185

5-{[1-(4-Chloro-2-fluoro-5-methoxyphenyl)-4-hydroxypiperidin-4-yl]methoxy}-8-fluoro-3,4-dihydroquinolin-2(1H)-one Synthesized analogous to Example 42.
(Ethyl acetate) m.p. 232.4-232.5° C.
$^1$HNMR (CDCl$_3$) δ ppm: 1.87-1.90 (2H, m), 1.93-1.99 (2H, m), 2.03 (1H, brs), 2.66 (2H, t, J=7.5 Hz), 3.02 (2H, t, J=7.5 Hz), 3.11-3.16 (2H, m), 3.26-3.29 (2H, m), 3.86 (2H, s), 3.88 (3H, s), 6.49 (1H, dd, J=9.0 Hz, 4.0 Hz), 6.60 (1H, d, J=7.5 Hz), 6.93 (1H, t, J=9.0 Hz), 7.08 (1H, d, J=11.5 Hz), 7.54 (1H, brs).

Example 186

5-{[1-(5,6-Dimethylpyridin-2-yl)-4-hydroxypiperidin-4-yl]methoxy}-8-fluoro-3,4-dihydroquinolin-2(1H)-one Synthesized analogous to Example 42.
(Ethyl acetate/methanol) m.p. 197.9-199.6° C.
$^1$HNMR (DMSO-d6) δ ppm: 1.52-1.60 (2H, m), 1.63-1.71 (2H, m), 2.08 (3H, s), 2.25 (3H, s), 2.38 (2H, t, J=7.5 Hz), 2.79 (2H, t, J=7.5 Hz), 3.07-3.15 (2H, m), 3.72 (2H, s), 3.92-4.00 (2H, m), 4.70 (1H, s), 6.51-6.57 (2H, m), 6.96 (1H, t, J=9.8 Hz), 7.22 (1H, d, J=8.5 Hz), 9.99 (1H, s).

Example 187

8-Chloro-5-{[1-(5,6-dimethylpyridin-2-yl)-4-hydroxypiperidin-4-yl]methoxy}-3,4-dihydroquinolin-2(1H)-one Synthesized analogous to Example 42.
(Ethyl acetate/hexane) m.p. 169.6-171.0° C.
$^1$HNMR (DMSO-d6) δ ppm: 1.53-1.60 (2H, m), 1.63-1.71 (2H, m), 2.08 (3H, s), 2.25 (3H, s), 2.40 (2H, t, J=7.5 Hz), 2.81 (2H, t, J=7.5 Hz), 3.08-3.16 (2H, m), 3.76 (2H, s), 3.92-3.98 (2H, m), 4.73 (1H, s), 6.55 (1H, d, J=8.5 Hz), 6.64 (1H, d, J=8.5 Hz), 7.19 (1H, d, J=8.5 Hz), 7.22 (1H, d, J=8.5 Hz), 9.34 (1H, s).

Example 188

8-Chloro-5-{[1-(3-chloro-5-ethoxypyridin-2-yl)-4-hydroxypiperidin-4-yl]methoxy}-3,4-dihydroquinolin-2(1H)-one Synthesized analogous to Example 33.
(Ethyl acetate/hexane) m.p. 169.0-170.4° C.
$^1$HNMR (DMSO-d6) δ ppm: 1.30 (3H, t, J=7.0 Hz), 1.62-1.68 (2H, m), 1.77-1.86 (2H, m), 2.46 (2H, t, J=7.5 Hz), 2.91 (2H, t, J=7.5 Hz), 3.05-3.13 (2H, m), 3.23-3.37 (2H, m), 3.80 (2H, s), 4.03 (2H, q, J=7.0 Hz), 4.69 (1H, s), 6.67 (1H, d, J=9.0 Hz), 7.21 (1H, d, J=9.0 Hz), 7.51 (1H, d, J=2.5 Hz), 7.96 (1H, d, J=2.5 Hz), 9.34 (1H, s).

Example 189

5-{[1-(4-Chloro-5-ethyl-2-fluorophenyl)-4-hydroxypiperidin-4-yl]methoxy}-8-fluoro-3,4-dihydroquinolin-2(1H)-one Synthesized analogous to Example 42.
(Ethyl acetate/dichloromethane) m.p. 201.3-202.4° C.
$^1$HNMR (CDCl$_3$) δ ppm: 1.21 (3H, t, J=7.5 Hz), 1.86-1.89 (2H, m), 1.92-1.98 (2H, m), 2.03 (1H, brs), 2.64-2.71 (4H, m), 3.03 (2H, t, J=7.5 Hz), 3.09-3.14 (2H, m), 3.24-3.26 (2H, m), 3.86 (2H, s), 6.49 (1H, dd, J=9.0 Hz, 4.0 Hz), 6.85 (1H, d, J=9.0 Hz), 6.93 (1H, t, J=9.0 Hz), 7.04 (1H, d, J=12.0 Hz), 7.56 (1H, brs).

Example 190

8-Chloro-5-{[1-(4-chloro-2-fluoro-5-methoxyphenyl)-4-hydroxypiperidin-4-yl]methoxy}-3,4-dihydroquinolin-2(1H)-one Synthesized analogous to Example 42.
(Ethyl acetate/methanol) m.p. 228.7-228.9° C.
$^1$HNMR (DMSO-d6) δ ppm: 1.67-1.70 (2H, m), 1.83-1.89 (2H, m), 2.47 (2H, t, J=7.5 Hz), 2.93 (2H, t, J=7.5 Hz), 3.06-3.11 (2H, m), 3.18-3.21 (2H, m), 3.82 (2H, s), 3.85 (3H, s), 4.76 (1H, brs), 6.69 (1H, d, J=9.0 Hz), 6.75 (1H, d, J=8.0 Hz), 7.24 (1H, d, J=9.0 Hz), 7.20 (1H, d, J=12.0 Hz), 9.36 (1H, brs).

Example 191

5-{[1-(3-Chloro-5-ethoxypyridin-2-yl)-4-hydroxypiperidin-4-yl]methoxy}-8-fluoro-3,4-dihydroquinolin-2(1H)-one Synthesized analogous to Example 33.
(Ethyl acetate/hexane) m.p. 187.9-190.2° C.
$^1$HNMR (DMSO-d6) δ ppm: 1.30 (3H, t, J=7.0 Hz), 1.62-1.68 (2H, m), 1.80-1.88 (2H, m), 2.44 (2H, t, J=7.5 Hz), 2.90 (2H, t, J=7.5 Hz), 3.06-3.14 (2H, m), 3.25-3.33 (2H, m), 3.77 (2H, s), 4.04 (2H, q, J=7.0 Hz), 4.67 (1H, s), 6.57 (1H, dd, J=9.0 Hz, 4.0 Hz), 6.98 (1H, t, J=9.5 Hz), 7.52 (1H, d, J=2.5 Hz), 7.98 (1H, d, J=2.5 Hz), 10.01 (1H, s).

Example 192

5-{[1-(5-Bromo-3-fluoropyridin-2-yl)-4-hydroxypiperidin-4-yl]methoxy}-8-fluoro-3,4-dihydroquinolin-2(1H)-one Synthesized analogous to Example 33.
(Ethyl acetate/methanol) m.p. 197.4-203.9° C.
$^1$HNMR (DMSO-d6) δ ppm: 1.66-1.73 (2H, m), 1.82-1.90 (2H, m), 2.45 (2H, t, J=7.5 Hz), 2.91 (2H, t, J=7.5 Hz), 3.04-3.11 (2H, m), 3.13-3.20 (2H, m), 3.80 (2H, s), 4.77 (1H, s), 6.58 (1H, dd, J=9.0 Hz, 4.0 Hz), 6.98 (1H, t, J=9.5 Hz), 7.78 (1H, d, J=2.0 Hz), 8.16 (1H, d, J=2.0 Hz), 10.02 (1H, s).

Example 193

5-{[1-(5-Bromo-3-fluoropyridin-2-yl)-4-hydroxypiperidin-4-yl]methoxy}-8-chloro-3,4-dihydroquinolin-2(1H)-one Synthesized analogous to Example 33.
(Ethyl acetate/methanol) m.p. 231.2-233.5° C.
$^1$HNMR (DMSO-d6) δ ppm: 1.67-1.74 (2H, m), 1.81-1.90 (2H, m), 2.43 (2H, t, J=7.5 Hz), 2.92 (2H, t, J=7.5 Hz), 3.04-3.11 (2H, m), 3.15-3.21 (2H, m), 3.84 (2H, s), 4.79 (1H, s), 6.65 (1H, d, J=9.0 Hz), 7.23 (1H, d, J=9.0 Hz), 7.77 (1H, d, J=2.2 Hz), 8.16 (1H, d, J=2.2 Hz), 9.37 (1H, s).

Example 194

5-{[1-(4-Chloro-2-fluorophenyl)-4-hydroxypiperidin-4-yl]methoxy}-7-fluoro-3,4-dihydroquinolin-2(1H)-one Synthesized analogous to Example 42.
¹HNMR (DMSO-d6) δ ppm: 1.60-1.74 (2H, m), 1.75-1.92 (2H, m), 2.43 (2H, t, J=7.7 Hz), 2.82 (2H, t, J=7.7 Hz), 2.96-3.20 (4H, m), 3.81 (2H, s), 4.74 (1H, s), 6.29 (1H, dd, J=9.9 Hz, 2.1 Hz), 6.52 (1H, dd, J=9.9 Hz, 2.1 Hz), 7.05-7.19 (2H, m), 7.31 (1H, dd, J=12.6 Hz, 2.1 Hz), 10.11 (1H, s).

Example 195

8-Chloro-5-{[1-(4-chloro-2-fluorophenyl)-4-hydroxypiperidin-4-yl]methoxy}-7-fluoro-3,4-dihydroquinolin-2(1H)-one Synthesized analogous to Example 42.
¹HNMR (DMSO-d6) δ ppm: 1.61-1.89 (4H, m), 2.42-2.53 (2H, m), 2.89 (2H, t, J=7.4 Hz), 2.96-3.20 (4H, m), 3.84 (2H, s), 4.78 (1H, s), 6.84 (1H, d, J=11.4 Hz), 7.04-7.20 (2H, m), 7.31 (1H, dd, J=12.5 Hz, 2.3 Hz), 9.68 (1H, brs).

Example 196

5-{[1-(4-Chloro-2,6-difluorophenyl)-4-hydroxypiperidin-4-yl]methoxy}-7-fluoro-3,4-dihydroquinolin-2(1H)-one Synthesized analogous to Example 42.
¹HNMR (DMSO-d6) δ ppm: 1.58-1.87 (4H, m), 2.43 (2H, t, J=7.9 Hz), 2.83 (2H, t, J=7.9 Hz), 2.92-3.03 (2H, m), 3.28-3.46 (2H, m), 3.80 (2H, s), 4.73 (1H, s), 6.29 (1H, dd, J=9.9 Hz, 2.4 Hz), 6.52 (1H, dd, J=9.9 Hz, 2.4 Hz), 7.20-7.33 (2H, m), 10.11 (1H, brs).

Example 197

8-Chloro-5-{[4-hydroxy-1-(2,2,6-trifluoro-1,3-benzodioxol-5-yl)piperidin-4-yl]methoxy}-3,4-dihydroquinolin-2(1H)-one Synthesized analogous to Example 42.
(Ethyl acetate) m.p. 213.4-213.5° C. ¹HNMR (CDCl₃) δ ppm: 1.87-1.89 (2H, m), 1.93-1.99 (2H, m), 1.99 (1H, brs), 2.65 (2H, t, J=7.5 Hz), 3.02 (2H, t, J=7.5 Hz), 3.06-3.12 (2H, m), 3.15-3.17 (2H, m), 3.88 (2H, s), 6.55 (1H, d, J=8.5 Hz), 6.83 (1H, d, J=7.0 Hz), 6.86 (1H, d, J=10.0 Hz), 7.20 (1H, d, J=8.5 Hz), 7.75 (1H, brs).

Example 198

5-{[1-(5-Chloropyridin-2-yl)-4-hydroxypiperidin-4-yl]methoxy}-8-fluoro-3,4-dihydroquinolin-2(1H)-one Synthesized analogous to Example 33.
(Ethyl acetate) m.p. 192.0-192.3° C.
¹HNMR (DMSO-d6) δ ppm: 1.55-1.62 (2H, m), 1.65-1.74 (2H, m), 2.40 (2H, t, J=7.5 Hz), 2.80 (2H, t, J=7.5 Hz), 3.17-3.27 (2H, m), 3.74 (2H, s), 4.00-4.07 (2H, m), 4.80 (1H, s), 6.54 (1H, dd, J=9.0 Hz, 3.5 Hz), 6.89 (1H, d, J=9.0 Hz), 6.97 (1H, t, J=9.8 Hz), 7.55 (1H, dd, J=9.0 Hz, 2.0 Hz), 8.09 (1H, d, J=3.0 Hz), 10.01 (1H, s).

Example 199

8-Chloro-5-({1-[2-chloro-4-(methylsulfanyl)phenyl]-4-hydroxypiperidin-4-yl}methoxy)-3,4-dihydroquinolin-2(1H)-one Synthesized analogous to Example 42.
(Ethyl acetate) m.p. 160.7-160.9° C.
¹HNMR (CDCl₃) δ ppm: 1.86-1.89 (2H, m), 1.94-2.00 (2H, m), 2.01 (1H, brs), 2.46 (3H, s), 2.65 (2H, t, J=7.5 Hz), 3.03 (2H, t, J=7.5 Hz), 3.05-3.10 (2H, m), 3.18-3.20 (2H, m), 3.89 (2H, s), 6.55 (1H, d, J=9.0 Hz), 7.03 (1H, d, J=8.5 Hz), 7.15 (1H, dd, J=8.5 Hz, 2.0 Hz), 7.20 (1H, d, J=9.0 Hz), 7.30 (1H, d, J=2.0 Hz), 7.75 (1H, brs).

Example 200

5-{[1-(5-Chloro-1-oxidopyridin-2-yl)-4-hydroxypiperidin-4-yl]methoxy}-8-fluoro-3,4-dihydroquinolin-2(1H)-one To a solution of 5-{[1-(5-chloropyridin-2-yl)-4-hydroxypiperidin-4-yl]methoxy}-8-fluoro-3,4-dihydroquinolin-2(1H)-one (183 mg) in chloroform (33 mL) was added m-chloroperoxybenzoic acid (75%) (156 mg) and the reaction mixture was stirred at room temperature for 20 h. To the reaction solution was added sodium carbonate aqueous solution to extract the product. The organic layer was dried over anhydrous sodium sulfate, the solvent was distilled off, the residue was recrystallized from ethyl acetate, and the precipitate was collected on a filter and dried under reduced pressure to provide the title compound (55 mg).
m.p. 189.0-189.5° C.
¹HNMR (DMSO-d6) δ ppm: 1.56-1.67 (2H, m), 2.40-2.60 (2H, m), 2.57-2.67 (2H, m), 2.73-2.84 (2H, m), 2.94 (2H, t, J=7.5 Hz), 3.84 (2H, s), 4.20-4.30 (2H, m), 5.01 (1H, s), 6.56-6.66 (1H, m), 6.97-7.06 (1H, m), 8.16-8.25 (1H, m), 8.51-8.59 (1H, m), 8.61 (1H, s), 10.04 (1H, s).

Example 201

8-Chloro-5-{[1-(4-chloro-2,6-difluorophenyl)-4-hydroxypiperidin-4-yl]methoxy}-7-fluoro-3,4-dihydroquinolin-2(1H)-one Synthesized analogous to Example 42.
¹HNMR (DMSO-d6) δ ppm: 1.68-1.85 (4H, m), 2.42-2.54 (2H, m), 2.82-3.04 (4H, m), 3.28-3.42 (2H, m), 3.83 (2H, s), 4.76 (1H, s), 6.84 (1H, d, J=11.7 Hz), 7.20-7.33 (2H, m), 9.67 (1H, brs).

Example 202

8-Fluoro-5-{[4-hydroxy-1-(2,2,6-trifluoro-1,3-benzodioxol-5-yl)piperidin-4-yl]methoxy}-3,4-dihydroquinolin-2(1H)-one Synthesized analogous to Example 42.
(Ethyl acetate/methanol) m.p. 226.6-226.7° C.
¹HNMR (CDCl₃) δ ppm: 1.87-1.89 (2H, m), 1.92-1.98 (2H, m), 2.03 (1H, brs), 2.66 (2H, t, J=7.5 Hz), 3.03 (2H, t, J=7.5 Hz), 3.06-3.12 (2H, m), 3.15-3.17 (2H, m), 3.85 (2H, s), 6.48 (1H, dd, J=9.0 Hz, 4.0 Hz), 6.84 (1H, d, J=7.0 Hz), 6.86 (1H, d, J=10.0 Hz), 6.93 (1H, t, J=9.0 Hz), 7.55 (1H, brs).

Example 203

5-({1-[2-Chloro-4-(methylsulfanyl)phenyl]-4-hydroxypiperidin-4-yl}methoxy)-8-fluoro-3,4-dihydroquinolin-2(1H)-one Synthesized analogous to Example 42.
(Ethyl acetate) m.p. 207.4-207.6° C.
$^1$HNMR (CDCl$_3$) δ ppm: 1.87-1.89 (2H, m), 1.93-1.99 (2H, m), 2.02 (1H, brs), 2.46 (3H, s), 2.66 (2H, t, J=7.5 Hz), 3.03 (2H, t, J=7.5 Hz), 3.05-3.10 (2H, m), 3.18-3.20 (2H, m), 3.87 (2H, s), 6.49 (1H, dd, J=9.0 Hz, 4.0 Hz), 6.93 (1H, t, J=9.0 Hz), 7.04 (1H, d, J=8.5 Hz), 7.15 (1H, dd, J=8.5 Hz, 2.5 Hz), 7.30 (1H, d, J=2.5 Hz), 7.52 (1H, brs).

Example 204

8-Chloro-5-{[1-(5-ethoxy-2,4-difluorophenyl)-4-hydroxypiperidin-4-yl]methoxy}-3,4-dihydroquinolin-2(1H)-one Synthesized analogous to Example 42.
(Ethyl acetate) m.p. 182.1-182.4° C.
$^1$HNMR (CDCl$_3$) δ ppm: 1.42 (3H, t, J=7.0 Hz), 1.86-1.89 (2H, m), 1.93-1.99 (2H, m), 2.00 (1H, brs), 2.64 (2H, t, J=7.5 Hz), 3.02 (2H, t, J=7.5 Hz), 3.06-3.12 (2H, m), 3.18-3.20 (2H, m), 3.88 (2H, s), 4.08 (2H, q, 7.0 Hz), 6.55 (1H, d, J=9.0 Hz), 6.68 (1H, t, J=8.5 Hz), 6.85 (1H, t, J=11.0 Hz), 7.20 (1H, d, J=9.0 Hz), 7.76 (1H, brs).

Example 205

8-Chloro-5-{[1-(2,4-difluoro-5-methoxyphenyl)-4-hydroxypiperidin-4-yl]methoxy}-3,4-dihydroquinolin-2(1H)-one Synthesized analogous to Example 42.
(Ethyl acetate) m.p. 191.4-191.7° C.
$^1$HNMR (CDCl$_3$) δ ppm: 1.87-1.89 (2H, m), 1.93-1.99 (2H, m), 2.01 (1H, brs), 2.64 (2H, t, J=7.5 Hz), 3.02 (2H, t, J=7.5 Hz), 3.08-3.13 (2H, m), 3.19-3.22 (2H, m), 3.87 (3H, s), 3.88 (2H, s), 6.55 (1H, d, J=9.0 Hz), 6.68 (1H, t, J=8.5 Hz), 6.86 (1H, t, J=11.0 Hz), 7.20 (1H, d, J=9.0 Hz), 7.76 (1H, brs).

Example 206

5-{[1-(2,4-Dichloro-5-fluorophenyl)-4-hydroxypiperidin-4-yl]methoxy}-7-fluoro-8-methyl-3,4-dihydroquinolin-2(1H)-one Synthesized analogous to Example 42.
$^1$HNMR (DMSO-d6) δ ppm: 1.68-1.72 (2H, m), 1.75-1.90 (2H, m), 2.03 (3H, s), 2.40 (2H, t, J=7.2 Hz), 2.83 (2H, t, J=7.2 Hz), 2.96-3.11 (4H, m), 3.79 (2H, s), 4.72 (1H, s), 6.54 (1H, d, J=12.0 Hz), 7.23 (1H, d, J=11.4 Hz), 7.68 (1H, d, J=7.8 Hz), 9.54 (1H, s).

Example 207

5-{[1-(4-Bromo-2-fluorophenyl)-4-hydroxypiperidin-4-yl]methoxy}-7-fluoro-8-methyl-3,4-dihydroquinolin-2(1H)-one Synthesized analogous to Example 42.
$^1$HNMR (DMSO-d6) δ ppm: 1.63-1.71 (2H, m), 1.75-1.86 (2H, m), 2.03 (3H, s), 2.39 (2H, t, J=7.2 Hz), 2.81 (2H, t, J=7.2 Hz), 3.01-3.20 (4H, m), 3.77 (2H, s), 4.70 (1H, s), 6.54 (1H, d, J=12.0 Hz), 6.99-7.05 (1H, m), 7.25-7.29 (1H, m), 7.36-7.41 (1H, m), 9.53 (1H, s).

Example 208

5-{[1-(4-Chloro-2,6-difluorophenyl)-4-hydroxypiperidin-4-yl]methoxy}-7-fluoro-8-methyl-3,4-dihydroquinolin-2(1H)-one Synthesized analogous to Example 42.
$^1$HNMR (DMSO-d6) δ ppm: 1.60-1.72 (2H, m), 1.74-1.81 (2H, m), 1.99 (3H, s), 2.41 (2H, t, J=7.2 Hz), 2.83 (2H, t, J=7.2 Hz), 2.90-2.98 (2H, m), 3.25-3.45 (2H, m), 3.77 (2H, s), 4.69 (1H, s), 6.54 (1H, d, J=12.0 Hz), 7.25 (2H, d, J=9.0 Hz), 9.54 (1H, s).

Example 209

5-({1-[4-(Difluoromethoxy)-2,6-difluorophenyl]-4-hydroxypiperidin-4-yl}methoxy)-7,8-difluoro-3,4-dihydroquinolin-2(1H)-one Synthesized analogous to Example 42.
$^1$HNMR (DMSO-d6) δ ppm: 1.59-1.65 (2H, m), 1.71-1.79 (2H, m), 2.42-2.48 (2H, m), 2.84-2.93 (4H, m), 3.30-3.38 (2H, m), 3.77 (2H, s), 4.70 (1H, s), 6.74 (1H, dd, J=12.9 Hz, 6.3 Hz), 6.95-7.05 (2H, m), 7.22 (1H, s), 10.27 (1H, s).

Example 210

5-{[1-(4-Ethoxy-2,6-difluorophenyl)-4-hydroxypiperidin-4-yl]methoxy}-7,8-difluoro-3,4-dihydroquinolin-2(1H)-one Synthesized analogous to Example 42.
$^1$HNMR (DMSO-d6) δ ppm: 1.29 (3H, t, J=7.2 Hz), 1.59-1.64 (2H, m), 1.72-1.79 (2H, m), 2.44-2.48 (2H, m), 2.79-2.91 (4H, m), 3.32-3.36 (2H, m), 3.78 (2H, s), 3.98 (2H, q, J=7.2 Hz), 4.66 (1H, s), 6.65 (2H, d, J=11.4 Hz), 6.75 (1H, dd, J=12.9 Hz, 6.3 Hz), 10.28 (1H, s).

Example 211

8-Chloro-5-{[1-(4-chloro-2,5-difluorophenyl)-4-hydroxypiperidin-4-yl]methoxy}-7-fluoro-3,4-dihydroquinolin-2(1H)-one Synthesized analogous to Example 42.
$^1$HNMR (DMSO-d6) δ ppm: 1.61-1.73 (2H, m), 1.74-1.89 (2H, m), 2.41-2.53 (2H, m), 2.82-2.94 (2H, m), 2.97-3.12 (2H, m), 3.13-3.27 (2H, m), 3.84 (2H, s), 4.80 (1H, s), 6.83 (1H, d, J=11.4 Hz), 7.12 (1H, dd, J=11.4 Hz, 7.8 Hz), 7.48 (1H, dd, J=12.0 Hz, 7.2 Hz), 9.66 (1H, brs).

Example 212

8-Chloro-5-{[1-(2,4-dichloro-5-fluorophenyl)-4-hydroxypiperidin-4-yl]methoxy}-7-fluoro-3,4-dihydroquinolin-2(1H)-one Synthesized analogous to Example 42.
$^1$HNMR (DMSO-d6) δ ppm: 1.63-1.90 (4H, m), 2.42-2.53 (2H, m), 2.83-2.95 (2H, m), 2.96-3.18 (4H, m), 3.86

(2H, s), 4.79 (1H, s), 6.84 (1H, d, J=11.7 Hz), 7.25 (1H, d, J=13.8 Hz), 7.70 (1H, d, J=7.8 Hz), 9.66 (1H, brs).

Example 213

5-{[1-(4-Bromo-2-fluorophenyl)-4-hydroxypiperidin-4-yl]methoxy}-8-chloro-7-fluoro-3,4-dihydroquinolin-2(1H)-one Synthesized analogous to Example 42.
$^1$HNMR (DMSO-d6) δ ppm: 1.61-1.90 (4H, m), 2.41-2.58 (2H, m), 2.83-2.94 (2H, m), 2.97-3.21 (4H, m), 3.84 (2H, s), 4.77 (1H, s), 6.84 (1H, d, J=11.4 Hz), 6.99-7.10 (1H, m), 7.25-7.34 (1H, m), 7.35-7.46 (1H, m), 9.65 (1H, brs).

Example 214

8-Chloro-7-fluoro-5-{[4-hydroxy-1-(2,4,6-trifluorophenyl)piperidin-4-yl]methoxy}-3,4-dihydroquinolin-2(1H)-one Synthesized analogous to Example 42.
$^1$HNMR (DMSO-d6) δ ppm: 1.58-1.84 (4H, m), 2.43-2.54 (2H, m), 2.82-2.98 (4H, m), 3.25-3.40 (2H, m), 3.83 (2H, s), 4.73 (1H, s), 6.84 (1H, d, J=11.7 Hz), 7.03-7.20 (2H, m), 9.66 (1H, brs).

Example 215

7,8-Difluoro-5-({1-[2-fluoro-4-(2,2,2-trifluoroethoxy)phenyl]-4-hydroxypiperidin-4-yl}methoxy)-3,4-dihydroquinolin-2(1H)-one Synthesized analogous to Example 42.
$^1$HNMR (DMSO-d6) δ ppm: 1.64-1.69 (2H, m), 1.79-1.83 (2H, m), 2.42-2.48 (2H, m), 2.85-2.91 (2H, m), 2.96-3.02 (4H, m), 3.79 (2H, s), 4.66-4.76 (3H, m), 6.72-6.84 (2H, m), 6.94-7.19 (2H, m), 10.28 (1H, s).

Example 216

5-{[1-(4-Chloro-2-fluorophenyl)-4-hydroxypiperidin-4-yl]methoxy}-7,8-difluoro-1-methyl-3,4-dihydroquinolin-2(1H)-one To a solution of 5-{[1-(4-chloro-2-fluorophenyl)-4-hydroxypiperidin-4-yl]methoxy}-7,8-difluoro-3,4-dihydroquinolin-2(1H)-one (135 mg) in N,N-dimethylformamide-tetrahydrofuran (1:1) (2 mL) was added sodium hydride (60% in oil) (15 mg), and the reaction mixture was stirred at room temperature for 30 min, and methyl iodide (0.024 mL) was then added to the mixture, which was then stirred at room temperature. To the reaction solution was added water, and the solution was extracted with ethyl acetate, the organic layer was dried over anhydrous sodium sulfate, and then the solvent was distilled off. The residue was purified by silica gel column chromatography (basic silica gel; hexane/ethyl acetate) to provide the title compound (44 mg).
$^1$HNMR (Methanol-d4) δ ppm: 1.76-1.81 (2H, m), 1.92-2.02 (2H, m), 2.52-2.57 (2H, m), 2.89-2.94 (2H, m), 3.04-3.12 (2H, m), 3.17-3.22 (3H, m), 3.39 (3H, s), 4.07 (2H, s), 6.77 (1H, dd, J=12.3 Hz, 6.3 Hz), 7.01-7.11 (3H, m).

Example 217

8-Chloro-5-({1-[2-fluoro-4-(2,2,2-trifluoroethoxy)phenyl]-4-hydroxypiperidin-4-yl}methoxy)-3,4-dihydroquinolin-2(1H)-one Synthesized analogous to Example 42.
(Ethyl acetate/hexane) m.p. 148.6-148.7° C.
$^1$HNMR (CDCl$_3$) δ ppm: 1.87-1.89 (2H, m), 1.93-1.99 (2H, m), 1.98 (1H, brs), 2.65 (2H, t, J=7.5 Hz), 3.03 (2H, t, J=7.5 Hz), 3.06-3.11 (2H, m), 3.18-3.20 (2H, m), 3.88 (2H, s), 4.28-4.33 (2H, m), 6.55 (1H, d, J=9.0 Hz), 6.66-6.69 (1H, m), 6.73 (1H, dd, J=13.0 Hz, 3.0 Hz), 6.99 (1H, t, J=9.0 Hz), 7.20 (1H, t, J=9.0 Hz), 7.75 (1H, brs).

Example 218

5-{[1-(4-Bromo-2-fluorophenyl)-4-hydroxypiperidin-4-yl]methoxy}-8-chloro-3,4-dihydroquinolin-2(1H)-one Synthesized analogous to Example 42.
(Ethyl acetate/methanol) m.p. 223.1-223.2° C. $^1$HNMR (DMSO-d6) δ ppm: 1.65-1.67 (2H, m), 1.81-1.86 (2H, m), 2.46 (2H, t, J=7.5 Hz), 2.91 (2H, t, J=7.5 Hz), 2.99-3.04 (2H, m), 3.12-3.14 (2H, m), 3.79 (2H, s), 4.76 (1H, brs), 6.67 (1H, d, J=9.0 Hz), 7.03 (1H, t, J=8.5 Hz), 7.22 (1H, d, J=9.0 Hz), 7.27 (1H, dd, J=8.5 Hz, 2.0 Hz), 7.39 (1H, dd, J=12.0 Hz, 2.0 Hz), 9.35 (1H, brs).

Example 219

5-{[1-(4-Bromo-2,6-difluorophenyl)-4-hydroxypiperidin-4-yl]methoxy}-8-fluoro-3,4-dihydroquinolin-2(1H)-one Synthesized analogous to Example 42.
(Ethyl acetate/methanol) m.p. 217.7-217.9° C.
$^1$HNMR (CDCl$_3$) δ ppm: 1.80-1.83 (2H, m), 1.85-1.91 (2H, m), 2.02 (1H, brs), 2.66 (2H, t, J=7.5 Hz), 3.02 (2H, t, J=7.5 Hz), 3.08-3.10 (2H, m), 3.45-3.49 (2H, m), 3.85 (2H, s), 6.48 (1H, dd, J=9.0 Hz, 4.0 Hz), 6.93 (1H, t, J=9.0 Hz), 7.00-7.05 (2H, m), 7.53 (1H, brs).

Example 220

5-{[1-(4-Bromo-2,6-difluorophenyl)-4-hydroxypiperidin-4-yl]methoxy}-8-chloro-3,4-dihydroquinolin-2(1H)-one Synthesized analogous to Example 42.
(Ethyl acetate/methanol) m.p. 195.3-195.4° C.
$^1$HNMR (CDCl$_3$) δ ppm: 1.80-1.83 (2H, m), 1.86-1.92 (2H, m), 2.00 (1H, brs), 2.64 (2H, t, J=7.5 Hz), 3.02 (2H, t, J=7.5 Hz), 3.08-3.10 (2H, m), 3.45-3.49 (2H, m), 3.87 (2H, s), 6.55 (1H, d, J=9.0 Hz), 7.00-7.05 (2H, m), 7.19 (1H, d, J=9.0 Hz), 7.75 (1H, brs).

Example 221

5-[(1-{4-Chloro-2-fluoro-5-[2-(4-fluorophenoxy)ethyl]phenyl}-4-hydroxypiperidin-4-yl)methoxy]-8-fluoro-3,4-dihydroquinolin-2(1H)-one Synthesized analogous to Example 42.
(Ethyl acetate/hexane) m.p. 156.0-156.1° C.
$^1$HNMR (CDCl$_3$) δ ppm: 1.86-1.88 (2H, m), 1.91-1.97 (2H, m), 2.01 (1H, brs), 2.66 (2H, t, J=7.5 Hz), 3.02 (2H, t, J=7.5 Hz), 3.08-3.15 (4H, m), 3.24-3.26 (2H, m), 3.85 (2H, s), 4.11-4.14 (2H, m), 6.48 (1H, dd, J=9.0 Hz, 4.0 Hz), 6.81-6.83 (2H, m), 6.91-6.97 (4H, m), 7.08 (1H, d, J=12.0 Hz), 7.52 (1H, brs).

Example 222

5-{[1-(5-Ethyl-2,4-difluorophenyl)-4-hydroxypiperidin-4-yl]methoxy}-8-fluoro-3,4-dihydroquinolin-2(1H)-one Synthesized analogous to Example 42.
(Ethyl acetate) m.p. 186.7-186.8° C.
$^1$HNMR (CDCl$_3$) δ ppm: 1.21 (3H, t, J=7.5 Hz), 1.87-1.89 (2H, m), 1.93-1.99 (2H, m), 2.01 (1H, brs), 2.61 (2H, q, J=7.5 Hz), 2.66 (2H, t, J=7.5 Hz), 3.03 (2H, t, J=7.5 Hz), 3.07-3.12 (2H, m), 3.18-3.20 (2H, m), 3.86 (2H, s), 6.49 (1H, dd, J=9.0 Hz, 4.0 Hz), 6.76 (1H, dd, J=12.0 Hz, 9.5 Hz), 6.84 (1H, dd, J=9.0 Hz, 8.0 Hz), 6.93 (1H, t, J=9.0 Hz), 7.54 (1H, brs).

Example 223

5-{[1-(2,4-Difluoro-5-propylphenyl)-4-hydroxypiperidin-4-yl]methoxy}-8-fluoro-3,4-dihydroquinolin-2(1H)-one Synthesized analogous to Example 42.
(Ethyl acetate/methanol) m.p. 184.7-184.8° C.
$^1$HNMR (CDCl$_3$) δ ppm: 0.95 (3H, t, J=7.0 Hz), 1.56-1.64 (2H, m), 1.86-1.89 (2H, m), 1.93-1.99 (2H, m), 2.02 (1H, brs), 2.55 (2H, t, J=7.5 Hz), 2.66 (2H, t, J=7.5 Hz), 3.03 (2H, t, J=7.5 Hz), 3.06-3.12 (2H, m), 3.17-3.20 (2H, m), 3.86 (2H, s), 6.49 (1H, dd, J=9.0 Hz, 4.0 Hz), 6.76 (1H, dd, J=12.0 Hz, 9.5 Hz), 6.82 (1H, dd, J=9.5 Hz, 8.0 Hz), 6.93 (1H, t, J=9.0 Hz), 7.55 (1H, brs).

Example 224

8-Chloro-5-{[1-(2,4-difluoro-5-propylphenyl)-4-hydroxypiperidin-4-yl]methoxy}-3,4-dihydroquinolin-2(1H)-one Synthesized analogous to Example 42.
(Ethyl acetate/hexane) m.p. 156.9-157.0° C.
$^1$HNMR (CDCl$_3$) δ ppm: 0.94 (3H, t, J=7.0 Hz), 1.54-1.64 (2H, m), 1.86-1.89 (2H, m), 1.93-1.99 (2H, m), 1.98 (1H, brs), 2.55 (2H, t, J=7.5 Hz), 2.65 (2H, t, J=7.5 Hz), 3.03 (2H, t, J=7.5 Hz), 3.06-3.12 (2H, m), 3.17-3.20 (2H, m), 3.88 (2H, s), 6.55 (1H, d, J=9.0 Hz), 6.76 (1H, dd, J=11.5 Hz, 9.5 Hz), 6.81 (1H, dd, J=9.5 Hz, 8.0 Hz), 7.20 (1H, d, J=9.0 Hz), 7.75 (1H, brs).

Example 225

8-Chloro-5-{[1-(5-ethyl-2,4-difluorophenyl)-4-hydroxypiperidin-4-yl]methoxy}-3,4-dihydroquinolin-2(1H)-one Synthesized analogous to Example 42.
(Ethyl acetate) m.p. 178.8-178.9° C.
$^1$HNMR (CDCl$_3$) δ ppm: 1.21 (3H, t, J=7.5 Hz), 1.86-1.89 (2H, m), 1.93-1.99 (2H, m), 1.99 (1H, brs), 2.61 (2H, q, J=7.5 Hz), 2.65 (2H, t, J=7.5 Hz), 3.03 (2H, t, J=7.5 Hz), 3.07-3.12 (2H, m), 3.18-3.20 (2H, m), 3.88 (2H, s), 6.55 (1H, d, J=9.0 Hz), 6.76 (1H, dd, J=11.5 Hz, 9.5 Hz), 6.84 (1H, dd, J=9.0 Hz, 8.0 Hz), 7.20 (1H, t, J=9.0 Hz), 7.75 (1H, brs).

Example 226

8-Chloro-5-({1-[4-(ethylsulfanyl)-2,6-difluorophenyl]-4-hydroxypiperidin-4-yl}methoxy)-3,4-dihydroquinolin-2(1H)-one Synthesized analogous to Example 42.
(Ethyl acetate/hexane) m.p. 157.4-157.5° C.
$^1$HNMR (CDCl$_3$) δ ppm: 1.32 (3H, t, J=7.5 Hz), 1.80-1.83 (2H, m), 1.87-1.93 (2H, m), 1.99 (1H, brs), 2.64 (2H, t, J=7.5 Hz), 2.90 (2H, q, J=7.5 Hz), 3.02 (2H, t, J=7.5 Hz), 3.08-3.10 (2H, m), 3.44-3.49 (2H, m), 3.87 (2H, s), 6.55 (1H, d, J=9.0 Hz), 6.78-6.84 (2H, m), 7.19 (1H, d, J=9.0 Hz), 7.75 (1H, brs).

Example 227

8-Fluoro-5-{[1-(2-fluoro-4-{[5-(trifluoromethyl)pyridin-2-yl]methoxy}phenyl)-4-hydroxypiperidin-4-yl]methoxy}-3,4-dihydroquinolin-2(1H)-one Synthesized analogous to Example 148.
(Ethyl acetate) m.p. 194.9-195.1° C.
$^1$HNMR (CDCl$_3$) δ ppm: 1.86-1.89 (2H, m), 1.93-1.99 (2H, m), 2.01 (1H, brs), 2.66 (2H, t, J=7.5 Hz), 3.03 (2H, t, J=7.5 Hz), 3.05-3.11 (2H, m), 3.16-3.19 (2H, m), 3.85 (2H, s), 5.22 (2H, s), 6.49 (1H, dd, J=9.0 Hz, 4.0 Hz), 6.68-6.71 (1H, m), 6.76 (1H, dd, J=13.5 Hz, 2.5 Hz), 6.93 (1H, t, J=9.0 Hz), 6.98 (1H, t, J=9.0 Hz), 7.53 (1H, d, J=2.0 Hz), 7.66 (1H, d, J=8.5 Hz), 7.96 (1H, dd, J=8.5 Hz, 2.0 Hz), 8.86 (1H, brs).

Example 228

5-({1-[2,6-Difluoro-4-(2,2,2-trifluoroethoxy)phenyl]-4-hydroxypiperidin-4-yl}methoxy)-8-fluoro-3,4-dihydroquinolin-2(1H)-one Synthesized analogous to Example 42.
(Ethyl acetate/hexane) m.p. 189.8-189.9° C.
$^1$HNMR (CDCl$_3$) δ ppm: 1.81-1.83 (2H, m), 1.87-1.92 (2H, m), 2.03 (1H, brs), 2.66 (2H, t, J=7.5 Hz), 2.98-3.02 (2H, m), 3.02 (2H, t, J=7.5 Hz), 3.42-3.47 (2H, m), 3.85 (2H, s), 4.26-4.31 (2H, m), 6.46-6.52 (3H, m), 6.93 (1H, t, J=9.0 Hz), 7.52 (1H, brs).

Example 229

8-Chloro-5-({1-[2,6-difluoro-4-(2,2,2-trifluoroethoxy)phenyl]-4-hydroxypiperidin-4-yl}methoxy)-3,4-dihydroquinolin-2(1H)-one Synthesized analogous to Example 42.
(Ethyl acetate/hexane) m.p. 178.6-178.7° C.
$^1$HNMR (CDCl$_3$) δ ppm: 1.81-1.83 (2H, m), 1.87-1.93 (2H, m), 2.01 (1H, brs), 2.64 (2H, t, J=7.5 Hz), 2.98-3.02 (2H, m), 3.02 (2H, t, J=7.5 Hz), 3.42-3.47 (2H, m), 3.87 (2H, s), 4.26-4.31 (2H, m), 6.46-6.52 (2H, m), 6.55 (1H, d, J=9.0 Hz), 7.19 (1H, d, J=9.0 Hz), 7.75 (1H, brs).

Example 230

8-Chloro-5-({1-[4-chloro-2-fluoro-5-(2-methoxyethyl)phenyl]-4-hydroxypiperidin-4-yl}methoxy)-3,4-dihydroquinolin-2(1H)-one Synthesized analogous to Example 42.
$^1$HNMR (CDCl$_3$) δ ppm: 1.86-1.89 (2H, m), 1.92-1.98 (2H, m), 1.99 (1H, brs), 2.65 (2H, t, J=7.5 Hz), 2.95 (2H, t, J=7.0 Hz), 3.02 (2H, t, J=7.5 Hz), 3.09-3.14 (2H, m), 3.24-3.26 (2H, m), 3.37 (3H, s), 3.58 (2H, t, J=7.0 Hz), 3.88 (2H, s), 6.55 (1H, d, J=9.0 Hz), 6.90 (1H, d, J=9.0 Hz), 7.05 (1H, d, J=11.5 Hz), 7.20 (1H, d, J=9.0 Hz), 7.75 (1H, brs).

Example 231

8-Chloro-7-fluoro-5-{[4-hydroxy-1-(2,2,6-trifluoro-1,3-benzodioxol-5-yl)piperidin-4-yl]methoxy}-3,4-dihydroquinolin-2(1H)-one Synthesized analogous to Example 42.
(Ethyl acetate/methanol) m.p. 249.4-250.5° C. (dec)
$^1$HNMR (DMSO-d6) δ ppm: 1.68-1.70 (2H, m), 1.80-1.86 (2H, m), 2.48 (2H, t, J=7.5 Hz), 2.90 (2H, t, J=7.5 Hz), 2.99-3.08 (4H, m), 3.84 (2H, s), 4.83 (1H, brs), 6.84 (1H, d, J=11.5 Hz), 7.28 (1H, d, J=7.5 Hz), 7.47 (1H, d, J=10.5 Hz), 9.67 (1H, brs).

Example 232

7,8-Difluoro-5-{[4-hydroxy-1-(2,2,6-trifluoro-1,3-benzodioxol-5-yl)piperidin-4-yl]methoxy}-3,4-dihydroquinolin-2(1H)-one Synthesized analogous to Example 42.
White powder (Acetic acid/water) (5:2) m.p. 258.9-259.0° C. (dec)
$^1$HNMR (DMSO-d6) δ ppm: 1.67-1.69 (2H, m), 1.80-1.86 (2H, m), 2.47 (2H, t, J=7.5 Hz), 2.88 (2H, t, J=7.5 Hz), 2.99-3.07 (4H, m), 3.80 (2H, s), 4.81 (1H, brs), 6.74 (1H, dd, J=12.5 Hz, 6.0 Hz), 7.27 (1H, d, J=7.5 Hz), 7.47 (1H, d, J=11.0 Hz), 10.30 (1H, brs).

Example 233

5-{[1-(4-Bromo-2,6-difluorophenyl)-4-hydroxypiperidin-4-yl]methoxy}-8-chloro-7-fluoro-3,4-dihydroquinolin-2(1H)-one Synthesized analogous to Example 42.
(Ethyl acetate) m.p. 200.5-200.8° C.
$^1$HNMR (CDCl$_3$) δ ppm: 1.79-1.82 (2H, m), 1.86-1.92 (2H, m), 1.94 (1H, brs), 2.64 (2H, t, J=7.5 Hz), 2.98 (2H, t, J=7.5 Hz), 3.08-3.10 (2H, m), 3.44-3.49 (2H, m), 3.85 (2H, s), 6.46 (1H, d, J=10.5 Hz), 7.00-7.06 (2H, m), 7.76 (1H, brs).

Example 234

5-{[1-(4-Bromo-2,6-difluorophenyl)-4-hydroxypiperidin-4-yl]methoxy}-7,8-difluoro-3,4-dihydroquinolin-2(1H)-one Synthesized analogous to Example 42.
(Ethyl acetate/methanol) m.p. 233.1-233.2° C.
$^1$HNMR (CDCl$_3$) δ ppm: 1.79-1.82 (2H, m), 1.85-1.91 (2H, m), 1.96 (1H, brs), 2.65 (2H, t, J=7.5 Hz), 2.97 (2H, t, J=7.5 Hz), 3.08-3.10 (2H, m), 3.44-3.49 (2H, m), 3.81 (2H, s), 6.41 (1H, dd, J=12.0 Hz, 6.5 Hz), 7.00-7.06 (2H, m), 7.58 (1H, brs).

Example 235

5-{[1-(4-Chloro-2-fluorophenyl)-4-hydroxypiperidin-4-yl]methoxy}-7-fluoro-8-methyl-3,4-dihydroquinolin-2(1H)-one Synthesized analogous to Example 42.
$^1$HNMR (DMSO-d6) δ ppm: 1.64-1.72 (2H, m), 1.79-1.87 (2H, m), 2.04 (3H, d, J=1.5 Hz), 2.43 (2H, t, J=7.2 Hz), 2.83 (2H, t, J=7.2 Hz), 2.98-3.06 (2H, m), 3.11-3.20 (2H, m), 3.77 (2H, s), 4.72 (1H, s), 6.54 (1H, d, J=12.0 Hz), 7.05-7.18 (2H, m), 7.30 (1H, dd, J=12.0 Hz, 2.4 Hz), 9.56 (1H, s).

Example 236

5-{[1-(4-Chloro-2,5-difluorophenyl)-4-hydroxypiperidin-4-yl]methoxy}-7-fluoro-8-methyl-3,4-dihydroquinolin-2(1H)-one Synthesized analogous to Example 42.
$^1$HNMR (DMSO-d6) δ ppm: 1.60-1.74 (2H, m), 1.78-1.83 (2H, m), 2.04 (3H, d, J=2.9 Hz), 2.40 (2H, t, J=7.2 Hz), 2.82 (2H, t, J=7.2 Hz), 3.04-3.08 (2H, m), 3.17-3.23 (2H, m), 3.77 (2H, s), 4.71 (1H, s), 6.54 (1H, d, J=12.0 Hz), 7.12 (1H, dd, J=9.0 Hz, 7.8 Hz), 7.48 (1H, dd, J=12.0 Hz, 7.2 Hz), 9.56 (1H, s).

Example 237

5-({1-[2,6-Difluoro-4-(2,2,2-trifluoroethoxy)phenyl]-4-hydroxypiperidin-4-yl}methoxy)-7,8-difluoro-3,4-dihydroquinolin-2(1H)-one Synthesized analogous to Example 42.
$^1$HNMR (CDCl$_3$) δ ppm: 1.79-1.82 (2H, m), 1.86-1.92 (2H, m), 1.96 (1H, brs), 2.65 (2H, t, J=7.5 Hz), 2.98 (2H, t, J=7.5 Hz), 2.99-3.02 (2H, m), 3.42-3.46 (2H, m), 3.81 (2H, s), 4.26-4.31 (2H, m), 6.41 (1H, dd, J=11.5 Hz, 6.0 Hz), 6.47-6.52 (2H, m), 7.56 (1H, brs).

Example 238

8-Chloro-5-({1-[2,6-difluoro-4-(2,2,2-trifluoroethoxy)phenyl]-4-hydroxypiperidin-4-yl}methoxy)-7-fluoro-3,4-dihydroquinolin-2(1H)-one Synthesized analogous to Example 42.
$^1$HNMR (CDCl$_3$) δ ppm: 1.80-1.82 (2H, m), 1.87-1.93 (2H, m), 1.96 (1H, brs), 2.64 (2H, t, J=7.5 Hz), 2.98 (2H, t, J=7.5 Hz), 3.00-3.02 (2H, m), 3.42-3.46 (2H, m), 3.85 (2H, s), 4.26-4.31 (2H, m), 6.47 (1H, d, J=10.5 Hz), 6.47-6.52 (2H, m), 7.77 (1H, brs).

Example 239

5-{[1-(4-Chloro-2-fluorophenyl)-4-hydroxypiperidin-4-yl]methoxy}-8-ethyl-7-fluoro-3,4-dihydroquinolin-2(1H)-one Synthesized analogous to Example 42.
¹HNMR (DMSO-d6) δ ppm: 0.98 (3H, t, J=7.5 Hz), 1.66 (2H, m), 1.79-1.88 (2H, m), 2.37-2.43 (2H, m), 2.59-2.62 (2H, m), 2.82 (2H, t, J=7.5 Hz), 3.01-3.06 (2H, m), 3.11-3.13 (2H, m), 3.77 (2H, s), 4.71 (12H, s), 6.53 (1H, d, J=12.0 Hz), 7.08-7.15 (2H, m), 7.29 (1H, dd, J=12.0 Hz, 2.4 Hz), 9.58 (1H, s).

Example 240

5-{[1-(4-Chloro-2-fluorophenyl)-4-hydroxypiperidin-4-yl]methoxy}-8-fluoro-7-hydroxy-3,4-dihydroquinolin-2(1H)-one To a mixture of 5-{[1-(4-chloro-2-fluorophenyl)-4-hydroxypiperidin-4-yl]methoxy}-8-fluoro-1-(4-methoxybenzyl)-7-(tetrahydro-2H-pyran-2-yloxy)-3,4-dihydroquinolin-2(1H)-one (350 mg) and anisole (0.12 mL) was added trifluoroacetic acid (10 mL), the reaction mixture was stirred at 60° C. for 30 min, and the reaction solution was concentrated. To the residue was added water, and the precipitate was collected on a filter. The product was crystallized from methanol, the obtained crystal was collected on a filter, and air-dried (60° C.) to provide the title compound (160 mg).
¹HNMR (DMSO-d6) δ ppm: 1.58-1.70 (2H, m), 1.80-1.87 (2H, m), 2.41 (2H, t, J=6.9 Hz), 2.82 (2H, t, J=7.8 Hz), 2.98-3.05 (2H, m), 3.10-3.15 (2H, m), 3.72 (2H, s), 4.68 (1H, s), 6.53 (1H, d, J=12.0 Hz), 7.05-7.18 (2H, m), 7.30 (1H, dd, J=12.0 Hz, 2.4 Hz), 9.6910 (12H, brs), 9.89 (1H, s).

Example 241

8-Bromo-5-{[1-(4-chloro-2,6-difluorophenyl)-4-hydroxypiperidin-4-yl]methoxy}-7-fluoro-3,4-dihydroquinolin-2(1H)-one To a suspension of 5-{[1-(4-chloro-2,6-difluorophenyl)-4-hydroxypiperidin-4-yl]methoxy}-7-fluoro-3,4-dihydroquinolin-2(1H)-one (400 mg) in acetic acid (10 mL) was added bromine (0.049 mL), and the reaction mixture was stirred at 50° C. for 40 min. The solvent was distilled off, the residue was purified by silica gel column chromatography (basic silica gel; dichloromethane), and washed with acetonitrile to provide the title compound (237 mg).
¹HNMR (DMSO-d6) δ ppm: 1.60-1.83 (4H, m), 2.42-2.56 (2H, m), 2.83-3.03 (4H, m), 3.27-3.42 (2H, m), 3.84 (2H, m), 4.76 (1H, brs), 6.84 (1H, d, J=11.1 Hz), 7.20-7.32 (2H, m), 9.24 (1H, brs).

Example 242

5-{[1-(4-Chloro-2,6-difluorophenyl)-4-hydroxypiperidin-4-yl]methoxy}-7-fluoro-8-iodo-3,4-dihydroquinolin-2(1H)-one To a suspension of 5-{[1-(4-chloro-2,6-difluorophenyl)-4-hydroxypiperidin-4-yl]methoxy}-7-fluoro-3,4-dihydroquinolin-2(1H)-one (1.0 g) in acetic acid (25 mL) was added N-iodosuccinimide (0.536 g), and the reaction mixture was stirred at 60° C. for 1 h. The solvent was distilled off, the residue was purified by silica gel column chromatography (basic silica gel/dichloromethane), and washed with acetonitrile to provide the title compound (382 mg).
¹HNMR (DMSO-d6) δ ppm: 1.59-1.83 (4H, m), 2.42-2.53 (2H, m), 2.83-3.03 (4H, m), 3.25-3.41 (2H, m), 3.84 (2H, s), 4.76 (1H, s), 6.78 (1H, d, J=10.5 Hz), 7.20-7.32 (2H, m), 8.58 (1H, brs).

Example 243

5-{[1-(2,2-Difluoro-1,3-benzodioxol-5-yl)-4-hydroxypiperidin-4-yl]methoxy}-8-fluoro-3,4-dihydroquinolin-2(1H)-one Synthesized analogous to Example 42.
(Ethyl acetate/hexane) m.p. 198.4-198.5° C.
¹HNMR (CDCl₃) δ ppm: 1.86-1.93 (4H, m), 2.03 (1H, brs), 2.66 (2H, t, J=7.5 Hz), 3.02 (2H, t, J=7.5 Hz), 3.13-3.19 (2H, m), 3.34-3.37 (2H, m), 3.84 (2H, s), 6.48 (1H, dd, J=9.0 Hz, 4.0 Hz), 6.63 (1H, dd, J=9.0 Hz, 2.5 Hz), 6.75 (1H, d, J=2.5 Hz), 6.91-6.95 (2H, m), 7.54 (1H, brs).

Example 244

5-{[1-(4-Chloro-2-fluorophenyl)-4-hydroxypiperidin-4-yl]methoxy}-7-fluoro-8-hydroxy-3,4-dihydroquinolin-2(1H)-one A suspension of 5-(benzyloxy)-7-fluoro-8-(tetrahydro-2H-pyran-2-yloxy)-3,4-dihydroquinolin-2(1H)-one (290 mg), potassium carbonate (300 mg) and 20% palladium hydroxide on carbon (300 mg) in 2-propanol (9 mL) was stirred at room temperature for 1 h under hydrogen atmosphere. After insoluble materials were filtered off, the solvent was distilled off. To a residue were added 6-(4-chloro-2-fluorophenyl)-1-oxa-6-azaspiro[2.5]octane (377 mg), sodium hydroxide (156 mg) and N,N-dimethylformamide/2-propanol (1:1) (10 mL), and the reaction mixture was stirred at 70° C. for 7 h. To the reaction solution was added water, and the solution was extracted with ethyl acetate. The organic layer was washed with brine, dried over anhydrous sodium sulfate, and the solvent was distilled off. The residue was purified by silica gel column chromatography (basic silica gel; hexane/ethyl acetate→ethyl acetate) to give 5-{[1-(4-chloro-2-fluorophenyl)-4-hydroxypiperidin-4-yl]methoxy}-7-fluoro-8-(tetrahydro-2H-pyran-2-yloxy)-3,4-dihydroquinolin-2(1H)-one (110 mg). The obtained product was dissolved into trifluoroacetic acid (1 mL), the solution was stirred at room temperature for 3 min and the reaction solution was concentrated. Water was added to the residue, the precipitate was collected on a filter and washed with ethanol to provide the title compound (80 mg).
¹HNMR (DMSO-d6) δ ppm: 1.62-1.7568 (2H, m), 1.79-1.86 (2H, m), 2.41 (2H, m), 2.82 (2H, m), 2.97-3.16 (4H, m), 3.71 (2H, s), 6.53 (1H, d, J=12.0 Hz), 7.05-7.18 (2H, m), 7.30 (1H, dd, J=12.0 Hz, 2.4 Hz), 9.11 (2H, s).

Example 245

8-Fluoro-5-{[4-hydroxy-1-(1-methyl-1H-benzimidazol-2-yl)piperidin-4-yl]methoxy}-3,4-dihydroquinolin-2(1H)-one A solution of 8-fluoro-5-[(4-hydroxypiperidin-4-yl)methoxy]-3,4-dihydroquinolin-2(1H)-one (0.25 g), 2-chloro-1-methyl-1H-benzimidazole (0.156 g) and triethylamine (0.355 mL) in N-methyl-2-pyrrolidone (NMP) (0.3 mL) was stirred at 95° C. for 48 h. To the reaction solution were added water and ethyl acetate, and the insoluble precipitate was collected on a filter. The obtained solid was purified by silica gel column chromatography (basic silica gel; dichloromethane/methanol) and recrystallized from ethanol/water. The precipitate was collected on a filter, and air-dried (60° C.) to provide the title compound (0.14 g).

(Ethanol/water) m.p. 229-230° C.

$^1$HNMR (DMSO-d6) δ ppm: 1.65-1.72 (2H, m), 1.89-2.00 (2H, m), 2.44 (2H, t, J=7.6 Hz), 2.91 (2H, t, J=7.6 Hz), 3.24-3.36 (2H, m), 3.37-3.45 (2H, m), 3.60 (3H, s), 3.80 (2H, s), 4.80 (1H, s), 6.60 (1H, dd, J=9.1 Hz, 3.8 Hz), 7.01 (1H, t, J=9.7 Hz), 7.05-7.11 (2H, m), 7.29-7.34 (1H, m), 7.37-7.42 (1H, m), 10.02 (1H, s).

Example 246

5-{[1-(1,3-Benzoxazol-2-yl)-4-hydroxypiperidin-4-yl]methoxy}-8-fluoro-3,4-dihydroquinolin-2(1H)-one A solution of 8-fluoro-5-[(4-hydroxypiperidin-4-yl)methoxy]-3,4-dihydroquinolin-2(1H)-one (0.25 g), 2-chlorobenzoxazole (0.107 mL) and potassium carbonate (0.141 g) in N,N-dimethylformamide (3 mL) was stirred at room temperature for 24 h. To a solution were added water and ethyl acetate, and the insoluble precipitate was collected on a filter. The obtained solid was purified by silica gel column chromatography (dichloromethane/methanol), and recrystallized from ethanol/water. The precipitate was collected on a filter and dried under reduced pressure (100° C.) to provide the title compound (0.22 g).

(Ethanol/water) m.p. 207-208° C.

$^1$HNMR (DMSO-d6) δ ppm: 1.66-1.73 (2H, m), 1.74-1.84 (2H, m), 2.40 (2H, t, J=7.6 Hz), 2.86 (2H, t, J=7.6 Hz), 3.41-3.50 (2H, m), 3.78 (2H, s), 3.97-4.04 (2H, m), 4.93 (1H, s), 6.57 (1H, dd, J=9.1 Hz, 3.8 Hz), 6.97-7.04 (2H, m), 7.14 (1H, dt, J=1.1 Hz, 7.7 Hz), 7.27 (1H, d, J=7.1 Hz), 7.39 (1H, d, J=7.8 Hz), 10.01 (1H, s).

Example 247

5-{[1-(6-Chloro-1,3-benzoxazol-2-yl)-4-hydroxypiperidin-4-yl]methoxy}-8-fluoro-3,4-dihydroquinolin-2(1H)-one Synthesized analogous to Example 246.
(Acetic acid/water) m.p. 249-250° C.

$^1$HNMR (DMSO-d6) δ ppm: 1.65-1.74 (2H, m), 1.74-1.83 (2H, m), 2.41 (2H, t, J=7.6 Hz), 2.87 (2H, t, J=7.6 Hz), 3.41-3.51 (2H, m), 3.78 (2H, s), 3.95-4.04 (2H, m), 4.94 (1H, s), 6.57 (1H, dd, J=9.1 Hz, 3.8 Hz), 7.00 (1H, t, J=9.7 Hz), 7.19 (1H, dd, J=8.3 Hz, 2.0 Hz), 7.26 (1H, d, J=8.3 Hz), 7.56 (1H, d, J=2.0 Hz), 10.01 (1H, s).

Example 248

5-{[1-(2-Bromo-4-chloro-6-fluorophenyl)-4-hydroxypiperidin-4-yl]methoxy}-8-fluoro-3,4-dihydroquinolin-2(1H)-one Synthesized analogous to Example 42.

$^1$HNMR (DMSO-d6) δ ppm: 1.63 (2H, d, J=12.4 Hz), 1.82-1.88 (2H, m), 2.46 (2H, t, J=7.7 Hz), 2.88-2.95 (4H, m), 3.38 (2H, t, J=11.7 Hz), 3.77 (2H, s), 4.71 (1H, s), 6.59 (1H, dd, J=9.1 Hz, 3.0 Hz), 7.01 (1H, t, J=11.1 Hz), 7.48 (1H, dd, J=11.9 Hz, 2.4 Hz), 7.61 (1H, m), 10.02 (1H, s).

Example 249

5-{[(3S*,4S*)-1-(3,5-Dichloropyridin-2-yl)-3,4-dihydroxypiperidin-4-yl]methoxy}-8-fluoro-3,4-dihydroquinolin-2(1H)-one Synthesized analogous to Example 33.
(2-Propanol) m.p. 202.6-204.8° C.

$^1$HNMR (DMSO-d6) δ ppm: 1.67-1.75 (1H, m), 1.88-1.99 (1H, m), 2.44 (2H, t, J=7.7 Hz), 2.77-2.90 (2H, m), 2.93-3.05 (1H, m), 3.07-3.16 (1H, m), 3.53-3.64 (2H, m), 3.68 (1H, d, J=8.8 Hz), 3.76-3.84 (1H, m), 4.01 (1H, d, J=8.8 Hz), 4.55 (1H, brs), 4.92 (1H, d, J=6.4 Hz), 6.57 (1H, dd, J=9.2 Hz, 3.8 Hz), 7.01 (1H, t, J=9.4 Hz), 8.02 (1H, d, J=2.4 Hz), 8.26 (1H, d, J=2.4 Hz), 10.00 (1H, brs).

Example 250

5-{[(3S*,4S*)-1-(2,4-Dichlorophenyl)-3,4-dihydroxypiperidin-4-yl]methoxy}-8-fluoro-3,4-dihydroquinolin-2(1H)-one To a mixture of 5-{[(3S*,4S*)-1-(2,4-dichlorophenyl)-3,4-dihydroxypiperidin-4-yl]methoxy}-8-fluoro-1-(4-methoxybenzyl)-3,4-dihydroquinolin-2(1H)-one (40 mg) and anisole (0.05 mL) was added trifluoroacetic acid (5 mL), the reaction mixture was stirred at 60° C. for 3 h, and the reaction solution was concentrated. The residue was dissolved into methanol, neutralized with aqueous sodium hydroxide, methanol was distilled off and insoluble precipitate was collected on a filter. The obtained solid was purified by silica gel column chromatography (dichloromethane/ethyl acetate→dichloromethane/methanol), and the obtained product was washed with dichloromethane/hexane to provide the title compound (14 mg).

$^1$HNMR (DMSO-d6) δ ppm: 1.71-1.79 (1H, m), 1.90-2.01 (1H, m), 2.47 (2H, t, J=7.7 Hz), 2.78-2.85 (1H, m), 2.86-2.95 (2H, m), 2.95-3.04 (2H, m), 3.07-3.14 (1H, m), 3.71 (1H, d, J=8.9 Hz), 3.77-3.85 (1H, m), 4.02 (1H, d, J=8.9 Hz), 4.52 (1H, brs), 4.91 (1H, d, J=6.4 Hz), 6.58 (1H, dd, J=9.1 Hz, 3.8 Hz), 7.02 (1H, t, J=9.6 Hz), 7.18 (1H, d, J=8.6 Hz), 7.35 (1H, dd, J=8.6 Hz, 2.4 Hz), 7.54 (1H, d, J=2.4 Hz), 10.01 (1H, brs).

Example 251

5-{[(3R,4R)-1-(3,5-Dichloropyridin-2-yl)-3,4-dihydroxypiperidin-4-yl]methoxy}-8-fluoro-3,4-dihydroquinolin-2(1H)-one Synthesized analogous to Example 33.

$^1$HNMR (DMSO-d6) δ ppm: 1.70-1.73 (1H, m), 1.90-1.97 (1H, m), 2.44 (2H, t, J=7.7 Hz), 2.80-2.87 (2H, m), 2.97 (1H, t, J=11.3 Hz), 3.11 (1H, dt, J=2.3 Hz, 12.6 Hz), 3.55-3.62 (2H, m), 3.68 (1H, d, J=8.8 Hz), 3.78-3.82 (1H, m), 4.02 (1H, d, J=8.9 Hz), 4.57 (1H, s), 4.94 (1H, d, J=6.4 Hz), 6.57 (1H, dd, J=9.1 Hz, 3.8 Hz), 7.01 (1H, t, J=9.7 Hz), 8.02 (1H, d, J=2.3 Hz), 8.26 (1H, d, J=2.3 Hz), 10.02 (1H, s).

Example 252

5-{[(3S,4S)-1-(3,5-Dichloropyridin-2-yl)-3,4-dihydroxypiperidin-4-yl]methoxy}-8-fluoro-3,4-dihydroquinolin-2(1H)-one Synthesized analogous to Example 33.
$^1$HNMR (DMSO-d6) δ ppm: 1.70-1.73 (1H, m), 1.90-1.97 (1H, m), 2.44 (2H, t, J=7.7 Hz), 2.80-2.87 (2H, m), 2.97 (1H, t, J=11.3 Hz), 3.11 (1H, dt, J=2.3 Hz, 12.6 Hz), 3.55-3.62 (2H, m), 3.68 (1H, d, J=8.8 Hz), 3.78-3.82 (1H, m), 4.02 (1H, d, J=8.9 Hz), 4.57 (1H, s), 4.94 (1H, d, J=6.4 Hz), 6.57 (1H, dd, J=9.1 Hz, 3.8 Hz), 7.01 (1H, t, J=9.7 Hz), 8.02 (1H, d, J=2.3 Hz), 8.26 (1H, d, J=2.3 Hz), 10.02 (1H, s).

Example 253

5-{[(3S*,4S*)-1-(4-Chloro-2-fluorophenyl)-3,4-dihydroxypiperidin-4-yl]methoxy}-8-fluoro-3,4-dihydroquinolin-2(1H)-one Synthesized analogous to Example 250.
(2-Propanol) m.p. 191.9-193.5° C.
$^1$HNMR (DMSO-d6) δ ppm: 1.69-1.78 (1H, m), 1.88-2.00 (1H, m), 2.46 (2H, t, J=7.5 Hz), 2.80-2.92 (3H, m), 2.93-3.03 (1H, m), 3.05-3.21 (2H, m), 3.68 (1H, d, J=8.8 Hz), 3.74-3.84 (1H, m), 4.02 (1H, d, J=8.8 Hz), 4.55 (1H, brs), 4.90-4.95 (1H, m), 6.57 (1H, dd, J=9.1 Hz, 3.8 Hz), 7.02 (1H, t, J=9.5 Hz), 7.08 (1H, t, J=9.5 Hz), 7.17 (1H, dd, J=8.6 Hz, 2.0 Hz), 7.32 (1H, d, J=12.5 Hz, 2.4 Hz), 10.01 (1H, brs).

Example 254

2-[(3R,4R)-4-{[(8-Fluoro-2-oxo-1,2,3,4-tetrahydroquinolin-5-yl)oxy]methyl}-3,4-dihydroxypiperidin-1-yl]-5-iodopyridine-3-carbonitrile Synthesized analogous to Example 6.
$^1$HNMR (CDCl$_3$) δ ppm: 1.88-2.01 (2H, m), 2.63 (2H, t, J=7.8 Hz), 2.74 (1H, s), 2.79 (1H, d, J=7.8 Hz), 2.91-3.00 (2H, m), 3.30 (1H, dd, J=12.9 Hz, 10.2 Hz), 3.43-3.49 (1H, m), 3.96-4.02 (3H, m), 4.17-4.30 (2H, m), 6.49 (1H, dd, J=9.1 Hz, 3.9 Hz), 6.92 (1H, t, J=9.5 Hz), 7.56 (1H, brs), 7.98 (1H, d, J=2.3 Hz), 8.47 (1H, d, J=2.3 Hz).

Example 255

2-[(3S,4S)-4-{[(8-Fluoro-2-oxo-1,2,3,4-tetrahydroquinolin-5-yl)oxy]methyl}-3,4-dihydroxypiperidin-1-yl]-5-iodopyridine-3-carbonitrile Synthesized analogous to Example 6.
$^1$HNMR (CDCl$_3$) δ ppm: 1.88-2.01 (2H, m), 2.63 (2H, t, J=7.8 Hz), 2.74 (1H, s), 2.79 (1H, d, J=7.8 Hz), 2.91-3.00 (2H, m), 3.30 (1H, dd, J=12.9 Hz, 10.2 Hz), 3.43-3.49 (1H, m), 3.96-4.02 (3H, m), 4.17-4.30 (2H, m), 6.49 (1H, dd, J=9.1 Hz, 3.9 Hz), 6.92 (1H, t, J=9.5 Hz), 7.56 (1H, brs), 7.98 (1H, d, J=2.3 Hz), 8.47 (1H, d, J=2.3 Hz).

Example 256

5-{[(3R*,4R*)-1-(4-Chloro-2,6-difluorophenyl)-3,4-dihydroxypiperidin-4-yl]methoxy}-8-fluoro-3,4-dihydroquinolin-2(1H)-one To a solution of 5-{[1-(4-chloro-2,6-difluorophenyl)-1,2,3,6-tetrahydropyridin-4-yl]methoxy}-8-fluoro-3,4-dihydroquinolin-2(1H)-one (285 mg) in acetone-water (3:1) (3 mL) were added aqueous solution of 4% osmium tetraoxide (428 mg) and aqueous solution of 4.8 M N-methylmorpholine N-oxide (NMO) (0.28 mL) under nitrogen atmosphere, and the reaction mixture was stirred at room temperature for 18 h. To the reaction solution was added tetrahydrofuran (THF) (2 mL), and the mixture was stirred at 50° C. for 1 h. To the mixture was added saturated sodium thiosulfate aqueous solution, the mixture was stirred at room temperature for 30 min, and the precipitate was collected on a filter. The obtained solid was purified by silica gel column chromatography (ethyl acetate) and recrystallized from ethyl acetate. The precipitate was collected on a filter and dried to provide the title compound (157 mg).
(Ethyl acetate) m.p. 199-201° C.
$^1$HNMR (DMSO-d6) δ ppm: 1.69 (1H, d, J=13.0 Hz), 1.91 (1H, dt, J=4.3 Hz, 13.0 Hz), 2.45-2.50 (2H, m), 2.84-2.98 (4H, m), 3.21 (1H, t, J=10.8 Hz), 3.30-3.35 (1H, m), 3.68 (1H, d, 8.8 Hz), 3.71-3.76 (1H, m), 4.02 (1H, d, J=8.8 Hz), 4.55 (1H, s), 4.88 (1H, d, J=6.5 Hz), 6.58 (1H, dd, J=9.1 Hz, 3.7 Hz), 7.02 (1H, t, J=9.1 Hz), 7.25-7.30 (2H, m), 10.03 (1H, s).

Example 257

8-Chloro-5-{[(3S*,4S*)-1-(4-chloro-2,6-difluorophenyl)-3,4-dihydroxypiperidin-4-yl]methoxy}-3,4-dihydroquinolin-2(1H)-one To a solution of 8-chloro-5-{[1-(4-chloro-2,6-difluorophenyl)-1,2,3,6-tetrahydropyridin-4-yl]methoxy}-3,4-dihydroquinolin-2(1H)-one (415 mg) in tetrahydrofuran (8 ml)/water (2 ml) were added Osmium Oxide, Immobilized Catalyst I (content: 7%) (172 mg) and aqueous solution of 4.8 M N-methylmorpholine-N-oxide (NMO) (0.394 mL), and the reaction mixture was stirred at room temperature for 16 h, then at 50° C. for 1 h. To the reaction solution was added saturated sodium thiosulfate aqueous solution, the solution was stirred at room temperature for 30 min, and the precipitate was collected on a filter. The obtained solid was purified by silica gel column chromatography (ethyl acetate) and recrystallized from ethyl acetate. The precipitate was collected on a filter and dried to provide the title compound (145 mg).
m.p. 195-198° C.
$^1$HNMR (DMSO-d6) δ ppm: 1.70 (1H, d, J=13.0 Hz), 1.90 (1H, dt, J=4.5 Hz, 13.0 Hz), 2.47-2.51 (2H, m), 2.87-2.98 (4H, m), 3.21 (1H, t, J=10.8 Hz), 3.29-3.35 (1H, m), 3.70-3.75 (2H, m), 4.05 (1H, d, J=8.8 Hz), 4.57 (1H, s), 4.89 (1H, d, J=6.4 Hz), 6.68 (1H, d, J=9.0 Hz), 7.25 (1H, d, J=9.0 Hz), 7.27-7.30 (2H, m), 9.38 (1H, s).

Example 258

5-{[(3S*,4S*)-1-(4-Chloro-2,6-difluorophenyl)-3,4-dihydroxypiperidin-4-yl]methoxy}-7,8-difluoro-3,4-dihydroquinolin-2(1H)-one Synthesized analogous to Example 257.
(Ethyl acetate) m.p. 215-217° C.
$^1$HNMR (DMSO-d6) δ ppm: 1.69 (1H, d, J=12.9 Hz), 1.87 (1H, dt, J=4.7 Hz, 12.9 Hz), 2.45-2.50 (2H, m), 2.80-2.90 (3H, m), 2.96 (1H, dd, J=10.8 Hz, 4.7 Hz), 3.20 (1H, t, J=10.8 Hz), 3.30-3.34 (1H, m), 3.68-3.73 (2H, m), 4.02 (1H, d, J=9.5 Hz), 4.56 (1H, s), 4.89 (1H, d, J=6.4 Hz), 6.74 (1H, dd, J=12.7 Hz, 6.2 Hz), 7.25-7.31 (2H, m), 10.31 (1H, s).

Example 259

5-{[(3R,4R)-1-(4-Chloro-2-fluorophenyl)-3,4-dihydroxypiperidin-4-yl]methoxy}-8-fluoro-3,4-dihydroquinolin-2(1H)-one A solution of 5-{[(3R,4R)-3-{[tert-butyl(dimethyl) silyl]oxy}-1-(4-chloro-2-fluorophenyl)-4-hydroxypiperidin-4-yl]methoxy}-8-fluoro-1-(4-methoxybenzyl)-3,4-dihydroquinolin-2(1H)-one (1.0 g), anisole (0.1 mL) in trifluoroacetic acid (10 mL) was stirred at 60° C. for 4 h, methanol (10 mL) was added thereto and the mixture was stirred at 60° C. overnight. The reaction solution was concentrated, the residue was purified by silica gel column chromatography (dichloromethane→dichloromethane/ethyl acetate), and recrystallized from ethanol. The precipitate was collected on a filter and dried to provide the title compound (417 mg, >99% ee).

(Ethanol) m.p. 184-185° C.
$^1$HNMR (DMSO-d6) δ ppm: 1.69-1.78 (1H, m), 1.88-2.00 (1H, m), 2.46 (2H, t, J=7.6 Hz), 2.80-2.92 (3H, m), 2.93-3.03 (1H, m), 3.05-3.21 (2H, m), 3.69 (1H, d, J=8.8 Hz), 3.75-3.84 (1H, m), 4.02 (1H, d, J=8.8 Hz), 4.56 (1H, brs), 4.90-4.96 (1H, m), 6.58 (1H, dd, J=9.1 Hz, 3.8 Hz), 7.02 (1H, t, J=9.5 Hz), 7.08 (1H, t, J=9.5 Hz), 7.17 (1H, dd, J=8.6 Hz, 2.0 Hz), 7.32 (1H, d, J=12.8 Hz, 2.4 Hz), 10.01 (1H, brs).

Example 260

5-{[(3R,4R)-1-(4-Chloro-2,6-difluorophenyl)-3,4-dihydroxypiperidin-4-yl]methoxy}-8-fluoro-3,4-dihydroquinolin-2(1H)-one A solution of bis(dihydroquinidinyl)phthalazine ((DHQD)$_2$PHAL) (44.2 mg) and potassium osmate(VI) dihydrate (5.23 mg) in acetone-water (2:1) (24 mL) was stirred at room temperature for 15 min, aqueous solution of 4.8 M N-methylmorpholine-N-oxide (0.296 mL) and 5-{[1-(4-chloro-2,6-difluorophenyl)-1,2,3,6-tetrahydropyridin-4-yl]methoxy}-8-fluoro-3,4-dihydroquinolin-2(1H)-one (400 mg) were added thereto under ice-cooling, and the mixture was stirred at room temperature for 3 days. To the reaction solution was added saturated sodium sulfite aqueous solution, and the reaction mixture was stirred at room temperature for 30 min. The reaction mixture was extracted with ethyl acetate. The extract was purified by silica gel column chromatography (ethyl acetate), and the residue was recrystallized form acetic acid/water. The precipitate was collected on a filter, and dried under reduced pressure (60° C.) to provide the title compound (210 mg, >99% ee).

m.p. 193-195° C.
$^1$HNMR (DMSO-d6) δ ppm: 1.69 (1H, d, J=13.1 Hz), 1.91 (1H, dt, J=4.7 Hz, 13.1 Hz), 2.45-2.51 (2H, m), 2.86-2.91 (3H, m), 2.96 (1H, dd, J=10.7 Hz, 5.9 Hz), 3.21 (1H, t, J=10.7 Hz), 3.30-3.34 (1H, m), 3.67 (1H, d, J=8.8 Hz), 3.70-3.76 (1H, m), 4.02 (1H, d, J=8.8 Hz), 4.54 (1H, s), 4.88 (1H, d, J=6.4 Hz), 6.57 (1H, dd, J=9.2 Hz, 3.8 Hz), 7.02 (1H, t, J=9.2 Hz), 7.25-7.30 (2H, m), 10.03 (1H, s).

Example 261

5-{[(3S,4S)-1-(4-Chloro-2,6-difluorophenyl)-3,4-dihydroxypiperidin-4-yl]methoxy}-8-fluoro-3,4-dihydroquinolin-2(1H)-one By the procedures analogous to Example 260, with (DHQ)$_2$PHAL instead of (DHQD)$_2$PHAL, the title compound was obtained.

(Acetic acid) m.p. 190-193° C.
$^1$HNMR (DMSO-d6) δ ppm: 1.68 (1H, d, J=13.1 Hz), 1.90 (1H, dt, J=4.8 Hz, 13.1 Hz), 2.45-2.50 (2H, m), 2.84-2.91 (3H, m), 2.96 (1H, dd, J=10.9 Hz, 5.8 Hz), 3.21 (1H, t, J=10.9 Hz), 3.30-3.34 (1H, m), 3.67 (1H, d, 8.8 Hz), 3.72-3.74 (1H, m), 4.02 (1H, d, J=8.8 Hz), 4.55 (1H, s), 4.88 (1H, d, J=5.6 Hz), 6.57 (1H, dd, J=9.4 Hz, 3.8 Hz), 7.02 (1H, t, J=9.4 Hz), 7.25-7.31 (2H, m), 10.03 (1H, s).

Example 262

5-{[(3R*,4R*)-3,4-Dihydroxy-1-(2,2,6-trifluoro-1,3-benzodioxol-5-yl)piperidin-4-yl]methoxy}-8-fluoro-3,4-dihydroquinolin-2(1H)-one Synthesized analogous to Example 259.
(Ethanol) m.p. 197.4-197.5° C. $^1$HNMR (CDCl$_3$) δ ppm: 1.96-2.04 (2H, m), 2.53 (1H, brs), 2.65 (2H, t, J=7.5 Hz), 2.65 (1H, brs), 2.91 (1H, t, J=10.0 Hz), 2.99-3.10 (4H, m), 3.26-3.30 (1H, m), 3.99 (1H, d, J=9.0 Hz), 4.03-4.07 (1H, m), 4.04 (1H, d, J=9.0 Hz), 6.52 (1H, dd, J=9.0 Hz, 4.0 Hz), 6.82 (1H, d, J=7.0 Hz), 6.87 (1H, d, J=10.0 Hz), 6.94 (1H, t, J=9.0 Hz), 7.56 (1H, brs).

Example 263

8-Chloro-5-{[(3R,4R)-1-(4-chloro-2,6-difluorophenyl)-3,4-dihydroxypiperidin-4-yl]methoxy}-3,4-dihydroquinolin-2(1H)-one Synthesized analogous to Example 260.
(Acetic acid) m.p. 197-199° C.
$^1$HNMR (DMSO-d6) δ ppm: 1.70 (1H, d, J=13.0 Hz), 1.90 (1H, dt, J=4.8 Hz, 13.0 Hz), 2.47-2.52 (2H, m), 2.88-2.98 (4H, m), 3.21 (1H, t, J=10.7 Hz), 3.31-3.35 (1H, m), 3.70-3.76 (2H, m), 4.05 (1H, d, J=8.9 Hz), 4.58 (1H, s), 4.90 (1H, d, J=6.0 Hz), 6.68 (1H, d, J=9.0 Hz), 7.24-7.29 (3H, m), 9.38 (1H, s).

Example 264

5-{[(3R,4R)-1-(4-Chloro-2,6-difluorophenyl)-3,4-dihydroxypiperidin-4-yl]methoxy}-7,8-difluoro-3,4-dihydroquinolin-2(1H)-one Synthesized analogous to Example 260.
(Acetic acid/water) m.p. 199-201° C.
$^1$HNMR (DMSO-d6) δ ppm: 1.69 (1H, d, J=12.8 Hz), 1.87 (1H, dt, J=4.8 Hz, 12.8 Hz), 2.46-2.51 (2H, m), 2.82-2.90 (3H, m), 2.96 (1H, dd, J=10.6 Hz, 5.0 Hz), 3.20 (1H, t, J=10.6 Hz), 3.29-3.34 (1H, m), 3.68-3.73 (2H, m), 4.01 (1H, d, J=9.0 Hz), 4.57 (1H, s), 4.89 (1H, d, J=6.4 Hz), 6.73 (1H, dd, J=12.6 Hz, 6.1 Hz), 7.25-7.30 (2H, m), 10.31 (1H, s).

Example 265

5-{[(3S,4S)-1-(4-Chloro-2-fluorophenyl)-3,4-dihydroxypiperidin-4-yl]methoxy}-8-fluoro-3,4-dihydroquinolin-2(1H)-one Synthesized analogous to Example 259.
$^1$HNMR (DMSO-d6) δ ppm: 1.69-1.77 (1H, m), 1.89-2.00 (1H, m), 2.46 (2H, t, J=7.6 Hz), 2.80-2.92 (3H, m), 2.93-3.03 (1H, m), 3.05-3.21 (2H, m), 3.69 (1H, d, J=8.8 Hz), 3.75-3.84 (1H, m), 4.02 (1H, d, J=8.8 Hz), 4.54 (1H, brs), 4.88-4.95 (1H, m), 6.57 (1H, dd, J=9.1 Hz, 3.8 Hz), 7.02 (1H, t, J=9.5 Hz), 7.08 (1H, t, J=9.5 Hz), 7.17 (1H, dd, J=8.6 Hz, 2.0 Hz), 7.32 (1H, d, J=12.8 Hz, 2.4 Hz), 10.00 (1H, brs).

Example 266

5-{[(3S*,4S*)-1-(4-Bromo-2-fluorophenyl)-3,4-dihydroxypiperidin-4-yl]methoxy}-8-fluoro-3,4-dihydroquinolin-2(1H)-one Synthesized analogous to Example 257.
$^1$HNMR (DMSO-d6) δ ppm: 1.73 (1H, d, J=13.1 Hz), 1.95 (1H, dt, J=5.2 Hz, 13.1 Hz), 2.46 (2H, t, J=7.7 Hz), 2.81-2.92 (3H, m), 2.97 (1H, t, J=11.0 Hz), 3.09-3.19 (2H, m), 3.68 (1H, d, J=8.8 Hz), 3.79 (1H, brs), 4.02 (1H, d, J=8.8 Hz), 4.57 (1H, brs), 4.94 (1H, brs), 6.57 (1H, dd, J=9.2 Hz, 3.8 Hz), 7.00-7.05 (2H, m), 7.29 (1H, dd, J=8.7 Hz, 1.6 Hz), 7.42 (1H, dd, J=12.3 Hz, 2.3 Hz), 10.03 (1H, s).

Example 267

5-{[(3R,4R)-1-(4-Bromo-2-fluorophenyl)-3,4-dihydroxypiperidin-4-yl]methoxy}-8-fluoro-3,4-dihydroquinolin-2(1H)-one A solution of bis(dihydroquinidinyl)phthalazine ((DHQD)$_2$PHAL) (30.3 mg), potassium osmate(VI) dihydrate (5.74 mg) and methanesulfonamide (111 mg) in acetone-water (1:1) (10 mL) was stirred at room temperature for 15 min, aqueous solution of 4.8 M N-methylmorpholine-N-oxide (43.4 mg) and 5-{[1-(4-bromo-2-fluorophenyl)-1,2,3,6-tetrahydropyridin-4-yl]methoxy}-8-fluoro-3,4-dihydroquinolin-2(1H)-one (350 mg) was added thereto under ice-cooling, and the reaction mixture was stirred at room temperature for 10 days. To the reaction solution was added saturated sodium sulfite aqueous solution, and the reaction mixture was stirred at room temperature for 30 min. The reaction mixture was extracted with ethyl acetate. The obtained extract was filtered with silica gel, and the filtrate was concentrated. To the residue were added acetic acid and water, the precipitate was filtered off, water was added to the filtrate and the precipitate was collected on a filter. The resultant precipitate was purified by silica gel column chromatography (hexane/ethyl acetate) to provide the title compound (35 mg, 97% ee).
$^1$HNMR (DMSO-d6) δ ppm: 1.73 (1H, d, J=13.1 Hz), 1.95 (1H, dt, J=4.4 Hz, 13.1 Hz), 2.46 (2H, t, J=7.7 Hz), 2.81-3.00 (4H, m), 3.08-3.12 (1H, m), 3.17 (1H, dd, J=10.8 Hz, 4.5 Hz), 3.68 (1H, d, J=8.7 Hz), 3.77-3.82 (1H, m), 4.02 (1H, d, J=8.7 Hz), 4.57 (1H, s), 4.94 (1H, d, J=6.4 Hz), 6.57 (1H, dd, J=9.0 Hz, 3.7 Hz), 7.00-7.05 (2H, m), 7.29 (1H, dd, J=8.3 Hz, 1.9 Hz), 7.42 (1H, dd, J=12.3 Hz, 2.3 Hz), 10.03 (1H, s).

Example 268

5-{[(3R,4R)-3,4-Dihydroxy-1-(2,2,6-trifluoro-1,3-benzodioxol-5-yl)piperidin-4-yl]methoxy}-8-fluoro-3,4-dihydroquinolin-2(1H)-one Synthesized analogous to Example 259.
$^1$HNMR (CDCl$_3$) δ ppm: 1.98-2.01 (2H, m), 2.53-2.54 (1H, m), 2.63-2.66 (3H, m), 2.89-3.29 (5H, m), 3.26-3.29 (1H, m), 3.99 (1H, d, J=9.1 Hz), 4.03-4.08 (2H, m), 6.52 (1H, dd, J=3.9 Hz, 9.1 Hz), 6.82 (1H, t, J=7.0 Hz), 6.87 (1H, d, J=10.3 Hz), 6.94 (1H, t, J=9.4 Hz), 7.55 (1H, brs).

Example 269

5-{[(3R*,4R*)-1-(4-Bromo-2-fluorophenyl)-3,4-dihydroxypiperidin-4-yl]methoxy}-8-chloro-3,4-dihydroquinolin-2(1H)-one Synthesized analogous to Example 257.
(Acetic acid/water) m.p. 190-192° C.
$^1$HNMR (DMSO-d6) δ ppm: 1.74 (1H, d, J=13.1 Hz), 1.94 (1H, dt, J=4.9 Hz, 13.1 Hz), 2.45-2.50 (2H, m), 2.81-3.00 (4H, m), 3.10 (1H, d, J=9.6 Hz), 3.17 (1H, dd, J=10.7 Hz, 4.9 Hz), 3.73 (1H, d, J=8.9 Hz), 3.78-3.80 (1H, m), 4.05 (1H, d, J=8.9 Hz), 4.60 (1H, s), 4.96 (1H, brs), 6.68 (1H, d, J=9.0 Hz), 7.02 (1H, t, J=9.0 Hz), 7.25 (1H, d, J=9.0 Hz), 7.29 (1H, dd, J=8.6 Hz, 1.6 Hz), 7.42 (1H, dd, J=12.2 Hz, 2.3 Hz), 9.37 (1H, s).

Example 270

5-{[(3R*,4R*)-1-(4-Bromo-2-fluorophenyl)-3,4-dihydroxypiperidin-4-yl]methoxy}-7,8-difluoro-3,4-dihydroquinolin-2(1H)-one Synthesized analogous to Example 257.
(Acetic acid/water) m.p. 214-216° C.
$^1$HNMR (DMSO-d6) δ ppm: 1.73 (1H, d, J=12.9 Hz), 1.91 (1H, dt, J=4.4 Hz, 12.9 Hz), 2.46 (2H, t, J=7.7 Hz), 2.81-3.00 (4H, m), 3.10 (1H, d, J=11.6 Hz), 3.17 (1H, dd, J=10.6 Hz, 4.5 Hz), 3.73 (1H, d, J=9.0 Hz), 3.74-3.79 (1H, m), 4.01 (1H, d, J=9.0 Hz), 4.59 (1H, s), 4.96 (1H, d, J=6.1 Hz), 6.73 (1H, dd, J=12.7 Hz, 6.2 Hz), 7.02 (1H, t, J=9.1 Hz), 7.29 (1H, dd, J=8.6 Hz, 1.6 Hz), 7.42 (1H, dd, J=12.3 Hz, 2.3 Hz), 10.31 (1H, s).

Example 271

5-{[(3R,4R)-1-(4-Bromo-2-fluorophenyl)-3,4-dihydroxypiperidin-4-yl]methoxy}-8-chloro-3,4-dihydroquinolin-2(1H)-one Synthesized analogous to Example 260.
(Acetic acid/water) m.p. 183-184° C.
$^1$HNMR (DMSO-d6) δ ppm: 1.74 (1H, d, J=13.2 Hz), 1.94 (1H, dt, J=4.6 Hz, 13.2 Hz), 2.45-2.49 (2H, m), 2.82-3.00 (4H, m), 3.10 (1H, d, J=10.1 Hz), 3.17 (1H, dd, J=11.0 Hz, 4.4 Hz), 3.73 (1H, d, J=8.9 Hz), 3.78 (1H, brs), 4.05 (1H, d, J=8.9 Hz), 4.60 (1H, brs), 4.96 (1H, brs), 6.68 (1H, d, J=8.8 Hz), 7.02 (1H, t, J=9.1 Hz), 7.25 (1H, d, J=8.8 Hz), 7.29 (1H, dd, J=8.6 Hz, 1.5 Hz), 7.42 (1H, dd, J=12.2 Hz, 2.3 Hz), 9.37 (1H, s).

Example 272

5-{[(3R,4R)-1-(4-Bromo-2-fluorophenyl)-3,4-dihydroxypiperidin-4-yl]methoxy}-7,8-difluoro-3,4-dihydroquinolin-2(1H)-one Synthesized analogous to Example 42.
$^1$HNMR (DMSO-d6) δ ppm: 1.72-1.75 (1H, m), 1.88-1.94 (1H, m), 2.46 (2H, t, J=7.5 Hz), 2.78-2.89 (3H, m), 2.94-3.00 (1H, m), 3.09-3.11 (1H, m), 3.16-3.19 (1H, m), 3.72 (1H, d, J=9.0 Hz), 3.75-3.79 (1H, m), 4.02 (1H, d, J=9.0 Hz), 4.59 (1H, brs), 4.95 (1H, d, J=6.5 Hz), 6.73 (1H, dd, J=12.5 Hz, 5.5 Hz), 7.02 (1H, t, J=9.0 Hz), 7.28-7.30 (1H, m), 7.42 (1H, dd, J=12.0 Hz, 2.5 Hz), 10.31 (1H, brs).

Example 273

8-Chloro-5-{[(3R,4R)-1-(2-chloro-4-fluorophenyl)-3,4-dihydroxypiperidin-4-yl]methoxy}-3,4-dihydroquinolin-2(1H)-one Synthesized analogous to Example 259.
$^1$HNMR (DMSO-d6) δ ppm: 1.74-1.77 (1H, m), 1.91-1.97 (1H, m), 2.47-2.50 (2H, m), 2.81 (1H, t, J=10.5 Hz), 2.85-2.96 (4H, m), 3.04 (1H, dd, J=10.4 Hz, 4.8 Hz), 3.76 (1H, d, J=8.9 Hz), 3.79-3.83 (1H, m), 4.05 (1H, d, J=9.0 Hz), 4.54 (1H, s), 4.91 (1H, d, J=6.4 Hz), 6.69 (1H, d, J=9.0 Hz), 7.15-7.26 (3H, m), 7.40 (1H, dd, J=8.6 Hz, 2.9 Hz), 9.37 (1H, s).

Example 274

8-Chloro-5-{[(3S,4S)-1-(2-chloro-4-fluorophenyl)-3,4-dihydroxypiperidin-4-yl]methoxy}-3,4-dihydroquinolin-2(1H)-one Synthesized analogous to Example 259.
$^1$HNMR (DMSO-d6) δ ppm: 1.74-1.77 (1H, m), 1.91-1.97 (1H, m), 2.47-2.50 (2H, m), 2.81 (1H, t, J=10.5 Hz), 2.85-2.96 (4H, m), 3.04 (1H, dd, J=10.4 Hz, 4.8 Hz), 3.76 (1H, d, J=8.9 Hz), 3.79-3.83 (1H, m), 4.05 (1H, d, J=9.0 Hz), 4.54 (1H, s), 4.91 (1H, d, J=6.4 Hz), 6.69 (1H, d, J=9.0 Hz), 7.15-7.26 (3H, m), 7.40 (1H, dd, J=8.6 Hz, 2.9 Hz,), 9.37 (1H, s).

Example 275

8-Chloro-5-{[(3R,4R)-1-(2-chloro-4-fluorophenyl)-3,4-dihydroxypiperidin-4-yl]methoxy}-7-fluoro-3,4-dihydroquinolin-2(1H)-one Synthesized analogous to Example 259.
(Ethanol/water) m.p. 175.7-177.0° C.
$^1$HNMR (CDCl$_3$) δ ppm: 1.96-2.07 (2H, m), 2.61-2.64 (3H, m), 2.70 (1H, s), 2.93-3.07 (5H, m), 3.23-3.26 (1H, m), 4.02 (2H, s), 4.03-4.08 (1H, m), 6.51 (1H, d, J=10.6 Hz), 6.94-6.98 (1H, m), 7.06 (1H, dd, J=8.9 Hz, 5.4 Hz), 7.15 (1H, dd, J=8.2 Hz, 2.9 Hz), 7.79 (1H, brs).

Example 276

8-Chloro-5-{[(3R*,4R*)-1-(2-chloro-4-fluorophenyl)-3,4-dihydroxypiperidin-4-yl]methoxy}-7-fluoro-3,4-dihydroquinolin-2(1H)-one Synthesized analogous to Example 259.
$^1$HNMR (CDCl$_3$) δ ppm: 1.96-2.07 (2H, m), 2.30-2.40 (1H, m), 2.61-2.64 (3H, m), 2.93-3.07 (5H, m), 3.23-3.26 (1H, m), 4.02 (2H, s), 4.03-4.08 (1H, m), 6.51 (1H, d, J=10.6 Hz), 6.94-6.98 (1H, m), 7.06 (1H, dd, J=8.9 Hz, 5.4 Hz), 7.15 (1H, dd, J=8.2 Hz, 2.9 Hz), 7.76 (1H, brs).

Example 277

8-Chloro-5-{[(3R*,4R*)-1-(4-chloro-2,6-difluorophenyl)-3,4-dihydroxypiperidin-4-yl]methoxy}-7-fluoro-3,4-dihydroquinolin-2(1H)-one Synthesized analogous to Example 257.
(Ethyl acetate) m.p. 201-204° C.
$^1$HNMR (DMSO-d6) δ ppm: 1.70 (1H, d, J=13.0 Hz), 1.83-1.91 (1H, m), 2.47-2.50 (2H, m), 2.80-2.96 (4H, m), 3.21 (1H, t, J=10.8 Hz), 3.29-3.34 (1H, m), 3.68-3.73 (1H, m), 3.76 (1H, d, J=9.0 Hz), 4.05 (1H, d, J=9.0 Hz), 4.59 (1H, s), 4.90 (1H, d, J=6.4 Hz), 6.81 (1H, d, J=11.5 Hz), 7.24-7.31 (2H, m), 9.70 (1H, s).

Example 278

8-Chloro-5-{[(3R,4R)-1-(4-chloro-2,6-difluorophenyl)-3,4-dihydroxypiperidin-4-yl]methoxy}-7-fluoro-3,4-dihydroquinolin-2(1H)-one Synthesized analogous to Example 260.
(Acetic acid/water) m.p. 192-194° C.
$^1$HNMR (DMSO-d6) δ ppm: 1.70 (1H, d, J=13.5 Hz), 1.83-1.91 (1H, m), 2.47-2.51 (2H, m), 2.81-2.98 (4H, m), 3.21 (1H, t, J=10.7 Hz), 3.30-3.36 (1H, m), 3.68-3.73 (1H, m), 3.76 (1H, d, J=9.0 Hz), 4.05 (1H, d, J=9.0 Hz), 4.60 (1H, s), 4.91 (1H, d, J=6.2 Hz), 6.81 (1H, d, J=11.4 Hz), 7.24-7.31 (2H, m), 9.69 (1H, s).

Example 279

5-{[(3R,4R)-1-(4-Chloro-2,5-difluorophenyl)-3,4-dihydroxypiperidin-4-yl]methoxy}-8-fluoro-3,4-dihydroquinolin-2(1H)-one Synthesized analogous to Example 259.
(Ethanol) m.p. 199.0-199.7° C.
$^1$HNMR (DMSO-d6) δ ppm: 1.71-1.74 (1H, m), 1.91-1.99 (1H, m), 2.45 (2H, t, J=7.7 Hz), 2.81-2.92 (3H, m), 2.98-3.03 (1H, m), 3.13-3.16 (1H, m), 3.22-3.25 (1H, m), 3.69 (1H, d, J=8.8 Hz), 3.76-3.81 (1H, m), 4.02 (1H, d, J=8.8 Hz), 4.59 (1H, s), 4.96 (1H, d, J=6.4 Hz), 6.57 (1H, dd, J=9.1 Hz, 3.7 Hz), 7.02 (1H, t, J=9.7 Hz), 7.11 (1H, dd, J=11.3 Hz, 7.9 Hz), 7.50 (1H, dd, J=12.2 Hz, 7.1 Hz), 10.02 (1H, s).

Example 280

5-{[(3R,4R)-1-(2,4-Dichlorophenyl)-3,4-dihydroxypiperidin-4-yl]methoxy}-8-fluoro-3,4-dihydroquinolin-2(1H)-one Synthesized analogous to Example 259.
$^1$HNMR (DMSO-d6) δ ppm: 1.73-1.76 (1H, m), 1.92-1.98 (1H, m), 2.47 (2H, t, J=7.7 Hz), 2.79-3.11 (6H, m), 3.71 (1H, d, J=8.9 Hz), 3.79-3.83 (1H, m), 4.03 (1H, d, J=8.8 Hz), 4.53 (1H, s), 4.92 (1H, d, J=6.4 Hz), 6.58 (1H, dd, J=9.1 Hz, 3.7 Hz), 7.02 (1H, t, J=9.7 Hz), 7.19 (1H, d, J=8.7 Hz), 7.36 (1H, dd, J=8.6 Hz, 2.5 Hz), 7.54 (1H, d, J=2.5 Hz), 10.03 (1H, s).

Example 281

5-{[(3R,4R)-1-(2,4-Dichloro-5-fluorophenyl)-3,4-dihydroxypiperidin-4-yl]methoxy}-8-fluoro-3,4-dihydroquinolin-2(1H)-one Synthesized analogous to Example 259.
$^1$HNMR (DMSO-d6) δ ppm: 1.73-1.76 (1H, m), 1.92-1.98 (1H, m), 2.47 (2H, t, J=7.7 Hz), 2.80-3.05 (5H, m), 3.15-3.18 (1H, m), 3.71 (1H, d, J=8.9 Hz), 3.79-3.83 (1H, m), 4.03 (1H, d, J=8.9 Hz), 4.56 (1H, s), 4.96 (1H, d, J=6.4 Hz), 6.58 (1H, dd, J=9.1 Hz, 3.7 Hz), 7.02 (1H, t, J=9.7 Hz), 7.24 (1H, d, J=11.2 Hz), 7.71 (1H, d, J=7.8 Hz), 10.03 (1H, s).

Example 282

5-{[(3R,4R)-1-(2,5-Dichloro-4-fluorophenyl)-3,4-dihydroxypiperidin-4-yl]methoxy}-8-fluoro-3,4-dihydroquinolin-2(1H)-one Synthesized analogous to Example 259.
(Ethanol/water) m.p. 216.0-216.3° C.
$^1$HNMR (DMSO-d6) δ ppm: 1.73-1.75 (1H, m), 1.92-1.98 (1H, m), 2.47 (2H, t, J=7.7 Hz), 2.80-3.09 (6H, m), 3.71 (1H, d, J=8.8 Hz), 3.79-3.83 (1H, m), 4.03 (1H, d, J=8.8 Hz), 4.54 (1H, s), 4.93 (1H, d, J=6.3 Hz), 6.58 (1H, dd, J=9.1 Hz, 3.7 Hz), 7.03 (1H, t, J=9.7 Hz), 7.34 (1H, d, J=7.3 Hz), 7.66 (1H, d, J=9.1 Hz), 10.03 (1H, s).

Example 283

5-{[(3R,4R)-1-(4-Ethoxy-2-fluorophenyl)-3,4-dihydroxypiperidin-4-yl]methoxy}-8-fluoro-3,4-dihydroquinolin-2(1H)-one Synthesized analogous to Example 259.
$^1$HNMR (DMSO-d6) δ ppm: 1.30 (3H, t, J=7.0 Hz), 1.70-1.72 (1H, m), 1.91-1.97 (1H, m), 2.47 (2H, t, J=7.7 Hz), 2.77-3.05 (6H, m), 3.68 (1H, d, J=8.8 Hz), 3.77-3.81 (1H, m), 3.97 (2H, q, J=7.0 Hz), 4.02 (1H, d, J=8.8 Hz), 4.47 (1H, s), 4.86 (1H, d, J=6.5 Hz), 6.57 (1H, dd, J=9.1 Hz, 3.7 Hz), 6.68 (1H, dd, J=8.7 Hz, 2.4 Hz), 6.77 (1H, dd, J=14.1 Hz, 2.8 Hz), 6.98-7.04 (2H, m), 10.02 (1H, s).

Example 284

5-{[(3R,4R)-1-(4-Bromo-2-fluorophenyl)-3,4-dihydroxypiperidin-4-yl]methoxy}-8-chloro-7-fluoro-3,4-dihydroquinolin-2(1H)-one Synthesized analogous to Example 260.
$^1$HNMR (DMSO-d6) δ ppm: 1.74 (1H, d, J=13.6 Hz), 1.87-1.95 (1H, m), 2.46-2.50 (2H, m), 2.82-3.00 (4H, m), 3.10 (1H, d, J=11.1 Hz), 3.17 (1H, dd, J=11.1 Hz, 3.9 Hz), 3.75-3.78 (2H, m), 4.07 (1H, d, J=9.0 Hz), 4.60 (1H, brs), 4.95 (1H, brs), 6.80 (1H, d, J=11.4 Hz), 7.02 (1H, t, J=9.1 Hz), 7.29 (1H, dd, J=7.4 Hz, 1.2 Hz), 7.42 (1H, dd, J=12.2 Hz, 2.3 Hz), 9.66 (1H, s).

Example 285

5-{[(3R*,4R*)-1-(4-Bromo-2-fluorophenyl)-3,4-dihydroxypiperidin-4-yl]methoxy}-8-chloro-7-fluoro-3,4-dihydroquinolin-2(1H)-one Synthesized analogous to Example 257.
(Ethyl acetate) m.p. 194° C.
$^1$HNMR (DMSO-d6) δ ppm: 1.74 (1H, d, J=13.6 Hz), 1.87-1.95 (1H, m), 2.46-2.49 (2H, m), 2.82-3.00 (4H, m), 3.08-3.12 (1H, m), 3.17 (1H, dd, J=11.1 Hz, 4.5 Hz), 3.74-3.78 (2H, m), 4.06 (1H, d, J=9.1 Hz), 4.60 (1H, s), 4.95 (1H, d, J=6.2 Hz), 6.80 (1H, d, J=11.4 Hz), 7.02 (1H, t, J=9.1 Hz), 7.29 (1H, dd, J=8.6 Hz, 1.6 Hz), 7.42 (1H, dd, J=12.3 Hz, 2.3 Hz), 9.66 (1H, s).

Example 286

5-{[(3R,4R)-1-(2-Chloro-4-fluorophenyl)-3,4-dihydroxypiperidin-4-yl]methoxy}-7,8-difluoro-3,4-dihydroquinolin-2(1H)-one Synthesized analogous to Example 259.
(Acetic acid/water) m.p. 192.2-193.2° C.
$^1$HNMR (DMSO-d6) δ ppm: 1.73-1.76 (1H, m), 1.89-1.95 (1H, m), 2.46-2.49 (2H, m), 2.78-3.05 (6H, m), 3.74-3.81 (2H, m), 4.02 (1H, d, J=9.1 Hz), 4.53 (1H, s), 4.91 (1H, d, J=6.4 Hz), 6.76 (1H, dd, J=12.6 Hz, 6.2 Hz), 7.15-7.23 (2H, m), 7.40 (1H, dd, J=8.6 Hz, 2.9 Hz), 10.03 (1H, s).

Example 287

5-{[(3R*,4R*)-1-(2-Chloro-4-fluorophenyl)-3,4-dihydroxypiperidin-4-yl]methoxy}-7,8-difluoro-3,4-dihydroquinolin-2(1H)-one Synthesized analogous to Example 259.
$^1$HNMR (DMSO-d6) δ ppm: 1.73-1.76 (1H, m), 1.89-1.95 (1H, m), 2.46-2.49 (2H, m), 2.78-3.05 (6H, m), 3.74-3.81 (2H, m), 4.02 (1H, d, J=9.1 Hz), 4.53 (1H, s), 4.91 (1H, d, J=6.4 Hz), 6.76 (1H, dd, J=12.6 Hz, 6.2 Hz), 7.15-7.23 (2H, m), 7.40 (1H, dd, J=8.6 Hz, 2.9 Hz), 10.03 (1H, s).

Example 288

5-{[(3R,4R)-1-(3-Bromo-6-chloroquinolin-2-yl)-3,4-dihydroxypiperidin-4-yl]methoxy}-8-fluoro-3,4-dihydroquinolin-2(1H)-one Synthesized analogous to Example 33.
$^1$HNMR (CDCl$_3$) δ ppm: 1.89-1.96 (1H, m), 1.97-2.05 (1H, m), 2.63 (2H, t, J=7.7 Hz), 2.93 (1H, brs), 2.94-3.06 (2H, m), 3.45-3.55 (2H, m), 3.68-3.75 (1H, m), 3.78-4.00 (2H, m), 4.04-4.10 (2H, m), 4.11-4.16 (1H, m), 6.53 (1H, dd, J=9.1 Hz, 3.9 Hz), 6.93 (1H, t, J=9.8 Hz), 7.55 (1H, brs), 7.57 (1H, dd, J=9.0 Hz, 2.4 Hz), 7.62 (1H, d, J=2.3 Hz), 7.75 (1H, d, J=9.0 Hz), 8.21 (1H, s).

Example 289

5-{[(3R,4R)-1-(6-Chloroquinolin-2-yl)-3,4-dihydroxypiperidin-4-yl]methoxy}-8-fluoro-3,4-dihydroquinolin-2(1H)-one Synthesized analogous to Example 33.
$^1$HNMR (CDCl$_3$) δ ppm: 1.83-1.91 (1H, m), 1.94-2.00 (1H, m), 2.50-2.60 (2H, m), 2.81 (1H, brs), 2.85-2.91 (2H, m), 3.07 (1H, brs), 3.34 (1H, dd, J=13.0 Hz, 10.0 Hz), 3.39-3.47 (1H, m), 3.93-4.00 (3H, m), 4.21-4.28 (1H, m), 4.44-4.51 (1H, m), 6.46 (1H, dd, J=9.2 Hz, 4.0 Hz), 6.90 (1H, t, J=9.3 Hz), 7.05 (1H, d, J=9.2 Hz), 7.47 (1H, dd, J=8.9 Hz, 2.6 Hz), 7.58 (1H, d, J=2.4 Hz), 7.59-7.64 (2H, m), 7.82 (1H, d, J=9.2 Hz).

Example 290

8-Chloro-5-{[(3R,4R)-1-(2,4-dichlorophenyl)-3,4-dihydroxypiperidin-4-yl]methoxy}-3,4-dihydroquinolin-2(1H)-one Synthesized analogous to Example 259.
(Ethanol/water) m.p. 184.1-185.1° C.
$^1$HNMR (DMSO-d6) δ ppm: 1.75-1.77 (1H, m), 1.92-1.98 (1H, m), 2.47-2.49 (2H, m), 2.80-3.12 (6H, m), 3.76 (1H, d, J=8.9 Hz), 3.79-3.83 (1H, m), 4.06 (1H, d, J=8.9 Hz), 4.55 (1H, s), 4.93 (1H, d, J=6.4 Hz), 6.69 (1H, d, J=9.0 Hz), 7.19 (1H, d, J=8.7 Hz), 7.25 (1H, d, J=8.9 Hz), 7.36 (1H, dd, J=8.7 Hz, 2.5 Hz), 7.53 (1H, d, J=2.5 Hz), 9.35 (1H, s).

Example 291

8-Chloro-5-{[(3R,4R)-1-(2,5-dichloro-4-fluorophenyl)-3,4-dihydroxypiperidin-4-yl]methoxy}-3,4-dihydroquinolin-2(1H)-one Synthesized analogous to Example 259.
(Acetic acid/water) m.p. 237.7-238.6° C.
$^1$HNMR (DMSO-d6) δ ppm: 1.74-1.77 (1H, m), 1.91-1.97 (1H, m), 2.47-2.49 (2H, m), 2.80-3.09 (6H, m), 3.75 (1H, d, J=8.9 Hz), 3.79-3.83 (1H, m), 4.06 (1H, d, J=8.9 Hz), 4.55 (1H, s), 4.93 (1H, d, J=6.4 Hz), 6.69 (1H, d, J=9.0 Hz), 7.25 (1H, d, J=8.9 Hz), 7.34 (1H, d, J=7.4 Hz,), 7.66 (1H, d, J=9.1 Hz), 9.36 (1H, s).

Example 292

8-Chloro-5-{[(3R,4R)-1-(2,4-dichloro-5-fluorophenyl)-3,4-dihydroxypiperidin-4-yl]methoxy}-3,4-dihydroquinolin-2(1H)-one Synthesized analogous to Example 259.
(Ethanol/water) m.p. 180.2-180.6° C.
$^1$HNMR (DMSO-d6) δ ppm: 1.74-1.77 (1H, m), 1.91-1.97 (1H, m), 2.47-2.49 (2H, m), 2.80-3.18 (6H, m), 3.76 (1H, d, J=8.9 Hz), 3.79-3.83 (1H, m), 4.06 (1H, d, J=8.9 Hz), 4.57 (1H, s), 4.95 (1H, d, J=6.4 Hz), 6.69 (1H, d, J=9.0 Hz), 7.22-7.26 (2H, m), 7.71 (1H, d, J=7.8 Hz), 9.35 (1H, s).

Example 293

5-{[(3R,4R)-1-(2-Chloro-4-fluorophenyl)-3,4-dihydroxypiperidin-4-yl]methoxy}-8-fluoro-3,4-dihydroquinolin-2(1H)-one Synthesized analogous to Example 259.
$^1$HNMR (DMSO-d6) δ ppm: 1.73-1.76 (1H, m), 1.93-1.99 (1H, m), 2.46-2.49 (2H, m), 2.79-3.06 (6H, m), 3.72 (1H, d, J=8.9 Hz), 3.79-3.84 (1H, m), 4.03 (1H, d, J=8.9 Hz), 4.49 (1H, s), 4.88 (1H, d, J=6.4 Hz), 6.59 (1H, dd, J=9.1 Hz, 3.8 Hz), 7.02 (1H, t, J=9.7 Hz), 7.15-7.19 (1H, m), 7.22 (1H, dd, J=9.0 Hz, 5.7 Hz), 7.39 (1H, dd, J=8.6 Hz, 2.9 Hz), 10.01 (1H, s).

Example 294

8-Chloro-5-{[(3R,4R)-1-(4-chloro-2,5-difluorophenyl)-3,4-dihydroxypiperidin-4-yl]methoxy}-3,4-dihydroquinolin-2(1H)-one Synthesized analogous to Example 259.
$^1$HNMR (DMSO-d6) δ ppm: 1.72-1.75 (1H, m), 1.90-1.96 (1H, m), 2.45-2.48 (2H, m), 2.82-3.25 (6H, m), 3.73 (1H, d, J=8.8 Hz), 3.76-3.80 (1H, m), 4.05 (1H, d, J=8.9 Hz), 4.62 (1H, s), 4.98 (1H, d, J=6.3 Hz), 6.67 (1H, d, J=9.0 Hz), 7.12 (1H, dd, J=11.3 Hz, 7.9 Hz), 7.25 (1H, d, J=8.9 Hz), 7.50 (1H, dd, J=12.2 Hz, 7.1 Hz), 9.37 (1H, s).

Example 295

5-{[(3R,4R)-1-(4-Chloro-2,5-difluorophenyl)-3,4-dihydroxypiperidin-4-yl]methoxy}-7,8-difluoro-3,4-dihydroquinolin-2(1H)-one Synthesized analogous to Example 259.
$^1$HNMR (DMSO-d6) δ ppm: 1.72-1.75 (1H, m), 1.87-1.93 (1H, m), 2.47 (2H, t, J=7.7 Hz), 2.77-3.25 (6H, m), 3.71-3.78 (2H, m), 4.02 (1H, d, J=9.0 Hz), 4.62 (1H, s), 4.98 (1H, d, J=6.3 Hz), 6.73 (1H, dd, J=12.6 Hz, 6.1 Hz), 7.11 (1H, dd, J=11.3 Hz, 7.9 Hz), 7.50 (1H, dd, J=12.2 Hz, 7.1 Hz), 10.31 (1H, s).

Example 296

5-Chloro-2-[(3R,4R)-4-{[(8-fluoro-2-oxo-1,2,3,4-tetrahydroquinolin-5-yl)oxy]methyl}-3,4-dihydroxypiperidin-1-yl]benzonitrile Synthesized analogous to Example 33.
$^1$HNMR (CDCl$_3$) δ ppm: 1.98-2.03 (1H, m), 2.04-2.12 (1H, m), 2.58-2.68 (2H, m), 2.73 (1H, brs), 2.79-2.83 (1H, m), 2.96-3.07 (3H, m), 3.15-3.23 (1H, m), 3.31-3.37 (1H, m), 3.46-3.52 (1H, m), 3.98-4.04 (2H, m), 4.09-4.15 (1H, m), 6.51 (1H, dd, J=9.1 Hz, 3.9 Hz), 6.93 (1H, t, J 5=9.5 Hz), 7.01 (1H, d, J=8.9 Hz), 7.46 (1H, dd, J=8.9 Hz, 2.6 Hz), 7.53 (1H, d, J=2.3 Hz), 7.58 (1H, brs).

Example 297

5-{[(3R,4R)-1-(5-Chloro-3-fluoropyridin-2-yl)-3,4-dihydroxypiperidin-4-yl]methoxy}-8-fluoro-3,4-dihydroquinolin-2(1H)-one Synthesized analogous to Example 33.
$^1$HNMR (CDCl$_3$) δ ppm: 1.88-1.94 (2H, m), 2.60-2.67 (2H, m), 2.73 (1H, brs), 2.77-2.80 (1H, m), 2.89-3.00 (2H, m), 3.19-3.27 (1H, m), 3.30-3.37 (1H, m), 3.79-3.85 (1H, m), 3.95-4.03 (4H, m), 6.50 (1H, dd, J=9.1 Hz, 3.9 Hz), 6.92 (1H, t, J=9.4 Hz), 7.29 (1H, dd, J=12.0 Hz, 2.2 Hz), 7.57 (1H, brs), 7.97 (1H, dd, J=2.2 Hz, 0.5 Hz).

Example 298

3,5-Difluoro-2-[(3R,4R)-4-{[(8-fluoro-2-oxo-1,2,3,4-tetrahydroquinolin-5-yl)oxy]methyl}-3,4-dihydroxypiperidin-1-yl]benzonitrile Synthesized analogous to Example 33.
$^1$HNMR (CDCl$_3$) δ ppm: 1.97-2.03 (2H, m), 2.51-2.55 (1H, m), 2.61-2.68 (3H, m), 2.95-3.04 (3H, m), 3.11-3.18 (1H, m), 3.26-3.32 (1H, m), 3.42-3.48 (1H, m), 3.97-4.08 (3H, m), 6.52 (1H, dd, J=9.2 Hz, 3.9 Hz), 6.84-6.88 (1H, m), 6.89-6.97 (2H, m), 7.53 (1H, brs).

Example 299

4-Chloro-5-fluoro-2-[(3R,4R)-4-{[(8-fluoro-2-oxo-1,2,3,4-tetrahydroquinolin-5-yl)oxy]methyl}-3,4-dihydroxypiperidin-1-yl]benzonitrile Synthesized analogous to Example 33.
$^1$HNMR (CDCl$_3$) δ ppm: 1.98-2.12 (2H, m), 2.62-2.67 (2H, m), 2.69-2.73 (2H, m), 2.94-3.06 (3H, m), 3.18 (1H, dt, J=11.6 Hz, 3.1 Hz), 3.26-3.32 (1H, m), 3.41-3.47 (1H, m), 4.09-4.15 (3H, m), 6.51 (1H, dd, J=9.1 Hz, 3.9 Hz), 6.93 (1H, t, J=9.4 Hz), 7.12 (1H, d, J=6.3 Hz), 7.36 (1H, d, J=8.1 Hz), 7.55 (1H, brs).

Example 300

5-{[(3R,4R)-1-(4-Chlorophenyl)-3,4-dihydroxypiperidin-4-yl]methoxy}-8-fluoro-3,4-dihydroquinolin-2(1H)-one Synthesized analogous to Example 259.
$^1$HNMR (DMSO-d6) δ ppm: 1.67-1.70 (1H, m), 1.87-1.93 (1H, m), 2.39-2.42 (2H, m), 2.70-2.99 (4H, m), 3.47-3.50 (2H, m), 3.66 (1H, d, J=8.8 Hz), 3.70-3.75 (1H, m), 4.01 (1H, d, J=8.8 Hz), 4.57 (1H, s), 4.89 (1H, d, J=6.6 Hz), 6.55 (1H, dd, J=9.1 Hz, 3.8 Hz), 6.93-6.97 (2H, m), 6.98-7.03 (1H, m), 7.20-7.23 (2H, m), 10.01 (1H, s).

Example 301

5-{[(3R*,4R*)-1-(4-Bromo-2,6-difluorophenyl)-3,4-dihydroxypiperidin-4-yl]methoxy}-8-fluoro-3,4-dihydroquinolin-2(1H)-one Synthesized analogous to Example 257.
(Ethyl acetate) m.p. 191-193° C.
$^1$HNMR (DMSO-d6) δ ppm: 1.69 (1H, d, J=13.4 Hz), 1.87-1.94 (1H, m), 2.45-2.49 (2H, m), 2.84-2.99 (4H, m), 3.20 (1H, t, J=10.7 Hz), 3.30-3.35 (1H, m), 3.68 (1H, d, J=8.8 Hz), 3.71-3.76 (1H, m), 4.02 (1H, d, J=8.8 Hz), 4.53 (1H, s), 4.87 (1H, d, J=6.5 Hz), 6.57 (1H, dd, J=9.2 Hz, 3.8 Hz), 7.02 (1H, t, J=9.7 Hz), 7.35-7.40 (2H, m), 10.02 (1H, s).

Example 302

5-{[(3R,4R)-1-(4-Bromo-2,6-difluorophenyl)-3,4-dihydroxypiperidin-4-yl]methoxy}-8-fluoro-3,4-dihydroquinolin-2(1H)-one Synthesized analogous to Example 260.
(Acetic acid/water) m.p. 197-198° C.
$^1$HNMR (DMSO-d6) δ ppm: 1.69 (1H, d, J=13.4 Hz), 1.87-1.94 (1H, m), 2.45-2.49 (2H, m), 2.82-2.99 (4H, m), 3.20 (1H, t, J=10.9 Hz), 3.28-3.33 (1H, m), 3.68 (1H, d, J=8.7 Hz), 3.70-3.76 (1H, m), 4.02 (1H, d, J=8.7 Hz), 4.53 (1H, s), 4.87 (1H, d, J=6.4 Hz), 6.57 (1H, dd, J=9.2 Hz, 3.8 Hz), 7.02 (1H, t, J=9.7 Hz), 7.35-7.40 (2H, m), 10.01 (1H, s).

Example 303

5-{[(3R*,4R*)-1-(2-Chloro-4,6-difluorophenyl)-3,4-dihydroxypiperidin-4-yl]methoxy}-8-fluoro-3,4-dihydroquinolin-2(1H)-one Synthesized analogous to Example 257.
(Ethyl acetate/hexane) m.p. 215-218° C.
$^1$HNMR (DMSO-d6) δ ppm: 1.68 (1H, d, J=13.3 Hz), 1.91-1.99 (1H, m), 2.45-2.49 (2H, m), 2.75-2.95 (4H, m), 3.20-3.37 (2H, m), 3.69 (1H, d, J=8.9 Hz), 3.74-3.79 (1H, m), 4.02 (1H, d, J=8.9 Hz), 4.49 (1H, s), 4.82 (1H, d, J=6.5 Hz), 6.58 (1H, dd, J=9.1 Hz, 3.8 Hz), 7.02 (1H, t, J=9.7 Hz), 7.26-7.36 (2H, m), 10.02 (1H, s).

Example 304

5-{[(3R,4R)-1-(2-Chloro-4,6-difluorophenyl)-3,4-dihydroxypiperidin-4-yl]methoxy}-8-fluoro-3,4-dihydroquinolin-2(1H)-one Synthesized analogous to Example 260.
(Acetic acid/water) m.p. 188-189° C.
$^1$HNMR (DMSO-d6) δ ppm: 1.68 (1H, d, J=13.3 Hz), 1.90-1.99 (1H, m), 2.45-2.49 (2H, m), 2.75-2.95 (4H, m), 3.21-3.37 (2H, m), 3.69 (1H, d, J=8.8 Hz), 3.74-3.80 (1H, m), 4.03 (1H, d, J=8.8 Hz), 4.49 (1H, s), 4.82 (1H, d, J=6.5 Hz), 6.59 (1H, dd, J=9.1 Hz, 3.8 Hz), 7.02 (1H, t, J=9.7 Hz), 7.26-7.35 (2H, m), 10.01 (1H, s).

Example 305

5-{[(3R*,4R*)-3,4-Dihydroxy-1-(2,4,6-trifluorophenyl)piperidin-4-yl]methoxy}-8-fluoro-3,4-dihydroquinolin-2(1H)-one Synthesized analogous to Example 257.
(Acetic acid/water) m.p. 198-199° C.
$^1$HNMR (DMSO-d6) δ ppm: 1.65-1.72 (1H, m), 1.86-1.96 (1H, m), 2.48 (2H, t, J=7.7 Hz), 2.77-2.97 (4H, m), 3.21 (1H, t, J=10.6 Hz), 3.28-3.38 (1H, m), 3.68 (1H, d, J=8.8 Hz), 3.70-3.78 (1H, m), 4.02 (1H, d, J=8.8 Hz), 4.51 (1H, s), 4.84 (1H, d, J=6.6 Hz), 6.58 (1H, dd, J=9.1 Hz, 3.8 Hz), 7.02 (1H, t, J=9.7 Hz), 7.08-7.18 (2H, m), 10.03 (1H, s).

Example 306

5-{[(3R,4R)-3,4-Dihydroxy-1-(2,4,6-trifluorophenyl)piperidin-4-yl]methoxy}-8-fluoro-3,4-dihydroquinolin-2(1H)-one Synthesized analogous to Example 260.
(Acetic acid/water) m.p. 191-192° C.
$^1$HNMR (DMSO-d6) δ ppm: 1.65-1.72 (1H, m), 1.86-1.96 (1H, m), 2.48 (2H, t, J=7.7 Hz), 2.77-2.97 (4H, m), 3.21 (1H, t, J=10.6 Hz), 3.28-3.38 (1H, m), 3.68 (1H, d, J=8.8 Hz), 3.70-3.78 (1H, m), 4.02 (1H, d, J=8.8 Hz), 4.51 (1H, s), 4.84 (1H, d, J=6.6 Hz), 6.58 (1H, dd, J=9.1 Hz, 3.8 Hz), 7.02 (1H, t, J=9.7 Hz), 7.08-7.18 (2H, m), 10.03 (1H, s).

Example 307

3,5-Dichloro-2-[(3R,4R)-4-{[(8-fluoro-2-oxo-1,2,3,4-tetrahydroquinolin-5-yl)oxy]methyl}-3,4-dihydroxypiperidin-1-yl]benzonitrile Synthesized analogous to Example 33.
$^1$HNMR (CDCl$_3$) δ ppm: 1.94-2.01 (1H, m), 2.05-2.13 (1H, m), 2.56-2.60 (1H, m), 2.61-2.69 (3H, m), 2.95-3.13 (3H, m), 3.28-3.34 (1H, m), 3.47-3.54 (1H, m), 3.63-3.69 (1H, m), 3.99-4.05 (2H, m), 4.07-4.14 (1H, m), 6.51 (1H, dd, J=9.1 Hz, 3.9 Hz), 6.93 (1H, t, J=9.3 Hz), 7.47 (1H, d, J=2.5 Hz), 7.52 (1H, brs), 7.56 (1H, d, J=2.5 Hz).

Example 308

8-Fluoro-5-({(3R,4R)-1-[2-fluoro-4-(trifluoromethoxy)phenyl]-3,4-dihydroxypiperidin-4-yl}methoxy)-3,4-dihydroquinolin-2(1H)-one Synthesized analogous to Example 259.
(Ethanol/water) m.p. 161.6-161.9° C.
$^{1}$HNMR (DMSO-d6) δ ppm: 1.72-1.75 (1H, m), 1.92-1.98 (1H, m), 2.46 (2H, t, J=7.7 Hz), 2.82-3.21 (6H, m), 3.69 (1H, d, J=8.8 Hz), 3.78-3.81 (1H, m), 4.03 (1H, d, J=8.8 Hz), 4.57 (1H, s), 4.95 (1H, d, J=5.9 Hz), 6.58 (1H, dd, J=9.2 Hz, 3.7 Hz), 7.02 (1H, t, J=9.7 Hz), 7.15-7.18 (2H, m), 7.31-7.33 (1H, m), 10.03 (1H, s).

Example 309

8-Fluoro-5-{[(3R,4R)-1-(2-fluorophenyl)-3,4-dihydroxypiperidin-4-yl]methoxy}-3,4-dihydroquinolin-2(1H)-one Synthesized analogous to Example 259.
(Ethanol) m.p. 177.7-178.0° C.
$^{1}$HNMR (DMSO-d6) δ ppm: 1.72-1.75 (1H, m), 1.93-1.99 (1H, m), 2.46 (2H, t, J=7.8 Hz), 2.82-3.20 (6H, m), 3.69 (1H, d, J=8.8 Hz), 3.79-3.83 (1H, m), 4.03 (1H, d, J=8.8 Hz), 4.52 (1H, s), 4.91 (1H, d, J=6.4 Hz), 6.58 (1H, dd, J=9.1 Hz, 3.8 Hz), 6.93-7.14 (5H, m), 10.03 (1H, s).

Example 310

5-({(3R*,4R*)-1-[2,6-Difluoro-4-(2,2,2-trifluoroethoxy)phenyl]-3,4-dihydroxypiperidin-4-yl}methoxy)-8-fluoro-3,4-dihydroquinolin-2(1H)-one Synthesized analogous to Example 257.
(Ethyl acetate-diisopropyl ether) m.p. 201-202° C.
$^{1}$HNMR (DMSO-d6) δ ppm: 1.68 (1H, d, J=13.6 Hz), 1.86-1.94 (1H, m), 2.46-2.51 (2H, m), 2.76-2.95 (4H, m), 3.18-3.34 (2H, m), 3.68 (1H, d, J=8.8 Hz), 3.70-3.75 (1H, m), 4.02 (1H, d, J=8.8 Hz), 4.47 (1H, s), 4.73-4.81 (3H, m), 6.58 (1H, dd, J=9.2 Hz, 3.8 Hz), 6.84-6.91 (2H, m), 7.02 (1H, t, J=9.7 Hz), 10.01 (1H, s).

Example 311

5-({(3R,4R)-1-[2,6-Difluoro-4-(2,2,2-trifluoroethoxy)phenyl]-3,4-dihydroxypiperidin-4-yl}methoxy)-8-fluoro-3,4-dihydroquinolin-2(1H)-one Synthesized analogous to Example 260.
(Acetic acid/water) m.p. 187° C.
$^{1}$HNMR (DMSO-d6) δ ppm: 1.68 (1H, d, J=13.6 Hz), 1.86-1.94 (1H, m), 2.46-2.50 (2H, m), 2.76-2.93 (4H, m), 3.18-3.32 (2H, m), 3.68 (1H, d, J=8.8 Hz), 3.70-3.75 (1H, m), 4.02 (1H, d, J=8.8 Hz), 4.47 (1H, s), 4.73-4.81 (3H, m), 6.58 (1H, dd, J=9.1 Hz, 3.8 Hz), 6.85-6.91 (2H, m), 7.02 (1H, t, J=9.8 Hz), 10.01 (1H, s).

Example 312

5-{[(3R*,4R*)-1-(2,4-Dichloro-6-fluorophenyl)-3,4-dihydroxypiperidin-4-yl]methoxy}-8-fluoro-3,4-dihydroquinolin-2(1H)-one Synthesized analogous to Example 257.
$^{1}$HNMR (DMSO-d6) δ ppm: 1.68 (1H, d, J=13.5 Hz), 1.91-1.98 (1H, m), 2.44-2.50 (2H, m), 2.86-2.95 (4H, m), 3.23-3.36 (2H, m), 3.69 (1H, d, J=8.8 Hz), 3.75-3.80 (1H, m), 4.03 (1H, d, J=8.8 Hz), 4.53 (1H, s), 4.86 (1H, d, J=6.4 Hz), 6.59 (1H, dd, J=9.2 Hz, 3.8 Hz), 7.03 (1H, t, J=9.7 Hz), 7.43-7.47 (2H, m), 10.03 (1H, s).

Example 313

5-{[(3R,4R)-1-(2,4-Dichloro-6-fluorophenyl)-3,4-dihydroxypiperidin-4-yl]methoxy}-8-fluoro-3,4-dihydroquinolin-2(1H)-one Synthesized analogous to Example 260.
$^{1}$HNMR (DMSO-d6) δ ppm: 1.68 (1H, d, J=13.3 Hz), 1.91-1.99 (1H, m), 2.47 (2H, t, J=7.7 Hz), 2.82-2.95 (4H, m), 3.20-3.36 (2H, m), 3.69 (1H, d, J=8.8 Hz), 3.75-3.80 (1H, m), 4.03 (1H, d, J=8.8 Hz), 4.53 (1H, s), 4.87 (1H, d, J=6.4 Hz), 6.59 (1H, dd, J=9.2 Hz, 3.8 Hz), 7.03 (1H, t, J=9.7 Hz), 7.43-7.47 (2H, m), 10.03 (1H, s).

Example 314

5-({(3R*,4R*)-1-[4-(Difluoromethoxy)-2,6-difluorophenyl]-3,4-dihydroxypiperidin-4-yl}methoxy)-8-fluoro-3,4-dihydroquinolin-2(1H)-one Synthesized analogous to Example 257.
(Ethyl acetate-diisopropyl ether) m.p. 167-169° C.
$^{1}$HNMR (DMSO-d6) δ ppm: 1.68 (1H, d, J=13.3 Hz), 1.87-1.95 (1H, m), 2.46-2.50 (2H, m), 2.83-2.93 (4H, m), 3.18-3.35 (2H, m), 3.68 (1H, d, J=8.8 Hz), 3.71-3.76 (1H, m), 4.02 (1H, d, J=8.8 Hz), 4.51 (1H, s), 4.84 (1H, d, J=6.5 Hz), 6.57 (1H, dd, J=9.2 Hz, 3.8 Hz), 7.00-7.06 (3H, m), 7.24 (1H, t, J=73.5 Hz), 10.02 (1H, s).

Example 315

5-({(3R,4R)-1-[4-(Difluoromethoxy)-2,6-difluorophenyl]-3,4-dihydroxypiperidin-4-yl}methoxy)-8-fluoro-3,4-dihydroquinolin-2(1H)-one Synthesized analogous to Example 260.
(Acetic acid/water) m.p. 166° C.
$^{1}$HNMR (DMSO-d6) δ ppm: 1.69 (1H, d, J=13.5 Hz), 1.87-1.95 (1H, m), 2.46-2.50 (2H, m), 2.83-2.93 (4H, m), 3.19-3.35 (2H, m), 3.68 (1H, d, J=8.8 Hz), 3.71-3.76 (1H, m), 4.02 (1H, d, J=8.8 Hz), 4.51 (1H, s), 4.85 (1H, d, J=6.5 Hz), 6.57 (1H, dd, J=9.2 Hz, 3.8 Hz), 7.00-7.06 (3H, m), 7.24 (1H, t, J=73.5 Hz), 10.02 (1H, s).

Example 316

5-{[(3R*,4R*)-1-(4-Ethoxy-2,6-difluorophenyl)-3,4-dihydroxypiperidin-4-yl]methoxy}-8-fluoro-3,4-dihydroquinolin-2(1H)-one Synthesized analogous to Example 257.
(Ethyl acetate-diisopropyl ether) m.p. 199-202° C.
$^{1}$HNMR (DMSO-d6) δ ppm: 1.29 (3H, t, J=7.0 Hz), 1.67 (1H, d, J=13.5 Hz), 1.86-1.93 (1H, m), 2.42-2.49 (2H, m), 2.72-2.93 (4H, m), 3.17-3.32 (2H, m), 3.68 (1H, d, J=8.8 Hz), 3.69-3.75 (1H, m), 3.97-4.04 (3H, m), 4.45 (1H, s), 4.78 (1H, d, J=6.5 Hz), 6.58 (1H, dd, J=9.1 Hz, 3.8 Hz), 6.64-6.68 (2H, m), 7.02 (1H, t, J=9.7 Hz), 10.01 (1H, s).

Example 317

5-{[(3R,4R)-1-(4-Ethoxy-2,6-difluorophenyl)-3,4-dihydroxypiperidin-4-yl]methoxy}-8-fluoro-3,4-dihydroquinolin-2(1H)-one Synthesized analogous to Example 260.
(Acetic acid/water) m.p. 176-178° C.
$^1$HNMR (DMSO-d6) δ ppm: 1.29 (3H, t, J=7.0 Hz), 1.67 (1H, d, J=13.4 Hz), 1.86-1.93 (1H, m), 2.46-2.50 (2H, m), 2.72-2.93 (4H, m), 3.17-3.32 (2H, m), 3.67 (1H, d, J=8.8 Hz), 3.69-3.75 (1H, m), 3.97-4.02 (3H, m), 4.45 (1H, s), 4.78 (1H, d, J=6.5 Hz), 6.57 (1H, dd, J=9.1 Hz, 3.8 Hz), 6.64-6.68 (2H, m), 7.02 (1H, t, J=9.7 Hz), 10.01 (1H, s).

Example 318

5-{[(3R,4R)-1-(2-Chlorophenyl)-3,4-dihydroxypiperidin-4-yl]methoxy}-8-fluoro-3,4-dihydroquinolin-2(1H)-one Synthesized analogous to Example 259.
(Ethanol/water) m.p. 161.3-161.4° C.
$^1$HNMR (DMSO-d6) δ ppm: 1.74-1.76 (1H, m), 1.94-2.00 (1H, m), 2.47 (2H, t, J=7.7 Hz), 2.80-3.14 (6H, m), 3.72 (1H, d, J=8.8 Hz), 3.80-3.85 (1H, m), 4.03 (1H, d, J=8.8 Hz), 4.50 (1H, s), 4.89 (1H, d, J=6.4 Hz), 6.59 (1H, dd, J=9.1 Hz, 3.7 Hz), 7.01-7.05 (2H, m), 7.18 (1H, d, J=7.3 Hz), 7.28-7.31 (1H, m), 7.40 (1H, dd, J=7.9 Hz, 0.9 Hz), 10.03 (1H, s).

Example 319

5-{[(3R,4R)-1-(2,4-Difluorophenyl)-3,4-dihydroxypiperidin-4-yl]methoxy}-8-fluoro-3,4-dihydroquinolin-2(1H)-one Synthesized analogous to Example 259.
(Ethanol/water) m.p. 175.2-176.1° C.
$^1$HNMR (DMSO-d6) δ ppm: 1.72-1.74 (1H, m), 1.92-1.97 (1H, m), 2.47 (2H, t, J=7.8 Hz), 2.80-3.11 (6H, m), 3.69 (1H, d, J=8.8 Hz), 3.78-3.82 (1H, m), 4.02 (1H, d, J=8.8 Hz), 4.53 (1H, s), 4.91 (1H, d, J=6.4 Hz), 6.58 (1H, dd, J=9.1 Hz, 3.8 Hz), 6.97-7.21 (4H, m), 10.03 (1H, s).

Example 320

5-{[(3R,4R)-1-(2,6-Difluorophenyl)-3,4-dihydroxypiperidin-4-yl]methoxy}-8-fluoro-3,4-dihydroquinolin-2(1H)-one Synthesized analogous to Example 259.
$^1$HNMR (DMSO-d6) δ ppm: 1.68-1.70 (1H, m), 1.89-1.95 (1H, m), 2.45-2.49 (2H, m), 2.84-2.99 (4H, m), 3.21-3.25 (1H, m), 3.32-3.38 (1H, m), 3.68 (1H, d, J=8.8 Hz), 3.72-3.77 (1H, m), 4.02 (1H, d, J=8.8 Hz), 4.51 (1H, s), 4.85 (1H, d, J=6.5 Hz), 6.58 (1H, dd, J=9.1 Hz, 3.7 Hz), 6.99-7.08 (4H, m), 10.03 (1H, s).

Example 321

5-{[(3R,4R)-3,4-Dihydroxy-1-phenylpiperidin-4-yl]methoxy}-8-fluoro-3,4-dihydroquinolin-2(1H)-one Synthesized analogous to Example 259.
(Ethanol/water) m.p. 202.8-203.5° C.
$^1$HNMR (DMSO-d6) δ ppm: 1.68-1.71 (1H, m), 1.88-1.94 (1H, m), 2.39-2.42 (2H, m), 2.72-2.86 (3H, m), 2.92-2.98 (1H, m), 3.46-3.51 (2H, m), 3.67 (1H, d, J=8.8 Hz), 3.72-3.77 (1H, m), 4.01 (1H, d, J=8.8 Hz), 4.53 (1H, s), 4.86 (1H, d, J=6.5 Hz), 6.56 (1H, dd, J=9.1 Hz, 3.8 Hz), 6.74 (1H, d, J=8.0 Hz), 6.94 (2H, d, J=8.0 Hz), 6.99-7.03 (1H, m), 7.20 (2H, dd, J=7.3 Hz, 8.7 Hz), 10.01 (1H, s).

Example 322

5-({(3R,4R)-3,4-Dihydroxy-1-[4-(trifluoromethoxy)phenyl]piperidin-4-yl}methoxy)-8-fluoro-3,4-dihydroquinolin-2(1H)-one Synthesized analogous to Example 259.
(Ethanol/water) m.p. 196.0-197.1° C.
$^1$HNMR (DMSO-d6) δ ppm: 1.68-1.71 (1H, m), 1.88-1.94 (1H, m), 2.38-2.41 (2H, m), 2.71-3.02 (4H, m), 3.50-3.53 (2H, m), 3.66 (1H, d, J=8.8 Hz), 3.71-3.75 (1H, m), 4.01 (1H, d, J=8.8 Hz), 4.58 (1H, s), 4.91 (1H, d, J=6.6 Hz), 6.56 (1H, dd, J=9.1 Hz, 3.7 Hz), 6.99-7.03 (3H, m), 7.18 (2H, d, J=8.6 Hz), 10.02 (1H, s).

Example 323

5-({(3R,4R)-1-[4-(Difluoromethoxy)phenyl]-3,4-dihydroxypiperidin-4-yl}methoxy)-8-fluoro-3,4-dihydroquinolin-2(1H)-one Synthesized analogous to Example 259.
(Ethanol/water) m.p. 163.1-164.6° C.
$^1$HNMR (DMSO-d6) δ ppm: 1.68-1.71 (1H, m), 1.88-1.95 (1H, m), 2.40-2.43 (2H, m), 2.75-2.86 (3H, m), 2.92-2.97 (1H, m), 3.43-3.51 (2H, m), 3.66 (1H, d, J=8.8 Hz), 3.72-3.77 (1H, m), 4.01 (1H, d, J=8.8 Hz), 4.54 (1H, s), 4.87 (1H, d, J=6.6 Hz), 6.56 (1H, dd, J=9.1 Hz, 3.8 Hz), 6.90-7.22 (6H, m), 10.01 (1H, s).

Example 324

5-{[(3R,4R)-1-(4-Chloro-2-fluorophenyl)-3,4-dihydroxypiperidin-4-yl]methoxy}-7,8-difluoro-3,4-dihydroquinolin-2(1H)-one Synthesized analogous to Example 259.
(Ethyl acetate) m.p. 192.6-193.4° C.
$^1$HNMR (DMSO-d6) δ ppm: 1.70-1.77 (1H, m), 1.87-1.95 (1H, m), 2.45 (2H, t, J=7.5 Hz), 2.77-2.90 (3H, m), 2.93-3.01 (1H, m), 3.06-3.13 (1H, m), 3.14-3.19 (1H, m), 3.71 (1H, d, J=9.0 Hz)), 3.74-3.80 (1H, m), 4.01 (1H, d, J=9.0 Hz), 4.59 (1H, s), 4.95 (1H, d, J=6.0 Hz), 6.71 (1H, dd, J=12.5 Hz, 6.0 Hz), 7.06 (1H, t, J=9.0 Hz), 7.16 (1H, dd, J=8.5 Hz, 2.0 Hz), 7.31 (1H, dd, J=12.5 Hz, 2.5 Hz), 10.31 (1H, s).

Example 325

5-{[(3R,4R)-1-(4-Bromo-2,6-difluorophenyl)-3,4-dihydroxypiperidin-4-yl]methoxy}-7,8-difluoro-3,4-dihydroquinolin-2(1H)-one Synthesized analogous to Example 42.
(Ethyl acetate) m.p. 204.5-204.6° C.
$^1$HNMR (DMSO-d6) δ ppm: 1.67-1.70 (1H, m), 1.84-1.90 (1H, m), 2.48 (2H, t, J=7.5 Hz), 2.80-2.91 (3H, m), 2.95-2.98 (1H, m), 3.17-3.22 (1H, m), 3.30-3.38 (1H, m), 3.68-3.72 (1H, m), 3.71 (1H, d, J=9.0 Hz), 4.01 (1H, d, J=9.0

Hz), 4.56 (1H, brs), 4.89 (1H, d, J=5.5 Hz), 6.73 (1H, dd, J=12.5 Hz, 6.0 Hz), 7.35-7.40 (2H, m), 10.31 (1H, brs).

Example 326

5-{[(3R,4R)-1-(4-Bromo-2,6-difluorophenyl)-3,4-dihydroxypiperidin-4-yl]methoxy}-8-chloro-3,4-dihydroquinolin-2(1H)-one Synthesized analogous to Example 42.
(Ethyl acetate/methanol) m.p. 203.6-203.7° C.
¹HNMR (DMSO-d6) δ ppm: 1.68-1.71 (1H, m), 1.86-1.92 (1H, m), 2.49 (2H, t, J=7.5 Hz), 2.85-2.92 (3H, m), 2.94-2.98 (1H, m), 3.18-3.23 (1H, m), 3.30-3.38 (1H, m), 3.70-3.75 (1H, m), 3.72 (1H, d, J=9.0 Hz), 4.05 (1H, d, J=9.0 Hz), 4.57 (1H, brs), 4.89 (1H, d, J=6.5 Hz), 6.68 (1H, d, J=9.0 Hz), 7.25 (1H, d, J=9.0 Hz), 7.35-7.41 (2H, m), 9.37 (1H, brs).

Example 327

8-Chloro-5-{[(3R,4R)-1-(4-chloro-2-fluorophenyl)-3,4-dihydroxypiperidin-4-yl]methoxy}-7-fluoro-3,4-dihydroquinolin-2(1H)-one Synthesized analogous to Example 259.
¹HNMR (DMSO-d6) δ ppm: 1.73-1.76 (1H, m), 1.88-1.94 (1H, m), 2.46-2.50 (2H, m), 2.79-3.18 (6H, m), 3.75-3.79 (2H, m), 4.06 (1H, d, J=9.1 Hz), 4.61 (1H, s), 4.96 (1H, d, J=6.3 Hz), 6.81 (1H, d, J=11.5 Hz), 7.08 (1H, t, J=9.2 Hz), 7.17 (1H, dd, J=8.7 Hz, 2.2 Hz), 7.32 (1H, dd, J=12.5 Hz, 2.5 Hz), 9.69 (1H, s).

Example 328

8-Chloro-5-{[(3R,4R)-1-(4-chloro-2-fluorophenyl)-3,4-dihydroxypiperidin-4-yl]methoxy}-3,4-dihydroquinolin-2(1H)-one Synthesized analogous to Example 259.
(Ethyl acetate/ethanol) m.p. 185.0-186.4° C.
¹HNMR (DMSO-d6) δ ppm: 1.70-1.77 (1H, m), 1.90-1.98 (1H, m), 2.46 (2H, t, J=7.5 Hz), 2.81-2.93 (3H, m), 2.93-3.02 (1H, m), 3.06-3.13 (1H, m), 3.14-3.19 (1H, m), 3.72 (1H, d, J=9.0 Hz)), 3.74-3.83 (1H, m), 4.04 (1H, d, J=9.0 Hz), 4.59 (1H, s), 4.94 (1H, d, J=6.0 Hz), 6.67 (1H, d, J=9.0 Hz), 7.06 (1H, t, J=9.0 Hz), 7.17 (1H, dd, J=9.0 Hz, 2.5 Hz), 7.24 (1H, d, J=9.0 Hz), 7.31 (1H, dd, J=12.5 Hz, 2.5 Hz), 9.37 (1H, s).

Example 329

5-{[(3R,4R)-1-(4-Bromo-2,6-difluorophenyl)-3,4-dihydroxypiperidin-4-yl]methoxy}-8-chloro-7-fluoro-3,4-dihydroquinolin-2(1H)-one Synthesized analogous to Example 42.
(Ethyl acetate/hexane) m.p. 199.0-199.6° C.
¹HNMR (CDCl₃) δ ppm: 1.91-2.00 (2H, m), 2.37 (1H, d, J=7.5 Hz), 2.58 (1H, brs), 2.64 (2H, t, J=7.5 Hz), 2.95-2.98 (2H, m), 3.03-3.06 (1H, m), 3.23-3.30 (2H, m), 3.34-3.39 (1H, m), 3.94-3.98 (1H, m), 4.00 (1H, d, J=9.0 Hz), 4.03 (1H, d, J=9.0 Hz), 6.50 (1H, d, J=10.5 Hz), 7.02-7.07 (2H, m), 7.56 (1H, brs).

Example 330

5-{[(3R*,4R*)-1-(4-Chloro-2-fluorophenyl)-3,4-dihydroxypiperidin-4-yl]methoxy}-7,8-difluoro-3,4-dihydroquinolin-2(1H)-one Synthesized analogous to Example 257.
(Ethyl acetate/methanol) m.p. 220.5-221.3° C.
¹HNMR (DMSO-d6) δ ppm: 1.68-1.76 (1H, m), 1.86-1.96 (1H, m), 2.45 (2H, t, J=7.5 Hz), 2.76-2.90 (3H, m), 2.93-3.00 (1H, m), 3.05-3.13 (1H, m), 3.14-3.19 (1H, m), 3.71 (1H, d, J=8.9 Hz), 3.73-3.79 (1H, m), 3.98-4.05 (1H, m), 4.59 (1H, s), 4.95 (1H, d, J=6.0 Hz), 6.71 (1H, dd, J=12.6 Hz, 6.1 Hz), 7.06 (1H, t, J=9.1 Hz), 7.16 (1H, dd, J=8.1 Hz, 2.1 Hz), 7.31 (1H, dd, J=12.5 Hz, 2.4 Hz), 10.31 (1H, s).

Example 331

5-{[(3R,4R)-1-(1,3-Benzoxazol-2-yl)-3,4-dihydroxypiperidin-4-yl]methoxy}-8-fluoro-3,4-dihydroquinolin-2(1H)-one Synthesized analogous to Example 246.
(Ethanol/ethyl acetate) m.p. 190-191° C.
¹HNMR (DMSO-d6) δ ppm: 1.76-1.82 (1H, m), 1.84-1.93 (1H, m), 2.36 (2H, t, J=7.7 Hz), 2.71-2.86 (2H, m), 3.19-3.27 (1H, m), 3.30-3.41 (1H, m), 3.69-3.76 (2H, m), 3.93-4.02 (2H, m), 4.03 (1H, d, J=8.9 Hz), 4.80 (1H, s), 5.17 (1H, d, J=6.1 Hz), 6.56 (1H, dd, J=9.2 Hz, 3.8 Hz), 6.97-7.04 (2H, m), 7.15 (1H, dt, J=1.1 Hz, 7.7 Hz), 7.28 (1H, d, J=7.3 Hz), 7.40 (1H, d, J=7.8 Hz), 10.00 (1H, s).

Example 332

5-{[(3R,4R)-3,4-Dihydroxy-1-(1-methyl-1H-benzimidazol-2-yl)piperidin-4-yl]methoxy}-8-fluoro-3,4-dihydroquinolin-2(1H)-one Synthesized analogous to Example 245.
(Ethanol) m.p. 138-147° C.
¹HNMR (DMSO-d6) δ ppm: 1.69-1.75 (1H, m), 2.01-2.10 (1H, m), 2.41 (2H, t, J=7.6 Hz), 2.79-2.91 (2H, m), 3.11 (1H, t, J=11.3 Hz), 3.20-3.29 (1H, m), 3.36-3.44 (2H, m), 3.60 (3H, s), 3.70 (1H, d, J=8.8 Hz), 3.92-4.01 (1H, m), 4.04 (1H, d, J=8.8 Hz), 4.62 (1H, s), 4.96 (1H, d, J=6.4 Hz), 6.58 (1H, dd, J=9.1 Hz, 3.8 Hz), 7.02 (1H, t, J=9.7 Hz), 7.05-7.11 (2H, m), 7.29-7.35 (1H, m), 7.37-7.42 (1H, m), 10.02 (1H, s).

Example 333

5-{[(3R,4R)-1-(6-Chloro-1,3-benzoxazol-2-yl)-3,4-dihydroxypiperidin-4-yl]methoxy}-8-fluoro-3,4-dihydroquinolin-2(1H)-one Synthesized analogous to Example 246.
(Ethanol) m.p. 219-220° C.
¹HNMR (DMSO-d6) δ ppm: 1.76-1.83 (1H, m), 1.83-1.93 (1H, m), 2.38 (2H, t, J=7.7 Hz), 2.73-2.88 (2H, m), 3.24 (1H, t, J=11.5 Hz), 3.35-3.43 (1H, m), 3.67-3.77 (2H, m), 3.91-4.00 (2H, m), 4.03 (1H, d, J=8.9 Hz), 4.82 (1H, s), 5.19 (1H, d, J=6.0 Hz), 6.56 (1H, dd, J=9.1 Hz, 3.8 Hz), 7.01 (1H, t, J=9.7 Hz), 7.19 (1H, dd, J=8.4 Hz, 2.0 Hz), 7.26 (1H, d, J=8.4 Hz), 7.58 (1H, d, J=2.0 Hz), 10.01 (1H, s).

Example 334

8-Chloro-5-{[(3R*,4R*)-1-(4-chloro-2-fluorophenyl)-3,4-dihydroxypiperidin-4-yl]methoxy}-3,4-dihydroquinolin-2(1H)-one Synthesized analogous to Example 257.
(Ethyl acetate) m.p. 195.5-195.6° C.
$^1$HNMR (CDCl$_3$) δ ppm: 1.95-2.02 (2H, m), 2.42 (2H, d, J=7.0 Hz), 2.59 (1H, s), 2.62 (2H, t, J=7.5 Hz), 2.91-3.02 (3H, m), 3.02-3.09 (1H, m), 3.15-3.21 (1H, m), 3.99-4.08 (3H, m), 6.57 (1H, d, J=9.0 Hz), 6.90-6.94 (1H, m), 7.04-7.08 (2H, m), 7.19 (1H, d, J=9.0 Hz), 7.75 (1H, brs).

Example 335

5-{[(3R,4R)-1-(1H-Benzimidazol-2-yl)-3,4-dihydroxypiperidin-4-yl]methoxy}-8-fluoro-3,4-dihydroquinolin-2(1H)-one Synthesized analogous to Example 245.
(Ethanol/water) m.p. 279-281° C.
$^1$HNMR (DMSO-d6) δ ppm: 1.69-1.77 (1H, m), 1.82-1.92 (1H, m), 2.31 (2H, t, J=7.7 Hz), 2.66-2.80 (2H, m), 3.08 (1H, t, J=11.5 Hz), 3.18-3.27 (1H, m), 3.69 (1H, d, J=8.9 Hz), 3.69-3.76 (1H, m), 3.83-3.91 (1H, m), 3.97 (1H, dd, J=12.3 Hz, 4.8 Hz), 4.02 (1H, d, J=8.9 Hz), 4.68 (1H, s), 5.05 (1H, d, J=6.7 Hz), 6.56 (1H, dd, J=9.1 Hz, 3.8 Hz), 6.88-6.95 (2H, m), 7.00 (1H, t, J=9.7 Hz), 7.15-7.21 (2H, m), 9.99 (1H, s), 11.46 (1H, brs).

Example 336

8-Fluoro-5-{[(3R*,4R*)-1-(4-fluorophenyl)-3,4-dihydroxypiperidin-4-yl]methoxy}-3,4-dihydroquinolin-2(1H)-one Synthesized analogous to Example 42.
(Ethyl acetate) m.p. 182.4-182.5° C.
$^1$HNMR (DMSO-d6) δ ppm: 1.68-1.71 (1H, m), 1.89-1.96 (1H, m), 2.42 (2H, t, J=8.0 Hz), 2.75-2.84 (3H, m), 2.90-2.94 (1H, m), 3.37-3.41 (2H, m), 3.66 (1H, d, J=8.5 Hz), 3.73-3.78 (1H, m), 4.01 (1H, d, J=8.5 Hz), 4.53 (1H, brs), 4.86 (1H, d, J=6.5 Hz), 6.56 (1H, dd, J=9.0 Hz, 4.0 Hz), 6.95-7.06 (5H, m), 10.02 (1H, brs).

Example 337

8-Fluoro-5-{[(3R,4R)-1-(4-fluorophenyl)-3,4-dihydroxypiperidin-4-yl]methoxy}-3,4-dihydroquinolin-2(1H)-one Synthesized analogous to Example 42.
(Ethyl acetate) m.p. 185.2-185.3° C.
$^1$HNMR (DMSO-d6) δ ppm: 1.68-1.71 (1H, m), 1.89-1.96 (1H, m), 2.42 (2H, t, J=8.0 Hz), 2.75-2.84 (3H, m), 2.90-2.94 (1H, m), 3.37-3.41 (2H, m), 3.66 (1H, d, J=9.0 Hz), 3.73-3.78 (1H, m), 4.01 (1H, d, J=9.0 Hz), 4.53 (1H, brs), 4.86 (1H, d, J=6.5 Hz), 6.56 (1H, dd, J=9.0 Hz, 4.0 Hz), 6.95-7.06 (5H, m), 10.02 (1H, brs).

Example 338

8-Bromo-5-{[(3R,4R)-1-(4-chloro-2-fluorophenyl)-3,4-dihydroxypiperidin-4-yl]methoxy}-3,4-dihydroquinolin-2(1H)-one Synthesized analogous to Example 42.
$^1$HNMR (DMSO-d6) δ ppm: 1.71-1.78 (1H, m), 1.90-1.98 (1H, m), 2.48 (2H, t, J=7.7 Hz), 2.81-2.94 (3H, m), 2.95-3.02 (1H, m), 3.07-3.13 (1H, m), 3.14-3.21 (1H, m), 3.73 (1H, d, J=8.8 Hz), 3.76-3.83 (1H, m), 4.05 (1H, d, J=8.8 Hz), 4.60 (1H, brs), 4.94-4.98 (1H, m), 6.65 (1H, d, J=9.0 Hz), 7.08 (1H, t, J=9.0 Hz), 7.17 (1H, dd, J=8.7 Hz, 2.2 Hz), 7.32 (1H, dd, J=12.5 Hz, 2.2 Hz), 7.40 (1H, d, J=8.7 Hz), 8.95 (1H, brs).

Example 339

5-{[(3R*,4R*)-1-(4-Bromo-2,6-difluorophenyl)-3,4-dihydroxypiperidin-4-yl]methoxy}-8-chloro-3,4-dihydroquinolin-2(1H)-one Synthesized analogous to Example 257.
(Ethyl acetate) m.p. 195-198° C.
$^1$HNMR (DMSO-d6) δ ppm: 1.70 (1H, d, J=13.5 Hz), 1.86-1.93 (1H, m), 2.46-2.50 (2H, m), 2.85-2.99 (4H, m), 3.18-3.34 (2H, m), 3.70-3.75 (2H, m), 4.06 (1H, d, J=8.7 Hz), 4.56 (1H, s), 4.88 (1H, d, J=6.4 Hz), 6.68 (1H, d, J=8.9 Hz), 7.25 (1H, d, J=8.9 Hz), 7.34-7.41 (2H, m), 9.36 (1H, s).

Example 340

5-{[(3R*,4R*)-1-(2-Bromo-4-chloro-6-fluorophenyl)-3,4-dihydroxypiperidin-4-yl]methoxy}-8-fluoro-3,4-dihydroquinolin-2(1H)-one To a solution of 5-{[(3R*,4R*)-1-(2-bromo-4-chloro-6-fluorophenyl)-3-{[tert-butyl(dimethyl)silyl]oxy}-4-hydroxypiperidin-4-yl]methoxy}-8-fluoro-3,4-dihydroquinolin-2(1H)-one (0.16 g) in tetrahydrofuran (THF) (3.2 mL) was added 1.0 M tetra-n-butylammonium fluoride (TBAF) tetrahydrofuran (THF) solution (0.304 mL), and the reaction mixture was stirred at room temperature for 30 min. To the reaction solution was added water, and the precipitate was collected on a filter. The obtained crystal was washed with acetone, the crystal was collected on a filter, and dried under reduced pressure (60° C.) to provide the title compound (0.11 g).
$^1$HNMR (DMSO-d6) δ ppm: 1.68 (1H, d, J=13.4 Hz), 1.73-1.80 (1H, m), 1.87-2.06 (1H, m), 2.47 (2H, t, J=7.7 Hz), 2.73-2.85 (1H, m), 2.85-2.99 (2H, m), 3.16-3.28 (1H, m), 3.28-3.40 (1H, m), 3.68 (1H, d, J=8.9 Hz), 3.75-3.86 (1H, m), 4.03 (1H, d, J=8.9 Hz), 4.51 (1H, s), 4.84 (1H, d, J=6.6 Hz), 6.58 (1H, dd, J=9.1 Hz, 3.8 Hz), 7.02 (1H, t, J=6.3 Hz), 7.49 (1H, dd, J=11.5 Hz, 2.4 Hz), 7.59-7.65 (1H, m), 10.02 (1H, brs).

Example 341

8-Bromo-5-{[(3R,4R)-1-(4-chloro-2,6-difluorophenyl)-3,4-dihydroxypiperidin-4-yl]methoxy}-3,4-dihydroquinolin-2(1H)-one Synthesized analogous to Example 42.
¹HNMR (DMSO-d6) δ ppm: 1.66-1.74 (1H, m), 1.85-1.94 (1H, m), 2.49 (2H, t, J=7.7 Hz), 2.85-2.95 (4H, m), 3.08-3.15 (1H, m), 3.30-3.38 (1H, m), 3.69-3.76 (2H, m), 4.05 (1H, d, J=8.9 Hz), 4.58 (1H, brs), 4.88-4.92 (1H, m), 6.65 (1H, d, J=9.0 Hz), 7.24-7.31 (2H, m), 7.40 (1H, d, J=9.0 Hz), 8.95 (1H, brs).

Example 342

5-{[(3R*,4R*)-1-(4-Chloro-2,5-difluorophenyl)-3,4-dihydroxypiperidin-4-yl]methoxy}-8-fluoro-3,4-dihydroquinolin-2(1H)-one Synthesized analogous to Example 257.
¹HNMR (DMSO-d6) δ ppm: 1.66-1.77 (1H, m), 1.86-1.98 (1H, m), 2.45 (2H, t, J=7.7 Hz), 2.74-2.94 (3H, m), 2.96-3.07 (1H, m), 3.09-3.20 (1H, m), 3.20-3.26 (1H, m), 3.69 (1H, d, J=8.8 Hz), 3.74-3.86 (1H, m), 4.02 (1H, d, J=8.8 Hz), 4.59 (1H, s), 4.96 (1H, d, J=6.4 Hz), 6.57 (1H, dd, J=9.1 Hz, 3.8 Hz), 7.01 (1H, t, J=9.7 Hz), 7.11 (1H, dd, J=11.3 Hz, 7.9 Hz), 7.50 (1H, dd, J=10.6 Hz, 7.1 Hz), 10.02 (1H, brs).

Example 343

5-{[(3R,4R)-1-(5,6-Difluoro-1-methyl-1H-benzimidazol-2-yl)-3,4-dihydroxypiperidin-4-yl]methoxy}-8-fluoro-3,4-dihydroquinolin-2(1H)-one Synthesized analogous to Example 245.
¹HNMR (DMSO-d6) δ ppm: 1.68-1.74 (1H, m), 1.98-2.08 (1H, m), 2.41 (2H, t, J=7.6 Hz), 2.79-2.90 (2H, m), 3.11 (1H, t, J=11.4 Hz), 3.19-3.28 (1H, m), 3.36-3.44 (2H, m), 3.59 (3H, s), 3.70 (1H, d, J=8.9 Hz), 3.90-3.97 (1H, m), 4.03 (1H, d, J=8.9 Hz), 4.63 (1H, s), 4.96 (1H, d, J=6.4 Hz), 6.58 (1H, dd, J=9.1 Hz, 3.8 Hz), 7.02 (1H, t, J=9.7 Hz), 7.43 (1H, dd, J=11.3 Hz, 7.5 Hz), 7.51 (1H, dd, J=10.8 Hz, 7.4 Hz), 10.01 (1H, s).

Example 344

5-({(3R,4R)-3,4-Dihydroxy-1-[1-(methoxymethyl)-1H-benzimidazol-2-yl]piperidin-4-yl}methoxy)-8-fluoro-3,4-dihydroquinolin-2(1H)-one Synthesized analogous to Example 245.
¹HNMR (DMSO-d6) δ ppm: 1.68-1.75 (1H, m), 1.99-2.09 (1H, m), 2.40 (2H, t, J=7.7 Hz), 2.79-2.91 (2H, m), 3.13 (1H, t, J=11.4 Hz), 3.23-3.32 (1H, m), 3.36 (3H, s), 3.50-3.60 (2H, m), 3.70 (1H, d, J=8.9 Hz), 3.89-3.97 (1H, m), 4.03 (1H, d, J=8.9 Hz), 4.62 (1H, s), 4.96 (1H, d, J=6.6 Hz), 5.33 (2H, s), 6.58 (1H, dd, J=9.2 Hz, 3.8 Hz), 7.02 (1H, t, J=9.7 Hz), 7.08-7.15 (2H, m), 7.38-7.42 (1H, m), 7.43-7.47 (1H, m), 10.01 (1H, s).

Example 345

8-Fluoro-5-{[(3R,4R)-1-(2-fluoro-4-hydroxyphenyl)-3,4-dihydroxypiperidin-4-yl]methoxy}-3,4-dihydroquinolin-2(1H)-one Under nitrogen atmosphere, a solution of 5-{[(3R,4R)-1-(4-bromo-2-fluorophenyl)-3,4-dihydroxypiperidin-4-yl]methoxy}-8-fluoro-3,4-dihydroquinolin-2(1H)-one (707 mg), tris(dibenzylideneacetone)dipalladium (0) (13.4 mg), di-tert-butyl[3,4,5,6-tetramethyl-2',4',6'-tri(propan-2-yl)biphenyl-2-yl]phosphane (14.07 mg) and potassium hydroxide (386 mg) in 1,4-dioxane-water (1:1) (1.5 mL) was stirred at 100° C. for 5 h. To the reaction solution was added 2 N hydrochloric acid, and the precipitate was collected on a filter. The obtained solid was washed with water and ethyl acetate, and vacuum-dried (100° C.) to provide the title compound (411 mg).
¹HNMR (DMSO-d6) δ ppm: 1.77-1.80 (1H, m), 2.13-2.18 (1H, m), 2.48 (2H, t, J=7.5 Hz), 2.88-2.98 (2H, m), 3.10-3.30 (4H, m), 3.71 (1H, d, J=9.0 Hz), 3.98-4.04 (1H, m), 4.05 (1H, d, J=9.0 Hz), 6.59 (1H, dd, J=9.0 Hz, 4.0 Hz), 6.63-6.64 (1H, m), 6.67-6.70 (1H, m), 7.03 (1H, t, J=9.0 Hz), 7.27-7.35 (1H, m), 10.04 (1H, brs).

Example 346

5-{[(3R,4R)-1-(4-Chloro-2,6-difluorophenyl)-3,4-dihydroxypiperidin-4-yl]methoxy}-3,4-dihydroquinolin-2(1H)-one A suspension of 5-hydroxy-3,4-dihydroquinolin-2(1H)-one (0.4 g), (3R,4R)-6-(4-chloro-2,6-difluorophenyl)-1-oxa-6-azaspiro[2.5]octan-4-ol (0.614 g) and potassium bicarbonate (0.021 mL) in N,N-dimethylformamide:2-propanol (1:4) (3 mL) was stirred at 70° C. for 21 h. To the reaction solution were added water and diisopropyl ether, the insoluble precipitate was collected on a filter, and the obtained solid was recrystallized form acetic acid/water. The precipitate was collected on a filter, and dried under reduced pressure (70° C.) to provide the title compound (0.73 g, 98% ee).

m.p. 211-212° C.
¹HNMR (DMSO-d6) δ ppm: 1.65-1.72 (1H, m), 1.86-1.98 (1H, m), 2.43 (2H, t, J=7.8 Hz), 2.77-2.94 (3H, m), 2.94-3.00 (1H, m), 3.21 (1H, t, J=10.7 Hz), 3.29-3.44 (1H, m, overlapping with H₂O signal), 3.68 (1H, d, J=8.8 Hz), 3.71-3.79 (1H, m), 4.04 (1H, d, J=8.8 Hz), 4.54 (1H, s), 4.88 (1H, d, J=6.5 Hz), 6.49 (1H, d, J=8.1 Hz), 6.59 (1H, d, J=8.1 Hz), 7.09 (1H, t, J=8.1 Hz), 7.23-7.32 (2H, m), 10.04 (1H, s).

Example 347

5-{[(3R,4R)-1-(4-Bromo-2-fluorophenyl)-3,4-dihydroxypiperidin-4-yl]methoxy}-3,4-dihydroquinolin-2(1H)-one Synthesized analogous to Example 346.
(Acetic acid/water) m.p. 226-227° C.
¹HNMR (DMSO-d6) δ ppm: 1.69-1.78 (1H, m), 1.91-2.01 (1H, m), 2.42 (2H, t, J=7.8 Hz), 2.75-2.90 (3H, m), 2.94-3.03 (1H, m), 3.06-3.14 (1H, m), 3.14-3.22 (1H, m), 3.69 (1H, d, J=8.8 Hz), 3.78-3.85 (1H, m), 4.04 (1H, d, J=8.8 Hz), 4.57 (1H, s), 4.95 (1H, d, J=6.4 Hz), 6.49 (1H, d, J=8.1 Hz), 6.59 (1H, d, J=8.1 Hz), 7.03 (1H, t, J=9.1 Hz), 7.08 (1H, t, J=8.1 Hz), 7.30 (1H, dd, J=8.6 Hz, 1.8 Hz), 7.42 (1H, dd, J=12.3 Hz, 2.3 Hz), 10.03 (1H, s).

Example 348

5-{[(3R,4R)-1-(2,6-Difluoro-4-hydroxyphenyl)-3,4-dihydroxypiperidin-4-yl]methoxy}-8-fluoro-3,4-dihydroquinolin-2(1H)-one Synthesized analogous to Example 345.
$^1$HNMR (DMSO-d6) δ ppm: 1.64-1.67 (1H, m), 1.85-1.92 (1H, m), 2.46-2.50 (2H, m), 2.66-2.72 (1H, m), 2.75-2.79 (1H, m), 2.83-2.97 (2H, m), 3.16-3.21 (1H, m), 3.26-3.32 (1H, m), 3.67 (1H, d, J=11.0 Hz), 3.68-3.74 (1H, m), 4.00 (1H, d, J=11.0 Hz), 4.43 (1H, brs), 4.76 (1H, d, J=8.0 Hz), 6.37-6.44 (2H, m), 6.56 (1H, dd, J=11.5 Hz, 4.5 Hz), 7.02 (1H, t, J=11.5 Hz), 10.00 (1H, brs), 10.02 (1H, brs).

Example 349

5-{[(3R*,4R*)-1-(4-Chloro-2,6-difluorophenyl)-3,4-dihydroxypiperidin-4-yl]methoxy}-3,4-dihydroquinolin-2(1H)-one Synthesized analogous to Example 346.
(Acetic acid/water) m.p. 233° C.
$^1$HNMR (DMSO-d6) δ ppm: 1.65-1.72 (1H, m), 1.86-1.98 (1H, m), 2.43 (2H, t, J=7.8 Hz), 2.77-2.94 (3H, m), 2.94-3.00 (1H, m), 3.21 (1H, t, J=10.7 Hz), 3.29-3.44 (1H, m, overlapping with H$_2$O signal), 3.68 (1H, d, J=8.8 Hz), 3.71-3.79 (1H, m), 4.04 (1H, d, J=8.8 Hz), 4.54 (1H, s), 4.88 (1H, d, J=6.5 Hz), 6.49 (1H, d, J=8.1 Hz), 6.59 (1H, d, J=8.1 Hz), 7.09 (1H, t, J=8.1 Hz), 7.23-7.32 (2H, m), 10.04 (1H, s).

Example 350

5-{[(3R*,4R*)-1-(4-Bromo-2-fluorophenyl)-3,4-dihydroxypiperidin-4-yl]methoxy}-3,4-dihydroquinolin-2(1H)-one Synthesized analogous to Example 346.
$^1$HNMR (DMSO-d6) δ ppm: 1.69-1.78 (1H, m), 1.91-2.01 (1H, m), 2.42 (2H, t, J=7.8 Hz), 2.75-2.90 (3H, m), 2.94-3.03 (1H, m), 3.06-3.14 (1H, m), 3.14-3.22 (1H, m), 3.69 (1H, d, J=8.8 Hz), 3.78-3.85 (1H, m), 4.04 (1H, d, J=8.8 Hz), 4.57 (1H, s), 4.95 (1H, d, J=6.4 Hz), 6.49 (1H, d, J=8.1 Hz), 6.59 (1H, d, J=8.1 Hz), 7.03 (1H, t, J=9.1 Hz), 7.08 (1H, t, J=8.1 Hz), 7.30 (1H, dd, J=8.6 Hz, 1.8 Hz), 7.42 (1H, dd, J=12.3 Hz, 2.3 Hz), 10.03 (1H, s).

Example 351

5-{[(3R,4R)-1-(4-Chloro-2,6-difluorophenyl)-3,4-dihydroxypiperidin-4-yl]methoxy}-6,8-difluoro-3,4-dihydroquinolin-2(1H)-one A solution of 6,8-difluoro-5-hydroxy-3,4-dihydroquinolin-2(1H)-one (23 mg), (3R,4R)-6-(4-chloro-2,6-difluorophenyl)-1-oxa-6-azaspiro[2.5]octan-4-ol (31.8 mg) and potassium carbonate (3.19 mg) in 2-propanol-water (5:1) (0.5 mL) was heated to reflux for 2 h. The reaction solution was purified by silica gel column chromatography (hexane/ethyl acetate) to provide the title compound (38 mg).
$^1$HNMR (CDCl$_3$) δ ppm: 1.88-1.95 (2H, m), 2.60 (1H, d, J=6.5 Hz), 2.64 (2H, t, J=7.5 Hz), 2.81 (1H, brs), 3.01-3.05 (1H, m), 3.08 (2H, t, J=7.5 Hz), 3.26 (2H, d, J=7.0 Hz), 3.33-3.39 (1H, m), 3.99 (1H, d, J=9.0 Hz), 4.00-4.04 (1H, m), 4.12 (1H, d, J=9.0 Hz), 6.85 (1H, t, J=10.0 Hz), 6.86-6.92 (2H, m), 7.53 (1H, brs).

Example 352

5-{[(3R,4R)-1-(2,6-Difluoro-4-methoxyphenyl)-3,4-dihydroxypiperidin-4-yl]methoxy}-8-fluoro-3,4-dihydroquinolin-2(1H)-one To a suspension of 5-{[(3R,4R)-1-(2,6-difluoro-4-hydroxyphenyl)-3,4-dihydroxypiperidin-4-yl]methoxy}-8-fluoro-3,4-dihydroquinolin-2(1H)-one (244 mg) and potassium carbonate (230 mg) in N,N-dimethylformamide (2.4 mL) was added methyl iodide (0.313 mL), and the reaction mixture was stirred at 90-100° C. for 8 h. To the reaction solution was added water, and the solution was extracted with ethyl acetate. The organic layer was washed with brine, dried over anhydrous sodium sulfate, and the solvent was distilled off. The residue was purified by silica gel column chromatography (hexane/ethyl acetate), and the product obtained from higher polarity fractions was recrystallized from ethyl acetate/hexane. The precipitate was collected on a filter and dried to provide the title compound (78 mg).
m.p. 167.1-167.3° C.
$^1$HNMR (DMSO-d6) δ ppm: 1.66-1.68 (1H, m), 1.86-1.92 (1H, m), 2.47 (2H, t, J=8.0 Hz), 2.72-2.74 (1H, m), 2.80-2.83 (1H, m), 2.84-2.95 (2H, m), 3.18-3.22 (1H, m), 3.28-3.35 (1H, m), 3.67 (1H, d, J=9.0 Hz), 3.70-3.74 (1H, m), 3.73 (3H, s), 4.01 (1H, d, J=9.0 Hz), 4.46 (1H, brs), 4.79 (1H, d, J=6.5 Hz), 6.58 (1H, dd, J=9.0 Hz, 4.0 Hz), 6.66-6.72 (2H, m), 7.02 (1H, t, J=9.0 Hz), 10.03 (1H, brs).

Example 353

5-{[(3R,4R)-1-(2,6-Difluoro-4-methoxyphenyl)-3,4-dihydroxypiperidin-4-yl]methoxy}-8-fluoro-1-methyl-3,4-dihydroquinolin-2(1H)-one The lower polarity fractions of Example 352 was vacuum-dried (100° C.) to provide the title compound (68 mg).
$^1$HNMR (CDCl$_3$) δ ppm: 1.92-1.95 (2H, m), 2.56-2.60 (2H, m), 2.73 (1H, d, J=8.0 Hz), 2.74 (1H, brs), 2.85-2.99 (3H, m), 3.18-3.24 (2H, m), 3.26-3.32 (1H, m), 3.42 (3H, d, J=7.0 Hz), 3.75 (3H, s), 3.95-3.98 (1H, m), 4.00 (1H, d, J=9.5 Hz), 4.07 (1H, d, J=9.5 Hz), 6.40-6.46 (2H, m), 6.63 (1H, dd, J=9.0 Hz, 3.0 Hz), 6.95 (1H, dd, J=12.5 Hz, 9.0 Hz).

Example 354

5-{[(3R,4R)-1-(2,6-Difluoro-4-propoxyphenyl)-3,4-dihydroxypiperidin-4-yl]methoxy}-8-fluoro-3,4-dihydroquinolin-2(1H)-one Synthesized analogous to Example 148.
(Ethyl acetate/hexane) m.p. 194.8-195.0° C.
$^1$HNMR (DMSO-d6) δ ppm: 0.95 (3H, t, J=7.0 Hz), 1.66-1.73 (3H, m), 1.86-1.92 (1H, m), 2.48 (2H, t, J=7.5 Hz), 2.71-2.74 (1H, m), 2.79-2.83 (1H, m), 2.84-2.95 (2H, m), 3.18-3.22 (1H, m), 3.28-3.35 (1H, m), 3.67 (1H, d, J=9.0 Hz), 3.70-3.74 (1H, m), 3.90 (2H, t, J=6.5 Hz), 4.01 (1H, d, J=9.0 Hz), 4.46 (1H, brs), 4.79 (1H, d, J=6.5 Hz), 6.58 (1H, dd, J=9.0 Hz, 4.0 Hz), 6.64-6.70 (2H, m), 7.02 (1H, t, J=9.0 Hz), 10.03 (1H, brs).

Example 355

5-{[(3R,4R)-1-(4-Butoxy-2,6-difluorophenyl)-3,4-dihydroxypiperidin-4-yl]methoxy}-8-fluoro-3,4-dihydroquinolin-2(1H)-one Synthesized analogous to Example 148.
(Ethyl acetate/hexane) m.p. 185.8-186.2° C.
$^1$HNMR (DMSO-d6) δ ppm: 0.92 (3H, t, J=7.0 Hz), 1.37-1.44 (2H, m), 1.63-1.69 (3H, m), 1.86-1.91 (1H, m), 2.48 (2H, t, J=7.5 Hz), 2.71-2.74 (1H, m), 2.79-2.82 (1H, m), 2.85-2.96 (2H, m), 3.18-3.22 (1H, m), 3.28-3.35 (1H, m), 3.67 (1H, d, J=8.5 Hz), 3.70-3.74 (1H, m), 3.93 (2H, t, J=6.5 Hz), 4.01 (1H, d, J=8.5 Hz), 4.46 (1H, brs), 4.79 (1H, d, J=6.5 Hz), 6.58 (1H, dd, J=9.0 Hz, 3.5 Hz), 6.64-6.70 (2H, m), 7.02 (1H, t, J=9.0 Hz), 10.03 (1H, brs).

Example 356

5-{[(3R*,4S*)-1-(3,5-Dichloropyridin-2-yl)-3,4-dihydroxypiperidin-4-yl]methoxy}-8-fluoro-3,4-dihydroquinolin-2(1H)-one A solution of tert-butyl (1S*,6S*)-6-{[(8-fluoro-2-oxo-1,2,3,4-tetrahydroquinolin-5-yl)oxy]methyl}-7-oxa-3-azabicyclo[4.1.0]heptane-3-carboxylate (392 mg) in trifluoroacetic acid (10 mL) was stirred at 60° C. for 3 h, and the reaction solution was concentrated. To the residue were added 2,3,5-trichloropyridine (219 mg), potassium carbonate (691 mg) and N-methyl-2-pyrrolidone (NMP) (5 mL), the mixture was stirred at 100° C. for 5 h, water was added thereto, and the solution was extracted with ethyl acetate. The organic layer was washed with water and brine, dried over anhydrous sodium sulfate, and the solvent was distilled off. The residue was purified by silica gel column chromatography (dichloromethane/ethyl acetate), washed with diethyl ether and dried to provide the title compound (188 mg).
$^1$HNMR (DMSO-d6) δ ppm: 1.45-1.43 (1H, m), 2.03-2.11 (1H, m), 2.45 (2H, t, J=7.6 Hz), 2.89-2.99 (2H, m), 3.16-3.27 (2H, m), 3.40-3.50 (2H, m), 3.60-3.70 (3H, m), 3.80 (1H, d, J=9.4 Hz), 3.94 (1H, d, J=9.4 Hz), 6.56 (1H, dd, J=9.1 Hz, 3.8 Hz), 6.99 (1H, t, J=9.7 Hz), 7.94 (1H, d, J=2.3 Hz), 8.20 (1H, d, J=2.3 Hz), 9.99 (1H, brs).

Example 357

5-{[(3R*,4S*)-1-(4-Chloro-2-fluorophenyl)-3,4-dihydroxypiperidin-4-yl]methoxy}-8-fluoro-3,4-dihydroquinolin-2(1H)-one To a mixture of 5-{[(3R*,4S*)-3-{[tert-butyl(dimethyl)silyl]oxy}-1-(4-chloro-2-fluorophenyl)-4-hydroxypiperidin-4-yl]methoxy}-8-fluoro-1-(4-methoxybenzyl)-3,4-dihydroquinolin-2(1H)-one (360 mg) and anisole (0.117 mL) was added trifluoroacetic acid (5 mL), the reaction mixture was stirred at 60° C. for 4 h, and the solvent was distilled off. The residue was dissolved into tetrahydrofuran (THF) (5 mL), and tetra-n-butylammonium fluoride (TBAF) (1 M tetrahydrofuran (THF) solution) (1.07 mL) was added thereto at 0° C. The solution was stirred at room temperature for 5 h, and the solvent was distilled off. The residue was purified by silica gel column chromatography (dichloromethane/ethyl acetate) and washed with diethyl ether to provide the title compound (65 mg).
$^1$HNMR (DMSO-d6) δ ppm: 1.52-1.59 (1H, m), 1.99-2.07 (1H, m), 2.45 (2H, t, J=7.9 Hz), 2.94 (2H, t, J=8.0 Hz), 3.01-3.08 (1H, m), 3.09-3.17 (2H, m), 3.20-3.26 (1H, m), 3.68 (1H, brs), 3.85 (1H, d, J=9.4 Hz), 3.96 (1H, d, J=9.4 Hz), 4.82 (2H, s), 6.57 (1H, dd, J=9.2 Hz, 3.8 Hz), 7.00 (1H, t, J=9.8 Hz), 7.06 (1H, t, J=9.3 Hz), 7.14 (1H, dd, J=8.7 Hz, 2.3 Hz), 7.29 (1H, dd, J=12.6 Hz, 2.4 Hz), 10.01 (1H, brs).

Example 358

5-{[(3R*,4S*)-1-(2,4-Dichlorophenyl)-3,4-dihydroxypiperidin-4-yl]methoxy}-8-fluoro-3,4-dihydroquinolin-2(1H)-one Synthesized analogous to Example 357.
$^1$HNMR (CDCl$_3$) δ ppm: 1.73-1.79 (1H, m), 2.07-2.05 (1H, m), 2.44 (1H, brs), 2.65 (2H, t, J=7.8 Hz), 2.95-3.05 (2H, m), 3.06-3.16 (2H, m), 3.22-3.27 (1H, m), 3.30 (1H, d, J=9.9 Hz), 3.35-3.39 (1H, m), 3.78-3.83 (1H, m), 3.89 (1H, d, J=8.9 Hz), 4.21 (1H, d, J=8.9 Hz), 6.55 (1H, dd, J=9.2 Hz, 4.0 Hz), 6.93 (1H, t, J=9.4 Hz), 7.08 (1H, d, J=8.6 Hz), 7.23 (1H, dd, J=8.6 Hz, 2.4 Hz), 7.40 (1H, d, J=2.5 Hz), 7.66 (1H, brs).

Example 359

5-{[(3R*,4S*)-1-(4-Chloro-2,6-difluorophenyl)-3,4-dihydroxypiperidin-4-yl]methoxy}-8-fluoro-3,4-dihydroquinolin-2(1H)-one To a solution of 5-({(3R*,4S*)-1-(4-chloro-2,6-difluorophenyl)-4-hydroxy-3-[(4-methoxybenzyl)oxy]piperidin-4-yl}methoxy)-8-fluoro-3,4-dihydroquinolin-2(1H)-one (68 mg) and anisole (0.026 mL) in dichloromethane (0.7 mL) was added trifluoroacetic acid (0.8 mL) at 0° C., and the reaction mixture was stirred at room temperature for 28.5 h. To the reaction solution was added water, neutralized with 5 N aqueous sodium hydroxide, and the solution was extracted with ethyl acetate. The organic layer was washed with brine, dried over anhydrous sodium sulfate, and the solvent was distilled off. The residue was purified by silica gel column chromatography (hexane/ethyl acetate), washed with hexane/ethyl acetate and dried to provide the title compound (19 mg).
$^1$HNMR (DMSO-d6) δ ppm: 1.49-1.52 (1H, m), 1.99-2.05 (1H, m), 2.45 (2H, t, J=7.5 Hz), 2.94 (2H, t, J=7.5 Hz), 2.95-3.00 (2H, m), 3.28-3.35 (1H, m), 3.52-3.54 (1H, m), 3.60-3.62 (1H, m), 3.83 (1H, d, J=9.5 Hz), 3.95 (1H, d, J=9.5 Hz), 4.70 (1H, d, J=5.0 Hz), 4.82 (1H, brs), 6.57 (1H, dd, J=9.0 Hz, 4.0 Hz), 7.00 (1H, t, J=9.0 Hz), 7.22-7.28 (2H, m), 10.01 (1H, brs).

Example 360

5-{[(3R,4S)-1-(4-Chloro-2,6-difluorophenyl)-3,4-dihydroxypiperidin-4-yl]methoxy}-8-fluoro-3,4-dihydroquinolin-2(1H)-one Synthesized analogous to Example 359.
$^1$HNMR (DMSO-d6) δ ppm: 1.49-1.52 (1H, m), 1.99-2.05 (1H, m), 2.45 (2H, t, J=7.5 Hz), 2.94 (2H, t, J=7.5 Hz), 2.95-3.00 (2H, m), 3.28-3.35 (1H, m), 3.52-3.54 (1H, m), 3.60-3.62 (1H, m), 3.83 (1H, d, J=9.5 Hz), 3.95 (1H, d, J=9.5 Hz), 4.69 (1H, d, J=5.5 Hz), 4.82 (1H, brs), 6.57 (1H, dd, J=9.0 Hz, 4.0 Hz), 7.00 (1H, t, J=9.0 Hz), 7.22-7.28 (2H, m), 10.01 (1H, brs).

Example 361

5-{[(3S,4R)-1-(4-Chloro-2,6-difluorophenyl)-3,4-dihydroxypiperidin-4-yl]methoxy}-8-fluoro-3,4-dihydroquinolin-2(1H)-one Synthesized analogous to Example 359.
(Acetic acid/water) m.p. 206.0-206.1° C.
$^1$HNMR (DMSO-d6) δ ppm: 1.49-1.52 (1H, m), 1.99-2.05 (1H, m), 2.45 (2H, t, J=7.5 Hz), 2.94 (2H, t, J=7.5 Hz), 2.95-3.00 (2H, m), 3.28-3.35 (1H, m), 3.52-3.54 (1H, m), 3.60-3.62 (1H, m), 3.83 (1H, d, J=9.5 Hz), 3.95 (1H, d, J=9.5 Hz), 4.69 (1H, d, J=5.5 Hz), 4.82 (1H, brs), 6.57 (1H, dd, J=9.0 Hz, 4.0 Hz), 7.00 (1H, t, J=9.0 Hz), 7.22-7.28 (2H, m), 9.99 (1H, brs).

Example 362

5-{[(3S,4R)-1-(4-Chloro-2-fluorophenyl)-3,4-dihydroxypiperidin-4-yl]methoxy}-8-fluoro-3,4-dihydroquinolin-2(1H)-one Synthesized analogous to Example 359.
(Acetic acid/water) m.p. 198.6-198.8° C.
$^1$HNMR (DMSO-d6) δ ppm: 1.54-1.57 (1H, m), 2.00-2.06 (1H, m), 2.45 (2H, t, J=7.5 Hz), 2.94 (2H, t, J=7.5 Hz), 3.02-3.06 (1H, m), 3.10-3.15 (2H, m), 3.22-3.24 (1H, m), 3.67-3.70 (1H, m), 3.85 (1H, d, J=9.5 Hz), 3.96 (1H, d, J=9.5 Hz), 4.82 (1H, brs), 4.82 (1H, d, J=4.5 Hz), 6.57 (1H, dd, J=9.0 Hz, 4.0 Hz), 7.00 (1H, t, J=9.0 Hz), 7.06 (1H, t, J=9.0 Hz), 7.13-7.15 (1H, m), 7.28 (1H, dd, J=12.5 Hz, 2.0 Hz), 10.01 (1H, brs).

Example 363

5-{[(3R,4S)-1-(4-Bromo-2-fluorophenyl)-3,4-dihydroxypiperidin-4-yl]methoxy}-8-fluoro-3,4-dihydroquinolin-2(1H)-one Synthesized analogous to Example 42.
(Ethyl acetate/methanol) m.p. 194.7-194.8° C.
$^1$HNMR (DMSO-d6) δ ppm: 1.54-1.56 (1H, m), 2.00-2.06 (1H, m), 2.45 (2H, t, J=7.5 Hz), 2.94 (2H, t, J=7.5 Hz), 3.03-3.07 (1H, m), 3.10-3.16 (2H, m), 3.22-3.24 (1H, m), 3.67-3.70 (1H, m), 3.84 (1H, d, J=9.5 Hz), 3.96 (1H, d, J=9.5 Hz), 4.82 (1H, brs), 4.83 (1H, d, J=6.0 Hz), 6.57 (1H, dd, J=9.0 Hz, 3.5 Hz), 6.98-7.03 (2H, m), 7.25-7.27 (1H, m), 7.38 (1H, dd, J=12.5 Hz, 2.0 Hz), 10.01 (1H, brs).

Example 364

5-{[(3R,4S)-1-(4-Bromo-2-fluorophenyl)-3,4-dihydroxypiperidin-4-yl]methoxy}-8-chloro-3,4-dihydroquinolin-2(1H)-one Synthesized analogous to Example 42.
(Ethanol/water) m.p. 185.8-186.0° C.
$^1$HNMR (DMSO-d6) δ ppm: 1.54-1.57 (1H, m), 2.01-2.06 (1H, m), 2.47 (2H, t, J=7.5 Hz), 2.96 (2H, t, J=7.5 Hz), 3.03-3.07 (1H, m), 3.11-3.17 (2H, m), 3.22-3.25 (1H, m), 3.68-3.70 (1H, m), 3.88 (1H, d, J=9.5 Hz), 3.99 (1H, d, J=9.5 Hz), 4.86 (1H, brs), 4.86 (1H, brs), 6.67 (1H, d, J=9.0 Hz), 7.01 (1H, t, J=9.5 Hz), 7.23 (1H, d, J=9.0 Hz), 7.23-7.27 (1H, m), 7.38 (1H, dd, J=12.5 Hz, 2.0 Hz), 9.35 (1H, brs).

Example 365

5-{[(3R*,4S*)-1-(4-Chloro-2,5-difluorophenyl)-3,4-dihydroxypiperidin-4-yl]methoxy}-8-fluoro-3,4-dihydroquinolin-2(1H)-one Synthesized analogous to Example 357.
(Ethanol/water) m.p. 184-185° C.
$^1$HNMR (DMSO-d6) δ ppm: 1.49-1.59 (1H, m), 1.95-2.06 (1H, m), 2.45 (2H, t, J=7.7 Hz), 2.94 (2H, t, J=7.7 Hz), 3.03-3.15 (1H, m), 3.15-3.35 (3H, m), 3.62-3.70 (1H, m), 3.83 (1H, d, J=9.3 Hz), 3.95 (1H, d, J=9.3 Hz), 4.85 (1H, s), 4.89 (1H, d, J=5.4 Hz), 6.56 (1H, dd, J=9.2 Hz, 3.8 Hz), 7.02 (1H, t, J=9.7 Hz), 7.09 (1H, dd, J=11.3 Hz, 7.9 Hz), 7.45 (1H, dd, J=12.3 Hz, 7.2 Hz), 10.01 (1H, s).

Example 366

5-{[(3S*,4R*)-1-(4-Bromo-2,6-difluorophenyl)-3,4-dihydroxypiperidin-4-yl]methoxy}-8-fluoro-3,4-dihydroquinolin-2(1H)-one Synthesized analogous to Example 359.
(Ethanol) m.p. 209-210° C.
$^1$HNMR (DMSO-d6) δ ppm: 1.46-1.54 (1H, m), 1.97-2.06 (1H, m), 2.45 (2H, t, J=7.7 Hz), 2.90-2.96 (2H, m), 2.96-3.03 (2H, m), 3.27-3.35 (1H, m), 3.49-3.56 (1H, m), 3.59-3.64 (1H, m), 3.82 (1H, d, J=9.4 Hz), 3.95 (1H, d, J=9.4 Hz), 4.69 (1H, d, J=5.5 Hz), 4.81 (1H, s), 6.57 (1H, dd, J=9.2 Hz, 3.8 Hz), 7.00 (1H, t, J=9.7 Hz), 7.31-7.38 (2H, m), 10.01 (1H, s).

Example 367

5-{[(3R,4R)-1-(4-Chloro-2,6-difluorophenyl)-3,4-dihydroxypiperidin-4-yl]methoxy}-8-fluoroquinolin-2(1H)-one Synthesized analogous to Example 42.
(Acetic acid/water) m.p. 247.4-247.5° C.
$^1$HNMR (DMSO-d6) δ ppm: 1.79-1.82 (1H, m), 1.88-1.94 (1H, m), 2.92-2.94 (1H, m), 2.97-3.00 (1H, m), 3.22-3.30 (2H, m), 3.74-3.77 (1H, m), 3.88 (1H, d, J=8.5 Hz), 4.12 (1H, d, J=8.5 Hz), 4.66 (1H, brs), 4.91 (1H, brs), 6.57 (1H, d, J=9.5 Hz), 6.67 (1H, dd, J=9.0 Hz, 3.5 Hz), 7.25-7.31 (2H, m), 7.34 (1H, t, J=9.0 Hz), 8.10 (1H, d, J=9.5 Hz), 11.74 (1H, brs).

Example 368

8-Chloro-5-{[(3R,4R)-1-(4-chloro-2,6-difluorophenyl)-3,4-dihydroxypiperidin-4-yl]methoxy}quinolin-2(1H)-one Synthesized analogous to Example 42.
(Acetic acid/water) m.p. 228.8-229.5° C.
$^1$HNMR (DMSO-d6) δ ppm: 1.80-1.83 (1H, m), 1.87-1.93 (1H, m), 2.92-2.94 (1H, m), 2.97-3.00 (1H, m), 3.22-3.28 (2H, m), 3.74-3.75 (1H, m), 3.93 (1H, d, J=9.0 Hz), 4.14 (1H, d, J=9.0 Hz), 4.70 (1H, brs), 4.93 (1H, brs), 6.60 (1H, d, J=10.0 Hz), 6.80 (1H, d, J=9.0 Hz), 7.25-7.31 (2H, m), 7.59 (1H, d, J=9.0 Hz), 8.15 (1H, d, J=10.0 Hz), 10.92 (1H, brs).

Example 369

5-{[(3R*,4R*)-1-(4-Bromo-2-fluorophenyl)-3,4-dihydroxypiperidin-4-yl]methoxy}-8-fluoroquinolin-2(1H)-one Synthesized analogous to Example 42.
$^1$HNMR (DMSO-d6) δ ppm: 1.83-1.86 (1H, m), 1.93-1.99 (1H, m), 2.88 (1H, t, J=11.0 Hz), 3.00 (1H, t, J=11.0 Hz), 3.12-3.15 (1H, m), 3.18-3.21 (1H, m), 3.81-3.85 (1H, m), 3.88 (1H, d, J=9.0 Hz), 4.12 (1H, d, J=9.0 Hz), 4.73 (1H, brs), 5.02 (1H, d, J=6.5 Hz), 6.55 (1H, d, J=10.0 Hz), 6.68 (1H, dd, J=9.0 Hz, 3.5 Hz), 7.34 (1H, t, J=9.0 Hz), 7.30-7.37 (2H, m), 7.43 (1H, dd, J=7.5 Hz, 2.0 Hz), 8.10 (1H, d, J=10.0 Hz), 11.76 (1H, brs).

Example 370

5-{[(3R,4R)-1-(4-Bromo-2-fluorophenyl)-3,4-dihydroxypiperidin-4-yl]methoxy}-8-fluoroquinolin-2(1H)-one Synthesized analogous to Example 42.
(Acetic acid/water) m.p. 224.5° C. (dec)
$^1$HNMR (DMSO-d6) δ ppm: 1.83-1.86 (1H, m), 1.93-1.99 (1H, m), 2.88 (1H, t, J=11.0 Hz), 3.00 (1H, t, J=11.0 Hz), 3.12-3.15 (1H, m), 3.18-3.21 (1H, m), 3.81-3.85 (1H, m), 3.88 (1H, d, J=9.0 Hz), 4.12 (1H, d, J=9.0 Hz), 4.73 (1H, brs), 5.02 (1H, d, J=6.5 Hz), 6.55 (1H, d, J=10.0 Hz), 6.68 (1H, dd, J=9.0 Hz, 3.5 Hz), 7.34 (1H, t, J=9.0 Hz), 7.30-7.37 (2H, m), 7.43 (1H, dd, J=7.5 Hz, 2.0 Hz), 8.10 (1H, d, J=10.0 Hz), 11.76 (1H, brs).

Example 371

5-{[(3R*,4R*)-1-(4-Chloro-2,6-difluorophenyl)-3,4-dihydroxypiperidin-4-yl]methoxy}-8-fluoroquinolin-2(1H)-one Synthesized analogous to Example 42.
(Acetic acid/water) m.p. 232° C.
$^1$HNMR (DMSO-d6) δ ppm: 1.77-1.84 (1H, m), 1.86-1.95 (1H, m), 2.88-2.96 (1H, m), 2.96-3.02 (1H, m), 3.24 (1H, t, J=10.7 Hz), 3.30-3.45 (1H, m, overlapping with H2O signal), 3.72-3.79 (1H, m), 3.88 (1H, d, J=9.0 Hz), 4.11 (1H, d, J=9.0 Hz), 4.69 (1H, s), 4.93 (1H, d, J=6.5 Hz), 6.57 (1H, d, J=9.8 Hz), 6.67 (1H, dd, J=9.0 Hz, 3.4 Hz), 7.24-7.32 (2H, m), 7.35 (1H, dd, J=10.8 Hz, 9.0 Hz), 8.10 (1H, dd, J=9.8 Hz, 1.4 Hz), 11.76 (1H, s).

Example 372

5-({[1-(3,5-Dichloropyridin-2-yl)-4-hydroxypiperidin-4-yl]methyl}amino)-8-fluoro-3,4-dihydroquinolin-2(1H)-one A solution of 5-amino-8-fluoro-3,4-dihydroquinolin-2(1H)-one (0.20 g), 6-(3,5-dichloropyridin-2-yl)-1-oxa-6-azaspiro[2.5]octane (0.432 g) in acetic acid (4 mL) was stirred at 60° C. for 7 h. The reaction solution was concentrated, saturated aqueous sodium hydrogencarbonate and ethyl acetate were added to the residue, insoluble materials were filtered off, and the filtrate was extracted with ethyl acetate. The organic layer was washed with water and brine, dried over anhydrous sodium sulfate, and the solvent was distilled off. The residue was purified by silica gel column chromatography (basic silica gel; dichloromethane/ethyl acetate) to provide the title compound (55.2 mg).
(Ethanol) m.p. 193-194° C.
$^1$HNMR (CDCl$_3$) δ ppm: 1.71 (1H, s), 1.79-1.94 (4H, m), 2.68 (2H, t, J=7.6 Hz), 2.82 (2H, t, J=7.6 Hz), 3.16 (2H, d, J=2.9 Hz), 3.21-3.30 (2H, m), 3.56-3.64 (2H, m), 3.72-3.81 (1H, m), 6.33 (1H, dd, J=9.0 Hz, 4.2 Hz), 6.89 (1H, t, J=9.4 Hz), 7.51 (1H, brs), 7.60 (1H, d, J=2.3 Hz), 8.12 (1H, d, J=2.3 Hz).

Example 373

5-({[1-(2,4-Dichlorophenyl)-4-hydroxypiperidin-4-yl]methyl}amino)-8-fluoro-3,4-dihydroquinolin-2(1H)-one Synthesized analogous to Example 372.
(Ethyl acetate/ethanol) m.p. 226-227° C. $^1$HNMR (CDCl$_3$) δ ppm: 1.70 (1H, s), 1.81-1.88 (2H, m), 1.89-1.98 (2H, m), 2.68 (2H, t, J=7.7 Hz), 2.82 (2H, t, J=7.7 Hz), 2.98-3.07 (2H, m), 3.12-3.21 (4H, m), 3.72-3.79 (1H, m), 6.35 (1H, dd, J=9.0 Hz, 4.3 Hz), 6.89 (1H, t, J=9.4 Hz), 7.01 (1H, d, J=8.7 Hz), 7.20 (1H, dd, J=8.7 Hz, 2.5 Hz), 7.37 (1H, d, J=2.5 Hz), 7.52 (1H, brs).

Example 374

5-({[1-(2,5-Dichloro-4-fluorophenyl)-4-hydroxypiperidin-4-yl]methyl}amino)-8-fluoro-3,4-dihydroquinolin-2(1H)-one Synthesized analogous to Example 372.
$^1$HNMR (CDCl$_3$) δ ppm: 1.67 (1H, s), 1.81-1.88 (2H, m), 1.88-1.97 (2H, m), 2.68 (2H, t, J=7.7 Hz), 2.83 (2H, t, J=7.7 Hz), 2.97-3.05 (2H, m), 3.09-3.15 (2H, m), 3.17 (2H, brs), 3.75 (1H, brs), 6.35 (1H, dd, J=9.0 Hz, 4.2 Hz), 6.90 (1H, t, J=9.5 Hz), 7.11 (1H, d, J=7.2 Hz), 7.21 (1H, d, J=8.6 Hz), 7.50 (1H, brs).

Example 375

5-({[1-(2-Chloro-4-fluorophenyl)-4-hydroxypiperidin-4-yl]methyl}amino)-8-fluoro-3,4-dihydroquinolin-2(1H)-one Synthesized analogous to Example 372.
(Acetic acid/ethyl acetate) m.p. 214-215° C.
$^1$HNMR (CDCl$_3$) δ ppm: 1.70 (1H, s), 1.81-1.87 (2H, m), 1.90-1.97 (2H, m), 2.69 (2H, t, J=7.6 Hz), 2.83 (2H, t, J=7.6 Hz), 2.97-3.05 (2H, m), 3.08-3.15 (2H, m), 3.17 (2H, brs), 3.77 (1H, brs), 6.35 (1H, dd, J=9.0 Hz, 4.3 Hz), 6.90 (1H, t, J=9.5 Hz), 6.92-6.98 (1H, m), 7.06 (1H, dd, J=9.0 Hz, 5.5 Hz), 7.14 (1H, dd, J=8.3 Hz, 3.0 Hz), 7.51 (1H, brs).

Example 376

5-({[1-(4-Chloro-2-fluorophenyl)-4-hydroxypiperidin-4-yl]methyl}amino)-8-fluoro-3,4-dihydroquinolin-2(1H)-one Synthesized analogous to Example 372.
(Acetic acid/ethyl acetate) m.p. 225-226° C.
$^1$HNMR (CDCl$_3$) δ ppm: 1.70 (1H, s), 1.81-1.87 (2H, m), 1.87-1.97 (2H, m), 2.68 (2H, t, J=7.6 Hz), 2.82 (2H, t, J=7.6 Hz), 3.02-3.10 (2H, m), 3.15 (2H, s), 3.19-3.25 (2H, m),

Example 377

5-[{[1-(2,4-Dichlorophenyl)-4-hydroxypiperidin-4-yl]methyl}(methyl)amino]-8-fluoro-3,4-dihydroquinolin-2(1H)-one Synthesized analogous to Example 6.
(Ethanol) m.p. 156-157° C.
$^1$HNMR (CDCl$_3$) δ ppm: 1.52-1.59 (2H, m), 1.68-1.76 (2H, m), 2.61 (1H, s), 2.62-2.67 (2H, m), 2.73 (3H, s), 2.92-3.00 (2H, m), 3.04-3.14 (6H, m), 6.90 (1H, dd, J=8.9 Hz, 4.8 Hz), 6.95-7.00 (2H, m), 7.17 (1H, dd, J=8.7 Hz, 2.5 Hz), 7.34 (1H, d, J=2.5 Hz), 7.53 (1H, brs).

Example 378

5-({[1-(2,4-Dichloro-5-fluorophenyl)-4-hydroxypiperidin-4-yl]methyl}amino)-8-fluoro-3,4-dihydroquinolin-2(1H)-one Synthesized analogous to Example 6.
$^1$HNMR (DMSO-d6) δ ppm: 1.65-1.75 (4H, brs), 2.43-2.50 (2H, m), 2.75 (2H, t, J=7.8 Hz), 2.90-3.10 (6H, m), 4.49-4.55 (1H, m), 4.70 (1H, s), 6.29 (1H, dd, J=9.0 Hz, 4.2 Hz), 6.81-6.92 (1H, m), 7.24 (1H, d, J=11.4 Hz), 7.70 (1H, d, J=7.8 Hz), 9.82 (1H, s).

Example 379

5-({[1-(4-Chloro-2,5-difluorophenyl)-4-hydroxypiperidin-4-yl]methyl}amino)-8-fluoro-3,4-dihydroquinolin-2(1H)-one Synthesized analogous to Example 6.
$^1$HNMR (DMSO-d6) δ ppm: 1.60-1.80 (4H, m), 2.40-2.60 (2H, m), 2.74 (2H, t, J=7.8 Hz), 2.87-3.22 (6H, m), 4.40-4.60 (1H, m), 4.72 (1H, brs), 6.28 (1H, dd, J=9.4 Hz, 3.9 Hz), 6.88 (1H, t, J=9.4 Hz), 7.12 (1H, dd, J=11.8 Hz, 7.4 Hz), 7.49 (1H, dd, J=11.8 Hz, 7.4 Hz), 9.82 (1H, s).

Example 380

5-({[1-(4-Chloro-2,6-difluorophenyl)-4-hydroxypiperidin-4-yl]methyl}amino)-8-fluoro-3,4-dihydroquinolin-2(1H)-one Synthesized analogous to Example 6.
$^1$HNMR (DMSO-d6) δ ppm: 1.57-1.77 (4H, m), 2.40-2.57 (2H, m), 2.74 (2H, t, J=7.8 Hz), 2.89-3.08 (4H, m), 3.20-3.45 (2H, m), 4.40-4.55 (1H, m), 4.68 (1H, brs), 6.29 (1H, dd, J=9.5 Hz, 4.1 Hz), 6.88 (1H, t, J=9.5 Hz), 7.19-7.35 (2H, m), 9.82 (1H, s).

Example 381

5-({[1-(2,4-Dichloro-6-fluorophenyl)-4-hydroxypiperidin-4-yl]methyl}amino)-8-fluoro-3,4-dihydroquinolin-2(1H)-one Synthesized analogous to Example 6.
$^1$HNMR (DMSO-d6) δ ppm: 1.62-1.74 (4H, m), 2.41-2.55 (2H, m), 2.69-2.79 (2H, m), 2.83-2.95 (2H, m), 3.03 (2H, d, J=5.4 Hz), 3.25-3.45 (2H, m), 4.42-4.55 (1H, m), 4.71 (1H, brs), 6.30 (1H, dd, J=9.2 Hz, 4.1 Hz), 6.89 (1H, t, J=9.2 Hz), 7.38-7.50 (2H, m), 9.82 (1H, s).

Example 382

5-({[1-(2-Chloro-4,6-difluorophenyl)-4-hydroxypiperidin-4-yl]methyl}amino)-8-fluoro-3,4-dihydroquinolin-2(1H)-one Synthesized analogous to Example 6.
$^1$HNMR (DMSO-d6) δ ppm: 1.62-1.72 (3H, m), 2.25-2.30 (1H, m), 2.40-2.55 (2H, m), 2.69-2.78 (2H, m), 2.79-2.88 (2H, m), 2.97-3.08 (2H, m), 3.25-3.40 (2H, m), 4.41-4.52 (1H, m), 4.66 (1H, s), 6.30 (1H, dd, J=9.2 Hz, 4.1 Hz), 6.82-6.95 (1H, m), 7.20-7.40 (2H, m), 9.82 (1H, s).

Example 383

8-Fluoro-5-({[4-hydroxy-1-(2,4,6-trifluorophenyl)piperidin-4-yl]methyl}amino)-3,4-dihydroquinolin-2(1H)-one Synthesized analogous to Example 6.
$^1$HNMR (CDCl$_3$) δ ppm: 1.57 (1H, brs), 1.76-1.82 (2H, m), 1.83-1.91 (2H, m), 2.68 (2H, t, J=8.0 Hz), 2.82 (2H, t, J=7.9 Hz), 3.00-3.06 (2H, m), 3.15 (2H, s), 3.33-3.41 (2H, m), 3.78 (1H, brs), 6.34 (1H, dd, J=9.1 Hz, 4.3 Hz), 6.59-6.67 (2H, m), 6.89 (1H, t, J=9.4 Hz), 7.51 (1H, brs).

Example 384

5-({[1-(2-Chloro-4-propylphenyl)-4-hydroxypiperidin-4-yl]methyl}amino)-8-fluoro-3,4-dihydroquinolin-2(1H)-one Synthesized analogous to Example 6.
$^1$HNMR (DMSO-d6) δ ppm: 0.87 (3H, t, J=7.4 Hz), 1.55 (2H, q, J=7.4 Hz), 1.64-1.78 (4H, m), 2.41-2.57 (2H, m), 2.70-2.79 (2H, m), 2.90-3.09 (6H, m), 3.30-3.38 (2H, m), 4.42-4.52 (1H, m), 4.65 (1H, s), 6.30 (1H, dd, J=9.2 Hz, 4.4 Hz), 6.81-6.97 (1H, m), 7.04-7.28 (3H, m), 9.82 (1H, s).

Example 385

5-({[1-(2-Chloro-4-ethylphenyl)-4-hydroxypiperidin-4-yl]methyl}amino)-8-fluoro-3,4-dihydroquinolin-2(1H)-one Synthesized analogous to Example 6.
$^1$HNMR (DMSO-d6) δ ppm: 1.14 (3H, t, J=7.5 Hz), 1.65-1.78 (4H, m), 2.40-2.60 (2H, m), 2.69-2.79 (2H, m), 2.90-3.09 (6H, m), 3.30-3.38 (2H, m), 4.42-4.55 (1H, m), 4.65 (1H, s), 6.30 (1H, dd, J=9.0 Hz, 4.2 Hz), 6.59 (1H, t, J=9.0 Hz), 7.05-7.28 (3H, m), 9.83 (1H, s).

Example 386

5-[({1-[2-Chloro-4-(trifluoromethoxy)phenyl]-4-hydroxypiperidin-4-yl}methyl)amino]-8-fluoro-3,4-dihydroquinolin-2(1H)-one Synthesized analogous to Example 6.
$^1$HNMR (DMSO-d6) δ ppm: 1.65-1.75 (4H, brs), 2.43-2.50 (2H, m), 2.75 (2H, t, J=7.8 Hz), 2.90-3.10 (6H, m), 4.49-4.55 (1H, m), 4.70 (1H, s), 6.31 (1H, dd, J=8.7 Hz, 4.2 Hz), 6.85-6.93 (1H, m), 7.26-7.35 (2H, m), 7.51 (1H, s), 9.82 (1H, s).

Example 387

8-Fluoro-5-[({1-[2-fluoro-4-(propan-2-yloxy)phenyl]-4-hydroxypiperidin-4-yl}methyl)amino]-3,4-dihydroquinolin-2(1H)-one Synthesized analogous to Example 6.
$^1$HNMR (DMSO-d6) δ ppm: 1.21 (6H, d, J=6 Hz), 1.65-1.75 (4H, brs), 2.43-2.50 (2H, m), 2.73 (2H, t, J=7.8 Hz), 2.90-2.96 (4H, m), 3.01 (1H, d, J=5.4 Hz), 4.46-4.53 (2H, m), 4.65 (1H, s), 4.69 (1H, s), 6.27 (1H, dd, J=9.3 Hz, 4.2 Hz), 6.66 (1H, dd, J=11.1 Hz, 2.7 Hz), 6.75 (1H, dd, J=14.1 Hz, 2.7 Hz), 6.88 (1H, d, J=9.0 Hz), 6.98 (1H, d, J=9.0 Hz), 9.84 (1H, s).

Example 388

5-({[1-(4-Ethoxy-2-fluorophenyl)-4-hydroxypiperidin-4-yl]methyl}amino)-8-fluoro-3,4-dihydroquinolin-2(1H)-one Synthesized analogous to Example 6.
$^1$HNMR (DMSO-d6) δ ppm: 1.28 (3H, t, J=6.9 Hz), 1.65-1.75 (4H, brs), 2.43-2.50 (2H, m), 2.73 (2H, t, J=7.8 Hz), 2.90-2.96 (4H, m), 3.11 (1H, d, J=5.4 Hz), 3.95 (2H, t, J=6.9 Hz), 4.47-4.50 (1H, m), 4.69 (1H, s), 6.27 (1H, dd, J=9.3 Hz, 4.2 Hz), 6.66 (1H, dd, J=8.7 Hz, 2.7 Hz), 6.75 (1H, dd, J=14.1 Hz, 2.7 Hz), 6.88 (1H, d, J=9.0 Hz), 7.00 (1H, d, J=9.0 Hz), 9.84 (1H, s).

Example 389

8-Fluoro-5-[({1-[2-fluoro-4-(trifluoromethoxy)phenyl]-4-hydroxypiperidin-4-yl}methyl)amino]-3,4-dihydroquinolin-2(1H)-one A solution of N-[8-fluoro-1-(4-methoxybenzyl)-2-oxo-1,2,3,4-tetrahydroquinolin-5-yl]acetamide (100 mg), 6-[2-fluoro-4-(trifluoromethoxy)phenyl]-1-oxa-6-azaspiro[2.5]octane (110 mg) and tripotassium phosphate (31.0 mg) in N,N-dimethylformamide (0.5 mL) was stirred at 100° C. for 16 h, 5 N aqueous sodium hydroxide (1.5 mL) was added thereto and the reaction solution was stirred at 90° C. for 3 h (reaction solution 1). Separately, a solution of N-[8-fluoro-1-(4-methoxybenzyl)-2-oxo-1,2,3,4-tetrahydroquinolin-5-yl]acetamide (100 mg), 6-[2-fluoro-4-(trifluoromethoxy)phenyl]-1-oxa-6-azaspiro[2.5]octane (110 mg) and tripotassium phosphate (31.0 mg) in N,N-dimethylformamide/2-propanol (1:1) (0.8 mL) was stirred at 100° C. for 18 h, 5 N aqueous sodium hydroxide (1 mL) was added thereto and the reaction mixture was stirred at 90° C. for 2 h (reaction solution 2). Reaction solutions 1 and 2 were combined, to which water was added, and the solution was extracted with ethyl acetate. The organic layer was washed with brine, dried over anhydrous sodium sulfate, and the solvent was distilled off. The residue was dissolved into ethanol (2 mL), a solution of sodium hydroxide (370 mg) in water (1.5 mL) was added to the solution, and the reaction mixture was heated to reflux for 2 h. To the reaction solution was added water, and the precipitate was collected on a filter and recrystallized from methanol to give 8-fluoro-5-[({1-[2-fluoro-4-(trifluoromethoxy)phenyl]-4-hydroxypiperidin-4-yl}methyl)amino]-1-(4-methoxybenzyl)-3,4-dihydroquinolin-2(1H)-one. Anisole (70 mg) and trifluoroacetic acid (2 mL) were added to the product, the reaction mixture was heated to reflux for 2 h, and the solvent was distilled off. To the residue was added water, the solution was neutralized with diluted aqueous sodium hydroxide, and extracted with ethyl acetate. The organic layer was washed with brine, dried over anhydrous sodium sulfate and the solvent was distilled off. The residue was washed with diethyl ether, the obtained solid was recrystallized from ethanol. The precipitate was collected on a filter and dried to provide the title compound (120 mg).
$^1$HNMR (DMSO-d6) δ ppm: 1.06 (3H, t, J=7.1 Hz), 1.61-1.72 (4H, m), 2.41-2.56 (2H, m), 2.68-2.80 (2H, m), 2.90-3.16 (6H, m), 4.36 (2H, t, J=5.1 Hz), 4.42-4.53 (1H, m), 4.68 (1H, s), 6.29 (1H, dd, J=9.4, 4.1 Hz), 6.88 (1H, t, J=9.4 Hz), 7.08-7.21 (2H, m), 7.23-7.34 (1H, m), 9.78 (1H, s).

Example 390

N-(8-Fluoro-2-oxo-1,2,3,4-tetrahydroquinolin-5-yl)-N-{[4-hydroxy-1-(2,4,6-trifluorophenyl)piperidin-4-yl]methyl}acetamide A solution of N-[8-fluoro-1-(4-methoxybenzyl)-2-oxo-1,2,3,4-tetrahydroquinolin-5-yl]acetamide (2.0 g), 6-(2,4,6-trifluorophenyl)-1-oxa-6-azaspiro[2.5]octane (2.13 g) and tripotassium phosphate (0.62 g) in N,N-dimethylformamide/2-propanol (1:1) (20 mL) was stirred at 90° C. for 16 h. To the reaction solution was added sodium hydroxide (0.351 g), and the reaction mixture was stirred at 90° C. for 3 days. The solvent was distilled off, water was added to the residue, and the solution was extracted with ethyl acetate. The organic layer was washed with brine, dried over anhydrous sodium sulfate, and the solvent was distilled off. The residue was purified by silica gel column chromatography (hexane/ethyl acetate) to give N-[8-fluoro-1-(4-methoxybenzyl)-2-oxo-1,2,3,4-tetrahydroquinolin-5-yl]-N-{[4-hydroxy-1-(2,4,6-trifluorophenyl)piperidin-4-yl]methyl}acetamide (0.22 g). Reactions analogous to Example 6 were done with the obtained compound, and the product was recrystallized from methanol. The precipitate was collected on a filter and dried to provide the title compound (131 mg).
$^1$HNMR (DMSO-d6) δ ppm: 1.46-1.88 (7H, m), 2.40-2.54 (3H, m), 2.64-2.78 (1H, m), 2.79-3.01 (2H, m), 3.15-3.42 (3H, m), 3.90 (1H, d, J=14.1 Hz), 4.14 (1H, s), 6.80-7.15 (4H, m), 9.59 (1H, brs). DMSO at 90 deg.

Example 391

8-Chloro-5-({[1-(4-chloro-2-fluorophenyl)-4-hydroxypiperidin-4-yl]methyl}amino)-3,4-dihydroquinolin-2(1H)-one Synthesized analogous to Example 6.
$^1$HNMR (DMSO-d6) δ ppm: 1.62-1.80 (4H, m), 2.44-2.54 (2H, m), 2.70-2.79 (2H, m), 2.95-3.15 (6H, m), 4.58 (1H, s), 4.70-4.74 (1H, m), 6.42 (1H, d, J=9.0 Hz), 7.00-7.18 (3H, m), 7.25 (1H, dd, J=12.5 Hz, 2.3 Hz), 8.81 (1H, brs).

Example 392

8-Chloro-5-({[1-(2,4-dichloro-5-fluorophenyl)-4-hydroxypiperidin-4-yl]methyl}amino)-3,4-dihydroquinolin-2(1H)-one Synthesized analogous to Example 6.
$^1$HNMR (DMSO-d6) δ ppm: 1.65-1.77 (4H, m), 2.43-2.54 (2H, m), 2.70-2.80 (2H, m), 2.92-3.14 (6H, m), 4.60

(1H, brs), 4.71-4.74 (1H, m), 6.43 (1H, d, J=8.9 Hz), 7.06 (1H, d, J=8.9 Hz), 7.20 (1H, d, J=11.4 Hz), 7.64 (1H, d, J=7.8 Hz), 8.82 (1H, brs).

Example 393

8-Chloro-5-({[1-(4-chloro-2,6-difluorophenyl)-4-hydroxypiperidin-4-yl]methyl}amino)-3,4-dihydroquinolin-2(1H)-one Synthesized analogous to Example 6.
¹HNMR (DMSO-d6) δ ppm: 1.58-1.76 (4H, m), 2.44-2.55 (2H, m), 2.70-2.79 (2H, m), 2.89-3.00 (2H, m), 3.02-3.11 (2H, m), 3.23-3.39 (2H, m), 4.63 (1H, m), 4.73-4.78 (1H, m), 6.42 (1H, d, J=8.9 Hz), 7.06 (1H, d, J=8.9 Hz), 7.19-7.28 (2H, m), 8.95 (1H, s).

Example 394

8-Chloro-5-({[4-hydroxy-1-(2,4,6-trifluorophenyl)piperidin-4-yl]methyl}amino)-3,4-dihydroquinolin-2(1H)-one Synthesized analogous to Example 6.
¹HNMR (DMSO-d6) δ ppm: 1.69-1.73 (4H, m), 2.44-2.55 (2H, m), 2.69-2.78 (2H, m), 2.81-2.93 (2H, m), 3.07 (2H, d, =5.7 Hz), 3.22-3.48 (2H, m), 4.61 (1H, s), 4.74-4.77 (1H, m), 6.42 (1H, d, J=9.0 Hz), 7.00-7.18 (3H, m), 8.95 (1H, brs).

Example 395

8-Chloro-5-({[1-(4-ethoxy-2-fluorophenyl)-4-hydroxypiperidin-4-yl]methyl}amino)-3,4-dihydroquinolin-2(1H)-one Synthesized analogous to Example 6.
¹HNMR (DMSO-d6) δ ppm: 1.29 (3H, t, J=6.9 Hz), 1.61-1.79 (4H, m), 2.45-2.53 (2H, m), 2.70-2.78 (2H, m), 2.89-2.99 (4H, m), 3.07 (2H, d, J=5.4 Hz), 3.96 (2H, q, J=6.9 Hz), 4.59 (1H, s), 4.73-4.77 (1H, m), 6.41 (1H, d, J=9.0 Hz), 6.61-6.79 (2H, m), 6.95-7.10 (2H, m), 8.95 (1H, brs).

Example 396

8-Chloro-5-({[1-(4-chloro-2,5-difluorophenyl)-4-hydroxypiperidin-4-yl]methyl}amino)-3,4-dihydroquinolin-2(1H)-one Synthesized analogous to Example 6.
¹HNMR (DMSO-d6) δ ppm: 1.61-1.78 (4H, m), 2.44-2.53 (2H, m), 2.69-2.78 (2H, m), 2.93-3.22 (6H, m), 4.70 (1H, s), 4.75-4.82 (1H, m), 6.41 (1H, d, J=9.0 Hz), 7.05-7.13 (2H, m), 7.47 (1H, dd, J=12.2 Hz, 7.1 Hz), 9.02 (1H, s).

Example 397

5-({[1-(4-Chloro-2-fluorophenyl)-4-hydroxypiperidin-4-yl]methyl}amino)-7,8-difluoro-3,4-dihydroquinolin-2(1H)-one Synthesized analogous to Example 6.
¹HNMR (DMSO-d6) δ ppm: 1.62-1.76 (4H, m), 2.47 (2H, t, J=7.6 Hz), 2.70 (2H, t, J=7.6 Hz), 2.92 (6H, m), 4.54-4.86 (2H, m), 6.35 (1H, dd, J=15.8 Hz, 6.5 Hz), 7.07 (1H, t, J=9.1 Hz), 7.16 (1H, dd, J=8.7 Hz, 2.2 Hz), 7.30 (1H, dd, J=12.4 Hz, 2.5 Hz), 10.05 (1H, brs).

Example 398

5-({[1-(4-Bromo-2-fluorophenyl)-4-hydroxypiperidin-4-yl]methyl}amino)-7,8-difluoro-3,4-dihydroquinolin-2(1H)-one Synthesized analogous to Example 6.
¹HNMR (DMSO-d6) δ ppm: 1.56-1.79 (4H, m), 2.47 (2H, t, J=7.6 Hz), 2.70 (2H, t, J=7.6 Hz), 2.92-3.15 (6H, m), 4.67 (1H, s), 4.77 (1H, t, J=5.3 Hz), 6.35 (1H, dd, J=13.9 Hz, 6.5 Hz), 7.02 (1H, t, J=9.1 Hz), 7.28 (1H, dd, J=8.5 Hz, 1.7 Hz), 7.40 (1H, dd, J=12.2 Hz, 2.3 Hz), 10.04 (1H, s).

Example 399

5-{[1-(3,5-Dichloropyridin-2-yl)piperidin-4-yl]methoxy}-8-fluoro-3,4-dihydroquinolin-2(1H)-one Synthesized analogous to Example 33.
(Ethanol/ethyl acetate) m.p. 194-195° C.
¹HNMR (CDCl₃) δ ppm: 1.52-1.63 (2H, m), 1.89-1.96 (2H, m), 1.96-2.08 (1H, m), 2.60-2.67 (2H, m), 2.82-2.90 (2H, m), 3.01 (2H, t, J=8.0 Hz), 3.82-3.88 (4H, m), 6.46 (1H, dd, J=9.1 Hz, 4.0 Hz), 6.91 (1H, t, J=9.4 Hz), 7.51 (1H, brs), 7.60 (1H, d, J=2.3 Hz), 8.12 (1H, d, J=2.3 Hz).

Example 400

8-Chloro-5-{[1-(3,5-dichloropyridin-2-yl)piperidin-4-yl]methoxy}-3,4-dihydroquinolin-2(1H)-one Synthesized analogous to Example 33.
(Ethyl acetate) m.p. 190-191° C.
¹HNMR (CDCl₃) δ ppm: 1.53-1.63 (2H, m), 1.89-1.96 (2H, m), 1.98-2.09 (1H, m), 2.58-2.65 (2H, m), 2.82-2.90 (2H, m), 3.01 (2H, t, J=8.0 Hz), 3.82-3.90 (4H, m), 6.52 (1H, d, J=8.9 Hz), 7.17 (1H, d, J=8.9 Hz), 7.60 (1H, d, J=2.3 Hz), 7.73 (1H, brs), 8.12 (1H, d, J=2.3 Hz).

Example 401

1-(3,5-Dichloropyridin-2-yl)-4-{[(8-fluoro-2-oxo-1,2,3,4-tetrahydroquinolin-5-yl)oxy]methyl}piperidine-4-carboxylic acid Synthesized analogous to Example 6.
(Acetic acid) m.p. 276-277° C.
¹HNMR (DMSO-d6) δ ppm: 1.69-1.79 (2H, m), 2.14-2.23 (2H, m), 2.44 (2H, t, J=7.6 Hz), 2.80 (2H, t, J=7.6 Hz), 2.97-3.08 (2H, m), 3.52-3.61 (2H, m), 4.03 (2H, s), 6.61 (1H, dd, J=9.1 Hz, 3.8 Hz), 7.01 (1H, t, J=9.5 Hz), 8.03 (1H, d, J=2.3 Hz), 8.26 (1H, d, J=2.3 Hz), 10.03 (1H, s), 12.72 (1H, brs).

Example 402

5-{[1-(3,5-Dichloropyridin-2-yl)-4-(dimethylamino)piperidin-4-yl]methoxy}-8-fluoro-3,4-dihydroquinolin-2(1H)-one To a solution of 5-{[4-amino-1-(3,5-dichloropyridin-2-yl)piperidin-4-yl]methoxy}-8-fluoro-3,4-dihydroquinolin-2(1H)-one (0.3 g) in N-methyl-2-pyrrolidone (NMP) (3 mL) were added formalin aqueous solution (37%) (0.5 mL) and sodium triacetoxyborohydride (0.342 g), and the reaction mixture was stirred at room temperature for 1.25 h. To the reaction solution was added 0.5 N aqueous sodium hydroxide, and the insoluble precipitate was collected on a filter. The obtained solid was purified by silica gel column chromatography (basic silica gel: dichloromethane/ethyl acetate) and recrystallized from ethyl acetate. The precipitate was collected on a filter, and air-dried (60° C.) to provide the title compound (0.22 g).

m.p. 202-203° C.

$^1$HNMR (CDCl$_3$) δ ppm: 1.83-1.91 (2H, m), 2.01-2.09 (2H, m), 2.44 (6H, s), 2.62-2.68 (2H, m), 3.00 (2H, t, J=7.7 Hz), 3.33-3.45 (4H, m), 3.95 (2H, s), 6.47 (1H, dd, J=9.1 Hz, 3.9 Hz), 6.92 (1H, t, J=9.5 Hz), 7.51 (1H, brs), 7.58 (1H, d, J=2.3 Hz), 8.11 (1H, d, J=2.3 Hz).

Example 403

5-{[1-(3,5-Dichloropyridin-2-yl)-4-methoxypiperidin-4-yl]methoxy}-8-fluoro-3,4-dihydroquinolin-2(1H)-one Synthesized analogous to Example 6.
(Ethyl acetate) m.p. 181-182° C.
$^1$HNMR (CDCl$_3$) δ ppm: 1.82-1.90 (2H, m), 1.99-2.06 (2H, m), 2.61-2.67 (2H, m), 3.03 (2H, t, J=7.7 Hz), 3.18-3.26 (2H, m), 3.35 (3H, s), 3.55-3.62 (2H, m), 3.92 (2H, s), 6.47 (1H, dd, J=9.1 Hz, 3.9 Hz), 6.92 (1H, t, J=9.5 Hz), 7.51 (1H, brs), 7.60 (1H, d, J=2.3 Hz), 8.12 (1H, d, J=2.3 Hz).

Example 404

5-{[1-(3,5-Dichloropyridin-2-yl)-4-fluoropiperidin-4-yl]methoxy}-8-fluoro-3,4-dihydroquinolin-2(1H)-one To a suspension of 5-{[1-(3,5-dichloropyridin-2-yl)-4-hydroxypiperidin-4-yl]methoxy}-8-fluoro-3,4-dihydroquinolin-2(1H)-one (0.4 g) in dichloromethane (8 mL) was added bis(2-methoxyethyl)aminosulfur trifluoride (0.335 mL) dropwise at −70° C., and the reaction mixture was stirred at 0° C. for 3.5 h. To the reaction solution was added saturated aqueous sodium hydrogencarbonate, and the solution was extracted with dichloromethane. The organic layer was washed with water and brine, dried over anhydrous sodium sulfate, and the solvent was distilled off. The residue was purified by silica gel column chromatography (dichloromethane/ethyl acetate), then further purified by HPLC. The obtained product was recrystallized from ethyl acetate. The precipitate was collected on a filter, and air-dried (60° C.) to provide the title compound (0.10 g).

m.p. 186-187° C.

$^1$HNMR (CDCl$_3$) δ ppm: 1.91-2.15 (4H, m), 2.61-2.67 (2H, m), 3.03 (2H, t, J=7.7 Hz), 3.19-3.29 (2H, m), 3.68-3.75 (2H, m), 4.00 (2H, d, J=18.1 Hz), 6.46 (1H, dd, J=9.1 Hz, 3.9 Hz), 6.92 (1H, t, J=9.4 Hz), 7.50 (1H, brs), 7.61 (1H, d, J=2.3 Hz), 8.13 (1H, d, J=2.3 Hz).

Example 405

5-{[1-(3,5-Dichloropyridin-2-yl)-4-(hydroxymethyl)piperidin-4-yl]methoxy}-8-fluoro-3,4-dihydroquinolin-2(1H)-one Synthesized analogous to Example 6.
$^1$HNMR (CDCl$_3$) δ ppm: 1.72 (1H, t, J=5.6 Hz), 1.78-1.84 (4H, m), 2.61-2.67 (2H, m), 2.99 (2H, t, J=7.7 Hz), 3.30-3.36 (4H, m), 3.78 (2H, d, J=5.7 Hz), 3.96 (2H, s), 6.51 (1H, dd, J=9.1 Hz, 4.0 Hz), 6.92 (1H, t, J=9.5 Hz), 7.50 (1H, brs), 7.60 (1H, d, J=2.4 Hz), 8.13 (1H, d, J=2.4 Hz).

Example 406

Methyl [1-(3,5-dichloropyridin-2-yl)-4-{[(8-fluoro-2-oxo-1,2,3,4-tetrahydroquinolin-5-yl)oxy]methyl}piperidin-4-yl]carbamate Synthesized analogous to Example 6.
(Ethyl acetate) m.p. 183° C.
$^1$HNMR (CDCl$_3$) δ ppm: 1.92-2.02 (2H, m), 2.23-2.32 (2H, m), 2.61-2.67 (2H, m), 2.99 (2H, t, J=7.7 Hz), 3.09-3.18 (2H, m), 3.57-3.64 (2H, m), 3.64 (3H, s), 4.12 (2H, s), 4.69 (1H, s), 6.48 (1H, dd, J=9.1 Hz, 4.0 Hz), 6.90 (1H, t, J=9.5 Hz), 7.52 (1H, brs), 7.61 (1H, d, J=2.3 Hz), 8.12 (1H, d, J=2.3 Hz).

Example 407

5-{[1-(3,5-Dichloropyridin-2-yl)-4-(methylamino)piperidin-4-yl]methoxy}-8-fluoro-3,4-dihydroquinolin-2(1H)-one To a solution of methyl [1-(3,5-dichloropyridin-2-yl)-4-{[(8-fluoro-2-oxo-1,2,3,4-tetrahydroquinolin-5-yl)oxy]methyl}piperidin-4-yl]methylcarbamate (0.2 g) in acetic acid (4 mL) was added conc. hydrochloric acid (3 mL), and the reaction mixture was stirred at 100° C. for 6 h. After the solvent was distilled off, to the residue was added water, the reaction mixture was made basic with 5 N aqueous sodium hydroxide, and the solution was extracted with dichloromethane. The organic layer was washed with brine, dried over anhydrous sodium sulfate, and the solvent was distilled off. The residue was purified by silica gel column chromatography (hexane/ethyl acetate) and recrystallized from ethyl acetate. The precipitate was collected on a filter, and air-dried (60° C.) to provide the title compound (29 mg).

m.p. 182-184° C.

$^1$HNMR (CDCl$_3$) δ ppm: 1.33-1.76 (1H, broad signal), 1.76-1.89 (4H, m), 2.37 (3H, s), 2.62-2.68 (2H, m), 3.01 (2H, t, J=7.7 Hz), 3.32-3.41 (2H, m), 3.41-3.49 (2H, m), 3.86 (2H, s), 6.50 (1H, dd, J=9.1 Hz, 4.0 Hz), 6.92 (1H, t, J=9.5 Hz), 7.52 (1H, brs), 7.59 (1H, d, J=2.3 Hz), 8.11 (1H, d, J=2.3 Hz).

Example 408

N-[1-(3,5-Dichloropyridin-2-yl)-4-{[(8-fluoro-2-oxo-1,2,3,4-tetrahydroquinolin-5-yl)oxy]methyl}piperidin-4-yl]-N2,N2-dimethylglycinamide To a solution of 5-{[4-amino-1-(3,5-dichloropyridin-2-yl)piperidin-4-yl]methoxy}-8-fluoro-3,4-dihydroquinolin-2(1H)-one (300 mg) in N,N-dimethylformamide (8 mL) were added triethylamine (0.32 mL) and dimethylaminoacetyl chloride hydrochloride (190 mg) at 0° C., and the reaction mixture was stirred at room temperature for 3 h. To the reaction solution was added sodium hydrogen carbonate aqueous solution, and the solution was extracted with dichloromethane. The organic layer was dried over anhydrous sodium sulfate, and the solvent was distilled off. The residue was purified by silica gel column chromatography (dichloromethane/methanol), the obtained product was recrystallized from hexane/ethyl acetate, and the precipitate was collected on a filter and dried to provide the title compound (0.28 g).

m.p. 188.9-190.8° C.

¹HNMR (CDCl₃) δ ppm: 1.93-2.012 (2H, m), 2.31 (6H, s), 2.39-2.47 (2H, m), 2.58-2.64 (2H, m), 2.88 (2H, s), 2.95-3.00 (2H, m), 3.05-3.13 (2H, m), 3.63-3.70 (2H, m), 4.21 (2H, s), 6.47 (1H, dd, J=9.0 Hz, 3.5 Hz), 6.87 (1H, t J=9.5 Hz), 7.36 (1H, brs), 7.62 (1H, d, J=2.0 Hz), 8.13 (1H, d, J=1.5 Hz), 8.18 (1H, brs).

Example 409

N-[1-(2-Cyano-4-fluorophenyl)-4-{[(8-fluoro-2-oxo-1,2,3,4-tetrahydroquinolin-5-yl)oxy]methyl}piperidin-4-yl]acetamide To a solution of 5-fluoro-2-(4-{[(8-fluoro-2-oxo-1,2,3,4-tetrahydroquinolin-5-yl)oxy]methyl}-4-hydroxypiperidin-1-yl)benzonitrile (349 mg) in acetonitrile (40 mL)/dichloromethane (20 mL), conc. sulfuric acid (2 mL) was added dropwise at 0° C., and the reaction mixture was stirred at room temperature for 30 min, then at 50° C. for 4 h. To the reaction solution were added 3 N aqueous sodium hydroxide and sodium hydrogen carbonate aqueous solution under ice-cooling to make the reaction solution basic, the solution was extracted with dichloromethane, and the solvent was distilled off. The residue was purified by silica gel column chromatography (dichloromethane/methanol), recrystallized from ethyl acetate, the precipitate was collected on a filter and dried to provide the title compound (88 mg).

m.p. 214.0-215.9° C.

¹HNMR (CDCl₃) δ ppm: 2.02 (3H, s), 2.02-2.10 (2H, m), 2.40-2.46 (2H, m), 2.97 (2H, t, J=7.8 Hz), 2.97 (2H, t, J=7.8 Hz), 3.00-3.07 (2H, m), 3.30-3.36 (2H, m), 4.22 (2H, s), 5.16 (1H, s), 6.48 (1H, dd, J=9.0 Hz, 4.0 Hz), 6.89 (1H, t, J=9.5 Hz), 7.02 (1H, dd, J=9.0 Hz, 5.0 Hz), 7.20-7.25 (1H, m), 7.28 (1H, dd, J=8.0 Hz, 3.0 Hz), 7.49 (1H, brs).

Example 410

N-[1-(3-Cyano-5-fluoropyridin-2-yl)-4-{[(8-fluoro-2-oxo-1,2,3,4-tetrahydroquinolin-5-yl)oxy]methyl}piperidin-4-yl]acetamide Synthesized analogous to Example 409.
(Ethyl acetate) m.p. 237.8-238.2° C.

¹HNMR (CDCl₃) δ ppm: 1.85-1.93 (2H, m), 1.99 (3H, s), 2.38-2.47 (2H, m), 2.58 (2H, t, J=7.5 Hz), 2.96 (2H, t, J=7.5 Hz), 3.30-3.36 (2H, m), 3.95-4.03 (2H, m), 4.18 (2H, s), 6.46 (1H, dd, J=9.0 Hz, 4.0 Hz), 6.81 (1H, s), 6.86 (1H, t, J=9.8 Hz), 7.58 (1H, dd, J=7.3 Hz, 3.0 Hz), 8.25 (1H, d, J=3.0 Hz), 8.52 (1H, brs).

Example 411

5-{[4-(Aminooxy)-1-(3,5-dichloropyridin-2-yl)piperidin-4-yl]methoxy}-8-fluoro-3,4-dihydroquinolin-2(1H)-one Synthesized analogous to Example 6.
White powder (Ethyl acetate) m.p. 147-149° C.

¹HNMR (CDCl₃) δ ppm: 1.81-1.88 (2H, m), 2.08-2.14 (2H, m), 2.64 (2H, t, J=7.7 Hz), 3.03 (2H, t, J=7.7 Hz), 3.12-3.20 (2H, m), 3.55-3.62 (2H, m), 3.99 (2H, s), 4.99 (2H, s), 6.51 (1H, dd, J=9.1 Hz, 4.0 Hz), 6.92 (1H, t, J=9.5 Hz), 7.52 (1H, brs), 7.60 (1H, d, J=2.3 Hz), 8.12 (1H, d, J=2.3 Hz).

Example 412

2-[4-(Aminooxy)-4-{[(8-fluoro-2-oxo-1,2,3,4-tetrahydroquinolin-5-yl)oxy]methyl}piperidin-1-yl]-5-fluorobenzonitrile Synthesized analogous to Example 6.
(Ethyl acetate/ethanol) m.p. 207-208° C.

¹HNMR (CDCl₃) δ ppm: 1.87-1.96 (2H, m), 2.16-2.21 (2H, m), 2.65 (2H, t, J=7.7 Hz), 3.00-3.11 (4H, m), 3.24-3.32 (2H, m), 4.00 (2H, s), 4.99 (2H, s), 6.51 (1H, dd, J=9.1 Hz, 4.0 Hz), 6.92 (1H, t, J=9.5 Hz), 7.03 (1H, dd, J=9.1 Hz, 4.6 Hz), 7.19-7.25 (1H, m), 7.28 (1H, dd, J=7.8 Hz, 3.1 Hz), 7.53 (1H, brs).

Example 413

2-[4-(Aminooxy)-4-{[(8-fluoro-2-oxo-1,2,3,4-tetrahydroquinolin-5-yl)oxy]methyl}piperidin-1-yl]-5-fluoropyridine-3-carbonitrile Synthesized analogous to Example 6.

¹HNMR (CDCl₃) δ ppm: 1.77-1.86 (2H, m), 2.11-2.18 (2H, m), 2.61-2.67 (2H, m), 3.02 (2H, t, J=7.7 Hz), 3.30-3.38 (2H, m), 3.94-4.01 (2H, m), 3.98 (2H, s), 5.01 (2H, s), 6.50 (1H, dd, J=9.1 Hz, 4.0 Hz), 6.91 (1H, t, J=9.5 Hz), 7.50-7.56 (2H, m), 8.24 (1H, d, J=3.1 Hz).

Example 414

5-{[(3S*,4S*)-1-(3,5-Dichloropyridin-2-yl)-3-hydroxypiperidin-4-yl]methoxy}-8-fluoro-3,4-dihydroquinolin-2(1H)-one Synthesized analogous to Example 33.

¹HNMR (CDCl₃) δ ppm: 1.63-1.72 (1H, m), 1.91-2.05 (2H, m), 2.63 (2H, t, J=7.8 Hz), 2.65 (1H, d, J=4.2 Hz), 2.80 (1H, dd, J=11.8 Hz, 9.1 Hz), 2.93 (1H, dt, J=11.8 Hz, 2.8 Hz), 2.94-3.05 (2H, m), 3.77-3.83 (1H, m), 3.88-3.98 (2H, m), 4.07-4.16 (2H, m), 6.52 (1H, dd, J=9.1 Hz, 4.0 Hz), 6.92 (1H, t, J=9.3 Hz), 7.59 (1H, brs), 7.61 (1H, d, J=2.4 Hz), 8.12 (1H, d, J=2.4 Hz).

Example 415

5-Fluoro-2-[(3S*,4S*)-4-{[(8-fluoro-2-oxo-1,2,3,4-tetrahydroquinolin-5-yl)oxy]methyl}-3-hydroxypiperidin-1-yl]pyridine-3-carbonitrile Synthesized analogous to Example 33.

¹HNMR (CDCl₃) δ ppm: 1.63-1.73 (1H, m), 1.95-2.06 (2H, m), 2.61 (1H, d, J=2.7 Hz), 2.63 (2H, t, J=7.7 Hz), 2.91 (1H, dd, J=12.7 Hz, 9.9 Hz), 2.93-3.03 (2H, m), 3.07 (1H, dt, J=12.7 Hz, 2.7 Hz), 3.85-3.93 (1H, m), 4.07-4.16 (2H, m), 4.16-4.22 (1H, m), 4.28-4.34 (1H, m), 6.51 (1H, dd, J=9.1 Hz, 3.9 Hz), 6.92 (1H, t, J=9.4 Hz), 7.55 (1H, dd, J=7.3 Hz, 3.0 Hz), 7.58 (1H, brs), 8.25 (1H, d, J=3.1 Hz).

Example 416

5-{[(3R*,4S*)-1-(3,5-Dichloropyridin-2-yl)-3-hydroxypiperidin-4-yl]methoxy}-8-fluoro-3,4-dihydroquinolin-2(1H)-one To a solution of (3R*,4S*)-1-(3,5-dichloropyridin-2-yl)-4-{[(8-fluoro-2-oxo-1,2,3,4-tetrahydroquinolin-5-yl)oxy]methyl}piperidin-3-yl 4-nitrobenzoate (1.0 g) in tetrahydrofuran (THF) (20 mL) was added 2 N lithium hydroxide aqueous solution (20 mL), and the reaction mixture was stirred at room temperature overnight. To the reaction solution was added water, and the solution was extracted with ethyl acetate. The organic layer was washed with water and brine, dried over anhydrous sodium sulfate, and the solvent was distilled off. The residue was purified by silica gel column chromatography (hexane/ethyl acetate) and washed with diethyl ether to provide the title compound (0.35 g).

$^1$HNMR (CDCl$_3$) δ ppm: 1.63-1.70 (2H, m), 2.06-2.14 (1H, m), 2.63 (2H, t, J=7.7 Hz), 2.94-3.04 (2H, m), 3.05-3.17 (2H, m), 3.82-3.89 (2H, m), 4.00 (1H, dt, J=13.7 Hz, 2.5 Hz), 4.07-4.14 (2H, m), 4.37 (1H, d, J=7.4 Hz), 6.51 (1H, dd, J=9.1 Hz, 4.0 Hz), 6.90 (1H, t, J=9.5 Hz), 7.56 (1H, brs), 7.65 (1H, d, J=2.3 Hz), 8.10 (1H, d, J=2.3 Hz).

Example 417

1-(3,5-Dichloropyridin-2-yl)-4-{[(8-fluoro-2-oxo-1,2,3,4-tetrahydroquinolin-5-yl)oxy]methyl}piperidine-4-carbonitrile Synthesized analogous to Example 33.
(Ethyl acetate) m.p. 218° C.
$^1$HNMR (CDCl$_3$) δ ppm: 1.85-1.95 (2H, m), 2.16-2.24 (2H, m), 2.63-2.69 (2H, m), 3.07 (2H, t, J=7.7 Hz), 3.19-3.30 (2H, m), 3.83-3.92 (2H, m), 4.01 (2H, s), 6.44 (1H, dd, J=9.1 Hz, 3.9 Hz), 6.93 (1H, t, J=9.4 Hz), 7.54 (1H, brs), 7.63 (1H, d, J=2.3 Hz), 8.15 (1H, d, J=2.3 Hz).

Example 418

5-{[(3R*,4R*)-1-(2,4-Dichlorophenyl)-3-hydroxypiperidin-4-yl]methoxy}-8-fluoro-3,4-dihydroquinolin-2(1H)-one A solution of 8-fluoro-5-hydroxy-3,4-dihydroquinolin-2(1H)-one (0.42 g), [(3R*,4R*)-1-(2,4-dichlorophenyl)-3-hydroxypiperidin-4-yl]methyl 4-methylbenzenesulfonate (1.0 g) and cesium carbonate (0.756 g) in N-methyl-2-pyrrolidone (NMP) (10 mL) was stirred at 100° C. for 3 h. To the reaction solution was added water, and the solution was extracted with ethyl acetate. The organic layer was washed with water and brine, dried over anhydrous sodium sulfate, and the solvent was distilled off. The residue was washed with ethyl acetate, and recrystallized from 2-propanol. The precipitate was collected on a filter and dried to provide the title compound (0.34 g).

(2-Propanol) m.p. 222-224° C.
$^1$HNMR (DMSO-d6) δ ppm: 1.57-1.76 (2H, m), 1.91-1.98 (1H, m), 2.38-2.52 (3H, m), 2.60-2.70 (1H, m), 2.87 (2H, d, J=7.2 Hz), 3.19-3.27 (1H, m), 3.35-3.43 (1H, m), 3.55-3.65 (1H, m), 3.97-4.06 (1H, m), 4.13-4.19 (1H, m), 5.07 (1H, d, J=5.5 Hz), 6.61 (1H, dd, J=9.2 Hz, 3.8 Hz), 7.02 (1H, t, J=9.2 Hz), 7.16 (1H, d, J=8.7 Hz), 7.36 (1H, dd, J=8.7 Hz, 2.5 Hz), 7.54 (1H, d, J=2.5 Hz), 10.01 (1H, brs).

Example 419

5-{[(3R*,4R*)-1-(4-Chloro-2-fluorophenyl)-3-hydroxypiperidin-4-yl]methoxy}-8-fluoro-3,4-dihydroquinolin-2(1H)-one To a solution of 5-{[(3R*,4R*)-3-{[tert-butyl(dimethyl)silyl]oxy}-1-(4-chloro-2-fluorophenyl)piperidin-4-yl]methoxy}-8-fluoro-3,4-dihydroquinolin-2(1H)-one (0.12 g) in tetrahydrofuran (THF) (4 mL) was added a solution of 1M tetra-n-butylammonium fluoride (TBAF) in tetrahydrofuran (THF) (0.268 mL), and the reaction mixture was stirred at room temperature overnight. To the reaction solution were added water and ethyl acetate, and the precipitate was collected on a filter. The obtained solid was recrystallized from 2-propanol, the precipitate was collected on a filter and dried to provide the title compound (83 mg).

m.p. 177.3-182.9° C.
$^1$HNMR (DMSO-d6) δ ppm: 1.57-1.76 (2H, m), 1.88-1.97 (1H, m), 2.40-2.51 (3H, m), 2.61-2.70 (1H, m), 2.86 (2H, d, J=7.2 Hz), 3.28-3.33 (1H, m), 3.41-3.48 (1H, m), 3.54-3.64 (1H, m), 3.97-4.05 (1H, m), 4.10-4.16 (1H, m), 5.07 (1H, d, J=5.5 Hz), 6.60 (1H, dd, J=9.2 Hz, 3.8 Hz), 7.02 (1H, t, J=9.3 Hz), 7.05 (1H, t, J=9.3 Hz), 7.17 (1H, dd, J=8.6 Hz, 2.4 Hz), 7.32 (1H, dd, J=12.3 Hz, 2.4 Hz), 10.00 (1H, brs).

Example 420

5-{[1-(2,4-Dichlorophenyl)-4-(hydroxymethyl)piperidin-4-yl]methoxy}-8-fluoro-3,4-dihydroquinolin-2(1H)-one Synthesized analogous to Example 6.
$^1$HNMR (DMSO-d6) δ ppm: 1.69 (4H, t, J=5.4 Hz), 2.46 (2H, t, J=7.6 Hz), 2.88 (2H, t, J=7.6 Hz), 2.96 (4H, t, J=5.4 Hz), 3.50 (2H, d, J=5.3 Hz), 3.87 (2H, s), 4.68 (1H, t, J=5.4 Hz), 6.64 (1H, dd, J=9.1 Hz, 3.8 Hz), 7.01 (1H, t, J=9.7 Hz), 7.19 (1H, d, J=8.7 Hz), 7.35 (1H, dd, J=8.6 Hz, 2.5 Hz), 7.52 (1H, d, J=2.5 Hz), 10.00 (1H, s).

Example 421

5-{[(3R*,4R*)-1-(4-Chloro-2,5-difluorophenyl)-3-hydroxypiperidin-4-yl]methoxy}-8-fluoro-3,4-dihydroquinolin-2(1H)-one Synthesized analogous to Example 6.
(2-Propanol) m.p. 168.9-172.7° C.
$^1$HNMR (DMSO-d6) δ ppm: 1.56-1.77 (2H, m), 1.88-1.97 (1H, m), 2.41-2.49 (3H, m), 2.64-2.73 (1H, m), 2.86 (2H, d, J=7.3 Hz), 3.33-3.39 (1H, m), 3.47-3.63 (2H, m), 3.97-4.04 (1H, m), 4.09-4.15 (1H, m), 5.10 (1H, d, J=5.5 Hz), 6.60 (1H, dd, J=9.2 Hz, 4.0 Hz), 7.02 (1H, t, J=9.6 Hz), 7.09 (1H, dd, J=11.3 Hz, 7.8 Hz), 7.50 (1H, dd, J=12.1 Hz, 7.1 Hz), 10.00 (1H, brs).

Example 422

5-{[(3R*,4R*)-1-(3,5-Dichloropyridin-2-yl)-4-hydroxy-3-(methylamino)piperidin-4-yl]methoxy}-8-fluoro-3,4-dihydroquinolin-2(1H)-one Synthesized analogous to Example 33.
$^1$HNMR (DMSO-d6) δ ppm: 1.52-1.62 (2H, m), 1.83-1.93 (1H, m), 2.29 (3H, s), 2.45 (2H, t, J=7.6 Hz), 2.55-2.61 (1H, m), 2.86-3.03 (2H, m), 3.20-3.35 (2H, m), 3.52-3.54 (2H, m), 3.89 (1H, d, J=9.4 Hz), 4.04 (1H, d, J=9.4 Hz), 4.80 (1H, brs), 6.58 (1H, dd, J=9.1 Hz, 3.8 Hz), 6.99 (1H, t, J=9.6 Hz), 8.03 (1H, d, J=2.3 Hz), 8.27 (1H, d, J=2.3 Hz), 9.99 (1H, brs).

Example 423

5-{[(3S*,4R*)-1-(3,5-Dichloropyridin-2-yl)-4-hydroxy-3-methoxypiperidin-4-yl]methoxy}-8-fluoro-3,4-dihydroquinolin-2(1H)-one Synthesized analogous to Example 6.
(Ethanol) m.p. 186-187° C.
$^1$HNMR (CDCl$_3$) δ ppm: 1.64-1.70 (1H, m), 2.19-2.27 (1H, m), 2.39 (1H, s), 2.66 (2H, t, J=7.7 Hz), 2.96-3.07 (2H, m), 3.31 (3H, s), 3.33-3.40 (2H, m), 3.46 (1H, dd, J=13.7 Hz, 2.0 Hz), 3.62-3.68 (1H, m), 3.88 (1H, d, J=9.1 Hz), 3.96 (1H, dd, J=13.8 Hz, 3.0 Hz), 4.15 (1H, d, J=9.1 Hz), 6.52 (1H, dd, J=9.2 Hz, 4.0 Hz), 6.93 (1H, t, J=9.4 Hz), 7.56 (1H, brs), 7.58 (1H, d, J=2.3 Hz), 8.11 (1H, d, J=2.3 Hz).

Example 424

5-{[(3S*,4S*)-1-(3,5-Dichloropyridin-2-yl)-4-hydroxy-3-methoxypiperidin-4-yl]methoxy}-8-fluoro-3,4-dihydroquinolin-2(1H)-one Synthesized analogous to Example 6.
(2-Propanol) m.p. 162.8-164.0° C.
$^1$HNMR (CDCl$_3$) δ ppm: 1.81-1.88 (1H, m), 2.05-2.15 (1H, m), 2.45-2.49 (1H, m), 2.64 (2H, t, J=7.7 Hz), 2.92-3.07 (3H, m), 3.16-3.25 (1H, m), 3.43 (3H, s), 3.63-3.73 (2H, m), 3.78 (1H, d, J=8.8 Hz), 3.93-4.00 (1H, m), 4.03 (1H, d, J=8.8 Hz), 6.50 (1H, dd, J=9.1 Hz, 3.9 Hz), 6.93 (1H, t, J=9.3 Hz), 7.53 (1H, brs), 7.62 (1H, d, J=2.3 Hz), 8.13 (1H, d, J=2.3 Hz).

Example 425

5-{[(3S*,4S*)-1-(3,5-Dichloropyridin-2-yl)-4-hydroxy-3-methylpiperidin-4-yl]methoxy}-8-fluoro-3,4-dihydroquinolin-2(1H)-one Synthesized analogous to Example 33.
(ethanol/acetic acid) m.p. 222-223° C.
$^1$HNMR (CDCl$_3$) δ ppm: 1.13 (3H, d, J=7.1 Hz), 1.69-1.77 (1H, m), 2.05-2.15 (2H, m), 2.22 (1H, brs), 2.66 (2H, t, J=7.7 Hz), 3.02 (2H, t, J=7.7 Hz), 3.32-3.42 (2H, m), 3.42-3.56 (2H, m), 3.88-3.98 (2H, m), 6.50 (1H, dd, J=9.1 Hz, 3.9 Hz), 6.93 (1H, t, J=9.4 Hz), 7.59 (1H, d, J=2.4 Hz), 7.62 (1H, brs), 8.12 (1H, d, J=2.4 Hz).

Example 426

5-{[(3R*,4R*)-3-Amino-1-(3,5-dichloropyridin-2-yl)-4-hydroxypiperidin-4-yl]methoxy}-8-fluoro-3,4-dihydroquinolin-2(1H)-one Synthesized analogous to Example 33.
$^1$HNMR (CDCl$_3$) δ ppm: 1.72-1.75 (1H, m), 2.04-2.10 (1H, m), 2.35 (1H, s), 2.65 (2H, t, J=7.7 Hz), 3.02 (2H, t, J=7.7 Hz), 3.09 (1H, brs), 3.28-3.33 (1H, m), 3.49-3.55 (3H, m), 3.97 (1H, d, J=9.1 Hz), 4.23 (1H, d, J=9.1 Hz), 6.55 (1H, dd, J=9.1 Hz, 3.9 Hz), 6.93 (1H, t, J=9.5 Hz), 7.56 (1H, brs), 7.62 (1H, d, J=2.3 Hz), 8.14 (1H, d, J=2.3 Hz).

Example 427

5-{[(3R*,4S*)-1-(3,5-Dichloropyridin-2-yl)-3-fluoro-4-hydroxypiperidin-4-yl]methoxy}-8-fluoro-3,4-dihydroquinolin-2(1H)-one Synthesized analogous to Example 6.
$^1$HNMR (DMSO-d6) δ ppm: 1.61-1.69 (1H, m), 1.98-2.08 (1H, m), 2.46 (2H, t, J=7.6 Hz), 2.85-3.03 (2H, m), 3.12-3.21 (1H, m), 3.35-3.52 (1H, m), 3.63-3.71 (1H, m), 3.82-3.87 (1H, m), 3.88-4.00 (2H, m), 4.69 (1H, d, J=46.0 Hz), 5.37 (1H, brs), 6.61 (1H, dd, J=9.1 Hz, 3.8 Hz), 7.00 (1H, t, J=9.5 Hz), 8.02 (1H, d, J=2.3 Hz), 8.26 (1H, d, J=2.3 Hz), 10.01 (1H, brs).

Example 428

(3R*,4S*)-1-(3,5-Dichloropyridin-2-yl)-4-{[(8-fluoro-2-oxo-1,2,3,4-tetrahydroquinolin-5-yl)oxy]methyl}-4-hydroxypiperidine-3-carbonitrile Synthesized analogous to Example 6.
(Ethanol/water) m.p. 206-207° C. $^1$HNMR (CDCl$_3$) δ ppm: 1.81-1.88 (1H, m), 2.20-2.28 (1H, m), 2.61-2.64 (1H, m), 2.64-2.69 (2H, m), 2.97-3.08 (2H, m), 3.11-3.15 (1H, m), 3.26-3.34 (1H, m), 3.54 (1H, dd, J=13.0 Hz, 2.8 Hz), 3.66-3.73 (1H, m), 3.92-3.99 (1H, m), 4.04 (1H, d, J=9.4 Hz), 4.24 (1H, d, J=9.4 Hz), 6.55 (1H, dd, J=9.1 Hz, 3.9 Hz), 6.96 (1H, t, J=9.4 Hz), 7.63-7.69 (2H, m), 8.15 (1H, d, J=2.3 Hz).

Example 429

5-{[(3R*,4S*)-1-(3,5-Dichloropyridin-2-yl)-3,4-dihydroxy-3-methylpiperidin-4-yl]methoxy}-8-fluoro-3,4-dihydroquinolin-2(1H)-one To a solution of tert-butyl (1S*,6S*)-6-({[8-fluoro-1-(4-methoxybenzyl)-2-oxo-1,2,3,4-tetrahydroquinolin-5-yl]oxy}methyl)-1-methyl-7-oxa-3-azabicyclo[4.1.0]heptane-3-carboxylate (493 mg) in anisole (0.05 mL) was added trifluoroacetic acid (5 mL), the reaction mixture was stirred at 65° C. for 3 h, and the solvent was distilled off. To the residue were added 2,3,5-trichloropyridine (1095 mg), potassium carbonate (553 mg) and N,N-dimethylformamide (5 mL), and the mixture was stirred at 100° C. for 9 h. To the reaction solution was added water, the solution was extracted with ethyl acetate, the organic layer was washed with water and brine, and dried over anhydrous sodium sulfate. The solvent was distilled off, and the residue was purified by silica gel column chromatography (dichloromethane/ethyl acetate) to provide the title compound (105 mg).
$^1$HNMR (DMSO-d6) δ ppm: 1.17 (3H, s), 1.69-1.78 (1H, m), 2.11-2.21 (1H, m), 2.42-2.49 (2H, m), 2.84-3.04 (2H, m), 3.14-3.23 (1H, m), 3.24-3.31 (1H, m), 3.35-3.43 (1H, m), 3.60-3.70 (1H, m), 3.96 (1H, d, J=9.6 Hz), 4.06 (1H, d, J=9.6 Hz), 4.48 (1H, brs), 4.82 (1H, brs), 6.57 (1H, dd, J=9.2 Hz, 3.8 Hz), 7.00 (1H, t, J=9.5 Hz), 7.94 (1H, d, J=2.3 Hz), 8.20 (1H, d, J=2.3 Hz), 9.99 (1H, brs).

Example 430

5-{[(3S*,4S*)-1-(3,5-Dichloropyridin-2-yl)-3,4-dihydroxy-3-methylpiperidin-4-yl]methoxy}-8-fluoro-3,4-dihydroquinolin-2(1H)-one Synthesized analogous to Example 6.
(2-Propanol) m.p. 182.6-187.5° C.
$^1$HNMR (DMSO-d6) δ ppm: 1.25 (3H, s), 1.85-1.93 (1H, m), 1.98-2.07 (1H, m), 2.42-2.49 (2H, m), 2.79-2.91 (1H, m), 2.92-3.02 (1H, m), 3.14-3.33 (3H, m), 3.42-3.49 (1H, m), 3.88 (1H, d, J=9.6 Hz), 4.04 (1H, d, J=9.6 Hz), 4.52 (1H, brs), 4.58 (1H, brs), 6.62 (1H, dd, J=9.2 Hz, 3.8 Hz), 7.02 (1H, t, J=9.5 Hz), 8.01 (1H, d, J=2.3 Hz), 8.25 (1H, d, J=2.3 Hz), 10.01 (1H, brs).

Example 431

5-{[(3S*,4S*)-1-(4-Chloro-2-fluorophenyl)-3,4-dihydroxy-3-methylpiperidin-4-yl]methoxy}-8-fluoro-3,4-dihydroquinolin-2(1H)-one Synthesized analogous to Example 6.
$^1$HNMR (CDCl$_3$) δ ppm: 1.47 (3H, s), 1.91-2.08 (2H, m), 2.62-2.69 (2H, m), 2.91-3.09 (6H, m), 3.10-3.17 (2H, m), 3.94 (1H, d, J=9.3 Hz), 4.22 (1H, d, J=9.3 Hz), 6.54 (1H, dd, J=9.1 Hz, 3.9 Hz), 6.85-7.00 (2H, m), 7.02-7.09 (2H, m), 7.56 (1H, brs).

Example 432

5-{[(3S*,4R*)-3-Amino-1-(3,5-dichloropyridin-2-yl)-4-hydroxypiperidin-4-yl]methoxy}-8-fluoro-3,4-dihydroquinolin-2(1H)-one To a solution of O-benzyl carbamate (337 mg) in 1-propanol (4 mL) were added 1 N aqueous sodium hydroxide (3.05 mL) and tert-butyl hypochlorite (0.480 mL), and the reaction mixture was stirred at room temperature for 5 min. To the mixture were added a solution of bis(dihydroquinidinyl)phthalazine ((DHQD)$_2$PHAL) (38.9 mg) in 1-propanol (3.5 mL), a solution of tert-butyl 4-({[8-fluoro-1-(4-methoxybenzyl)-2-oxo-1,2,3,4-tetrahydroquinolin-5-yl]oxy}methyl)-3,6-dihydropyridine-1(2H)-carboxylate (497 mg) in 1-propanol (6.5 mL) and potassium osmate(VI) dihydrate (14.74 mg), and the reaction mixture was stirred at room temperature for 3 days. Under ice-cooling, saturated sodium sulfite aqueous solution was added to the mixture, the solution was stirred for 10 min, and the solution was extracted with ethyl acetate. The organic layer was washed with saturated sodium chloride aqueous solution, dried over anhydrous magnesium sulfate, and the solvent was distilled off. The residue was purified by silica gel column chromatography (hexane/ethyl acetate), and further purified by silica gel column chromatography (basic silica gel; dichloromethane/ethyl acetate) to give tert-butyl (3R,4S)-3-(benzyloxycarbonylamino)-4-({[8-fluoro-1-(4-methoxybenzyl)-2-oxo-1,2,3,4-tetrahydroquinolin-5-yl]oxy}methyl)-4-hydroxypiperidine-1-carboxylate. The obtained product was dissolved into ethanol (6 mL), 10% palladium on carbon (containing water) (30 mg) was added to the solution, and the reaction mixture was stirred at room temperature for 1 h under hydrogen atmosphere. Insoluble materials were filtered off with Celite, and the solvent was distilled off. To the residue were added anisole (0.020 mL) and trifluoroacetic acid (4 mL), and the reaction mixture was stirred at 60° C. for 1 h. The reaction solution was concentrated, 2-bromo-3,5-dichloropyridine (48.8 mg), potassium carbonate (82 mg) and N-methyl-2-pyrrolidone (NMP) (4 mL) were added to the residue, and the mixture was stirred at 100° C. for 5 h. To the reaction solution was added water, and the solution was extracted with ethyl acetate. The organic layer was washed with water and saturated sodium chloride aqueous solution, dried over anhydrous magnesium sulfate, and the solvent was distilled off. The residue was purified by silica gel column chromatography (basic silica gel; dichloromethane/methanol), washed with ethyl acetate-2-propanol, and the insoluble precipitate was collected on a filtered off to provide optically active compound 1 (27 mg, 19% ee). On the other hand, the reactions identical to the above was repeated by using bis(dihydroquinidyl)phthalazine ((DHQ)$_2$PHAL) in place of bis(dihydroquinidinyl)phthalazine ((DHQD)$_2$PHAL), another optically active compound 2 (38 mg, 34% ee) was obtained. Optically active compound 1 (11 mg) and optically active compound 2 (6 mg) were dissolved into a solvent mixture of ethyl acetate/ethanol/dichloromethane, the solvent was distilled off, and the residue was washed with ethyl acetate and 2-propanol. The insoluble precipitate was collected on a filter and dried under reduced pressure to provide the title compound (6 mg, <1% ee).
$^1$HNMR (CDCl$_3$) δ ppm: 1.13 (1H, d, J=6.2 Hz), 1.87-1.90 (1H, m), 1.96-2.01 (1H, m), 2.64 (2H, t, J=7.7 Hz), 2.95-3.07 (3H, m), 3.23-3.28 (1H, m), 3.37 (1H, dd, J=9.8 Hz, 4.4 Hz) 3.43-3.69 (3H, m), 3.92 (2H, s), 6.50 (1H, dd, J=9.0 Hz, 3.4 Hz), 6.92 (1H, t, J=9.5 Hz), 7.54 (1H, brs), 7.61 (1H, s), 8.12 (1H, s).

Example 433

(3S*,4S*)-1-(4-Chloro-2-fluorophenyl)-4-{[(8-fluoro-2-oxo-1,2,3,4-tetrahydroquinolin-5-yl)oxy]methyl}-4-hydroxypiperidin-3-yl acetate To a solution of 5-{[(3S*,4S*)-1-(4-chloro-2-fluorophenyl)-3,4-dihydroxypiperidin-4-yl]methoxy}-8-fluoro-3,4-dihydroquinolin-2(1H)-one (100 mg) in pyridine (1 mL) were added acetic anhydride (0.032 mL) and 4-(dimethylamino)pyridine (2.78 mg), and the reaction mixture was stirred at room temperature for 10 days. To the reaction solution was added water, and the solution was extracted with ethyl acetate, the organic layer was concentrated, the residue was purified by silica gel column chromatography (hexane/ethyl acetate) and recrystallized from ethyl acetate. The precipitate was collected on a filter and dried to provide the title compound (74 mg).
(Ethyl acetate) m.p. 182-185° C.
$^1$HNMR (DMSO-d6) δ ppm: 1.82 (1H, d, J=14.0 Hz), 1.98-2.05 (4H, m), 2.45 (2H, t, J=7.9 Hz), 2.81-2.88 (2H, m), 3.01-3.27 (4H, m), 3.77 (1H, d, J=9.2 Hz), 3.88 (1H, d, J=9.2 Hz), 5.01 (1H, dd, J=10.4 Hz, 4.6 Hz), 5.15 (1H, s), 6.56 (1H, dd, J=9.1 Hz, 3.8 Hz), 7.01 (1H, t, J=9.7 Hz), 7.13-7.20 (2H, m), 7.34 (1H, dd, J=12.4 Hz, 2.3 Hz), 10.03 (1H, s).

Example 434

(3R,4R)-1-(4-Chloro-2,6-difluorophenyl)-4-{[(8-fluoro-2-oxo-1,2,3,4-tetrahydroquinolin-5-yl)oxy]methyl}-4-hydroxypiperidin-3-yl acetate Synthesized analogous to Example 433.
(Ethyl acetate-diisopropyl ether) m.p. 163-165° C.
$^1$HNMR (DMSO-d6) δ ppm: 1.79 (1H, d, J=13.6 Hz), 1.95-2.02 (4H, m), 2.46 (2H, t, J=7.4 Hz), 2.86-3.08 (4H, m), 3.30-3.40 (2H, m), 3.76 (1H, d, J=9.2 Hz), 3.87 (1H, d, J=9.2 Hz), 4.95 (1H, dd, J=10.2 Hz, 4.8 Hz), 5.14 (1H, s), 6.56 (1H, dd, J=9.2 Hz, 3.8 Hz), 7.01 (1H, t, J=9.7 Hz), 7.27-7.33 (2H, m), 10.03 (1H, s).

Example 435

(3R,4R)-1-(4-Chloro-2,6-difluorophenyl)-4-{[(8-fluoro-2-oxo-1,2,3,4-tetrahydroquinolin-5-yl)oxy]methyl}-4-hydroxypiperidin-3-yl pyrazine-2-carboxylate A solution of 5-{[(3R,4R)-1-(4-chloro-2,6-difluorophenyl)-3,4-dihydroxypiperidin-4-yl]methoxy}-8-fluoro-3,4- dihydroquinolin-2(1H)-one (100 mg), 2-pyrazinecarboxylic acid (97.8 mg), 4-(dimethylamino)pyridine (2.67 mg) and 1-(3-dimethylaminopropyl)-3-ethylcarbodiimide hydrochloride (151.2 mg) in N,N-dimethylformamide (2 mL) was stirred at room temperature overnight. To the reaction solution was added water, the precipitate was collected on a filter and purified by silica gel column chromatography (hexane/ethyl acetate). The obtained product was washed with ethyl acetate/diisopropyl ether and dried to provide the title compound (53 mg).

$^1$HNMR (DMSO-d6) δ ppm: 1.88 (1H, d, J=13.6 Hz), 2.02-2.09 (1H, m), 2.43 (2H, t, J=7.6 Hz), 2.87 (2H, t, J=7.6 Hz), 3.03 (1H, d, J=11.5 Hz), 3.26-3.30 (1H, m), 3.41-3.54 (2H, m), 3.92 (1H, d, J=9.5 Hz), 4.00 (1H, d, J=9.5 Hz), 5.28 (1H, dd, J=10.1 Hz, 4.8 Hz), 5.38 (1H, s), 6.55 (1H, dd, J=9.2 Hz, 3.8 Hz), 6.93 (1H, t, J=9.7 Hz), 7.28-7.35 (2H, m), 8.82 (1H, dd, J=2.4 Hz, 1.4 Hz), 8.88 (1H, d, J=2.4 Hz), 9.42 (1H, d, J=1.4 Hz), 9.99 (1H, s).

Example 436

5-{[(4R)-1-(4-Chloro-2,6-difluorophenyl)-4-hydroxy-3-oxopiperidin-4-yl]methoxy}-8-fluoro-3,4-dihydroquinolin-2(1H)-one To a solution of dimethyl sulfoxide (0.078 mL) in dichloromethane (3 mL) was added oxalyl chloride (0.057 mL) at −80° C., and the mixture was stirred at the same temperature for 10 min. To the mixture was added a solution of 5-{[(3R,4R)-1-(4-chloro-2,6-difluorophenyl)-3,4-dihydroxypiperidin-4-yl]methoxy}-8-fluoro-3,4-dihydroquinolin-2(1H)-one (100 mg) in dichloromethane/dimethyl sulfoxide (1 mL/0.33 mL), the mixture was stirred at the same temperature for 20 min, then triethylamine (0.183 mL) was added thereto, and the reaction mixture was stirred at room temperature overnight. To the reaction solution was added water, the solution was extracted with ethyl acetate, the solvent of the organic layer was distilled off, and then the residue was purified by silica gel column chromatography (hexane/ethyl acetate), and recrystallized from ethyl acetate/diisopropyl ether/hexane. The precipitate was collected on a filter and dried to provide the title compound (21 mg).

m.p. 127-130° C.

$^1$HNMR (DMSO-d6) δ ppm: 1.96-2.06 (1H, m), 2.20-2.26 (1H, m), 2.43 (2H, t, J=7.7 Hz), 2.76-2.85 (2H, m), 3.28-3.38 (2H, m), 3.51-3.55 (1H, m), 3.67 (1H, d, J=14.7 Hz), 3.99 (1H, d, J=14.7 Hz), 4.05 (1H, d, J=9.6 Hz), 4.17 (1H, d, J=9.6 Hz), 6.63 (1H, dd, J=9.1 Hz, 3.8 Hz), 7.03 (1H, t, J=9.7 Hz), 7.26-7.38 (2H, m), 10.03 (1H, s).

Example 437

(3R,4R)-1-(5-Chloro-3-fluoropyridin-2-yl)-4-{[(8-fluoro-2-oxo-1,2,3,4-tetrahydroquinolin-5-yl)oxy]methyl}-4-hydroxypiperidin-3-yl acetate Synthesized analogous to Example 433.
White Powder
$^1$HNMR (CDCl$_3$) δ ppm: 1.91-1.96 (1H, m), 2.06-2.10 (1H, m), 2.08 (3H, s), 2.34-2.36 (1H, m), 2.61-2.65 (2H, m), 2.91-3.03 (2H, m), 3.28 (1H, dd, J=12.3 Hz, 10.5 Hz), 3.35 (1H, dt, J=12.5 Hz, 2.8 Hz), 3.80 (1H, d, J=9.1 Hz), 3.83-3.89 (1H, m), 3.87 (1H, d, J=9.1 Hz), 3.98-4.04 (1H, m), 5.22 (1H, dd, J=10.4 Hz, 4.9 Hz), 6.44 (1H, dd, J=9.1 Hz, 3.9 Hz), 6.90 (1H, t, J=9.5 Hz), 7.29 (1H, dd, J=12.0 Hz, 2.1 Hz), 7.54 (1H, brs), 7.98 (1H, d, J=2.1 Hz).

Example 438

5-{1-[1-(4-Chloro-2,6-difluorophenyl)-4-hydroxypiperidin-4-yl]ethoxy}-8-fluoro-3,4-dihydroquinolin-2(1H)-one A suspension of 8-fluoro-5-hydroxy-3,4-dihydroquinolin-2(1H)-one (110 mg), 1-[1-(4-chloro-2,6-difluorophenyl)-4-hydroxypiperidin-4-yl]ethyl 4-methylbenzenesulfonate (284 mg) and potassium carbonate (126 mg) in acetonitrile (2 mL) was stirred at 70° C. for 1 h. To the reaction solution was added ethyl acetate, the precipitate was filtered off, and the filtrate was concentrated. To the residue were added tripotassium phosphate (25.8 mg) and N,N-dimethylformamide/2-propanol (1:1) (4 mL), and the mixture was stirred at 70° C. for 7 days. To the reaction solution was added water, the solution was extracted with ethyl acetate, and the solvent of the organic layer was distilled off. The residue was purified by silica gel column chromatography (hexane/ethyl acetate), and recrystallized form diisopropyl ether/hexane. The precipitate was collected on a filter and dried to provide the title compound (38 mg).

$^1$HNMR (DMSO-d6) δ ppm: 1.18 (3H, d, J=6.0 Hz), 1.48 (1H, d, J=13.6 Hz), 1.70-1.80 (3H, m), 2.44 (2H, t, J=7.5 Hz), 2.79-2.99 (4H, m), 3.28-3.39 (2H, m), 4.14 (1H, q, J=6.0 Hz), 4.52 (1H, s), 6.62 (1H, dd, J=9.2 Hz, 3.9 Hz), 7.00 (1H, t, J=9.7 Hz), 7.23-7.28 (2H, m), 9.99 (1H, s).

Example 439

5-{[(3S*,4R*)-1-(4-Chloro-2,6-difluorophenyl)-3-fluoro-4-hydroxypiperidin-4-yl]methoxy}-8-fluoro-3,4-dihydroquinolin-2(1H)-one Synthesized analogous to Example 42.
(Acetic acid/water) m.p. 223-224° C.
$^1$HNMR (DMSO-d6) δ ppm: 1.59-1.66 (1H, m), 1.87-1.97 (1H, m), 2.46 (2H, t, J=7.8 Hz), 2.85-3.04 (3H, m), 3.25-3.45 (2H, m), 3.50-3.65 (1H, m), 3.84 (1H, dd, J=9.8 Hz, 2.8 Hz), 3.97 (1H, dd, J=9.8 Hz, 1.9 Hz), 4.62 (1H, d, J=46.6 Hz), 5.34 (1H, d, J=1.0 Hz), 6.61 (1H, dd, J=9.1 Hz, 3.8 Hz), 7.01 (1H, t, J=9.7 Hz), 7.25-7.32 (2H, m), 10.03 (1H, s).

Example 440

5-{[(3R*,4R*)-1-(4-Chloro-2,6-difluorophenyl)-3-fluoro-4-hydroxypiperidin-4-yl]methoxy}-8-fluoro-3,4-dihydroquinolin-2(1H)-one Synthesized analogous to Example 42.
(Acetic acid/water) m.p. 222-223° C.
$^1$HNMR (DMSO-d6) δ ppm: 1.74-1.81 (1H, m), 1.89-1.98 (1H, m), 2.45-2.52 (2H, m), 2.84-2.97 (3H, m), 3.20-3.28 (1H, m), 3.28-3.38 (1H, m), 3.44-3.52 (1H, m), 3.81 (1H, d, J=9.1 Hz), 4.04 (1H, d, J=9.1 Hz), 4.73 (1H, ddd, J=47.4 Hz, 10.1 Hz, 5.1 Hz), 5.30 (1H, s), 6.61 (1H, dd, J=9.1 Hz, 3.8 Hz), 7.03 (1H, t, J=9.7 Hz), 7.28-7.35 (2H, m), 10.04 (1H, s).

Example 441

5-{[(3S*,4R*)-1-(4-Chloro-2-fluorophenyl)-3-fluoro-4-hydroxypiperidin-4-yl]methoxy}-8-fluoro-3,4-dihydroquinolin-2(1H)-one Synthesized analogous to Example 42.
(Acetic acid/water) m.p. 190-191° C.
$^1$HNMR (DMSO-d6) δ ppm: 1.64-1.71 (1H, m), 1.90-1.99 (1H, m), 2.46 (2H, t, J=7.8 Hz), 2.86-3.03 (2H, m), 3.05-3.14 (1H, m), 3.16-3.23 (2H, m), 3.51 (1H, t, J=13.1 Hz), 3.86 (1H, dd, J=9.8 Hz, 2.8 Hz), 3.97 (1H, dd, J=9.8 Hz, 1.8 Hz), 4.68 (1H, d, J=46.1 Hz), 5.36 (1H, d, J=1.3 Hz), 6.61 (1H, dd, J=9.1 Hz, 3.8 Hz), 7.01 (1H, t, J=9.7 Hz), 7.10 (1H, t, J=9.1 Hz), 7.17 (1H, dd, J=8.8 Hz, 2.0 Hz), 7.32 (1H, dd, J=12.5 Hz, 2.4 Hz), 10.03 (1H, s).

Example 442

5-{[(3R*,4R*)-1-(4-Chloro-2-fluorophenyl)-3-fluoro-4-hydroxypiperidin-4-yl]methoxy}-8-fluoro-3,4-dihydroquinolin-2(1H)-one Synthesized analogous to Example 42.
(Acetic acid/water) m.p. 194-195° C.
$^1$HNMR (DMSO-d6) δ ppm: 1.78-1.86 (1H, m), 1.92-2.02 (1H, m), 2.47 (2H, t, J=7.9 Hz), 2.89 (2H, t, J=7.4 Hz), 2.96-3.04 (1H, m), 3.09-3.21 (2H, m), 3.35-3.43 (1H, m), 3.82 (1H, d, J=9.1 Hz), 4.04 (1H, d, J=9.1 Hz), 4.81 (1H, ddd, J=47.1 Hz, 10.3 Hz, 5.0 Hz), 5.31 (1H, s), 6.60 (1H, dd, J=9.2 Hz, 3.8 Hz), 7.03 (1H, t, J=9.7 Hz), 7.11-7.22 (2H, m), 7.35 (1H, dd, J=12.4 Hz, 2.3 Hz), 10.04 (1H, s).

Example 443

5-{[(3S*,4R*)-1-(2-Chloro-4-fluorophenyl)-3-fluoro-4-hydroxypiperidin-4-yl]methoxy}-8-fluoro-3,4-dihydroquinolin-2(1H)-one Synthesized analogous to Example 42.
(Acetic acid/water) m.p. 204-205° C.
$^1$HNMR (DMSO-d6) δ ppm: 1.65-1.71 (1H, m), 1.93-2.02 (1H, m), 2.46 (2H, t, J=7.8 Hz), 2.86-3.09 (4H, m), 3.16-3.39 (2H, m), 3.88 (1H, dd, J=9.8 Hz, 2.8 Hz), 3.99 (1H, dd, J=9.8 Hz, 1.9 Hz), 4.68 (1H, d, J=46.4 Hz), 5.32 (1H, d, J=1.2 Hz), 6.62 (1H, dd, J=9.2 Hz, 3.8 Hz), 7.02 (1H, t, J=9.7 Hz), 7.15-7.21 (1H, m), 7.26 (1H, dd, J=9.1 Hz, 5.6 Hz), 7.40 (1H, dd, J=8.6 Hz, 3.0 Hz), 10.03 (1H, s).

Example 444

5-{[(3R*,4R*)-1-(2-Chloro-4-fluorophenyl)-3-fluoro-4-hydroxypiperidin-4-yl]methoxy}-8-fluoro-3,4-dihydroquinolin-2(1H)-one Synthesized analogous to Example 42.
(Acetic acid/water) m.p. 218-220° C.
$^1$HNMR (DMSO-d6) δ ppm: 1.79-1.87 (1H, m), 1.93-2.02 (1H, m), 2.44-2.51 (2H, m), 2.85-2.96 (2H, m), 2.96-3.02 (2H, m), 3.11-3.19 (1H, m), 3.23-3.31 (1H, m), 3.84 (1H, d, J=9.1 Hz), 4.06 (1H, d, J=9.1 Hz), 4.81 (1H, ddd, J=47.3 Hz, 10.2 Hz, 5.0 Hz), 5.29 (1H, s), 6.62 (1H, dd, J=9.1 Hz, 3.8 Hz), 7.03 (1H, t, J=9.7 Hz), 7.15-7.21 (1H, m), 7.30 (1H, dd, J=9.0 Hz, 5.6 Hz), 7.42 (1H, dd, J=8.6 Hz, 3.0 Hz), 10.05 (1H, s).

Example 445

5-{[(3R*,5R*)-1-(4-Chloro-2,6-difluorophenyl)-3,4,5-trihydroxypiperidin-4-yl]methoxy}-8-fluoro-3,4-dihydroquinolin-2(1H)-one Synthesized analogous to Example 42.
(Ethyl acetate/methanol) m.p. 221.5-222.0° C.
$^1$HNMR (CDCl$_3$) δ ppm: 2.43 (1H, d, J=9.0 Hz), 2.65 (2H, t, J=7.5 Hz), 2.79 (1H, brs), 2.92-3.08 (4H, m), 3.18-3.21 (1H, m), 3.26-3.30 (1H, m), 3.73 (1H, d, J=12.5 Hz), 3.92-3.94 (1H, m), 4.00-4.05 (1H, m), 4.32-4.36 (2H, m), 6.60 (1H, dd, J=9.0 Hz, 4.0 Hz), 6.93-6.96 (3H, m), 7.53 (1H, brs).

Example 446

5-{[(3R,4S)-1-(4-Chloro-2,6-difluorophenyl)-3-fluoro-4-hydroxypiperidin-4-yl]methoxy}-8-fluoro-3,4-dihydroquinolin-2(1H)-one Synthesized analogous to Example 42.
(Ethanol) m.p. 224-225° C. $^1$HNMR (DMSO-d6) δ ppm: 1.59-1.66 (1H, m), 1.87-1.97 (1H, m), 2.46 (2H, t, J=7.8 Hz), 2.85-3.04 (3H, m), 3.25-3.45 (2H, m), 3.50-3.65 (1H, m), 3.84 (1H, dd, J=9.8 Hz, 2.8 Hz), 3.97 (1H, dd, J=9.8 Hz, 1.9 Hz), 4.62 (1H, d, J=46.6 Hz), 5.34 (1H, s), 6.61 (1H, dd, J=9.1 Hz, 3.8 Hz), 7.01 (1H, t, J=9.7 Hz), 7.25-7.32 (2H, m), 10.03 (1H, s).

Example 447

5-{[(3S,4R)-1-(4-Chloro-2,6-difluorophenyl)-3-fluoro-4-hydroxypiperidin-4-yl]methoxy}-8-fluoro-3,4-dihydroquinolin-2(1H)-one Synthesized analogous to Example 42.
(Ethanol) m.p. 224-225° C.
$^1$HNMR (DMSO-d6) δ ppm: 1.59-1.66 (1H, m), 1.87-1.97 (1H, m), 2.46 (2H, t, J=7.8 Hz), 2.85-3.04 (3H, m), 3.25-3.45 (2H, m), 3.50-3.65 (1H, m), 3.84 (1H, dd, J=9.8 Hz, 2.8 Hz), 3.97 (1H, dd, J=9.8 Hz, 1.9 Hz), 4.62 (1H, d, J=46.6 Hz), 5.34 (1H, s), 6.61 (1H, dd, J=9.1 Hz, 3.8 Hz), 7.01 (1H, t, J=9.7 Hz), 7.25-7.32 (2H, m), 10.03 (1H, s).

Example 448

5-{[(3R,4R)-1-(4-Chloro-2,6-difluorophenyl)-3-fluoro-4-hydroxypiperidin-4-yl]methoxy}-8-fluoro-3,4-dihydroquinolin-2(1H)-one Synthesized analogous to Example 42.
(Acetic acid/water) m.p. 207-209° C.
$^1$HNMR (DMSO-d6) δ ppm: 1.74-1.81 (1H, m), 1.89-1.98 (1H, m), 2.45-2.52 (2H, m), 2.84-2.97 (3H, m), 3.20-3.28 (1H, m), 3.28-3.38 (1H, m), 3.44-3.52 (1H, m), 3.81 (1H, d, J=9.1 Hz), 4.04 (1H, d, J=9.1 Hz), 4.73 (1H, ddd, J=47.4 Hz, 10.1 Hz, 5.1 Hz), 5.30 (1H, s), 6.61 (1H, dd, J=9.1 Hz, 3.8 Hz), 7.03 (1H, t, J=9.7 Hz), 7.28-7.35 (2H, m), 10.05 (1H, s).

Example 449

5-{[(3S,4S)-1-(4-Chloro-2,6-difluorophenyl)-3-fluoro-4-hydroxypiperidin-4-yl]methoxy}-8-fluoro-3,4-dihydroquinolin-2(1H)-one Synthesized analogous to Example 42.
(Acetic acid/water) m.p. 209-210° C.
$^1$HNMR (DMSO-d6) δ ppm: 1.74-1.81 (1H, m), 1.89-1.98 (1H, m), 2.45-2.52 (2H, m), 2.84-2.97 (3H, m), 3.20-3.28 (1H, m), 3.28-3.38 (1H, m), 3.44-3.52 (1H, m), 3.81 (1H, d, J=9.1 Hz), 4.04 (1H, d, J=9.1 Hz), 4.73 (1H, ddd, J=47.4 Hz, 10.1 Hz, 5.1 Hz), 5.29 (1H, s), 6.61 (1H, dd, J=9.1 Hz, 3.8 Hz), 7.03 (1H, t, J=9.7 Hz), 7.28-7.35 (2H, m), 10.05 (1H, s).

Example 450

(3R,4R)-1-(4-chloro-2,6-difluorophenyl)-4-{[(8-fluoro-2-oxo-1,2,3,4-tetrahydroquinolin-5-yl)oxy]methyl}-4-hydroxypiperidin-3-yl ethyl carbonate To a suspension of 5-{[(3R,4R)-1-(4-chloro-2,6-difluorophenyl)-3,4-dihydroxypiperidin-4-yl]methoxy}-8-fluoro-3,4-dihydroquinolin-2(1H)-one (200 mg) in dichloromethane (4 mL) was added pyridine (0.053 mL), then ethyl chloroformate (0.063 mL) was added at 0° C., and the mixture was stirred at room temperature for 1 h. To the reaction solution was added water and the solution was extracted with dichloromethane. The organic layer was washed with water and brine, dried over anhydrous sodium sulfate, and the solvent was distilled off. The residue was purified by silica gel column chromatography (hexane/ethyl acetate) to provide the title compound (122 mg).
$^1$HNMR (CDCl$_3$) δ ppm: 1.26 (3H, t, J=7.2 Hz), 1.84-1.90 (1H, m), 2.05-2.13 (1H, m), 2.40 (1H, d, J=2.0 Hz), 2.63-2.68 (2H, m), 3.00-3.06 (3H, m), 3.30-3.36 (1H, m), 3.43-3.53 (2H, m), 3.87-3.94 (2H, m), 4.07-4.21 (2H, m), 5.04 (1H, dd, J=10.2 Hz, 5.2 Hz), 6.46 (1H, dd, J=9.1 Hz, 4.0 Hz), 6.86-6.95 (3H, m), 7.56 (1H, brs).

Example 451

4-{[(3R,4R)-1-(4-Chloro-2,6-difluorophenyl)-4-{[(8-fluoro-2-oxo-1,2,3,4-tetrahydroquinolin-5-yl)oxy]methyl}-4-hydroxypiperidin-3-yl]oxy}-4-oxobutanoic acid A solution of 5-{[(3R,4R)-1-(4-chloro-2,6-difluorophenyl)-3,4-dihydroxypiperidin-4-yl]methoxy}-8-fluoro-3,4-dihydroquinolin-2(1H)-one (300 mg), 4-(dimethylamino)pyridine (16.1 mg) and succinic anhydride (99 mg) in N-methyl-2-pyrrolidone (NMP) (2 mL) was stirred at 100° C. for 2 h. To the reaction solution were added water and diethyl ether, and the precipitate was collected on a filter. The obtained solid was purified by silica gel column chromatography (ethyl acetate/methanol), and washed with ethyl acetate/diethyl ether to give the title compound (203 mg).
$^1$HNMR (DMSO-d6) δ ppm: 1.78-1.84 (1H, m), 1.93-2.01 (1H, m), 2.43-2.50 (5H, m), 2.82-2.95 (3H, m), 3.01-3.07 (1H, m), 3.30-3.42 (1H, m), 3.75-3.89 (2H, m), 4.93-4.98 (1H, m), 5.11 (1H, brs), 6.56 (1H, dd, J=9.2 Hz, 3.6 Hz), 7.00 (1H, t, J=9.6 Hz), 7.26-7.33 (2H, m), 10.03 (1H, brs), 12.30 (1H, brs).

Example 452

(3R,4R)-1-(4-Chloro-2,6-difluorophenyl)-4-{[(8-fluoro-2-oxo-1,2,3,4-tetrahydroquinolin-5-yl)oxy]methyl}-4-hydroxypiperidin-3-yl ethylcarbamate A solution of 5-{[(3R,4R)-1-(4-chloro-2,6-difluorophenyl)-3,4-dihydroxypiperidin-4-yl]methoxy}-8-fluoro-3,4-dihydroquinolin-2(1H)-one (200 mg), dimethylaminopyridine (10.7 mg) and ethyl isocyanate (0.052 mL) in tetrahydrofuran (6 mL) was heated to reflux for 3 days. After 3 days, the reaction solution was concentrated, and the residue was purified by silica gel column chromatography (hexane/ethyl acetate). The obtained product was recrystallized from ethyl acetate/diethyl ether, the precipitate was collected on a filter and dried to provide the title compound (177 mg).
m.p. 167-169° C.
$^1$HNMR (CDCl$_3$) δ ppm: 1.10 (3H, t, J=7.3 Hz), 1.91-1.97 (1H, m), 2.02-2.10 (1H, m), 2.37 (1H, brs), 2.61-2.68 (2H, m), 2.96-3.09 (3H, m), 3.14-3.24 (2H, m), 3.26-3.32 (1H, m), 3.39-3.47 (2H, m), 3.84-3.96 (2H, m), 4.72-4.78 (1H, m), 5.03-5.09 (1H, m), 6.46 (1H, dd, J=9.1 Hz, 3.9 Hz), 6.85-6.94 (3H, m), 7.64 (1H, brs).

Example 453

(3R,4R)-1-(4-Chloro-2-fluorophenyl)-4-{[(8-fluoro-2-oxo-1,2,3,4-tetrahydroquinolin-5-yl)oxy]methyl}-4-hydroxypiperidin-3-yl ethyl carbonate Synthesized analogous to Example 450.
(Ethyl acetate/diethyl ether) m.p. 171-172° C.
$^1$HNMR (CDCl$_3$) δ ppm: 1.26 (3H, t, J=7.2 Hz), 1.89-1.95 (1H, m), 2.08-2.16 (1H, m), 2.54 (1H, d, J=2.0 Hz), 2.59-2.69 (2H, m), 2.94-3.07 (2H, m), 3.10-3.18 (2H, m), 3.23-3.29 (1H, m), 3.47-3.53 (1H, m), 3.88-3.94 (2H, m), 4.09-4.22 (2H, m), 5.12 (1H, dd, J=10.4 Hz, 5.0 Hz), 6.46 (1H, dd, J=9.1 Hz, 3.9 Hz), 6.88-6.96 (2H, m), 7.03-7.09 (2H, m), 7.84 (1H, brs).

Example 454

(3R,4R)-1-(4-Chloro-2-fluorophenyl)-4-{[(8-fluoro-2-oxo-1,2,3,4-tetrahydroquinolin-5-yl)oxy]methyl}-4-hydroxypiperidin-3-yl acetate Synthesized analogous to Example 433.
$^1$HNMR (CDCl$_3$) δ ppm: 1.91-1.98 (1H, m), 2.09 (3H, s), 2.09-2.16 (1H, m), 2.32-2.34 (1H, m), 2.64 (2H, d, J=7.6 Hz), 2.95-3.07 (2H, m), 3.09 (1H, t, J=10.6 Hz), 3.15 (1H, dd, J=12.1 Hz, 2.6 Hz), 3.24-3.30 (1H, m), 3.38-3.43 (1H, m), 3.82 (1H, d, J=9.0 Hz), 3.89 (1H, d, J=9.0 Hz), 5.28 (1H, dd, J=10.3 Hz, 5.0 Hz), 6.45 (1H, dd, J=9.1 Hz, 3.9 Hz), 6.88-6.95 (2H, m), 7.03-7.08 (2H, m), 7.61 (1H, brs).

Example 455

(3R,4R)-1-(4-Chloro-2-fluorophenyl)-4-{[(8-fluoro-2-oxo-1,2,3,4-tetrahydroquinolin-5-yl)oxy]methyl}piperidine-3,4-diyl diacetate Synthesized analogous to Example 433.
$^1$HNMR (CDCl$_3$) δ ppm: 2.03 (3H, s), 2.14-2.22 (1H, m), 2.17 (3H, s), 2.61-2.68 (2H, m), 2.75-2.81 (1H, m), 2.86-2.93 (1H, m), 2.93-3.04 (2H, m), 3.16 (1H, t, J=10.5 Hz), 3.29-3.36 (1H, m), 3.37-3.43 (1H, m), 4.15 (1H, d, J=9.0

Hz), 4.68 (1H, d, J=9.0 Hz), 5.43 (1H, dd, J=10.1 Hz, 4.6 Hz), 6.45 (1H, dd, J=9.2 Hz, 3.9 Hz), 6.87-6.95 (2H, m), 7.03-7.09 (2H, m), 7.63 (1H, brs).

Example 456

(3R,4R)-1-(4-Chloro-2-fluorophenyl)-4-{[(8-fluoro-2-oxo-1,2,3,4-tetrahydroquinolin-5-yl)oxy]methyl}-4-hydroxypiperidin-3-yl ethylcarbamate Synthesized analogous to Example 452.
(Ethyl acetate/diethyl ether) m.p. 156-157° C.
$^1$HNMR (CDCl$_3$) δ ppm: 1.11 (3H, t, J=7.3 Hz), 1.98-2.01 (1H, m), 2.04-2.13 (1H, m), 2.46 (1H, brs), 2.58-2.68 (2H, m), 2.94-3.06 (2H, m), 3.07-3.30 (5H, m), 3.41-3.47 (1H, m), 3.86 (1H, d, J=9.0 Hz), 3.93 (1H, d, J=9.0 Hz), 4.77-4.84 (1H, m), 5.11-5.17 (1H, m), 6.46 (1H, dd, J=9.1 Hz, 3.9 Hz), 6.88-6.96 (2H, m), 7.03-7.09 (2H, m), 7.84 (1H, brs).

Example 457

(3R,4R)-1-(4-Chloro-2-fluorophenyl)-4-{[(8-fluoro-2-oxo-1,2,3,4-tetrahydroquinolin-5-yl)oxy]methyl}-4-hydroxypiperidin-3-yl hydrogen phosphonate To a solution of diphenyl phosphite (1.309 mL) in pyridine (6 mL) was added, 5-{[(3R,4R)-1-(4-chloro-2-fluorophenyl)-3,4-dihydroxypiperidin-4-yl]methoxy}-8-fluoro-3,4-dihydroquinolin-2(1H)-one (1.0 g) at 0° C., and the reaction mixture was stirred at room temperature for 2 h. To the reaction solution were added water and ethyl acetate for extraction. The aqueous layer was left to stand a day, the precipitated crystal was collected on a filter and dried to provide the title compound (0.85 g).
$^1$HNMR (DMSO-d6) δ ppm: 1.76-1.83 (1H, m), 1.96-2.05 (1H, m), 2.46 (2H, t, J=7.9 Hz), 2.89 (2H, t, J=7.9 Hz), 3.00-3.07 (1H, m), 3.11-3.18 (2H, m), 3.34-3.40 (1H, m), 3.70-3.85 (2H, m), 3.96 (1H, d, J=9.0 Hz), 4.48-4.56 (1H, m), 5.99 (0.5H, s), 6.58 (1H, dd, J=9.1 Hz, 3.8 Hz), 7.03 (1H, t, J=9.5 Hz), 7.14 (1H, t, J=9.1 Hz), 7.19 (1H, dd, J=8.8 Hz, 2.3 Hz), 7.33 (0.5H, s), 7.35 (1H, dd, J=12.3 Hz, 2.3 Hz), 10.04 (1H, brs).

Example 458

4-{[(3R,4R)-1-(4-Chloro-2-fluorophenyl)-4-{[(8-fluoro-2-oxo-1,2,3,4-tetrahydroquinolin-5-yl)oxy]methyl}-4-hydroxypiperidin-3-yl]oxy}-4-oxobutanoic acid Synthesized analogous to Example 451.
$^1$HNMR (DMSO-d6) δ ppm: 1.81-1.88 (1H, m), 1.95-2.04 (1H, m), 2.41-2.52 (6H, m), 2.80-2.92 (2H, m), 2.98-3.11 (2H, m), 3.14-3.20 (1H, m), 3.21-3.27 (1H, m), 3.79 (1H, d, J=9.2 Hz), 3.87 (1H, d, J=9.2 Hz), 5.02 (1H, dd, J=10.4 Hz, 4.6 Hz), 5.14 (1H, brs), 6.56 (1H, dd, J=9.1 Hz, 3.5 Hz), 7.00 (1H, t, J=9.9 Hz), 7.12 (1H, t, J=9.2 Hz), 7.18 (1H, dd, J=8.7 Hz, 2.2 Hz), 7.34 (1H, dd, J=12.3 Hz, 2.2 Hz), 10.02 (1H, brs), 12.20 (1H, brs).

Example 459

(3R,4R)-1-(4-Chloro-2,6-difluorophenyl)-4-{[(8-fluoro-2-oxo-1,2,3,4-tetrahydroquinolin-5-yl)oxy]methyl}piperidine-3,4-diyl diacetate Synthesized analogous to Example 433.
$^1$HNMR (CDCl$_3$) δ ppm: 2.02 (3H, s), 2.12-2.19 (1H, m), 2.18 (3H, s), 2.62-2.67 (2H, m), 2.70-2.76 (1H, m), 2.93-3.05 (2H, m), 3.06-3.12 (1H, m), 3.15-3.29 (2H, m), 3.44-3.51 (1H, m), 4.17 (1H, d, J=9.0 Hz), 4.68 (1H, d, J=9.0 Hz), 5.35 (1H, dd, J=9.7 Hz, 4.6 Hz), 6.45 (1H, dd, J=9.2 Hz, 3.9 Hz), 6.85-6.95 (3H, m), 7.63 (1H, brs).

Example 460

5-({[1-(4-Chloro-2-fluorophenyl)-4-hydroxypiperidin-4-yl]methyl}sulfanyl)-8-fluoro-3,4-dihydroquinolin-2(1H)-one Synthesized analogous to Example 6.
(Acetic acid/water) m.p. 171-172° C.
$^1$HNMR (CDCl$_3$) δ ppm: 1.75-1.88 (4H, m), 2.04 (1H, s), 2.64-2.71 (2H, m), 2.99-3.08 (2H, m), 3.06 (2H, s), 3.14-3.23 (4H, m), 6.87-6.92 (1H, m), 6.97 (1H, t, J=9.3 Hz), 7.01-7.07 (2H, m), 7.15 (1H, dd, J=8.8 Hz, 5.1 Hz), 7.62 (1H, brs).

Example 461

5-({[1-(4-Chloro-2-fluorophenyl)-4-hydroxypiperidin-4-yl]methyl}sulfinyl)-8-fluoro-3,4-dihydroquinolin-2(1H)-one A suspension of 5-({[1-(4-chloro-2-fluorophenyl)-4-hydroxypiperidin-4-yl]methyl}-sulfanyl)-8-fluoro-3,4-dihydroquinolin-2(1H)-one (0.22 g) and m-chloroperoxybenzoic acid (75%) (0.144 g) in chloroform (10 mL) was stirred at room temperature for 7.5 h. The solvent was distilled off and to the residue were added saturated aqueous sodium hydrogencarbonate and ethyl acetate. The insoluble precipitate was collected on a filter, the obtained solid was purified by silica gel column chromatography (dichloromethane/methanol), and recrystallized from ethanol. The precipitate was collected on a filter and dried to provide the title compound (86 mg).
m.p. 241° C.
$^1$HNMR (DMSO-d6) δ ppm: 1.67-1.74 (1H, m), 1.77-1.85 (1H, m), 1.85-2.00 (2H, m), 2.47-2.61 (2H, m), 2.82-3.13 (8H, m), 5.15 (1H, s), 7.08 (1H, t, J=9.1 Hz), 7.16 (1H, dd, J=8.6 Hz, 1.9 Hz), 7.30 (1H, dd, J=12.4 Hz, 2.5 Hz), 7.38 (1H, t, J=9.5 Hz), 7.45 (1H, dd, J=8.8 Hz, 5.0 Hz), 10.34 (1H, s).

Example 462

5-({[1-(4-Chloro-2-fluorophenyl)-4-hydroxypiperidin-4-yl]methyl}sulfonyl)-8-fluoro-3,4-dihydroquinolin-2(1H)-one To a suspension of 5-({[1-(4-chloro-2-fluorophenyl)-4-hydroxy-1-oxidopiperidin-4-yl]methyl}sulfonyl)-8-fluoro-3,4-dihydroquinolin-2(1H)-one (0.1 g) in methanol (3 mL) was added carbon disulfide (3 mL), the mixture was heated to reflux for 3 h, and the solvent was distilled off. To the residue were added methanol/chloroform (1:1) (4 mL) and carbon disulfide (8 mL), and the reaction mixture was heated to reflux for 6 h. The solvent was distilled off, the residue was purified by silica gel column chromatography (dichloromethane/methanol), and recrystallized from ethyl acetate/ethanol. The precipitate was collected on a filter, and air-dried (60° C.) to provide the title compound (54 mg).
m.p. 236-238° C.

¹HNMR (CDCl₃) δ ppm: 1.93-2.02 (2H, m), 2.04-2.11 (2H, m), 2.69-2.76 (2H, m), 3.08-3.15 (2H, m), 3.15-3.21 (2H, m), 3.31 (2H, s), 3.48-3.54 (2H, m), 3.59 (1H, s), 6.90 (1H, t, J=8.8 Hz), 7.02-7.07 (2H, m), 7.21 (1H, t, J=9.1 Hz), 7.72 (1H, brs), 7.76 (1H, dd, J=8.9 Hz, 5.3 Hz).

Example 463

5-{2-[1-(4-Chloro-2,6-difluorophenyl)-4-hydroxypiperidin-4-yl]ethyl}-8-fluoro-3,4-dihydroquinolin-2(1H)-one Synthesized analogous to Example 6.
¹HNMR (DMSO-d6) δ ppm: 1.53-1.62 (6H, m), 2.45-2.49 (2H, m), 2.60-2.64 (2H, m), 2.88-2.94 (4H, m), 3.29-3.34 (2H, m), 4.35 (1H, s), 6.80 (1H, dd, J=8.6 Hz, 5.2 Hz), 6.96-7.00 (1H, m), 7.22-7.29 (2H, m), 9.96 (1H, s).

Example 464

5-({trans-4-(4-Chloro-2-fluorophenyl)-1-hydroxy-4-[(4-methoxybenzyl)oxy]cyclohexyl}methoxy)-8-fluoro-3,4-dihydroquinolin-2(1H)-one Synthesized analogous to Example 42.
¹HNMR (DMSO-d6) δ ppm: 1.49 (2H, d, J=12.4 Hz), 1.97-2.25 (6H, m), 2.31 (2H, t, J=8.8 Hz), 2.75 (2H, t, J=7.6 Hz), 3.70 (2H, s), 3.74 (3H, s), 4.02 (2H, s), 4.62 (1H, s), 6.55 (1H, dd, J=9.1 Hz, 3.8 Hz), 6.87-6.93 (2H, m), 6.99 (1H, t, J=9.7 Hz), 7.19-7.25 (2H, m), 7.33 (1H, dd, J=8.5 Hz, 2.1 Hz), 7.42 (1H, dd, J=11.9 Hz, 2.2 Hz), 7.50 (1H, t, J=8.6 Hz), 10.00 (1H, brs).

Example 465

5-{[trans-4-(4-Chloro-2-fluorophenyl)-1,4-dihydroxycyclohexyl]methoxy}-8-fluoro-3,4-dihydroquinolin-2(1H)-one To a solution of 5-({trans-4-(4-chloro-2-fluorophenyl)-1-hydroxy-4-[(4-methoxybenzyl)oxy]cyclohexyl}methoxy)-8-fluoro-3,4-dihydroquinolin-2(1H)-one (0.30 g) in dichloromethane (6 mL) were added water (3 mL) and 2,3-dichloro-5,6-dicyano-p-benzoquinone (0.146 g), and the mixture was stirred vigorously at room temperature for 30 min. To the reaction solution was added water, and the solution was extracted with ethyl acetate. The organic layer was washed with brine, dried over anhydrous sodium sulfate, and the solvent was distilled off. The residue was purified by silica gel column chromatography (hexane/ethyl acetate), washed with diisopropyl ether and dried under reduced pressure (40° C.) to provide the title compound (87 mg).
¹HNMR (CDCl₃) δ ppm: 1.71-1.83 (4H, m), 1.89-1.97 (2H, m), 1.97-2.09 (2H, m), 2.39-2.53 (2H, m), 2.60-2.70 (2H, m), 3.02 (2H, t, J=7.7 Hz), 3.85 (2H, s), 6.49 (1H, dd, J=9.1 Hz, 3.9 Hz), 6.93 (1H, t, J=9.5 Hz), 7.10 (1H, dd, J=12.0 Hz, 2.1 Hz), 7.15 (1H, dd, J=8.5 Hz, 2.2 Hz), 7.49 (1H, t, J=8.7 Hz), 7.56 (1H, brs).

Example 466

5-({cis-4-(4-Chloro-2-fluorophenyl)-1-hydroxy-4-[(4-methoxybenzyl)oxy]cyclohexyl}-methoxy)-8-fluoro-3,4-dihydroquinolin-2(1H)-one Synthesized analogous to Example 42.
(Isopropylalcohol) m.p. 171.4-173.1° C.
¹HNMR (CDCl₃) δ ppm: 1.75-1.88 (2H, m), 1.98-2.19 (4H, m), 2.22-2.33 (3H, m), 2.58-2.68 (2H, m), 2.98 (2H, t, J=7.7 Hz), 3.80 (3H, s), 3.95 (2H, s), 4.17 (2H, s), 6.49 (1H, dd, J=9.1 Hz, 3.9 Hz), 6.83-6.96 (3H, m), 7.06-7.17 (2H, m), 7.20-7.26 (2H, m), 7.39 (1H, t, J=22 Hz), 7.56 (1H, brs).

Example 467

5-{[cis-4-(4-Chloro-2-fluorophenyl)-1,4-dihydroxycyclohexyl]methoxy}-8-fluoro-3,4-dihydroquinolin-2(1H)-one Synthesized analogous to Example 465.
¹HNMR (DMSO-d6) δ ppm: 1.58-1.68 (2H, m), 1.69-1.78 (2H, m), 1.78-1.90 (2H, m), 1.96-2.09 (2H, m), 2.43 (2H, t, J=7.7 Hz), 2.85 (2H, t, J=7.6 Hz), 3.90 (2H, s), 4.67 (1H, s), 5.21 (1H, s), 6.61 (1H, dd, J=9.1 Hz, 3.8 Hz), 7.01 (1H, t, J=9.7 Hz), 7.23-7.33 (2H, m), 7.63 (1H, t, J=8.7 Hz), 10.00 (1H, s).

Example 468

5-{[trans-4-(4-Chloro-2-fluorophenyl)-1-hydroxycyclohexyl]methoxy}-8-fluoro-3,4-dihydroquinolin-2(1H)-one Synthesized analogous to Example 42.
(Isopropylalcohol) m.p. 166.2-168.4° C.
¹HNMR (CDCl₃) δ ppm: 1.48-1.65 (2H, m), 1.68-1.81 (2H, m), 1.83-1.98 (2H, m), 2.09-2.21 (2H, m), 2.38 (1H, s), 2.61-2.70 (2H, m), 2.83-2.97 (1H, m), 3.02 (2H, t, J=7.7 Hz), 4.04 (2H, s), 6.53 (1H, dd, J=9.1 Hz, 4.0 Hz), 6.94 (1H, t, J=9.4 Hz), 7.02-7.08 (2H, m), 7.08-7.17 (1H, m), 7.55 (1H, brs).

Example 469

5-{[cis-4-(4-Chloro-2-fluorophenyl)-1-hydroxycyclohexyl]methoxy}-8-fluoro-3,4-dihydroquinolin-2(1H)-one Synthesized analogous to Example 42.
¹HNMR (CDCl₃) δ ppm: 1.54-1.70 (2H, m), 1.70-1.81 (2H, m), 1.85-2.25 (5H, m), 2.56-2.73 (2H, m), 2.78-2.95 (1H, m), 3.02 (2H, t, J=7.7 Hz), 3.81 (2H, s), 6.48 (1H, dd, J=9.1 Hz, 4.0 Hz), 6.92 (1H, t, J=9.4 Hz), 7.05 (1H, dd, J=10.1 Hz, 2.1 Hz), 7.10 (1H, dd, J=8.3 Hz, 2.0 Hz), 7.24 (1H, t, J=8.2 Hz), 7.59 (1H, brs).

Example 470

5-{[(1R*,2R*,4S*)-4-(4-Chloro-2-fluorophenyl)-1,2-dihydroxycyclohexyl]methoxy}-8-fluoro-3,4-dihydroquinolin-2(1H)-one Synthesized analogous to Example 6.
¹HNMR (CDCl₃) δ ppm: 1.53-1.68 (1H, m), 1.80-1.94 (3H, m), 2.00-2.18 (2H, m), 2.57-2.72 (4H, m), 3.00 (2H, t, J=7.7 Hz), 3.30-3.45 (1H, m), 4.05-4.15 (3H, m), 6.51 (1H, dd, J=9.1 Hz, 3.9 Hz), 6.95 (1H, t, J=9.4 Hz), 7.02-7.10 (2H, m), 7.13 (1H, t, J=7.7 Hz), 7.54 (1H, brs).

Example 471

5-{[(1R*,2R*,4R*)-4-(4-Chloro-2-fluorophenyl)-1,2-dihydroxycyclohexyl]methoxy}-8-fluoro-3,4-dihydroquinolin-2(1H)-one Synthesized analogous to Example 6.
$^1$HNMR (DMSO-d6) δ ppm: 1.44-1.56 (2H, m), 1.61-1.96 (4H, m), 2.47 (2H, t, J=7.8 Hz), 2.77-3.00 (3H, m), 3.64 (1H, d, J=8.6 Hz), 3.68-3.76 (1H, m), 4.02 (1H, d, J=5.2 Hz), 4.40 (1H, s), 4.64 (1H, d, J=6.5 Hz), 6.56 (1H, dd, J=9.1 Hz, 3.8 Hz), 7.01 (1H, t, J=9.7 Hz), 7.26 (1H, dd, J=8.4 Hz, 2.0 Hz), 7.32-7.42 (2H, m), 10.01 (1H, brs).

Example 472

(1R,2R,5S)-5-(4-Chloro-2-fluorophenyl)-2-{[(8-fluoro-2-oxo-1,2,3,4-tetrahydroquinolin-5-yl)oxy]methyl}-2,5-dihydroxycyclohexyl acetate Synthesized analogous to Example 465.
$^1$HNMR (DMSO-d6) δ ppm: 1.37-1.51 (1H, m), 1.57-1.76 (2H, m), 1.93 (3H, s), 2.10-2.27 (1H, m), 2.29-2.44 (2H, m), 2.44-2.56 (2H, m), 2.90 (2H, t, J=7.6 Hz), 3.69 (1H, d, J=9.1 Hz), 3.83 (1H, d, J=9.1 Hz), 4.91 (1H, s), 5.35 (1H, dd, J=11.2 Hz, 4.8 Hz), 5.44 (1H, s), 6.54 (1H, dd, J=9.2 Hz), 7.00 (1H, t, J=9.7 Hz), 7.29 (1H, dd, J=8.5 Hz, 2.1 Hz), 7.33 (1H, dd, J=11.7 Hz, 2.1 Hz), 7.63 (1H, t, J=8.7 Hz), 10.03 (1H, s).

Example 473

5-{[(1R*,2R*,4S*)-4-(4-Chloro-2-fluorophenyl)-1,2,4-trihydroxycyclohexyl]methoxy}-8-fluoro-3,4-dihydroquinolin-2(1H)-one To a solution of (1R*,2R*,5S*)-5-(4-chloro-2-fluorophenyl)-2-{[(8-fluoro-2-oxo-1,2,3,4-tetrahydroquinolin-5-yl)oxy]methyl}-2,5-dihydroxycyclohexyl acetate (0.30 g) in N,N-dimethylformamide/methanol (5:3) (8 mL) was added potassium carbonate (0.167 g), and the reaction mixture was stirred at room temperature for 30 min. The reaction solution was concentrated, to the residue was added water, the precipitate was collected on a filter, and dried to provide the title compound (0.25 g).
$^1$HNMR (DMSO-d6) δ ppm: 1.36-1.46 (1H, m), 1.47-1.61 (1H, m), 1.61-1.74 (1H, m), 2.06-2.20 (1H, m), 2.22-2.38 (2H, m), 2.38-2.58 (2H, m), 2.81-3.03 (2H, m), 3.63 (1H, d, J=8.7 Hz), 3.97-4.11 (2H, m), 4.39 (2H, brs), 5.22 (1H, brs), 6.58 (1H, dd, J=9.1 Hz, 3.8 Hz), 7.01 (1H, t, J=9.7 Hz), 7.28 (1H, dd, J=8.4 Hz, 2.2 Hz), 7.31 (1H, dd, J=11.6 Hz, 2.1 Hz), 7.63 (1H, t, J=8.6 Hz), 10.03 (1H, brs).

Example 474

(1R*,2R*,5R*)-5-(4-Chloro-2-fluorophenyl)-2-{[(8-fluoro-2-oxo-1,2,3,4-tetrahydroquinolin-5-yl)oxy]methyl}-2,5-dihydroxycyclohexyl acetate Synthesized analogous to Example 465.
$^1$HNMR (DMSO-d6) δ ppm: 1.37-1.58 (1H, m), 1.63-1.76 (1H, m), 1.87-2.03 (4H, m), 2.07 (1H, t, J=12.2 Hz), 2.21-2.37 (3H, m), 2.37-2.60 (3H, m), 3.61 (1H, d, J=9.2 Hz), 3.77 (1H, d, J=9.2 Hz), 4.77 (1H, dd, J=11.6 Hz, 3.9 Hz), 5.02 (1H, s), 5.38 (1H, s), 6.46 (1H, dd, J=9.1 Hz, 3.7 Hz), 6.95 (1H, t, J=9.7 Hz), 7.32 (1H, dd, J=8.5 Hz, 2.2 Hz), 7.40 (1H, dd, J=12.2 Hz, 2.2 Hz), 7.68 (1H, t, J=8.7 Hz), 9.98 (1H, s).

Example 475

5-{[(1R*,2R*,4R*)-4-(4-Chloro-2-fluorophenyl)-1,2,4-trihydroxycyclohexyl]methoxy}-8-fluoro-3,4-dihydroquinolin-2(1H)-one Synthesized analogous to Example 473.
$^1$HNMR (DMSO-d6) δ ppm: 1.45-1.60 (1H, m), 1.63-1.77 (1H, m), 1.79-1.90 (1H, m), 1.90-2.01 (1H, m), 2.16-2.27 (1H, m), 2.28-2.37 (2H, m), 2.37-2.57 (3H, m), 3.48-3.61 (2H, m), 3.93 (1H, d, J=9.0 Hz), 4.49 (1H, brs), 4.84 (1H, brs), 5.42 (1H, brs), 6.67 (1H, dd, J=9.1 Hz, 3.7 Hz), 6.97 (1H, t, J=9.8 Hz), 7.30 (1H, dd, J=8.5 Hz, 2.2 Hz), 7.37 (1H, dd, J=12.2 Hz, 2.2 Hz), 7.54 (1H, t, J=8.7 Hz), 9.99 (1H, brs).

Example 476 trans-1-(4-Chloro-2-fluorophenyl)-4-{[(8-fluoro-2-oxo-1,2,3,4-tetrahydroquinolin-5-yl)oxy]methyl}-4-hydroxycyclohexanecarbonitrile Synthesized analogous to Example 42.
$^1$HNMR (DMSO-d6) δ ppm: 1.69-1.87 (2H, m), 1.92-2.05 (2H, m), 2.05-2.17 (2H, m), 2.17-2.31 (2H, m), 2.37-2.48 (2H, m), 2.95 (2H, t, J=7.6 Hz), 3.78 (2H, s), 4.86 (1H, s), 6.60 (1H, dd, J=9.1 Hz), 7.02 (1H, t, J=9.7 Hz), 7.40 (1H, dd, J=8.5 Hz, 2.0 Hz), 7.52-7.66 (2H, m), 10.03 (1H, brs).

Example 477

5-{[trans-4-(4-Chloro-2-fluorophenyl)-1-hydroxy-4-methoxycyclohexyl]methoxy}-8-fluoro-3,4-dihydroquinolin-2(1H)-one Synthesized analogous to Example 42.
$^1$HNMR (DMSO-d6) δ ppm: 1.45-1.57 (2H, m), 1.77-1.90 (2H, m), 1.90-2.00 (2H, m), 2.06-2.20 (2H, m), 2.43-2.49 (2H, m), 2.92 (2H, t, J=7.6 Hz), 2.96 (3H, s), 3.72 (2H, s), 4.56 (1H, s), 6.58 (1H, dd, J=9.1 Hz, 3.8 Hz), 7.00 (1H, t, J=9.7 Hz), 7.30 (1H, dd, J=8.5 Hz, 2.1 Hz), 7.38 (1H, dd, J=11.9 Hz, 2.1 Hz), 7.44 (1H, t, J=8.6 Hz), 10.0 (1H, brs).

Example 478

5-{[trans-4-(4-Chloro-2,6-difluorophenyl)-1,4-dihydroxycyclohexyl]methoxy}-8-fluoro-3,4-dihydroquinolin-2(1H)-one Synthesized analogous to Example 42.
(Methanol) m.p. 213.0-213.4° C.
$^1$HNMR (CDCl$_3$) δ ppm: 1.66-1.79 (2H, m), 1.93 (1H, s), 1.99-2.12 (4H, m), 2.45-2.58 (3H, m), 2.61-2.70 (2H, m), 3.02 (2H, t, J=7.7 Hz), 3.82 (2H, s), 6.48 (1H, dd, J=9.1 Hz, 4.0 Hz), 6.86-7.00 (3H, m), 7.54 (1H, brs).

Example 479

5-{[cis-4-(4-Chloro-2-fluorophenyl)-1-hydroxy-4-methoxycyclohexyl]methoxy}-8-fluoro-3,4-dihydro-quinolin-2(1H)-one Synthesized analogous to Example 42.
(2-Propanol) m.p. 155.4-158.8° C.
$^1$HNMR (CDCl$_3$) δ ppm: 1.73-1.87 (2H, m), 1.91-2.20 (6H, m), 2.30 (1H, s), 2.62-2.68 (2H, m), 2.98 (2H, t, J=7.7 Hz), 3.11 (3H, s), 3.95 (2H, s), 6.49 (1H, dd, J=9.1 Hz, 4.0 Hz), 6.91 (1H, t, J=9.4 Hz), 7.07 (1H, dd, J=11.2 Hz, 2.1 Hz), 7.13 (1H, dd, J=8.5 Hz, 2.1 Hz), 7.33 (1H, t, J=8.5 Hz), 7.65 (1H, s).

Example 480

5-{[cis-4-(4-Chloro-2,6-difluorophenyl)-1,4-dihydroxycyclohexyl]methoxy}-8-fluoro-3,4-dihydroquinolin-2(1H)-one Synthesized analogous to Example 42.
$^1$HNMR (DMSO-d6) δ ppm: 1.54-1.70 (2H, m), 1.71-1.82 (2H, m), 1.88-2.02 (2H, m), 2.10-2.25 (2H, m), 2.40 (2H, t, J=7.6 Hz), 2.71 (2H, t, J=7.6 Hz), 3.77 (2H, s), 4.63 (1H, s), 5.33 (1H, s), 6.55 (1H, dd, J=9.1 Hz, 3.8 Hz), 6.98 (1H, t, J=9.7 Hz), 7.20-7.32 (2H, m), 9.99 (1H, s).

Test Example 1

Antibacterial Test (Agar Plate Dilution Method)

The minimum inhibitory concentration against *Mycobacterium tuberculosis* (*M. tuberculosis* H37Rv) of the fused heterocyclyl compound obtained from Example 259 was determined by using 7H11 medium (BBL). The bacterial strain was previously cultured on 7H9 medium (BBL), cryopreserved at −80° C., and the viable bacterial count was calculated. The preserved bacterial solution was used to prepare the bacterial solution in which the final viable bacterial count was about 10$^6$ CFU/mL. About 5 μL of this bacterial solution was inoculated into the 7H11 agar medium containing the test compound. After incubated at 37° C. for 14 days, the minimum inhibitory concentration was determined.

The minimum inhibitory concentration against *M. tuberculosis* H37Rv was <0.39 μg/mL.

Test Example 2

Antibacterial Test (Agar Dilution Method)

Regarding the test compounds shown in the following table, the respective minimum inhibitory concentrations against *Mycobacterium tuberculosis* (*M. tuberculosis* Kurono) were determined by using 7H11 medium (BBL). The bacterial strain was previously cultured on 7H9 medium (BBL), cryopreserved at −80° C., and the viable bacterial count was calculated. The preserved bacterial suspension was used to prepare the bacterial suspension in which the final viable bacterial count was about 10$^6$ CFU/mL. About 5 μL of this bacterial suspension was inoculated into the 7H11 agar medium containing the test compound, and incubated at 37° C. for 14 days, the minimum inhibitory concentration was determined.

The results are shown in the following Table.

TABLE 1

| Test Compounds | Minimum inhibitory concentration (MIC) kurono (μg/mL) |
|---|---|
| Compound of Example 1 | <0.39 |
| Compound of Example 14 | <0.39 |
| Compound of Example 17 | <0.39 |
| Compound of Example 49 | <0.39 |
| Compound of Example 52 | <0.39 |
| Compound of Example 85 | <0.39 |
| Compound of Example 102 | <0.39 |
| Compound of Example 130 | <0.39 |
| Compound of Example 138 | <0.39 |
| Compound of Example 139 | <0.39 |
| Compound of Example 152 | <0.39 |
| Compound of Example 175 | <0.39 |
| Compound of Example 194 | <0.39 |
| Compound of Example 206 | <0.39 |
| Compound of Example 214 | <0.39 |
| Compound of Example 251 | <0.39 |
| Compound of Example 252 | <0.39 |
| Compound of Example 259 | <0.39 |
| Compound of Example 260 | <0.39 |
| Compound of Example 265 | <0.39 |
| Compound of Example 288 | <0.39 |
| Compound of Example 347 | <0.39 |
| Compound of Example 361 | <0.39 |
| Compound of Example 364 | <0.39 |
| Compound of Example 369 | <0.39 |
| Compound of Example 372 | <0.39 |
| Compound of Example 399 | <0.39 |
| Compound of Example 404 | <0.39 |
| Compound of Example 419 | <0.39 |
| Compound of Example 446 | <0.39 |
| Compound of Example 447 | <0.39 |
| Compound of Example 448 | <0.39 |
| Compound of Example 449 | <0.39 |
| Compound of Example 450 | <0.39 |
| Compound of Example 454 | <0.39 |
| Compound of Example 460 | <0.39 |
| Compound of Example 463 | <0.39 |
| Compound of Example 465 | <0.39 |
| Compound of Example 469 | <0.39 |
| Compound of Example 471 | <0.39 |
| Compound of Example 473 | <0.39 |
| Compound of Example 476 | <0.39 |
| Compound of Example 477 | <0.39 |

INDUSTRIAL APPLICABILITY

The present invention can provide compounds with an excellent antibacterial activity against tuberculosis bacteria, multidrug-resistant tuberculosis bacteria and/or non-tuberculous mycobacteria.

The invention claimed is:
1. A compound of the general formula (1):

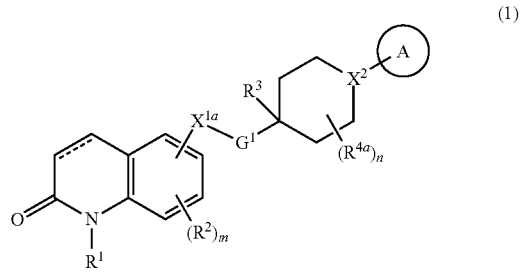

or a salt thereof, wherein R¹ is
(1) hydrogen,
(2) amino which may have one or two of the same or different lower alkyl or
(3) lower alkyl;

R² is
(1) halogen,
(2) amino which may have one or two of the same or different lower alkyl,
(3) lower alkyl,
(4) lower alkoxy or
(5) hydroxy;

m is an integer of 0 to 3;
provided that when m is 2 or 3, R² may be different from each other;

a partial structure (Y) of formula (1) is represented by the following partial structure:

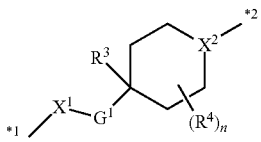
(Y)

wherein *1 is a binding point to a partial structure (X) of formula (1) and *2 is a binding point to Ring A, and the partial structure (X) of formula (1) is represented by the following partial structure:

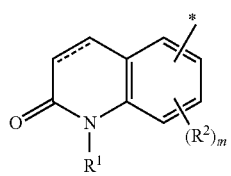
(X)

wherein * is a binding point to X¹, the partial structure (Y) is any one of the structures selected from the group consisting of the following formulae (Y1) to (Y8):

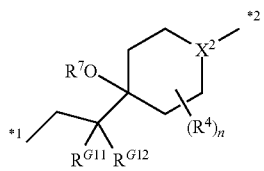
(Y1)

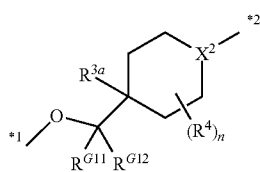
(Y2)

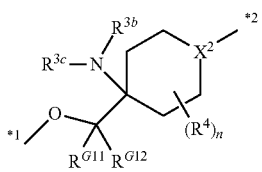
(Y3)

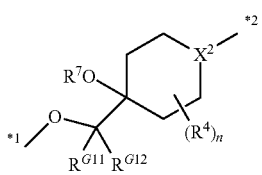
(Y4)

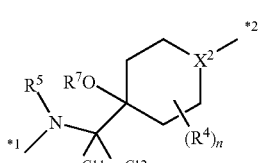
(Y5)

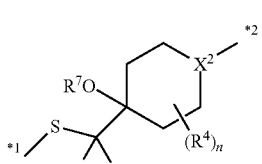
(Y6)

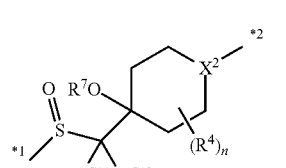
(Y7)

and

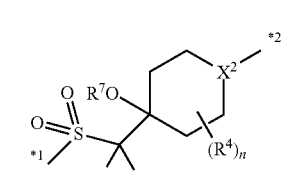
(Y8)

wherein $R^{3a}$ is
(1) hydrogen,
(2) carboxy,
(3) halogen,
(4) lower alkyl, which may have one or more hydroxy, or
(5) cyano;

$R^{3b}$ and $R^{3c}$ are each independently
(1) hydrogen,
(2) lower alkyl, or
(3) —C(=O)—R⁶;

$R^{G11}$ and $R^{G12}$ are each independently hydrogen or lower alkyl;
the total number of carbon atoms in $R^{G11}$ and $R^{G12}$ is 0 to 5;

R⁵ is
(1) hydrogen,
(2) lower alkyl or
(3) lower alkanoyl;

R⁶ is
- (1) lower alkoxy or
- (2) lower alkyl, wherein the lower alkyl may have amino which may have one or two of the same or different lower alkyl;

R⁷ is
- (1) hydrogen,
- (2) amino,
- (3) lower alkanoyl or
- (4) lower alkyl;

R⁴ is
- (1) amino which may have one or two of the same or different lower alkyl,
- (2) halogen,
- (3) cyano,
- (4) lower alkyl,
- (5) oxo,
- (6) —O—R⁸ or
- (7) —O—C(=O)—R⁹;

R⁸ is
- (1) hydrogen,
- (2) lower alkyl,
- (3) —PH(=O)OH or
- (4) benzyl which may have one or more of the same or different lower alkoxy;

R⁹ is
- (1) lower alkyl,
- (2) -G²-COOH,
- (3) amino which may have one or two of the same or different lower alkyl,
- (4) lower alkoxy or
- (5) pyrazinyl;

G² is lower alkylene;

n is an integer of 0 to 8;
provided that when n is 2 or more, each of R⁴, R⁸, R⁹, and G² may be different from each other and may be substituted on the same carbon atom;

X² is N or CH;
provided that when X² is CH, H of the group may be replaced with R⁴ which is defined as above, wherein multiple R⁴s in formula (1) may be the same or different from each other;

Ring A is
- (1) aryl which may have one or more substituents, or
- (2) heterocyclyl which may have one or more substituents; and a moiety of formula:
represents single bond or double bond.

2. The compound of claim 1, or a salt thereof, wherein the partial structure (X)
is any one of the structures selected from the group consisting of the following formulae (X1) to (X6):

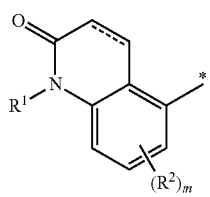
(X1)

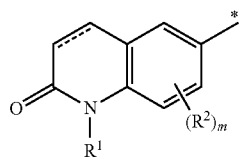
(X2)

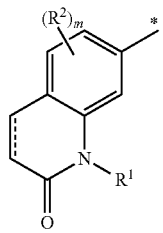
(X3)

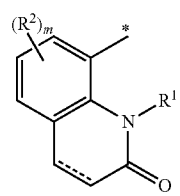
(X4)

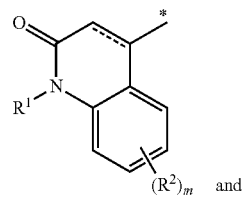
(X5)

and

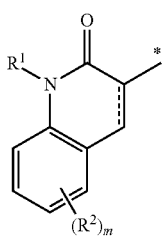
(X6)

wherein the symbols are as defined in the above and claim 1.

3. The compound of claim 1, or a salt thereof, wherein Ring A is aryl or heterocyclyl which may have 1 to 5 substituents independently selected from:
- (a) halogen;
- (b) cyano;
- (c) nitro;
- (d) hydroxy;
- (e) lower alkyl which may have one or more substituents independently selected from:
  - (i) halogen,
  - (ii) hydroxy,
  - (iii) lower alkoxy, and
  - (iv) aryloxy which may have one or more of the same or different halogen;
- (f) lower alkoxy which may have one or more substituents independently selected from:
  - (i) halogen,
  - (ii) lower alkoxy which may have one or more of the same or different lower alkoxy,
  - (iii) aryloxy which may have one or more of the same or different halogen, (iv) heterocyclyl which may have one or more of the same or different lower alkyl which may have one or more of the same or different halogen, and
(v) amino which may have one or two of the same or different lower alkyl;
(g) lower alkoxycarbonyl;
(h) lower alkylsulfanyl;
(i) aryl which may have one or more of the same or different halogen;
(j) aryloxy; and
(k) aralkyloxy which may have one or more substituents independently selected from:
  (i) halogen,
  (ii) lower alkyl which may have one or more of the same or different halogen, and
  (iii) lower alkoxy which may have one or more of the same or different halogen.

4. The compound of claim 1, or a salt thereof, wherein $R^1$ is hydrogen.

5. The compound of claim 1, or a salt thereof, wherein $R^2$ is halogen.

6. The compound of claim 1, or a salt thereof, wherein m is 0, 1 or 2.

7. The compound of claim 1, or a salt thereof, wherein n is 0, 1 or 2.

8. The compound of claim 1, or a salt thereof, wherein the partial structure (X) is a structure of a formula selected from the group consisting of the formulae (X1-1), (X1-2), (X1-3), (X1-4), (X1-6), and (X1-7):

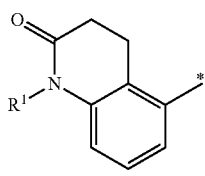
(X1-1)

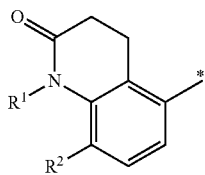
(X1-2)

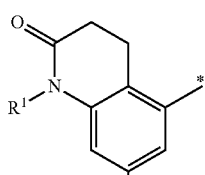
(X1-3)

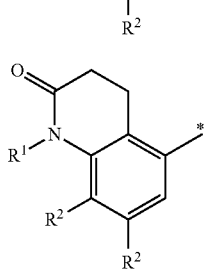
(X1-4)

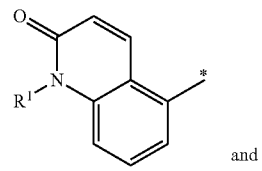
(X1-6)

and

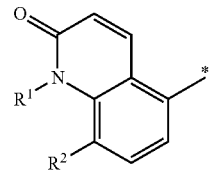
(X1-7)

wherein * is binding point to $X^1$;

$R^1$ is hydrogen;

$R^2$ is substituent selected from (1) halogen or (2) lower alkyl;

provided that when $R^2$ may be multiple, each of them may be different from each other;

the partial structure (Y) is a structure of a formula selected from the group consisting of the formulae (Y1-1), (Y2-1), (Y3-1), (Y4-1), (Y5-1), and (Y6-1):

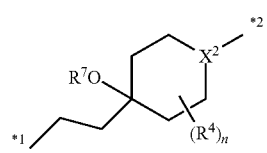
(Y1-1)

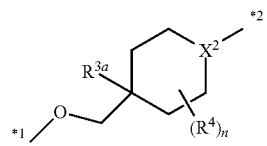
(Y2-1)

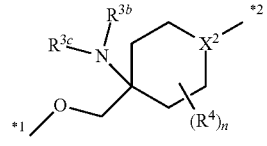
(Y3-1)

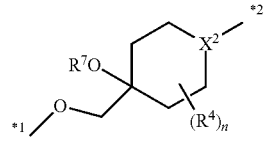
(Y4-1)

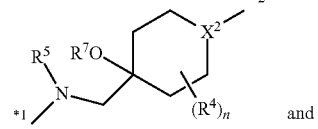
(Y5-1)

and

-continued (Y6-1)

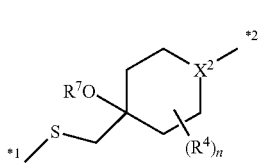

wherein *1 is binding point to the partial structure (X);
*2 is binding point to Ring A;
$R^5$ is hydrogen;
$R^{3a}$ is (1) hydrogen or (2) halogen;
$R^{3b}$ and $R^{3c}$ are each hydrogen;
$R^7$ is hydrogen;
$R^4$ is substituent selected from (1) halogen, (2) —O—$R^8$, (3) —O—C(=O)—$R^9$, or (4) cyano;
$R^8$ is (1) hydrogen or (2) lower alkyl;
$R^9$ is (1) lower alkyl or (2) lower alkoxy;
n is an integer of 0 to 2;
provided that when n is 2, each of $R^4$, $R^8$, and $R^9$ may be different from each other and may be substituted on the same carbon atom;
$X^2$ is N or CH;
provided that when $X^2$ is CH, H of the group may be substituted with $R^4$ which is defined as above or may be different from the other $R^4$; and
Ring A is phenyl or pyridyl which may have 1 to 3 groups independently selected from:
(a) halogen;
(b) lower alkoxy which may have (i) halogen and (ii) lower alkoxy; or
(c) aralkyloxy which may have one or more of the same or different lower alkoxy which may have one or more of the same or different halogen; or
quinolyl which may have 1 to 2 halogen.

9. The compound of claim 1, which is selected from the group consisting of the following compounds:
5-{[4-amino-1-(3,5-dichloropyridin-2-yl)piperidin-4-yl]methoxy}-8-fluoro-3,4-dihydroquinolin-2(1H)-one;
5-{[4-amino-1-(4-chloro-2-fluorophenyl)piperidin-4-yl]methoxy}-8-chloro-3,4-dihydroquinolin-2(1H)-one;
5-{[4-amino-1-(4-chloro-2-fluorophenyl)piperidin-4-yl]methoxy}-8-chloroquinolin-2(1H)-one;
5-{[1-(4-chlorophenyl)-4-hydroxypiperidin-4-yl]methoxy}-8-fluoro-3,4-dihydroquinolin-2(1H)-one;
5-{[1-(4-chloro-2-fluorophenyl)-4-hydroxypiperidin-4-yl]methoxy}-8-fluoro-3,4-dihydroquinolin-2(1H)-one;
5-{[1-(4-ethoxy-2-fluorophenyl)-4-hydroxypiperidin-4-yl]methoxy}-8-fluoro-3,4-dihydroquinolin-2(1H)-one;
8-chloro-5-{[1-(4-chloro-2,6-difluorophenyl)-4-hydroxypiperidin-4-yl]methoxy}-3,4-dihydroquinolin-2(1H)-one;
5-{[1-(4-bromo-2-fluorophenyl)-4-hydroxypiperidin-4-yl]methoxy}-7,8-difluoro-3,4-dihydroquinolin-2(1H)-one;
5-{[1-(4-chloro-2-fluorophenyl)-4-hydroxypiperidin-4-yl]methoxy}quinolin-2(1H)-one;
8-chloro-5-{[1-(3,5-dichloropyridin-2-yl)-4-hydroxypiperidin-4-yl]methoxy}-3,4-dihydroquinolin-2(1H)-one;
8-fluoro-5-{[1-(2-fluoro-4-[{4-(trifluoromethoxy)benzyl]oxy}phenyl)-4-hydroxypiperidin-4-yl]methoxy}-3,4-dihydroquinolin-2(1H)-one;
8-chloro-5-({1-[4-chloro-2-fluoro-5-(2-methoxyethoxy)phenyl]-4-hydroxypiperidin-4-yl}methoxy)-3,4-dihydroquinolin-2(1H)-one;
5-{[1-(4-chloro-2-fluorophenyl)-4-hydroxypiperidin-4-yl]methoxy}-7-fluoro-3,4-dihydroquinolin-2(1H)-one;
5-{[1-(2,4-dichloro-5-fluorophenyl)-4-hydroxypiperidin-4-yl]methoxy}-7-fluoro-8-methyl-3,4-dihydroquinolin-2(1H)-one;
8-chloro-7-fluoro-5-{[4-hydroxy-1-(2,4,6-trifluorophenyl)piperidin-4-yl]methoxy}-3,4-dihydroquinolin-2(1H)-one;
5-{[(3R,4R)-1-(3,5-dichloropyridin-2-yl)-3,4-dihydroxypiperidin-4-yl]methoxy}-8-fluoro-3,4-dihydroquinolin-2(1H)-one;
5-{[(3S,4S)-1-(3,5-dichloropyridin-2-yl)-3,4-dihydroxypiperidin-4-yl]methoxy}-8-fluoro-3,4-dihydroquinolin-2(1H)-one;
5-{[(3R,4R)-1-(4-chloro-2-fluorophenyl)-3,4-dihydroxypiperidin-4-yl]methoxy}-8-fluoro-3,4-dihydroquinolin-2(1H)-one;
5-{[(3R,4R)-1-(4-chloro-2,6-difluorophenyl)-3,4-dihydroxypiperidin-4-yl]methoxy}-8-fluoro-3,4-dihydroquinolin-2(1H)-one;
5-{[(3S,4S)-1-(4-chloro-2-fluorophenyl)-3,4-dihydroxypiperidin-4-yl]methoxy}-8-fluoro-3,4-dihydroquinolin-2(1H)-one;
5-{[(3R,4R)-1-(3-bromo-6-chloroquinolin-2-yl)-3,4-dihydroxypiperidin-4-yl]methoxy}-8-fluoro-3,4-dihydroquinolin-2(1H)-one;
5-{[(3R,4R)-1-(4-bromo-2-fluorophenyl)-3,4-dihydroxypiperidin-4-yl]methoxy}-3,4-dihydroquinolin-2(1H)-one;
5-{[(3S,4R)-1-(4-chloro-2,6-difluorophenyl)-3,4-dihydroxypiperidin-4-yl]methoxy}-8-fluoro-3,4-dihydroquinolin-2(1H)-one;
5-{[(3R,4S)-1-(4-bromo-2-fluorophenyl)-3,4-dihydroxypiperidin-4-yl]methoxy}-8-chloro-3,4-dihydroquinolin-2(1H)-one;
5-{[(3R*,4R*)-1-(4-bromo-2-fluorophenyl)-3,4-dihydroxypiperidin-4-yl]methoxy}-8-fluoroquinolin-2(1H)-one;
5-({[1-(3,5-dichloropyridin-2-yl)-4-hydroxypiperidin-4-yl]methyl}amino)-8-fluoro-3,4-dihydroquinolin-2(1H)-one;
5-{[1-(3,5-dichloropyridin-2-yl)piperidin-4-yl]methoxy}-8-fluoro-3,4-dihydroquinolin-2(1H)-one;
5-{[1-(3,5-dichloropyridin-2-yl)-4-fluoropiperidin-4-yl]methoxy}-8-fluoro-3,4-dihydroquinolin-2(1H)-one;
5-{[(3R*,4R*)-1-(4-chloro-2-fluorophenyl)-3-hydroxypiperidin-4-yl]methoxy}-8-fluoro-3,4-dihydroquinolin-2(1H)-one;
5-{[(3R,4S)-1-(4-chloro-2,6-difluorophenyl)-3-fluoro-4-hydroxypiperidin-4-yl]methoxy}-8-fluoro-3,4-dihydroquinolin-2(1H)-one;
5-{[(3S,4R)-1-(4-chloro-2,6-difluorophenyl)-3-fluoro-4-hydroxypiperidin-4-yl]methoxy}-8-fluoro-3,4-dihydroquinolin-2(1H)-one;
5-{[(3R,4R)-1-(4-chloro-2,6-difluorophenyl)-3-fluoro-4-hydroxypiperidin-4-yl]methoxy}-8-fluoro-3,4-dihydroquinolin-2(1H)-one;
5-{[(3S,4S)-1-(4-chloro-2,6-difluorophenyl)-3-fluoro-4-hydroxypiperidin-4-yl]methoxy}-8-fluoro-3,4-dihydroquinolin-2(1H)-one;
(3R,4R)-1-(4-chloro-2,6-difluorophenyl)-4-{[(8-fluoro-2-oxo-1,2,3,4-tetrahydroquinolin-5-yl)oxy]methyl}-4-hydroxypiperidin-3-yl ethyl carbonate;
(3R,4R)-1-(4-chloro-2-fluorophenyl)-4-{[(8-fluoro-2-oxo-1,2,3,4-tetrahydroquinolin-5-yl)oxy]methyl}-4-hydroxypiperidin-3-yl acetate;

5-({[1-(4-chloro-2-fluorophenyl)-4-hydroxypiperidin-4-yl]methyl}sulfanyl)-8-fluoro-3,4-dihydroquinolin-2(1H)-one;
5-{2-[1-(4-chloro-2,6-difluorophenyl)-4-hydroxypiperidin-4-yl]ethyl}-8-fluoro-3,4-dihydroquinolin-2(1H)-one;
5-{[trans-4-(4-chloro-2-fluorophenyl)-1,4-dihydroxycyclohexyl]methoxy}-8-fluoro-3,4-dihydroquinolin-2(1H)-one;
5-{[cis-4-(4-chloro-2-fluorophenyl)-1-hydroxycyclohexyl]methoxy}-8-fluoro-3,4-dihydroquinolin-2(1H)-one;
5-{[(1R*,2R*,4R*)-4-(4-chloro-2-fluorophenyl)-1,2-dihydroxycyclohexyl]methoxy}-8-fluoro-3,4-dihydroquinolin-2(1H)-one;
5-{[1R,2R,4S)-4-(4-chloro-2-fluorophenyl)-1,2,4-trihydroxycyclohexyl]methoxy}-8-fluoro-3,4-dihydroquinolin-2(1H)-one;
trans-1-(4-chloro-2-fluorophenyl)-4-{[(8-fluoro-2-oxo-1,2,3,4-tetrahydroquinolin-5-yl)oxy]methyl}-4-hydroxycyclohexanecarbonitrile; and
5-{[trans-4-(4-chloro-2-fluorophenyl)-1-hydroxy-4-methoxycyclohexyl]methoxy}-8-fluoro-3,4-dihydroquinolin-2(1H)-one, or a salt thereof.

10. The compound of claim 1, which is selected from the group consisting of the following compounds:

5-{[4-amino-1-(3,5-dichloropyridin-2-yl)piperidin-4-yl]methoxy}-8-fluoro-3,4-dihydroquinolin-2(1H)-one;
5-{[4-amino-1-(4-chloro-2-fluorophenyl)piperidin-4-yl]methoxy}-8-chloro-3,4-dihydroquinolin-2(1H)-one;
5-{[4-amino-1-(4-chloro-2-fluorophenyl)piperidin-4-yl]methoxy}-8-chloroquinolin-2(1H)-one;
5-{[1-(4-chlorophenyl)-4-hydroxypiperidin-4-yl]methoxy}-8-fluoro-3,4-dihydroquinolin-2(1H)-one;
5-{[1-(4-chloro-2-fluorophenyl)-4-hydroxypiperidin-4-yl]methoxy}-8-fluoro-3,4-dihydroquinolin-2(1H)-one;
5-{[1-(4-ethoxy-2-fluorophenyl)-4-hydroxypiperidin-4-yl]methoxy}-8-fluoro-3,4-dihydroquinolin-2(1H)-one;
8-chloro-5-{[1-(4-chloro-2,6-difluorophenyl)-4-hydroxypiperidin-4-yl]methoxy}-3,4-dihydroquinolin-2(1H)-one;
5-{[1-(4-bromo-2-fluorophenyl)-4-hydroxypiperidin-4-yl]methoxy}-7,8-difluoro-3,4-dihydroquinolin-2(1H)-one;
5-{[1-(4-chloro-2-fluorophenyl)-4-hydroxypiperidin-4-yl]methoxy}quinolin-2(1H)-one;
8-chloro-5-{[1-(3,5-dichloropyridin-2-yl)-4-hydroxypiperidin-4-yl]methoxy}-3,4-dihydroquinolin-2(1H)-one;
8-fluoro-5-{[1-(2-fluoro-4-{[4-(trifluoromethoxy)benzyl]oxy}phenyl)-4-hydroxypiperidin-4-yl]methoxy}-3,4-dihydroquinolin-2(1H)-one;
8-chloro-5-({1-[4-chloro-2-fluoro-5-(2-methoxyethoxy)phenyl]-4-hydroxypiperidin-4-yl}methoxy)-3,4-dihydroquinolin-2(1H)-one;
5-{[1-(4-chloro-2-fluorophenyl)-4-hydroxypiperidin-4-yl]methoxy}-7-fluoro-3,4-dihydroquinolin-2(1H)-one;
5-{[1-(2,4-dichloro-5-fluorophenyl)-4-hydroxypiperidin-4-yl]methoxy}-7-fluoro-8-methyl-3,4-dihydroquinolin-2(1H)-one;
8-chloro-7-fluoro-5-{[4-hydroxy-1-(2,4,6-trifluorophenyl)piperidin-4-yl]methoxy}-3,4-dihydroquinolin-2(1H)-one;
5-{[(3R,4R)-1-(3,5-dichloropyridin-2-yl)-3,4-dihydroxypiperidin-4-yl]methoxy}-8-fluoro-3,4-dihydroquinolin-2(1H)-one;
5-{[(3S,4S)-1-(3,5-dichloropyridin-2-yl)-3,4-dihydroxypiperidin-4-yl]methoxy}-8-fluoro-3,4-dihydroquinolin-2(1H)-one;
5-{[(3R,4R)-1-(4-chloro-2-fluorophenyl)-3,4-dihydroxypiperidin-4-yl]methoxy}-8-fluoro-3,4-dihydroquinolin-2(1H)-one;
5-{[(3R,4R)-1-(4-chloro-2,6-difluorophenyl)-3,4-dihydroxypiperidin-4-yl]methoxy}-8-fluoro-3,4-dihydroquinolin-2(1H)-one;
5-{[(3S,4S)-1-(4-chloro-2-fluorophenyl)-3,4-dihydroxypiperidin-4-yl]methoxy}-8-fluoro-3,4-dihydroquinolin-2(1H)-one;
5-{[(3R,4R)-1-(3-bromo-6-chloroquinolin-2-yl)-3,4-dihydroxypiperidin-4-yl]methoxy}-8-fluoro-3,4-dihydroquinolin-2(1H)-one;
5-{[(3R,4R)-1-(4-bromo-2-fluorophenyl)-3,4-dihydroxypiperidin-4-yl]methoxy}-3,4-dihydroquinolin-2(1H)-one;
5-{[(3S,4R)-1-(4-chloro-2,6-difluorophenyl)-3,4-dihydroxypiperidin-4-yl]methoxy}-8-fluoro-3,4-dihydroquinolin-2(1H)-one;
5-{[(3R,4S)-1-(4-bromo-2-fluorophenyl)-3,4-dihydroxypiperidin-4-yl]methoxy}-8-chloro-3,4-dihydroquinolin-2(1H)-one;
5-{[(3R*,4R*)-1-(4-bromo-2-fluorophenyl)-3,4-dihydroxypiperidin-4-yl]methoxy}-8-fluoroquinolin-2(1H)-one;
5-({[1-(3,5-dichloropyridin-2-yl)-4-hydroxypiperidin-4-yl]methyl}amino)-8-fluoro-3,4-dihydroquinolin-2(1H)-one;
5-{[1-(3,5-dichloropyridin-2-yl)piperidin-4-yl]methoxy}-8-fluoro-3,4-dihydroquinolin-2(1H)-one;
5-{[1-(3,5-dichloropyridin-2-yl)-4-fluoropiperidin-4-yl]methoxy}-8-fluoro-3,4-dihydroquinolin-2(1H)-one;
5-{[(3R*,4R*)-1-(4-chloro-2-fluorophenyl)-3-hydroxypiperidin-4-yl]methoxy}-8-fluoro-3,4-dihydroquinolin-2(1H)-one;
5-{[(3R,4S)-1-(4-chloro-2,6-difluorophenyl)-3-fluoro-4-hydroxypiperidin-4-yl]methoxy}-8-fluoro-3,4-dihydroquinolin-2(1H)-one;
5-{[(3S,4R)-1-(4-chloro-2,6-difluorophenyl)-3-fluoro-4-hydroxypiperidin-4-yl]methoxy}-8-fluoro-3,4-dihydroquinolin-2(1H)-one;
5-{[(3R,4R)-1-(4-chloro-2,6-difluorophenyl)-3-fluoro-4-hydroxypiperidin-4-yl]methoxy}-8-fluoro-3,4-dihydroquinolin-2(1H)-one;
5-{[(3S,4S)-1-(4-chloro-2,6-difluorophenyl)-3-fluoro-4-hydroxypiperidin-4-yl]methoxy}-8-fluoro-3,4-dihydroquinolin-2(1H)-one;
(3R,4R)-1-(4-chloro-2,6-difluorophenyl)-4-{[(8-fluoro-2-oxo-1,2,3,4-tetrahydroquinolin-5-yl)oxy]methyl}-4-hydroxypiperidin-3-yl ethyl carbonate;
(3R,4R)-1-(4-chloro-2-fluorophenyl)-4-{[(8-fluoro-2-oxo-1,2,3,4-tetrahydroquinolin-5-yl)oxy]methyl}-4-hydroxypiperidin-3-yl acetate;
5-({[1-(4-chloro-2-fluorophenyl)-4-hydroxypiperidin-4-yl]methyl}sulfanyl)-8-fluoro-3,4-dihydroquinolin-2(1H)-one;
5-{2-[1-(4-chloro-2,6-difluorophenyl)-4-hydroxypiperidin-4-yl]ethyl}-8-fluoro-3,4-dihydroquinolin-2(1H)-one;
5-{[trans-4-(4-chloro-2-fluorophenyl)-1,4-dihydroxycyclohexyl]methoxy}-8-fluoro-3,4-dihydroquinolin-2(1H)-one;
5-{[cis-4-(4-chloro-2-fluorophenyl)-1-hydroxycyclohexyl]methoxy}-8-fluoro-3,4-dihydroquinolin-2(1H)-one;

5-{[(1R*,2R*,4R*)-4-(4-chloro-2-fluorophenyl)-1,2-dihydroxycyclohexyl]methoxy}-8-fluoro-3,4-dihydroquinolin-2(1H)-one;

5-{[(1R,2R,4S)-4-(4-chloro-2-fluorophenyl)-1,2,4-trihydroxycyclohexyl]methoxy}-8-fluoro-3,4-dihydroquinolin-2(1H)-one;

trans-1-(4-chloro-2-fluorophenyl)-4-{[(8-fluoro-2-oxo-1,2,3,4-tetrahydroquinolin-5-yl)oxy]methyl}-4-hydroxycyclohexanecarbonitrile; and 5-{[trans-4-(4-chloro-2-fluorophenyl)-1-hydroxy-4-methoxycyclohexyl]methoxy}-8-fluoro-3,4-dihydroquinolin-2(1H)-one.

11. A pharmaceutical composition, comprising the compound of claim 1, or a salt thereof and a pharmaceutically acceptable carrier.

12. The compound of claim 1, which is 8-chloro-5-{[1-(4-chloro-2,6-difluorophenyl)-4-hydroxypiperidin-4-yl]methoxy}-3,4-dihydroquinolin-2(1H)-one, or a salt thereof.

13. The compound of claim 1, which is 8-chloro-5-{[1-(4-chloro-2,6-difluorophenyl)-4-hydroxypiperidin-4-yl]methoxy}-3,4-dihydroquinolin-2(1H)-one.

14. The compound of claim 1, which is 5-{[1-(4-bromo-2-fluorophenyl)-4-hydroxypiperidin-4-yl]methoxy}-7,8-difluoro-3,4-dihydroquinolin-2(1H)-one, or a salt thereof.

15. The compound of claim 1, which is 5-{[1-(4-bromo-2-fluorophenyl)-4-hydroxypiperidin-4-yl]methoxy}-7,8-difluoro-3,4-dihydroquinolin-2(1H)-one.

16. The compound of claim 1, which is 5-{[1-(2,4-dichloro-5-fluorophenyl)-4-hydroxypiperidin-4-yl]methoxy}-7-fluoro-8-methyl-3,4-dihydroquinolin-2(1H)-one, or a salt thereof.

17. The compound of claim 1, which is 5-{[1-(2,4-dichloro-5-fluorophenyl)-4-hydroxypiperidin-4-yl]methoxy}-7-fluoro-8-methyl-3,4-dihydroquinolin-2(1H)-one.

18. The compound of claim 1, which is 5-{[(3R,4R)-1-(4-chloro-2,6-difluorophenyl)-3,4-dihydroxypiperidin-4-yl]methoxy}-8-fluoro-3,4-dihydroquinolin-2(1H)-one, or a salt thereof.

19. The compound of claim 1, which is 5-{[(3R,4R)-1-(4-chloro-2,6-difluorophenyl)-3,4-dihydroxypiperidin-4-yl]methoxy}-8-fluoro-3,4-dihydroquinolin-2(1H)-one.

20. The compound of claim 1, which is (3R,4R)-1-(4-chloro-2-fluorophenyl)-4-{[(8-fluoro-2-oxo-1,2,3,4-tetrahydroquinolin-5-yl)oxy]methyl}-4-hydroxypiperidin-3-yl acetate, or a salt thereof.

21. The compound of claim 1, which is (3R,4R)-1-(4-chloro-2-fluorophenyl)-4-{[(8-fluoro-2-oxo-1,2,3,4-tetrahydroquinolin-5-yl)oxy]methyl}-4-hydroxypiperidin-3-yl acetate.

* * * * *

UNITED STATES PATENT AND TRADEMARK OFFICE
CERTIFICATE OF CORRECTION

PATENT NO. : 10,053,446 B2
APPLICATION NO. : 15/506887
DATED : August 21, 2018
INVENTOR(S) : Hiroshi Shimizu et al.

Page 1 of 1

It is certified that error appears in the above-identified patent and that said Letters Patent is hereby corrected as shown below:

In Claim 1, in Column 405, Lines 51-52 should read as follows:
a moiety of formula:

represents single bond or double bond.

Signed and Sealed this
Third Day of November, 2020

Andrei Iancu
*Director of the United States Patent and Trademark Office*